United States Patent
Zhang et al.

(10) Patent No.: US 11,597,949 B2
(45) Date of Patent: *Mar. 7, 2023

(54) OPTIMIZED CRISPR-CAS DOUBLE NICKASE SYSTEMS, METHODS AND COMPOSITIONS FOR SEQUENCE MANIPULATION

(71) Applicants: The Broad Institute, Inc., Cambridge, MA (US); Massachusetts Institute of Technology, Cambridge, MA (US); President and Fellows of Harvard College, Cambridge, MA (US)

(72) Inventors: Feng Zhang, Cambridge, MA (US); Patrick Hsu, Cambridge, MA (US); Chie-Yu Lin, Cambridge, MA (US); Fei Ran, Cambridge, MA (US)

(73) Assignees: THE BROAD INSTITUTE, INC., Cambridge, MA (US); MASSACHUSETTS INSTITUTE OF TECHNOLOGY, Cambridge, MA (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 242 days.

This patent is subject to a terminal disclaimer.

(21) Appl. No.: 16/844,548

(22) Filed: Apr. 9, 2020

(65) Prior Publication Data

US 2020/0377912 A1    Dec. 3, 2020

Related U.S. Application Data

(63) Continuation of application No. 14/972,523, filed on Dec. 17, 2015, now Pat. No. 10,711,285, which is a continuation-in-part of application No. PCT/US2014/041803, filed on Jun. 10, 2014, which is a continuation-in-part of application No. PCT/US2013/074667, filed on Dec. 12, 2013.

(60) Provisional application No. 61/915,383, filed on Dec. 12, 2013, provisional application No. 61/871,301, filed on Aug. 28, 2013, provisional application No. 61/862,355, filed on Aug. 5, 2013, provisional application No. 61/847,537, filed on Jul. 17, 2013, provisional application No. 61/836,123, filed on Jun. 17, 2013.

(51) Int. Cl.
| | |
|---|---|
| *C12N 15/90* | (2006.01) |
| *C12N 9/22* | (2006.01) |
| *C12N 15/10* | (2006.01) |
| *C12N 15/63* | (2006.01) |
| *A61K 48/00* | (2006.01) |

(52) U.S. Cl.
CPC .......... *C12N 15/907* (2013.01); *A61K 48/005* (2013.01); *C12N 9/22* (2013.01); *C12N 15/102* (2013.01); *C12N 15/1082* (2013.01); *C12N 15/63* (2013.01); *C12N 2800/80* (2013.01)

(58) Field of Classification Search
CPC .................................................. C12N 15/907
See application file for complete search history.

(56) References Cited

U.S. PATENT DOCUMENTS

| | | | |
|---|---|---|---|
| 5,622,856 | A | 4/1997 | Natsoulis |
| 6,251,677 | B1 | 6/2001 | Wilson et al. |
| 7,601,492 | B2 | 10/2009 | Fu et al. |
| 7,691,995 | B2 | 4/2010 | Zamore et al. |
| 8,697,359 | B1 | 4/2014 | Zhang |
| 8,771,945 | B1 | 7/2014 | Zhang |
| 8,865,406 | B2 | 10/2014 | Zhang et al. |
| 8,871,445 | B2 | 10/2014 | Cong et al. |
| 8,889,418 | B2 | 11/2014 | Zhang et al. |
| 8,895,308 | B1 | 11/2014 | Zhang et al. |
| 8,932,814 | B2 | 1/2015 | Cong et al. |
| 8,945,839 | B2 | 2/2015 | Zhang |
| 8,993,233 | B2 | 3/2015 | Zhang et al. |
| 9,512,446 | B1 | 12/2016 | Joung et al. |
| 9,549,901 | B2 | 1/2017 | Shi et al. |
| 9,597,357 | B2 | 3/2017 | Gregory et al. |
| 9,623,071 | B2 | 4/2017 | Guo et al. |
| 9,637,739 | B2 | 5/2017 | Siksnys et al. |
| 9,701,964 | B2 | 7/2017 | Clube et al. |
| 9,834,791 | B2 | 12/2017 | Zhang et al. |

(Continued)

FOREIGN PATENT DOCUMENTS

| | | |
|---|---|---|
| BR | 112015013784 | 7/2017 |
| CN | 101228176 | 7/2008 |

(Continued)

OTHER PUBLICATIONS

Declaration of Interference—PTAB, *The Broad Institute, Inc., Massachusetts Institute of Technology, and President and Fellows of Harvard College v. Toolgen, Inc.*, filed Dec. 14, 2020, in Patent Interference No. 106,126 (DK), 19 pages.

(Continued)

*Primary Examiner* — Ram R Shukla
*Assistant Examiner* — David A Montanari
(74) *Attorney, Agent, or Firm* — Foley & Lardner LLP

(57) ABSTRACT

The invention provides for delivery, engineering and optimization of systems, methods, and compositions for manipulation of sequences and/or activities of target sequences. Provided are vectors and vector systems, some of which encode one or more components of a CRISPR complex, as well as methods for the design and use of such vectors. Also provided are methods of directing CRISPR complex formation in prokaryotic and eukaryotic cells to ensure enhanced specificity for target recognition and avoidance of toxicity.

27 Claims, 78 Drawing Sheets

Specification includes a Sequence Listing.

(56) References Cited

U.S. PATENT DOCUMENTS

| | | | |
|---|---|---|---|
| 9,873,894 B2 | 1/2018 | Conway et al. |
| 10,301,651 B2 | 5/2019 | Doudna et al. |
| 10,494,621 B2 | 12/2019 | Zhang et al. |
| 10,660,943 B2 | 5/2020 | Bikard et al. |
| 10,781,444 B2 | 9/2020 | Zhang et al. |
| 10,930,367 B2 | 2/2021 | Zhang et al. |
| 2003/0186238 A1 | 10/2003 | Allawi et al. |
| 2004/0111221 A1 | 6/2004 | Beattie et al. |
| 2005/0196851 A1 | 9/2005 | Uckun |
| 2005/0220796 A1 | 10/2005 | Dynan et al. |
| 2006/0178297 A1 | 8/2006 | Troy et al. |
| 2006/0234247 A1 | 10/2006 | Puttaraju et al. |
| 2007/0016012 A1 | 1/2007 | Hartlep et al. |
| 2007/0244031 A1 | 10/2007 | Lu et al. |
| 2008/0293655 A1 | 11/2008 | Aygun et al. |
| 2010/0055798 A1 | 3/2010 | Battersby |
| 2010/0076057 A1 | 3/2010 | Sontheimer et al. |
| 2010/0081707 A1 | 4/2010 | Ali et al. |
| 2010/0093617 A1 | 4/2010 | Barrangou et al. |
| 2010/0233084 A1 | 9/2010 | Narasimhaswamy et al. |
| 2011/0016540 A1 | 1/2011 | Weinstein et al. |
| 2011/0059502 A1 | 3/2011 | Chalasani |
| 2011/0189776 A1 | 8/2011 | Terns et al. |
| 2011/0223638 A1 | 9/2011 | Wiedenheft et al. |
| 2011/0239315 A1 | 9/2011 | Bonas et al. |
| 2012/0029891 A1 | 2/2012 | Behlke et al. |
| 2013/0096182 A1 | 4/2013 | Chatterjee et al. |
| 2013/0130248 A1 | 5/2013 | Haurwitz et al. |
| 2013/0315831 A1 | 11/2013 | Shi et al. |
| 2014/0068797 A1 | 3/2014 | Doudna et al. |
| 2014/0294771 A1 | 10/2014 | Schaffer et al. |
| 2014/0295557 A1 | 10/2014 | Joung et al. |
| 2014/0315985 A1 | 10/2014 | May et al. |
| 2014/0342456 A1 | 11/2014 | Mali et al. |
| 2014/0356956 A1 | 12/2014 | Church et al. |
| 2014/0357530 A1 | 12/2014 | Zhang et al. |
| 2015/0045546 A1 | 2/2015 | Siksnys et al. |
| 2015/0071899 A1 | 3/2015 | Liu et al. |
| 2015/0071903 A1 | 3/2015 | Liu et al. |
| 2015/0071906 A1 | 3/2015 | Liu et al. |
| 2015/0232881 A1 | 8/2015 | Glucksmann et al. |
| 2015/0247150 A1 | 9/2015 | Zhang et al. |
| 2015/0291965 A1 | 10/2015 | Zhang et al. |
| 2015/0322457 A1 | 11/2015 | Kim et al. |
| 2015/0353905 A1 | 12/2015 | Weiss et al. |
| 2016/0017366 A1 | 1/2016 | Chen et al. |
| 2016/0024510 A1 | 1/2016 | Bikard et al. |
| 2016/0024524 A1 | 1/2016 | Joung et al. |
| 2016/0130609 A1 | 5/2016 | Doudna et al. |
| 2016/0237456 A1 | 8/2016 | Church et al. |
| 2016/0251648 A1 | 9/2016 | Wang et al. |
| 2016/0281072 A1 | 9/2016 | Zhang |
| 2016/0298135 A1 | 10/2016 | Chen et al. |
| 2016/0298137 A1 | 10/2016 | Chen et al. |
| 2016/0324938 A1 | 11/2016 | Bikard et al. |
| 2016/0340662 A1 | 11/2016 | Zhang et al. |
| 2017/0175144 A1 | 6/2017 | Zhang et al. |
| 2017/0191082 A1 | 7/2017 | Chen et al. |
| 2017/0327806 A1 | 11/2017 | Joung et al. |
| 2018/0127783 A1 | 5/2018 | Zhang et al. |
| 2018/0230495 A1 | 8/2018 | Doudna et al. |
| 2019/0010471 A1 | 1/2019 | Zhang et al. |
| 2020/0282026 A1 | 9/2020 | Bikard et al. |
| 2020/0282027 A1 | 9/2020 | Bikard et al. |
| 2021/0060140 A1 | 3/2021 | Bikard et al. |
| 2021/0060141 A1 | 3/2021 | Bikard et al. |

FOREIGN PATENT DOCUMENTS

| | | |
|---|---|---|
| CN | 103343120 | 10/2013 |
| CN | 103388006 | 11/2013 |
| CN | 103668472 | 3/2014 |
| CN | 104520429 A | 4/2015 |
| CN | 104854241 A | 8/2015 |
| CN | 107532161 A | 1/2018 |
| EP | 2 591 770 A2 | 5/2013 |
| EP | 2 784 162 | 1/2014 |
| EP | 2 764 103 | 8/2014 |
| EP | 2 771 468 | 9/2014 |
| EP | 2 828 386 A1 | 1/2015 |
| FR | 2872170 A1 | 12/2005 |
| IN | 49/2015 | 12/2015 |
| JP | 2004-519245 A | 7/2004 |
| JP | 2004-537285 A | 12/2004 |
| JP | 2005-509409 A | 4/2005 |
| JP | 2006-513694 A | 4/2006 |
| JP | 2006-518996 A | 8/2006 |
| JP | 2007-501626 A | 2/2007 |
| JP | 2009-502170 A | 1/2009 |
| JP | 2009-536827 A | 10/2009 |
| JP | 2010-522547 A | 7/2010 |
| JP | 2012-508235 | 4/2012 |
| JP | 2012-510812 A | 5/2012 |
| JP | 2012-511332 A | 5/2012 |
| JP | 2012-523234 A | 10/2012 |
| JP | 2012-529287 A | 11/2012 |
| JP | 2013-500045 A | 1/2013 |
| JP | 2013-513389 A | 4/2013 |
| JP | 2013-518602 A | 5/2013 |
| JP | 2013-544077 A | 12/2013 |
| JP | 2014-526279 A | 10/2014 |
| JP | 2015-523856 A | 8/2015 |
| JP | 2016-500003 A | 1/2016 |
| JP | 2016-500262 A | 1/2016 |
| JP | 2016-501531 | 1/2016 |
| JP | 2016-501532 A | 1/2016 |
| JP | 2016-025710 A | 2/2016 |
| JP | 2016-502840 A | 2/2016 |
| JP | 2016-504026 A | 2/2016 |
| JP | 2016-505256 A | 2/2016 |
| JP | 2016-093196 | 5/2016 |
| JP | 2016-516169 A | 6/2016 |
| JP | 2016-517954 A | 6/2016 |
| JP | 2016-131404 A | 7/2016 |
| JP | 2016-520317 A | 7/2016 |
| JP | 2016-521554 A | 7/2016 |
| JP | 2016-521975 A | 7/2016 |
| JP | 2016-521995 | 7/2016 |
| JP | 2016-523082 A | 8/2016 |
| JP | 2016-524472 | 8/2016 |
| JP | 2016-182140 A | 10/2016 |
| JP | 2017-501151 A | 1/2017 |
| JP | 2017-501699 | 1/2017 |
| JP | 6395765 | 9/2018 |
| RU | 2009136452 A | 4/2011 |
| WO | WO-02/074968 A1 | 9/2002 |
| WO | WO-02/080851 A2 | 10/2002 |
| WO | WO-03/014318 A2 | 2/2003 |
| WO | WO-03/104414 A2 | 12/2003 |
| WO | WO-2004/029219 A2 | 4/2004 |
| WO | WO-2004/046321 A2 | 6/2004 |
| WO | WO-2004/062618 A2 | 7/2004 |
| WO | WO-2005/014791 | 2/2005 |
| WO | WO-2005/049642 A2 | 6/2005 |
| WO | WO-2007/014275 A2 | 2/2007 |
| WO | WO-2007/134161 A2 | 11/2007 |
| WO | WO-2008/093152 A1 | 8/2008 |
| WO | WO-2008/108989 | 9/2008 |
| WO | WO-2008/116860 A2 | 10/2008 |
| WO | WO-2010/054108 | 5/2010 |
| WO | WO-2010/065123 A1 | 6/2010 |
| WO | WO-2010/068816 A1 | 6/2010 |
| WO | WO-2010/075424 A2 | 7/2010 |
| WO | WO-2010/079430 A1 | 7/2010 |
| WO | WO-2010/143917 | 12/2010 |
| WO | WO-2011/011767 A1 | 1/2011 |
| WO | WO-2011/016840 A2 | 2/2011 |
| WO | WO-2011/036510 A1 | 3/2011 |
| WO | WO-2011/064736 A1 | 6/2011 |
| WO | WO-2011/076873 A1 | 6/2011 |
| WO | WO-2011/100058 | 8/2011 |
| WO | WO-2011/146121 A1 | 11/2011 |
| WO | WO-2012/012738 A1 | 1/2012 |
| WO | WO-2012/031205 | 3/2012 |

(56) References Cited

FOREIGN PATENT DOCUMENTS

| | | |
|---|---|---|
| WO | WO-2012/051343 A1 | 4/2012 |
| WO | WO-2012/149470 A1 | 11/2012 |
| WO | WO-2012/164565 A1 | 12/2012 |
| WO | WO-2013/044008 A2 | 3/2013 |
| WO | WO-2013/052681 | 4/2013 |
| WO | WO-2013/071440 A1 | 5/2013 |
| WO | WO-2013/078400 A1 | 5/2013 |
| WO | WO-2013/082519 A2 | 6/2013 |
| WO | WO-2013/098244 | 7/2013 |
| WO | WO-2013/130824 A1 | 9/2013 |
| WO | WO-2013/141680 A1 | 9/2013 |
| WO | WO-2013/142578 A1 | 9/2013 |
| WO | WO-2013/155572 | 10/2013 |
| WO | WO-2013/176772 A1 | 11/2013 |
| WO | WO-2014/165349 A1 | 3/2014 |
| WO | WO-2014/065596 A1 | 5/2014 |
| WO | WO-2014/089290 A1 | 6/2014 |
| WO | WO-2014/093479 | 6/2014 |
| WO | WO-2014/093595 | 6/2014 |
| WO | WO-2014/093622 A2 | 6/2014 |
| WO | WO-2014/093635 A1 | 6/2014 |
| WO | WO-2014/093655 | 6/2014 |
| WO | WO-2014/093661 | 6/2014 |
| WO | WO-2014/093694 A1 | 6/2014 |
| WO | WO-2014/093701 A1 | 6/2014 |
| WO | WO-2014/093709 | 6/2014 |
| WO | WO-2014/093712 A1 | 6/2014 |
| WO | WO-2014/093718 | 6/2014 |
| WO | WO-2014/099744 | 6/2014 |
| WO | WO-2014/099750 A2 | 6/2014 |
| WO | WO-2015/031775 | 8/2014 |
| WO | WO-2014/144761 A2 | 9/2014 |
| WO | WO-2014/186585 A2 | 11/2014 |
| WO | WO-2014/191518 A1 | 12/2014 |
| WO | WO-2014/197568 A2 | 12/2014 |
| WO | WO-2014/197748 A2 | 12/2014 |
| WO | WO-2014/204724 A1 | 12/2014 |
| WO | WO-2014/204725 | 12/2014 |
| WO | WO-2014/204726 A1 | 12/2014 |
| WO | WO-2014/204727 A1 | 12/2014 |
| WO | WO-2014/204728 | 12/2014 |
| WO | WO-2014/204729 A1 | 12/2014 |
| WO | WO-2015/006747 A2 | 1/2015 |
| WO | WO-2015/035136 A2 | 3/2015 |
| WO | WO-2015/048577 | 4/2015 |
| WO | WO-2015/048690 | 4/2015 |
| WO | WO-2015/065964 A1 | 5/2015 |
| WO | WO-2015/070083 A1 | 5/2015 |
| WO | WO-2015/071474 A2 | 5/2015 |
| WO | WO-2015/089351 A1 | 6/2015 |
| WO | WO-2015/089364 | 6/2015 |
| WO | WO-2015/089419 A2 | 6/2015 |
| WO | WO-2015/089427 A1 | 6/2015 |
| WO | WO-2015/113063 A1 | 7/2015 |
| WO | WO-2016/022866 A1 | 2/2016 |
| WO | WO-2016/141224 A1 | 9/2016 |

OTHER PUBLICATIONS

Decision on Motions—PTAB, *The Regents of the University of California v. The Broad Institute, Inc.*, filed Sep. 10, 2020, in Patent Interference No. 106,115 (DK), 113 pages.

Hirano et al., "Structure and Engineering of Francisella novicida Cas9," Cell, vol. 164, Feb. 25, 2016, pp. 950-961.

Ran, F.A., "CRISPR-Cas: Development and Applications for Mammalian Genome Editing", Ph.D. Dissertation, Harvard University, Apr. 2014.

Redeclaration—PTAB, *The Regents of the University of California v. The Broad Institute, Inc.*, filed Aug. 26, 2019, in Patent Interference No. 106,115 (DK), 20 pages.

Redeclaration—PTAB, *The Regents of the University of California v. The Broad Institute, Inc.*, filed Sep. 10, 2020, in Patent Interference No. 106,115 (DK), 3 pages.

Yamada et al., "Crystal Structure of the Minimal Cas9 from Campylobacter jejuni Reveals the Molecular Diversity in the CRISPR-Cas9 Systems," Molecular Cell, vol. 65, Mar. 16, 2017, pp. 1109-1121.

"Crispr Genome Engineering Resources" XP055167591, Oct. 5, 2013, https://web.archive.org/web/2013100500 [retrieved on Feb. 5, 2015].

"Fixes, extra genomes, and improvements to the CRISPR Design Tool" Google Groups, XP055167583, Oct. 21, 2013, URL:https://groups.google.com/forum/#!topic/crispr/g9Q8U1tNSis [retrieved on Feb. 5, 2015].

"The CRISPR Revolution," Catalyst Magazine, College of Chemistry, University of California, Berkeley, http://catalyst.berkeley.edu/slideshow/the-crispr-revolution/[Dec. 19, 2014 12:40:53] (Jul. 9, 2014).

A. Amsterdam et al., "Identification of 315 genes essential for early zebrafish development," proc Natl Acad Sci., vol. 101, Aug. 31, 2004, pp. 12792-12797, 6 pages.

A. Fire et al., "Potent and specific genetic interference by double-stranded RNA in Caenorhabditis elegans," Nature, vol. 391, Feb. 19, 1998, pp. 806-811, 6 pages.

A. Subramanian et al., "Gene set enrichment analysis: a knowledge-based approach for interpreting genome-wide expression profiles," Proc Natl Acad Sci., vol. 102, Oct. 25, 2005, pp. 15545-15550, 6 pages.

A.C. Spradling et al., "The Berkeley Drosophila Genome Project Gene Disruption Project: Single P-Element Insertions Mutating 25% of Vital *Drosophila* Genes," Genetics, vol. 153, Sep. 1999, pp. 135-177, 43 pages.

A.H. Tong et al., "Global mapping of the yeast genetic interaction network," Science, vol. 303, Feb. 6, 2004, pp. 808-813, 6 pages.

A.L. Lin and D.H Gutmann, "Advances in the treatment of neurofibromatosis-associated tumours," Nature, vol. 10, Nov. 2013, pp. 616-624, 9 pages.

A.P. Blanchard and L. Hood, "Sequence to array: probing the genome's secrets," Nat Biotechnol, vol. 14, Dec. 14, 1996, p. 1649.

Abudayyeh, et al., "C2c2 is a single-component programmable RNA-guided RNA-targeting CRISPR effector," Science, vol. 10, Jun. 2, 2016, pp. 1-16, 18 pages.

Addgene Materials, "CRISPR/cas Plasmids and Resources", downloaded from https://www.addgene.org/crispr/, May 6, 2015, 3 pages.

Addgene Materials, "Engineering with Addgene's Help", Addgene Newsletter, Mar. 2013, downloaded from https://archive.constantcontact.com/fs126/1103481513180/archive/1112756362265.html, Oct. 14, 2014, 4 pages.

Addgene Reagent distribution list for Zhang Lab with Plasmid Name, date unknown (prior to May 10, 2015), 2 pages.

Addgene, "gRNA_Cloning Vector", retrieved on Jan. 30, 2019, <https://www/addgenen.org/41824/> 2 pages.

Al-Attar, et al., "Clustered regularly interspaced short palindromic repeats (CRISPRs): the hallmark of an ingenious antiviral defense mechanism in prokaryotes" Biol Chem., vol. 392, No. 4, Apr. 2011, pp. 277-289, 13 pages.

Alberts, et al., "Intracellular Compartments and Protein Sorting," Garland Science, 4 ed., 2002, pp. 671-676, 8 pages.

Allen, et al., "Liposomal drug delivery systems: From concept to clinical applications" Advanced Drug Delivery Reviews, vol. 65, 2013, pp. 36-48, 13 pages.

Andreas, et al., "Enhanced efficiency through nuclear localization signal fusion on phage C31-integrase: activity comparison with Cre and FLPe recombinase in mammalian cells", Nucleic Acids Research, Apr. 15, 2002, vol. 30, No. 11, pp. 2299-2306, 8 pages.

*Arbitron, Inc. v. Kiefl*, No. 09-CV-04013 PAC, 2010 WL 3239414, at *1 (S.D.N.Y. Aug. 13, 2010), 7 pages.

Asuri, P., et al., "Directed Evolution of Adeno-Associated Virus for Enhanced Gene Delivery and Gene Targeting in Human Pluripotent Stem Cells," Molecular Therapy, vol. 30, 2012, No. pp. 329-338, 10 pages.

Au, et al., "Characterization of a baculovirus nuclear localization signal domain in the late express factor 3 protein", Virology, vol. 385, 2009, pp. 209-217.

(56) References Cited

OTHER PUBLICATIONS

Ausubel, et al. "Compendium of Methods from Current Protocols in Molecular Biology", Short Protocols in Molecular Biology, 4 ed., 1999, 9-0, 9-4, 5 pages.

Autofluorescence MIT Flow Cytometry Core Facility (2018), 6 pages.

B. Langmead et al., "Ultrafast and memory-efficient alignment of short DNA sequences to the human genome," Genome biology, vol. 10, Mar. 4, 2009, 10 pages.

B.Langmead and S.L. Salzberg, "Fast gapped-read alignment with Bowtie 2," Nat Meth, vol. 9, 2012, pp. 357-359, 3 pages.

B.Scappini et al., "Changes associated with the development of resistance to imatinib (STI571) in two leukemia cell lines expressing p210 Bcr/Abl protein," Cancer, vol. 100, Apr. 1, 2004, pp. 1459-1471, 13 pages.

B.Sonnichsen et al., "Full-genome RNAi profiling of early embryogenesis in Caenorhabditis elegans," Nature, vol. 434, Mar. 24, 2005, pp. 462-469, 8 pages.

Bae, T. and Schneewind, O. "Allelic replacement in *Staphylococcus aureus* with inducible counter-selection," Plasmid, vol. 55, 2006, pp. 58-63, 6 pages.

Baena-Lopez, L., et al., "Accelerated homologous recombination and subsequent genome modification in *Drosophila*," Development, vol. 140, 2013, pp. 4818-4835, including Supplementary Material, 8 pages.

Baiker, et al. "The Immediate-Early 63 Protein of Varicella-Zoster Virus: Analysis of Functional Domains Required for Replication In Vitro and for T-Cell and Skin Tropism in the SCIDhu Model In Vivo", Journal of Virology, 2004, vol. 78 pp. 1181-1194, 14 pages.

Baker, M., "Gene editing at CRISPR Speed," Nature Biotechnology, vol. 32, 2014, pp. 309-312, 4 pages.

Balboa, et al., "Conditionally Stabilized dCas9 Activator for Controlling Gene Expression in Human Cell Reprogramming and Differentiation. (plus Supplemental Information)", Stem Cell Reports, vol. 5, Sep. 8, 2015, pp. 448-459, 12 pages.

Banaszewska, A., et al., "Proprotein Convertase Subtilisin/Kexin Type 9: A New Target Molecule for Gene Therapy," Cellular & Molecular Biology Letters, vol. 17, 2012, pp. 228-239, 12 pages.

Barrangou and Van Der Oost (Eds.), "CRISPR-Cas Systems," Springer Heidelberg, 2013, pp. i-299.

Barrangou, R. et al., "CRISPR provides acquired resistance against viruses in prokaryotes," Science, vol. 315, Mar. 23, 2007, pp. 1709-1712, 6 pages.

Barrangou, R., "RNA-mediated programmable DNA cleavage," Nature Biotechnology, vol. 30, 2012, pp. 836-388, 13 pages.

Bassett, et al. "Highly Efficient Targeted Mutagenesis of *Drosophila* with the CRISPR/Cas9 System" Cell Reports, vol. 4, Jul. 11, 2013, p. 220.

Bassett, et al., "A Genome-Wide CRISPR Library for High-Throughput Genetic Screening in *Drosophila* Cells," Journal of Genetics and Genomics, vol. 42, Apr. 18, 2015, pp. 301-309, 9 pages.

Bauer, et al, "An Erythroid Enhancer of BCL11A Subject to Genetic Variation Determines Fetal Hemoglobin Level," Science, vol. 342, Oct. 11, 2013, pp. 253-257, 4 pages.

Beerli, et al. "Positive and negative regulation of endogenous genes by designed transcription factors" PNAS, vol. 97, Feb. 15, 2000, pp. 1495-1500.

Beerli, et al., "Toward controlling gene expression at will: Specific regulation of the erbB-2/HER-2 promoter by using polydactyl zinc finger proteins constructed from modular building blocks", Proc. Natl. Acad. Sci., vol. 95, Oct. 7, 1998, pp. 14628-14633.

Beerli, R., et al., "Engineering polydactyl zinc-finger transcription factors," Nature Biotechnology, vol. 20, Feb. 2002, pp. 135-141.

Bennett, et al., "Stable transgene expression in rod photoreceptors after recombinant adeno-associated virus-mediated gene transfer to monkey retina", Proc. Natl. Acad. Sci., vol. 96, Aug. 1999, pp. 9920-9925.

Bergemann, et al., Excision of specific DNA-sequences from integrated retroviral vectors via site-specific recombination:, Nucleic Acids Res., vol. 23, Oct. 2, 1995, pp. 4451-4456.

Berns, K., et al., "A Large-Scale RNAi Screen in Human Cells Identifies New Components of the p53 Pathway," Nature, vol. 428, Mar. 25, 2004, pp. 431-437.

Bhaya, D., et al., "CRISPR-Cas Systems in Bacteria and Archaea: Versatile Small RNAs for Adaptive Defense and Regulation," Annual Review of Genetics, vol. 45, 2011, pp. 273-297.

Bikard, et al. "CRISPR Interference Can Prevent Natural Transformation and Virulence Acquisition During In Vivo Bacterial Infection," Cell Host & Microbe, vol. 12, 2012, pp. 177-186.

Bikard, et al., Supplementary Information for: "CRISPR Interference Can Prevent Natural Transformation and Virulence Acquisition During In Vivo Bacterial Infection," Cell Host & Microbe, vol. 12, 2012, pp. 177-186.

Birch, et al., "Plant Transformation: Problems and Strategies for Practical Application", Annu. Rev. Plant Physiol. Plant Mol. Biol., vol. 48, 1997, pp. 297-326.

Bloom, et al., "Inactivation of hepatitis B virus replication in cultured cells and in vivo with engineered transcription activator-like effector nucleases", Molecular Therapy, vol. 21, Oct. 2013, pp. 1889-1897.

Bobis-Wozowicz, S., et al., "Targeted genome editing in pluripotent stem cells using zinc-finger nucleases," Methods, vol. 53, 2012, pp. 339-346.

Boch, et al., "Breaking the Code of DNA Binding Specificity of TAL-Type III Effectors". Science, vol. 326, 2009, pp. 1509-1512.

Boch, et al., "Xanthomonas AvrBs3 Family-Type III Effectors: Discovery and Function", Annu. Rev. Phytopathol, vol. 48, 2010, pp. 419-436.

Boden, et al., "Efficient Gene Transfer of HIV-1-Specific Short Hairpin RNA into Human Lymphocytic Cells Using Recombinant Adeno-associated Virus Vectors", Molecular Therapy, vol. 9, 2004, pp. 396-402.

Bogdanove, et al., "TAL Effectors: Customizable Proteins for DNA Targeting", Science, vol. 333, 2011, pp. 1843-1846.

Bohm et al., "The computer program LUDI: A new method forthe de novo design of enzyme inhibitors", Journal of Computer-Aided Molecular Design, vol. 6, 1992, pp. 61-78.

Botta, S. et al, "Transcriptional Repression with Zinc-Finger and Tale Protein Scaffold", Molecular Therapy, 2013, Supplement 1, p. S208, Abstract No. 539.

Bouard, et al., "Themed Section: Vector Design and Drug Delivery Review, Viral vectors: from virology to transgene expression", British Journal of Pharmacology, vol. 157, 2009, pp. 153-165.

Boutros, et al., "Genome-wide RNAi analysis of growth and viability in *Drosophila* cells," Science, American Association for the Advancement of Science, vol. 303, Feb. 6, 2004, pp. 832-835.

Branden, C., and Tooze, J., "Prediction, Engineering, and Design of Protein Structures: Introduction to Protein Structure," Garland Publishing, Inc., Chapter 16, 1991, p. 247.

Briner, et al., "Guide RNA Functional Modules Direct Cas9 Activity and Orthogonality", Molecular Cell, vol. 56, 2014, pp. 333-339.

Brouns, S., "A Swiss Army Knife of Immunity," Science, vol. 337, 2012, pp. 808-809.

Brouns, S., et al., "Small CRISPR RNAs Guide Antiviral Defense in Prokaryotes," Science, vol. 321, Aug. 15, 2008, pp. 960-964.

Brummelkamp TR et al., "A system for stable expression of short interfering RNAs in mammalian cells," Science, vol. 296, Apr. 19, 2002, pp. 550-553.

C. Cayrol et al., "The THAP-zinc finger protein THAP1 regulates endothelial cell proliferation through modulation of pRB/E2F cell-cycle target genes," Blood, vol. 109, 2007, pp. 584-594.

C. Trapnell et al., "Differential gene and transcript expression analysis of RNA-seq experiments with TopHat and Cufflinks," Nature protocols, vol. 7, 2012, p. 562.

C. Trapnell et al., "TopHat: discovering splice junctions with RNA-Seq.," Bioinformatics, vol. 25, 2009, pp. 1105-1111.

C.J, Echeverri et al., "Minimizing the risk of reporting false positives in large-scale RNAi screens," Nature methods, vol. 3, Oct. 2006, p. 777.

(56) References Cited

OTHER PUBLICATIONS

C.M Johannessen et al., "COT drives resistance to RAF inhibition through MAP kinase pathway reactivation," Nature, vol. 468, Dec. 16, 2010, p. 968.

C.M. Johnston et al., "Large-scale population study of human cell lines indicate that dosage compensation is virtually complete," PLoS Genet., vol. 4, Jan. 2008, pp. 88-98, 11 pages.

Campeau, et al., "A Versatile Viral System for Expression and Depletion of Proteins in Mammalian Cells", PLoS One, vol. 4, 2009, pp. 1-17.

Canver, et al., "BCL11A enhancer dissection by Cas9-mediated in situ saturating mutagenesis," Nature, vol. 527, 2015, pp. 192-197, including Supplementary Material.

Carr, et al., "Genome engineering", Nature Biotechnology, vol. 27, 2009, pp. 1151-1162.

Carroll, D., "A CRISPR Approach to Gene Targeting," Molecular Therapy, vol. 20, 2012, pp. 1658-1660.

Carroll., "Genome Engineering With Zing-Finger Nucleases", Genetics, vol. 188, 2011, pp. 773-782.

Carroll., "Progress and prospects: Zinc-finger nucleases as gene therapy agents", Gene Therapy, vol. 15, 2008, pp. 1463-1468.

Carte, J., et al., "Cas6 is an endoribonuclease that generates guide RNAs for invader defense in prokaryotes," Genes Dev., vol. 22, 2008, pp. 3489-3496.

Cermak, T., et al., "Efficient design and assembly of custom TALEN and other TAL Effector-Based Constructs for DNA Targeting", Nucleic Acids Research, vol. 39, 2011, pp. 1-11.

Chadderton, N., et al., "Improved Retinal Function in a Mouse Model of Dominant Retinitis Pigmentosa Following AAV-delivered Gene Therapy", Molecular Therapy, vol. 17, Apr. 2009, pp. 593-599.

Chan, et al. "Characterization of the Kinetochore Binding Domain of CENP-E Reveals Interactions with the Kinetochore Proteins CENP-F and hBuBR1", The Journal of Cell Biology, vol. 143, 1998, pp. 49-63.

Chan, Wai-Ting, et al., "Toxin-Antitoxin Genes of the Gram-Positive Pathogen *Streptococcus pneumoniae*: So Few and Yet So Many", Microbiology and Molecular Biology Reviews, vol. 76, 2012, pp. 773-791.

Chang, N., et al. "Genome editing with RNA-guided Cas9 nuclease in Zebrafish embryos", Cell Research, vol. 23, 2013, pp. 465-472.

Chen, B., et al., "Dynamic Imaging of Genomic Loci in Living Human Cells by an Optimized CRISPR/Cas System," Cell, vol. 155, 2013, pp. 1479-1491.

Chen, Fuqiang, et al., "High-frequency genome editing using ssDNA oligonucleotides with zinc-finger nucleases". Nature Methods, 2011, vol. 8, pp. 753-755, including Supplemental Online Methods.

Chen, Jieliang, et al., "An Efficient Antiviral Strategy for Targeting Hepatitis B Virus Genome Using Transcription Activator-Like Effector Nucelases", Molecular Therapy, vol. 22, 2014, pp. 303-311.

Chen, S., et al., "Genome-wide CRISPR Screen in a Mouse Model of Tumor Growth and Metastasis", Cell, vol. 160, 2015, pp. 1-15, http://dx.doi.org/10.1016/j.cell.2015.02.038.

Chevalier et al., "Homing endonuclease: structural and functional insight into the catalysts of intron/intein mobility," Oxford University Press., vol. 29, 2001, pp. 3757-3774.

Chinnasamy, D., et al., "Multicistronic lentiviral vectors containing the FMCV 2A Cleavage factor demonstrate robust expression of encoded genes at limiting MOI," Virology Journal, vol. 3, 2006, pp. 1-16.

Chiu, et al., "Engineered GFP as a vital reporter in plants", Current Biology, vol. 6, 1996, pp. 325-330.

Cho, A., et al., "Generation of Transgenic Mice," Current Protocols in Cell Biology, Chapter Unit 19.11, 2009, pp. 1-29.

Cho, Minseon, et al., "Quantitative selection and parallel characterization of aptamers," PNAS, vol. 110, Nov. 12, 2013, pp. 18460-18465.

Cho, Seung Woo, et al. "Analysis off-target effects of CRISPR/Cas-derived RNA-guided endonucleases and nickases" Genome Research, vol. 24, 2014, pp. 132-141.

Cho, Seung Woo, et al., "Targeted genome engineering in human cells with the Cas9 RNA-guided endonuclease," Nature Biotechnology, vol. 31 pp. 230-232, including Supplementary Information, 14 pages.

Chou, JY, and Mansfield, BC., "Recombinant AAV-directed gene therapy for type I glycogen storage diseases," Expert Opinion on Biological Therapy, vol. 11, Aug. 2011, pp. 1011-1024.

Choulika, et al., "Transfer of Single Gene-Containing Long Terminal Repeats into the Genome of Mammalian Cells by a Retroviral Vector Carrying the cre Gene and the IoxP site", Journal of Virology, vol. 70, 1996, pp. 1792-1798.

Christian, et al., "Supporting Information-Targeting DNA Double-Strand Breaks With TAL Effector Nucleases", Genetics, 2010, pp. 1-8, DOI:10.1534/110.120717:1 SI-8SI.

Christian, et al., "Targeting DNA Double-Strand Breaks With TAL Effector Nucleases", Genetics, vol. 186, 2010, pp. 757-761.

Chylinski, et al., "Classification and evolution of type II CRISPR-Cas systems", Nucleic Acids Research, vol. 42, 2014, pp. 6091-6105, doi:10.1093lnarlgku241.

Chylinski, K., et al., "The tracrRNA and Cas9 Families of Type II CRISPR-Cas Immunity Systems," RNA Biology, vol. 10, 2013, pp. 726-737.

Claims of Broad/Zhang patent granted by EPO over Jinek 2012 and UCB Applications, Sep. 9, 2015.

Clark, K., et al., "A TALE of Two Nucleases: Gene Targeting forthe Masses?" Zebrafish, vol. 8, No. 3, 2011, pp. 147-149.

Cockrell, "Berkeley's Wikipedian-in-residence is a first," NewsCenter, Feb. 25, 2014, downloaded from https://newscenter.berkeley.edu/2014/02/25/berkeleys-wikipedian-in-residence-is-a-first/, May 8, 2015, 3 pages.

Community Corner, "CRISPR technology for gene therapy," Nature Medicine, vol. 20, May 2014, pp. 476-477.

Cong, et al., Octobers, 2012 Manuscript including Supplementary Materials, "CRISPR-Assisted Mammalian Genome Engineering," published as "Multiplex Genome Engineering Using CRISPR-Cas Systems," Science, vol. 339, 2013, pp. 819-823.

Cong, L., et al., "Comprehensive interrogation of natural TALE DNA-binding modules and transcriptional repressor domains," Nature Communications, vol. 3, Jul. 24, 2012, pp. 968-973.

Cong, L., et al., "In Vivo Genome Engineering With AAV Vector Carrying CRISPR-Cas9 System," Molecular Therapy, vol. 22, May 2014, Supplement 1, p. S214.

Cong, L., et al., "Multiplex Genome Engineering Using CRISPR-Cas Systems," Science, vol. 339, 2013, pp. 819-823.

Cong, L., et al., Supplementary Material for: "Multiplex Genome Engineering Using CRISPR-Cas Systems," Science, vol. 339, 2013, pp. 819-823.

Connor, S., "Scientific split—the human genome breakthrough dividing former colleagues," The Independent, http://www.independent.co.uk/news/science/scientific-split--the-human-genome-breakthrough-dividing-former-colleagues-9300456.html, dated Apr. 25, 2014, 5 pages.

Costantino, et al., "Enhanced levels of alpha Red-mediated recombinants in mismatch repair mutants", PNAS, vol. 100, 2003, pp. 15748-15753.

Cotropia, et al., "Copying in Patent Law," N.C.L. Rev., Stanford Public Law Working Paper No. 1270160, 2009, pp. 1-46.

Cummings et al., "Fourteen and counting: unraveling trinucleotide repeat diseases", Human Molecular Genetics, vol. 9, 2000, pp. 909-916.

D.J.Burgess et al., "Topoisomerase levels determine chemotherapy response in vitro and in vivo," Proceedings of the National Academy of Sciences, vol. 105, Jul. 1, 2008, pp. 9053-9058.

Daboussi, F., et al., "Chromosomal context and epigenetic mechanisms control the efficacy of genome editing by rare-cutting designer endonucleases," Nucleic Acids Research, vol. 40, 2012, pp. 6367-6379.

Dahlman, J., et al., "In vivo endothelial siRNA delivery using polymeric nanoparticles with low molecular weight," Nature Nanotechnology, vol. 9, 2014, pp. 648-655.

Dai, et al. "Genes:Structures and Regulation: The Transcription Factors GATA4 and dHAND Physically Interact to Synergistically

(56) References Cited

OTHER PUBLICATIONS

Activate Cardiac Gene Expression through a p300-dependent Mechanism", J. Biol. Chem., vol. 277, 2002 pp. 24390-24398.
Daley, J., and Wilson, T., "Rejoining of DNA Double-Strand Breaks as a Function of Overhang Length," Molecular and Cellular Biology, vol. 25, 2005, pp. 896-906.
Damian, M., and Porteus, M., "A Crisper Look at Genome Editing: RNA-guided Genome Modification," Molecular Therapy, vol. 21, Apr. 2013, pp. 720-722.
Database GenBank, "*Staphylococcus aureus* subsp.*aureus* ORFX gene and pseudo SCCmec-SCC-SCCCRISPR element, strain M06/0171," Accession No. HE980450, http://www.ncbi.nlm.nih.gov/nuccore/HE980450, dated Aug. 18, 2016, 22 pages.
Database GenBank: "CRISPR-associated protein, Csn1 family, *Staphylococcus pseudintermedius* ED99," Accession No. ADX75954, http://www.uniprot.org/uniprot/G1 UFN3.txt?version=3, dated Nov. 21, 2011, 1 page.
Database UniProt: "CRISPR-associated endonuclease Cas9: *Staphylococcus aureus*," UniProtKB, J7RUA5 (CAS9_STAAU), XP002738511M, https://www.uniprot.org/uniprot/J7RUA5#, dated Oct. 31, 2012, 7 pages.
Database UniProtKB/TrEMBL [online], Accession No. Q0P897, "The genome sequence of the food-borne pathogen *Campylobacter jejuni* reveals hypervariable sequences," Subname: Full=Putative CRISPR-associated protein, Oct. 3, 2012 uploaded, [retrieved on Nov. 22, 2017], URL, http://www.uniprot.org/uniprot/Q0P897.txt?version=28.
Database UniProtKB/TrEMBL, Accession No. D0W2Z9, http://www.uniprot.org/uniprot/D0W2Z9.txt?version=4, dated Oct. 3, 2012, 1 page.
Database UniProtKB/TrEMBL, Accession No. G1UFN3, http://www.uniprot.org/uniprot/G1UFN3.txt?version=3, dated Oct. 3, 2012, 1 page.
Database UniProtKB/TrEMBL, Accession No. J3TRJ9, http://www.uniprot.org/uniprot/J3TRJ9.txt?version=2, dated Oct. 31, 2012, 1 page.
Database UniProtKB/TrEMBL, Accession No. Q6NKI3, http://www.uniprot.org/uniprot/Q6NKI3.txt?version=43, dated Jun. 13, 2012, 1 page.
Database UniProtKB/TrEMBL, Accession No. Q73QW6, http://www.uniprot.org/uniprot/Q73QW6.txt?version=4, dated Nov. 28, 2012, 2 pages.
Database WPI, Week 201437 Thomson Scientific, London, GB; AN 2014-J79552, XP-002737563, 2 pages.
Datsenko, et al. "Molecular memory of prior infections activates the CRISPR/Cas adaptive bacterial immunity system", Nature Communications, vol. 3, 2012, pp. 1-7.
Dean., "Recent Advances in Drug Design Methods: Where Will They Lead?", BioEssays, vol. 16, Sep. 1994, pp. 683-687.
Declaration of Feng Zhang for U.S. Appl. No. 14/054,414 dated Jan. 30, 2014 (10 pages).
Declaration of Technical Expert Paul Simons dated Dec. 22, 2015, 76 pages.
Deltcheva, E., et al., "CRISPR RNA maturation by trans-encoded small RNA and host Factor RNase III," Nature, vol. 471, 2011, pp. 602-609.
Deltcheva, et al., "Supplementary Information: CRISPR RNA Maturation by Trans-Encoded Small RNA and Host Factor RNase III" Nature, pp. 1-35.
Deveau, H. et al., "Phage response to CRISPR-encoded resistance in *Streptococcus thermophilus*," Journal of Bacteriology, vol. 190, Feb. 2008, pp. 1390-1400.
Deveau, H., et al., "CRISPR/Cas system and its role in phage-bacteria interactions," Annu. Rev. Microbiol., vol. 64, 2010, pp. 475-493.
Dicarlo, et al., "Genome engineering in *Saccharomyces cerevisiae* using CRISPTR-Cas systems", Nucleic Acids Research, vol. 41, 2013 pp. 4336-4343.

Dingwall, et al. "A Polypeptide Domain That Specifies Migration of Nucleoplasmin into the Nucleus", Cell, vol. 30, 1982, pp. 449-458, (Abstract only).
Dingwall, et al., "The Nucleoplasmin Nuclear Location Sequence is Larger and More Complex than That of SV-40 Large T Antigen", The Journal of Cell Biology, vol. 107, 1988, pp. 841-849.
Do, et al., "Identification of multiple nuclear localization signals in murine Elf3, an ETS transcription factor" FEBS Letters, vol. 580, 2006, pp. 1865-1871.
Doench, et al., "Rational design of highly active sgRNAs for CRISPR-Cas9-mediated gene inactivation," Nature Biotechnology, vol. 32, 2014, pp. 1262-1267, including Supplementary Material, 17 pages.
Dominguez, et al., "Beyond editing: repurposing CRISPR-Cas 9 for precision genome regulation and interrogation" Nat Rev Mol Cell Biol., vol. 17, 2016, 17 pp. 5-15.
Dong, et al., "The crystal structure of Cpf1 in complex with CRISPR RNA," Nature, vol. 532, 2016, pp. 523-525.
Drittanti, et al. "High throughput production, screening and anyalysis of adeno-associated viral vectors", Gene Therapy, vol. 7, 2000, pp. 924-929.
Dworetzky, S., et al., "The Effects of Variations in the Number and Sequence of Targeting Signals on Nuclear Uptake," The Journal of Cell Biology, vol. 107, 1988, pp. 1279-1287.
E.S. Lander, "Initial impact of the sequencing of the human genome," Nature, vol. 470, Feb. 10, 2011, p. 187-197.
Ebina, H., et al., "Harnessing the CRISPR/Cas9 system to disrupt latent HIV-1 provirus," Scientific Reports, vol. 3, 2013, pp. 1-7, art. 2510.
Edgar, R. and Qimron, U., "The *Escherichia coli* CRISPR system protects from λ lysogenization, lysogens, and prophage induction," Journal of Bacteriology, vol. 192, Dec. 2010, pp. 6291-6294.
Ellis, B., et al., "Zinc-finger nuclease-mediated gene correction using single AAV vector transduction and enhanced by Food and Drug Administration-Approved Drugs," Gene Therapy, vol. 20, 2013, pp. 35-42.
Ellis, et al., "Macromolecular Crowding: Obvious but Underappreciated", Trends in Biochemical Sciences, vol. 26, 2001, pp. 597-604.
Ellis, Hilary, et al., "High efficiency mutagenesis, repair, and engineering of chromosomal DNA using single-stranded oligonucleotids" PNAS, vol. 98, 2001, pp. 6742-6746.
Enyeart, et al., "Biotechnological applications of mobile group II introns and their reverse transcriptases: gene targeting, RNA-seq, and non-coding RNA analysis", Mobile DNA, vol. 5, 2014, pp. 1-19 http://www.mobilednajournal.com/contents5/1/2.
Espinoza, et al., "Characterization of the structure, function, and mechanism of B2 RNA, an ncRNA repressor of RNA polymerase II transcription", RNA, vol. 13, 2007, pp. 583-596.
Esvelt et. al., "Orthogonal Cas9 proteins for RNA-guided gene regulation and editing", Nature Methods, vol. 10, No. 11, Nov. 2013 (available online Sep. 29, 2013), pp. 1116-1123.
Excerpt from Dr. Feng Zhang's Jan. 30, 2014 Declaration (Exhibit C1), 11 pages.
Federal Circuit decision in *Dow Chemical Co.* v. *Nova Chemicals Corp.*, Appeal Nos. 2014-1431, 2014-1462 (Fed. Cir. Aug. 28, 2015) (*Dow* v. *Nova*), 25 pages.
Feldgarden et al., "*Staphylococcus aureus* M0408 acrHk-supercont1. 1, whole genome shotgun sequence", NCBI Reference Sequence: NK_KB821326.1, Direct Submission, Dec. 10, 2012, pp. 1-4.
Fieck, et al., "Modifications of the *E.coli* Lac repressor for expression in eukaryotic cells: effects of nuclear signal sequences on protein activity and nuclear accumulation", Nucleic Acids Research, vol. 20, 1992, pp. 1785-1791.
Fischer, S. et al., "An archaeal immune system can detect multiple Protospacer Adjacent Motifs (PAMs) to target invader DNA," J. Biol. Chem., vol. 287, Sep. 28, 2012, pp. 33351-33363.
Fischer-Fantuzzi, L., and Vesco, C., "Cell-dependent efficiency of reiterated nuclear signals in a mutant simian virus 40 oncoprotein targeted to the nucleus," Molecular and Cellular Biology, vol. 8, 1988, pp. 5495-5503.

(56) References Cited

OTHER PUBLICATIONS

Flannery, J. G., "Ribozyme-Mediated Gene Therapy for Autosomal Dominant Retinal Degeneration", Retinal Degenerative Diseases and Experimental Therapy, 1999, pp. 277-291.
Fleming, J., et al., "Adeno-Associated Virus and Lentivirus Vectors Mediate Efficient and Sustained Transduction of Cultured Mouse and Human Dorsal Root Ganglia Sensory Neurons," Human Gene Therapy, vol. 12, Jan. 1, 2001, pp. 77-86.
Foecking, et al. "Powerful and versatile enhance-promoter unit for mammalian expression vectors", Gene, vol. 45, 1986, pp. 101-105.
Fonfara et al., "Phylogeny of Cas9 determines functional exchangeability ofdual-RNA and Cas9 among orthologous type II CRISPR-Cas systems", Nucleic Acids Research, 2014, vol. 42, No. 4, pp. 2577-2590.
Freitas, et al., "Mechanisms and Signals for the Nuclear Import of Proteins", Current Genomics, vol. 10, 2009, pp. 550-557.
Fu, et al., "High-frequency off-target mutagenesis induced by CRISPR-Cas nucleases in human cells", Nature Biotechnology, vol. 31, 2013, pp. 822-826.
Fu, et al., "Targeted genome editing in human cells using CRISPR/Cas nucleases and truncated guide RNAs", The Use of CRISPR/Cas9 ZFNs and Talens in Generating Site-Specific Genome Alterations; Elsevier Inc., 2014, pp. 21-45.
G. Giaever et al., "Functional profiling of the *Saccharomyces cerevisiae* genome," Nature, vol. 418, Jul. 25, 2002, pp. 387-391.
G. Guo et al., "Mismatch repair genes identified using genetic screens in Blm-deficient embryonic stem cells," Nature, vol. 429, Jun. 24, 2004, p. 891.
Gabriel, R., et al., "An unbiased genome-wide analysis of zinc-finger nuclease specificity," Nature Biotechnology, vol. 29, 2011, pp. 816-823.
Gaj, T., et al., "Targeted Gene knockout by direct delivery of zinc-finger nuclease proteins," Nature Methods, vol. 9, 2012, pp. 805-807, including supplemental pages.
Gaj, T., et al., "ZFN, TALEN, and CRISPR/Cas-Based Methods for Genome Engineering," Trends in Biotechnology, vol. 31, 2013, pp. 397-405.
Gama Sosa, M., et al., "Animal transgenesis: an overview," Brain Structure and Function, vol. 214,0 2010, pp. 91-109.
Gao, et al. "Engineered Cpf1 variants with altered PAM specificities", Nature Biotechnology, vol. 35, Jun. 8, 2017, pp. 1-4 (789-792), doi:10.1038/nbt.3900, advanced online publication including Supplementary Information.
Gao, et al., "A Sustained, Cytoplasmic Transgene Expression System delivered by Cationic Liposomes", Biochemical and Biophysical Research Communications, vol. 200, May 16, 1994, pp. 1201-1206.
Garcia-Bustos, et al., "Nuclear protein localization", Biochimica et Biophysica Acta, vol. 1071, 1991, pp. 83-101.
Gardlik, R., et al., "Vectors and delivery systems in gene therapy," Medical Science Monitor, vol. 11, No. 4, pp. RA110-RA121, dated Apr. 1, 2005, 12 pages.
Garg, et al. "Engineering synthetic TAL effectors with orthogonal target sites", Nucleic Acids Research, 2012, vol. 40, pp. 7584-7595, doi:10.1093/nar/gks404.
Garneau, et al., "The CRISPR-Cas bacterial immune systems cleaves bacteriophage and plasmid DNA", Nature, vol. 468, 2010, pp. 67-71.
Garriga-Canut, M., et al., "Synthetic zinc finger repressors reduce mutant huntingtin expression in the brain of R6/2 mice," Proceedings of the National Academy of Sciences, vol. 109, Oct. 10, 2012, pp. E3136-E3145.
Gasiunas, G, et al., "Cas9-crRNA ribonucleoprotein complex mediates specific DNA cleavage for adaptive immunity in bacteria," Proceedings of the National Academy of Sciences, vol. 109, 2012, p. E2579-2586.
Geibler, et al., "Transcriptional Activators of Human Genes with Programmable DNA-Specificity", PLone, vol. 6, 2011, pp. 1-7 Doi:10.1371/hournal.pone.0019509.

Geisinger, et al., "In vivo blunt-end cloning through CRISPR/CAS9-facilitated non-homologous end-joining", Nucleic Acid Research Advance Access, vol. 44, 2016, pp. 1-15.
GenBank: "CRISPR-associated protein Cas9/Csn1 [*Staphylococcus aureus* subsp. *aureus*]", GenBank: CCK74173.1, Year: 2012, http://www.ncbi.nlm.nih.gov/protein/403411236?sat=16&satkey=13804560, dated Dec. 14, 2016, 2 pages.
Gibson, D.G. et al., "Enzymatic assembly of DNA molecules up to several hundred kilobases," Nat methods, vol. 6, 2009, pp. 343-345.
Gilbert, L., et al., "CRISPR-Mediated Modular RNA-Guided Regulation of Transcription in Eukaryotes," Cell, vol. 154, 2013, pp. 442-451.
Goldfarb, et al. "Synthetic peptides as nuclear localization signals", Nature, vol. 322, 1986, pp. 641-644.
Gomaa, et al. "Programmable removal of bacterial strains by use of genome-targeting CRISPR-Cas systems", MBio., vol. 5, 2014, pp. 1-9.
Goncalves, M., et al., "Concerted nicking of donor and chromosomal acceptor DNA promotes homology-directed gene targeting in Human Cells," Nucleic Acids Research, vol. 40, 2012, pp. 3443-3455.
Gratz, et al., "Genome Engineering of *Drosophila* with the CRISPR RNA-Guided Cas9 Nuclease", Genetics, vol. 194, 2013, pp. 1029-1035.
Greenspan, et al., "Two Nuclear Location Signals in the Influenza Virus NS1 Nonstructural Protein", Journal of Virology, vol. 62, 1988, pp. 3020-3026.
Greenwald, D L, et al., "Engineered Zinc Finger Nuclease-Mediated Homologous Recombination of the Human Rhodopsin Gene", Investigative Ophthalmology & Visual Science, vol. 51, Dec. 2010, pp. 6374-6380.
Grens, "Enzyme Improves CRISPR A smaller Cas9 protein enables in vivo genome engineering via viral vectors", The Scientist, Apr. 1, 2015.
Grieger, J., and Samulski, R., "Packaging Capacity of Adeno-Associated Virus Serotypes: Impact of Larger Genomes on Infectivity and Postentry Steps," Journal of Virology, vol. 79, 2005, pp. 9933-9944.
Grissa, I., et al., "CRISPRFinder: a web tool to identify clustered regularly interspaced short palindromic repeats," Nucleic Acids Research, vol. 35, 2007, pp. W52-W57.
Grosse, et al. "Meganuclease-medicated Inhibition of HSV1 Infection in Cultured Cells", Molecular Therapy, vol. 19, No. 4, Apr. 1, 2011, pp. 694-702.
Guan, et al., "Heritable endogenous gene regulation in plants with designed polydactyl zinc finger transcription factors", PNAS, vol. 99, 2002, pp. 13296-13301.
Gudbergsdottir, S. et al., "Dynamic properties of the Sulfolobus CRISPR/Cas and CRISPR/Cmr systems when challenged with vector-borne viral and plasmid genes and protospacers," Mol. Microbiology, vol. 79, 2011, pp. 35-49.
Gustafsson, et al. "Codon Bias and heterologous protein expression", Trends in Biotechnology, Jul. 2004, vol. 22, pp. 346-353.
H. Davies et al., "Mutations of the BRAF gene in human cancer," Nature, vol. 417, Jun. 27, 2002, p. 949-954.
H.W Cheung et al., "Systematic investigation of genetic vulnerabilities across cancer cell lines reveals lineage-specific dependencies in ovarian cancer," Proceedings of the National Academy of Sciences, vol. 108, Jul. 26, 2011, p. 12372-12377.
Habib, N., Assignment to Broad Institute, dated Jun. 9, 2014, 4 pages.
Haft, D., et al., "A Guild of 45 CRISPR-Associated (Cas) Protein Families and Multiple CRISPR/Cas Subtypes Exist in Prokaryotic Genomes," PLoS Computational Biology, vol. 1, 2005, pp. 0474-0483.
Haft, D.H., "HMM Summary Page: TIGR04330", 2012, XP-002757584, http://jcvi.org/cgi-bin/tigrfams/HmmReportPage.cgi?acc=TIGR04330, 1 page.
Hale, et al. "Essential Features and Rational Design of CRISPR RNAs that Function With the Cas RAMP Module Complex to Cleave RNAs", Molecular Cell, vol. 45, 2012, pp. 292-302.
Hale, et al. "RNA-Guided RNA Cleavage by a CRISPR RNA-Cas Protein Complex", Cell, vol. 139, 2009, pp. 945-956.

(56) References Cited

OTHER PUBLICATIONS

Hale, et al., "Prokaryotic siliencing (psi) RNAs in Pyrococcus furiosus", RNA, vol. 14, 2008, pp. 2572-2579.
Hall, B., et al., "Overview: Generation of Gene Knockout Mice," Current Protocols in Cell Biology, unit 19.12, suppl. 44, Sep. 2009, pp. 1-17.
Handel, E., et al., "Versatile and Efficient Genome Editing in Human Cells by Combining Zinc-Finger Nucleases With Adeno-Associated Viral-Vectors," Human Gene Therapy, vol. 23, 2012, pp. 321-329.
Harrison, et al., "A CRISPR view of development", Genes & Development, vol. 28, 2014, pp. 1859-1872.
Hatoum-Aslan, A., et al., "Mature clustered, regularly interspaced, short palindromic repeats RNA (crRNA) length is measured by a ruler mechanism anchored at the precursor processing site," Proc. Natl. Acad. Sci., vol. 108, Dec. 27, 2011, pp. 21218-21222.
Haurwitz, R.E., et al., "Sequence- and structure-specific RNA processing by a CRISPR endonuclease," Science, vol. 329, 2010, pp. 1355-1358.
Havarstein, L.S., et al., "An unmodified heptadecapeptide pheromone induces competence for genetic transformation in *Streptococcus pneumoniae*," Proc. Natl. Acad. Sci., vol. 92, Nov. 1995, pp. 11140-11144.
Heintze, et al. "A CRISPR CASe for high-throughput silencing", Frontiers in Genetics, vol. 4, 2013, pp. 1-6 DOI:10.3389/gfene.2013.00193.
Hemann et al., "An epi-allelic series of p53 hypomorphs created by stable RNAi produces distinct tumor phenotypes in vivo," Nat Genetics, vol. 33, Mar. 2003, pp. 396-400.
Hibbitt, O., et al., "RNAi-mediated knockdown of HMG CoA reductase enhances gene expression from physiologically regulated low-density lipoprotein receptor therapeutic vectors in vivo," Gene Therapy, vol. 19, 2012, pp. 463-467.
Hicks, et al. "Protein Import Into the Nucleus: An Integrated View", Annu. Rev. Cell Dev. Biology, vol. 11, 1995, pp. 155-188.
Ho, et al., "Targeting non-coding RNAs with the CRISPR/Cas9 system in human cell lines," Nucleic Acids Research, vol. 43, 2015, pp. 1-11.
Hockemeyer, et al., "Highly efficient gene targeting of expressed and silent genes in human ESCs and iPSCs using zinc finger nucleases", Nat Biotechnology, vol. 27, 2009, pp. 851-857, doi:10.1038/nbt.1562.
Holkers, M., et al., "Adenoviral vector DNA for accurate genome editing with engineered nucleases," Nature Methods, vol. 11, 2014, pp. 1051-1057, (Only Abstract Available).
Holmes, "CRISPR Genome Engineering Resources" XP055167586, Oct. 2, 2013, https://groups.google/forum/#!top1c/crispr/5BpJj_Y3ylG [retrieved on Feb. 5, 2015].
Holmes, "Understanding Scores" XP055167918, Oct. 23, 2013, https://groups.google.com/forum/#!profo_nt50txrP9Yb6e_LXccolb9hNf7gKeMLt6rgaVQ4fOsQ/crispr/fkhX7Fu3r-1/rziHxKT76pYJ [retrieved on Feb. 6, 2015].
Horinouchi, S. and Weisblum, B., "Nucleotide sequence and functional map of pC194, a plasmid that specifies inducible chloramphenicol resistance," J. Bacteriology, vol. 150, May 1982, pp. 815-825.
Horton, R.M., "In Vitro recombination and Mutagenesis of DNA: SOEing Together Tailor-Made Genes," Methods Mol. Biology, vol. 15, 1993, pp. 251-261.
Horvath, P. and Barrangou, R. "CRISPR/Cas, the immune system of bacteria and archaea," Science, vol. 327, Jan. 8, 2010, pp. 167-170.
Horvath, P., and Barrangou, R., "RNA-guided genome editing a la carte," Cell Research, vol. 23, 2013, pp. 733-734.
Hosaka, T. et al., "The novel mutation K87E in ribosomal protein S12 enhances protein synthesis activity during the late growth phase in *Escherichia coli*," Mol. Gen. Genomics, vol. 271, 2004, pp. 317-324.
Hoskins, J. et al., "Genome of the bacterium *Streptococcus pneumoniae* strain R6," Journal of Bacteriology, vol. 183, Oct. 2001, pp. 5709-5717.

Hou, Z., et al., "Efficient genome engineering in human pluripotent stem cells using Cas9 from Neisseria meningitides," Proceedings of the National Academy of Sciences, vol. 110, 2013, pp. 15644-15649.
Houdebine, L., "The methods to generate transgenic animals and to control transgene expression," Journal of Biotechnology, vol. 98, 2002, pp. 145-160.
Hsu et al., "Supplementary Information-DNA targeting specificity of RNA-guided Cas9 nucleases," Nature Biotechnology, 2013, doi:10.1038/nbt.2647.
Hsu, et al., "DNA targeting specificity of RNA-guided Cas9 nucleases," Nature Biotechnology, vol. 31, 2013, pp. 827-834.
Hsu, P., et al., "Development and Applications of CRISPR-Cas9 for Genome Engineering," Cell, vol. 157, 2014, pp. 1262-1278.
*Huang v. California Institute of Technology*, 2004 WL 2296330 (C.D. Cal. Feb. 18, 2004), 20 pages.
Hung, S., et al., "AAV-Mediated CRISPR/Cas Gene Editing of Retinal Cells in Vivo," Investigative Ophthalmology & Visual Science, vol. 57, 2016, pp. 3470-3476.
Husmann, L.K.,et al., "Expression of the Arp protein, a member of the M protein family, is not sufficient to inhibit phagocytosis of *Streptococcus pyogenes*," Infection and immunity, vol. 63, Jan. 1995, pp. 345-348.
Hwang W., et al., "Efficient In Vivo Genome Editing Using RNA-Guided Nucleases," Nature Biotechnology, vol. 31, No. 3, Mar. 2013, pp. 227-229 (12 pages).
Hwang, W.Y., et al., "Efficient Genome Editing in Zebrafish Using a CRISPR-Cas System", Nature Biotechnology, vol. 31, No. 3, Jan. 29, 2013, pp. 227-229.
Imagawa, et al., "Two nuclear localization signals are required for nuclear translocation of nuclear factor 1-A", FEBS Letters, vol. 484, 2000, pp. 118-124.
Incontro, S., et al., "Efficient, Complete Deletion of Synaptic Proteins using CRISPR," Neuron, vol. 83, 2014, pp. 1051-1057, 13 pages.
Ishino Y. et al., "Nucleotide sequence of the iap gene, responsible for alkaline phosphatase isozyme conversion in *Escherichia coli*, and identification of the gene product," J. Bacteriology, vol. 169, Dec. 1987, pp. 5429-5433, 5 pages.
Iwamoto et al., "A General Chemical Method to Regulate Protein Stability in the Mammalian Central Nervous System", Chemistry and Biology, Current Biology, vol. 17, Sep. 24, 2010, pp. 981-988, 8 pages.
J. Merkin et al., "Evolutionary dynamics of gene and isoform regulation in Mammalian tissues," Science, vol. 338, Dec. 21, 2012, p. 1593-1599, 7 pages. Includes Supplementary Information, 34 pages.
J.E. Carette et al., "Haploid genetic screens in human cells identify host factors used by pathogens," Science, vol. 326, Nov. 27, 2009, p. 1231-1235, 5 pages.
J.F. Rual et al., "Toward Improving Caenorhabditis elegans Phenome Mapping with an ORFeome-Based RNAi Library," Genome Research, vol. 14, 2004, pp. 2162-2168, 7 pages.
J.M. Engreitz et al., "The Xist lncRNA exploits three-dimensional genome architecture to spread across the X chromosome," Science, vol. 341, Aug. 16, 2013, pp. 1-8, 8 pages.
Jackson, A., et al., "Widespread siRNA "off-target" transcript silencing mediated by seed region sequence complementarity," RNA vol. 12, 2006, pp. 1179-1187, 10 pages.
Jansen R. et al., "Identification of genes that are associated with DNA repeats in prokaryotes," Molecular Microbiology, vol. 43, 2002, pp. 1565-1575, 11 pages.
Janssen, et al., "Mouse Models of K-ras-Initiated Carcinogenesis", Biochimicia et Biophysica Acta, vol. 1756 2005, pp. 145-154, 10 pages.
Jao, et al., "Efficient multiplex biallelic zebrafish genome editing using a CRISPR nuclease system", Proceeding of the National Academy of Sciences, PNAS 2013, pp. 1-6, includes supplementary information, pp. 1-10. www.pnas.org/cgi/doi/10.1073/pnas.1308335110.
Jiang, W., et al., "RNA-guided editing of bacterial genomes using CRISPR-Cas systems," Nature Biotechnology, vol. 31, Mar. 2013, pp. 233-239, 30 pages. including supplementary information.

(56) References Cited

OTHER PUBLICATIONS

Jinek, M., et al., "A Programmable Dual-RNA-Guided DNA Endonuclease in Adaptive Bacterial Immunity," Science, vol. 337, Aug. 17, 2012 pp. 816-821, including supplementary information, 45 pages.
Jinek, M., et al., "RNA-programmed genome editing in human cells", eLIFE, vol. 2, No. e00471, 2013, 9 pages.
Jinek, M., et al., Figures and figure supplements for: "RNA-programmed genome editing in human cells," eLIFE, vol. 2, 2013, 5 pages.
JL. Mummery-Widmer et al., "Genome-wide analysis of Notch signalling in Drosophila by transgenic RNAi," Nature, vol. 458, Apr. 23, 2009, pp. 987-992, 6 pages. Includes Supplementary information, 2 pages.
Joseph, T., and Osman, R., "Thermodynamic basis of selectivity in guide-target-mismatched RNA interference," Proteins, vol. 80, 2012, pp. 1283-1298, 26 pages.
Joshi, et al., "Evolution of I-SceI homing endonucleases with increased DNA recognition site specificity", Journal of Molecular Biology, 2011, vol. 405, pp. 185-200, 16 pages. Includes supplementary information, 14 pages.
Joung, et al., "TALENs: a widely applicable technology for targeted genome editing", Nat Ref. Mol. Cell Biology, vol. 14, 2013, pp. 49-55, 7 pages. doi:10.1038/nrm3586.
K. Yoshimoto et al., "Complex DNA repair pathways as possible therapeutic targets to overcome temozolomide resistance in glioblastoma," Front Oncology, vol. 2, Dec. 2012, pp. 1-8, 8 pages.
K.T Flaherty et al., "Inhibition of mutated, activated BRAF in metastatic melanoma," The New England Journal of Medicine, vol. 363, Aug. 26, 2010, pp. 1-22, 22 pages.
Kalderon, et al., "A Short Amino Acid Sequence Able to Specify Nuclear Location", Cell, vol. 39, 1984, pp. 499-509, 11 pages.
Kanasty, R., et al., "Delivery materials for siRNA therapeutics," Nature Materials, vol. 12, 2013, pp. 967-977, 11 pages.
Karvelis, et al., "crRNA and tracrRNA guide Cas9-mediated DNA interference in Streptococcus thermophiles" RNA Biology, vol. 10, 2013, pp. 841-851, 11 pages.
Karvelis, et al., "Supplemental Material to: crRNA and tracrRNA guide Cas9-mediated DNA interference in Streptococcus thermophiles", Landes Bioscience, vol. 10, 2013, pp. 1-8, 9 pages. http://dx.doi.org/10.4161/rna.24203.
Kiani, et al., "CAS9 gRNA engineering for genome editing, activation and repression", Nature Methods, Advanced Online Publication, 2015, pp. 1-6. DOI:10.1038/NMETH.3580.
Kim et al., "High Cleavage Efficiency of a 2A Peptide Derived from Porcine Teschovirus-1 in Human Cell Lines, Zebrafish and Mice," PLoS One, vol. 6, Apr. 2011, pp. 1-8, 8 pages.
Kim, E., et al., "Precision genome engineering with programmable DNA-nicking enzymes," Genome Research, vol. 22, 2012, pp. 1327-1333, 8 pages.
Kim, et al., "Crystal structure of Cas1 from Archaeoglobus fulgidus and characterization of its nucleolytic activity", Biochemical and Biophysical Research Communications, 2013, vol. 441, 2013, pp. 720-725, 6 pages.
Kim, S., et al., "CRISPER RNAs trigger innate immune responses in human cells," Genome Research, 2018, pp. 1-7, 8 pages.
Kinnevey, P., et al., "Emergence of Sequence Type 779 Methicillin-Resistant Staphylococcus aureus Harboring a Novel Pseudo Staphylococcal Cassette Chromosome mec (SCCmec)-SCC-SCC CRISPR Composite Element in Irish Hospitals," Antimicrobial Agents and Chemotherapy, vol. 57, 2013, pp. 524-531, 8 pages. Includes Supplementary information, 9 pages.
Kleinstiver et al., "High-fidelity CRISP-Cas9 nucleases with no detectable genome-wide off-target effects", Nature, vol. 529, Jan. 28, 2016, pp. 490-495, 6 pages. Includes Supplementary information, 12 pages.
Kleinstiver, et al. "Engineered CRISPR-Cas9 nucleases with altered PAM specificities," Nature, vol. 523,vol. 523, 2015, pp. 1-27, 27 pages.

Koike-Yusa, H., et al., "Genome-wide recessive genetic screening in mammalian cells with a lentiviral CRISPR-guide RNA library," Nat Biotechnology, vol. 32, Mar. 2014, pp. 267-273, 7 pages. Including Supplemental information, 3 pages. doi:10.1038/nbt.2800.
Kondo, et al., "Highly Improved Gene Targeting by Germline-Specific Cas9 Expression in Drosphila", Genetics, vol. 195, 2013, pp. 715-721, 7 pages. Including Supplemental information 14 pages.
Konermann, et al., "Genome-scale transcriptional activation by an engineered CRISPR-Cas9 complex", Nature, vol. 517, 2015, pp. 583-588, 6 pages. Including Supplemental information, 12 pages.
Koo et al., "Measuring and Reducing Off-Target Activities of Programmable Nucleases Including CRISPR-Cas9", Molecules and Cells, vol. 38, 2015, pp. 475-481, 7 pages.
Koornneef, A., et al., "Apoliprotein B Knockdown by AAV-Delivered shRNA Lowers Plasma Cholesterol in Mice," Molecular Therapy, vol. 19, 2011, pp. 731-740, 10 pages.
Kosugi, et al. "Six Classes of Nuclear Localization Signals Specific to Different Binding Grooves of Importin a . . . " The Journal of Biological Chemistry, 2009, vol. 284 pp. 478-485, 8 pages. Including Supplemental information, 21 pages.
Kowalski, Thomas J., PowerPoint Presentation, Presented and Discussed during Sep. 9, 2015 Interview (Exhibit B), 51 pages.
Krauer, et al. "Identification of the nuclear localization signals within the Epstein-Barr virus EBNA-6 protein", Journal of General Virology, vol. 85, 2005, pp. 165-172, 8 pages.
Kuhlman, et al. "A place for everything—Chromosomal intergration of large constructs", Bioengineered Bugs, vol. 1, 2010, pp. 296-299, 4 pages.
Kuhlman, et al., "Site-specific chromosomal integration of large synthetic constructs", Nucleic Acids Research, 2010, vol. 38, pp. 1-10, 10 pages. doi:10.1093/nar/gkp1193.
Kumar, M., et al., "Systematic Determination of the Packaging Limit of Lentiviral Vectors," Human Gene Therapy, vol. 12, Oct. 10, 2001, pp. 1893-1905, 21 pages.
Kuwayama, H., "Enhancement of Homologous Recombination Efficiency by Homologous Oligonucleotides," Cell 2012, pp. 233-244, 12 pages. IntechOpen, DOI: 10.5772/47779.
Laganiere et. al., "An Engineered Zinc Finger Protein Activator of the Endogenous Glial Cell Line-Derived Neurotrophic Factor Gene Provides Functional Neuroprotection in a Rat Model of Parkinson's Disease", The Journal of Neuroscience, vol. 30, Dec. 8, 2010, pp. 16469-16474, 6 pages.
Lambowitz, et al., "Group II Introns: Mobile Ribozymes that Invade DNA", Cold Spring Harb Perspect Biology, 2011, pp. 1-20, 20 pages. 3:a003616.
Lanford, et al., "Induction of Nuclear Transport with a Synthetic Peptide Homologous to the SV40 T Antigen Transport Signal", Cell, vol. 46, Aug. 15, 1986, pp. 575-582, 8 pages.
Lange, et al. "Classical Nuclear Localization Signals: Definition, Function, and Interaction with Importin$2026" J. Biology, vol. 282, 2007, pp. 5101-5105, 5 pages. including Supplemental information, 5 pages.
Larson, et al., "CRISPR interference (CRISPRi) for sequence-specific control of gene expression", Nature Protocols, vol. 8, 2013, pp. 2180-2196, 17 pages.
Lebherz, C., et al., "Gene therapy with novel adeno-associated virus vectors substantially diminished atherosclerosis in a murine model of familial hypercholesterolemia," The Journal of Gene Medicine, vol. 6, 2004, pp. 663-672, 10 pages.
Lee, C., et al., "Correction of the F508 Mutation in the Cystic Fibrosis Transmembrane Conductance Regulator Gene by Zinc-Finger Nuclease Homology-Directed Repair," Bioresearch Open Access, vol. 1, No. 3, pp. 99-108, dated 2012, 12 pages.
Leenay, et al., "Identifying and Visualizing Functional PAM Diversity across CRISPR-Cas Systems", Molecular Cell, vol. 62, 2016, pp. 137-147, 11 pages.
Lemay, et al., "Folding of the Adenine Riboswitch", Chemistry & Biology, vol. 13, 2006, pp. 857-868, 12 pages.

(56) References Cited

OTHER PUBLICATIONS

Levitt, J., et al., "Intrinsic fluorescence and redox changes associated with apoptosis of primary human epithelial cells," Journal of Biomedical Optics, vol. 11, No. 6, pp. 064012-1 to 064012-10, dated Nov./Dec. 2006, 10 pages.
Lewin, et al., "Nuclear localization sequences target proteins to the nucleus" Cells, vol. 5, 2006, 224.
Lewis, et al., "The c-myc and PyMT oncogenes induce different tumor types in a somatic mouse model for pancreatic cancer" Genes & Development, 2003, vol. 17 pp. 3127-3138, 14 pages.
Li et al., "Coevolution of CRISPR-Cas system with bacteria and phages", Hereditas, vol. 33, 2011, pp. 213-218, 6 pages.
Li, et al., "In vivo genome editing restores hemostasis in a mouse model of hemophilia" Nature, 2011, vol. 475, pp. 217-221, 5 pages. doi: 10.1038/nature10177.
Li, et al., "Multiplex and homologous recombination-mediated genome editing in *Arabidopsis* and Nicotaina benthamiana using guide RNA and Cas9" Nature Biotechnology, 2013, vol. 31 pp. 688-691, 4 pages.
Li, P., et al., "Biallelic knockout of alpha-1,3 galactosyltransferase gene in porcine liver-derived cells using zing finger nucleases," Journal of Surgical Research, vol. 181, 2013, pp. E39-E45, 7 pages.
Li, Ting, et al. "Modularly assembled designer TAL effector nucleases for targeted gene knockout and gene replacement in eukaryotes" Nucleic Acids Research, vol. 39, 2011, pp. 6315-6325, 11 pages.
Liu, et al. "Epstein-Barr Virus DNase Contains Two Nuclear Localization Signals Which Are Different in Sensitivity to the Hydrophobic Regions" Virology, vol. 247, pp. 62-73, 10 pages.
Lombardo, A., et al., "Gene editing in human stem cells using zinc finger nucleases and integrase-defective lentiviral vector delivery," Nature Biotechnology, vol. 25, 2007, pp. 1298-1306, 9 pages.
Los, et al., "Halotag Technology: Cell Imaging and Protein Analysis" Cell Notes, vol. 14, 2006, pp. 10-14, 5 pages.
Luo, B., et al., "Highly parallel identification of essential genes in cancer cells," Proceeding of the National Academy of Sciences, vol. 105, 2006, pp. 20380-20385, 6 pages.
Luo, Ming, et al., "Multiple Nuclear Localization Sequences Allow Modulation of 5-Lipoxygenase Nuclear Import" Traffic, 2004, vol. 5, pp. 847-854, 8 pages.
Lyssenko, et al., "Cognate putative nuclear localization signal effects strong nuclear localization of a GFP reporter and facilitates gene expression studies in Caenorhabditis elegans" BioTechniques, 2007, vol. 43 pp. 596-600, 5 pages.
M. Booker et al., "False negative rates in *Drosophila* cell-based RNAi screens: a case study," BMC Genomics, vol. 12, 2011, pp. 1-11, 11 pages.
M. Costanzo et al., "The genetic landscape of a cell," Science, vol. 327, Jan. 22, 2010, pp. 425-431, 8 pages.
Ma, M., et al., "A Guide RNA Sequence Design Platform for the CRISPR/Cas9 System for Model Organism Genomes," Hindawi, vol. 2013, 2013, art. 270805, pp. 1-5, 5 pages.
Maczuga, P., et al., "Embedding siRNA sequences targeting Apolipoprotein B100 in shRNA and miRNA scaffolds results in differential processing and in vivo efficacy," Molecular Therapy, vol. 21, 2013, pp. 217-227, 11 pages.
Madisen et al., "A robust and high-throughput Cre reporting and characterization system for the whole mouse brain," Nat. Neuroscience, vol. 13, Jan. 2010, pp. 133-140, 8 pages.
Maeder, et al., "CRISPR RNA-guided activation of endogenous human genes" Nature Methods, vol. 10, 2013, pp. 977-979, 3 pages. doi.10.1038/nmeth.2556.
Maeder, M., and Gersbach, C., "Genome-editing Technologies for Gene and Cell Therapy," Molecular Therapy, vol. 24, 2016, pp. 430-446, 17 pages.
Maeder, M., et al., "Robust, synergistic regulation of human gene expression using TALE activators," Nature Methods, vol. 10, 2013, pp. 243-245, 3 pages. Including Supplemental information, 6 pages.
Mahfouz, et al., "Targeted transcriptional repression using a chimeric TALE-SRDX repressor protein" Plant Mol Biology, vol. 78, 2012, pp. 311-321, 11 pages.

Mahfouz, M., et al., "De novo-engineered transcription activator-like effector (TALE) hybrid nuclease with novel DNA binding specificity creates double-strand breaks," Proceedings of the National Academy of Science, vol. 108, 2011, pp. 2623-2628, 6 pages.
Makarova, et al., "An updated evolutionary classification of CRISPR-Cas systems" Nature Reviews-Microbiology, vol. 13 2015, pp. 722-736, 15 pages.
Makarova, K., et al., "Evolution and classification of the CRISPR-CAS Systems," Nature Reviews Microbiology, vol. 9, 2011, pp. 467-477, 11 pages. Including Supplemental information, 23 pages.
Makarova, K., et al., "Unification of Cas protein families and a simple scenario for the origin and evolution of CRISPR-Cas systems," Biology Direct, vol. 6, No. 38, 2011, pp. 1-27, 27 pages.
Mali, et al. "RNA-Guided Human Genome Engineering Via Cas9" Science, vol. 339, pp. 823-826, dated Feb. 15, 2013, 41 pages. (Includes Supplemental Information).
Mali, et al., Supplementary Information for "Use of adjacent sgRNA: Cas9 complexes for transcriptional activation and genome engineering," Nature Biotechnology, pp. 1-36, 36 pages. doi:10.1037/nbt.2675.
Mali, P., et al., "CAS9 transcriptional activators for target specificity screening and paired nickases for cooperative genome engineering," Nature Biotechnology, vol. 31, No. 9, pp. 833-838, dated Aug. 1, 2013, 44 pages. (Includes Supplemental Information).
Mali, P., et al., Supplementary Information for: "RNA-Guided Human Genome Engineering via Cas9," Science, vol. 339, pp. 823-826, 2013, 8 pages.
Malina, A., et al., "Repurposing CRISPR/Cas9 for in situ functional assays," Genes & Development, vol. 27, 2013, pp. 2602-2614, 13 pages.
Manjunath, N., et al., "Newer Gene Editing Technologies toward HIV Gene Therapy," Viruses, vol. 5, pp. 2748-2766, 2013, 19 pages.
*Manning v. Paradis*, 296 F.3d 1098 (Fed. Cir. 2012), 9 pages.
Marraffini, L., "CRISPR-Cas Immunity against Phages: Its Effects on the Evolution and Survival of Bacterial Pathogens," PLoS, Dec. 12, 2013, pp. 1-6, 6 pages.
Marraffini, L., Assignment to Rockefeller University, dated Dec. 12, 2013, 3 pages.
Marraffini, L., et al., "Self vs. non-self discrimination during CRISPR RNA-directed immunity," Nature, vol. 463, 2010, pp. 568-571, 13 pages.
Marraffini, L.A., et al., "Sortases and the art of anchoring proteins to the envelopes of gram-positive bacteria," Microbiol. Mol. Biology Review vol. 70, Mar. 2006, pp. 192-221, 3 pages.
Martin, M., "Cutadapt removes adapter sequences from high-throughput sequencing reads," EMBnet.journal, vol. 17, 2011, pp. 10-12, 3 pages.
Mastroianni, et al., "Group II Intron-Based Gene Targeting Reactions in Eukaryotes" Plos One, vol. 3, 2008, pp. 1-15, 15 pages. Doi:10.1371/journal.pone.0003121.
*Maxwell v. The Stanley Works*, 2006 WL 1967012, *5 (M.D. Tenn. Jul. 11, 2006), 7 pages.
Meshorer, et al., "Chromatin in pluripotent embryonic stem cells and differentiation" Nature Reviews Molecular Cell Biology, vol. 7, 2006, pp. 540-546, 7 pages.
Miller, et al., "A TALE nuclease architecture for efficient genome editing" Nature Biotechnology, vol. 29, 2011, pp. 143-150, 8 pages.
Mincer, J., and Simon, S., "Simulations of nuclear pore transport yield mechanistic insights and quantitative predictions," Proceedings of the National Academy of Science, vol. 108, pp. E351-E358, 8 pages.
Minton, "How can biochemical reactions within cells differ from those in test tubes?" Journal of Cell Science, 2006, vol. 119, pp. 2863-2869, 7 pages.
Moffat J et al., "A lentiviral RNAi library for human and mouse genes applied to an arrayed viral high-content screen," Cell, vol. 124, Mar. 24, 2006, pp. 1283-1298, 16 pages.
Mojica F. J. M et al., "Biological significance of a family of regularly spaced repeats in the genomes of Archaea, Bacteria and mitochondria," Molecular Microbiology, vol. 36, 2000, pp. 244-246, 3 pages.

(56) References Cited

OTHER PUBLICATIONS

Mojica, F. J., et al., "Short motif sequences determine the targets of the prokaryotic CRISPR defence system," Microbiology, vol. 155, 2009, pp. 733-740, 8 pages.

Mojica, F. J., et al., Supplementary Material for: "Short motif sequences determine the targets of the prokaryotic CRISPR defence system," Microbiology, vol. 155, 2009, 37 pages.

Morbitzer, et al., "Assembly of custom TALE-type DNA binding domains by modular cloning," Nucleic Acids Research, vol. 39, pp. 5790-5799, 10 pages.

Morbitzer, et al., "Regulation of selected genome loci using de novo-engineered transcription activator-like effector (TALE)-type transcription factors" PNAS, vol. 108, 2010, pp. 21617-21622, 6 pages.

Morgan, et al., "Inducible Expression and Cytogenetic Effects of the EcoRI Restriction Endonuclease in Chinese Hamster Ovary Cells" Molecular and Cellular Biology, vol. 8, 1988, pp. 4204-4211, 8 pages.

Morin, et al., "Nuclear Localization of the Adenovirus DNA-Binding Protein: Requirement for Two Signals and Complementation during Viral Infection" Molecular and Cellular Biology, vol. 9, 1989, pp. 4372-4380, 9 pages.

Morris et al., "Distributed automated docking of flexible ligands to proteins: Parallel applications of AutoDock 2.4*", Journal of Computer-Aided Molecular Design, 1996, vol. 10, pp. 293-304.

Moscou, et al., "A Simple Cipher Governs DNA Regognition by TAL Effectors" Science, vol. 326, 2009, p. 1501.

Motamedi, M.R., et al., "Double-strand-break repair recombination in *Escherichia coli*: physical evidence for a DNA replication mechanism in vivo," Genes Dev., vol. 13, 1999, pp. 2889-2903.

Mukhopadyay, R., "On the Same Wavelength," ASBMB Today, http://www.asbmb.org/asbmbtoday/201408/Features/Doudna/, dated Aug. 2014, 6 pages.

Mussolino, et al., "TALE nucleases: tailored genome engineering made easy" Current Opinion in Biotechnology, vol. 23, 2012, pp. 644-650, 7 pages.

Musunuru, "Abstract 18593: Use of a CRISPR/Cas System for Cardiovascular Disease Modeling and Therapeutic Applications", Circulation, vol. 128, 2013, 4 pages (Meeting info: American Heart Association, 2013 Scientific Sessions and Resuscitation Science Symposium, Dallas, TX, US, Nov. 16-20, 2013).

Muther, N., et al., "Viral Hybrid Vectors for Somatic Integration—Are They the Better Solution?" Viruses, vol. 1, 2009, pp. 1295-1324, 30 pages.

Nagarajan, et al., "A Hierarchy of Nuclear Localization Signals Governs the Import of the Regulatory Factor X Complex Subunits and MHC Class II Expression" The Journal of Immunology, vol. 173, 2004, pp. 410-419, 11 pages.

Nakai, et al., "PSORT: a program for detecting sorting signals in proteins and predicting their subcellular localization" Trends in Biochem Sciences, vol. 24, 1999, pp. 34-35, 2 pages.

Nakamura, et al., "Codon usage tabulated from international DNA sequence databases: status for the year 2000" Nucleic Acids Research, vol. 28, 2000, p. 292.

Nishimasu, et al., "Crystal Structure of Cas9 in Complex with Guide RNA and Target DNA", Cell, Feb. 27, 2014, vol. 156, pp. 935-949.

Nishimasu, H., et al., "Crystal Structure of *Staphylococcus aureus* Cas9," Cell, vol. 162, Aug. 27, 2015, pp. 1113-1126, 15 pages.

Noguchi, et al., "PDX-1 Protein Containing Its Own Antennapedia-Like Protein Transduction Domain Can Transduce Pancreatic Duct and Islet Cells" Diabetes, 2003, vol. 52 pp. 1732-1737, 6 pages.

Nomura, S., et al., "Low-density lipoprotein receptor gene therapy using helper-dependent adenovirus produces long-term protection against atherosclerosis in a mouse model of familial hypercholesterolemia," Gene Therapy, vol. 11, 2004, pp. 1540-1548, 10 pages.

O'Hare, et al., "Transformation of mouse fibroblasts to methotrexate resistance by a recombinant plasmid expressing a prokaryotic dihydrofolate reductase" Proc. Natl. Acad. Sci., vol. 78 2011, 1527-1531, 5 pages.

Opposition Against Appl. Ser. No. EP13818570.7 submitted by Schlich dated Oct. 26, 2015, 8 pages.

Opposition Against EP Appl. Ser. No. 2771468-B1 dated Oct. 26, 2015, 40 pages.

Ozawa, K., "Gene therapy using AAV," Virus, vol. 57, pp. 47-55, dated, 2007, 13 pages. (with English Abstract; No English Translation).

Paddison et al., "A resource for large-scale RNA-interference-based screens in mammals," Nature, vol. 428, Mar. 25, 2004, pp. 427-431, 5 pages.

Pandika, et al., www.ozy.com/rising-stars-and-provocateurs/jennifer-doudna-crispr-code-killer/4690; Jan. 7, 2014.

Panyam, J., and Labhasetwar, V., "Biodegradable nanoparticles fordrug and gene delivery to cells and tissue," Advanced Drug Delivery Reviews, vol. 55, 2003, pp. 329-347, 19 pages.

Park, et al., "Regulation of Ribosomal S6 Kinase 2 by Mammalian Target of Rapamycin", The Journal of Biological Chemistry, vol. 277, 2002, pp. 31423-31429, 7 pages.

Pattanayak, et al., "High-throughput profiling of off-target DNA cleavage reveals RNA-programmed Cas9 nuclease specificity," Nature Biotechnology, vol. 31, 2013, pp. 839-843, 5 pages. Including Supplementary Materials, 2 pages.

Patterson, et al., "Codon optimization of bacterial luciferase (lux) for expression in mammalian cells" J. Ind. Microbio. Biotechnology, vol. 32, 2005, 115-123, 9 pages.

Perez-Pinera, et al., "Advances in Targeted Genome Editiong" CurrOpin Chem Biology, vol. 16, 2012, pp. 268-277, 10 pages. doi:10.1016/j.cbpa.2012.06.007, 17 pages.

Perez-Pinera, et al., "RNA-guided gene activation by CRISPR-Cas9-based transcription factors" Nature Methods, 2013, vol. 10, pp. 1-12.

Phillips, A., "The challenge of gene therapy and DNA delivery," The Journal of Pharmacy and Pharmacology, vol. 53, 2011, pp. 1169-1174, 6 pages.

Planey, et al. "Mechanisms of Signal Transduction: Inhibition of Glucocorticoid-induced Apoptosis in 697 Pre-B Lymphocytes by the Mineralocorticoid Receptor N-terminal Domain", Journal of Biological Chemistry, vol. 277, 2002, pp. 42188-42196, 9 pages.

Platt, R., et al., "CRISPR-Cas9 Knockin Mice for Genome Editing and Cancer Modeling," Cell, vol. 159, 2014, pp. 440-455, 16 pages.

Podbielski, A., et al., "R. Novel series of plasmid vectors for gene inactivation and expression analysis in group A streptococci (GAS)," Gene, vol. 177, 1996, pp. 137-147, 11 pages.

Porteus, et al., "Gene targeting using zinc finger nucleases" Nature Biotechnology, Aug. 2005, vol. 23 pp. 967-973, 7 pages.

Porteus, M., and Balitmore, D., "Chimeric Nucleases Stimulate Gene Targeting in Human Cells," Science, vol. 300, 2003, p. 763, 2 pages.

Posfai, et al., "Markerless gene replacement in *Escherichia coli* stimulated by a double-strand break in the chromosome" Nucleic Acids Resarch, vol. 27, 1999, pp. 4409-4415, 7 pages.

Pougach, et al., "Transcription, Processing and Function of CRISPR Cassettes in *Escherichia coli*" Mol. Microbiology, vol. 77, 2010, pp. 1367-1379, 14 pages.

Pougach, K.S., et al., "CRISPR Adaptive Immunity Systems of Prokaryotes," Molecular Biology, vol. 46, Apr. 2012, pp. 195-203, 1 page (English Abstract).

Pride, D., et al., "Analysis of Streptococcal CRISPRs from Human Saliva Reveals Substantial Sequence Diversity Within and Between Subjects Over Time," Genome Research, vol. 21, 2011, pp. 126-136, 11 pages.

Primo, et al., "Lentiviral vectors for cutaneous RNA managing" Experimental Dermatology, vol. 21, 2012. 162-170, 9 pages.

Qi, et al., "Repurposing CRISPR as an RNA-Guided Platform for Sequence-Specific Control of Gene Expression" Cell, vol. 152, 2013, pp. 1173-1183, 11 pages.

Qi, J., et al., "microRNAs regulate human embryonic stem cell division," Cell Cycle, vol. 8, 2009, pp. 3729-3741, 13 pages.

R. Rad et al., "PiggyBac transposon mutagenesis: a tool for cancer gene discovery in mice," Science, vol. 330, Nov. 19, 2010, p. 1104-1107, 4 pages.

(56) References Cited

OTHER PUBLICATIONS

R.D Kolodner and G.T. Marsischky, "Eukaryotic DNA mismatch repair," Current Opinion in Genetics and Development, vol. 9, 1999, p. 89-96, 8 pages.

R.Renella et al., "Codanin-1 mutations in congenital dyserthropoietic anemia type 1 affect HP1α localization in erythroblasts," Blood, vol. 117, Jun. 2011, pp. 6928-6938, 11 pages.

Radecke, S., et al., "Zinc-finger Nuclease-induced Gene Repair With Oligodeoxynucleotides: Wanted and Unwanted Target Locus Modifications," Molecular Therapy, vol. 18, Apr. 2010, pp. 743-753, 11 pages.

Radulovich, et al., "Modified gateway system for double shRNA expression and Cre/lox based gene expression" BMC Biotechnology, 2011, vol. 11, pp. 1-9, 10 pages.

Ran et al., "Double Nicking by RNA-guided CRISPR Cas9 for enhanced genome editing specificity", Cell, Sep. 12, 2013, vol. 154, pp. 1380-1389.

Ran, F., et al, "In vivo genome editing using *Staphylococcus aureus* Cas9," Nature, vol. 520, 2015, pp. 186-191, 6 pages. Includes Supplemental information, 12 pages.

Ran, F., et al., "Genome engineering using the CRISPR-Cas9 system," Nature Protocols, vol. 8, 2013, pp. 2281-2308, 28 pages.

Rand, et al. "Argonaute2 Cleaves the Anti-Guide Strand of siRNA during RISC Activation" Cell, vol. 123, 2005, pp. 621-629, 9 pages.

Raymond, et al. "High-Efficiency FLP and φC31 Site-Specific Recombination in Mammalian Cells" PLoS One, vol. 2, Jan. 2007, pp. 1-4. DOI. 10.1371/journal.pone.0000162.

Rebar, et al., "Induction of angiogenesis in a mouse model using engineered transcription factors" Nature Medicine, vol. 8, 2002, pp. 1427-1432, 6 pages.

Redeclaration—37 C.F.R. 41.203(c); filed Mar. 17, 2016 in Patent Interference No. 106,048 (DK), 14 pages.

Reiss, et al., "RecA protein stimulates homologous recombination in plants" Proc. Natl. Acad. Sci. vol. 93, 1996, pp. 3094-3098, 5 pages.

Response to Third Party Observations in EP No. 13824232.6 filed Oct. 2, 2014, with Redlined and Clean Amended Claims, 14 pages.

Rho, M., et al., "Diverse CRISPRs Evolving in Human Microbiomes," PLoS Genetics, vol. 8, Jun. 2012 e1002441, 12 pages.

Rhun, A., and Charpentier, E., "Small RNAs in streptococci," RNA Biology, vol. 9, 2012, pp. 414-426, 13 pages.

Roberts, et al. "Nuclear location signal-mediated protein transport" Biochimica et Biophysica Act, vol. 1008, 1989, pp. 263-280, 18 pages.

Roberts, et al., "The Effect of Protein Content on Nuclear Location Signal Function" Cell, vol. 50, 1989, pp. 465-475, 11 pages.

Rockefeller University and Broad Institute of MIT and Harvard announce update to CRISPR-Cas9 portfolio filed by Broad, Press Release dated Jan. 15, 2018, retrieved from: https://www.broadinstitute.org/news/rockefeller-university-and-broad-institute-mit-and-harvard-announce-update-crispr-cas9, 3 pages.

Rodrigues, et al., "Red Fluorescent Protein (DsRed) as a Reporter in *Saccharomyces cerevisiae*" Journal of Bacteriology, vol. 183, 2001, pp. 3791-3794, 4 pages.

Rodriguez et al., "AAV-CRISPR: A New Therapeutic Approach to Nucleotide Repeat Diseases", Molecular Therapy, vol. 22, 2014, Supplement 1, Abstract 247, p. S94.

Rolling, "Recombinant AAV-mediated gene transfer to the retina: gene therapy perspectives", Gene Therapy, vol. 11, 2004, pp. S26-S32, 5 pages.

*Rubin v. The General Hospital Corp.*, 2011-1439 (Fed. Cir. Mar. 28, 2013), 8 pages.

S. Huang et al., "MED12 Controls the Response to Multiple Cancer Drugs through Regulation of TGF-β; Receptor Signaling," Cell, vol. 151, 2012, pp. 937-950, 14 pages.

S. Konermann et al., "Optical control of mammalian endogenous transcription and epigenetic states," Nature, vol. 500, Aug. 22, 2013, pp. 472-476, 5 pages. Includes Supplemental Information, 13 pages.

S.H. Chen et al., "A Knockout Mouse Approach Reveals that TCTP Functions as an Essential Factor for Cell Proliferation and Survival in a Tissue- or Cell Type-specific Manner," Molecular Biology of the Cell, vol. 18, Jul. 2007, pp. 2525-2532, 8 pages.

S.R. Whittaker et al., "A Genome-Scale RNA Interference Screen Implicates NF1 Loss in Resistance to RAF Inhibition," Cancer Discovery, vol. 3, 2013, pp. 350-362, 14 pages.

S.S. Liu et al., "Identification and characterization of a novel gene, clorf109, encoding a CK2 substrate that is involved in cancer cell proliferation," Journal of Biomedical Science, vol. 19, 2012, 12 pages.

S.Xue and M. Barna, "Specialized ribosomes: a new frontier in gene regulation and organismal biology," Nat Rev Mol Cell Biology, vol. 13, Jun. 2012. pp. 355-369, 15 pages.

Sadowski, M., and Jones, D., "The sequence-structure relationship and protein function prediction," Current Opinion in Structural Biology, vol. 19, 2009, pp. 357-362, 6 pages.

Sambrook, et al., "Molecular Cloning, A Laboratory Manual on the Web", Cold Spring Harbor Laboratory Press, Chapter 16, 2001, downloaded from http://www.molecularcloning.com/members/chapter.jsp?chapter=127 on Feb. 19, 2002, 13 pages.

Sander, et al., "CRISPR-Cas systems for editing, regulating and targeting genomes," Nature Biotechnology, vol. 32, 2014, pp. 347-355, 9 pages.

Sanders, "Cheap and easy technique to snip DNA could revolutionize gene therapy", UC Berkeley Press Release, Jan. 7, 2013, available at http://newscenter.berkeley.edu/2013/01/07/cheap-and-easy-technique-to-snip-dna-could-revolutionize-gene-therarpy/.

Sanders, et al., "Use of a macromolecular crowding agent to dissect interactions and define functions in transcriptional activation by a DNA-tracking protein: Bacteriophage T4 gene 45 protein and late transcription" PNAS, vol. 9 2014, pp. 7703-7707, 5 pages.

Sanjana, et al., "Improved vectors and genome-wide libraries for CRISPR screening," HHS Public Access Author Manuscript, vol. 11, 2014, pp. 2145-2148, 4 pages.

Sanjana, N., et al., "A Transcription Activator-Like Effector (TALE) Toolbox for Genome Engineering," Nature Protocols, vol. 7, 2012, pp. 171-192, 39 pages.

Sapranauskas, R., et al., "The *Streptococcus thermophilus* CRISPR-Cas system provides immunity in *Escherichia coli*," Nucleic Acids Research, vol. 3, 2011, pp. 9275-9282, 8 pages.

Sarra, G., et al., "Gene replacement therapy in the retinal degeneration slow (rds) mouse: the effect on retinal degeneration following partial transduction of the retina", Human Molecular Genetics, vol. 10, 2001, pp. 2353-2361, 9 pages.

Sato, et al. "Generation of Adeno-Associated Virus Vector Enabling Functional Expressionof Oxytocin Receptor and Fluorescence Marker Genes Using the Human eIF4G Internal Ribosome Entry Site Elemet" Biosci. Biotechno. Biochem, vol. 73, 2009, pp. 2145-2148, 4 pages.

Sauer, "Functional Expression of the cre-lox Site-Specific Recombination System in the Yeast *Saccharomyces cerevisiae*" Mol. Cell. Biology, vol. 7, 1987, pp. 2087-2096, 10 pages.

Sauer, et al. "Site-specific DNA recombination in mammalian cells by the Cre recombinase of bacteriophage P1" Proc. Natl. Acad. Sci. vol. 85, 1988, pp. 5166-5170, 5 pages.

Schiffer, et al. "Targeted DNA Mutagenesis forthe Cure of Chronic Viral Infections" Journal of Virology, vol. 86, No. 17, Jun. 20, 2012, pp. 8920-8936.

Schiffer, et al., "Predictors of Hepatitis B Cure Using Gene Therapy to Deliver DNA Cleavage Enzymes: A Mathematical Modeling Approach" PLoS Computational Biology, vol. 9, 2013, pp. 1-16. www.ploscompbiol.org.

Scholze, et al., "TAL effector-DNA specificity", Virulence, vol. 1, No. 5, Sep. 1, 2010, pp. 428-432, 5 pages. DOI:10.4161/viru.1.5.12863.

Schramm et al., "Recruitment of RNA polymerase III to its target promoters" Genes & Development, vol. 16, 2002, 2593-2620, pages 28 pages.

Schunder et al., "First indication for a functional CRISPR/Cas system in Francisella tularensis", International Journal of Medical Microbiology, vol. 303, 2013, pp. 51-60, 10 pages.

Sebastiani, et al., "BCL11A enhancer haplotypes and fetal hemoglobin in sickle cell anemia," Blood Cells, vol. 54, 2015, pp. 2240230, 7 pages.

(56) References Cited

OTHER PUBLICATIONS

Sebo, et al., "A simplified and efficient germline-specific CRISPR/Cas9 system for *Drosophila* genomic engineering" Fly, 2014, vol. 8, pp. 52-57, 8 pages.
Seffernick, J., et al., "Melamine Deaminase and Atrazine Chlorohydrolase: 98 Percent Identical but Functionally Different," Journal of Bacteriology, vol. 183, No. 8, Apr. 2001, pp. 2405-2410, 6 pages.
Semenova, E. et al., "Interference by clustered regularly interspaced short palindromic repeat (CRISPR) RNA is governed by a seed sequence," Proc. Natl. Acad. Sci., vol. 108, Jun. 21, 2011, pp. 10089-10103, 7 pages.
Senis, E., et al., "CRISPR/Cas9-mediated genome engineering: An adeno-associated viral (AAV) vector toolbox," Biotechnology Journal, vol. 9, 2014, pp. 1402-1412, 12 pages.
Senturk et al., "A rapid and tunable method to temporally control cas9 expression enables the identification of essential genes and the interrogation of functional gene interactions in vitro and in vivo," vol. 9, 2015, pp. 1-27, XP002756303, doi:10.1101/023366, Retrieved from the Internet: URL:http://biorxiv.org/content/early/2015/07/28/023366 [retrieved on Apr. 11, 2016).
Shalem, et al., "High-throughput functional genomics using CRISP-Cas9," Nature Reviews Genetics, vol. 16, No. 5, pp. 299-311, May 2015.
Shalem, O., et al., "Genome-Scale CRISPR-Cas9 Knockout Screening in Human Cells," Science, vol. 343, 2014, pp. 84-87, 5 pages.
Sharan, et al., "Recombineering: A Homologous Recombination-Based Method of Genetic Engineering" Nat. Protoc., 2009, vol. 4 pp. 206-223, 18 pages. doi:10.1038/nprot.2008.227.
Shen, B., et al., "Generation of gene-modified mice via Cas9/RNA-mediated gene targeting," Cell Research, vol. 23, 2013, pp. 720-723.
Shen, et al., "Efficient genome modification by CRISPR-Cas9 mickase with minimal off-target effects" 2014, Nature Methods, vol. 11, pp. 399-404, 6 pages.
Shengdar Tsai et al., "Dimeric CRISPR RNS-guided FokI nucleases for highly specific genome editing", Nature Biotechnology, vol. 32, Jun. 2014, pp. 569-576, 18 pages.
Shieh, et al., "Nuclear Targeting of the Maize R. Protein Requires Two Nuclear Localization Sequences" Plant Physiol, 1993, vol. 101 pp. 353-361, 9 pages.
Siegl, et al., "I-ScelI endonuclease: a new tool for DNA repair studies and genetic manipulations in streptomycetes" Appl Microbiol Bitotechnol, vol. 87, 2010, pp. 1525-1532, 8 pages.
Sims, D., et al., "High-throughput RNA interference screening using pooled shRNA libraries and next generation sequencing," Genome Biology, vol. 12, 2011, pp. 1-13.
Singer, et al., "Applications of Lentiviral Vectors for shRNA Delivery and Transgenesis" Curr Gene Ther., vol. 8, 2008 pp. 483-488, 6 pages.
Slaymaker et al., "Rationally engineered Cas9 nucleases with improved specificity", Science, American Association for the Advancement of Science, US, vol. 351, Jan. 1, 2016, pp. 84-88.
Sontheimer, "Project 7: Establishing RNA-Directed DNA Targeting in Eukaryotic Cells" Physical Sciences-Onc., Nov. 16, 2011-Dec. 31, 2012, 2 pages. htt://groups.molbiosci.northwestern.edu/sontheimer/Sontheimer_cv.php) Molecular Biosciences, 2 pages.
Spencer, J.M., et al., "Development of a Nuclease Screen to Improve Cas9 Targeting Specificity", Molecular Therapy, May 2015, vol. 23, Suppl. 1, S136(340).
Stewart SA et al., "Lentivirus-delivered stable gene silencing by RNAi in primary cells," RNA, vol. 9, 2003, pp. 493-501, 9 pages.
Stolfi, et al., "Tissue-specific genome editing in Ciona embryos by CRISPR/Cas9," Development, vol. 141, 2014, pp. 4115-4120, 6 pages. doi:10.1242/dev.114488.
Stoller, J. and Aboussouan, L., "Alpha1-antitrypsin deficiency," The Lancet, Seminar, vol. 365, 2005, pp. 2225-2236, 12 pages.
Stratikopoulos, E., et al., "The hormonal action of IGF1 in postnatal mouse growth," Proceedings of the National Academy of Sciences, vol. 105, Dec. 9, 2008, pp. 19378-19383, 6 pages.

Straub, C., et al., "CRISPR/Cas9-Mediated Gene Knock-Down in Post-Mitotic Neurons," PLoS One, vol. 9, No. 8, art. E105584, pp. 1-5, dated Aug. 2014, 6 pages.
Sung, et al., "An rpsL Cassette, Janus, for Gene Replacement through Negative Selectionin *Streptococcus pneumoniae*" Applied and Environmental Microbiology, vol. 67, 2001, pp. 5190-5196, 7 pages.
Sung, M., et al., "The importance of valency in enhancing the import and cell routing potential of protein transduction domain-containing molecules," Biochimica et Biophysica Aeta, vol. 1758, pp. 355-363, dated 2006, 9 pages.
Sung, Young Hoon, et al., "Mouse genetics: Catalogue and scissors" BMB Reports, 2012, vol. 45 pp. 686-692, 7 pages.
Suzuki, K., et al., "In vivo genome editing via CRISPR/Cas9 mediated homology-independent targeted integration," Nature, vol. 540, art. 7631, 2015, pp. 1-44.
Swarthout, J., et al., "Zinc Finger Nucleases: A new era for transgenic animals," Annals of Neurosciences, vol. 18, 2011, pp. 25-28, 4 pages.
Swiech et al., "CRISPR-Mediated Genome Editing in the Mammalian Brain", Molecular Therapy, 747, vol. 22, 2014, p. S289.
Swiech, L., et al., "In vivo interrogation of gene function in the mammalian brain using CRISPR-Cas9," Nature Biotechnology, vol. 33, 2014, pp. 102-106, 5 pages. Including Supplemental information, 4 pages.
Symington et al., "Double-Strand Break End Resection and Repair Pathway Choice", Annual Review of Genetics, vol. 45, 2011, pp. 247-271, 25 pages.
T. Horii et al., "Generation of an ICF Syndrome Model by Efficient Genome Editing of Human Induced Pluripotent Stem Cells Using the CRISPR System," International Journal of Molecular Sciences, vol. 14, 2013, p. 19774-19781, 9 pages.
T.J. Cradick et al., "CRISPR/Cas9 systems targeting β-globin and CCR5 genes have substantial off-target activity," Nucleic Acids Research, vol. 41, 2013, 9584-9592, 9 pages.
T.Yan et al., "DNA mismatch repair (MMR) mediates 6-thioguanine genetoxicity by introducing single-strand breaks to signal a G2-M arrest in MMR-proficient RKO cells," Clinical Cancer Research, vol. 9, Jun. 2003, p. 2327-2334, 9 pages.
Takara Bio USA, Inc., "Lenti-X™ Tet-On © 3G CRISPR/Cas9 System User Manual", 2016, pp. 1-35.
Tang, T., et al., "A mouse knockout library for secreted and transmembrane proteins," Nature Biotechnology, vol. 28, No. 7, Jul. 2010, pp. 749-755, pages. 7 pages. Including Supplemental information, 2 pages.
Terns, M., and Terns, R., "CRISPR-based adaptive immune systems," Current Opinion in Microbiology, vol. 14, 2011, pp. 321-327, 8 pages.
*The Broad Inst.* v. *The Regents of University of UCA*—Decision on Motions for Patent Interference No. 106,048 filed Feb. 15, 2017, 51 pages.
Third Party Observation for Application No. EP20130824232 dated Sep. 22, 2014, 19 pages.
Third Party Observation in Application No. PCT/US2013/074819 dated Apr. 10, 2015, 10 pages.
Third Party Observation Under Article 115 EPC in Application No. 13818570.7 dated Oct. 1, 2014.
Third Party Observations Concerning App. No. GB1420270.9, dated Jun. 30, 2015, 71 pages.
Third Party Observations Concerning Appl. No. EP2800811, dated Jul. 24, 2015, 108 pages.
Third Party Observations Concerning Appl. No. EP2800811, dated Sep. 4, 2015.
Third Party Observations Concerning Appl. No. GB1420270.9 dated Jun. 30, 2015.
Third Party Observations Concerning Appl. No. GB1420270.9, dated Jul. 13, 2015.
Third Party Observations in Accordance with Article 115 EPC, Appl. No. EP13824232.6, Pub. No. EP2764103A, dated Mar. 25, 2015.
Third Party Observations submitted by Broad Institute Inc. Concerning Appl. Ser. No. EP13793997.1 dated Jul. 24, 2015, 108 pages.

(56) References Cited

OTHER PUBLICATIONS

Third Party Observations submitted by Broad Institute Inc. Concerning Appl. Ser. No. EP13793997.1 dated Sep. 4, 2015, 25 pages.
Third Party Observations submitted by Regents of the University of California et al. Concerning App. No. GB1420270.9 dated Jul. 13, 2015, 18 pages.
Third Party-Observations, Appl. No. 1382432.6, Pub. No. EP2764103, dated Feb. 16, 2015, 12 pages.
Third-Party Observation for Application No. EP20130824232 dated Sep. 8, 2014, 47 pages.
Tinland, et al., "The T-DNA-linked VirD2 protein contains two distinct functional nuclear localization signals" Proc. Natl. Acad. Sci, vol. 89, 1992, pp. 7442-7446, 5 pages.
Tiscornia, et al. "Development of Lentiviral Vectors Expressing siRNA" Gene Transfer-Delivery and Expression of DNA and RNA-A Laboratory Manual, 2007, Chapter 3 pp. 23-34, 12 pages.
Tolia, et al., "Slicer and the Argonautes" Nature Chemical Biology, vol. 3, 2007, pp. 36-43, 8 pages.
Trafton, A., "CRISPR-carrying nanoparticles edit the genome," MIT News, dated Nov. 13, 2017, 3 pages.
Trevino, et al., "Genome Editing Using Cas9 Nickases" Methods in Enxymology, vol. 546 pp. 161-174, 14 pages.
Tulpan, D., et al., "Free energy estimation of short DNA duplex hybridizations," BMC Bioinformatics, vol. 11, 2012, pp. 105-127, 23 pages.
Type V CRISPR-associated protein Cpfi [*Acidaminococcus* sp. Bv3L6], 2017, NCBI Reference Sequence: WP_02173622.1, Non-redundant Protein Sequence, 2 pages.
*Ultra-Precision Mfg. Ltd. v. Ford Motor Co.*, 2004 WL 3507671, *7, *11-12 (E.D. Mich. Mar. 30, 2004).
Urnov, et al., "Highly efficient endogenous human gene correction using designed zinc-finger nucleases" Nature, vol. 435, 2005, pp. 646-651, 6 pages.
Urnov, F., et al., "Genome editing with engineered zinc finger nucleases," Nature Reviews, Genetics, vol. 11, pp. 637-646, dated Sep. 2010, 11 pages.
Urrutia, et al., "KRAB-containing zing finger repressor proteins" Genome Biology, vol. 4, Sep. 23, 2003, pp. 231-231.8, 8 pages.
V.N. Ngo et al., "A loss-of-function RNA interference screen for molecular targets in cancer," Nature, vol. 441, May 4, 2006, pp. 106-110, 5 pages.
Van Den Ackerveken, et al., "Recognition of the Bacterial Avirulence Protein AvrBs3 Occurs inside the Host Plant Cell" Cell, vol. 87, Dec. 27, 1996, pp. 1307-1316, 10 pages.
Van Der Oost, "New tool for genome surgery", Science, vol. 339, Feb. 15, 2013, pp. 768-770, 3 pages.
Van Der Oost, J., et al., "CRISPR-based adaptive and heritable immunity in prokaryotes," Trends. Biochem. Sci., vol. 34, 2009, pp. 401-407, 7 pages.
Van Nierop, G., et al., "Stimulation of homology-directed gene targeting at an endogenous human locus by a nicking endonuclease," Nucleic Acids Research, vol. 37, 2009, pp. 5725-5736, 12 pages.
Venken et al., "P[acman]: A BAC Transgenic Platform for Targeted Insertion of Large DNA Fragments in *D. melanogaster*", Science, vol. 314, Dec. 15, 2006, pp. 1747-1751, 5 pages.
Vestergaard et al:., "CRISPR adaptive immune systems of Archaea", RNA Biology, vol. 11, 2014, pp. 156-167, 12 pages.
Villion, et al., "The double-edged sword of CRISPR-Cas systems" Cell Research, 2013, vol. 23 pp. 15-17, 3 pages.
W.G. Kaelin., "Use and Abuse of RNAi to Study Mammalian Gene Function," Science, vol. 337, Jul. 27, 2012, p. 421-422, 2 pages.
Wang, et al. "Genetic Screens in Human Cells Using the CRISPR-Cas9 System", Science, 2014, 343:80-84.
Wang, H., et al., "One-Step Generation of Mice Carrying Mutations in Multiple Genes by CRISPR/Cas-Mediated Genome Engineering," Cell, vol. 153, 2013, pp. 910-918, 9 pages.
Wang, H.H et al., "Genome-scale promoter engineering by coselection MAGE," Nat methods, vol. 9, Jun. 2012, pp. 591-593, 3 pages.
Wayengera, M., "Identity of zinc finger nucleases with specificity to herpes simplex virus type II genomic DNA; novel HSV-2 vaccine/therapy precursors", Theoretical Biology and Medical Modelling, vol. 8, No. 1, Jun. 24, 2011, p. 23.
Wayengera, M., "Zinc finger arrays binding human papillomavirus types 16 and 18 genomic DNA: precursors of gene-therapeutics for in-situ reversal of associated cervical neoplasia", Theoretical Biology and Medical Modeling, vol. 9, No. 1, Jul. 28, 2012, p. 30.
Weber et al., "TALENs Targeting HBV: Designer Endonuclease Therapies for Viral Infections", Molecular Therapy, vol. 21, Oct. 2013, pp. 1819-1821, 3 pages.
Welch, et al., "Designing Genes for Successful Protein Expression" Methods in Enzymology, 2011, vol. 498, pp. 43-66, 24 pages. DOI: 10.1016/B978-0-12-385120-8.00003-6.
Wiedenheft, B. et al., "RNA-guided complex from a bacterial immune system enhances target recognition through seed sequence interactions," Proc. Natl. Acad. Sci., vol. 108, Jun. 21, 2011, 10092-10097, 7 pages.
Wiedenheft, B. et al., "RNA-guided genetic silencing systems in bacteria and archaea", Nature, vol. 482, Feb. 16, 2012, pp. 331-338.
Wienert, B., et al., "In vitro transcribed guide RNAs trigger an innate immune response via the RIG-I pathway," BioRxiv Preprint, 2018, 1-28, 28 pages.
Witkowski, A., et al., "Conversion of a Beta-Ketoacyl Synthase to a Malonyl Decarboxylase by Replacement of the Active-Site Cysteine with Glutamine," Biochemistry, vol. 38, 1999, pp. 11643-11650, 8 pages.
Wittmann et al., "Engineered riboswitches: Expanding researchers' toolbox with synthetic RNA regulators", FEBS Letters, vol. 586, 2012, pp. 2076-2083, 8 pages.
Wolff, et al., "Nuclear security breached" Nature Biotechnology, Dec. 2001, vol. 19, 1118-1120, 3 pages.
Wu, X., et al., "Genome-wide binding of the CRISPR endonuclease Cas9 in mammalian cells," Nature Biotechnology, 2014, 1-7, 7 pages. Including Supplemental information, 2 pages.
Wu, Y., et al., "Correction of a Genetic Disease in Mouse via Use of CRISPR-Cas9," Cell Stem Cell, vol. 13, 2013, pp. 659-662, 4 pages.
Wu, Z., et al., "Effect of Genome Size on AAV Vector Packaging," The American Society of Gene & Cell Therapy, vol. 18, 2010, pp. 80-86, 7 pages.
X.Liu et al., "STAGA recruits Mediator to the MYC oncoprotein to stimulate transcription and cell proliferation," Molecular and cellular biology, vol. 28, Jan. 2008, p. 108-121, 14 pages.
Xiao, et al., "Chromosomal deletions and inversions mediated by TALENs and CRIPPR/Cas in zebrafish" Nucleic Acids Research, vol. 41, 2013, pp. 1-11, Including Supplemental information, 31 pages. doi:10.1093/nar/gkt464.
Xiao, et al., "Production of High-Titer Recombinant Adeno-Associated Virus Vectors in the Absence of Helper Adenovirus" Journal of Virology, Mar. 1998, vol. 72, No. 3, pp. 2224-2232, 9 pages.
Xiao, W., et al, "Gene Therapy Vectors Based on Adeno-Associated Virus Type 1", Journal of Virology, May 1999, vol. 73, No. 5, p. 3994-4003.
Xie, et al. "RNA-Guided Genome Editing in Plants Using a CRISPR-Cas System" Molecular Plant, vol. 6, Nov. 2013, 1975-1983, 9 pages.
Xu, Zhi-Li et al., "Regulated gene expression from adenovirus vectors: a systematic comparison of various inducible systems," Gene, vol. 309, 2003, pp. 145-151, 7 pages.
Yaghmai, et al., "Optimized Regulation of Gene Expression Using Artificial Transcription Factors", Molecular Therapy, Jun. 2002, vol. 5, No. 6, pp. 685-694.
Yamano, et al., "Crystal Structure of Cpf1 in Complex with Guide RNA and Target DNA" Cell, vol. 165, May 5, 2016, pp. 949-962, 14 pages.
Yanfang Fu et al., "Improving CRISPR-Cas nuclease specificity using truncated guide RNAs" (with Supplement Table), Nature Biotechnology, vol. 32, Mar. 2014, pp. 1-18.
Yang et al., "HIV-1 TAT-mediated protein transduction and subcellular localization using novel expression vectors," FEBS Letters, vol. 532, 2012, pp. 36-44, 9 pages.
Yang, H., et al., "One-Step Generation of Mice Carrying Reporter and Conditional Alleles by CRISPR/Cas-Mediated Genome Engi-

(56) References Cited

OTHER PUBLICATIONS neering," Cell, vol. 154, 2013, pp. 1370-1379, 10 pages. Including Supplemental information, 4 pages.

Yi, et al., "Current Advances in Retroviral Gene Therapy" Current Gene Therapy, vol. 11, 2011, pp. 218-228, 11 pages.

Yin, H., et al., "Structure-guided chemical modification of guide RNA enables potent non-viral in vivo genome editing," Nature Biotechnology, vol. 35, Dec. 2017, pp. 1-22.

Yu, et al., "An efficient recombination system for chromosome engineering in *Escherichia coli*" PNAS, 2000, vol. 97, pp. 5978-5983, 6 pages.

Yu, W., et al., "Nrl knockdown by AAV-delivered CRISPR/Cas9 prevents retinal degeneration in mice," Nature Communications, vol. 8, 2017, art. 14716, 15 pages.

Yu, Zhongshen, et al., "Highly Efficient Genome Modifications Mediated by CRISPR/Cas9 in *Drosophila*" Genetics, 2013, vol. 195 pp. 289-291, 3 pages.

Yusuke Miyazaki et al., Destabilizing Domains Derived from the Human Estrogen Receptor:, Journal of the American Chemical Society, vol. 134, Mar. 7, 2012, pp. 3942-3945, 4 pages.

Zahner, D. and Hakenbeck, R. "The *Streptococcus pneumoniae* beta-galactosidase is a surface protein," J. Bacteriology, vol. 182, Oct. 2000, pp. 5919-5921, 3 pages.

Zeng Y et al., "Both natural and designed micro RNAs can inhibit the expression of cognate mRNAs when expressed in human cells," Mol Cell., vol. 9, Jun. 2002, pp. 1327-1333, 7 pages.

Zetsche et al. "A split-Cas9 architecture for inducible genome editing and transcription modulation" Nature biotechnology, 2015, vol. 33, 139-142, 4 pages.

Zetsche et al., "Cpf1 is a single RNA-guided endonuclease of a class 2 CRISPR-Cas system", Cell, vol. 163, Oct. 22, 2015, pp. 759-771, 13 pages.

Zhang, "Processing-Independent CRISPR RNAs Limit Natural Transformation in Neisseria meningitidis", Molecular Cell, vol. 50, May 23, 2013 pp. 488-503.

Zhang, et al. "Optogenetic interrogation of neural circuits: technology for probing mammalian brain structures" Nat Protoc., 2010, 5(3):439-456, doi:10.1038/nprot.2009.226.

Zhang, et al., "Optimized CRISPR Design", MIT, XP055167487, Oct. 23, 2013, URL:http//crispr.mit.edu/about[retrieved on Feb. 5, 2015].

Zhang, et al., "Efficient construction of sequence-specific TAL effectors for modulating mammalian transcription" nature biotechnology, vol. 29, 2011, 149-154, 6 pages.

Zhang, F., PowerPoint Presentation: "Development and Applications of CRISPR-Cas9 for Genome Editing," Broad Institute/MIT, dated Sep. 9, 2015, 50 pages.

Zhang, L., et al., "Efficient Expression of CFTR Function with Adeno-Associated Virus Vectors that Carry Shortened CFTR Genes," Proceedings of the National Academy of Science USA, vol. 95, 1998, pp. 10158-10163, 6 pages.

Zhang, X. D., et al., "cSSMD: assessing collective activity for addressing off-target effects in genome-scale RNA interference screens," Bioinformatics, vol. 27, pp. 2775-2781, 2011, 7 pages.

Zhou, et al., "High-throughput screening of a CRISPR/Cas9 library for functional genomics in human cells," Nature, vol. 509, pp. 487-491, 5 pages.

Zhu, et al. "Crystal structure of Cmr2 suggests a nucleotide cyclase-related enzyme in type III CRISPR-Cas sytems" FEBS Letters, 2012, 939-945, 6 pages. Doi:10.1016/j.febslet2012.02.036.

Zolkiewska, et al., "ADAM Proteases:Ligand Processing and Modulation of the Notch Pathway" Cell Mol Life Sci, 2008, vol. 65 pp. 2056-2068, 13 pages.

Zuris, et al., "Cationic lipid-mediated delivery proteins enables efficient protein-based genome editing in vitro and in vivo", Nature Biotechnology, vol. 33, No. 1, Jan. 2015, pp. 73-80.

Zuris, et al., "Efficient Delivery of Genome-Editing Proteins In Vitro and In Vivo" Nature Biotechnology, vol. 33, No. 1, Jan. 2015, pp. 1-26.

Zuris, et al., Supplementary Information—"Cationic lipid-mediated delivery proteins enables efficient protein-based genome editing in vitro and in vivo" Nature Biotechnology, vol. 33, No. 1, Jan. 2015, pp. 1-49. doi:10.1038/nbt.3081.

Jinek et al., "RNA-programmed genome editing in human cells", eLife, vol. 2, 2013, DOI: 10.7554/eLife.00471 (9 pages).

Stoddard, "Homing endonuclease structure and function," Quarterly Reviews of Biophysics, Cambridge University Press, 2005 (pp. 1-47).

Voytas, Daniel F., "Plant genome engineering with sequence-specific nucleases," Annual Review of Plant Biology May 1, 2013, vol. 64 (pp. 327-350).

Wiles et al., "CRISPR-Cas9-medicated genome editing and guide RNA Design," Mammalian Genome, May 20, 2015, vol. 26, No. 9 (10 pages).

Workman et al., "A natural single-guide RNA repurposes Cas9 to autoregulate CRISPR-Cas expression," Cell Press, vol. 184, Feb. 4, 2021 (pp. 675-688).

Adhin et al.,"Complete nucleotide sequence of the group I RNA bacteriophage fr," Biochimica et Biophysica Acta, Elsevier, vol. 1050, 1990 pp. 104-109.

Anders et al., "Structural basis of PAM-dependent target DNA recognition by the Cas9 endonuclease," Nature, vol. 513, Sep. 25, 2014 pp. 569-573.

Anguela et al., "Robust ZFN-mediated genol ne editing in adult hemophilic mice", Blood, vol. 122, No. 19, Nov. 7, 2013, (pp. 3283-3287).

Bikard et al., "Exploiting CRISPR-Cas nucleases to produce sequence-specific antimicrobials", Nature Biotechnology, vol. 32, No. 11, Nov. 2014 (pp. 1146-1151).

Chapdelaine et al., "Meganucleases can restore the reading frame of a mutated dystrophin", Gene Therapy, vol. 17, 2010 (pp. 846-858).

Database UniPro Accession No. J7RUA5, 2012, [online] downloaded from https:/lwww.uniprot.org/uniprol/J7RUA5 on Mar. 23, 2021 (10 pages).

He et al., "Pollen fertility restoration by nuclear gene Fr in CMS common bean: an Fr linkage map and the mode of Fraction," Theor. Appl. Genet. vol. 90, 1995, pp. 1056-1062.

Hemphill et al., "Optical Control of CRISPR/Cas9 Gene Editing," Journal of the American Chemical Society, vol. 137, May 6, 2015 (9 pages).

Huang and Honkanen, "Molecular Cloning, Expression, and Characterization of a Novel Human Serine/Threonine Protein Phosphatase, PP7, That Is Homologous to '*Drosophila*' Retinal Degeneration C Gene Product (rdgC)*," The Journal of Biological Chemistry, vol. 273, No. 3, Iss. 16, 1998, pp. 1462-1468.

Koonin et al., "Diversity, classification and evolution of CRISPR-Cas systems", Current Opinion in Microbiology vol. 37, 2017 (pp. 67-78).

Sorek et al., "CRISPR-Mediated Adaptive Immune Systems in Bacteria and Archea", Annual Review of Biochemistry, vol. 82, 2013, (pp. 237-266).

Guilinger et al., "Fusion of catalytically inactive Cas9 to FokI nuclease improves the specificity of genome modification," Nature Biotechnology, vol. 32, No. 6, Jun. 2014 (pp. 577-582).

Slaymaker et al., "Rationally engineered Cas9 nucleases with improved specificity", Science, vol. 351, No. 6268, Jan. 1, 2016, pp. 84-88.

Taylor, G., "Introduction to phasing," Acta Crystallographica Section D Biological Crystallography, 2010, D66 (pp. 325-338).

Bhattacharya et al., "A simple genotyping method to detect small CRISPR-Cas9 induced indels by agarose gel electrophoresis," Scientific Reports, Mar. 14, 2019, vol. 9, No. 4437 (7 pages).

Cameron et al., "Mapping the genomic landscape of CRISPR-Cas9 cleavage," Nature Methods, Jun. 2017, vol. 14, No. 6 (pp. 600-606).

Finn et al., "A Single Administration of CRISPR/Cas9 Lipid Nanoparticles Achieves Robust and Persistent In Vivo Genome Editing," Cell Reports, Cell Press, 2018, vol. 22 (pp. 2227-2235).

Raveux et al., "Optimization of the production of knock-in alleles by CRISPR/Cas9 microinjection into the mouse zygote," Scientific Reports, Feb. 17, 2017, vol. 7, No. 42661 (11 pages).

(56) References Cited

OTHER PUBLICATIONS

Shapiro et al., "Increasing CRISPR Efficiency and Measuring Its Specificity in HSPCs Using a Clinically Relevant System," Molecular Therapy: Methods & Clinical Development, Jun. 12, 2020, vol. 17 (pp. 1097-1107).
U.S. Appl. No. 14/054,414, filed Oct. 15, 2013, Leith, Nancy J.
U.S. Appl. No. 14/104,837, filed Dec. 12, 2013, Poliakova-Georgan, Ekaterina.
U.S. Appl. No. 14/104,900, filed Dec. 12, 2013, Leith, Nancy J.
U.S. Appl. No. 14/104,977, filed Dec. 12, 2013, Holland, Paul J.
U.S. Appl. No. 14/104,990, filed Dec. 12, 2013, Leith, Nancy J.
U.S. Appl. No. 14/105,017, filed Dec. 12, 2013, Leith, Nancy J.
U.S. Appl. No. 14/105,031, filed Dec. 12, 2013, Leith, Nancy J.
U.S. Appl. No. 14/105,035, filed Dec. 12, 2013, Leith, Nancy J.
U.S. Appl. No. 14/183,429, filed Feb. 18, 2014, Leith, Nancy J.
U.S. Appl. No. 14/183,471, filed Feb. 18, 2014, Leith, Nancy J.
U.S. Appl. No. 14/183,486, filed Feb. 18, 2014, Leith, Nancy J.
U.S. Appl. No. 14/183,512, filed Feb. 18, 2014, Poliakova-Georgan, Ekaterina.
U.S. Appl. No. 14/222,930, filed Mar. 24, 2014, Leith, Nancy J.
U.S. Appl. No. 14/226,274, filed Mar. 26, 2014, Leith, Nancy J.
U.S. Appl. No. 14/256,912, filed Apr. 18, 2014, Leith, Nancy J.
U.S. Appl. No. 14/258,458, filed Apr. 22, 2014, Leith, Nancy J.
U.S. Appl. No. 14/259,420, filed Apr. 23, 2014, Leith, Nancy J.
U.S. Appl. No. 14/290,575, filed May 29, 2014, Whisenant, Ethan C.
U.S. Appl. No. 14/293,498, filed Jun. 2, 2014, Holland, Paul J.
U.S. Appl. No. 14/293,674, filed Jun. 2, 2014, Holland, Paul J.
U.S. Appl. No. 14/324,960, filed Jul. 7, 2014, Brown, Mindy G.
U.S. Appl. No. 14/463,253, filed Aug. 19, 2014, Zhang, Kaijiang.
U.S. Appl. No. 14/481,339, filed Sep. 9, 2014, Marvich, Maria.
U.S. Appl. No. 14/497,627, filed Sep. 26, 2014, Leith, Nancy J.
U.S. Appl. No. 14/523,799, filed Oct. 24, 2014, Leith, Nancy J.
U.S. Appl. No. 14/681,382, filed Apr. 8, 2015, Leith, Nancy J.
U.S. Appl. No. 14/703,511, filed May 4, 2015, Leith, Nancy J.
U.S. Appl. No. 14/704,551, filed May 5, 2015, Leonard, Arthur S.
U.S. Appl. No. 14/738,398, filed Jun. 12, 2015, Ramirez, Delia M.
U.S. Appl. No. 14/738,483, filed Jun. 12, 2015, Woitach, Joseph T.
U.S. Appl. No. 14/970,967, filed Dec. 16, 2015, Leith, Nancy J.
U.S. Appl. No. 14/971,169, filed Dec. 16, 2015, Aron, Kimberly A.
U.S. Appl. No. 14/971,356, filed Dec. 16, 2015, Noble, Marcia Stephens.
U.S. Appl. No. 14/972,523, filed Dec. 17, 2015, Montanari, David A.
U.S. Appl. No. 14/972,927, filed Dec. 17, 2015, Leonard, Arthur S.
U.S. Appl. No. 14/973,062, filed Dec. 17, 2015, Leith, Nancy J.
U.S. Appl. No. 14/990,444, filed Jan. 7, 2016, Leith, Nancy J.
U.S. Appl. No. 14/991,083, filed Jan. 8, 2016, Leith, Nancy J.
U.S. Appl. No. 15/160,710, filed May 20, 2016, Leith, Nancy J.
U.S. Appl. No. 15/217,489, filed Jul. 22, 2016, Brown, Mindy G.
U.S. Appl. No. 15/229,702, filed Aug. 5, 2016, Leith, Nancy J.
U.S. Appl. No. 15/230,161, filed Aug. 5, 2016, Leith, Nancy J.
U.S. Appl. No. 15/230,025, filed Aug. 5, 2016, Leith, Nancy J.
U.S. Appl. No. 15/330,876, filed Nov. 7, 2016, Holland, Paul J.
U.S. Appl. No. 15/349,603, filed Nov. 11, 2016, Marvich, Maria.
U.S. Appl. No. 15/430,260, filed Feb. 10, 2017, Leith, Nancy J.
U.S. Appl. No. 15/834,736, filed Dec. 7, 2017, Not Assigned.
U.S. Appl. No. 15/838,064, filed Dec. 11, 2017, Leith, Nancy J.
U.S. Appl. No. 15/887,377, filed Feb. 2, 2018, Leith, Nancy J.
U.S. Appl. No. 15/967,464, filed Apr. 30, 2018, Leith, Nancy J.
U.S. Appl. No. 15/967,495, filed Apr. 30, 2018, Leith, Nancy J.
U.S. Appl. No. 15/967,510, filed Apr. 30, 2018, Leith, Nancy J.
U.S. Appl. No. 16/012,692, filed Jun. 19, 2018, Leith, Nancy J.
U.S. Appl. No. 16/177,403, filed Oct. 31, 2018, Leith, Nancy J.
U.S. Appl. No. 16/178,551, filed Nov. 1, 2018, Leith, Nancy J.
U.S. Appl. No. 16/445,150, filed Jun. 18, 2019, Leith, Nancy J.
U.S. Appl. No. 16/445,156, filed Jun. 18, 2019, Leith, Nancy J.
U.S. Appl. No. 16/525,531, filed Jul. 29, 2019, Zhang, Kaijiang.
U.S. Appl. No. 16/532,442, filed Aug. 5, 2019, To Be Assigned.
U.S. Appl. No. 16/535,043, filed Aug. 7, 2019, To Be Assigned.
U.S. Appl. No. 16/800,988, filed Feb. 25, 2020, To Be Assigned.
U.S. Appl. No. 16/906,580, filed Jun. 19, 2020, To Be Assigned.
U.S. Appl. No. 16/938,110, filed Jul. 24, 2020, To Be Assigned.
U.S. Appl. No. 17/027,151, filed Sep. 21, 2020, To Be Assigned.
U.S. Appl. No. 17/034,754, filed Sep. 28, 2020, To Be Assigned.
U.S. Appl. No. 17/182,817, filed Feb. 23, 2021, To Be Assigned.
U.S. Appl. No. 17/201,347, filed Mar. 15, 2021, To Be Assigned.
U.S. Appl. No. 17/245,952, filed Apr. 30, 2021, To Be Assigned.
U.S. Appl. No. 17/321,872, filed May 17, 2021, To Be Assigned.
U.S. Appl. No. 17/503,928, filed Oct. 18, 2021, To Be Assigned.

FIG. 4A

FIG. 4D hSpCas9

```
5' CTGGAAGAGTCCTTCCTGGTGGAAGAGGATAAGAAGCACGAGCGGCACCCCATCTTCGGC
                                                                    360
            hSpCas9
    L   E   E   S   F   L   V   E   E   D   K   K   H   E   R   H   P   I   F   G
   101 102 103 104 105 106 107 108 109 110 111 112 113 114 115 116 117 118 119 120

5' AACATCGTGGACGAGGTGGCCTACCACGAGAAGTACCCCACCATCTACCACCTGAGAAAG
                                                                    420
            hSpCas9
    N   I   V   D   E   V   A   Y   H   E   K   Y   P   T   I   Y   H   L   R   K
   121 122 123 124 125 126 127 128 129 130 131 132 133 134 135 136 137 138 139 140

5' AAACTGGTGGACAGCACCGACAAGGCCGACCTGCGGCTGATCTATCTGGCCCTGGCCCAC
                                                                    480
            hSpCas9
    K   L   V   D   S   T   D   K   A   D   L   R   L   I   Y   L   A   L   A   H
   141 142 143 144 145 146 147 148 149 150 151 152 153 154 155 156 157 158 159 160

5' ATGATCAAGTTCCGGGGCCACTTCCTGATCGAGGGCGACCTGAACCCCGACAACAGCGAC
                                                                    540
            hSpCas9
    M   I   K   F   R   G   H   F   L   I   E   G   D   L   N   P   D   N   S   D
   161 162 163 164 165 166 167 168 169 170 171 172 173 174 175 176 177 178 179 180

5' GTGGACAAGCTGTTCATCCAGCTGGTGCAGACCTACAACCAGCTGTTCGAGGAAAACCCC
                                                                    600
            hSpCas9
    V   D   K   L   F   I   Q   L   V   Q   T   Y   N   Q   L   F   E   E   N   P
   181 182 183 184 185 186 187 188 189 190 191 192 193 194 195 196 197 198 199 200

5' ATCAACGCCAGCGGCGTGGACGCCAAGGCCATCCTGTCTGCCAGACTGAGCAAGAGCAGA
                                                                    660
            hSpCas9
    I   N   A   S   G   V   D   A   K   A   I   L   S   A   R   L   S   K   S   R
   201 202 203 204 205 206 207 208 209 210 211 212 213 214 215 216 217 218 219 220
```

FIG. 6B hSpCas9

```
5'  CGGCTGGAAAATCTGATCGCCCAGCTGCCCGGCGAGAAGAAGAATGGCCTGTTCGGCAAC  720
                              hSpCas9
    R   L   E   N   L   I   A   Q   L   P   G   E   K   K   N   G   L   F   G   N
    221 222 223 224 225 226 227 228 229 230 231 232 233 234 235 236 237 238 239 240

5'  CTGATTGCCCTGAGCCTGGGCCTGACCCCCAACTTCAAGAGCAACTTCGACCTGGCCGAG  780
                              hSpCas9
    L   I   A   L   S   L   G   L   T   P   N   F   K   S   N   F   D   L   A   E
    241 242 243 244 245 246 247 248 249 250 251 252 253 254 255 256 257 258 259 260

5'  GATGCCAAACTGCAGCTGAGCAAGGACACCTACGACGACGACCTGGACAACCTGCTGGCC  840
                              hSpCas9
    D   A   K   L   Q   L   S   K   D   T   Y   D   D   D   L   D   N   L   L   A
    261 262 263 264 265 266 267 268 269 270 271 272 273 274 275 276 277 278 279 280

5'  CAGATCGGCGACCAGTACGCCGACCTGTTTCTGGCCGCCAAGAACCTGTCCGACGCCATC  900
                              hSpCas9
    Q   I   G   D   Q   Y   A   D   L   F   L   A   A   K   N   L   S   D   A   I
    281 282 283 284 285 286 287 288 289 290 291 292 293 294 295 296 297 298 299 300

5'  CTGCTGAGCGACATCCTGAGAGTGAACACCGAGATCACCAAGGCCCCCCTGAGCGCCTCT  960
                              hSpCas9
    L   L   S   D   I   L   R   V   N   T   E   I   T   K   A   P   L   S   A   S
    301 302 303 304 305 306 307 308 309 310 311 312 313 314 315 316 317 318 319 320

5'  ATGATCAAGAGATACGACGAGCACCACCAGGACCTGACCCTGCTGAAAGCTCTCGTGCGG  1020
                              hSpCas9
    M   I   K   R   Y   D   E   H   H   Q   D   L   T   L   L   K   A   L   V   R
    321 322 323 324 325 326 327 328 329 330 331 332 333 334 335 336 337 338 339 340
```

FIG. 6C hSpCas9

5' CAGCAGCTGCCTGAGAAGTACAAAGAGATTTTCTTCGACCAGAGCAAGAACGGCTACGCC 1080
Q Q L P E K Y K E I F F D Q S K N G Y A
341 342 343 344 345 346 347 348 349 350 351 352 353 354 355 356 357 358 359 360

5' GGCTACATTGACGGCGGAGCCAGCCAGGAAGAGTTCTACAAGTTCATCAAGCCCATCCTG 1140
G Y I D G G A S Q E E F Y K F I K P I L
361 362 363 364 365 366 367 368 369 370 371 372 373 374 375 376 377 378 379 380

5' GAAAAGATGGACGGCACCGAGGAACTGCTCGTGAAGCTGAACAGAGAGGACCTGCTGCGG 1200
E K M D G T E E L L V K L N R E D L L R
381 382 383 384 385 386 387 388 389 390 391 392 393 394 395 396 397 398 399 400

5' AAGCAGCGGACCTTCGACAACGGCAGCATCCCCCACCAGATCCACCTGGGAGAGCTGCAC 1260
K Q R T F D N G S I P H Q I H L G E L H
401 402 403 404 405 406 407 408 409 410 411 412 413 414 415 416 417 418 419 420

5' GCCATTCTGCGGCGGCAGGAAGATTTTTACCCATTCCTGAAGGACAACCGGGAAAAGATC 1320
A I L R R Q E D F Y P F L K D N R E K I
421 422 423 424 425 426 427 428 429 430 431 432 433 434 435 436 437 438 439 440

5' GAGAAGATCCTGACCTTCCGCATCCCCTACTACGTGGGCCCTCTGGCCAGGGGAAACAGC 1380
E K I L T F R I P Y Y V G P L A R G N S
441 442 443 444 445 446 447 448 449 450 451 452 453 454 455 456 457 458 459 460

FIG. 6D

```
hSpCas9
5' AGATTCGCCTGGATGACCAGAAAGAGCGAGGAAACCATCACCCCCTGGAACTTCGAGGAA
                                                                    1440
    R  F  A  W  M  T  R  K  S  E  E  T  I  T  P  W  N  F  E  E
   461 462 463 464 465 466 467 468 469 470 471 472 473 474 475 476 477 478 479 480

5' GTGGTGGACAAGGGCGCTTCCGCCCAGAGCTTCATCGAGCGGATGACCAACTTCGATAAG
                                                                    1500
    V  V  D  K  G  A  S  A  Q  S  F  I  E  R  M  T  N  F  D  K
   481 482 483 484 485 486 487 488 489 490 491 492 493 494 495 496 497 498 499 500

5' AACCTGCCCAACGAGAAGGTGCTGCCCAAGCACAGCCTGCTGTACGAGTACTTCACCGTG
                                                                    1560
    N  L  P  N  E  K  V  L  P  K  H  S  L  L  Y  E  Y  F  T  V
   501 502 503 504 505 506 507 508 509 510 511 512 513 514 515 516 517 518 519 520

5' TATAACGAGCTGACCAAAGTGAAATACGTGACCGAGGGAATGAGAAAGCCCGCCTTCCTG
                                                                    1620
    Y  N  E  L  T  K  V  K  Y  V  T  E  G  M  R  K  P  A  F  L
   521 522 523 524 525 526 527 528 529 530 531 532 533 534 535 536 537 538 539 540

5' AGCGGCGAGCAGAAAAAGGCCATCGTGGACCTGCTGTTCAAGACCAACCGGAAAGTGACC
                                                                    1680
    S  G  E  Q  K  K  A  I  V  D  L  L  F  K  T  N  R  K  V  T
   541 542 543 544 545 546 547 548 549 550 551 552 553 554 555 556 557 558 559 560

5' GTGAAGCAGCTGAAAGAGGACTACTTCAAGAAAATCGAGTGCTTCGACTCCGTGGAAATC
                                                                    1740
    V  K  Q  L  K  E  D  Y  F  K  K  I  E  C  F  D  S  V  E  I
   561 562 563 564 565 566 567 568 569 570 571 572 573 574 575 576 577 578 579 580
```

FIG. 6E

```
hSpCas9
5'  TCCGGCGTGGAAGATCGGTTCAACGCCTCCCTGGGCACATACCACGATCTGCTGAAAATT
                                                                            1800
                            hSpCas9
     S   G   V   E   D   R   F   N   A   S   L   G   T   Y   H   D   L   L   K   I
     581 582 583 584 585 586 587 588 589 590 591 592 593 594 595 596 597 598 599 600

5'  ATCAAGGACAAGGACTTCCTGGACAATGAGGAAAACGAGGACATTCTGGAAGATATCGTG
                                                                            1860
                            hSpCas9
     I   K   D   K   D   F   L   D   N   E   E   N   E   D   I   L   E   D   I   V
     601 602 603 604 605 606 607 608 609 610 611 612 613 614 615 616 617 618 619 620

5'  CTGACCCTGACACTGTTTGAGGACAGAGAGATGATCGAGGAACGGCTGAAAACCTATGCC
                                                                            1920
                            hSpCas9
     L   T   L   T   L   F   E   D   R   E   M   I   E   E   R   L   K   T   Y   A
     621 622 623 624 625 626 627 628 629 630 631 632 633 634 635 636 637 638 639 640

5'  CACCTGTTCGACGACAAAGTGATGAAGCAGCTGAAGCGGCGGAGATACACCGGCTGGGGC
                                                                            1980
                            hSpCas9
     H   L   F   D   D   K   V   M   K   Q   L   K   R   R   R   Y   T   G   W   G
     641 642 643 644 645 646 647 648 649 650 651 652 653 654 655 656 657 658 659 660

5'  AGGCTGAGCCGGAAGCTGATCAACGGCATCCGGGACAAGCAGTCCGGCAAGACAATCCTG
                                                                            2040
                            hSpCas9
     R   L   S   R   K   L   I   N   G   I   R   D   K   Q   S   G   K   T   I   L
     661 662 663 664 665 666 667 668 669 670 671 672 673 674 675 676 677 678 679 680

5'  GATTTCCTGAAGTCCGACGGCTTCGCCAACAGAAACTTCATGCAGCTGATCCACGACGAC
                                                                            2100
                            hSpCas9
     D   F   L   K   S   D   G   F   A   N   R   N   F   M   Q   L   I   H   D   D
     681 682 683 684 685 686 687 688 689 690 691 692 693 694 695 696 697 698 699 700
```

FIG. 6F hSpCas9

```
5'  AGCCTGACCTTTAAAGAGGACATCCAGAAAGCCCAGGTGTCCGGCCAGGGCGATAGCCTG
                                                                    2160
    hSpCas9
    S   L   T   F   K   E   D   I   Q   K   A   Q   V   S   G   Q   G   D   S   L
    701 702 703 704 705 706 707 708 709 710 711 712 713 714 715 716 717 718 719 720

5'  CACGAGCACATTGCCAATCTGGCCGGCAGCCCCGCCATTAAGAAGGGCATCCTGCAGACA
                                                                    2220
    hSpCas9
    H   E   H   I   A   N   L   A   G   S   P   A   I   K   K   G   I   L   Q   T
    721 722 723 724 725 726 727 728 729 730 731 732 733 734 735 736 737 738 739 740

5'  GTGAAGGTGGTGGACGAGCTCGTGAAAGTGATGGGCCGGCACAAGCCCGAGAACATCGTG
                                                                    2280
    hSpCas9
                                                              RuvC II
    V   K   V   V   D   E   L   V   K   V   M   G   R   H   K   P   E   N   I   V
    741 742 743 744 745 746 747 748 749 750 751 752 753 754 755 756 757 758 759 760

5'  ATCGCCATGGCCAGAGAGAACCAGACCACCCAGAAGGGACAGAAGAACAGCCGCGAGAGA
                                                                    2340
    hSpCas9
        RuvC II
    E
    I   A   M   A   R   E   N   Q   T   T   Q   K   G   Q   K   N   S   R   E   R
    761 762 763 764 765 766 767 768 769 770 771 772 773 774 775 776 777 778 779 780

5'  ATGAAGCGGATCGAAGAGGGCATCAAAGAGCTGGGCAGCCAGATCCTGAAAGAACACCCC
                                                                    2400
    hSpCas9
    M   K   R   I   E   E   G   I   K   E   L   G   S   Q   I   L   K   E   H   P
    781 782 783 784 785 786 787 788 789 790 791 792 793 794 795 796 797 798 799 800
```

```
hSpCas9
5'  TACCCTAAGCTGGAAAGCGAGTTCGTGTACGGCGACTACAAGGTGTACGACGTGCGGAAG
                                                                              3060
    [hSpCas9]
     Y   P   K   L   E   S   E   F   V   Y   G   D   Y   K   V   Y   D   V   R   K
    1001 1002 1003 1004 1005 1006 1007 1008 1009 1010 1011 1012 1013 1014 1015 1016 1017 1018 1019 1020

5'  ATGATCGCCAAGAGCGAGCAGGAAATCGGCAAGGCTACCGCCAAGTACTTCTTCTACAGC
                                                                              3120
    [hSpCas9]
     M   I   A   K   S   E   Q   E   I   G   K   A   T   A   K   Y   F   F   Y   S
    1021 1022 1023 1024 1025 1026 1027 1028 1029 1030 1031 1032 1033 1034 1035 1036 1037 1038 1039 1040

5'  AACATCATGAACTTTTTCAAGACCGAGATTACCCTGGCCAACGGCGAGATCCGGAAGCGG
                                                                              3180
    [hSpCas9]
     N   I   M   N   F   F   K   T   E   I   T   L   A   N   G   E   I   R   K   R
    1041 1042 1043 1044 1045 1046 1047 1048 1049 1050 1051 1052 1053 1054 1055 1056 1057 1058 1059 1060

5'  CCTCTGATCGAGACAAACGGCGAAACCGGGGAGATCGTGTGGGATAAGGGCCGGGATTTT
                                                                              3240
    [hSpCas9]
     P   L   I   E   T   N   G   E   T   G   E   I   V   W   D   K   G   R   D   F
    1061 1062 1063 1064 1065 1066 1067 1068 1069 1070 1071 1072 1073 1074 1075 1076 1077 1078 1079 1080

5'  GCCACCGTGCGGAAAGTGCTGAGCATGCCCCAAGTGAATATCGTGAAAAAGACCGAGGTG
                                                                              3300
    [hSpCas9]
     A   T   V   R   K   V   L   S   M   P   Q   V   N   I   V   K   K   T   E   V
    1081 1082 1083 1084 1085 1086 1087 1088 1089 1090 1091 1092 1093 1094 1095 1096 1097 1098 1099 1100

5'  CAGACAGGCGGCTTCAGCAAAGAGTCTATCCTGCCCAAGAGGAACAGCGATAAGCTGATC
                                                                              3360
    [hSpCas9]
     Q   T   G   G   F   S   K   E   S   I   L   P   K   R   N   S   D   K   L   I
    1101 1102 1103 1104 1105 1106 1107 1108 1109 1110 1111 1112 1113 1114 1115 1116 1117 1118 1119 1120
```

FIG. 6J

```
hSpCas9
5'  GCCAGAAAGAAGGACTGGGACCCTAAGAAGTACGGCGGCTTCGACAGCCCCACCGTGGCC
                                                                              3420
         A  R  K  K  D  W  D  P  K  K  Y  G  G  F  D  S  P  T  V  A
        1121 1122 1123 1124 1125 1126 1127 1128 1129 1130 1131 1132 1133 1134 1135 1136 1137 1138 1139 1140

5'  TATTCTGTGCTGGTGGTGGCCAAAGTGGAAAAGGGCAAGTCCAAGAAACTGAAGAGTGTG
                                                                              3480
         Y  S  V  L  V  V  A  K  V  E  K  G  K  S  K  K  L  K  S  V
        1141 1142 1143 1144 1145 1146 1147 1148 1149 1150 1151 1152 1153 1154 1155 1156 1157 1158 1159 1160

5'  AAAGAGCTGCTGGGGATCACCATCATGGAAAGAAGCAGCTTCGAGAAGAATCCCATCGAC
                                                                              3540
         K  E  L  L  G  I  T  I  M  E  R  S  S  F  E  K  N  P  I  D
        1161 1162 1163 1164 1165 1166 1167 1168 1169 1170 1171 1172 1173 1174 1175 1176 1177 1178 1179 1180

5'  TTTCTGGAAGCCAAGGGCTACAAAGAAGTGAAAAAGGACCTGATCATCAAGCTGCCTAAG
                                                                              3600
         F  L  E  A  K  G  Y  K  E  V  K  K  D  L  I  I  K  L  P  K
        1181 1182 1183 1184 1185 1186 1187 1188 1189 1190 1191 1192 1193 1194 1195 1196 1197 1198 1199 1200

5'  TACTCCCTGTTCGAGCTGGAAAACGGCCGGAAGAGAATGCTGGCCTCTGCCGGCGAACTG
                                                                              3660
         Y  S  L  F  E  L  E  N  G  R  K  R  M  L  A  S  A  G  E  L
        1201 1202 1203 1204 1205 1206 1207 1208 1209 1210 1211 1212 1213 1214 1215 1216 1217 1218 1219 1220

5'  CAGAAGGGAAACGAACTGGCCCTGCCCTCCAAATATGTGAACTTCCTGTACCTGGCCAGC
                                                                              3720
         Q  K  G  N  E  L  A  L  P  S  K  Y  V  N  F  L  Y  L  A  S
        1221 1222 1223 1224 1225 1226 1227 1228 1229 1230 1231 1232 1233 1234 1235 1236 1237 1238 1239 1240
```

FIG. 6K hSpCas9

```
5' CACTATGAGAAGCTGAAGGGCTCCCCCGAGGATAATGAGCAGAAACAGCTGTTTGTGGAA
                                                                    3780
         hSpCas9
    H   Y   E   K   L   K   G   S   P   E   D   N   E   Q   K   Q   L   F   V   E
   1241 1242 1243 1244 1245 1246 1247 1248 1249 1250 1251 1252 1253 1254 1255 1256 1257 1258 1259 1260

5' CAGCACAAGCACTACCTGGACGAGATCATCGAGCAGATCAGCGAGTTCTCCAAGAGAGTG
                                                                    3840
         hSpCas9
    Q   H   K   H   Y   L   D   E   I   I   E   Q   I   S   E   F   S   K   R   V
   1261 1262 1263 1264 1265 1266 1267 1268 1269 1270 1271 1272 1273 1274 1275 1276 1277 1278 1279 1280

5' ATCCTGGCCGACGCTAATCTGGACAAAGTGCTGTCCGCCTACAACAAGCACCGGGATAAG
                                                                    3900
         hSpCas9
    I   L   A   D   A   N   L   D   K   V   L   S   A   Y   N   K   H   R   D   K
   1281 1282 1283 1284 1285 1286 1287 1288 1289 1290 1291 1292 1293 1294 1295 1296 1297 1298 1299 1300

5' CCCATCAGAGAGCAGGCCGAGAATATCATCCACCTGTTTACCCTGACCAATCTGGGAGCC
                                                                    3960
         hSpCas9
    P   I   R   E   Q   A   E   N   I   I   H   L   F   T   L   T   N   L   G   A
   1301 1302 1303 1304 1305 1306 1307 1308 1309 1310 1311 1312 1313 1314 1315 1316 1317 1318 1319 1320

5' CCTGCCGCCTTCAAGTACTTTGACACCACCATCGACCGGAAGAGGTACACCAGCACCAAA
                                                                    4020
         hSpCas9
    P   A   A   F   K   Y   F   D   T   T   I   D   R   K   R   Y   T   S   T   K
   1321 1322 1323 1324 1325 1326 1327 1328 1329 1330 1331 1332 1333 1334 1335 1336 1337 1338 1339 1340

5' GAGGTGCTGGACGCCACCCTGATCCACCAGAGCATCACCGGCCTGTACGAGACACGGATC
                                                                    4080
         hSpCas9
    E   V   L   D   A   T   L   I   H   Q   S   I   T   G   L   Y   E   T   R   I
   1341 1342 1343 1344 1345 1346 1347 1348 1349 1350 1351 1352 1353 1354 1355 1356 1357 1358 1359 1360
```

FIG. 6L

Cas9, Rosa26 targeting vector map

Cas9, Rosa26 targeting vector map

Cas9 Expression in Mouse Hippocampus (AAV)
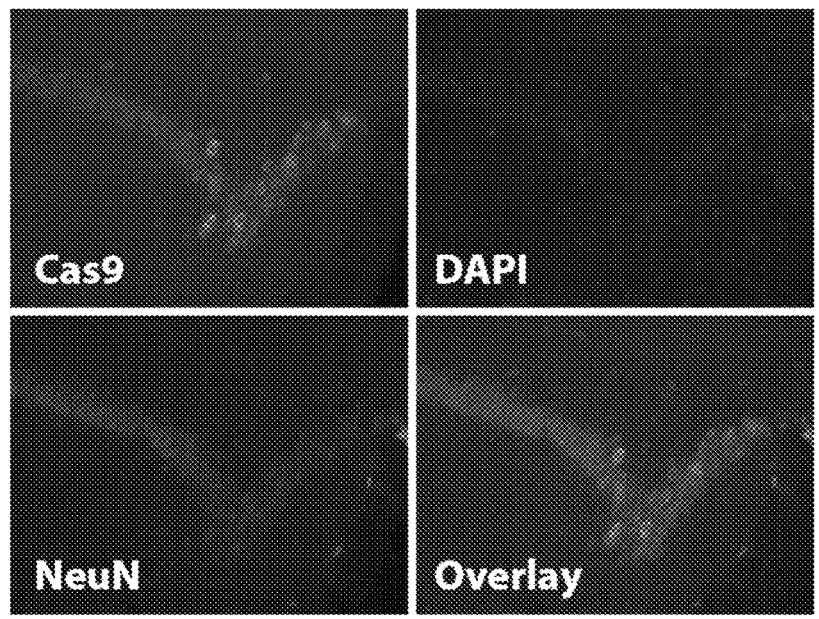
Cas9 Expression in Mouse Cortex (AAV)
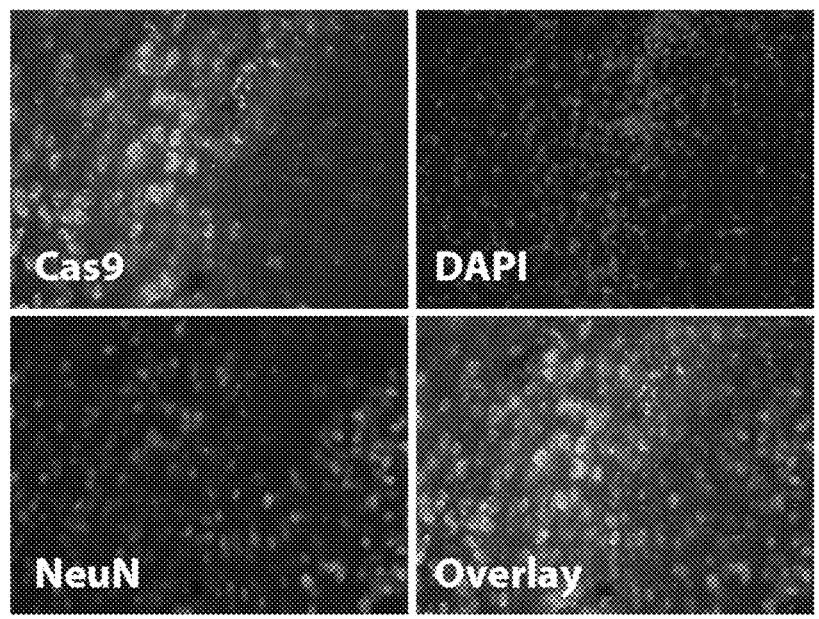
FIG. 9

Repair Strategy for Cystic Fibrosis deltaF508 Mutation

FIG 13A

```
                          CFTR gene
    G  T  I  K  E  N  I  I  G  V  S  Y  D  E  Y  R  Y  R  S
    500 501 502 503 504 505 506 507 509 510 511 512 513 514 515 516 517 518 519
1. human CFTR    GGCACCATTAAAGAAAATATCATTGGTGTTTCCTATGATGAATATAGATACAGAAGC
   genomic      +++++++++++++++++++++++++++++++++++++++++++++++++++++++++
   locus         CCGTGGTAATTTCTTTTATAGTAACCACAAAGGATACTACTTATATCTATGTCTTCG
                           Cas9 Target Site
```

FIG 13B

```
              5'- NNNNNNNNNNNNNNNNNNNNNNNGUUUUAGAGCUAG
                                         *|||||* ||||  A
2. human      GUUCAACUAUUGCCUGAUCGGAAUAAAAUU  CGAUA  A
   CFTRdeltaF508  A                              GAA
   targeting    A ||||
   chimeric guide  AAAGUGGCACCGA
   RNA              *|||||||G
              3'- UUUCGUGGCU
```

FIG 13C

```
                                    F508
              ...ATTAAAGAAAATATCATTGGCTTTGTTTCCTATGATGAATATAGATAC...
              +++++++++++++++++++++++++++++++++++++++++++++++++++
3. repair     ...TAATTTCTTTTATAGTAACCGAAACAAAGGATACTACTTATATCTATG...
   template                           repair template
   for deltaF508
   mutation
                I  K  E  N  I  I  G  F  V  S  Y  D  E  Y  R  Y
                502 503 504 505 506 507 508 509 510 511 512 513 514 515 516 517
```

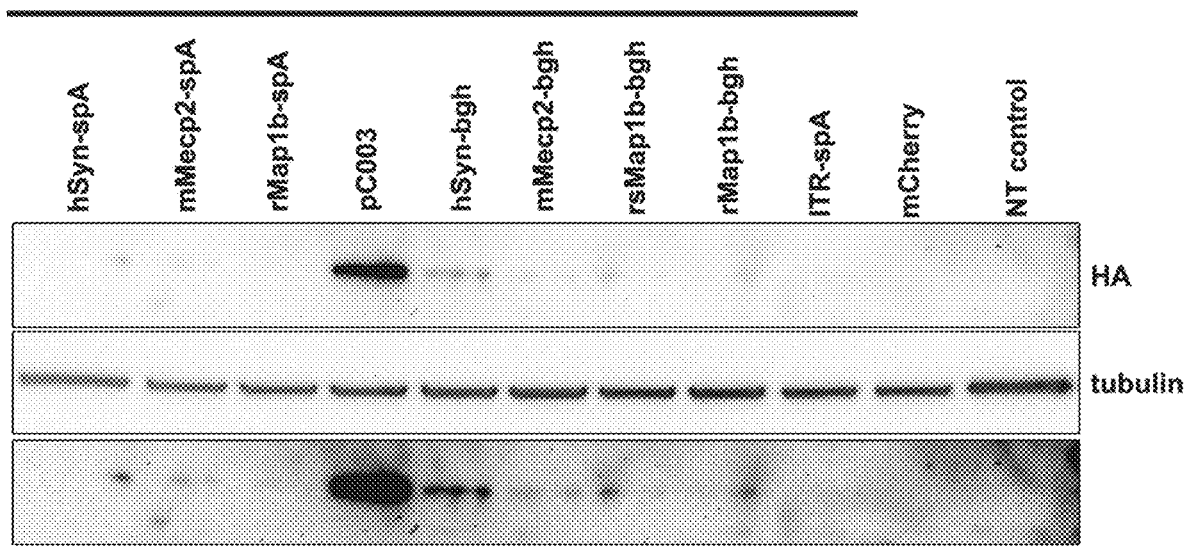
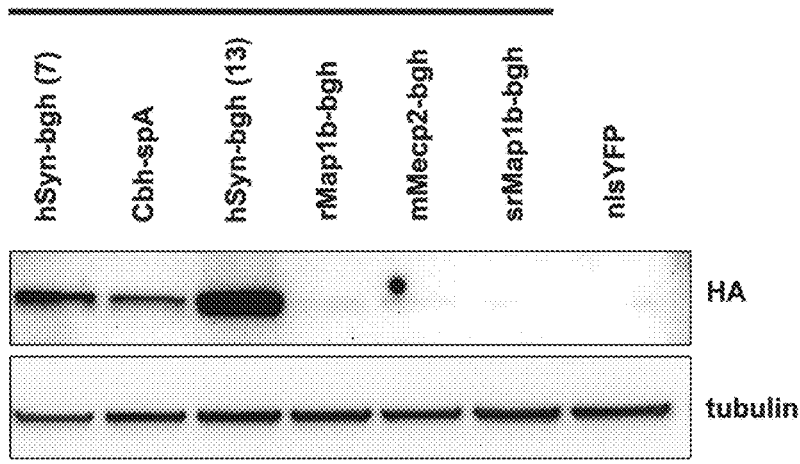
FIG. 24

FIG. 34

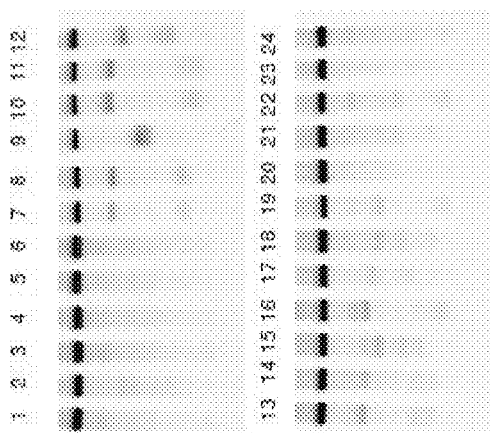

| lane # | Cas9 to use | Left gRNA | Right gRNA | Overhang (D10A) number of bases protruding from 5' |
|---|---|---|---|---|
| 1 | D10A | left 23 | left 12 | -36 |
| 2 | D10A | right 4 | left 9 | -25 |
| 3 | D10A | left 23 | right 23 | -16 |
| 4 | D10A | right 7 | left 10 | -15 |
| 5 | D10A | right 16 | left 3 | -8 |
| 6 | D10A | right 22 | right 6 | 26 |
| 7 | D10A | left 12 | right 15 | 31 |
| 8 | D10A | left 12 | right 13 | 34 |
| 9 | D10A | left 10 | right 1 | 38 |
| 10 | D10A | right 23 | right 15 | 51 |
| 11 | D10A | right 23 | right 13 | 54 |
| 12 | D10A | left 3 | right 7 | 57 |
| 13 | D10A | left 12 | right 4 | 65 |
| 14 | D10A | left 12 | right 3 | 69 |
| 15 | D10A | left 3 | right 10 | 76 |
| 16 | D10A | right 23 | right 4 | 85 |
| 17 | D10A | left 12 | right 9 | 95 |
| 18 | D10A | left 12 | right 10 | 115 |
| 19 | D10A | right 23 | right 10 | 135 |
| 20 | D10A | left 12 | right 2 | 145 |
| 21 | D10A | left 12 | left 22 | 181 |
| 22 | D10A | right 23 | left 22 | 201 |
| 23 | D10A | left 12 | right 6 | 222 |
| 24 | D10A | right 23 | right 6 | 242 |

FIG. 36

| Gene | Overhang Length (bp) | Overhang Type | Offset Length (bp) | Left sgRNA ID | Right sgRNA ID | Cas9n with left and right sgRNA indel (%) | left sgRNA target site guide sequence (5' to 3') | PAM | left sgRNA with wildtype Cas9 indel (%) | right sgRNA target site guide sequence (5' to 3') | PAM | right sgRNA with wildtype Cas9 indel (%) |
|---|---|---|---|---|---|---|---|---|---|---|---|---|
| EMX1 | 148 | 3' | -182 | 15 | 4 | N.D. | TGCGCCACCGGTTGATGTGA | TGG | 13.15 | AGGCCCCAGTGGCTGCTCTG | GGG | 27.29 |
| EMX1 | 101 | 3' | -135 | 23 | 1 | N.D. | ACTCTGCCCTCGTGGGTTTG | TGG | 24.7 | GAGTCCGAGCAGAAGAAGAA | TGG | 21.9 |
| EMX1 | 48 | 3' | -82 | 23 | 17 | N.D. | ACTCTGCCCTCGTGGGTTTG | TGG | 24.7 | CACGAAGCAGGCCAATGGGG | AGG | 13.57 |
| EMX1 | 25 | 3' | -59 | 10 | 13 | N.D. | CAAACGGCAGAAGCTGGAGG | AGG | 26.15 | GGAGCCCTTCTTCTTCTGCT | CGG | 33.17 |
| EMX1 | 15 | 3' | -49 | 4 | 5 | N.D. | AGGCCCCAGTGGCTGCTCTG | GGG | 27.29 | GGGGCACAGATGAGAAACTC | AGG | 26.56 |
| EMX1 | 8 | 3' | -42 | 7 | 9 | N.D. | TGAAGGTGTGGTTCCAGAAC | CGG | 36.02 | GCCGTTTGTACTTTGTCCTC | CGG | 30.49 |
| EMX1 | 26 | 5' | -8 | 9 | 19 | 13.7 ± 1.27 | GCCGTTTGTACTTTGTCCTC | CGG | 9.82 | GGCAGAGTGCTGCTTGCTGC | TGG | 26.15 |
| EMX1 | 30 | 5' | -4 | 9 | 10 | 19.72 ± 0.32 | GCCGTTTGTACTTTGTCCTC | CGG | 30.49 | CAAACGGCAGAAGCTGGAGG | AGG | 22.06 |
| EMX1 | 31 | 5' | -3 | 6 | 7 | 21.35 ± 2.23 | TCACCTGGGCCAGGGAGGGA | GGG | 10.75 | TGAAGGTGTGGTTCCAGAAC | CGG | 35.02 |
| EMX1 | 34 | 5' | 0 | 15 | 16 | 26.89 ± 1.54 | TGCGCCACCGGTTGATGTGA | TGG | 13.15 | TTGCCACAGAAGCAGGCCAAT | AGG | 13.77 |
| EMX1 | 38 | 5' | 4 | 15 | 17 | 36.31 ± 2.97 | TGCGCCACCGGTTGATGTGA | TGG | 14.49 | CACGAAGCAGGCCAATGGGG | AGG | 13.57 |
| EMX1 | 51 | 5' | 17 | 5 | 7 | 31.12 ± 0.25 | GGGGCACAGATGAGAAACTC | ACTC | 26.56 | TGAAGGTGTGGTTCCAGAAC | CGG | 36.02 |
| EMX1 | 54 | 5' | 20 | 5 | 8 | 32.41 ± 3.68 | GGGGCACAGATGAGAAACTC | ACTC | 26.56 | AGGTGTGGTTCCAGAAACGG | CGG | 35.53 |
| EMX1 | 65 | 5' | 31 | 6 | 10 | 13.45 ± 1.99 | TCACCTGGGCCAGGGAGGGGA | GGA | 10.75 | CAAACGGCAGAAGCTGGAGG | AGG | 26.15 |

FIG. 44A

| Gene | Overhang Length (bp) | Overhang Type | Offset Length (bp) | Left sgRNA ID | Right sgRNA ID | Cas9n with left and right sgRNA indel (%) | left sgRNA target site guide sequence (5' to 3') | PAM | left sgRNA with wildtype Cas9 indel (%) | right sgRNA target site guide sequence (5' to 3') | PAM | right sgRNA with wildtype Cas9 indel (%) |
|---|---|---|---|---|---|---|---|---|---|---|---|---|
| EMX1 | 69 | 5' | 35 | 6 | 11 | 12.39 ± 1.29 | TCACCTGGGCCAGGAGGGA | GG G | 10.75 | CGGCAGAAGCTGGAGGAGGA | AG G | 22.06 |
| EMX1 | 76 | 5' | 42 | 9 | 14 | 21.71 ± 1.66 | GCCGTTTGTACTTTGTCCTC | CG G | 30.49 | AGGGCTCCCATCACATCAAC | CG G | 41.27 |
| EMX1 | 85 | 5' | 51 | 5 | 10 | 21.89 ± 1.88 | GGGGCACAGATGAGAAACTC | AG G | 26.56 | CAAACGGCAGAAGCTGGAGG | AG G | 26.15 |
| EMX1 | 95 | 5' | 61 | 6 | 12 | 5.88 ± 1.81 | TCACCTGGGCCAGGAGGGA | GG G | 10.75 | TGAGTCCGAGCAGAAGAAGAAGA | AG G | 29.06 |
| EMX1 | 135 | 5' | 101 | 5 | 14 | 15.78 ± 2.19 | GGGGCACAGATGAGAAACTC | AG G | 26.56 | AGGGCTCCCATCACATCAAC | CG G | 41.27 |
| EMX1 | 145 | 5' | 111 | 6 | 16 | N.D. | TCACCTGGGCCAGGAGGGA | GG G | 10.75 | TTGCCACGAAGCAGGCCAAT | GG G | 13.77 |
| EMX1 | 181 | 5' | 147 | 6 | 18 | N.D. | TCACCTGGGCCAGGAGGGA | GG G | 10.75 | TCACCTCCAATGACTAGGGT | GG G | 25.14 |
| EMX1 | 201 | 5' | 167 | 5 | 18 | N.D. | GGGGCACAGATGAGAAACTC | AG G | 26.56 | TCACCTCCAATGACTAGGGT | GG G | 25.14 |
| EMX1 | 222 | 5' | 188 | 6 | 19 | N.D. | TCACCTGGGCCAGGAGGGA | GG G | 10.75 | GGCAGAGTGCTGCTTGCTGC | TG G | 10.75 |
| EMX1 | 242 | 5' | 208 | 5 | 19 | N.D. | GGGGCACAGATGAGAAACTC | AG G | 26.56 | GGCAGAGTGCTGCTTGCTGC | TG G | 17.22 |
| DYRK1A | 164 | 3' | -198 | 34 | 47 | N.D. | ATCTGGTCAGAATATGATAA | AG G | 10.65 ± 2.05 | AACCTCACTTATCTTCTTGT | AG G | 19.02 ± 4.32 |
| DYRK1A | 105 | 3' | -139 | 35 | 47 | N.D. | GTCACTGTACTGATGTGAAT | TG G | 16.71 ± 2.47 | AACCTCACTTATCTTCTTGT | AG G | 17.04 ± 1.30 |
| DYRK1A | 66 | 3' | -100 | 36 | 48 | N.D. | CATCTGAAGGCCAGCAGCAT | TG G | 8.82 ± 1.01 | CTCACTTATCTTCTTGTAGG | AG G | 18.79 ± 2.71 |
| DYRK1A | 25 | 3' | -59 | 35 | 49 | N.D. | GTCACTGTACTGATGTGAAT | TG G | 17.83 ± 0.43 | CCATGCTGCTGGCCTTCAGA | TG G | 17.15 ± 3.29 |

FIG. 44B

| Gene | Overhang Length (bp) | Overhang Type | Offset Length (bp) | Left sgRNA ID | Right sgRNA ID | Cas9n with left and right sgRNA indel (%) | left sgRNA target site | | | right sgRNA target site | | |
|---|---|---|---|---|---|---|---|---|---|---|---|---|
| | | | | | | | guide sequence (5' to 3') | PAM | left sgRNA with wildtype Cas9 indel (%) | guide sequence (5' to 3') | PAM | right sgRNA with wildtype Cas9 indel (%) |
| DYRK1A | 4 | 3' | -38 | 36 | 31 | N.D. | TGATAAGGCAGAAAAACCTGTT | TG G | 4.95 ± 0.66 | GCCAAACATAAGTGACCAAC | AG G | 15.38 ± 3.39 |
| DYRK1A | 17 | 5' | -17 | 37 | 47 | N.D. | GAAGATAAGTGAGGTTTAAA | AG G | 5.30 ± 1.98 | AACCTCACTTATCTTCTTGT | AG G | 24.18 ± 3.22 |
| DYRK1A | 21 | 5' | -13 | 38 | 33 | 10.54 ± 0.63 | GTATCATTGACATATCTAA | TG G | 26.90 ± 1.17 | TGTCAAATGATACAAACATT | AG G | 29.69 ± 0.86 |
| DYRK1A | 25 | 5' | -9 | 39 | 49 | 2.33 ± 0.11 | CAGCATGGAATGAAAATGAC | CG G | 3.33 ± 0.56 | CCATGCTGCTGGCCTTCAGA | TG G | 20.43 ± 2.40 |
| DYRK1A | 29 | 5' | -5 | 40 | 50 | 27.76 ± 0.84 | GCAGCATGGAATGAAAATGA | CG G | 17.84 ± 5.46 | GCTGCTGGCCTTCAGATGGC | TG G | 21.92 ± 3.46 |
| DYRK1A | 33 | 5' | -1 | 41 | 51 | 10.42 ± 0.90 | ATCTGGTCAGAATATGATAA | AG G | 9.13 ± 2.32 | TCAGCAACCTCTAACTAACC | AG G | 24.14 ± 2.95 |
| DYRK1A | 35 | 5' | 1 | 34 | 52 | 7.63 ± 0.51 | GTGCAAGCCGAACAGATGAA | AG G | 6.65 ± 2.19 | TCATTTTCATTCCATGCTGC | TG G | 20.61 ± 3.64 |
| DYRK1A | 36 | 5' | 2 | 42 | 29 | 38.46 ± 0.74 | GGAGTATCAGAAATGACTAT | TG G | 20.88 ± 9.09 | GGAGTATCAGAAATGACTAT | TG G | 30.3 ± 0.7 |
| DYRK1A | 41 | 5' | 7 | 28 | 31 | 34.41 ± 0.87 | GGTCACTGTACTGATGTGAA | TG G | 25.68 ± 5.95 | GCCAAACATAAGTGACCAAC | AG G | 33.1 ± 0.4 |
| DYRK1A | 42 | 5' | 8 | 30 | 31 | 38.36 ± 0.32 | TCACTGTACTGATGTGAATG | GG G | 24.68 ± 4.58 | GCCAAACATAAGTGACCAAC | AG G | 29.46 ± 3.30 |
| DYRK1A | 43 | 5' | 9 | 43 | 33 | 28.97 ± 0.32 | GTTCCTTAAATAAGAACTT | AG G | 23.60 ± 2.56 | TGTCAAATGATACAAACATT | AG G | 22.4 ± 1.6 |
| DYRK1A | 46 | 5' | 12 | 32 | 53 | 11.90 ± 1.65 | TCCTACAAGAGATAAGTGA | AG G | 6.57 ± 1.36 | CATGCAAACCTTCATCTGTT | CG G | 30.42 ± 1.14 |
| DYRK1A | 77 | 5' | 43 | 44 | 31 | 6.63 ± 0.27 | CATCTGAAGGCCAGCAGCAT | TG G | 10.02 ± 1.17 | GCCAAACATAAGTGACCAAC | AG G | 22.92 ± 5.16 |
| DYRK1A | 86 | 5' | 52 | 36 | 38 | 52 | N.D. | GAAGATAAGTGAGGTTTAAA | AG G | 2.90 ± 0.82 | TCATTTCATTCCATGCTGC | TG G | 17.30 ± 1.62 |

FIG. 44C

| Gene | Overhang Length (bp) | Overhang Type | Offset Length (bp) | Left sgRNA ID | Right sgRNA ID | Cas9n with left and right sgRNA indel (%) | left sgRNA target site guide sequence (5' to 3') | PAM | left sgRNA with wildtype Cas9 indel (%) | right sgRNA target site guide sequence (5' to 3') | PAM | right sgRNA with wildtype Cas9 indel (%) |
|---|---|---|---|---|---|---|---|---|---|---|---|---|
| DYRK1A | 97 | 5' | 63 | 38 | 49 | N.D. | GAAGATAAGTGAGGTTTAAA | AG G | 2.16 ± 0.48 | CCATGCTGCTGGCCTTCAGA | TG G | 24.75 ± 2.50 |
| DYRK1A | 131 | 5' | 97 | 45 | 52 | N.D. | TATCATTTGACATATCTAAT | TG G | 8.21 ± 2.83 | TCATTTTCATTCCATGCTGC | TG G | 14.61 ± 4.10 |
| DYRK1A | 155 | 5' | 121 | 44 | 31 | N.D. | TCCTACAAGAAGATAAGTGA | AG G | 9.99 ± 4.12 | GCCAAACATAAGTGACCAAC | AG G | 19.74 ± 2.91 |
| DYRK1A | 191 | 5' | 157 | 46 | 52 | N.D. | AACTTTCTAACTACAAACA | AG G | 5.74 ± 2.24 | TCATTTTCATTCCATGCTGC | TG G | 21.37 |
| GRIN2B | 165 | 3' | -199 | 70 | 82 | N.D. | CCAACACCAACCAGAACTTG | GG G | 2.95 ± 0.21 | CTGGTAGATGGAGTTGGTT | TG G | 17.25 ± 1.30 |
| GRIN2B | 67 | 3' | -101 | 71 | 83 | N.D. | ACAGCAATGCCAATGCTGGG | GG G | 18.00 ± 2.31 | AGTGCTGTTCTCCCAAGTTC | TG G | 28.64 ± 0.69 |
| GRIN2B | 42 | 3' | -76 | 72 | 84 | N.D. | GTGGAAATCATCTTTCTCGT | TG G | 14.56 ± 7.84 | GGCATTGCTGTCATCCTCGT | GG G | 21.26 ± 2.68 |
| GRIN2B | 16 | 3' | -50 | 73 | 85 | N.D. | TCTGCTGCCTGACACGGCCA | AG G | 4.24 ± 0.79 | TCCCAAGTTCTGGTTGGTGT | TG G | 19.64 ± 0.23 |
| GRIN2B | 2 | 3' | -36 | 74 | 86 | N.D. | CGAGCTGCTGCTGCCTGACAC | CG G | 2.99 ± 0.31 | TTGGCCGTCCTGGCCGTGTC | AG G | 4.74 ± 0.15 |
| GRIN2B | 9 | 5' | -25 | 75 | 87 | 1.04 ± 0.53 | TCCTTGATGGCCACCTCGTC | CG G | 2.25 ± 1.08 | TTCCGACGAGGTGGCCATCA | AG G | 17.13 ± 2.90 |
| GRIN2B | 18 | 5' | -16 | 76 | 88 | 5.93 ± 1.25 | ATGACAGCAATGCCAATGCT | TG G | 16.46 ± 2.28 | TGGCATTGCTGTCATCCTCG | TG G | 16.35 ± 1.25 |
| GRIN2B | 23 | 5' | -11 | 77 | 88 | 2.28 ± 0.34 | AGCAATGCCAATGCTGGGGG | GG G | 3.19 ± 0.51 | TGGCATTGCTGTCATCCTCG | TG G | 15.17 ± 2.02 |
| GRIN2B | 28 | 5' | -6 | 78 | 86 | 1.45 ± 0.12 | GCCAACACCAACCAGAACTT | TG G | 17.80 ± 2.30 | TTGGCCGTCCTGGCCGTGTC | AG G | 4.46 ± 1.35 |
| GRIN2B | 30 | 5' | -4 | 69 | 85 | 11.80 ± 0.29 | GGAGAACAGCACTCCGCTCT | TG G | 21.80 ± 1.40 | TCCCAAGTTCTGGTTGGTGT | TG G | 21.33 ± 0.63 |

FIG. 44D

| Gene | Overhang Length (bp) | Overhang Type | Offset Length (bp) | Left sgRNA AID | Right sgRNA AID | Cas9n with left and right sgRNA indel (%) | left sgRNA target site guide sequence (5' to 3') | PAM | left sgRNA with wildtype Cas9 indel (%) | right sgRNA target site guide sequence (5' to 3') | PAM | right sgRNA with wildtype Cas9 indel (%) |
|---|---|---|---|---|---|---|---|---|---|---|---|---|
| GRIN2B | 33 | 5' | -1 | 76 | 65 | 24.24 ± 0.23 | ATGACAGCAATGCCAATGCT | TG G | 19.48 ± 1.88 | CCTCGTGGGCACTTCCGACG | AG G | 21.19 ± 3.42 |
| GRIN2B | 34 | 5' | 0 | 79 | 65 | 20.83 ± 0.95 | TGACAGCAATGCCAATGCTG | GG G | 21.44 ± 3.02 | CCTCGTGGGCACTTCCGACG | AG G | 24.11 ± 0.14 |
| GRIN2B | 36 | 5' | 2 | 58 | 59 | 31.76 ± 1.00 | CCGGCAAGACCTTGAAGCC | AG G | 32.50 ± 0.50 | CTGGTTGTAGGATTGAGTT | AG G | 25.7 ± 2.9 |
| GRIN2B | 38 | 5' | 4 | 54 | 55 | 34.45 ± 0.45 | TATTACAGAATGAGAGACTG | TG G | 30.90 ± 1.40 | TTATTTCTGAAGAATATTAA | AG G | 27.6 ± 2.5 |
| GRIN2B | 38 | 5' | 4 | 56 | 57 | 44.22 ± 0.55 | AAAAGACCTAAACAAAAGAA | TG G | 23.20 ± 2.10 | TGTGTGAGGATAAAAGAGTT | GG G | 29.4 ± 2.7 |
| GRIN2B | 38 | 5' | 4 | 77 | 65 | 9.60 ± 0.25 | AGCAATGCCAATGCTGGGGG | GG G | 4.19 ± 0.58 | CCTCGTGGGCACTTCCGACG | AG G | 21.78 ± 1.70 |
| GRIN2B | 40 | 5' | 6 | 60 | 61 | 42.54 ± 1.39 | TCAGAGCTTCCTGACACCCA | TG G | 14.20 ± 1.50 | AATACCTAGTTACAGGCATT | TG G | 24.8 ± 1.0 |
| GRIN2B | 45 | 5' | 11 | 76 | 87 | 18.96 ± 0.93 | ATGACAGCAATGCCAATGCT | TG G | 20.45 ± 0.98 | TTCCGACGAGGTGGCCATCA | AG G | 13.21 ± 0.74 |
| GRIN2B | 50 | 5' | 16 | 77 | 87 | 5.33 ± 0.57 | AGCAATGCCAATGCTGGGGG | GG G | 4.93 ± 2.06 | TTCCGACGAGGTGGCCATCA | AG G | 12.51 ± 1.21 |
| GRIN2B | 89 | 5' | 55 | 80 | 89 | 7.31 ± 0.83 | GAGAACAGCACTCCGCTCTG | GG G | 3.09 ± 0.54 | CAGAAGAGCCCCCCAGCAT | TG G | 25.02 ± 1.86 |
| GRIN2B | 105 | 5' | 71 | 78 | 90 | 10.56 ± 1.21 | GCCAACACCAACCAGAACTT | TG G | 25.29 ± 1.65 | CGTGGGCACTTCCGACGAGG | TG G | 23.32 ± 0.78 |
| GRIN2B | 132 | 5' | 98 | 81 | 67 | 2.66 ± 0.89 | CTGCCTGACACGGCAGGAC | CG G | 4.34 ± 0.62 | TGATTTCCACCATCTCTCCG | TG G | 20.95 ± 0.79 |
| GRIN2B | 175 | 5' | 141 | 80 | 67 | N.D. | GAGAACAGCACTCCGCTCTG | GG G | 2.96 ± 0.93 | TGATTTCCACCATCTCTCCG | TG G | 19.77 ± 2.20 |
| GRIN2B | 231 | 5' | 197 | 81 | 91 | N.D. | CTGCCTGACACGGCAGGAC | CG G | 6.17 ± 2.09 | TGACCGGAAGATCCAGGGGG | TG G | 23.36 ± 2.34 |

FIG. 44E

| Gene | Overhang Length (bp) | Overhang Type | Offset Length (bp) | Left sgRNA ID | Right sgRNA ID | Cas9n with left and right sgRNA indel (%) | left sgRNA target site guide sequence (5' to 3') | PAM | left sgRNA with wildtype Cas9 indel (%) | right sgRNA target site guide sequence (5' to 3') | PAM | right sgRNA with wildtype Cas9 indel (%) |
|---|---|---|---|---|---|---|---|---|---|---|---|---|
| MeCP2 | 38 | 5' | 4 | 92 | 93 | 12.16 ± 2.58 | GTCCAACCTTCAGGCAAGGT | GG G | 24.11 ± 3.48 | AAGCTTAAACAAAGGAAGTC | TG G | 35.76 ± 2.65 |
| MeCP2 | 34 | 5' | 0 | 94 | 95 | 11.72 ± 2.40 | GCGCTGTTTGGGGGAAGCCG | AG G | N.T | GGCTCCATTATCCGTGACCG | GG G | N.T |
| VEGFA | 50 | 5' | 16 | 96 | 97 | 23.92 ± 0.54 | GGGTGGGGGAGTTTGCTCC | TG G | 14.15 ± 1.07 | TCCCTCTTTAGCCAGAGCCG | GG G | 33.59 ± 0.88 |
| VEGFA | 54 | 5' | 20 | 98 | 99 | 16.32 ± 1.01 | GACCCCCTCCACCCCGCCTC | CG G | 24.52 ± 1.80 | GAAACTTTCGTCCAACTTC | TG G | 10.45 ± 1.14 |

FIG. 44F

| gene | sgRNA ID | guide sequence (5' to 3') | PAM | strand | species |
|---|---|---|---|---|---|
| EMX1 | 1 | GAGTCCGAGCAGAAGAAGAA | GGG | + | H. sapiens |
| EMX1 | 2 | GGAAGGGCCTGAGTCCGAGCAGAAGAAGA | GGG | + | H. sapiens |
| EMX1 | 3 | GGCCTCCAAGGAGTCCGAGCAGAAGAAGAA | GGG | + | H. sapiens |
| EMX1 | 4 | AGGCCCCAGTGGCTGCTCTG | GGG | + | H. sapiens |
| EMX1 | 5 | GGGGCACAGATGAGAAACTC | AGG | — | H. sapiens |
| EMX1 | 6 | TCACCTGGGCCAGGGAGGGA | GGG | — | H. sapiens |
| EMX1 | 7 | TGAAGGTGTGGTTCCAGAAC | CGG | + | H. sapiens |
| EMX1 | 8 | AGGTGTGGTTCCAGAACCGG | AGG | + | H. sapiens |
| EMX1 | 9 | GCCGTTTGTACTTTGTCCTC | CGG | — | H. sapiens |
| EMX1 | 10 | CAAACGGCAGAAGCTGGAGG | AGG | + | H. sapiens |
| EMX1 | 11 | CGGCAGAAGCTGGAGGAGGA | AGG | + | H. sapiens |
| EMX1 | 12 | TGAGTCCGAGCAGAAGAAGA | AGG | + | H. sapiens |
| EMX1 | 13 | GGAGCCCTTCTTCTTCTGCT | CGG | — | H. sapiens |
| EMX1 | 14 | AGGGCTCCCATCACATCAAC | CGG | + | H. sapiens |
| EMX1 | 15 | TGCGCCACCGGTTGATGTGA | TGG | — | H. sapiens |
| EMX1 | 16 | TTGCCACGAAGCAGGCCAAT | GGG | + | H. sapiens |
| EMX1 | 17 | CACGAAGCAGGCCAATGGGG | AGG | + | H. sapiens |
| EMX1 | 18 | TCACCTCCAATGACTAGGGT | GGG | + | H. sapiens |
| EMX1 | 19 | GGCAGAGTGCTGCTTGCTGC | TGG | + | H. sapiens |
| EMX1 | 20 | GACATCGATGTCCTCCCCAT | TGG | — | H. sapiens |
| EMX1 | 21 | GTCACCTCCAATGACTAGGG | TGG | + | H. sapiens |
| EMX1 | 22 | GGGCAACCACAAACCCACGA | GGG | + | H. sapiens |
| EMX1 | 23 | ACTCTGCCCTCGTGGGTTTG | TGG | — | H. sapiens |
| EMX1 | 24 | CAAGCAGCACTCTGCCCTCG | TGG | — | H. sapiens |
| EMX1 | 25 | TTCTTCTTCTGCTCGGACTC | AGG | — | H. sapiens |
| EMX1 | 26 | CTCCCCATTGGCCTGCTTCG | AGG | — | H. sapiens |
| EMX1 | 27 | GTCACCTCCAATGACTAGGG | TGG | + | H. sapiens |
| DYRK1A | 28 | GAACTTACCTGGTTAGTTAG | AGG | — | H. sapiens |
| DYRK1A | 29 | GGAGTATCAGAAATGACTAT | TGG | + | H. sapiens |
| DYRK1A | 30 | GGTCACTGTACTGATGTGAA | TGG | — | H. sapiens |
| DYRK1A | 31 | GCCAAACATAAGTGACCAAC | AGG | + | H. sapiens |

FIG. 45A

| gene | sgRNA ID | guide sequence (5' to 3') | PAM | strand | species |
|---|---|---|---|---|---|
| DYRK1A | 32 | GTTCCTTAAATAAGAACTTT | AGG | − | H. sapiens |
| DYRK1A | 33 | TGTCAAATGATACAAACATT | AGG | + | H. sapiens |
| DYRK1A | 34 | ATCTGGTCAGAATATGATAA | AGG | − | H. sapiens |
| DYRK1A | 35 | GTCACTGTACTGATGTGAAT | TGG | − | H. sapiens |
| DYRK1A | 36 | CATCTGAAGGCCAGCAGCAT | TGG | − | H. sapiens |
| DYRK1A | 37 | TGATAAGGCAGAAACCTGTT | TGG | − | H. sapiens |
| DYRK1A | 38 | GAAGATAAGTGAGGTTTAAA | AGG | − | H. sapiens |
| DYRK1A | 39 | GTATCATTTGACATATCTAA | TGG | − | H. sapiens |
| DYRK1A | 40 | CAGCATGGAATGAAAATGAC | CGG | − | H. sapiens |
| DYRK1A | 41 | GCAGCATGGAATGAAAATGA | CGG | − | H. sapiens |
| DYRK1A | 42 | GTGCAAGCCGAACAGATGAA | AGG | − | H. sapiens |
| DYRK1A | 43 | TCACTGTACTGATGTGAATG | GGG | − | H. sapiens |
| DYRK1A | 44 | TCCTACAAGAAGATAAGTGA | AGG | − | H. sapiens |
| DYRK1A | 45 | TATCATTTGACATATCTAAT | TGG | − | H. sapiens |
| DYRK1A | 46 | AACTTTCTAACTACAAACA | AGG | − | H. sapiens |
| DYRK1A | 47 | AACCTCACTTATCTTCTTGT | AGG | + | H. sapiens |
| DYRK1A | 48 | CTCACTTATCTTCTTGTAGG | AGG | + | H. sapiens |
| DYRK1A | 49 | CCATGCTGCTGGCCTTCAGA | TGG | + | H. sapiens |
| DYRK1A | 50 | GCTGCTGGCCTTCAGATGGC | TGG | + | H. sapiens |
| DYRK1A | 51 | TCAGCAACCTCTAACTAACC | AGG | + | H. sapiens |
| DYRK1A | 52 | TCATTTCATTCCATGCTGC | TGG | + | H. sapiens |
| DYRK1A | 53 | CATGCAAACCTTCATCTGTT | CGG | + | H. sapiens |
| DYRK1A | 54 | TATTACAGAATGAGAGACTG | TGG | − | H. sapiens |
| DYRK1A | 55 | TTATTTCTGAAGAATATTAA | AGG | + | H. sapiens |
| DYRK1A | 56 | AAAAGACCTAAACAAAAGAA | TGG | − | H. sapiens |
| DYRK1A | 57 | TGTGTGAGGATAAAAGAGTT | GGG | + | H. sapiens |
| DYRK1A | 58 | CCGGCCAAGACCTTGAAGCC | AGG | − | H. sapiens |
| DYRK1A | 59 | CTGGTTGTAGGATTTGAGTT | AGG | + | H. sapiens |
| DYRK1A | 60 | TCAGAGCTTCCTGACACCCA | TGG | − | H. sapiens |
| DYRK1A | 61 | AATACCTAGTTACAGGCATT | TGG | + | H. sapiens |
| GRIN2B | 62 | GGTGATGATGCTCTTTGGGT | CGG | − | H. sapiens |

FIG. 45B

| gene | sgRNA ID | guide sequence (5' to 3') | PAM | strand | species |
|---|---|---|---|---|---|
| GRIN2B | 63 | TCTGTGATCTCATGTCTGAC | CGG | + | H. sapiens |
| GRIN2B | 64 | CAGCAATGCCAATGCTGGGG | GGG | — | H. sapiens |
| GRIN2B | 65 | CCTCGTGGGCACTTCCGACG | AGG | + | H. sapiens |
| GRIN2B | 66 | TTTCTCGTGGGCATCCTTGA | TGG | — | H. sapiens |
| GRIN2B | 67 | TGATTTCCACCATCTCTCCG | TGG | + | H. sapiens |
| GRIN2B | 68 | GGAGAACAGCACTCCGCTCT | GGG | — | H. sapiens |
| GRIN2B | 69 | CTGGTTGGTGTTGGCCGTCC | TGG | + | H. sapiens |
| GRIN2B | 70 | CCAACACCAACCAGAACTTG | GGG | — | H. sapiens |
| GRIN2B | 71 | ACAGCAATGCCAATGCTGGG | GGG | — | H. sapiens |
| GRIN2B | 72 | GTGGAAATCATCTTTCTCGT | TGG | — | H. sapiens |
| GRIN2B | 73 | TCTGCTGCCTGACACGGCCA | AGG | — | H. sapiens |
| GRIN2B | 74 | CGAGCTCTGCTGCCTGACAC | CGG | — | H. sapiens |
| GRIN2B | 75 | TCCTTGATGGCCACCTCGTC | CGG | — | H. sapiens |
| GRIN2B | 76 | ATGACAGCAATGCCAATGCT | TGG | — | H. sapiens |
| GRIN2B | 77 | AGCAATGCCAATGCTGGGGG | GGG | — | H. sapiens |
| GRIN2B | 78 | GCCAACACCAACCAGAACTT | TGG | — | H. sapiens |
| GRIN2B | 79 | TGACAGCAATGCCAATGCTG | GGG | — | H. sapiens |
| GRIN2B | 80 | GAGAACAGCACTCCGCTCTG | GGG | — | H. sapiens |
| GRIN2B | 81 | CTGCCTGACACGGCCAGGAC | CGG | — | H. sapiens |
| GRIN2B | 82 | CTGGTAGATGGAGTTGGGTT | TGG | + | H. sapiens |
| GRIN2B | 83 | AGTGCTGTTCTCCCAAGTTC | TGG | + | H. sapiens |
| GRIN2B | 84 | GGCATTGCTGTCATCCTCGT | GGG | + | H. sapiens |
| GRIN2B | 85 | TCCCAAGTTCTGGTTGGTGT | TGG | + | H. sapiens |
| GRIN2B | 86 | TTGGCCGTCCTGGCCGTGTC | AGG | + | H. sapiens |
| GRIN2B | 87 | TTCCGACGAGGTGGCCATCA | AGG | + | H. sapiens |
| GRIN2B | 88 | TGGCATTGCTGTCATCCTCG | TGG | + | H. sapiens |
| GRIN2B | 89 | CAGAAGAGCCCCCCCAGCAT | TGG | + | H. sapiens |
| GRIN2B | 90 | CGTGGGCACTTCCGACGAGG | TGG | + | H. sapiens |
| GRIN2B | 91 | TGACCGGAAGATCCAGGGGG | TGG | + | H. sapiens |
| MeCP2 | 92 | GTCCAACCTTCAGGCAAGGT | GGG | — | M. musculus |
| MeCP2 | 93 | AAGCTTAAACAAAGGAAGTC | TGG | + | M. musculus |

FIG. 45C

| gene | sgRNA ID | guide sequence (5' to 3') | PAM | strand | species |
|---|---|---|---|---|---|
| MeCP2 | 94 | GCGCTGTTTGGGGAAGCCG | AGG | — | M. musculus |
| MeCP2 | 95 | GGCTCCATTATCCGTGACCG | GGG | + | M. musculus |
| VEGFA | 96 | GGGTGGGGGGAGTTTGCTCC | TGG | — | H. sapiens |
| VEGFA | 97 | TCCCTCTTTAGCCAGAGCCG | GGG | + | H. sapiens |
| VEGFA | 98 | GACCCCCTCCACCCCGCCTC | CGG | — | H. sapiens |
| VEGFA | 99 | GAAACTTTTCGTCCAACTTC | TGG | + | H. sapiens |

FIG. 45D

SEQUENCE LISTING

<160> NUMBER OF SEQ ID NOS: 480

<210> SEQ ID NO 1
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 1
gcactgaggg cctatttccc atgattc                                         27

<210> SEQ ID NO 2

```
<211> LENGTH: 20
<212> TYPE: DNA
<213> ORGANISM: Homo sapiens

<400> SEQUENCE: 2
gagtccgagc agaagaagaa                                                    20

<210> SEQ ID NO 3
<211> LENGTH: 20
<212> TYPE: DNA
<213> ORGANISM: Homo sapiens

<400> SEQUENCE: 3
gagtcctagc aggagaagaa                                                    20

<210> SEQ ID NO 4
<211> LENGTH: 20
<212> TYPE: DNA
<213> ORGANISM: Homo sapiens

<400> SEQUENCE: 4
gagtctaagc agaagaagaa                                                    20

<210> SEQ ID NO 5
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(44)
<223> OTHER INFORMATION: a, c, u, g, unknown or other
<220> FEATURE:
<221> NAME/KEY: modified_base
<222> LOCATION: (47)..(60)
<223> OTHER INFORMATION: a, c, u, g, unknown or other

<400> SEQUENCE: 5
nnnnnnnnnn nnnnnnnnnn ccnnnnnnnn nnnnnnnnnn nnnnggnnnn nnnnnnnnnn        60

<210> SEQ ID NO 6
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(14)
<223> OTHER INFORMATION: a, c, u, g, unknown or other
<220> FEATURE:
<221> NAME/KEY: modified_base
<222> LOCATION: (17)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 6
nnnnnnnnnn nnnnccnnnn nnnnnnnnnn nnnnnnnngg nnnnnnnnnn nnnnnnnnnn        60
```

```
<210> SEQ ID NO 7
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(43)
<223> OTHER INFORMATION: a, c, u, g, unknown or other
<220> FEATURE:
<221> NAME/KEY: modified_base
<222> LOCATION: (46)..(60)
<223> OTHER INFORMATION: a, c, u, g, unknown or other

<400> SEQUENCE: 7
nnnnnnnnnn nnnnnnnnnn ccnnnnnnnn nnnnnnnnnn nnggnnnnnn nnnnnnnnnn      60

<210> SEQ ID NO 8
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(15)
<223> OTHER INFORMATION: a, c, u, g, unknown or other
<220> FEATURE:
<221> NAME/KEY: modified_base
<222> LOCATION: (18)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 8
nnnnnnnnnn nnnnnccnnn nnnnnnnnnn nnnnnnnngg nnnnnnnnnn nnnnnnnnnn      60

<210> SEQ ID NO 9
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(42)
<223> OTHER INFORMATION: a, c, u, g, unknown or other
<220> FEATURE:
<221> NAME/KEY: modified_base
<222> LOCATION: (45)..(60)
<223> OTHER INFORMATION: a, c, u, g, unknown or other

<400> SEQUENCE: 9
nnnnnnnnnn nnnnnnnnnn ccnnnnnnnn nnnnnnnnnn nnggnnnnnn nnnnnnnnnn      60
```

<210> SEQ ID NO 10
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(15)
<223> OTHER INFORMATION: a, c, u, g, unknown or other
<220> FEATURE:
<221> NAME/KEY: modified_base
<222> LOCATION: (18)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 10
nnnnnnnnnn nnnnccnnn nnnnnnnnnn nnnnnnnngg nnnnnnnnnn nnnnnnnnnn      60

<210> SEQ ID NO 11
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(41)
<223> OTHER INFORMATION: a, c, u, g, unknown or other
<220> FEATURE:
<221> NAME/KEY: modified_base
<222> LOCATION: (44)..(60)
<223> OTHER INFORMATION: a, c, u, g, unknown or other

<400> SEQUENCE: 11
nnnnnnnnnn nnnnnnnnnn ccnnnnnnnn nnnnnnnnnn nggnnnnnnn nnnnnnnnnn      60

<210> SEQ ID NO 12
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(17)
<223> OTHER INFORMATION: a, c, u, g, unknown or other
<220> FEATURE:
<221> NAME/KEY: modified_base
<222> LOCATION: (20)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 12
nnnnnnnnnn nnnnnnnccn nnnnnnnnnn nnnnnnnngg nnnnnnnnnn nnnnnnnnnn      60

-continued

```
<210> SEQ ID NO 13
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(40)
<223> OTHER INFORMATION: a, c, u, g, unknown or other
<220> FEATURE:
<221> NAME/KEY: modified_base
<222> LOCATION: (43)..(60)
<223> OTHER INFORMATION: a, c, u, g, unknown or other

<400> SEQUENCE: 13
nnnnnnnnnn nnnnnnnnnn ccnnnnnnnn nnnnnnnnnn ggnnnnnnnn nnnnnnnnnn      60

<210> SEQ ID NO 14
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(18)
<223> OTHER INFORMATION: a, c, u, g, unknown or other
<220> FEATURE:
<221> NAME/KEY: modified_base
<222> LOCATION: (21)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 14
nnnnnnnnnn nnnnnnnncc nnnnnnnnnn nnnnnnnngg nnnnnnnnnn nnnnnnnnnn      60

<210> SEQ ID NO 15
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(39)
<223> OTHER INFORMATION: a, c, u, g, unknown or other
<220> FEATURE:
<221> NAME/KEY: modified_base
<222> LOCATION: (42)..(60)
<223> OTHER INFORMATION: a, c, u, g, unknown or other

<400> SEQUENCE: 15
nnnnnnnnnn nnnnnnnnnn ccnnnnnnnn nnnnnnnnng gnnnnnnnnn nnnnnnnnnn      60

<210> SEQ ID NO 16
```

```
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(19)
<223> OTHER INFORMATION: a, c, u, g, unknown or other
<220> FEATURE:
<221> NAME/KEY: modified_base
<222> LOCATION: (22)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 16
nnnnnnnnnn nnnnnnnnnc cnnnnnnnnn nnnnnnnngg nnnnnnnnnn nnnnnnnnnn      60

<210> SEQ ID NO 17
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 17
nnnnnnnnnn nnnnnnnnnn ccnnnnnnnn nnnnnnnngg nnnnnnnnnn nnnnnnnnnn      60

<210> SEQ ID NO 18
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 18
nnnnnnnnnn nnnnnnnnnn ccnnnnnnnn nnnnnnnngg nnnnnnnnnn nnnnnnnnnn      60

<210> SEQ ID NO 19
<211> LENGTH: 60
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(37)
<223> OTHER INFORMATION: a, c, u, g, unknown or other
<220> FEATURE:
<221> NAME/KEY: modified_base
<222> LOCATION: (40)..(60)
<223> OTHER INFORMATION: a, c, u, g, unknown or other

<400> SEQUENCE: 19
nnnnnnnnnn nnnnnnnnnn ccnnnnnnnn nnnnnnnggn nnnnnnnnnn nnnnnnnnnn      60

<210> SEQ ID NO 20
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(21)
<223> OTHER INFORMATION: a, c, u, g, unknown or other
<220> FEATURE:
<221> NAME/KEY: modified_base
<222> LOCATION: (24)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 20
nnnnnnnnnn nnnnnnnnnn nccnnnnnnn nnnnnnnngg nnnnnnnnnn nnnnnnnnnn      60

<210> SEQ ID NO 21
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(36)
<223> OTHER INFORMATION: a, c, u, g, unknown or other
<220> FEATURE:
<221> NAME/KEY: modified_base
<222> LOCATION: (39)..(60)
<223> OTHER INFORMATION: a, c, u, g, unknown or other

<400> SEQUENCE: 21
nnnnnnnnnn nnnnnnnnnn ccnnnnnnnn nnnnnnggnn nnnnnnnnnn nnnnnnnnnn      60

<210> SEQ ID NO 22
<211> LENGTH: 60
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(22)
<223> OTHER INFORMATION: a, c, u, g, unknown or other
<220> FEATURE:
<221> NAME/KEY: modified_base
<222> LOCATION: (25)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 22
nnnnnnnnnn nnnnnnnnnn nnccnnnnnn nnnnnnnngg nnnnnnnnnn nnnnnnnnnn        60

<210> SEQ ID NO 23
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(35)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 23
nnnnnnnnnn nnnnnnnnnn ccnnnnnnnn nnnnggnnnn nnnnnnnnnn nnnnnnnnnn        60

<210> SEQ ID NO 24
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(23)
<223> OTHER INFORMATION: a, c, u, g, unknown or other
<220> FEATURE:
<221> NAME/KEY: modified_base
<222> LOCATION: (26)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 24
nnnnnnnnnn nnnnnnnnnn nnnccnnnnn nnnnnnnngg nnnnnnnnnn nnnnnnnnnn        60

<210> SEQ ID NO 25
<211> LENGTH: 60
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(34)
<223> OTHER INFORMATION: a, c, u, g, unknown or other
<220> FEATURE:
<221> NAME/KEY: modified_base
<222> LOCATION: (37)..(60)
<223> OTHER INFORMATION: a, c, u, g, unknown or other

<400> SEQUENCE: 25
nnnnnnnnnn nnnnnnnnnn ccnnnnnnnn nnnggnnnnn nnnnnnnnnn nnnnnnnnnn    60

<210> SEQ ID NO 26
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(24)
<223> OTHER INFORMATION: a, c, u, g, unknown or other
<220> FEATURE:
<221> NAME/KEY: modified_base
<222> LOCATION: (27)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 26
nnnnnnnnnn nnnnnnnnnn nnnnccnnnn nnnnnnnngg nnnnnnnnnn nnnnnnnnnn    60

<210> SEQ ID NO 27
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(33)
<223> OTHER INFORMATION: a, c, u, g, unknown or other
<220> FEATURE:
<221> NAME/KEY: modified_base
<222> LOCATION: (36)..(60)
<223> OTHER INFORMATION: a, c, u, g, unknown or other

<400> SEQUENCE: 27
nnnnnnnnnn nnnnnnnnnn ccnnnnnnnn nnnggnnnnn nnnnnnnnnn nnnnnnnnnn    60

<210> SEQ ID NO 28
<211> LENGTH: 60
<212> TYPE: RNA
<213> ORGANISM: Artificial Sequence
<220> FEATURE:
```

-continued

```
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(25)
<223> OTHER INFORMATION: a, c, u, g, unknown or other
<220> FEATURE:
<221> NAME/KEY: modified_base
<222> LOCATION: (28)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 28
nnnnnnnnnn nnnnnnnnnn nnnnnccnnn nnnnnnnngg nnnnnnnnnn nnnnnnnnnn      60

<210> SEQ ID NO 29
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(32)
<223> OTHER INFORMATION: a, c, u, g, unknown or other
<220> FEATURE:
<221> NAME/KEY: modified_base
<222> LOCATION: (35)..(60)
<223> OTHER INFORMATION: a, c, u, g, unknown or other

<400> SEQUENCE: 29
nnnnnnnnnn nnnnnnnnnn ccnnnnnnnn nnggnnnnnn nnnnnnnnnn nnnnnnnnnn      60

<210> SEQ ID NO 30
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(26)
<223> OTHER INFORMATION: a, c, u, g, unknown or other
<220> FEATURE:
<221> NAME/KEY: modified_base
<222> LOCATION: (29)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 30
nnnnnnnnnn nnnnnnnnnn nnnnnnccnn nnnnnnnngg nnnnnnnnnn nnnnnnnnnn      60

<210> SEQ ID NO 31
<211> LENGTH: 60
<212> TYPE: RNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(31)
<223> OTHER INFORMATION: a, c, u, g, unknown or other
<220> FEATURE:
<221> NAME/KEY: modified_base
<222> LOCATION: (34)..(60)
<223> OTHER INFORMATION: a, c, u, g, unknown or other

<400> SEQUENCE: 31
nnnnnnnnnn nnnnnnnnnn ccnnnnnnnn nggnnnnnnn nnnnnnnnnn nnnnnnnnnn      60

<210> SEQ ID NO 32
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(27)
<223> OTHER INFORMATION: a, c, u, g, unknown or other
<220> FEATURE:
<221> NAME/KEY: modified_base
<222> LOCATION: (30)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 32
nnnnnnnnnn nnnnnnnnnn nnnnnnnccn nnnnnnnngg nnnnnnnnnn nnnnnnnnnn      60

<210> SEQ ID NO 33
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(30)
<223> OTHER INFORMATION: a, c, u, g, unknown or other
<220> FEATURE:
<221> NAME/KEY: modified_base
<222> LOCATION: (33)..(60)
<223> OTHER INFORMATION: a, c, u, g, unknown or other

<400> SEQUENCE: 33
nnnnnnnnnn nnnnnnnnnn ccnnnnnnnn ggnnnnnnnn nnnnnnnnnn nnnnnnnnnn      60

<210> SEQ ID NO 34
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
```

```
      Synthetic oligonucleotide"
<220> FEATURE:
<221> NAME/KEY: modified_base
<222> LOCATION: (1)..(28)
<223> OTHER INFORMATION: a, c, u, g, unknown or other
<220> FEATURE:
<221> NAME/KEY: modified_base
<222> LOCATION: (31)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 34
nnnnnnnnnn nnnnnnnnnn nnnnnnnncc nnnnnnnngg nnnnnnnnnn nnnnnnnnnn     60

<210> SEQ ID NO 35
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(29)
<223> OTHER INFORMATION: a, c, u, g, unknown or other
<220> FEATURE:
<221> NAME/KEY: modified_base
<222> LOCATION: (32)..(60)
<223> OTHER INFORMATION: a, c, u, g, unknown or other

<400> SEQUENCE: 35
nnnnnnnnnn nnnnnnnnnn ccnnnnnnng gnnnnnnnnn nnnnnnnnnn nnnnnnnnnn     60

<210> SEQ ID NO 36
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(29)
<223> OTHER INFORMATION: a, c, u, g, unknown or other
<220> FEATURE:
<221> NAME/KEY: modified_base
<222> LOCATION: (32)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 36
nnnnnnnnnn nnnnnnnnnn nnnnnnnnnc nnnnnnnngg nnnnnnnnnn nnnnnnnnnn     60

<210> SEQ ID NO 37
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(28)
<223> OTHER INFORMATION: a, c, u, g, unknown or other
<220> FEATURE:
<221> NAME/KEY: modified_base
<222> LOCATION: (31)..(60)
<223> OTHER INFORMATION: a, c, u, g, unknown or other

<400> SEQUENCE: 37
nnnnnnnnnn nnnnnnnnn ccnnnnnngg nnnnnnnnnn nnnnnnnnnn nnnnnnnnnn        60

<210> SEQ ID NO 38
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(30)
<223> OTHER INFORMATION: a, c, u, g, unknown or other
<220> FEATURE:
<221> NAME/KEY: modified_base
<222> LOCATION: (33)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 38
nnnnnnnnnn nnnnnnnnnn nnnnnnnnnn ccnnnnnngg nnnnnnnnnn nnnnnnnnnn        60

<210> SEQ ID NO 39
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(27)
<223> OTHER INFORMATION: a, c, u, g, unknown or other
<220> FEATURE:
<221> NAME/KEY: modified_base
<222> LOCATION: (30)..(60)
<223> OTHER INFORMATION: a, c, u, g, unknown or other

<400> SEQUENCE: 39
nnnnnnnnnn nnnnnnnnnn ccnnnnnggn nnnnnnnnnn nnnnnnnnnn nnnnnnnnnn        60

<210> SEQ ID NO 40
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: modified_base
<222> LOCATION: (1)..(31)
<223> OTHER INFORMATION: a, c, u, g, unknown or other
<220> FEATURE:
<221> NAME/KEY: modified_base
<222> LOCATION: (34)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 40
nnnnnnnnnn nnnnnnnnnn nnnnnnnnnn nccnnnnngg nnnnnnnnnn nnnnnnnnnn      60

<210> SEQ ID NO 41
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(26)
<223> OTHER INFORMATION: a, c, u, g, unknown or other
<220> FEATURE:
<221> NAME/KEY: modified_base
<222> LOCATION: (29)..(60)
<223> OTHER INFORMATION: a, c, u, g, unknown or other

<400> SEQUENCE: 41
nnnnnnnnnn nnnnnnnnnn ccnnnnggnn nnnnnnnnnn nnnnnnnnnn nnnnnnnnnn      60

<210> SEQ ID NO 42
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(32)
<223> OTHER INFORMATION: a, c, u, g, unknown or other
<220> FEATURE:
<221> NAME/KEY: modified_base
<222> LOCATION: (35)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 42
nnnnnnnnnn nnnnnnnnnn nnnnnnnnnn nnccnnnngg nnnnnnnnnn nnnnnnnnnn      60

<210> SEQ ID NO 43
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
```

```
<222> LOCATION: (1)..(20)
<223> OTHER INFORMATION: a, c, u, g, unknown or other
<220> FEATURE:
<221> NAME/KEY: modified_base
<222> LOCATION: (23)..(25)
<223> OTHER INFORMATION: a, c, u, g, unknown or other
<220> FEATURE:
<221> NAME/KEY: modified_base
<222> LOCATION: (28)..(60)
<223> OTHER INFORMATION: a, c, u, g, unknown or other

<400> SEQUENCE: 43
nnnnnnnnnn nnnnnnnnnn ccnnnggnnn nnnnnnnnnn nnnnnnnnnn nnnnnnnnnn     60

<210> SEQ ID NO 44
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(33)
<223> OTHER INFORMATION: a, c, u, g, unknown or other
<220> FEATURE:
<221> NAME/KEY: modified_base
<222> LOCATION: (36)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 44
nnnnnnnnnn nnnnnnnnnn nnnnnnnnnn nnnccnnngg nnnnnnnnnn nnnnnnnnnn     60

<210> SEQ ID NO 45
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(24)
<223> OTHER INFORMATION: a, c, u, g, unknown or other
<220> FEATURE:
<221> NAME/KEY: modified_base
<222> LOCATION: (27)..(60)
<223> OTHER INFORMATION: a, c, u, g, unknown or other

<400> SEQUENCE: 45
nnnnnnnnnn nnnnnnnnnn ccnnggnnnn nnnnnnnnnn nnnnnnnnnn nnnnnnnnnn     60

<210> SEQ ID NO 46
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(34)
```

```
<223> OTHER INFORMATION: a, c, u, g, unknown or other
<220> FEATURE:
<221> NAME/KEY: modified_base
<222> LOCATION: (37)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 46 nnnnnnnnn nnnnnnnnn nnnnnnnnn nnnnccnngg nnnnnnnnnn nnnnnnnnnn     60

<210> SEQ ID NO 47
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(23)
<223> OTHER INFORMATION: a, c, u, g, unknown or other
<220> FEATURE:
<221> NAME/KEY: modified_base
<222> LOCATION: (26)..(60)
<223> OTHER INFORMATION: a, c, u, g, unknown or other

<400> SEQUENCE: 47
nnnnnnnnnn nnnnnnnnnn ccnggnnnnn nnnnnnnnnn nnnnnnnnnn nnnnnnnnnn     60

<210> SEQ ID NO 48
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(35)
<223> OTHER INFORMATION: a, c, u, g, unknown or other
<220> FEATURE:
<221> NAME/KEY: modified_base
<222> LOCATION: (38)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 48
nnnnnnnnnn nnnnnnnnnn nnnnnnnnnn nnnnccngg nnnnnnnnnn nnnnnnnnnn     60

<210> SEQ ID NO 49
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(21)
<223> OTHER INFORMATION: a, c, u, g, unknown or other
```

```
<220> FEATURE:
<221> NAME/KEY: modified_base
<222> LOCATION: (26)..(60)
<223> OTHER INFORMATION: a, c, u, g, unknown or other

<400> SEQUENCE: 49
nnnnnnnnnn nnnnnnnnnn nccggnnnnn nnnnnnnnnn nnnnnnnnnn nnnnnnnnnn      60

<210> SEQ ID NO 50
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(35)
<223> OTHER INFORMATION: a, c, u, g, unknown or other
<220> FEATURE:
<221> NAME/KEY: modified_base
<222> LOCATION: (40)..(60)
<223> OTHER INFORMATION: a, c, u, g, unknown or other

<400> SEQUENCE: 50
nnnnnnnnnn nnnnnnnnnn nnnnnnnnnn nnnnnccggn nnnnnnnnnn nnnnnnnnnn      60

<210> SEQ ID NO 51
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(23)
<223> OTHER INFORMATION: a, c, u, g, unknown or other
<220> FEATURE:
<221> NAME/KEY: modified_base
<222> LOCATION: (26)..(60)
<223> OTHER INFORMATION: a, c, u, g, unknown or other

<400> SEQUENCE: 51
nnnnnnnnnn nnnnnnnnnn nnnggnnnnn nnnnnnnnnn nnnnnnnnnn nnnnnnnnnn      60

<210> SEQ ID NO 52
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(33)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 52
nnnnnnnnnn nnnnnnnnnn nnnnnnnnnn nnnggccnnn nnnnnnnnnn nnnnnnnnnn      60

<210> SEQ ID NO 53
<211> LENGTH: 60
<212> TYPE: RNA
```

-continued

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(22)
<223> OTHER INFORMATION: a, c, u, g, unknown or other
<220> FEATURE:
<221> NAME/KEY: modified_base
<222> LOCATION: (26)..(60)
<223> OTHER INFORMATION: a, c, u, g, unknown or other

<400> SEQUENCE: 53
nnnnnnnnnn nnnnnnnnnn nncggnnnnn nnnnnnnnnn nnnnnnnnnn nnnnnnnnnn      60

<210> SEQ ID NO 54
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(32)
<223> OTHER INFORMATION: a, c, u, g, unknown or other
<220> FEATURE:
<221> NAME/KEY: modified_base
<222> LOCATION: (35)..(35)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 54
nnnnnnnnnn nnnnnnnnnn nnnnnnnnnn nnggnccnnn nnnnnnnnnn nnnnnnnnnn      60

<210> SEQ ID NO 55
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(31)
<223> OTHER INFORMATION: a, c, u, g, unknown or other
<220> FEATURE:
<221> NAME/KEY: modified_base
<222> LOCATION: (34)..(35)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 55
nnnnnnnnnn nnnnnnnnnn nnnnnnnnnn nggnnccnnn nnnnnnnnnn nnnnnnnnnn      60

<210> SEQ ID NO 56
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: modified_base
<222> LOCATION: (1)..(30)
<223> OTHER INFORMATION: a, c, u, g, unknown or other
<220> FEATURE:
<221> NAME/KEY: modified_base
<222> LOCATION: (33)..(35)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 56
nnnnnnnnnn nnnnnnnnnn nnnnnnnnnn ggnnnccnnn nnnnnnnnnn nnnnnnnnnn      60

<210> SEQ ID NO 57
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(29)
<223> OTHER INFORMATION: a, c, u, g, unknown or other
<220> FEATURE:
<221> NAME/KEY: modified_base
<222> LOCATION: (32)..(35)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 57
nnnnnnnnnn nnnnnnnnnn nnnnnnnnng gnnnccnnn nnnnnnnnnn nnnnnnnnnn      60

<210> SEQ ID NO 58
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(28)
<223> OTHER INFORMATION: a, c, u, g, unknown or other
<220> FEATURE:
<221> NAME/KEY: modified_base
<222> LOCATION: (31)..(35)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 58
nnnnnnnnnn nnnnnnnnnn nnnnnnnngg nnnnccnnn nnnnnnnnnn nnnnnnnnnn      60

<210> SEQ ID NO 59
<211> LENGTH: 12
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

```
<400> SEQUENCE: 59
guuuuagagc ua                                                          12

<210> SEQ ID NO 60
<211> LENGTH: 7
<212> TYPE: PRT
<213> ORGANISM: Simian virus 40

<400> SEQUENCE: 60

Pro Lys Lys Lys Arg Lys Val
1               5

<210> SEQ ID NO 61
<211> LENGTH: 16
<212> TYPE: PRT
<213> ORGANISM: Unknown
<220> FEATURE:
<221> NAME/KEY: source
<223> OTHER INFORMATION: /note="Description of Unknown:
      Nucleoplasmin bipartite NLS sequence"

<400> SEQUENCE: 61

Lys Arg Pro Ala Ala Thr Lys Lys Ala Gly Gln Ala Lys Lys Lys Lys
1               5                   10                  15

<210> SEQ ID NO 62
<211> LENGTH: 9
<212> TYPE: PRT
<213> ORGANISM: Unknown
<220> FEATURE:
<221> NAME/KEY: source
<223> OTHER INFORMATION: /note="Description of Unknown:
      c-myc NLS sequence"

<400> SEQUENCE: 62

Pro Ala Ala Lys Arg Val Lys Leu Asp
1               5

<210> SEQ ID NO 63
<211> LENGTH: 11
<212> TYPE: PRT
<213> ORGANISM: Unknown
<220> FEATURE:
<221> NAME/KEY: source
<223> OTHER INFORMATION: /note="Description of Unknown:
      c-myc NLS sequence"

<400> SEQUENCE: 63

Arg Gln Arg Arg Asn Glu Leu Lys Arg Ser Pro
1               5                   10

<210> SEQ ID NO 64
<211> LENGTH: 38
<212> TYPE: PRT
<213> ORGANISM: Homo sapiens

<400> SEQUENCE: 64

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35

<210> SEQ ID NO 65
```

```
<211> LENGTH: 42
<212> TYPE: PRT
<213> ORGANISM: Unknown
<220> FEATURE:
<221> NAME/KEY: source
<223> OTHER INFORMATION: /note="Description of Unknown:
      IBB domain from importin-alpha sequence"

<400> SEQUENCE: 65

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
                20                  25                  30

Asp Glu Gln Ile Leu Lys Arg Arg Asn Val
            35                  40

<210> SEQ ID NO 66
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      myoma T protein sequence"

<400> SEQUENCE: 66

Val Ser Arg Lys Arg Pro Arg Pro
1               5

<210> SEQ ID NO 67
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      myoma T protein sequence"

<400> SEQUENCE: 67

Pro Pro Lys Lys Ala Arg Glu Asp
1               5

<210> SEQ ID NO 68
<211> LENGTH: 8
<212> TYPE: PRT
<213> ORGANISM: Homo sapiens

<400> SEQUENCE: 68

Pro Gln Pro Lys Lys Lys Pro Leu
1               5

<210> SEQ ID NO 69
<211> LENGTH: 12
<212> TYPE: PRT
<213> ORGANISM: Mus musculus

<400> SEQUENCE: 69

Ser Ala Leu Ile Lys Lys Lys Lys Lys Met Ala Pro
1               5                   10

<210> SEQ ID NO 70
<211> LENGTH: 5
<212> TYPE: PRT
<213> ORGANISM: Influenza virus

<400> SEQUENCE: 70
```

```
Asp Arg Leu Arg Arg
1               5

<210> SEQ ID NO 71
<211> LENGTH: 7
<212> TYPE: PRT
<213> ORGANISM: Influenza virus

<400> SEQUENCE: 71

Pro Lys Gln Lys Lys Arg Lys
1               5

<210> SEQ ID NO 72
<211> LENGTH: 10
<212> TYPE: PRT
<213> ORGANISM: Hepatitis delta virus

<400> SEQUENCE: 72

Arg Lys Leu Lys Lys Lys Ile Lys Lys Leu
1               5                   10

<210> SEQ ID NO 73
<211> LENGTH: 10
<212> TYPE: PRT
<213> ORGANISM: Mus musculus

<400> SEQUENCE: 73

Arg Glu Lys Lys Lys Phe Leu Lys Arg Arg
1               5                   10

<210> SEQ ID NO 74
<211> LENGTH: 20
<212> TYPE: PRT
<213> ORGANISM: Homo sapiens

<400> SEQUENCE: 74

Lys Arg Lys Gly Asp Glu Val Asp Gly Val Asp Glu Val Ala Lys Lys
1               5                   10                  15

Lys Ser Lys Lys
            20

<210> SEQ ID NO 75
<211> LENGTH: 17
<212> TYPE: PRT
<213> ORGANISM: Homo sapiens

<400> SEQUENCE: 75

Arg Lys Cys Leu Gln Ala Gly Met Asn Leu Glu Ala Arg Lys Thr Lys
1               5                   10                  15

Lys

<210> SEQ ID NO 76
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(22)
```

```
<223> OTHER INFORMATION: a, c, t, g, unknown or other

<400> SEQUENCE: 76
nnnnnnnnnn nnnnnnnnnn nnagaaw                                          27

<210> SEQ ID NO 77
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(14)
<223> OTHER INFORMATION: a, c, t, g, unknown or other

<400> SEQUENCE: 77
nnnnnnnnnn nnnnagaaw                                                   19

<210> SEQ ID NO 78
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(22)
<223> OTHER INFORMATION: a, c, t, g, unknown or other

<400> SEQUENCE: 78
nnnnnnnnnn nnnnnnnnnn nnagaaw                                          27

<210> SEQ ID NO 79
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(13)
<223> OTHER INFORMATION: a, c, t, g, unknown or other

<400> SEQUENCE: 79
nnnnnnnnnn nnnagaaw                                                    18

<210> SEQ ID NO 80
<211> LENGTH: 137
<212> TYPE: DNA
<213> ORGANISM: Artificial Sequence
<220> FEATURE:
<221> NAME/KEY: source
```

<223> OTHER INFORMATION: /note="Description of Artificial Sequence:
     Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 80
nnnnnnnnnn nnnnnnnnnn gtttttgtac tctcaagatt tagaaataaa tcttgcagaa    60
gctacaaaga taaggcttca tgccgaaatc aacaccctgt cattttatgg cagggtgttt   120
tcgttattta attttt                                                   137

<210> SEQ ID NO 81
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 81
nnnnnnnnnn nnnnnnnnnn gtttttgtac tctcagaaat gcagaagcta caaagataag    60
gcttcatgcc gaaatcaaca ccctgtcatt ttatggcagg gtgttttcgt tatttaattt   120
ttt                                                                 123

<210> SEQ ID NO 82
<211> LENGTH: 110
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 82
nnnnnnnnnn nnnnnnnnnn gtttttgtac tctcagaaat gcagaagcta caaagataag    60
gcttcatgcc gaaatcaaca ccctgtcatt ttatggcagg gtgttttttt              110

<210> SEQ ID NO 83
<211> LENGTH: 102
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 83
nnnnnnnnnn nnnnnnnnnn gttttagagc tagaaatagc aagttaaaat aaggctagtc    60
cgttatcaac ttgaaaaagt ggcaccgagt cggtgctttt tt                      102

<210> SEQ ID NO 84

```
<211> LENGTH: 88
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t, g, unknown or other

<400> SEQUENCE: 84
nnnnnnnnnn nnnnnnnnnn gttttagagc tagaaatagc aagttaaaat aaggctagtc    60
cgttatcaac ttgaaaaagt gttttttt                                       88

<210> SEQ ID NO 85
<211> LENGTH: 76
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t, g, unknown or other

<400> SEQUENCE: 85
nnnnnnnnnn nnnnnnnnnn gttttagagc tagaaatagc aagttaaaat aaggctagtc    60
cgttatcatt tttttt                                                    76

<210> SEQ ID NO 86
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 86
aaactctaga gagggcctat ttcccatgat tc                                  32

<210> SEQ ID NO 87
<211> LENGTH: 153
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 87
acctctagaa aaaagcacc gactcggtgc cactttttca agttgataac ggactagcct    60
tattttaact tgctatgctg ttttgtttcc aaaacagcat agctctaaaa ccctagtca   120 ttggaggtga cggtgtttcg tcctttccac aag                               153

<210> SEQ ID NO 88
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

-continued

<400> SEQUENCE: 88
taatacgact cactataggga agtgcgccac catggcccca aagaagaagc gg          52

<210> SEQ ID NO 89
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 89
ggtttttttt tttttttttt tttttttttt ttttcttact ttttcttttt tgcctggccg    60

<210> SEQ ID NO 90
<211> LENGTH: 984
<212> TYPE: PRT
<213> ORGANISM: Campylobacter jejuni

<400> SEQUENCE: 90

```
Met Ala Arg Ile Leu Ala Phe Asp Ile Gly Ile Ser Ser Ile Gly Trp
1               5                   10                  15

Ala Phe Ser Glu Asn Asp Glu Leu Lys Asp Cys Gly Val Arg Ile Phe
            20                  25                  30

Thr Lys Val Glu Asn Pro Lys Thr Gly Glu Ser Leu Ala Leu Pro Arg
        35                  40                  45

Arg Leu Ala Arg Ser Ala Arg Lys Arg Leu Ala Arg Arg Lys Ala Arg
    50                  55                  60

Leu Asn His Leu Lys His Leu Ile Ala Asn Glu Phe Lys Leu Asn Tyr
65                  70                  75                  80

Glu Asp Tyr Gln Ser Phe Asp Glu Ser Leu Ala Lys Ala Tyr Lys Gly
                85                  90                  95

Ser Leu Ile Ser Pro Tyr Glu Leu Arg Phe Arg Ala Leu Asn Glu Leu
            100                 105                 110

Leu Ser Lys Gln Asp Phe Ala Arg Val Ile Leu His Ile Ala Lys Arg
        115                 120                 125

Arg Gly Tyr Asp Asp Ile Lys Asn Ser Asp Asp Lys Glu Lys Gly Ala
    130                 135                 140

Ile Leu Lys Ala Ile Lys Gln Asn Glu Glu Lys Leu Ala Asn Tyr Gln
145                 150                 155                 160

Ser Val Gly Glu Tyr Leu Tyr Lys Glu Tyr Phe Gln Lys Phe Lys Glu
                165                 170                 175

Asn Ser Lys Glu Phe Thr Asn Val Arg Asn Lys Lys Glu Ser Tyr Glu
            180                 185                 190

Arg Cys Ile Ala Gln Ser Phe Leu Lys Asp Glu Leu Lys Leu Ile Phe
        195                 200                 205

Lys Lys Gln Arg Glu Phe Gly Phe Ser Phe Ser Lys Lys Phe Glu Glu
    210                 215                 220

Glu Val Leu Ser Val Ala Phe Tyr Lys Arg Ala Leu Lys Asp Phe Ser
225                 230                 235                 240

His Leu Val Gly Asn Cys Ser Phe Phe Thr Asp Glu Lys Arg Ala Pro
                245                 250                 255

Lys Asn Ser Pro Leu Ala Phe Met Phe Val Ala Leu Thr Arg Ile Ile
            260                 265                 270

Asn Leu Leu Asn Asn Leu Lys Asn Thr Glu Gly Ile Leu Tyr Thr Lys
```

```
            275                 280                 285
Asp Asp Leu Asn Ala Leu Leu Asn Glu Val Leu Lys Asn Gly Thr Leu
    290                 295                 300
Thr Tyr Lys Gln Thr Lys Lys Leu Leu Gly Leu Ser Asp Asp Tyr Glu
305                 310                 315                 320
Phe Lys Gly Glu Lys Gly Thr Tyr Phe Ile Glu Phe Lys Lys Tyr Lys
                325                 330                 335
Glu Phe Ile Lys Ala Leu Gly Glu His Asn Leu Ser Gln Asp Asp Leu
            340                 345                 350
Asn Glu Ile Ala Lys Asp Ile Thr Leu Ile Lys Asp Glu Ile Lys Leu
            355                 360                 365
Lys Lys Ala Leu Ala Lys Tyr Asp Leu Asn Gln Asn Gln Ile Asp Ser
    370                 375                 380
Leu Ser Lys Leu Glu Phe Lys Asp His Leu Asn Ile Ser Phe Lys Ala
385                 390                 395                 400
Leu Lys Leu Val Thr Pro Leu Met Leu Glu Gly Lys Lys Tyr Asp Glu
                405                 410                 415
Ala Cys Asn Glu Leu Asn Leu Lys Val Ala Ile Asn Glu Asp Lys Lys
            420                 425                 430
Asp Phe Leu Pro Ala Phe Asn Glu Thr Tyr Tyr Lys Asp Glu Val Thr
            435                 440                 445
Asn Pro Val Val Leu Arg Ala Ile Lys Glu Tyr Arg Lys Val Leu Asn
    450                 455                 460
Ala Leu Leu Lys Lys Tyr Gly Lys Val His Lys Ile Asn Ile Glu Leu
465                 470                 475                 480
Ala Arg Glu Val Gly Lys Asn His Ser Gln Arg Ala Lys Ile Glu Lys
                485                 490                 495
Glu Gln Asn Glu Asn Tyr Lys Ala Lys Lys Asp Ala Glu Leu Glu Cys
            500                 505                 510
Glu Lys Leu Gly Leu Lys Ile Asn Ser Lys Asn Ile Leu Lys Leu Arg
            515                 520                 525
Leu Phe Lys Glu Gln Lys Glu Phe Cys Ala Tyr Ser Gly Glu Lys Ile
    530                 535                 540
Lys Ile Ser Asp Leu Gln Asp Glu Lys Met Leu Glu Ile Asp His Ile
545                 550                 555                 560
Tyr Pro Tyr Ser Arg Ser Phe Asp Asp Ser Tyr Met Asn Lys Val Leu
                565                 570                 575
Val Phe Thr Lys Gln Asn Gln Glu Lys Leu Asn Gln Thr Pro Phe Glu
            580                 585                 590
Ala Phe Gly Asn Asp Ser Ala Lys Trp Gln Lys Ile Glu Val Leu Ala
            595                 600                 605
Lys Asn Leu Pro Thr Lys Lys Gln Lys Arg Ile Leu Asp Lys Asn Tyr
    610                 615                 620
Lys Asp Lys Glu Gln Lys Asn Phe Lys Asp Arg Asn Leu Asn Asp Thr
625                 630                 635                 640
Arg Tyr Ile Ala Arg Leu Val Leu Asn Tyr Thr Lys Asp Tyr Leu Asp
                645                 650                 655
Phe Leu Pro Leu Ser Asp Asp Glu Asn Thr Lys Leu Asn Asp Thr Gln
            660                 665                 670
Lys Gly Ser Lys Val His Val Glu Ala Lys Ser Gly Met Leu Thr Ser
            675                 680                 685
Ala Leu Arg His Thr Trp Gly Phe Ser Ala Lys Asp Arg Asn Asn His
    690                 695                 700
```

Leu His His Ala Ile Asp Ala Val Ile Ile Ala Tyr Ala Asn Asn Ser
705                 710                 715                 720

Ile Val Lys Ala Phe Ser Asp Phe Lys Lys Glu Gln Glu Ser Asn Ser
            725                 730                 735

Ala Glu Leu Tyr Ala Lys Lys Ile Ser Glu Leu Asp Tyr Lys Asn Lys
        740                 745                 750

Arg Lys Phe Phe Glu Pro Phe Ser Gly Phe Arg Gln Lys Val Leu Asp
    755                 760                 765

Lys Ile Asp Glu Ile Phe Val Ser Lys Pro Glu Arg Lys Lys Pro Ser
770                 775                 780

Gly Ala Leu His Glu Glu Thr Phe Arg Lys Glu Glu Phe Tyr Gln
785                 790                 795                 800

Ser Tyr Gly Gly Lys Glu Gly Val Leu Lys Ala Leu Glu Leu Gly Lys
                805                 810                 815

Ile Arg Lys Val Asn Gly Lys Ile Val Lys Asn Gly Asp Met Phe Arg
            820                 825                 830

Val Asp Ile Phe Lys His Lys Lys Thr Asn Lys Phe Tyr Ala Val Pro
        835                 840                 845

Ile Tyr Thr Met Asp Phe Ala Leu Lys Val Leu Pro Asn Lys Ala Val
    850                 855                 860

Ala Arg Ser Lys Lys Gly Glu Ile Lys Asp Trp Ile Leu Met Asp Glu
865                 870                 875                 880

Asn Tyr Glu Phe Cys Phe Ser Leu Tyr Lys Asp Ser Leu Ile Leu Ile
                885                 890                 895

Gln Thr Lys Asp Met Gln Glu Pro Glu Phe Val Tyr Tyr Asn Ala Phe
            900                 905                 910

Thr Ser Ser Thr Val Ser Leu Ile Val Ser Lys His Asp Asn Lys Phe
        915                 920                 925

Glu Thr Leu Ser Lys Asn Gln Lys Ile Leu Phe Lys Asn Ala Asn Glu
    930                 935                 940

Lys Glu Val Ile Ala Lys Ser Ile Gly Ile Gln Asn Leu Lys Val Phe
945                 950                 955                 960

Glu Lys Tyr Ile Val Ser Ala Leu Gly Glu Val Thr Lys Ala Glu Phe
                965                 970                 975

Arg Gln Arg Glu Asp Phe Lys Lys
            980

<210> SEQ ID NO 91
<211> LENGTH: 91
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91
tataatctca taagaaattt aaaaagggac taaaataaag agtttgcggg actctgcggg      60
gttacaatcc cctaaaaccg cttttaaaat t                                    91

<210> SEQ ID NO 92
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 92
attttaccat aaagaaattt aaaaagggac taaaac          36

<210> SEQ ID NO 93
<211> LENGTH: 95
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other

<400> SEQUENCE: 93
nnnnnnnnnn nnnnnnnnnn guuuuagucc cgaaagggac uaaauaaag aguuugcggg          60 acucugcggg guuacaauuc ccuaaaaccg cuuuu          95

<210> SEQ ID NO 94
<211> LENGTH: 1115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 94

Met Ser Asp Leu Val Leu Gly Leu Asp Ile Gly Ile Gly Ser Val Gly
1               5                   10                  15

Val Gly Ile Leu Asn Lys Val Thr Gly Glu Ile Ile His Lys Asn Ser
            20                  25                  30

Arg Ile Phe Pro Ala Ala Gln Ala Glu Asn Asn Leu Val Arg Arg Thr
        35                  40                  45

Asn Arg Gln Gly Arg Arg Leu Ala Arg Arg Lys Lys His Arg Arg Val
    50                  55                  60

Arg Leu Asn Arg Leu Phe Glu Glu Ser Gly Leu Ile Thr Asp Phe Thr
65                  70                  75                  80

Lys Ile Ser Ile Asn Leu Asn Pro Tyr Gln Leu Arg Val Lys Gly Leu
                85                  90                  95

Thr Asp Glu Leu Ser Asn Glu Glu Leu Phe Ile Ala Leu Lys Asn Met
            100                 105                 110

Val Lys His Arg Gly Ile Ser Tyr Leu Asp Asp Ala Ser Asp Asp Gly
        115                 120                 125

Asn Ser Ser Val Gly Asp Tyr Ala Gln Ile Val Lys Glu Asn Ser Lys
    130                 135                 140

Gln Leu Glu Thr Lys Thr Pro Gly Gln Ile Gln Leu Glu Arg Tyr Gln
145                 150                 155                 160

Thr Tyr Gly Gln Leu Arg Gly Asp Phe Thr Val Glu Lys Asp Gly Lys
                165                 170                 175

Lys His Arg Leu Ile Asn Val Phe Pro Thr Ser Ala Tyr Arg Ser Glu
            180                 185                 190

Ala Leu Arg Ile Leu Gln Thr Gln Gln Glu Phe Asn Pro Gln Ile Thr
        195                 200                 205

Asp Glu Phe Ile Asn Arg Tyr Leu Glu Ile Leu Thr Gly Lys Arg Lys
    210                 215                 220

```
Tyr Tyr His Gly Pro Gly Asn Glu Lys Ser Arg Thr Asp Tyr Gly Arg
225                 230                 235                 240

Tyr Arg Thr Ser Gly Glu Thr Leu Asp Asn Ile Phe Gly Ile Leu Ile
            245                 250                 255

Gly Lys Cys Thr Phe Tyr Pro Asp Glu Phe Arg Ala Ala Lys Ala Ser
        260                 265                 270

Tyr Thr Ala Gln Glu Phe Asn Leu Leu Asn Asp Leu Asn Asn Leu Thr
    275                 280                 285

Val Pro Thr Glu Thr Lys Lys Leu Ser Lys Glu Gln Lys Asn Gln Ile
290                 295                 300

Ile Asn Tyr Val Lys Asn Glu Lys Ala Met Gly Pro Ala Lys Leu Phe
305                 310                 315                 320

Lys Tyr Ile Ala Lys Leu Leu Ser Cys Asp Val Ala Asp Ile Lys Gly
                325                 330                 335

Tyr Arg Ile Asp Lys Ser Gly Lys Ala Glu Ile His Thr Phe Glu Ala
            340                 345                 350

Tyr Arg Lys Met Lys Thr Leu Glu Thr Leu Asp Ile Glu Gln Met Asp
        355                 360                 365

Arg Glu Thr Leu Asp Lys Leu Ala Tyr Val Leu Thr Leu Asn Thr Glu
    370                 375                 380

Arg Glu Gly Ile Gln Glu Ala Leu Glu His Glu Phe Ala Asp Gly Ser
385                 390                 395                 400

Phe Ser Gln Lys Gln Val Asp Glu Leu Val Gln Phe Arg Lys Ala Asn
                405                 410                 415

Ser Ser Ile Phe Gly Lys Gly Trp His Asn Phe Ser Val Lys Leu Met
            420                 425                 430

Met Glu Leu Ile Pro Glu Leu Tyr Glu Thr Ser Glu Glu Gln Met Thr
        435                 440                 445

Ile Leu Thr Arg Leu Gly Lys Gln Lys Thr Thr Ser Ser Ser Asn Lys
    450                 455                 460

Thr Lys Tyr Ile Asp Glu Lys Leu Leu Thr Glu Glu Ile Tyr Asn Pro
465                 470                 475                 480

Val Val Ala Lys Ser Val Arg Gln Ala Ile Lys Ile Val Asn Ala Ala
                485                 490                 495

Ile Lys Glu Tyr Gly Asp Phe Asp Asn Ile Val Ile Glu Met Ala Arg
            500                 505                 510

Glu Asn Gln Thr Thr Gln Lys Gly Gln Lys Asn Ser Arg Glu Arg Met
        515                 520                 525

Lys Arg Ile Glu Glu Gly Ile Lys Glu Leu Gly Ser Gln Ile Leu Lys
    530                 535                 540

Glu His Pro Val Glu Asn Thr Gln Leu Gln Asn Glu Lys Leu Tyr Leu
545                 550                 555                 560

Tyr Tyr Leu Gln Asn Gly Arg Asp Met Tyr Val Asp Gln Glu Leu Asp
                565                 570                 575

Ile Asn Arg Leu Ser Asp Tyr Asp Val Asp His Ile Val Pro Gln Ser
            580                 585                 590

Phe Leu Lys Asp Asp Ser Ile Asp Asn Lys Val Leu Thr Arg Ser Asp
        595                 600                 605

Lys Asn Arg Gly Lys Ser Asp Asn Val Pro Ser Glu Glu Val Val Lys
    610                 615                 620

Lys Met Lys Asn Tyr Trp Arg Gln Leu Leu Asn Ala Lys Leu Ile Thr
625                 630                 635                 640
```

Gln Arg Lys Phe Asp Asn Leu Thr Lys Ala Glu Arg Gly Gly Leu Ser
                        645                 650                 655

Glu Leu Asp Lys Ala Gly Phe Ile Lys Arg Gln Leu Val Glu Thr Arg
            660                 665                 670

Gln Ile Thr Lys His Val Ala Gln Ile Leu Asp Ser Arg Met Asn Thr
        675                 680                 685

Lys Tyr Asp Glu Asn Asp Lys Leu Ile Arg Glu Val Lys Val Ile Thr
    690                 695                 700

Leu Lys Ser Lys Leu Val Ser Asp Phe Arg Lys Asp Phe Gln Phe Tyr
705                 710                 715                 720

Lys Val Arg Glu Ile Asn Asn Tyr His His Ala His Asp Ala Tyr Leu
                725                 730                 735

Asn Ala Val Val Gly Thr Ala Leu Ile Lys Lys Tyr Pro Lys Leu Glu
            740                 745                 750

Ser Glu Phe Val Tyr Gly Asp Tyr Lys Val Tyr Asp Val Arg Lys Met
        755                 760                 765

Ile Ala Lys Ser Glu Gln Glu Ile Gly Lys Ala Thr Ala Lys Tyr Phe
    770                 775                 780

Phe Tyr Ser Asn Ile Met Asn Phe Phe Lys Thr Glu Ile Thr Leu Ala
785                 790                 795                 800

Asn Gly Glu Ile Arg Lys Arg Pro Leu Ile Glu Thr Asn Gly Glu Thr
                805                 810                 815

Gly Glu Ile Val Trp Asp Lys Gly Arg Asp Phe Ala Thr Val Arg Lys
            820                 825                 830

Val Leu Ser Met Pro Gln Val Asn Ile Val Lys Lys Thr Glu Val Gln
        835                 840                 845

Thr Gly Gly Phe Ser Lys Glu Ser Ile Leu Pro Lys Arg Asn Ser Asp
    850                 855                 860

Lys Leu Ile Ala Arg Lys Lys Asp Trp Asp Pro Lys Lys Tyr Gly Gly
865                 870                 875                 880

Phe Asp Ser Pro Thr Val Ala Tyr Ser Val Leu Val Val Ala Lys Val
                885                 890                 895

Glu Lys Gly Lys Ser Lys Lys Leu Lys Ser Val Lys Glu Leu Leu Gly
            900                 905                 910

Ile Thr Ile Met Glu Arg Ser Ser Phe Glu Lys Asn Pro Ile Asp Phe
        915                 920                 925

Leu Glu Ala Lys Gly Tyr Lys Glu Val Lys Lys Asp Leu Ile Ile Lys
    930                 935                 940

Leu Pro Lys Tyr Ser Leu Phe Glu Leu Glu Asn Gly Arg Lys Arg Met
945                 950                 955                 960

Leu Ala Ser Ala Gly Glu Leu Gln Lys Gly Asn Glu Leu Ala Leu Pro
                965                 970                 975

Ser Lys Tyr Val Asn Phe Leu Tyr Leu Ala Ser His Tyr Glu Lys Leu
            980                 985                 990

Lys Gly Ser Pro Glu Asp Asn Glu Gln Lys Gln Leu Phe Val Glu Gln
        995                 1000                1005

His Lys His Tyr Leu Asp Glu Ile Ile Glu Gln Ile Ser Glu Phe
    1010                1015                1020

Ser Lys Arg Val Ile Leu Ala Asp Ala Asn Leu Asp Lys Val Leu
    1025                1030                1035

Ser Ala Tyr Asn Lys His Arg Asp Lys Pro Ile Arg Glu Gln Ala
    1040                1045                1050

Glu Asn Ile Ile His Leu Phe Thr Leu Thr Asn Leu Gly Ala Pro

```
                  1055                1060                1065

Ala Ala Phe Lys Tyr Phe Asp Thr Thr Ile Asp Arg Lys Arg Tyr
    1070                1075                1080

Thr Ser Thr Lys Glu Val Leu Asp Ala Thr Leu Ile His Gln Ser
    1085                1090                1095

Ile Thr Gly Leu Tyr Glu Thr Arg Ile Asp Leu Ser Gln Leu Gly
    1100                1105                1110

Gly Asp
    1115

<210> SEQ ID NO 95
<211> LENGTH: 1374
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 95

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285
```

```
Leu Phe Leu Ala Ala Lys Asn Leu Ser Asp Ala Ile Leu Ser Asp
            290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
690                 695                 700
```

```
Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Thr Asn
            755                 760                 765

Glu Asp Asp Glu Lys Lys Ala Ile Gln Lys Ile Gln Lys Ala Asn Lys
770                 775                 780

Asp Glu Lys Asp Ala Ala Met Leu Lys Ala Ala Asn Gln Tyr Asn Gly
785                 790                 795                 800

Lys Ala Glu Leu Pro His Ser Val Phe His Gly His Lys Gln Leu Ala
                805                 810                 815

Thr Lys Ile Arg Leu Trp His Gln Gln Gly Glu Arg Cys Leu Tyr Thr
                820                 825                 830

Gly Lys Thr Ile Ser Ile His Asp Leu Ile Asn Asn Ser Asn Gln Phe
            835                 840                 845

Glu Val Asp His Ile Leu Pro Leu Ser Ile Thr Phe Asp Asp Ser Leu
850                 855                 860

Ala Asn Lys Val Leu Val Tyr Ala Thr Ala Asn Gln Glu Lys Gly Gln
865                 870                 875                 880

Arg Thr Pro Tyr Gln Ala Leu Asp Ser Met Asp Asp Ala Trp Ser Phe
                885                 890                 895

Arg Glu Leu Lys Ala Phe Val Arg Glu Ser Lys Thr Leu Ser Asn Lys
            900                 905                 910

Lys Lys Glu Tyr Leu Leu Thr Glu Glu Asp Ile Ser Lys Phe Asp Val
            915                 920                 925

Arg Lys Lys Phe Ile Glu Arg Asn Leu Val Asp Thr Arg Tyr Ala Ser
930                 935                 940

Arg Val Val Leu Asn Ala Leu Gln Glu His Phe Arg Ala His Lys Ile
945                 950                 955                 960

Asp Thr Lys Val Ser Val Val Arg Gly Gln Phe Thr Ser Gln Leu Arg
                965                 970                 975

Arg His Trp Gly Ile Glu Lys Thr Arg Asp Thr Tyr His His Ala
            980                 985                 990

Val Asp Ala Leu Ile Ile Ala Ala  Ser Ser Gln Leu Asn  Leu Trp Lys
            995                 1000                1005

Lys Gln Lys Asn Thr Leu Val  Ser Tyr Ser Glu Asp  Gln Leu Leu
    1010                1015                1020

Asp Ile Glu Thr Gly Glu Leu  Ile Ser Asp Asp Glu  Tyr Lys Glu
    1025                1030                1035

Ser Val Phe Lys Ala Pro Tyr  Gln His Phe Val Asp  Thr Leu Lys
    1040                1045                1050

Ser Lys Glu Phe Glu Asp Ser  Ile Leu Phe Ser Tyr  Gln Val Asp
    1055                1060                1065

Ser Lys Phe Asn Arg Lys Ile  Ser Asp Ala Thr Ile  Tyr Ala Thr
    1070                1075                1080

Arg Gln Ala Lys Val Gly Lys  Asp Lys Ala Asp Glu  Thr Tyr Val
    1085                1090                1095

Leu Gly Lys Ile Lys Asp Ile  Tyr Thr Gln Asp Gly  Tyr Asp Ala
    1100                1105                1110

Phe Met Lys Ile Tyr Lys Lys  Asp Lys Ser Lys Phe  Leu Met Tyr
```

```
                      1115                1120                1125

Arg His Asp Pro Gln Thr Phe Glu Lys Val Ile Glu Pro Ile Leu
    1130                1135                1140

Glu Asn Tyr Pro Asn Lys Gln Ile Asn Glu Lys Gly Lys Glu Val
    1145                1150                1155

Pro Cys Asn Pro Phe Leu Lys Tyr Lys Glu His Gly Tyr Ile
    1160                1165                1170

Arg Lys Tyr Ser Lys Lys Gly Asn Gly Pro Glu Ile Lys Ser Leu
    1175                1180                1185

Lys Tyr Tyr Asp Ser Lys Leu Gly Asn His Ile Asp Ile Thr Pro
    1190                1195                1200

Lys Asp Ser Asn Asn Lys Val Val Leu Gln Ser Val Ser Pro Trp
    1205                1210                1215

Arg Ala Asp Val Tyr Phe Asn Lys Thr Thr Gly Lys Tyr Glu Ile
    1220                1225                1230

Leu Gly Leu Lys Tyr Ala Asp Leu Gln Phe Glu Lys Gly Thr Gly
    1235                1240                1245

Thr Tyr Lys Ile Ser Gln Glu Lys Tyr Asn Asp Ile Lys Lys Lys
    1250                1255                1260

Glu Gly Val Asp Ser Asp Ser Glu Phe Lys Phe Thr Leu Tyr Lys
    1265                1270                1275

Asn Asp Leu Leu Leu Val Lys Asp Thr Glu Thr Lys Glu Gln Gln
    1280                1285                1290

Leu Phe Arg Phe Leu Ser Arg Thr Met Pro Lys Gln Lys His Tyr
    1295                1300                1305

Val Glu Leu Lys Pro Tyr Asp Lys Gln Lys Phe Glu Gly Gly Glu
    1310                1315                1320

Ala Leu Ile Lys Val Leu Gly Asn Val Ala Asn Ser Gly Gln Cys
    1325                1330                1335

Lys Lys Gly Leu Gly Lys Ser Asn Ile Ser Ile Tyr Lys Val Arg
    1340                1345                1350

Thr Asp Val Leu Gly Asn Gln His Ile Ile Lys Asn Glu Gly Asp
    1355                1360                1365

Lys Pro Lys Leu Asp Phe
    1370

<210> SEQ ID NO 96
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 96

His His His His His His
1               5

<210> SEQ ID NO 97
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97
```

```
Gly Gly Gly Gly Ser Gly Gly Gly Ser Gly Gly Gly Ser
1               5                   10                  15
```

<210> SEQ ID NO 98
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

```
Glu Ala Ala Ala Lys Glu Ala Ala Ala Lys Glu Ala Ala Ala Lys
1               5                   10                  15
```

<210> SEQ ID NO 99
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

```
Gly Gly Gly Gly Gly Ser Gly Gly Gly Gly Ser Gly Gly Gly Gly
1               5                   10                  15

Gly Ser
```

<210> SEQ ID NO 100
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100
gccaaattgg acgaccctcg cgg                                              23

<210> SEQ ID NO 101
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101
cgaggagacc cccgtttcgg tgg                                              23

<210> SEQ ID NO 102
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 102
cccgccgccg ccgtggctcg agg                                              23

```
<210> SEQ ID NO 103
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 103
tgagctctac gagatccaca agg                                              23

<210> SEQ ID NO 104
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 104
ctcaaaattc ataccggttg tgg                                              23

<210> SEQ ID NO 105
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 105
cgttaaacaa caaccggact tgg                                              23

<210> SEQ ID NO 106
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 106
ttcaccccgc ggcgctgaat ggg                                              23

<210> SEQ ID NO 107
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 107
accactacca gtccgtccac agg                                              23

<210> SEQ ID NO 108
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 108
agcctttctg aacacatgca cgg                                              23

<210> SEQ ID NO 109
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109
cctgccatca atgtggccat gcatgtgttc agaaaggct                             39

<210> SEQ ID NO 110
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110
cctgccatca atgtggccgt gcatgtgttc agaaaggct                             39

<210> SEQ ID NO 111
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 111
cactgcttaa gcctcgctcg agg                                              23

<210> SEQ ID NO 112
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112
tcaccagcaa tattcgctcg agg                                              23

<210> SEQ ID NO 113
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 113
caccagcaat attccgctcg agg                                              23

<210> SEQ ID NO 114
<211> LENGTH: 23
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 114
tagcaacaga catacgctcg agg                                            23

<210> SEQ ID NO 115
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115
gggcagtagt aatacgctcg agg                                            23

<210> SEQ ID NO 116
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 116
ccaattccca tacattattg tac                                            23

<210> SEQ ID NO 117
<211> LENGTH: 4677
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 117
tctttcttgc gctatgacac ttccagcaaa aggtagggcg ggctgcgaga cggcttcccg     60
gcgctgcatg caacaccgat gatgcttcga ccccccgaag ctccttcggg gctgcatggg    120
cgctccgatg ccgctccagg gcgagcgctg tttaaatagc caggccccg attgcaaaga    180 cattatagcg agctaccaaa gccatattca aacacctaga tcactaccac ttctacacag    240
gccactcgag cttgtgatcg cactccgcta aggggcgcc tcttcctctt cgtttcagtc    300
acaacccgca acatgtacc catacgatgt tccagattac gcttcgccga agaaaaagcg    360
caaggtcgaa gcgtccgaca agaagtacag catcggcctg gacatcggca ccaactctgt    420
gggctgggcc gtgatcaccg acgagtacaa ggtgcccagc aagaaattca aggtgctggg    480
caacaccgac cggcacagca tcaagaagaa cctgatcgga gccctgctgt tcgacagcgg    540
cgaaacagcc gaggccaccc ggctgaagag aaccgccaga agaagataca ccagacggaa    600
gaaccggatc tgctatctgc aagagatctt cagcaacgag atggccaagg tggacgacag    660
cttcttccac agactggaag agtccttcct ggtggaagag ataagaagc acgagcggca    720 ccccatcttc ggcaacatcg tggacgaggt ggcctaccac gagaagtacc ccaccatcta    780
ccacctgaga aagaaactgg tggacagcac cgacaaggcc gacctgcggc tgatctatct    840
ggccctggcc cacatgatca agttccgggg ccacttcctg atcgagggcg acctgaaccc    900
```

```
cgacaacagc gacgtggaca agctgttcat ccagctggtg cagacctaca accagctgtt    960
cgaggaaaac cccatcaacg ccagcggcgt ggacgccaag gccatcctgt ctgccagact   1020
gagcaagagc agacggctgg aaaatctgat cgcccagctg cccggcgaga agaagaatgg   1080
cctgttcggc aacctgattg ccctgagcct gggcctgacc cccaacttca gagcaacttt   1140
cgacctggcc gaggatgcca aactgcagct gagcaaggac acctacgacg acgacctgga   1200
caacctgctg gcccagatcg gcgaccagta cgccgacctg tttctggccg ccaagaacct   1260
gtccgacgcc atcctgctga cgacatcct gagagtgaac accgagatca ccaaggcccc   1320
cctgagcgcc tctatgatca agagatacga cgagcaccac caggacctga ccctgctgaa   1380
agctctcgtg cggcagcagc tgcctgagaa gtacaaagag atttccttcg accagagcaa   1440
gaacggctac gccggctaca ttgacggcgg agccagccag aagagttcct acaagttcat   1500
caagcccatc ctggaaaaga tggacggcac cgaggaactg ctcgtgaagc tgaacagaga   1560
ggacctgctg cggaagcagc ggaccttcga caacggcagc atcccccacc agatccacct   1620
gggagagctg cacgccattc tgcggcggca ggaagatttt tacccattcc tgaaggacaa   1680
ccgggaaaag atcgaagaga tcctgacctt ccgcatcccc tactacgtgg ccctctggc   1740
caggggaaac agcagattcg cctggatgac cagaaagagc gaggaaacca tcacccctg   1800
gaacttcgag gaagtggtgg acaagggcgc ttccgcccag agcttcatcg agcggatgac   1860
caacttcgat aagaacctgc ccaacgagaa ggtgctgccc aagcacagcc tgctgtacga   1920
gtacttcacc gtgtataacg agctgaccaa agtgaaatac gtgaccgagg aatgagaaa   1980
gcccgccttc ctgagcggcg agcagaaaaa ggccatcgtg gacctgctgt tcaagaccaa   2040
ccggaaagtg accgtgaagc agctgaaaga ggactacttc aagaaaatcg agtgcttcga   2100
ctccgtggaa atctccggcg tggaagatcg gttcaacgcc tccctgggca taccacga   2160
tctgctgaaa attatcaagg acaaggactt cctggacaat gaggaaaacg aggacattct   2220
ggaagatatc gtgctgaccc tgacactgtt tgaggacaga gagatgatcg aggaacggct   2280
gaaaacctat gcccacctgt tcgacgacaa agtgatgaag cagctgaagc ggcggagata   2340
caccggctgg ggcaggctga gccggaagct gatcaacggc atccgggaca gcagtccgg   2400
caagacaatc ctggatttcc tgaagtccga cggcttcgcc aacagaaact tcatgcagct   2460
gatccacgac gacagcctga cctttaaaga ggacatccag aaagcccagg tgtccggcca   2520
gggcgatagc ctgcacgagc acattgccaa tctggccggc agccccgcca ttaagaaggg   2580
catcctgcag acagtgaagg tggtggacga gctcgtgaaa gtgatgggcc ggcacaagcc   2640
cgagaacatc gtgatcgaaa tggccagaga gaaccagacc acccagaagg acagaagaa   2700
cagccgcgag agaatgaagc ggatcgaaga gggcatcaaa gagctgggca gccagatcct   2760
gaaagaacac cccgtggaaa acacccagct gcagaacgag aagctgtacc tgtactacct   2820
gcagaatggg cgggatatgt acgtggacca ggaactggac atcaaccggc tgtccgacta   2880
cgatgtggac catatcgtgc ctcagagctt tctgaaggac gactccatcg acaacaaggt   2940
gctgaccaga agcgacaaga accggggcaa gagcgacaac gtgccctccg aagaggtcgt   3000
gaagaagatg aagaactact ggcggcagct gctgaacgcc aagctgatta cccagagaaa   3060
gttcgacaat ctgaccaagg ccgagagagg cggcctgagc gaactggata aggccggctt   3120
catcaagaga cagctggtgg aaacccggca gatcacaaag cacgtggcac agatcctgga   3180
ctcccggatg aacactaagt acgacgagaa tgacaagctg atccgggaag tgaaagtgat   3240
caccctgaag tccaagctgg tgtccgattt ccggaaggat ttccagtttt acaaagtgcg   3300
```

```
cgagatcaac aactaccacc acgcccacga cgcctacctg aacgccgtcg tgggaaccgc    3360
cctgatcaaa aagtacccta agctggaaag cgagttcgtg tacggcgact acaaggtgta    3420
cgacgtgcgg aagatgatcg ccaagagcga gcaggaaatc ggcaaggcta ccgccaagta    3480
cttcttctac agcaacatca tgaacttttt caagaccgag attaccctgg ccaacggcga    3540
gatccggaag cggcctctga tcgagacaaa cggcgaaacc ggggagatcg tgtgggataa    3600
gggccgggat tttgccaccg tgcggaaagt gctgagcatg ccccaagtga atatcgtgaa    3660
aaagaccgag gtgcagacag gcggcttcag caaagagtct atcctgccca gaggaacag    3720 cgataagctg atcgccagaa agaaggactg ggaccctaag aagtacggcg gcttcgacag    3780
ccccaccgtg gcctattctg tgctggtggt ggccaaagtg gaaaagggca agtccaagaa    3840
actgaagagt gtgaaagagc tgctggggat caccatcatg gaaagaagca gcttcgagaa    3900
gaatcccatc gactttctgg aagccaaggg ctacaaagaa gtgaaaaagg acctgatcat    3960
caagctgcct aagtactccc tgttcgagct ggaaaacggc cggaagagaa tgctggcctc    4020
tgccggcgaa ctgcagaagg gaaacgaact ggccctgccc tccaaatatg tgaacttcct    4080
gtacctggcc agccactatg agaagctgaa gggctccccc gaggataatg agcagaaaca    4140
gctgtttgtg gaacagcaca gcactacct ggacgagatc atcgagcaga tcagcgagtt    4200
ctccaagaga gtgatcctgg ccgacgctaa tctggacaaa gtgctgtccg cctacaacaa    4260
gcaccgggat aagcccatca gagagcaggc cgagaatatc atccacctgt ttaccctgac    4320
caatctggga gccctgccg ccttcaagta ctttgacacc accatcgacc ggaagaggta    4380
caccagcacc aaagaggtgc tggacgccac cctgatccac cagagcatca ccggcctgta    4440
cgagacacgg atcgacctgt ctcagctggg aggcgacagc cccaagaaga gagaaaggt    4500 ggaggccagc taaggatccg gcaagactgg ccccgcttgg caacgcaaca gtgagcccct    4560
ccctagtgtg tttggggatg tgactatgta ttcgtgtgtt ggccaacggg tcaacccgaa    4620
cagattgata cccgccttgg catttcctgt cagaatgtaa cgtcagttga tggtact     4677
```

<210> SEQ ID NO 118
<211> LENGTH: 3150
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 118

```
tctttcttgc gctatgacac ttccagcaaa aggtagggcg ggctgcgaga cggcttcccg     60
gcgctgcatg caacaccgat gatgcttcga ccccccgaag ctccttcggg gctgcatggg    120
cgctccgatg ccgctccagg gcgagcgctg tttaaatagc caggcccccg attgcaaaga    180
cattatagcg agctaccaaa gccatattca aacacctaga tcactaccac ttctacacag    240
gccactcgag cttgtgatcg cactccgcta aggggcgcc tcttcctctt cgtttcagtc    300
acaacccgca acatgcctta agaagaagag gaaggttaac acgattaaca tcgctaagaa    360
cgacttctct gacatcgaac tggctgctat cccgttcaac actctggctg accattacgg    420
tgagcgttta gctcgcgaac agttggccct tgagcatgag tcttacgaga tgggtgaagc    480
acgcttccgc aagatgtttg agcgtcaact taaagctggt gaggttgcgg ataacgctgc    540
cgccaagcct ctcatcacta ccctactccc taagatgatt gcacgcatca acgactggtt    600
```

```
tgaggaagtg aaagctaagc gcggcaagcg cccgacagcc ttccagttcc tgcaagaaat    660
caagccggaa gccgtagcgt acatcaccat taagaccact ctggcttgcc taaccagtgc    720
tgacaataca accgttcagg ctgtagcaag cgcaatcggt cgggccattg aggacgaggc    780
tcgcttcggt cgtatccgtg accttgaagc taagcacttc aagaaaaacg ttgaggaaca    840
actcaacaag cgcgtagggc acgtctacaa gaaagcattt atgcaagttg tcgaggctga    900
catgctctct aagggtctac tcggtggcga ggcgtggtct tcgtggcata aggaagactc    960
tattcatgta ggagtacgct gcatcgagat gctcattgag tcaaccggaa tggttagctt   1020
acaccgccaa aatgctggcg tagtaggtca agactctgag actatcgaac tcgcacctga   1080
atacgctgag gctatcgcaa cccgtgcagg tgcgctggct ggcatctctc cgatgttcca   1140
accttgcgta gttcctccta agccgtggac tggcattact ggtggtggct attgggctaa   1200
cggtcgtcgt cctctggcgc tggtgcgtac tcacagtaag aaagcactga tgcgctacga   1260
agacgtttac atgcctgagg tgtacaaagc gattaacatt gcgcaaaaca ccgcatggaa   1320
aatcaacaag aaagtcctag cggtcgccaa cgtaatcacc aagtggaagc attgtccggt   1380
cgaggacatc cctgcgattg agcgtgaaga actcccgatg aaaccggaag acatcgacat   1440
gaatcctgag gctctcaccg cgtggaaacg tgctgccgct gctgtgtacc gcaaggacaa   1500
ggctcgcaag tctcgccgta tcagccttga gttcatgctt gagcaagcca ataagtttgc   1560
taaccataag gccatctggt tcccttacaa catggactgg cgcggtcgtg tttacgctgt   1620
gtcaatgttc aacccgcaag gtaacgatat gaccaaagga ctgcttacgc tggcgaaagg   1680
taaaccaatc ggtaaggaag gttactactg gctgaaaatc cacggtgcaa actgtgcggg   1740
tgtcgacaag gttccgttcc ctgagcgcat caagttcatt gaggaaaacc acgagaacat   1800
catggcttgc gctaagtctc cactggagaa cacttggtgg gctgagcaag attctccgtt   1860
ctgcttcctt gcgttctgct ttgagtacgc tggggtacag caccacggcc tgagctataa   1920 ctgctcccctt ccgctggcgt ttgacgggtc ttgctctggc atccagcact tctccgcgat   1980
gctccgagat gaggtaggtg tcgcgcggt taacttgctt cctagtgaaa ccgttcagga   2040
catctacggg attgttgcta agaaagtcaa cgagattcta caagcagacg caatcaatgg   2100
gaccgataac gaagtagtta ccgtgaccga tgagaacact ggtgaaatct ctgagaaagt   2160
caagctgggc actaaggcac tggctggtca atggctggct tacggtgtta ctcgcagtgt   2220
gactaagcgt tcagtcatga cgctggctta cgggtccaaa gagttcggct tccgtcaaca   2280
agtgctggaa gataccattc agccagctat tgattccggc aagggtctga tgttcactca   2340
gccgaatcag gctgctggat acatggctaa gctgatttgg gaatctgtga gcgtgacggt   2400
ggtagctgcg gttgaagcaa tgaactggct taagtctgct gctaagctgc tggctgctga   2460
ggtcaaagat aagaagactg gagagattct tcgcaagcgt tgcgctgtgc attgggtaac   2520
tcctgatggt ttccctgtgt ggcaggaata caagaagcct attcagacgc gcttgaacct   2580
gatgttcctc ggtcagttcc gcttacagcc taccattaac accaacaaag atagcgagat   2640
tgatgcacac aaacaggagt ctggtatcgc tcctaacttt gtacacagcc aagacggtag   2700
ccaccttcgt aagactgtag tgtgggcaca cgagaagtac ggaatcgaat cttttgcact   2760
gattcacgac tccttcggta cgattccggc tgacgctgcg aacctgttca aagcagtgcg   2820
cgaaactatg gttgacacat atgagtcttg tgatgtactg gctgatttct acgaccagtt   2880
cgctgaccag ttgcacgagt ctcaattgga caaaatgcca gcacttccgg ctaaaggtaa   2940
cttgaacctc cgtgacatct tagagtcgga cttcgcgttc gcgtaaggat ccggcaagac   3000
```

```
tggccccgct tggcaacgca acagtgagcc cctccctagt gtgtttgggg atgtgactat   3060
gtattcgtgt gttggccaac gggtcaaccc gaacagattg atacccgcct tggcatttcc   3120
tgtcagaatg taacgtcagt tgatggtact                                   3150
```

<210> SEQ ID NO 119
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (23)..(42)
<223> OTHER INFORMATION: a, c, t, g, unknown or other

<400> SEQUENCE: 119

```
gaaattaata cgactcacta tannnnnnnn nnnnnnnnnn nngttttaga gctagaaata    60
gcaagttaaa ataaggctag tccgttatca acttgaaaaa gtggcaccga gtcggtgctt   120
ttttt                                                              125
```

<210> SEQ ID NO 120
<211> LENGTH: 8452
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 120

```
tgcggtattt cacaccgcat caggtggcac ttttcgggga atgtgcgcg gaacccctat     60 ttgtttattt ttctaaatac attcaaatat gtatccgctc atgagattat caaaaaggat   120
cttcacctag atccttttaa attaaaaatg aagttttaaa tcaatctaaa gtatatatga   180
gtaaacttgg tctgacagtt accaatgctt aatcagtgag gcacctatct cagcgatctg   240
tctatttcgt tcatccatag ttgcctgact ccccgtcgtg tagataacta cgatacggga   300
gggcttacca tctggcccca gtgctgcaat gataccgcga gacccacgct caccggctcc   360
agatttatca gcaataaacc agccagccgg aagggccgag cgcagaagtg gtcctgcaac   420
tttatccgcc tccatccagt ctattaattg ttgccgggaa gctagagtaa gtagttcgcc   480
agttaatagt ttgcgcaacg ttgttgccat tgctacaggc atcgtggtgt cacgctcgtc   540
gtttggtatg gcttcattca gctccggttc ccaacgatca aggcgagtta catgatcccc   600
catgttgtgc aaaaaagcgg ttagctcctt cggtcctccg atcgttgtca gaagtaagtt   660
ggccgcagtg ttatcactca tggttatggc agcactgcat aattctctta ctgtcatgcc   720
atccgtaaga tgcttttctg tgactggtga gtactcaacc aagtcattct gagaatagtg   780
tatgcggcga ccgagttgct cttgcccggc gtcaatacgg gataataccg cgccacatag   840
cagaacttta aaagtgctca tcattggaaa acgttcttcg gggcgaaaac tctcaaggat   900
cttaccgctg ttgagatcca gttcgatgta acccactcgt gcacccaact gatcttcagc   960
atcttttact ttcaccagcg tttctgggtg agcaaaaaca ggaaggcaaa atgccgcaaa  1020
aaagggaata agggcgacac ggaaatgttg aatactcata ctcttccttt ttcaatatta  1080
ttgaagcatt tatcagggtt attgtctcat gaccaaaatc ccttaacgtg agttttcgtt  1140
```

```
ccactgagcg tcagaccccg tagaaaagat caaaggatct tcttgagatc cttttttct    1200
gcgcgtaatc tgctgcttgc aaacaaaaaa accaccgcta ccagcggtgg tttgtttgcc   1260
ggatcaagag ctaccaactc tttttccgaa ggtaactggc ttcagcagag cgcagatacc   1320
aaatactgtt cttctagtgt agccgtagtt aggccaccac ttcaagaact ctgtagcacc   1380
gcctacatac ctcgctctgc taatcctgtt accagtggct gttgccagtg gcgataagtc   1440
gtgtcttacc gggttggact caagacgata gttaccggat aaggcgcagc ggtcgggctg   1500
aacgggggt tcgtgcacac agcccagctt ggagcgaacg acctacaccg aactgagata    1560
cctacagcgt gagctatgag aaagcgccac gcttcccgaa gggagaaagg cggacaggta   1620
tccggtaagc ggcagggtcg aacaggaga gcgcacgagg gagcttccag ggggaaacgc    1680
ctggtatctt tatagtcctg tcgggtttcg ccacctctga cttgagcgtc gattttgtg    1740
atgctcgtca ggggggcgga gcctatggaa aaacgccagc aacgcggcct ttttacggtt   1800
cctggccttt tgctggcctt tgctcacat gttctttcct gcgttatccc ctgattctgt    1860
ggataaccgt attaccgcct ttgagtgagc tgataccgct cgccgcagcc gaacgaccga   1920
gcgcagcgag tcagtgagcg aggaagcggt cgctgaggct tgacatgatt ggtgcgtatg   1980
tttgtatgaa gctacaggac tgatttggcg ggctatgagg gcggggaag ctctggaagg    2040
gccgcgatgg ggcgcgcggc gtccagaagg cgccatacgg cccgctggcg gcacccatcc   2100
ggtataaaag cccgcgaccc cgaacggtga cctccacttt cagcgacaaa cgagcactta   2160
tacatacgcg actattctgc cgctatacat aaccactcag ctagcttaag atcccatcaa   2220
gcttgcatgc cgggcgcgcc agaaggacg cagccaaacc aggatgatgt ttgatggggt    2280
atttgagcac ttgcaaccct tatccggaag cccctggcc cacaaaggct aggcgccaat    2340
gcaagcagtt cgcatgcagc ccctggacg gtgcctcct gataaaccgg ccagggggcc     2400
tatgttcttt acttttttac aagagaagtc actcaacatc ttaaaatggc caggtgagtc   2460
gacgagcaag cccggcggat caggcagcgt gcttgcagat ttgacttgca acgcccgcat   2520
tgtgtcgacg aaggcttttg gctcctctgt cgctgtctca agcagcatct aaccctgcgt   2580
cgccgttttcc atttgcagga gattcgaggt accatgtacc catacgatgt tccagattac   2640
gcttcgccga agaaaaagcg caaggtcgaa gcgtccgaca agaagtacag catcggcctg   2700
gacatcggca ccaactctgt gggctgggcc gtgatcaccg acgagtacaa ggtgcccagc   2760
aagaaattca aggtgctggg caacaccgac cggcacagca tcaagaagaa cctgatcgga   2820
gccctgctgt tcgacagcgg cgaaacagcc gaggccaccc ggctgaagag aaccgccaga   2880
agaagataca ccagacggaa gaaccggatc tgctatctgc aagagatctt cagcaacgag   2940
atggccaagg tggacgacag cttcttccac agactggaag agtccttcct ggtggaagag   3000
gataagaagc acgagcggca ccccatcttc ggcaacatcg tggacgaggt ggcctaccac   3060
gagaagtacc ccaccatcta ccacctgaga aagaaactgg tggacagcac cgacaaggcc   3120
gacctgcggc tgatctatct ggccctggcc cacatgatca gttccgggg ccacttcctg    3180
atcgagggcg acctgaaccc cgacaacagc gacgtggaca agctgttcat ccagctggtg   3240
cagacctaca accagctgtt cgaggaaaac cccatcaacg ccagcggcgt ggacgccaag   3300
gccatcctgt ctgccagact gagcaagagc agacggctgg aaaatctgat cgcccagctg   3360
cccggcgaga agaagaatgg cctgttcggc aacctgattg ccctgagcct gggcctgacc   3420
cccaacttca gagcaacttt cgacctgccc gaggatgcca actgcagct gagcaaggac    3480
acctacgacg acgacctgga caacctgctg gcccagatcg gcgaccagta cgccgacctg   3540
```

```
tttctggccg ccaagaacct gtccgacgcc atcctgctga gcgacatcct gagagtgaac    3600
accgagatca ccaaggcccc cctgagcgcc tctatgatca agagatacga cgagcaccac    3660
caggacctga ccctgctgaa agctctcgtg cggcagcagc tgcctgagaa gtacaaagag    3720
attttcttcg accagagcaa gaacggctac gccggctaca ttgacggcgg agccagccag    3780
gaagagttct acaagttcat caagcccatc ctggaaaaga tggacggcac cgaggaactg    3840
ctcgtgaagc tgaacagaga ggacctgctg cggaagcagc ggaccttcga caacggcagc    3900
atcccccacc agatccacct gggagagctg cacgccattc tgcggcggca ggaagatttt    3960
tacccattcc tgaaggacaa ccgggaaaag atcgagaaga tcctgacctt ccgcatcccc    4020
tactacgtgg gccctctggc caggggaaac agcagattcg cctggatgac cagaaagagc    4080
gaggaaacca tcaccccctg gaacttcgag gaagtggtgg acaagggcgc ttccgcccag    4140
agcttcatcg agcggatgac caacttcgat aagaacctgc ccaacgagaa ggtgctgccc    4200
aagcacagcc tgctgtacga gtacttcacc gtgtataacg agctgaccaa agtgaaatac    4260
gtgaccgagg gaatgagaaa gcccgccttc ctgagcggcg agcagaaaaa ggccatcgtg    4320
gacctgctgt tcaagaccaa ccggaaagtg accgtgaagc agctgaaaga ggactacttc    4380
aagaaaatcg agtgcttcga ctccgtggaa atctccggcg tggaagatcg gttcaacgcc    4440
tccctgggca cataccacga tctgctgaaa attatcaagg acaaggactt cctggacaat    4500
gaggaaaacg aggacattct ggaagatatc gtgctgaccc tgacactgtt tgaggacaga    4560
gagatgatcg aggaacggct gaaaacctat gcccacctgt tcgacgacaa agtgatgaag    4620
cagctgaagc ggcggagata caccggctgg ggcaggctga gccggaagct gatcaacggc    4680
atccgggaca gcagtccgg caagacaatc ctggatttcc tgaagtccga cggcttcgcc    4740
aacagaaact tcatgcagct gatccacgac gacagcctga cctttaaaga ggacatccag    4800
aaagcccagg tgtccggcca gggcgatagc ctgcacgagc acattgccaa tctggccggc    4860
agccccgcca ttaagaaggg catcctgcag acagtgaagg tggtggacga gctcgtgaaa    4920
gtgatgggcc ggcacaagcc cgagaacatc gtgatcgaaa tggccagaga gaaccagacc    4980
acccagaagg gacagaagaa cagccgcgag agaatgaagc ggatcgaaga gggcatcaaa    5040
gagctgggca gccagatcct gaaagaacac cccgtggaaa acacccagct gcagaacgag    5100
aagctgtacc tgtactacct gcagaatggg cgggatatgt acgtggacca ggaactggac    5160
atcaaccggc tgtccgacta cgatgtggac catatcgtgc ctcagagctt tctgaaggac    5220
gactccatcg acaacaaggt gctgaccaga agcgacaaga accggggcaa gagcgacaac    5280
gtgccctccg aagaggtcgt gaagaagatg aagaactact ggcggcagct gctgaacgcc    5340
aagctgatta cccagagaaa gttcgacaat ctgaccaagg ccgagagagg cggcctgagc    5400
gaactggata aggccggctt catcaagaga cagctggtgg aaacccggca gatcacaaag    5460
cacgtggcac agatcctgga ctcccggatg aacactaagt acgacgagaa tgacaagctg    5520
atccgggaag tgaaagtgat cacccctgaag tccaagctgg tgtccgattt ccggaaggat    5580
ttccagtttt acaaagtgcg cgagatcaac aactaccacc acgcccacga cgcctacctg    5640
aacgccgtcg tgggaaccgc cctgatcaaa aagtacccta gctgaaaag cgagttcgtg    5700 tacggcgact acaaggtgta cgacgtgcgg aagatgatcg ccaagagcga gcaggaaatc    5760
ggcaaggcta ccgccaagta cttcttctac agcaacatca tgaactttt caagaccgag    5820 attaccctgg ccaacggcga gatccggaag cggcctctga tcgagacaaa cggcgaaacc    5880
```

```
ggggagatcg tgtgggataa gggccgggat tttgccaccg tgcggaaagt gctgagcatg   5940
ccccaagtga atatcgtgaa aaagaccgag gtgcagacag gcggcttcag caaagagtct   6000
atcctgccca agaggaacag cgataagctg atcgccagaa agaaggactg ggaccctaag   6060
aagtacggcg gcttcgacag ccccaccgtg gcctattctg tgctggtggt ggccaaagtg   6120
gaaaagggca agtccaagaa actgaagagt gtgaaagagc tgctggggat caccatcatg   6180
gaaagaagca gcttcgagaa gaatcccatc gactttctgg aagccaaggg ctacaaagaa   6240
gtgaaaaagg acctgatcat caagctgcct aagtactccc tgttcgagct ggaaaacggc   6300
cggaagagaa tgctggcctc tgccggcgaa ctgcagaagg gaaacgaact ggccctgccc   6360
tccaaatatg tgaacttcct gtacctggcc agccactatg agaagctgaa gggctccccc   6420
gaggataatg agcagaaaca gctgtttgtg gaacagcaca gcactacct ggacgagatc   6480
atcgagcaga tcagcgagtt ctccaagaga gtgatcctgg ccgacgctaa tctggacaaa   6540
gtgctgtccg cctacaacaa gcaccgggat aagcccatca gagagcaggc cgagaatatc   6600
atccacctgt ttacctgac caatctggga gcccctgccg ccttcaagta ctttgacacc   6660
accatcgacc ggaagaggta caccagcacc aaagaggtgc tggacgccac cctgatccac   6720
cagagcatca ccggcctgta cgagacacgg atcgacctgt ctcagctggg aggcgacagc   6780
cccaagaaga gagaaaggt ggaggccagc taacatatga ttcgaatgtc tttcttgcgc   6840
tatgacactt ccagcaaaag gtagggcggg ctgcagacg gcttcccggc gctgcatgca   6900
acaccgatga tgcttcgacc ccccgaagct ccttcggggc tgcatgggcg ctccgatgcc   6960
gctccagggc gagcgctgtt taaatagcca ggcccccgat tgcaaagaca ttatagcgag   7020
ctaccaaagc catattcaaa cacctagatc actaccactt ctacacaggc cactcgagct   7080
tgtgatcgca ctccgctaag ggggcgcctc ttcctcttcg tttcagtcac aacccgcaaa   7140
catgacacaa gaatccctgt tacttctcga ccgtattgat tcggatgatt cctacgcgag   7200
cctgcggaac gaccaggaat ctgggaggt gagtcgacga gcaagcccgg cggatcaggc   7260
agcgtgcttg cagatttgac ttgcaacgcc cgcattgtgt cgacgaaggc ttttggctcc   7320
tctgtcgctg tctcaagcag catctaaccc tgcgtcgccg tttccatttg cagccgctgg   7380
cccgccgagc cctggaggag ctcgggctgc cggtgccgcc ggtgctgcgg gtgcccggcg   7440
agagcaccaa ccccgtactg gtcggcgagc ccggccggt gatcaagctg ttcggcgagc   7500
actggtgcgg tccggagagc ctcgcgtcgg agtcggaggc gtacgcggtc ctggcggacg   7560
ccccggtgcc ggtgccccgc ctcctcggcc gcggcgagtc gcggcccggc accgagcct   7620
ggccgtggcc ctacctggtg atgagccgga tgaccggcac cacctggcgg tccgcgatgg   7680
acggcacgac cgaccggaac gcgctgctcg ccctggcccg cgaactcggc cgggtgctcg   7740
gccggctgca cagggtgccg ctgaccggga acaccgtgct cacccccat tccgaggtct   7800
tcccggaact gctgcgggaa cgccgcgcg cgaccgtcga ggaccaccgc gggtggggct   7860
acctctcgcc ccgctgctg gaccgcctgg aggactggct gccggacgtg gacacgctgc   7920
tggccggccg cgaaccccgg ttcgtccacg gcgacctgca cgggaccaac atcttcgtgg   7980
acctggccgc gaccgaggtc accgggatcg tcgacttcac cgacgtctat gcgggagact   8040
cccgctacag cctggtgcaa ctgcatctca acgccttccg gggcgaccgc gagatcctgg   8100
ccgcgctgct cgacggggcg cagtggaagc ggaccgagga cttcgcccgc gaactgctcg   8160
ccttcacctt cctgcacgac ttcgaggtgt tcgaggagac cccgctggat ctctccggct   8220
tcaccgatcc ggaggaactg gcgcagttcc tctggggcc gccggacacc gcccccggcg   8280
```

```
cctgataagg atccggcaag actggccccg cttggcaacg caacagtgag cccctccta      8340 gtgtgtttgg ggatgtgact atgtattcgt gtgttggcca acgggtcaac ccgaacagat    8400
tgatacccgc cttggcattt cctgtcagaa tgtaacgtca gttgatggta ct            8452
```

<210> SEQ ID NO 121
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 121

```
ccgtgccggg cgggagaccg ccatgg                                           26
```

<210> SEQ ID NO 122
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 122

```
ggcccggctg tggctgagga gc                                               22
```

<210> SEQ ID NO 123
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 123

```
cggtctcccg cccggcacgg                                                  20
```

<210> SEQ ID NO 124
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 124

```
gctcctcagc cacagccggg ccgggt                                           26
```

<210> SEQ ID NO 125
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 125

```
cgaccctgga aa                                                          12
```

<210> SEQ ID NO 126

```
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 126
ccccgccgcc accc                                                      14

<210> SEQ ID NO 127
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 127
tttccagggt cgccatgg                                                  18

<210> SEQ ID NO 128
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 128
ggcggcgggg                                                           10

<210> SEQ ID NO 129
<211> LENGTH: 20
<212> TYPE: DNA
<213> ORGANISM: Homo sapiens

<400> SEQUENCE: 129
acccttgtta gccacctccc                                                20

<210> SEQ ID NO 130
<211> LENGTH: 20
<212> TYPE: DNA
<213> ORGANISM: Homo sapiens

<400> SEQUENCE: 130
gaacgcagtg ctcttcgaag                                                20

<210> SEQ ID NO 131
<211> LENGTH: 20
<212> TYPE: DNA
<213> ORGANISM: Homo sapiens

<400> SEQUENCE: 131
ctcacgccct gctccgtgta                                                20

<210> SEQ ID NO 132
<211> LENGTH: 20
<212> TYPE: DNA
<213> ORGANISM: Homo sapiens

<400> SEQUENCE: 132
ggcgacaact acttcctggt                                                20
```

```
<210> SEQ ID NO 133
<211> LENGTH: 20
<212> TYPE: DNA
<213> ORGANISM: Homo sapiens

<400> SEQUENCE: 133
ctcacgccct gctccgtgta                                              20

<210> SEQ ID NO 134
<211> LENGTH: 20
<212> TYPE: DNA
<213> ORGANISM: Homo sapiens

<400> SEQUENCE: 134
gggcgacaac tacttcctgg                                              20

<210> SEQ ID NO 135
<211> LENGTH: 20
<212> TYPE: DNA
<213> ORGANISM: Homo sapiens

<400> SEQUENCE: 135
cctcttcagg gccggggtgg                                              20

<210> SEQ ID NO 136
<211> LENGTH: 20
<212> TYPE: DNA
<213> ORGANISM: Homo sapiens

<400> SEQUENCE: 136
gaggacccag gtggaactgc                                              20

<210> SEQ ID NO 137
<211> LENGTH: 20
<212> TYPE: DNA
<213> ORGANISM: Homo sapiens

<400> SEQUENCE: 137
tcagctccag gcggtcctgg                                              20

<210> SEQ ID NO 138
<211> LENGTH: 20
<212> TYPE: DNA
<213> ORGANISM: Homo sapiens

<400> SEQUENCE: 138
agcagcagca gcagtggcag                                              20

<210> SEQ ID NO 139
<211> LENGTH: 20
<212> TYPE: DNA
<213> ORGANISM: Homo sapiens

<400> SEQUENCE: 139
tgggcaccgt cagctccagg                                              20

<210> SEQ ID NO 140
<211> LENGTH: 20
<212> TYPE: DNA
<213> ORGANISM: Homo sapiens

<400> SEQUENCE: 140
```
cagcagtggc agcggccacc                                           20

<210> SEQ ID NO 141
<211> LENGTH: 20
<212> TYPE: DNA
<213> ORGANISM: Homo sapiens

<400> SEQUENCE: 141
acctctcccc tggccctcat                                           20

<210> SEQ ID NO 142
<211> LENGTH: 20
<212> TYPE: DNA
<213> ORGANISM: Homo sapiens

<400> SEQUENCE: 142
ccaggaccgc ctggagctga                                           20

<210> SEQ ID NO 143
<211> LENGTH: 20
<212> TYPE: DNA
<213> ORGANISM: Homo sapiens

<400> SEQUENCE: 143
ccgtcagctc caggcggtcc                                           20

<210> SEQ ID NO 144
<211> LENGTH: 20
<212> TYPE: DNA
<213> ORGANISM: Homo sapiens

<400> SEQUENCE: 144
agcagcagca gcagtggcag                                           20

<210> SEQ ID NO 145
<211> LENGTH: 20
<212> TYPE: DNA
<213> ORGANISM: Homo sapiens

<400> SEQUENCE: 145
atgtgccaag caaagcctca                                           20

<210> SEQ ID NO 146
<211> LENGTH: 20
<212> TYPE: DNA
<213> ORGANISM: Homo sapiens

<400> SEQUENCE: 146
ttcggtcatg cccgtggatg                                           20

<210> SEQ ID NO 147
<211> LENGTH: 20
<212> TYPE: DNA
<213> ORGANISM: Homo sapiens

<400> SEQUENCE: 147
gtcgttgaaa ttcatcgtac                                           20

<210> SEQ ID NO 148
<211> LENGTH: 20
<212> TYPE: DNA
<213> ORGANISM: Homo sapiens

<400> SEQUENCE: 148
accacctgtg aagagtttcc 20

<210> SEQ ID NO 149
<211> LENGTH: 20
<212> TYPE: DNA
<213> ORGANISM: Homo sapiens

<400> SEQUENCE: 149
cgtcgttgaa attcatcgta 20

<210> SEQ ID NO 150
<211> LENGTH: 20
<212> TYPE: DNA
<213> ORGANISM: Homo sapiens

<400> SEQUENCE: 150
accacctgtg aagagtttcc 20

<210> SEQ ID NO 151
<211> LENGTH: 20
<212> TYPE: DNA
<213> ORGANISM: Mus musculus

<400> SEQUENCE: 151
gaacgcagtg cttttcgagg 20

<210> SEQ ID NO 152
<211> LENGTH: 20
<212> TYPE: DNA
<213> ORGANISM: Mus musculus

<400> SEQUENCE: 152
acccttgttg gccacctccc 20

<210> SEQ ID NO 153
<211> LENGTH: 20
<212> TYPE: DNA
<213> ORGANISM: Mus musculus

<400> SEQUENCE: 153
ggtgacaact actatctggt 20

<210> SEQ ID NO 154
<211> LENGTH: 20
<212> TYPE: DNA
<213> ORGANISM: Mus musculus

<400> SEQUENCE: 154
ctcacaccct gctccgtgta 20

<210> SEQ ID NO 155
<211> LENGTH: 20
<212> TYPE: DNA
<213> ORGANISM: Mus musculus

<400> SEQUENCE: 155
gggtgacaac tactatctgg 20

<210> SEQ ID NO 156
<211> LENGTH: 20
<212> TYPE: DNA
<213> ORGANISM: Mus musculus -continued

```
<400> SEQUENCE: 156
ctcacaccct gctccgtgta                                                  20

<210> SEQ ID NO 157
<211> LENGTH: 20
<212> TYPE: DNA
<213> ORGANISM: Mus musculus

<400> SEQUENCE: 157
cgagaacgca gtgcttttcg                                                  20

<210> SEQ ID NO 158
<211> LENGTH: 20
<212> TYPE: DNA
<213> ORGANISM: Mus musculus

<400> SEQUENCE: 158
acccttgttg gccacctccc                                                  20

<210> SEQ ID NO 159
<211> LENGTH: 20
<212> TYPE: DNA
<213> ORGANISM: Mus musculus

<400> SEQUENCE: 159
atgagccaag caaatcctca                                                  20

<210> SEQ ID NO 160
<211> LENGTH: 20
<212> TYPE: DNA
<213> ORGANISM: Mus musculus

<400> SEQUENCE: 160
ttccgtcatg cccgtggaca                                                  20

<210> SEQ ID NO 161
<211> LENGTH: 20
<212> TYPE: DNA
<213> ORGANISM: Mus musculus

<400> SEQUENCE: 161
cttcgttgaa aaccattgta                                                  20

<210> SEQ ID NO 162
<211> LENGTH: 20
<212> TYPE: DNA
<213> ORGANISM: Mus musculus

<400> SEQUENCE: 162
ccacctctga agagtttcct                                                  20

<210> SEQ ID NO 163
<211> LENGTH: 20
<212> TYPE: DNA
<213> ORGANISM: Mus musculus

<400> SEQUENCE: 163
cttcgttgaa aaccattgta                                                  20

<210> SEQ ID NO 164
<211> LENGTH: 20
<212> TYPE: DNA
<213> ORGANISM: Mus musculus
```

```
<400> SEQUENCE: 164
accacctctg aagagtttcc                                               20

<210> SEQ ID NO 165
<211> LENGTH: 20
<212> TYPE: DNA
<213> ORGANISM: Mus musculus

<400> SEQUENCE: 165
cttccactca ctctgcgatt                                               20

<210> SEQ ID NO 166
<211> LENGTH: 20
<212> TYPE: DNA
<213> ORGANISM: Mus musculus

<400> SEQUENCE: 166
accatgtctc agtgtcaagc                                               20

<210> SEQ ID NO 167
<211> LENGTH: 20
<212> TYPE: DNA
<213> ORGANISM: Mus musculus

<400> SEQUENCE: 167
ggcggcaaca gcggcaacag                                               20

<210> SEQ ID NO 168
<211> LENGTH: 20
<212> TYPE: DNA
<213> ORGANISM: Mus musculus

<400> SEQUENCE: 168
actgctctgc gtggctgcgg                                               20

<210> SEQ ID NO 169
<211> LENGTH: 20
<212> TYPE: DNA
<213> ORGANISM: Mus musculus

<400> SEQUENCE: 169
ccgcagccac gcagagcagt                                               20

<210> SEQ ID NO 170
<211> LENGTH: 20
<212> TYPE: DNA
<213> ORGANISM: Mus musculus

<400> SEQUENCE: 170
gcacctctcc tcgccccgat                                               20

<210> SEQ ID NO 171
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 171
gagggcctat ttcccatgat tcc                                           23
```

```
<210> SEQ ID NO 172
<211> LENGTH: 126
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (84)..(102)
<223> OTHER INFORMATION: a, c, t, g, unknown or other

<400> SEQUENCE: 172
aaaaaaagca ccgactcggt gccactttt caagttgata acggactagc cttattttaa      60
cttgctattt ctagctctaa aacnnnnnnn nnnnnnnnnn nnccggtgtt tcgtcctttc    120
cacaag                                                              126

<210> SEQ ID NO 173
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (6)..(24)
<223> OTHER INFORMATION: a, c, t, g, unknown or other

<400> SEQUENCE: 173
caccgnnnnn nnnnnnnnnn nnnn                                           24

<210> SEQ ID NO 174
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (5)..(23)
<223> OTHER INFORMATION: a, c, t, g, unknown or other

<400> SEQUENCE: 174
aaacnnnnnn nnnnnnnnnn nnnc                                           24

<210> SEQ ID NO 175
<211> LENGTH: 126
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 175
aaaaaaagca ccgactcggt gccactttt caagttgata acggactagc cttattttaa      60
cttgctattt ctagctctaa aaccccctagt cattggaggt gaccggtgtt tcgtcctttc    120
cacaag                                                              126

<210> SEQ ID NO 176
<211> LENGTH: 24
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 176
caccgtcacc tccaatgact aggg                                           24

<210> SEQ ID NO 177
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 177
aaacccctag tcattggagg tgac                                           24

<210> SEQ ID NO 178
<211> LENGTH: 192
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 178
cagaagaaga agggctccca tcacatcaac cggtggcgca ttgccacgaa gcaggccaat     60
ggggaggaca tcgatgtcac ctccaatgac aagcttgcta gcggtgggca accacaaacc    120
cacgagggca gagtgctgct tgctgctggc caggccctg cgtgggccca agctggactc     180
tggccactcc ct                                                       192

<210> SEQ ID NO 179
<211> LENGTH: 192
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 179
agggagtggc cagagtccag cttgggccca cgcaggggcc tggccagcag caagcagcac     60
tctgccctcg tgggtttgtg gttgcccacc gctagcaagc ttgtcattgg aggtgacatc    120
gatgtcctcc ccattggcct gcttcgtggc aatgcgccac cggttgatgt gatgggagcc    180
cttcttcttc tg                                                       192

<210> SEQ ID NO 180
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 180 ccatccccctt ctgtgaatgt                                               20
```

<210> SEQ ID NO 181
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 181
ggagattgga gacacggaga                                               20

<210> SEQ ID NO 182
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 182
ggctccctgg gttcaaagta                                               20

<210> SEQ ID NO 183
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 183 agagggtct ggatgtcgta a                                              21

<210> SEQ ID NO 184
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 184
cgccagggtt ttcccagtca cgac                                          24

<210> SEQ ID NO 185
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 185
gagggtctcg tccttgcggc cgcgctagcg agggcctatt tcccatgatt c            51

<210> SEQ ID NO 186
<211> LENGTH: 133
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

```
<220> FEATURE:
<221> NAME/KEY: modified_base
<222> LOCATION: (95)..(114)
<223> OTHER INFORMATION: a, c, t, g, unknown or other

<400> SEQUENCE: 186
ctcggtctcg gtaaaaaagc accgactcgg tgccactttt tcaagttgat aacggactag    60
ccttatttta acttgctatt tctagctcta aaacnnnnnn nnnnnnnnnn nnnnggtgtt   120
tcgtcctttc cac                                                      133

<210> SEQ ID NO 187
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 187
gagggtctct ttaccggtga gggcctattt cccatgattc c                        41

<210> SEQ ID NO 188
<211> LENGTH: 133
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (95)..(114)
<223> OTHER INFORMATION: a, c, t, g, unknown or other

<400> SEQUENCE: 188
ctcggtctcc tcaaaaaagc accgactcgg tgccactttt tcaagttgat aacggactag    60
ccttatttta acttgctatt tctagctcta aaacnnnnnn nnnnnnnnnn nnnnggtgtt   120
tcgtcctttc cac                                                      133

<210> SEQ ID NO 189
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 189
gagggtctct ttgagctcga gggcctattt cccatgattc                          40

<210> SEQ ID NO 190
<211> LENGTH: 133
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (96)..(115)
<223> OTHER INFORMATION: a, c, t, g, unknown or other

<400> SEQUENCE: 190
```

```
ctcggtctcg cgtaaaaaag caccgactcg gtgccacttt ttcaagttga taacggacta    60
gccttatttt aacttgctat ttctagctct aaaacnnnnn nnnnnnnnnn nnnnnggtgt   120
ttcgtccttt cca                                                     133
```

<210> SEQ ID NO 191
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 191

```
gagggtctct tacgcgtgtg tctagac                                       27
```

<210> SEQ ID NO 192
<211> LENGTH: 98
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 192

```
ctcggtctca aggacaggga agggagcagt ggttcacgcc tgtaatccca gcaatttggg    60
aggccaaggt gggtagatca cctgagatta ggagttgc                           98
```

<210> SEQ ID NO 193
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 193

```
cctgtccttg cggccgcgct agcgagggcc                                    30
```

<210> SEQ ID NO 194
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 194

```
cacgcggccg caaggacagg gaagggagca g                                  31
```

<210> SEQ ID NO 195
<211> LENGTH: 327
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 195

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Ser
225                 230                 235                 240

Gly Leu Arg Ser Arg Glu Glu Glu Glu Thr Asp Ser Arg Met Pro
                245                 250                 255

His Leu Asp Ser Pro Gly Ser Ser Gln Pro Arg Arg Ser Phe Leu Ser
            260                 265                 270

Arg Val Ile Arg Ala Ala Leu Pro Leu Gln Leu Leu Leu Leu Leu
        275                 280                 285

Leu Leu Leu Ala Cys Leu Leu Pro Ala Ser Glu Asp Asp Tyr Ser Cys
290                 295                 300

Thr Gln Ala Asn Asn Phe Ala Arg Ser Phe Tyr Pro Met Leu Arg Tyr
305                 310                 315                 320

Thr Asn Gly Pro Pro Pro Thr
                325

<210> SEQ ID NO 196
<211> LENGTH: 3243
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 196
accggtgcca ccatgtaccc atacgatgtt ccagattacg cttcgccgaa gaaaaagcgc    60
aaggtcgaag cgtccatgaa aggaactac attctggggc tggacatcgg gattacaagc   120
gtggggtatg ggattattga ctatgaaaca agggacgtga tcgacgcagg cgtcagactg   180
ttcaaggagg ccaacgtgga aaacaatgag ggacggagaa gcaagagggg agccaggcgc   240

```
ctgaaacgac ggagaaggca cagaatccag agggtgaaga aactgctgtt cgattacaac    300
ctgctgaccg accattctga gctgagtgga attaatcctt atgaagccag ggtgaaaggc    360
ctgagtcaga agctgtcaga ggaagagttt ccgcagctc tgctgcacct ggctaagcgc     420
cgaggagtgc ataacgtcaa tgaggtggaa gaggacaccg gcaacgagct gtctacaaag    480
gaacagatct cacgcaatag caaagctctg gaagagaagt atgtcgcaga gctgcagctg    540
gaacggctga gaaagatgg cgaggtgaga gggtcaatta ataggttcaa gacaagcgac     600
tacgtcaaag aagccaagca gctgctgaaa gtgcagaagg cttaccacca gctggatcag    660
agcttcatcg atacttatat cgacctgctg gagactcgga gaacctacta tgagggacca    720
ggagaaggga gcccttcgg atggaaagac atcaaggaat ggtacgagat gctgatggga    780
cattgcacct attttccaga agagctgaga agcgtcaagt acgcttataa cgcagatctg    840
tacaacgccc tgaatgacct gaacaacctg gtcatcacca gggatgaaaa cgagaaactg    900
gaatactatg agaagttcca gatcatcgaa aacgtgttta gcagaagaa aaagcctaca    960
ctgaaacaga ttgctaagga gatcctggtc aacgaagagg acatcaaggg ctaccgggtg   1020
acaagcactg aaaaccaga gttcaccaat ctgaaagtgt atcacgatat taaggacatc    1080
acagcacgga agaaatcat tgagaacgcc gaactgctgg atcagattgc taagatcctg    1140
actatctacc agagctccga ggacatccag gaagagctga ctaacctgaa cagcgagctg    1200
acccaggaag agatcgaaca gattagtaat ctgaaggggt acaccggaac acacaacctg    1260
tccctgaaag ctatcaatct gattctggat gagctgtggc atacaaacga caatcagatt    1320
gcaatctta accggctgaa gctggtccca aaaaggtgg acctgagtca gcagaaagag    1380
atcccaacca cactggtgga cgatttcatt ctgtcacccg tggtcaagcg gagcttcatc    1440
cagagcatca aagtgatcaa cgccatcatc aagaagtacg gcctgcccaa tgatatcatt    1500
atcgagctgg ctagggagaa aacagcaag gacgcacaga gatgatcaa tgagatgcag    1560
aaacgaaacc ggcagaccaa tgaacgcatt gaagagatta ccgaactac cgggaaagag    1620
aacgcaaagt acctgattga aaaaatcaag ctgcacgata tgcaggaggg aaagtgtctg    1680
tattctctgg aggccatccc cctggaggac ctgctgaaca atccattcaa ctacgaggtc    1740
gatcatatta tccccagaag cgtgtccttc gacaattcct ttaacaacaa ggtgctggtc    1800
aagcaggaag agaactctaa aaagggcaat aggactcctt ccagtacct gtctagttca    1860
gattccaaga tctcttacga aacctttaaa aagcacattc tgaatctggc caaaggaaag    1920
ggccgcatca gcaagaccaa aaaggagtac ctgctggaag agcgggacat caacagattc    1980
tccgtccaga aggatttat taaccggaat ctggtggaca aagatacgc tactcgcggc    2040
ctgatgaatc tgctgcgatc ctatttccgg gtgaacaatc tggatgtgaa agtcaagtcc    2100
atcaacggcg gttcacatc ttttctgagg cgcaaatgga gtttaaaaa ggagcgcaac    2160
aaagggtaca agcaccatgc cgaagatgct ctgattatcg caaatgccga cttcatcttt    2220
aaggagtgga aaagctgga caaagccaag aaagtgatgg agaaccagat gttcgaagag    2280
aagcaggccg aatctatgcc cgaaatcgag acagaacagg agtacaagga gatttcatc    2340
actcctcacc agatcaagca tatcaaggat ttcaaggact acagtactc tcaccgggtg   2400
gataaaagc ccaacagaga gctgatcaat gacaccctgt atagtacaag aaaagacgat    2460
aagggggaata ccctgattgt gaacaatctg aacggactgt acgacaaaga taatgacaag    2520
ctgaaaaagc tgatcaacaa aagtcccgag aagctgctga tgtaccacca tgatcctcag    2580
```

-continued

| | |
|---|---|
| acatatcaga aactgaagct gattatggag cagtacggcg acgagaagaa cccactgtat | 2640 |
| aagtactatg aagagactgg gaactacctg accaagtata gcaaaaagga taatggcccc | 2700 |
| gtgatcaaga agatcaagta ctatgggaac aagctgaatg cccatctgga catcacagac | 2760 |
| gattacccta acagtcgcaa caaggtggtc aagctgtcac tgaagccata cagattcgat | 2820 |
| gtctatctgg acaacggcgt gtataaattt gtgactgtca agaatctgga tgtcatcaaa | 2880 |
| aaggagaact actatgaagt gaatagcaag tgctacgaag aggctaaaaa gctgaaaaag | 2940 |
| attagcaacc aggcagagtt catcgcctcc ttttacaaca acgacctgat taagatcaat | 3000 |
| ggcgaactgt atagggtcat cggggtgaac aatgatctgc tgaaccgcat tgaagtgaat | 3060 |
| atgattgaca tcacttaccg agagtatctg gaaaacatga atgataagcg ccccctcga | 3120 |
| attatcaaaa caattgcctc taagactcag agtatcaaaa agtactcaac cgacattctg | 3180 |
| ggaaacctgt atgaggtgaa gagcaaaaag caccctcaga ttatcaaaaa gggctaagaa | 3240 |
| ttc | 3243 |

<210> SEQ ID NO 197
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 197
ccaggcttgg                                                             10

<210> SEQ ID NO 198
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 198
ggagctggtc tgttggagaa                                                  20

<210> SEQ ID NO 199
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 199
tcccaatcca taatcccacg tt                                               22

<210> SEQ ID NO 200
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 200
caggagggcc aggagatttg                                                  20

```
<210> SEQ ID NO 201
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 201
tgaaatcgag gatctgggcg                                                  20

<210> SEQ ID NO 202
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 202
caaaggaccc cagtcactcc                                                  20

<210> SEQ ID NO 203
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 203
gaggagggag caggaaagtg                                                  20

<210> SEQ ID NO 204
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 204
gacacttccc aaaggacccc                                                  20

<210> SEQ ID NO 205
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 205
tgagagccgt tccctctttg                                                  20

<210> SEQ ID NO 206
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

Synthetic primer"

<400> SEQUENCE: 206
gacaggggca aagtgagtga                                              20

<210> SEQ ID NO 207
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 207
ttcatggttt cggaggccc                                               19

<210> SEQ ID NO 208
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 208
tgagtgacct gcttttgggg                                              20

<210> SEQ ID NO 209
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 209
gttcatggtt tcggaggccc                                              20

<210> SEQ ID NO 210
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 210
ggaggacaaa gtacaaacgg c                                            21

<210> SEQ ID NO 211
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 211
atcgatgtcc tccccattgg                                              20

<210> SEQ ID NO 212
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 212
tgggagagag accccttctt                                                    20

<210> SEQ ID NO 213
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 213
tcctgctctc acttagactt tctc                                               24

<210> SEQ ID NO 214
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 214
gacattcctc ctgagggaaa a                                                  21

<210> SEQ ID NO 215
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 215
gataaaatgt attccttctc accattc                                            27

<210> SEQ ID NO 216
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 216
ccagactcag taaagcctgg a                                                  21

<210> SEQ ID NO 217
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 217
```
tggccccagt ctctcttcta                                          20

<210> SEQ ID NO 218
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 218
cacggccttt gcaaatagag                                          20

<210> SEQ ID NO 219
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 219
catgacttgg cctttgtagg a                                        21

<210> SEQ ID NO 220
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 220
tggggttaca gaaagaatag gg                                       22

<210> SEQ ID NO 221
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 221
ttctgagggc tgctacctgt                                          20

<210> SEQ ID NO 222
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 222
tgaagcaact ccagtcccaa                                          20

<210> SEQ ID NO 223
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 223
cccggctctg gctaaagag                                                19

<210> SEQ ID NO 224
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 224
tgggtgtgca catctaagga                                               20

<210> SEQ ID NO 225
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 225
ccactgagtc aactgtaagc a                                             21

<210> SEQ ID NO 226
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 226
gcagaggaat atgtgacatg agg                                           23

<210> SEQ ID NO 227
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 227
tactccctgc tgtcctctcc                                               20

<210> SEQ ID NO 228
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 228
ttcctggcca agtcgattcc                                               20

<210> SEQ ID NO 229

-continued

<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 229
ggataccagc atgggctacc                                                    20

<210> SEQ ID NO 230
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 230
actcttgaga ttggaacggg a                                                  21

<210> SEQ ID NO 231
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 231
ccacacttat ctacgcccca                                                    20

<210> SEQ ID NO 232
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 232
agccagaaga gaacatccac g                                                  21

<210> SEQ ID NO 233
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 233
agttgctctt tgttgagagg ga                                                 22

<210> SEQ ID NO 234
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 234

```
tgaccgggga cctatgtatg a                                              21
```

<210> SEQ ID NO 235
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 235

```
acaagacttg ctcttactta cttga                                          25
```

<210> SEQ ID NO 236
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 236

```
ggatggaggg agtttgctcc tgg                                            23
```

<210> SEQ ID NO 237
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 237

```
cgccctcccc accccgcctc cgg                                            23
```

<210> SEQ ID NO 238
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 238

```
taccccccac accccgcctc tgg                                            23
```

<210> SEQ ID NO 239
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 239

```
gggcccctcc accccgcctc tgg                                            23
```

<210> SEQ ID NO 240
<211> LENGTH: 23
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 240 ctaccctcc accccgcctc cgg                                              23

<210> SEQ ID NO 241
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 241
aggttgttgc tgttgcttta ca                                              22

<210> SEQ ID NO 242
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 242
aggtttcacc tggtttgggg                                                 20

<210> SEQ ID NO 243
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 243
agcacggtta atttgcatac atct                                            24

<210> SEQ ID NO 244
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 244
tccaggcagt tttcttctgg t                                               21

<210> SEQ ID NO 245
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 245
ccagagagcc agcattccaa                                                 20
```

```
<210> SEQ ID NO 246
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 246
agggctccca ctagaagagg                                                    20

<210> SEQ ID NO 247
<211> LENGTH: 352
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (250)..(269)
<223> OTHER INFORMATION: a, c, t, g, unknown or other

<400> SEQUENCE: 247
gagggcctat ttcccatgat tccttcatat ttgcatatac gatacaaggc tgttagagag        60
ataattggaa ttaatttgac tgtaaacaca aagatattag tacaaaatac gtgacgtaga       120
aagtaataat ttcttgggta gttttgcagtt ttaaaattat gttttaaaat ggactatcat      180
atgcttaccg taacttgaaa gtatttcgat ttccttggctt tatatatctt gtggaaagga     240
cgaaacaccn nnnnnnnnn nnnnnnnnng ttttagagct agaaatagca agttaaaata       300
aggctagtcc gttatcaact tgaaaaagtg gcaccgagtc ggtgcttttt tt              352

<210> SEQ ID NO 248
<211> LENGTH: 4269
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 248
atggactata aggaccacga cggagactac aaggatcatg atattgatta caaagacgat        60
gacgataaga tggccccaaa gaagaagcgg aaggtcggta tccacggagt cccagcagcc      120
gacaagaagt acagcatcgg cctggacatc ggcaccaact ctgtgggctg ggccgtgatc      180
accgacgagt acaaggtgcc cagcaagaaa ttcaaggtgc tgggcaacac cgaccggcac     240
agcatcaaga gaacctgat cggagccctg ctgttcgaca cggcgaaac agccgaggcc        300 acccggctga agagaaccgc cagaagaaga taccagac ggaagaaccg gatctgctat        360
ctgcaagaga tcttcagcaa cgagatggcc aaggtggacg acagcttctt ccacagactg      420
gaagagtcct tcctggtgga agaggataag aagcacgagc ggcaccccat cttcggcaac      480
atcgtggacg aggtggccta ccacgagaag tacccctcca tctaccacct gagaagaaaa     540
ctggtggaca gcaccgacaa ggccgacctg cggctgatct atctggccct ggcccacatg      600
atcaagttcc ggggccactt cctgatcgag ggcgacctga accccgacaa cagcgacgtg      660
gacaagctgt tcatccaggct ggtgcagacc tacaaccagc tgttcgagga aaaccccatc    720
aacgccagcg gcgtggacgc caaggccatc ctgtctgcca gactgagcaa gagcagacgg     780
```

```
ctggaaaatc tgatcgccca gctgcccggc gagaagaaga atggcctgtt cggcaacctg      840
attgccctga gcctgggcct gacccccaac ttcaagagca acttcgacct ggccgaggat      900
gccaaactgc agctgagcaa ggacacctac gacgacgacc tggacaacct gctggcccag      960
atcggcgacc agtacgccga cctgtttctg gccgccaaga acctgtccga cgccatcctg     1020
ctgagcgaca tcctgagagt gaacaccgag atcaccaagg ccccctgag cgcctctatg      1080
atcaagagat acgacgagca ccaccaggac ctgaccctgc tgaaagctct cgtgcggcag     1140
cagctgcctg agaagtacaa agagattttc ttcgaccaga gcaagaacgg ctacgccggc     1200
tacattgacg gcggagccag ccaggaagag ttctacaagt tcatcaagcc catcctggaa     1260
aagatggacg gcaccgagga actgctcgtg aagctgaaca gagaggacct gctgcggaag     1320
cagcggacct tcgacaacgg cagcatcccc accagatcc acctgggaga gctgcacgcc     1380
attctgcggc ggcaggaaga ttttacccca ttcctgaagg acaaccggga aaagatcgag     1440
aagatcctga ccttccgcat ccctactac gtgggccctc tggccagggg aaacagcaga     1500
ttcgcctgga tgaccagaaa gagcgaggaa accatcaccc cctggaactt cgaggaagtg     1560
gtggacaagg gcgcttccgc ccagagcttc atcgagcgga tgaccaactt cgataagaac     1620
ctgcccaacg agaaggtgct gcccaagcac agcctgctgt acgagtactt caccgtgtat     1680
aacgagctga ccaaagtgaa atacgtgacc gagggaatga gaaagcccgc cttcctgagc     1740
ggcgagcaga aaaaggccat cgtggacctg ctgttcaaga ccaaccggaa agtgaccgtg     1800
aagcagctga aggaggacta cttcaagaaa atcgagtgct tcgactccgt ggaaatctcc     1860
ggcgtggaag atcggttcaa cgcctccctg ggcacatacc acgatctgct gaaaattatc     1920
aaggacaagg acttcctgga caatgaggaa aacgaggaca ttctggaaga tatcgtgctg     1980
accctgcacac tgtttgagga cagagagatg atcgaggaac ggctgaaaac ctatgcccac     2040
ctgttcgacg acaaagtgat gaagcagctg aagcggcgga gatacaccgg ctggggcagg     2100
ctgagccgga agctgatcaa cggcatccgg gacaagcagt ccggcaagac aatcctggat     2160
ttcctgaagt ccgacggctt cgccaacaga aacttcatgc agctgatcca cgacgacagc     2220
ctgacctttta agaggacat ccagaaagcc caggtgtccg gccagggcga tagcctgcac     2280
gagcacattg ccaatctggc cggcagcccc gccattaaga agggcatcct gcagacagtg     2340
aaggtggtgg acgagctcgt gaaagtgatg ggccggcaca gcccgagaa catcgtgatc     2400
gaaatggcca gagagaacca gaccacccag aagggacaga agaacagccg cgagagaatg     2460
aagcggatcg aagagggcat caaagagctg ggcagccaga tcctgaaaga acaccccgtg     2520
gaaaacaccc agctgcagaa cgagaagctg tacctgtact acctgcagaa tgggcgggat     2580
atgtacgtgg accaggaact ggacatcaac cggctgtccg actacgatgt ggaccatatc     2640
gtgcctcaga gctttctgaa ggacgactcc atcgacaaca aggtgctgac cagaagcgac     2700
aagaaccggg gcaagagcga caacgtgccc tccgaagagg tcgtgaagaa gatgaagaac     2760
tactggcggc agctgctgaa cgccaagctg attacccaga gaaagttcga caatctgacc     2820
aaggccgaga aggcggcct gagcgaactg gataaggccg gcttcatcaa gagacagctg     2880
gtggaaaccc ggcagatcac aaagcacgtg gcacagatcc tggactcccg gatgaacact     2940
aagtacgacg agaatgacaa gctgatccgg gaagtgaaag tgatcaccct gaagtccaag     3000
ctggtgtccg atttccggaa ggatttccag ttttacaaag tgcgcgagat caacaactac     3060
caccacgccc acgacgccta cctgaacgcc gtcgtgggaa ccgccctgat caaaaagtac     3120
cctaagctgg aaagcgagtt cgtgtacggc gactacaagg tgtacgacgt gcggaagatg     3180
```

```
atcgccaaga gcgagcagga aatcggcaag gctaccgcca agtacttctt ctacagcaac    3240
atcatgaact ttttcaagac cgagattacc ctggccaacg gcgagatccg gaagcggcct    3300
ctgatcgaga caaacggcga aaccggggag atcgtgtggg ataagggccg ggattttgcc    3360
accgtgcgga aagtgctgag catgcccaa  gtgaatatcg tgaaaagac  cgaggtgcag    3420
```

```
atcgccaaga gcgagcagga aatcggcaag gctaccgcca agtacttctt ctacagcaac    3240
atcatgaact ttttcaagac cgagattacc ctggccaacg gcgagatccg gaagcggcct    3300
ctgatcgaga caaacggcga aaccggggag atcgtgtggg ataagggccg ggattttgcc    3360
accgtgcgga aagtgctgag catgcccaa  gtgaatatcg tgaaaagac  cgaggtgcag    3420 acaggcggct tcagcaaaga gtctatcctg cccaagagga acagcgataa gctgatcgcc    3480
agaaagaagg actgggaccc taagaagtac ggcggcttcg acagcccac  cgtgccctat    3540 tctgtgctgg tggtggccaa agtggaaaag ggcaagtcca agaaactgaa gagtgtgaaa    3600
gagctgctgg ggatcaccat catggaaaga agcagcttcg agaagaatcc catcgacttt    3660
ctggaagcca agggctacaa agaagtgaaa aaggacctga tcatcaagct gcctaagtac    3720
tccctgttcg agctggaaaa cggccggaag agaatgctgg cctctgccgg cgaactgcag    3780
aagggaaacg aactggccct gccctccaaa tatgtgaact tcctgtacct ggccagccac    3840
tatgagaagc tgaagggctc ccccgaggat aatgagcaga acagctgtt  tgtggaacag    3900 cacaagcact acctggacga gatcatcgag cagatcagcg agttctccaa gagagtgatc    3960
ctggccgacg ctaatctgga caaagtgctg tccgcctaca caagcaccg  ggataagccc    4020 atcagagagc aggccgagaa tatcatccac ctgtttaccc tgaccaatct gggagcccct    4080
gccgccttca gtactttga  caccaccatc gaccggaaga ggtacaccag caccaaagag    4140
gtgctggacg ccaccctgat ccaccagagc atcaccggcc tgtacgagac acggatcgac    4200
ctgtctcagc tgggaggcga caagcgtcct gctgctacta agaaagctgg tcaagctaag    4260
aaaaagaaa                                                             4269

<210> SEQ ID NO 249
<211> LENGTH: 4269
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 249
atggactata aggaccacga cggagactac aaggatcatg atattgatta caaagacgat      60
gacgataaga tggcccccaa gaagaagcgg aaggtcggta tccacggagt cccagcagcc     120
gacaagaagt acagcatcgg cctggccatc ggcaccaact ctgtgggctg ggccgtgatc     180
accgacgagt acaaggtgcc cagcaagaaa ttcaaggtgc tgggcaacac cgaccggcac     240
agcatcaaga gaacctgat  cggagccctg ctgttcgaca gcggcgaaac agccgaggcc     300
acccggctga gagaaccgc  cagaagaaga taccagcac  ggaagaaccg gatctgctat     360
ctgcaagaga tcttcagcaa cgagatggcc aaggtggacg acagcttctt ccacagactg     420
gaagagtcct tcctggtgga agaggataag aagcacgagc ggcaccccat cttcggcaac     480
atcgtggacg aggtggccta ccacgagaag taccccacca tctaccacct gagaaagaaa     540
ctggtggaca gcaccgacaa ggccgacctg cggctgatct atctggccct ggcccacatg     600
atcaagttcc ggggccactt cctgatcgag ggcgacctga accccgacaa cagcgacgtg     660
gacaagctgt tcatccagct ggtgcagacc tacaaccagc tgttcgagga aaacccaatc     720
aacgccagcg gcgtggacgc caaggccatc ctgtctgcca gactgagcaa gagcagacgg     780
ctggaaaatc tgatcgccca gctgcccggc gagaagaaga atggcctgtt cggcaacctg     840
```

```
attgccctga gcctgggcct gacccccaac ttcaagagca acttcgacct ggccgaggat    900
gccaaactgc agctgagcaa ggacacctac gacgacgacc tggacaacct gctggcccag    960
atcggcgacc agtacgccga cctgtttctg gccgccaaga acctgtccga cgccatcctg   1020
ctgagcgaca tcctgagagt gaacaccgag atcaccaagg ccccctgag cgcctctatg    1080
atcaagagat acgacgagca ccaccaggac ctgaccctgc tgaaagctct cgtgcggcag   1140
cagctgcctg agaagtacaa agagattttc ttcgaccaga gcaagaacgg ctacgccggc   1200
tacattgacg gcggagccag ccaggaagag ttctacaagt tcatcaagcc catcctggaa   1260
aagatggacg gcaccgagga actgctcgtg aagctgaaca gagaggacct gctgcggaag   1320
cagcggacct tcgacaacgg cagcatcccc caccagatcc acctgggaga gctgcacgcc   1380
attctgcggc ggcaggaaga tttttaccca ttcctgaagg acaaccggga aaagatcgag   1440
aagatcctga ccttccgcat ccctactac gtgggccctc tggccagggg aaacagcaga    1500
ttcgcctgga tgaccagaaa gagcgaggaa accatcaccc cctggaactt cgaggaagtg   1560
gtggacaagg gcgcttccgc ccagagcttc atcgagcgga tgaccaactt cgataagaac   1620
ctgcccaacg agaaggtgct gcccaagcac agcctgctgt acgagtactt caccgtgtat   1680
aacgagctga ccaaagtgaa atacgtgacc gagggaatga gaaagcccgc cttcctgagc   1740
ggcgagcaga aaaaggccat cgtggacctg ctgttcaaga ccaaccggaa agtgaccgtg   1800
aagcagctga agaggactac cttcaagaaa atcgagtgct tcgactccgt ggaaatctcc   1860
ggcgtggaag atcggttcaa cgcctccctg ggcacatacc acgatctgct gaaaattatc   1920
aaggacaagg acttcctgga caatgaggaa acgaggaca ttctggaaga tatcgtgctg    1980
accctgacac tgtttgagga cagagagatg atcgaggaac ggctgaaaac ctatgcccac   2040
ctgttcgacg acaaagtgat gaagcagctg aagcggcgga gatacaccgg ctggggcagg   2100
ctgagccgga agctgatcaa cggcatccgg gacaagcagt ccggcaagac aatcctggat   2160
ttcctgaagt ccgacggctt cgccaacaga aacttcatgc agctgatcca cgacgacagc   2220
ctgacctta aagaggacat ccagaaagcc caggtgtccg gccagggcga tagcctgcac   2280
gagcacattg ccaatctggc cggcagcccc gccattaaga agggcatcct gcagacagtg   2340
aaggtggtgg acgagctcgt gaaagtgatg ggccggcaca gcccgagaa catcgtgatc    2400
gaaatggcca gagagaacca gaccacccag aagggacaga agaacagccg cgagagaatg   2460
aagcggatcg aagagggcat caaagagctg ggcagccaga tcctgaaaga acaccccgtg   2520
gaaaacaccc agctgcagaa cgagaagctg tacctgtact acctgcagaa tgggcgggat   2580
atgtacgtgg accaggaact ggacatcaac cggctgtccg actacgatgt ggaccatatc   2640
gtgcctcaga gctttctgaa ggacgactcc atcgacaaca aggtgctgac cagaagcgac   2700
aagaaccggg gcaagagcga caacgtgccc tccgaagagg tcgtgaagaa gatgaagaac   2760
tactggcggc agctgctgaa cgccaagctg attacccaga gaaagttcga caatctgacc   2820
aaggccgaga gaggcggcct gagcgaactg gataaggccg gcttcatcaa gagacagctg   2880
gtggaaaccc ggcagatcac aaagcacgtg gcacagatcc tggactcccg gatgaacact   2940
aagtacgacg agaatgacaa gctgatccgg gaagtgaaag tgatcaccct gaagtccaag   3000
ctggtgtccg atttccggaa ggatttccag ttttacaaag tgcgcgagat caacaactac   3060
caccacgccc acgacgccta cctgaacgcc gtcgtgggaa ccgccctgat caaaaagtac   3120
cctaagctgg aaagcgagtt cgtgtacggc gactacaagg tgtacgacgt gcggaagatg   3180
atcgccaaga gcgagcagga aatcggcaag gctaccgcca agtacttctt ctacagcaac   3240
```

```
atcatgaact ttttcaagac cgagattacc ctggccaacg gcgagatccg gaagcggcct    3300
ctgatcgaga caaacggcga aaccggggag atcgtgtggg ataagggccg ggattttgcc    3360
accgtgcgga aagtgctgag catgccccaa gtgaatatcg tgaaaaagac cgaggtgcag    3420
acaggcggct tcagcaaaga gtctatcctg cccaagagga cagcgataa gctgatcgcc    3480 agaaagaagg actgggaccc taagaagtac ggcggcttcg acagcccac cgtggcctat    3540 tctgtgctgg tggtggccaa agtggaaaag ggcaagtcca agaaactgaa gagtgtgaaa    3600
gagctgctgg ggatcaccat catggaaaga agcagcttcg agaagaatcc catcgacttt    3660
ctggaagcca agggctacaa agaagtgaaa aaggacctga tcatcaagct gcctaagtac    3720
tccctgttcg agctggaaaa cggccggaag agaatgctgg cctctgccgg cgaactgcag    3780
aagggaaacg aactggccct gccctccaaa tatgtgaact tcctgtacct ggccagccac    3840
tatgagaagc tgaagggctc ccccgaggat aatgagcaga aacagctgtt tgtggaacag    3900
cacaagcact acctggacga gatcatcgag cagatcagcg agttctccaa gagagtgatc    3960
ctggccgacg ctaatctgga caaagtgctg tccgcctaca caagcaccg ggataagccc    4020 atcagagagc aggccgagaa tatcatccac ctgtttaccc tgaccaatct gggagcccct    4080
gccgccttca agtactttga caccaccatc gaccggaaga ggtacaccag caccaaagag    4140
gtgctggacg ccaccctgat ccaccagagc atcaccggcc tgtacgagac acggatcgac    4200
ctgtctcagc tgggaggcga caagcgtcct gctgctacta agaaagctgg tcaagctaag    4260
aaaaagaaa                                                            4269
```

<210> SEQ ID NO 250
<211> LENGTH: 4341
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 250

```
gccaccggtt aatacgactc actatagggc caccatggac tataaggacc acgacggaga    60
ctacaaggat catgatattg attacaaaga cgatgacgat aagatggccc caagaagaa    120 gcggaaggtc ggtatccacg gagtcccagc agccgacaag aagtacagca tcggcctgga    180
catcggcacc aactctgtgg gctgggccgt gatcaccgac gagtacaagg tgcccagcaa    240
gaaattcaag gtgctgggca acaccgaccg gcacagcatc aagaagaacc tgatcggagc    300
cctgctgttc gacagcggcg aaacagccga ggccacccgg ctgaagagaa ccgccagaag    360
aagatacacc agacgcaaga accggatctg ctatctgcaa gagatcttca gcaacgagat    420
ggccaaggtg gacgacagct tcttccacag actggaagag tccttcctgg tggaagagga    480
taagaagcac gagcggcacc ccatcttcgg caacatcgtg gacgaggtgg cctaccacga    540
gaagtacccc accatctacc acctgagaaa gaaactggtg gacagcaccg acaaggccga    600
cctgcggctg atctatctgg ccctggccca catgatcaag ttccggggcc acttcctgat    660
cgagggcgac ctgaacccg acaacagcga cgtggacaag ctgttcatcc agctggtgca    720
gacctacaac cagctgttcg aggaaaaccc catcaacgcc agcggcgtgg acgccaaggc    780
catcctgtct gccagactga gcaagagcag acggctggaa aatctgatcg cccagctgcc    840
cggcgagaag aagaatggcc tgttcggcaa cctgattgcc ctgagcctgg gcctgacccc    900
```

```
caacttcaag agcaacttcg acctggccga ggatgccaaa ctgcagctga gcaaggacac    960
ctacgacgac gacctggaca acctgctggc ccagatcggc gaccagtacg ccgacctgtt   1020
tctggccgcc aagaacctgt ccgacgccat cctgctgagc gacatcctga gagtgaacac   1080
cgagatcacc aaggcccccc tgagcgcctc tatgatcaag agatacgacg agcaccacca   1140
ggacctgacc ctgctgaaag ctctcgtgcg gcagcagctg cctgagaagt acaaagagat   1200
tttcttcgac cagagcaaga acggctacgc cggctacatt gacggcggag ccagccagga   1260
agagttctac aagttcatca gcccatcct ggaaaagatg gacggcaccg aggaactgct   1320
cgtgaagctg aacagagagg acctgctgcg gaagcagcgg accttcgaca acggcagcat   1380
cccccaccag atccacctgg agagctgca cgccattctg cggcggcagg aagattttta   1440
cccattcctg aaggacaacc gggaaaagat cgagaagatc ctgaccttcc gcatccccta   1500
ctacgtgggc cctctggcca ggggaaacag cagattcgcc tggatgacca aaagagcga   1560
ggaaaccatc accccctgga acttcgagga agtggtggac aagggcgctt ccgcccagag   1620
cttcatcgag cggatgacca acttcgataa gaacctgccc aacgagaagg tgctgcccaa   1680
gcacagcctg ctgtacgagt acttcaccgt gtataacgag ctgaccaaag tgaaatacgt   1740
gaccgaggga atgagaaagc ccgccttcct gagcggcgag cagaaaaagg ccatcgtgga   1800
cctgctgttc aagaccaacc ggaaagtgac cgtgaagcag ctgaaagagg actacttcaa   1860
gaaaatcgag tgcttcgact ccgtggaaat tccggcgtg aagatcggt tcaacgcctc   1920
cctgggcaca taccacgatc tgctgaaaat tatcaaggac aaggacttcc tggacaatga   1980
ggaaaacgag gacattctgg aagatatcgt gctgaccctg acactgtttg aggacagaga   2040
gatgatcgag gaacggctga aaacctatgc ccacctgttc gacgacaaag tgatgaagca   2100
gctgaagcgg cggagataca ccggctgggg caggctgagc cggaagctga tcaacggcat   2160
ccgggacaag cagtccggca agacaatcct ggatttcctg aagtccgacg gcttcgccaa   2220
cagaaacttc atgcagctga tccacgacga cagcctgacc tttaaagagg acatccagaa   2280
agcccaggtg tccggccagg gcgatagcct gcacgagcac attgccaatc tggccggcag   2340
ccccgccatt aagaagggca tcctgcagac agtgaaggtg gtggacgagc tcgtgaaagt   2400
gatgggccgg cacaagcccg agaacatcgt gatcgaaatg gccagagaga accagaccac   2460
ccagaaggga cagaagaaca gccgcgagag aatgaagcgg atcgaagagg gcatcaaaga   2520
gctgggcagc cagatcctga aagaacaccc cgtggaaaac acccagctgc agaacgagaa   2580
gctgtacctg tactacctgc agaatgggcg ggatatgtac gtggaccagg aactggacat   2640
caaccggctg tccgactacg atgtggacca tatcgtgcct cagagctttc tgaaggacga   2700
ctccatcgac aacaaggtgc tgaccagaag cgacaagaac cggggcaaga gcgacaacgt   2760
gcccttccgaa gaggtcgtga agaagatgaa gaactactgg cggcagctgc tgaacgccaa   2820
gctgattacc cagagaaagt tcgacaatct gaccaaggcc gagagaggcg gcctgagcga   2880
actggataag gccggcttca tcaagagaca gctggtggaa acccgcaga tcacaaagca   2940
cgtggcacag atcctggact cccggatgaa cactaagtac gacgagaatg acaagctgat   3000
ccgggaagtg aaagtgatca ccctgaagtc caagctggtg tccgattcc ggaaggattt   3060
ccagttttac aaagtgcgcg agatcaacaa ctaccaccac gcccacgacg cctacctgaa   3120
cgccgtcgtg ggaaccgccc tgatcaaaaa gtaccctaag ctggaaagcg agttcgtgta   3180
cggcgactac aaggtgtacg acgtgcgcaa gatgatcgcc aagagcgagc aggaaatcgg   3240
caaggctacc gccaagtact tcttctacag caacatcatg aacttttcca agaccgagat   3300
```

```
taccctggcc aacggcgaga tccggaagcg gcctctgatc gagacaaacg gcgaaaccgg    3360
ggagatcgtg tgggataagg gccgggattt tgccaccgtg cggaaagtgc tgagcatgcc    3420
ccaagtgaat atcgtgaaaa agaccgaggt gcagacaggc ggcttcagca agagtctat    3480 cctgcccaag aggaacagcg ataagctgat cgccagaaag aaggactggg accctaagaa    3540
gtacggcggc ttcgacagcc ccaccgtggc ctattctgtg ctggtggtgg ccaaagtgga    3600
aaagggcaag tccaagaaac tgaagagtgt gaaagagctg ctggggatca ccatcatgga    3660
aagaagcagc ttcgagaaga tcccatcga ctttctggaa gccaagggct acaaagaagt    3720
gaaaaaggac ctgatcatca agctgcctaa gtactccctg ttcgagctgg aaaacggccg    3780
gaagagaatg ctggcctctg ccggcgaact gcagaaggga acgaactgg ccctgccctc    3840 caaatatgtg aacttcctgt acctggccag ccactatgag aagctgaagg gctccccga    3900 ggataatgag cagaaacagc tgtttgtgga acagcacaag cactacctgg acgagatcat    3960
cgagcagatc agcgagttct ccaagagagt gatcctggcc gacgctaatc tggacaaagt    4020
gctgtccgcc tacaacaagc accgggataa gcccatcaga gagcaggccg agaatatcat    4080
ccacctgttt accctgacca atctgggagc ccctgccgcc ttcaagtact ttgacaccac    4140
catcgaccgg aagaggtaca ccagcaccaa agaggtgctg gacgccaccc tgatccacca    4200
gagcatcacc ggcctgtacg agacacggat cgacctgtct cagctgggag cgacaaaag    4260 gccggcggcc acgaaaaagg ccggccaggc aaaaaagaaa aagtaagaaa aaaaaaaaa    4320 aaaaaaaaaa aaaaaaaac c                                              4341

<210> SEQ ID NO 251
<211> LENGTH: 4341
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 251
gccaccggtt aatacgactc actatagggc caccatggac tataaggacc acgacggaga     60
ctacaaggat catgatattg attacaaaga cgatgacgat aagatggccc caagaagaa    120 gcggaaggtc ggtatccacg gagtcccagc agccgacaag aagtacagca tcggcctggc    180
catcggcacc aactctgtgg gctgggccgt gatcaccgac gagtacaagg tgcccagcaa    240
gaaattcaag gtgctgggca caccgaccg gcacagcatc aagaagaacc tgatcggagc    300
cctgctgttc gacagcggcg aaacagccga ggccacccgg ctgaagagaa ccgccagaag    360
aagatacacc agacgaagaa accggatctg ctatctgcaa gagatcttca gcaacgagat    420
ggccaaggtg gacgacagct tcttccacag actggaagag tccttcctgg tggaagagga    480
taagaagcac gagcggcacc ccatcttcgg caacatcgtg gacgaggtgg cctaccacga    540
gaagtacccc accatctacc acctgagaaa gaaactggtg gacagcaccg acaaggccga    600
cctgcggctg atctatctgg ccctggccca catgatcaag ttccggggcc acttcctgat    660
cgagggcgac ctgaacccg acaacagcga cgtggacaag ctgttcatcc agctggtgca    720
gacctacaac cagctgttcg aggaaaaccc catcaacgcc agcggcgtgg acgccaaggc    780
catcctgtct gccagactga gcaagagcag acggctggaa atctgatcg cccagctgcc    840 cggcgagaag aagaatggcc tgttcggcaa cctgattgcc ctgagcctgg gcctgacccc    900
```

```
caacttcaag agcaacttcg acctggccga ggatgccaaa ctgcagctga gcaaggacac    960
ctacgacgac gacctggaca acctgctggc ccagatcggc gaccagtacg ccgacctgtt   1020
tctggccgcc aagaacctgt ccgacgccat cctgctgagc gacatcctga gagtgaacac   1080
cgagatcacc aaggcccccc tgagcgcctc tatgatcaag agatacgacg agcaccacca   1140
ggacctgacc ctgctgaaag ctctcgtgcg gcagcagctg cctgagaagt acaaagagat   1200
tttcttcgac cagagcaaga acggctacgc cggctacatt gacggcggag ccagccagga   1260
agagttctac aagttcatca gcccatcct ggaaaagatg gacggcaccg aggaactgct   1320
cgtgaagctg aacagagagg acctgctgcg gaagcagcgg accttcgaca acggcagcat   1380
cccccaccag atccacctgg gagagctgca cgccattctg cggcggcagg aagattttta   1440
cccattcctg aaggacaacc gggaaaagat cgagaagatc ctgaccttcc gcatcccta   1500
ctacgtgggc cctctggcca ggggaaacag cagattcgcc tggatgacca aaagagcga   1560
ggaaaccatc accccctgga acttcgagga agtggtggac aagggcgctt ccgcccagag   1620
cttcatcgag cggatgacca acttcgataa gaacctgccc aacgagaagg tgctgcccaa   1680
gcacagcctg ctgtacgagt acttcaccgt gtataacgag ctgaccaaag tgaaatacgt   1740
gaccgaggga atgagaaagc ccgccttcct gagcggcgag cagaaaaagg ccatcgtgga   1800
cctgctgttc aagaccaacc ggaaagtgac cgtgaagcag ctgaaagagg actacttcaa   1860
gaaaatcgag tgcttcgact ccgtggaaat ctccggcgtg gaagatcggt tcaacgcctc   1920
cctgggcaca taccacgatc tgctgaaaat tatcaaggac aaggacttcc tggacaatga   1980
ggaaaacgag gacattctgg aagatatcgt gctgaccctg acactgtttg aggacagaga   2040
gatgatcgag gaacggctga aaacctatgc ccacctgttc gacgacaaag tgatgaagca   2100
gctgaagcgc cggagataca ccggctgggg caggctgagc cggaagctga tcaacggcat   2160
ccgggacaag cagtccggca gacaatcct ggatttcctg aagtccgacg gcttcgccaa   2220
cagaaacttc atgcagctga tccacgacga cagcctgacc tttaaagagg acatccagaa   2280
agcccaggtg tccggccagg gcgatagcct gcacgagcac attgccaatc tggccggcag   2340
ccccgccatt aagaagggca tcctgcagac agtgaaggtg gtggacgagc tcgtgaaagt   2400
gatgggccgg cacaagcccg agaacatcgt gatcgaaatg gccagagaga accagaccac   2460
ccagaaggga cagaagaaca ccgcgagag aatgaagcgg atcgaagagg gcatcaaaga   2520
gctgggcagc cagatcctga aagaacaccc cgtggaaaac acccagctgc agaacgagaa   2580
gctgtacctg tactacctgc agaatgggcg ggatatgtac gtggaccagg aactggacat   2640
caaccggctg tccgactacg atgtggacca tatcgtgcct cagagctttc tgaaggacga   2700
ctccatcgac aacaaggtgc tgaccagaag cgacaagaac cggggcaaga gcgacaacgt   2760
gcccctccgaa gaggtcgtga agaagatgaa gaactactgg cggcagctgc tgaacgccaa   2820
gctgattacc cagagaaagt tcgacaatct gaccaaggcc gagagaggcg gcctgagcga   2880
actggataag gccggcttca tcaagagaca gctggtggaa acccggcaga tcacaaagca   2940
cgtggcacag atcctggact cccggatgaa cactaagtac gacgagaatg acaagctgat   3000
ccgggaagtg aaagtgatca ccctgaagtc caagctggtg tccgatttcc ggaaggattt   3060
ccagttttac aaagtgcgcg agatcaacaa ctaccaccac gcccacgacg cctacctgaa   3120
cgccgtcgtg ggaaccgccc tgatcaaaaa gtaccctaag ctggaaagcg agttcgtgta   3180
cggcgactac aaggtgtacg acgtgcggaa gatgatcgcc aagagcgagc aggaaatcgg   3240
caaggctacc gccaagtact tcttctacag caacatcatg aactttttca agaccgagat   3300
```

```
taccctggcc aacggcgaga tccggaagcg gcctctgatc gagacaaacg gcgaaaccgg   3360
ggagatcgtg tgggataagg gccgggattt tgccaccgtg cggaaagtgc tgagcatgcc   3420
ccaagtgaat atcgtgaaaa agaccgaggt gcagacaggc ggcttcagca aagagtctat   3480
cctgcccaag aggaacagcg ataagctgat cgccagaaag aaggactggg accctaagaa   3540
gtacggcggc ttcgacagcc ccaccgtggc ctattctgtg ctggtggtgg ccaaagtgga   3600
aaagggcaag tccaagaaac tgaagagtgt gaaagagctg ctggggatca ccatcatgga   3660
aagaagcagc ttcgagaaga atcccatcga ctttctggaa gccaagggct acaaagaagt   3720
gaaaaaggac ctgatcatca agctgcctaa gtactccctg ttcgagctgg aaaacggccg   3780
gaagagaatg ctggcctctg ccggcgaact gcagaaggga aacgaactgg ccctgccctc   3840
caaatatgtg aacttcctgt acctggccag ccactatgag aagctgaagg gctcccccga   3900
ggataatgag cagaaacagc tgtttgtgga acagcacaag cactacctgg acgagatcat   3960
cgagcagatc agcgagttct ccaagagagt gatcctggcc gacgctaatc tggacaaagt   4020
gctgtccgcc tacaacaagc accgggataa gcccatcaga gagcaggccg agaatatcat   4080
ccacctgttt accctgacca atctgggagc ccctgccgcc ttcaagtact ttgacaccac   4140
catcgaccgg aagaggtaca ccagcaccaa agaggtgctg gacgccaccc tgatccacca   4200
gagcatcacc ggcctgtacg agacacggat cgacctgtct cagctgggag cgacaaaag   4260 gccggcggcc acgaaaaagg ccggccaggc aaaaaagaaa aagtaagaaa aaaaaaaaa   4320 aaaaaaaaaa aaaaaaaac c                                             4341

<210> SEQ ID NO 252
<211> LENGTH: 191
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 252
agcaggccaa tggggaggac atcgatgtca cctccaatga ctactaccca tacgatgttc     60
cagattacgc tatggactat aaggaccacg acggagacta caaggatcat gatattgatt    120
acaaagacga tgacgataag aagcttgaaa tggcatcaat gcagaagctg atctcagagg    180
aggacctgta a                                                         191

<210> SEQ ID NO 253
<211> LENGTH: 191
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 253
tagtcattgg aggtgacatc gatgtcctcc ccattggcct gctttacagg tcctcctctg     60
agatcagctt ctgcattgat gccatttcaa gcttcttatc gtcatcgtct ttgtaatcaa    120
tatcatgatc cttgtagtct ccgtcgtggt ccttatagtc catagcgtaa tctggaacat    180
cgtatgggta g                                                         191

<210> SEQ ID NO 254
```

<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 254
ggggccacta gggacaggat                                              20

<210> SEQ ID NO 255
<211> LENGTH: 102
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 255
gttttagagc tatgctgttt tgaatggtcc caaaacggaa gggcctgagt ccgagcagaa    60
gaagaagttt tagagctatg ctgttttgaa tggtcccaaa ac                      102

<210> SEQ ID NO 256
<211> LENGTH: 100
<212> TYPE: DNA
<213> ORGANISM: Homo sapiens

<400> SEQUENCE: 256
cggaggacaa agtacaaacg gcagaagctg gaggaggaag ggcctgagtc cgagcagaag    60
aagaagggct cccatcacat caaccggtgg cgcattgcca                         100

<210> SEQ ID NO 257
<211> LENGTH: 50
<212> TYPE: DNA
<213> ORGANISM: Homo sapiens

<400> SEQUENCE: 257
agctggagga ggaagggcct gagtccgagc agaagaagaa gggctcccac              50

<210> SEQ ID NO 258
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 258
gaguccgagc agaagaagaa guuuuagagc                                    30

<210> SEQ ID NO 259
<211> LENGTH: 49
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 259
agctggagga ggaagggcct gagtccgagc agaagagaag ggctcccat               49

-continued

<210> SEQ ID NO 260
<211> LENGTH: 53
<212> TYPE: DNA
<213> ORGANISM: Homo sapiens

<400> SEQUENCE: 260
ctggaggagg aagggcctga gtccgagcag aagaagaagg gctcccatca cat    53

<210> SEQ ID NO 261
<211> LENGTH: 52
<212> TYPE: DNA
<213> ORGANISM: Homo sapiens

<400> SEQUENCE: 261
ctggaggagg aagggcctga gtccgagcag aagagaaggg ctcccatcac at    52

<210> SEQ ID NO 262
<211> LENGTH: 54
<212> TYPE: DNA
<213> ORGANISM: Homo sapiens

<400> SEQUENCE: 262
ctggaggagg aagggcctga gtccgagcag aagaaagaag gctcccatc acat    54

<210> SEQ ID NO 263
<211> LENGTH: 50
<212> TYPE: DNA
<213> ORGANISM: Homo sapiens

<400> SEQUENCE: 263
ctggaggagg aagggcctga gtccgagcag aagaagggct cccatcacat    50

<210> SEQ ID NO 264
<211> LENGTH: 47
<212> TYPE: DNA
<213> ORGANISM: Homo sapiens

<400> SEQUENCE: 264
ctggaggagg aagggcctga gcccgagcag aagggctccc atcacat    47

<210> SEQ ID NO 265
<211> LENGTH: 4104
<212> TYPE: DNA
<213> ORGANISM: Homo sapiens
<220> FEATURE:
<221> NAME/KEY: CDS
<222> LOCATION: (1)..(4104)

<400> SEQUENCE: 265

```
atg gac aag aag tac agc atc ggc ctg gac atc ggc acc aac tct gtg      48
Met Asp Lys Lys Tyr Ser Ile Gly Leu Asp Ile Gly Thr Asn Ser Val
1               5                   10                  15 ggc tgg gcc gtg atc acc gac gag tac aag gtg ccc agc aag aaa ttc      96
Gly Trp Ala Val Ile Thr Asp Glu Tyr Lys Val Pro Ser Lys Lys Phe
            20                  25                  30 aag gtg ctg ggc aac acc gac cgg cac agc atc aag aag aac ctg atc     144
Lys Val Leu Gly Asn Thr Asp Arg His Ser Ile Lys Lys Asn Leu Ile
        35                  40                  45 gga gcc ctg ctg ttc gac agc ggc gaa aca gcc gag gcc acc cgg ctg     192
Gly Ala Leu Leu Phe Asp Ser Gly Glu Thr Ala Glu Ala Thr Arg Leu
    50                  55                  60 aag aga acc gcc aga aga aga tac acc aga cgg aag aac cgg atc tgc     240
Lys Arg Thr Ala Arg Arg Arg Tyr Thr Arg Arg Lys Asn Arg Ile Cys
65                  70                  75                  80
```

```
tat ctg caa gag atc ttc agc aac gag atg gcc aag gtg gac gac agc      288
Tyr Leu Gln Glu Ile Phe Ser Asn Glu Met Ala Lys Val Asp Asp Ser
                85                  90                  95 ttc ttc cac aga ctg gaa gag tcc ttc ctg gtg gaa gag gat aag aag      336
Phe Phe His Arg Leu Glu Glu Ser Phe Leu Val Glu Glu Asp Lys Lys
            100                 105                 110 cac gag cgg cac ccc atc ttc ggc aac atc gtg gac gag gtg gcc tac      384
His Glu Arg His Pro Ile Phe Gly Asn Ile Val Asp Glu Val Ala Tyr
            115                 120                 125 cac gag aag tac ccc acc atc tac cac ctg aga aag aaa ctg gtg gac      432
His Glu Lys Tyr Pro Thr Ile Tyr His Leu Arg Lys Lys Leu Val Asp
            130                 135                 140 agc acc gac aag gcc gac ctg cgg ctg atc tat ctg gcc ctg gcc cac      480
Ser Thr Asp Lys Ala Asp Leu Arg Leu Ile Tyr Leu Ala Leu Ala His
145                 150                 155                 160 atg atc aag ttc cgg ggc cac ttc ctg atc gag ggc gac ctg aac ccc      528
Met Ile Lys Phe Arg Gly His Phe Leu Ile Glu Gly Asp Leu Asn Pro
                165                 170                 175 gac aac agc gac gtg gac aag ctg ttc atc cag ctg gtg cag acc tac      576
Asp Asn Ser Asp Val Asp Lys Leu Phe Ile Gln Leu Val Gln Thr Tyr
                180                 185                 190 aac cag ctg ttc gag gaa aac ccc atc aac gcc agc ggc gtg gac gcc      624
Asn Gln Leu Phe Glu Glu Asn Pro Ile Asn Ala Ser Gly Val Asp Ala
            195                 200                 205 aag gcc atc ctg tct gcc aga ctg agc aag agc aga cgg ctg gaa aat      672
Lys Ala Ile Leu Ser Ala Arg Leu Ser Lys Ser Arg Arg Leu Glu Asn
            210                 215                 220 ctg atc gcc cag ctg ccc ggc gag aag aag aat ggc ctg ttc ggc aac      720
Leu Ile Ala Gln Leu Pro Gly Glu Lys Lys Asn Gly Leu Phe Gly Asn
225                 230                 235                 240 ctg att gcc ctg agc ctg ggc ctg acc ccc aac ttc aag agc aac ttc      768
Leu Ile Ala Leu Ser Leu Gly Leu Thr Pro Asn Phe Lys Ser Asn Phe
                245                 250                 255 gac ctg gcc gag gat gcc aaa ctg cag ctg agc aag gac acc tac gac      816
Asp Leu Ala Glu Asp Ala Lys Leu Gln Leu Ser Lys Asp Thr Tyr Asp
                260                 265                 270 gac gac ctg gac aac ctg ctg gcc cag atc ggc gac cag tac gcc gac      864
Asp Asp Leu Asp Asn Leu Leu Ala Gln Ile Gly Asp Gln Tyr Ala Asp
            275                 280                 285 ctg ttt ctg gcc gcc aag aac ctg tcc gac gcc atc ctg ctg agc gac      912
Leu Phe Leu Ala Ala Lys Asn Leu Ser Asp Ala Ile Leu Leu Ser Asp
            290                 295                 300 atc ctg aga gtg aac acc gag atc acc aag gcc ccc ctg agc gcc tct      960
Ile Leu Arg Val Asn Thr Glu Ile Thr Lys Ala Pro Leu Ser Ala Ser
305                 310                 315                 320 atg atc aag aga tac gac gag cac cac cag gac ctg acc ctg ctg aaa     1008
Met Ile Lys Arg Tyr Asp Glu His His Gln Asp Leu Thr Leu Leu Lys
                325                 330                 335 gct ctc gtg cgg cag cag ctg cct gag aag tac aaa gag att ttc ttc     1056
Ala Leu Val Arg Gln Gln Leu Pro Glu Lys Tyr Lys Glu Ile Phe Phe
            340                 345                 350 gac cag agc aag aac ggc tac gcc ggc tac att gac ggc gga gcc agc     1104
Asp Gln Ser Lys Asn Gly Tyr Ala Gly Tyr Ile Asp Gly Gly Ala Ser
            355                 360                 365 cag gaa gag ttc tac aag ttc atc aag ccc atc ctg gaa aag atg gac     1152
Gln Glu Glu Phe Tyr Lys Phe Ile Lys Pro Ile Leu Glu Lys Met Asp
            370                 375                 380 ggc acc gag gaa ctg ctc gtg aag ctg aac aga gag gac ctg ctg cgg     1200
Gly Thr Glu Glu Leu Leu Val Lys Leu Asn Arg Glu Asp Leu Leu Arg
```

|  |  |
|---|---|
| 385 390 395 400 | |
| aag cag cgg acc ttc gac aac ggc agc atc ccc cac cag atc cac ctg<br>Lys Gln Arg Thr Phe Asp Asn Gly Ser Ile Pro His Gln Ile His Leu<br>                    405                   410              415 | 1248 |
| gga gag ctg cac gcc att ctg cgg cgg cag gaa gat ttt tac cca ttc<br>Gly Glu Leu His Ala Ile Leu Arg Arg Gln Glu Asp Phe Tyr Pro Phe<br>          420                   425                   430 | 1296 |
| ctg aag gac aac cgg gaa aag atc gag aag atc ctg acc ttc cgc atc<br>Leu Lys Asp Asn Arg Glu Lys Ile Glu Lys Ile Leu Thr Phe Arg Ile<br>                  435                   440              445 | 1344 |
| ccc tac tac gtg ggc cct ctg gcc agg gga aac agc aga ttc gcc tgg<br>Pro Tyr Tyr Val Gly Pro Leu Ala Arg Gly Asn Ser Arg Phe Ala Trp<br>450                     455                   460 | 1392 |
| atg acc aga aag agc gag gaa acc atc acc ccc tgg aac ttc gag gaa<br>Met Thr Arg Lys Ser Glu Glu Thr Ile Thr Pro Trp Asn Phe Glu Glu<br>465                     470                   475              480 | 1440 |
| gtg gtg gac aag ggc gct tcc gcc cag agc ttc atc gag cgg atg acc<br>Val Val Asp Lys Gly Ala Ser Ala Gln Ser Phe Ile Glu Arg Met Thr<br>                  485                   490              495 | 1488 |
| aac ttc gat aag aac ctg ccc aac gag aag gtg ctg ccc aag cac agc<br>Asn Phe Asp Lys Asn Leu Pro Asn Glu Lys Val Leu Pro Lys His Ser<br>                  500                   505              510 | 1536 |
| ctg ctg tac gag tac ttc acc gtg tat aac gag ctg acc aaa gtg aaa<br>Leu Leu Tyr Glu Tyr Phe Thr Val Tyr Asn Glu Leu Thr Lys Val Lys<br>              515                   520              525 | 1584 |
| tac gtg acc gag gga atg aga aag ccc gcc ttc ctg agc ggc gag cag<br>Tyr Val Thr Glu Gly Met Arg Lys Pro Ala Phe Leu Ser Gly Glu Gln<br>          530                   535                   540 | 1632 |
| aaa aag gcc atc gtg gac ctg ctg ttc aag acc aac cgg aaa gtg acc<br>Lys Lys Ala Ile Val Asp Leu Leu Phe Lys Thr Asn Arg Lys Val Thr<br>545                     550                   555              560 | 1680 |
| gtg aag cag ctg aaa gag gac tac ttc aag aaa atc gag tgc ttc gac<br>Val Lys Gln Leu Lys Glu Asp Tyr Phe Lys Lys Ile Glu Cys Phe Asp<br>                  565                   570              575 | 1728 |
| tcc gtg gaa atc tcc ggc gtg gaa gat cgg ttc aac gcc tcc ctg ggc<br>Ser Val Glu Ile Ser Gly Val Glu Asp Arg Phe Asn Ala Ser Leu Gly<br>              580                   585              590 | 1776 |
| aca tac cac gat ctg ctg aaa att atc aag gac aag gac ttc ctg gac<br>Thr Tyr His Asp Leu Leu Lys Ile Ile Lys Asp Lys Asp Phe Leu Asp<br>          595                   600                   605 | 1824 |
| aat gag gaa aac gag gac att ctg gaa gat atc gtg ctg acc ctg aca<br>Asn Glu Glu Asn Glu Asp Ile Leu Glu Asp Ile Val Leu Thr Leu Thr<br>610                     615                   620 | 1872 |
| ctg ttt gag gac aga gag atg atc gag gaa cgg ctg aaa acc tat gcc<br>Leu Phe Glu Asp Arg Glu Met Ile Glu Glu Arg Leu Lys Thr Tyr Ala<br>625                     630                   635              640 | 1920 |
| cac ctg ttc gac gac aaa gtg atg aag cag ctg aag cgg cgg aga tac<br>His Leu Phe Asp Asp Lys Val Met Lys Gln Leu Lys Arg Arg Arg Tyr<br>                  645                   650              655 | 1968 |
| acc ggc tgg ggc agg ctg agc cgg aag ctg atc aac ggc atc cgg gac<br>Thr Gly Trp Gly Arg Leu Ser Arg Lys Leu Ile Asn Gly Ile Arg Asp<br>          660                   665                   670 | 2016 |
| aag cag tcc ggc aag aca atc ctg gat ttc ctg aag tcc gac ggc ttc<br>Lys Gln Ser Gly Lys Thr Ile Leu Asp Phe Leu Lys Ser Asp Gly Phe<br>                  675                   680              685 | 2064 |
| gcc aac aga aac ttc atg cag ctg atc cac gac gac agc ctg acc ttt<br>Ala Asn Arg Asn Phe Met Gln Leu Ile His Asp Asp Ser Leu Thr Phe<br>690                     695                   700 | 2112 |
| aaa gag gac atc cag aaa gcc cag gtg tcc ggc cag ggc gat agc ctg | 2160 |

```
Lys Glu Asp Ile Gln Lys Ala Gln Val Ser Gly Gln Gly Asp Ser Leu
705                 710                 715                 720 cac gag cac att gcc aat ctg gcc ggc agc ccc gcc att aag aag ggc     2208
His Glu His Ile Ala Asn Leu Ala Gly Ser Pro Ala Ile Lys Lys Gly
                725                 730                 735 atc ctg cag aca gtg aag gtg gtg gac gag ctc gtg aaa gtg atg ggc     2256
Ile Leu Gln Thr Val Lys Val Val Asp Glu Leu Val Lys Val Met Gly
            740                 745                 750 cgg cac aag ccc gag aac atc gtg atc gcc atg gcc aga gag aac cag     2304
Arg His Lys Pro Glu Asn Ile Val Ile Ala Met Ala Arg Glu Asn Gln
        755                 760                 765 acc acc cag aag gga cag aag aac agc cgc gag aga atg aag cgg atc     2352
Thr Thr Gln Lys Gly Gln Lys Asn Ser Arg Glu Arg Met Lys Arg Ile
    770                 775                 780 gaa gag ggc atc aaa gag ctg ggc agc cag atc ctg aaa gaa cac ccc     2400
Glu Glu Gly Ile Lys Glu Leu Gly Ser Gln Ile Leu Lys Glu His Pro
785                 790                 795                 800 gtg gaa aac acc cag ctg cag aac gag aag ctg tac ctg tac tac ctg     2448
Val Glu Asn Thr Gln Leu Gln Asn Glu Lys Leu Tyr Leu Tyr Tyr Leu
                805                 810                 815 cag aat ggg cgg gat atg tac gtg gac cag gaa ctg gac atc aac cgg     2496
Gln Asn Gly Arg Asp Met Tyr Val Asp Gln Glu Leu Asp Ile Asn Arg
            820                 825                 830 ctg tcc gac tac gat gtg gac gcc atc gtg cct cag agc ttt ctg aag     2544
Leu Ser Asp Tyr Asp Val Asp Ala Ile Val Pro Gln Ser Phe Leu Lys
        835                 840                 845 gac gac tcc atc gac gcc aag gtg ctg acc aga agc gac aag gcc cgg     2592
Asp Asp Ser Ile Asp Ala Lys Val Leu Thr Arg Ser Asp Lys Ala Arg
    850                 855                 860 ggc aag agc gac aac gtg ccc tcc gaa gag gtc gtg aag aag atg aag     2640
Gly Lys Ser Asp Asn Val Pro Ser Glu Glu Val Val Lys Lys Met Lys
865                 870                 875                 880 aac tac tgg cgg cag ctg ctg aac gcc aag ctg att acc cag aga aag     2688
Asn Tyr Trp Arg Gln Leu Leu Asn Ala Lys Leu Ile Thr Gln Arg Lys
                885                 890                 895 ttc gac aat ctg acc aag gcc gag aga ggc ggc ctg agc gaa ctg gat     2736
Phe Asp Asn Leu Thr Lys Ala Glu Arg Gly Gly Leu Ser Glu Leu Asp
            900                 905                 910 aag gcc ggc ttc atc aag aga cag ctg gtg gaa acc cgg cag atc aca     2784
Lys Ala Gly Phe Ile Lys Arg Gln Leu Val Glu Thr Arg Gln Ile Thr
        915                 920                 925 aag cac gtg gca cag atc ctg gac tcc cgg atg aac act aag tac gac     2832
Lys His Val Ala Gln Ile Leu Asp Ser Arg Met Asn Thr Lys Tyr Asp
    930                 935                 940 gag aat gac aag ctg atc cgg gaa gtg aaa gtg atc acc ctg aag tcc     2880
Glu Asn Asp Lys Leu Ile Arg Glu Val Lys Val Ile Thr Leu Lys Ser
945                 950                 955                 960 aag ctg gtg tcc gat ttc cgg aag gat ttc cag ttt tac aaa gtg cgc     2928
Lys Leu Val Ser Asp Phe Arg Lys Asp Phe Gln Phe Tyr Lys Val Arg
                965                 970                 975 gag atc aac aac tac cac cac gcc cac gcc gcc tac ctg aac gcc gtc     2976
Glu Ile Asn Asn Tyr His His Ala His Ala Ala Tyr Leu Asn Ala Val
            980                 985                 990 gtg gga acc gcc ctg atc aaa aag tac cct aag ctg gaa agc gag ttc     3024
Val Gly Thr Ala Leu Ile Lys Lys Tyr Pro Lys Leu Glu Ser Glu Phe
        995                 1000                1005 gtg tac ggc gac tac aag gtg tac gac gtg cgg aag atg atc gcc         3069
Val Tyr Gly Asp Tyr Lys Val Tyr Asp Val Arg Lys Met Ile Ala
    1010                1015                1020
```

-continued

| | | | | | | | | | | | | |
|---|---|---|---|---|---|---|---|---|---|---|---|---|
| aag | agc | gag | cag | gaa | atc | ggc | aag | gct | acc | gcc | aag | tac ttc ttc | 3114 |
| Lys | Ser | Glu | Gln | Glu | Ile | Gly | Lys | Ala | Thr | Ala | Lys | Tyr Phe Phe |
| | 1025 | | | | 1030 | | | | | 1035 | | |

| tac | agc | aac | atc | atg | aac | ttt | ttc | aag | acc | gag | att | acc ctg gcc | 3159 |
| Tyr | Ser | Asn | Ile | Met | Asn | Phe | Phe | Lys | Thr | Glu | Ile | Thr Leu Ala |
| | 1040 | | | | 1045 | | | | | 1050 | | |

| aac | ggc | gag | atc | cgg | aag | cgg | cct | ctg | atc | gag | aca | aac ggc gaa | 3204 |
| Asn | Gly | Glu | Ile | Arg | Lys | Arg | Pro | Leu | Ile | Glu | Thr | Asn Gly Glu |
| | 1055 | | | | 1060 | | | | | 1065 | | |

| acc | ggg | gag | atc | gtg | tgg | gat | aag | ggc | cgg | gat | ttt | gcc acc gtg | 3249 |
| Thr | Gly | Glu | Ile | Val | Trp | Asp | Lys | Gly | Arg | Asp | Phe | Ala Thr Val |
| | 1070 | | | | 1075 | | | | | 1080 | | |

| cgg | aaa | gtg | ctg | agc | atg | ccc | caa | gtg | aat | atc | gtg | aaa aag acc | 3294 |
| Arg | Lys | Val | Leu | Ser | Met | Pro | Gln | Val | Asn | Ile | Val | Lys Lys Thr |
| | 1085 | | | | 1090 | | | | | 1095 | | |

| gag | gtg | cag | aca | ggc | ggc | ttc | agc | aaa | gag | tct | atc | ctg ccc aag | 3339 |
| Glu | Val | Gln | Thr | Gly | Gly | Phe | Ser | Lys | Glu | Ser | Ile | Leu Pro Lys |
| | 1100 | | | | 1105 | | | | | 1110 | | |

| agg | aac | agc | gat | aag | ctg | atc | gcc | aga | aag | aag | gac | tgg gac cct | 3384 |
| Arg | Asn | Ser | Asp | Lys | Leu | Ile | Ala | Arg | Lys | Lys | Asp | Trp Asp Pro |
| | 1115 | | | | 1120 | | | | | 1125 | | |

| aag | aag | tac | ggc | ggc | ttc | gac | agc | ccc | acc | gtg | gcc | tat tct gtg | 3429 |
| Lys | Lys | Tyr | Gly | Gly | Phe | Asp | Ser | Pro | Thr | Val | Ala | Tyr Ser Val |
| | 1130 | | | | 1135 | | | | | 1140 | | |

| ctg | gtg | gtg | gcc | aaa | gtg | gaa | aag | ggc | aag | tcc | aag | aaa ctg aag | 3474 |
| Leu | Val | Val | Ala | Lys | Val | Glu | Lys | Gly | Lys | Ser | Lys | Lys Leu Lys |
| | 1145 | | | | 1150 | | | | | 1155 | | |

| agt | gtg | aaa | gag | ctg | ctg | ggg | atc | acc | atc | atg | gaa | aga agc agc | 3519 |
| Ser | Val | Lys | Glu | Leu | Leu | Gly | Ile | Thr | Ile | Met | Glu | Arg Ser Ser |
| | 1160 | | | | 1165 | | | | | 1170 | | |

| ttc | gag | aag | aat | ccc | atc | gac | ttt | ctg | gaa | gcc | aag | ggc tac aaa | 3564 |
| Phe | Glu | Lys | Asn | Pro | Ile | Asp | Phe | Leu | Glu | Ala | Lys | Gly Tyr Lys |
| | 1175 | | | | 1180 | | | | | 1185 | | |

| gaa | gtg | aaa | aag | gac | ctg | atc | atc | aag | ctg | cct | aag | tac tcc ctg | 3609 |
| Glu | Val | Lys | Lys | Asp | Leu | Ile | Ile | Lys | Leu | Pro | Lys | Tyr Ser Leu |
| | 1190 | | | | 1195 | | | | | 1200 | | |

| ttc | gag | ctg | gaa | aac | ggc | cgg | aag | aga | atg | ctg | gcc | tct gcc ggc | 3654 |
| Phe | Glu | Leu | Glu | Asn | Gly | Arg | Lys | Arg | Met | Leu | Ala | Ser Ala Gly |
| | 1205 | | | | 1210 | | | | | 1215 | | |

| gaa | ctg | cag | aag | gga | aac | gaa | ctg | gcc | ctg | ccc | tcc | aaa tat gtg | 3699 |
| Glu | Leu | Gln | Lys | Gly | Asn | Glu | Leu | Ala | Leu | Pro | Ser | Lys Tyr Val |
| | 1220 | | | | 1225 | | | | | 1230 | | |

| aac | ttc | ctg | tac | ctg | gcc | agc | cac | tat | gag | aag | ctg | aag ggc tcc | 3744 |
| Asn | Phe | Leu | Tyr | Leu | Ala | Ser | His | Tyr | Glu | Lys | Leu | Lys Gly Ser |
| | 1235 | | | | 1240 | | | | | 1245 | | |

| ccc | gag | gat | aat | gag | cag | aaa | cag | ctg | ttt | gtg | gaa | cag cac aag | 3789 |
| Pro | Glu | Asp | Asn | Glu | Gln | Lys | Gln | Leu | Phe | Val | Glu | Gln His Lys |
| | 1250 | | | | 1255 | | | | | 1260 | | |

| cac | tac | ctg | gac | gag | atc | atc | gag | cag | atc | agc | gag | ttc tcc aag | 3834 |
| His | Tyr | Leu | Asp | Glu | Ile | Ile | Glu | Gln | Ile | Ser | Glu | Phe Ser Lys |
| | 1265 | | | | 1270 | | | | | 1275 | | |

| aga | gtg | atc | ctg | gcc | gac | gct | aat | ctg | gac | aaa | gtg | ctg tcc gcc | 3879 |
| Arg | Val | Ile | Leu | Ala | Asp | Ala | Asn | Leu | Asp | Lys | Val | Leu Ser Ala |
| | 1280 | | | | 1285 | | | | | 1290 | | |

| tac | aac | aag | cac | cgg | gat | aag | ccc | atc | aga | gag | cag | gcc gag aat | 3924 |
| Tyr | Asn | Lys | His | Arg | Asp | Lys | Pro | Ile | Arg | Glu | Gln | Ala Glu Asn |
| | 1295 | | | | 1300 | | | | | 1305 | | |

| atc | atc | cac | ctg | ttt | acc | ctg | acc | aat | ctg | gga | gcc | cct gcc gcc | 3969 |
| Ile | Ile | His | Leu | Phe | Thr | Leu | Thr | Asn | Leu | Gly | Ala | Pro Ala Ala |
| | 1310 | | | | 1315 | | | | | 1320 | | |

```
ttc aag tac ttt gac acc acc atc gac cgg aag agg tac acc agc        4014
Phe Lys Tyr Phe Asp Thr Thr Ile Asp Arg Lys Arg Tyr Thr Ser
    1325                1330                1335 acc aaa gag gtg ctg gac gcc acc ctg atc cac cag agc atc acc        4059
Thr Lys Glu Val Leu Asp Ala Thr Leu Ile His Gln Ser Ile Thr
    1340                1345                1350 ggc ctg tac gag aca cgg atc gac ctg tct cag ctg gga ggc gac        4104
Gly Leu Tyr Glu Thr Arg Ile Asp Leu Ser Gln Leu Gly Gly Asp
    1355                1360                1365
```

<210> SEQ ID NO 266
<211> LENGTH: 1368
<212> TYPE: PRT
<213> ORGANISM: Homo sapiens

<400> SEQUENCE: 266

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
```

```
                305                 310                 315                 320
            Met Ile Lys Arg Tyr Asp Glu His His Gln Asp Leu Thr Leu Leu Lys
                            325                 330                 335
            Ala Leu Val Arg Gln Gln Leu Pro Glu Lys Tyr Lys Glu Ile Phe Phe
                            340                 345                 350
            Asp Gln Ser Lys Asn Gly Tyr Ala Gly Tyr Ile Asp Gly Gly Ala Ser
                            355                 360                 365
            Gln Glu Glu Phe Tyr Lys Phe Ile Lys Pro Ile Leu Glu Lys Met Asp
                            370                 375                 380
            Gly Thr Glu Glu Leu Leu Val Lys Leu Asn Arg Glu Asp Leu Leu Arg
            385                 390                 395                 400
            Lys Gln Arg Thr Phe Asp Asn Gly Ser Ile Pro His Gln Ile His Leu
                            405                 410                 415
            Gly Glu Leu His Ala Ile Leu Arg Arg Gln Glu Asp Phe Tyr Pro Phe
                            420                 425                 430
            Leu Lys Asp Asn Arg Glu Lys Ile Glu Lys Ile Leu Thr Phe Arg Ile
                            435                 440                 445
            Pro Tyr Tyr Val Gly Pro Leu Ala Arg Gly Asn Ser Arg Phe Ala Trp
                            450                 455                 460
            Met Thr Arg Lys Ser Glu Glu Thr Ile Thr Pro Trp Asn Phe Glu Glu
            465                 470                 475                 480
            Val Val Asp Lys Gly Ala Ser Ala Gln Ser Phe Ile Glu Arg Met Thr
                            485                 490                 495
            Asn Phe Asp Lys Asn Leu Pro Asn Glu Lys Val Leu Pro Lys His Ser
                            500                 505                 510
            Leu Leu Tyr Glu Tyr Phe Thr Val Tyr Asn Glu Leu Thr Lys Val Lys
                            515                 520                 525
            Tyr Val Thr Glu Gly Met Arg Lys Pro Ala Phe Leu Ser Gly Glu Gln
                            530                 535                 540
            Lys Lys Ala Ile Val Asp Leu Leu Phe Lys Thr Asn Arg Lys Val Thr
            545                 550                 555                 560
            Val Lys Gln Leu Lys Glu Asp Tyr Phe Lys Lys Ile Glu Cys Phe Asp
                            565                 570                 575
            Ser Val Glu Ile Ser Gly Val Glu Asp Arg Phe Asn Ala Ser Leu Gly
                            580                 585                 590
            Thr Tyr His Asp Leu Leu Lys Ile Ile Lys Asp Lys Asp Phe Leu Asp
                            595                 600                 605
            Asn Glu Glu Asn Glu Asp Ile Leu Glu Asp Ile Val Leu Thr Leu Thr
                            610                 615                 620
            Leu Phe Glu Asp Arg Glu Met Ile Glu Glu Arg Leu Lys Thr Tyr Ala
            625                 630                 635                 640
            His Leu Phe Asp Asp Lys Val Met Lys Gln Leu Lys Arg Arg Arg Tyr
                            645                 650                 655
            Thr Gly Trp Gly Arg Leu Ser Arg Lys Leu Ile Asn Gly Ile Arg Asp
                            660                 665                 670
            Lys Gln Ser Gly Lys Thr Ile Leu Asp Phe Leu Lys Ser Asp Gly Phe
                            675                 680                 685
            Ala Asn Arg Asn Phe Met Gln Leu Ile His Asp Asp Ser Leu Thr Phe
                            690                 695                 700
            Lys Glu Asp Ile Gln Lys Ala Gln Val Ser Gly Gln Gly Asp Ser Leu
            705                 710                 715                 720
            His Glu His Ile Ala Asn Leu Ala Gly Ser Pro Ala Ile Lys Lys Gly
                            725                 730                 735
```

-continued

Ile Leu Gln Thr Val Lys Val Asp Glu Leu Val Lys Val Met Gly
             740                 745                 750

Arg His Lys Pro Glu Asn Ile Val Ile Ala Met Ala Arg Glu Asn Gln
             755                 760                 765

Thr Thr Gln Lys Gly Lys Asn Ser Arg Glu Arg Met Lys Arg Ile
770              775                 780

Glu Glu Gly Ile Lys Glu Leu Gly Ser Gln Ile Leu Lys Glu His Pro
785              790                 795                 800

Val Glu Asn Thr Gln Leu Gln Asn Glu Lys Leu Tyr Leu Tyr Tyr Leu
             805                 810                 815

Gln Asn Gly Arg Asp Met Tyr Val Asp Gln Glu Leu Asp Ile Asn Arg
             820                 825                 830

Leu Ser Asp Tyr Asp Val Asp Ala Ile Val Pro Gln Ser Phe Leu Lys
             835                 840                 845

Asp Asp Ser Ile Asp Ala Lys Val Leu Thr Arg Ser Asp Lys Ala Arg
850              855                 860

Gly Lys Ser Asp Asn Val Pro Ser Glu Glu Val Val Lys Lys Met Lys
865              870                 875                 880

Asn Tyr Trp Arg Gln Leu Leu Asn Ala Lys Leu Ile Thr Gln Arg Lys
             885                 890                 895

Phe Asp Asn Leu Thr Lys Ala Glu Arg Gly Gly Leu Ser Glu Leu Asp
             900                 905                 910

Lys Ala Gly Phe Ile Lys Arg Gln Leu Val Glu Thr Arg Gln Ile Thr
             915                 920                 925

Lys His Val Ala Gln Ile Leu Asp Ser Arg Met Asn Thr Lys Tyr Asp
             930                 935                 940

Glu Asn Asp Lys Leu Ile Arg Glu Val Lys Val Ile Thr Leu Lys Ser
945              950                 955                 960

Lys Leu Val Ser Asp Phe Arg Lys Asp Phe Gln Phe Tyr Lys Val Arg
             965                 970                 975

Glu Ile Asn Asn Tyr His His Ala His Ala Ala Tyr Leu Asn Ala Val
             980                 985                 990

Val Gly Thr Ala Leu Ile Lys Lys Tyr Pro Lys Leu Glu Ser Glu Phe
             995                 1000                1005

Val Tyr Gly Asp Tyr Lys Val Tyr Asp Val Arg Lys Met Ile Ala
             1010                1015                1020

Lys Ser Glu Gln Glu Ile Gly Lys Ala Thr Ala Lys Tyr Phe Phe
             1025                1030                1035

Tyr Ser Asn Ile Met Asn Phe Phe Lys Thr Glu Ile Thr Leu Ala
             1040                1045                1050

Asn Gly Glu Ile Arg Lys Arg Pro Leu Ile Glu Thr Asn Gly Glu
             1055                1060                1065

Thr Gly Glu Ile Val Trp Asp Lys Gly Arg Asp Phe Ala Thr Val
             1070                1075                1080

Arg Lys Val Leu Ser Met Pro Gln Val Asn Ile Val Lys Lys Thr
             1085                1090                1095

Glu Val Gln Thr Gly Gly Phe Ser Lys Glu Ser Ile Leu Pro Lys
             1100                1105                1110

Arg Asn Ser Asp Lys Leu Ile Ala Arg Lys Lys Asp Trp Asp Pro
             1115                1120                1125

Lys Lys Tyr Gly Gly Phe Asp Ser Pro Thr Val Ala Tyr Ser Val
             1130                1135                1140

| | | | | | | | | | | |
|---|---|---|---|---|---|---|---|---|---|---|
| Leu | Val | Val | Ala | Lys | Val | Glu | Lys | Gly | Lys | Ser | Lys | Lys | Leu | Lys |
| | 1145 | | | | 1150 | | | | 1155 | |
| Ser | Val | Lys | Glu | Leu | Leu | Gly | Ile | Thr | Ile | Met | Glu | Arg | Ser | Ser |
| | 1160 | | | | 1165 | | | | 1170 | |
| Phe | Glu | Lys | Asn | Pro | Ile | Asp | Phe | Leu | Glu | Ala | Lys | Gly | Tyr | Lys |
| | 1175 | | | | 1180 | | | | 1185 | |
| Glu | Val | Lys | Lys | Asp | Leu | Ile | Ile | Lys | Leu | Pro | Lys | Tyr | Ser | Leu |
| | 1190 | | | | 1195 | | | | 1200 | |
| Phe | Glu | Leu | Glu | Asn | Gly | Arg | Lys | Arg | Met | Leu | Ala | Ser | Ala | Gly |
| | 1205 | | | | 1210 | | | | 1215 | |
| Glu | Leu | Gln | Lys | Gly | Asn | Glu | Leu | Ala | Leu | Pro | Ser | Lys | Tyr | Val |
| | 1220 | | | | 1225 | | | | 1230 | |
| Asn | Phe | Leu | Tyr | Leu | Ala | Ser | His | Tyr | Glu | Lys | Leu | Lys | Gly | Ser |
| | 1235 | | | | 1240 | | | | 1245 | |
| Pro | Glu | Asp | Asn | Glu | Gln | Lys | Gln | Leu | Phe | Val | Glu | Gln | His | Lys |
| | 1250 | | | | 1255 | | | | 1260 | |
| His | Tyr | Leu | Asp | Glu | Ile | Ile | Glu | Gln | Ile | Ser | Glu | Phe | Ser | Lys |
| | 1265 | | | | 1270 | | | | 1275 | |
| Arg | Val | Ile | Leu | Ala | Asp | Ala | Asn | Leu | Asp | Lys | Val | Leu | Ser | Ala |
| | 1280 | | | | 1285 | | | | 1290 | |
| Tyr | Asn | Lys | His | Arg | Asp | Lys | Pro | Ile | Arg | Glu | Gln | Ala | Glu | Asn |
| | 1295 | | | | 1300 | | | | 1305 | |
| Ile | Ile | His | Leu | Phe | Thr | Leu | Thr | Asn | Leu | Gly | Ala | Pro | Ala | Ala |
| | 1310 | | | | 1315 | | | | 1320 | |
| Phe | Lys | Tyr | Phe | Asp | Thr | Thr | Ile | Asp | Arg | Lys | Arg | Tyr | Thr | Ser |
| | 1325 | | | | 1330 | | | | 1335 | |
| Thr | Lys | Glu | Val | Leu | Asp | Ala | Thr | Leu | Ile | His | Gln | Ser | Ile | Thr |
| | 1340 | | | | 1345 | | | | 1350 | |
| Gly | Leu | Tyr | Glu | Thr | Arg | Ile | Asp | Leu | Ser | Gln | Leu | Gly | Gly | Asp |
| | 1355 | | | | 1360 | | | | 1365 | |

<210> SEQ ID NO 267
<211> LENGTH: 15
<212> TYPE: DNA
<213> ORGANISM: Homo sapiens

<400> SEQUENCE: 267
cagaagaaga agggc                                                       15

<210> SEQ ID NO 268
<211> LENGTH: 51
<212> TYPE: DNA
<213> ORGANISM: Homo sapiens

<400> SEQUENCE: 268
ccaatgggga ggacatcgat gtcacctcca atgactaggg tggtgggcaa c               51

<210> SEQ ID NO 269
<211> LENGTH: 15
<212> TYPE: DNA
<213> ORGANISM: Homo sapiens

<400> SEQUENCE: 269
ctctggccac tccct                                                       15

<210> SEQ ID NO 270
<211> LENGTH: 52
<212> TYPE: DNA

```
<213> ORGANISM: Homo sapiens

<400> SEQUENCE: 270
acatcgatgt cacctccaat gacaagcttg ctagcggtgg gcaaccacaa ac        52

<210> SEQ ID NO 271
<211> LENGTH: 57
<212> TYPE: DNA
<213> ORGANISM: Homo sapiens
<220> FEATURE:
<221> NAME/KEY: CDS
<222> LOCATION: (1)..(57)

<400> SEQUENCE: 271 ggc acc att aaa gaa aat atc att ggt gtt tcc tat gat gaa tat aga    48
Gly Thr Ile Lys Glu Asn Ile Ile Gly Val Ser Tyr Asp Glu Tyr Arg
1               5                   10                  15 tac aga agc                                                        57
Tyr Arg Ser <210> SEQ ID NO 272
<211> LENGTH: 19
<212> TYPE: PRT
<213> ORGANISM: Homo sapiens

<400> SEQUENCE: 272

Gly Thr Ile Lys Glu Asn Ile Ile Gly Val Ser Tyr Asp Glu Tyr Arg
1               5                   10                  15

Tyr Arg Ser

<210> SEQ ID NO 273
<211> LENGTH: 99
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other

<400> SEQUENCE: 273
nnnnnnnnnn nnnnnnnnnn guuuuagagc uagaaauagc aaguuaaaau aaggcuaguc    60
cguuaucaac uugaaaaagu ggcaccgagu cggugcuuu                          99

<210> SEQ ID NO 274
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: CDS
<222> LOCATION: (1)..(48)

<400> SEQUENCE: 274 att aaa gaa aat atc att ggc ttt gtt tcc tat gat gaa tat aga tac    48
Ile Lys Glu Asn Ile Ile Gly Phe Val Ser Tyr Asp Glu Tyr Arg Tyr
1               5                   10                  15

<210> SEQ ID NO 275
<211> LENGTH: 16
```

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 275

Ile Lys Glu Asn Ile Ile Gly Phe Val Ser Tyr Asp Glu Tyr Arg Tyr
1               5                   10                  15

<210> SEQ ID NO 276
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(48)
<223> OTHER INFORMATION: a, c, t, g, unknown or other

<400> SEQUENCE: 276
ccnnnnnnnn nnnnnnnnnn nnnnnnnnnn nnnnnnnnnn nnnnnnnngg         50

<210> SEQ ID NO 277
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(44)
<223> OTHER INFORMATION: a, c, t, g, unknown or other

<400> SEQUENCE: 277
ccnnnnnnnn nnnnnnnnnn nnnnnnnnnn nnnnnnnnnn nnnngg             46

<210> SEQ ID NO 278
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(40)
<223> OTHER INFORMATION: a, c, t, g, unknown or other

<400> SEQUENCE: 278
ccnnnnnnnn nnnnnnnnnn nnnnnnnnnn nnnnnnnnnn gg                 42

<210> SEQ ID NO 279
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(36)
<223> OTHER INFORMATION: a, c, t, g, unknown or other -continued

<400> SEQUENCE: 279
ccnnnnnnnn nnnnnnnnnn nnnnnnnnnn nnnnnngg                              38

<210> SEQ ID NO 280
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(32)
<223> OTHER INFORMATION: a, c, t, g, unknown or other

<400> SEQUENCE: 280
ccnnnnnnnn nnnnnnnnnn nnnnnnnnnn nngg                                  34

<210> SEQ ID NO 281
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(28)
<223> OTHER INFORMATION: a, c, t, g, unknown or other

<400> SEQUENCE: 281
ccnnnnnnnn nnnnnnnnnn nnnnnnnngg                                       30

<210> SEQ ID NO 282
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(24)
<223> OTHER INFORMATION: a, c, t, g, unknown or other

<400> SEQUENCE: 282
ccnnnnnnnn nnnnnnnnnn nnnngg                                           26

<210> SEQ ID NO 283
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(20)
<223> OTHER INFORMATION: a, c, t, g, unknown or other

<400> SEQUENCE: 283
ccnnnnnnnn nnnnnnnnnn gg                                               22

<210> SEQ ID NO 284

```
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(16)
<223> OTHER INFORMATION: a, c, t, g, unknown or other

<400> SEQUENCE: 284
ccnnnnnnnn nnnnnngg                                                 18

<210> SEQ ID NO 285
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(14)
<223> OTHER INFORMATION: a, c, t, g, unknown or other

<400> SEQUENCE: 285
ccnnnnnnnn nnnngg                                                   16

<210> SEQ ID NO 286
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(13)
<223> OTHER INFORMATION: a, c, t, g, unknown or other

<400> SEQUENCE: 286
ccnnnnnnnn nnngg                                                    15

<210> SEQ ID NO 287
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(12)
<223> OTHER INFORMATION: a, c, t, g, unknown or other

<400> SEQUENCE: 287
ccnnnnnnnn nngg                                                     14

<210> SEQ ID NO 288
<211> LENGTH: 13
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: modified_base
<222> LOCATION: (3)..(11)
<223> OTHER INFORMATION: a, c, t, g, unknown or other

<400> SEQUENCE: 288
ccnnnnnnnn ngg                                                          13

<210> SEQ ID NO 289
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(10)
<223> OTHER INFORMATION: a, c, t, g, unknown or other

<400> SEQUENCE: 289
ccnnnnnnnn gg                                                           12

<210> SEQ ID NO 290
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(9)
<223> OTHER INFORMATION: a, c, t, g, unknown or other

<400> SEQUENCE: 290
ccnnnnnnng g                                                            11

<210> SEQ ID NO 291
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(8)
<223> OTHER INFORMATION: a, c, t, g, unknown or other

<400> SEQUENCE: 291 ccnnnnnngg                                                              10

<210> SEQ ID NO 292
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(10)
<223> OTHER INFORMATION: a, c, t, g, unknown or other

<400> SEQUENCE: 292
```

```
ggnnnnnnnn cc                                                             12
```

<210> SEQ ID NO 293
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 293

```
aaaaaaagca ccgactcggt gccactttt caagttgata acggactagc cttattttaa       60
cttgctattt ctagctctaa aactcacatc aaccggtggc gcaggtgttt cgtccttcc      120 acaag                                                                 125
```

<210> SEQ ID NO 294
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 294

```
aaaaaaagca ccgactcggt gccactttt caagttgata acggactagc cttattttaa       60
cttgctattt ctagctctaa aactcacatc aaccggtggc gcaggtgttt cgtccttcc      120 acaag                                                                 125
```

<210> SEQ ID NO 295
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 295

```
aaaaaaagca ccgactcggt gccactttt caagttgata acggactagc cttattttaa       60
cttgctattt ctagctctaa aacgaggaca aagtacaaac ggcggtgttt cgtccttcc      120 acaag                                                                 125
```

<210> SEQ ID NO 296
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 296

```
aaaaaaagca ccgactcggt gccactttt caagttgata acggactagc cttattttaa       60
cttgctattt ctagctctaa aacgaggaca aagtacaaac ggcggtgttt cgtccttcc      120 acaag                                                                 125
```

<210> SEQ ID NO 297
<211> LENGTH: 125
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic primer"

<400> SEQUENCE: 297
aaaaaaagca ccgactcggt gccactttt caagttgata acggactagc cttattttaa      60
cttgctattt ctagctctaa aacgtggcgc attgccacga agcggtgttt cgtccttcc     120 acaag                                                                125

<210> SEQ ID NO 298
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 298
aaaaaaagca ccgactcggt gccactttt caagttgata acggactagc cttattttaa      60
cttgctattt ctagctctaa aaccgagggc agagtgctgc ttgggtgttt cgtccttcc     120 acaag                                                                125

<210> SEQ ID NO 299
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 299
aaaaaaagca ccgactcggt gccactttt caagttgata acggactagc cttattttaa      60
cttgctattt ctagctctaa aacgagtccg agcagaagaa gaaggtgttt cgtccttcc     120 acaag                                                                125

<210> SEQ ID NO 300
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 300
aaaaaaagca ccgactcggt gccactttt caagttgata acggactagc cttattttaa      60
cttgctattt ctagctctaa aacgaggaca aagtacaaac ggcggtgttt cgtccttcc     120 acaag                                                                125

<210> SEQ ID NO 301
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 301
```
aaaaaaagca ccgactcggt gccactttt caagttgata acggactagc cttattttaa    60
cttgctattt ctagctctaa aacagcagaa gaagaagggc tccggtgttt cgtccttcc   120 acaag                                                              125

<210> SEQ ID NO 302
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 302
aaaaaaagca ccgactcggt gccactttt caagttgata acggactagc cttattttaa    60
cttgctattt ctagctctaa aactcacatc aaccggtggc gcaggtgttt cgtccttcc   120 acaag                                                              125

<210> SEQ ID NO 303
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 303
aaaaaaagca ccgactcggt gccactttt caagttgata acggactagc cttattttaa    60
cttgctattt ctagctctaa aaccctggc ccaggtgaag gtgggtgttt cgtccttcc   120 acaag                                                              125

<210> SEQ ID NO 304
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 304
aaaaaaagca ccgactcggt gccactttt caagttgata acggactagc cttattttaa    60
cttgctattt ctagctctaa aactccctcc ctggcccagg tgaggtgttt cgtccttcc   120 acaag                                                              125

<210> SEQ ID NO 305
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 305
aaaaaaagca ccgactcggt gccactttt caagttgata acggactagc cttattttaa    60
cttgctattt ctagctctaa aacgaaccgg aggacaaagt acaggtgttt cgtccttcc   120 acaag                                                              125

```
<210> SEQ ID NO 306
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 306
aaaaaaagca ccgactcggt gccactttt  caagttgata acggactagc cttattttaa    60
cttgctattt ctagctctaa aacaggtgaa ggtgtggttc cagggtgttt cgtccttcc    120 acaag                                                                125

<210> SEQ ID NO 307
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 307
aaaaaaagca ccgactcggt gccactttt  caagttgata acggactagc cttattttaa    60
cttgctattt ctagctctaa aacggtgaag gtgtggttcc agaggtgttt cgtccttcc    120 acaag                                                                125

<210> SEQ ID NO 308
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 308
aaaaaaagca ccgactcggt gccactttt  caagttgata acggactagc cttattttaa    60
cttgctattt ctagctctaa aacgaaccgg aggacaaagt acaggtgttt cgtccttcc    120 acaag                                                                125

<210> SEQ ID NO 309
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 309
aaaaaaagca ccgactcggt gccactttt  caagttgata acggactagc cttattttaa    60
cttgctattt ctagctctaa aaccctggc  ccaggtgaag gtgggtgttt cgtccttcc    120 acaag                                                                125

<210> SEQ ID NO 310
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic primer"

<400> SEQUENCE: 310
aaaaaaagca ccgactcggt gccactttt caagttgata acggactagc cttatttaa      60 cttgctattt ctagctctaa aacaggtgaa ggtgtggttc cagggtgttt cgtccttcc    120 acaag                                                                125

<210> SEQ ID NO 311
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 311
aaaaaaagca ccgactcggt gccactttt caagttgata acggactagc cttatttaa      60 cttgctattt ctagctctaa aacgaggaca aagtacaaac ggcggtgttt cgtcctttcc   120
acaag                                                                125

<210> SEQ ID NO 312
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 312
aaaaaaagca ccgactcggt gccactttt caagttgata acggactagc cttatttaa      60 cttgctattt ctagctctaa aacgggaggg aggggcacag atgggtgttt cgtcctttcc   120
acaag                                                                125

<210> SEQ ID NO 313
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 313
aaaaaaagca ccgactcggt gccactttt caagttgata acggactagc cttatttaa      60 cttgctattt ctagctctaa aaccacctc acctgggcca ggggtgttt cgtcctttcc    120 acaag                                                                125

<210> SEQ ID NO 314
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 314
aaaaaaagca ccgactcggt gccactttt caagttgata acggactagc cttatttaa      60 cttgctattt ctagctctaa aacaccctag tcattggagg tgaggtgttt cgtcctttcc   120

```
acaag                                                          125

<210> SEQ ID NO 315
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 315
aaaaaaagca ccgactcggt gccactttt caagttgata acggactagc cttatttaa    60 cttgctattt ctagctctaa aaccagagca gccactgggg cctggtgttt cgtccttcc   120 acaag                                                              125

<210> SEQ ID NO 316
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 316
aaaaaaagca ccgactcggt gccactttt caagttgata acggactagc cttatttaa    60 cttgctattt ctagctctaa aaccaccttc acctgggcca gggggtgttt cgtccttcc   120 acaag                                                              125

<210> SEQ ID NO 317
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 317
aaaaaaagca ccgactcggt gccactttt caagttgata acggactagc cttatttaa    60 cttgctattt ctagctctaa aaccccatt ggcctgcttc gtgggtgttt cgtccttcc    120 acaag                                                              125

<210> SEQ ID NO 318
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 318
aaaaaaagca ccgactcggt gccactttt caagttgata acggactagc cttatttaa    60 cttgctattt ctagctctaa aacattggcc tgcttcgtgg caaggtgttt cgtccttcc   120 acaag                                                              125

<210> SEQ ID NO 319
<211> LENGTH: 125
<212> TYPE: DNA
```

<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 319
aaaaaaagca ccgactcggt gccactttt caagttgata acggactagc cttattttaa    60
cttgctattt ctagctctaa aactcctcct ccagcttctg ccgggtgttt cgtccttttcc   120 acaag                                                                125

<210> SEQ ID NO 320
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 320
aaaaaaagca ccgactcggt gccactttt caagttgata acggactagc cttattttaa    60
cttgctattt ctagctctaa aaccctccag cttctgccgt tgggtgttt cgtccttttcc   120 acaag                                                                125

<210> SEQ ID NO 321
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 321
aaaaaaagca ccgactcggt gccactttt caagttgata acggactagc cttattttaa    60
cttgctattt ctagctctaa aacattggcc tgcttcgtgg caaggtgttt cgtccttttcc   120 acaag                                                                125

<210> SEQ ID NO 322
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 322
aaaaaaagca ccgactcggt gccactttt caagttgata acggactagc cttattttaa    60
cttgctattt ctagctctaa aacgcagcaa gcagcactct gccggtgttt cgtccttttcc   120 acaag                                                                125

<210> SEQ ID NO 323
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 323

```
aaaaaaagca ccgactcggt gccactttt caagttgata acggactagc cttatttta          60 cttgctattt ctagctctaa aacttcttct tctgctcgga ctcggtgttt cgtcctttcc       120
acaag                                                                   125
```

<210> SEQ ID NO 324
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 324

```
aaaaaaagca ccgactcggt gccactttt caagttgata acggactagc cttatttta          60 cttgctattt ctagctctaa aacaccggag acaaagtac aaaggtgttt cgtcctttcc        120
acaag                                                                   125
```

<210> SEQ ID NO 325
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 325

```
aaaaaaagca ccgactcggt gccactttt caagttgata acggactagc cttatttta          60 cttgctattt ctagctctaa aactcttct ctgctcggac tcaggtgttt cgtcctttcc       120
acaag                                                                   125
```

<210> SEQ ID NO 326
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 326

```
aaaaaaagca ccgactcggt gccactttt caagttgata acggactagc cttatttta          60 cttgctattt ctagctctaa aacgttgatg tgatgggagc cctggtgttt cgtcctttcc       120
acaag                                                                   125
```

<210> SEQ ID NO 327
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 327

```
aaaaaaagca ccgactcggt gccactttt caagttgata acggactagc cttatttta          60 cttgctattt ctagctctaa aacgggccag ggagggaggg gcaggtgttt cgtcctttcc       120
acaag                                                                   125
```

<210> SEQ ID NO 328
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 328
aaaaaaagca ccgactcggt gccactttt caagttgata acggactagc cttattttaa      60
cttgctattt ctagctctaa aacgggaggg aggggcacag atgggtgttt cgtccttcc     120 acaag                                                                125

<210> SEQ ID NO 329
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 329
aaaaaaagca ccgactcggt gccactttt caagttgata acggactagc cttattttaa      60
cttgctattt ctagctctaa aacccggttc tggaaccaca cctggtgttt cgtccttcc     120 acaag                                                                125

<210> SEQ ID NO 330
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 330
aaaaaaagca ccgactcggt gccactttt caagttgata acggactagc cttattttaa      60
cttgctattt ctagctctaa aactcacctg ggccagggag ggaggtgttt cgtccttcc     120 acaag                                                                125

<210> SEQ ID NO 331
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 331
aaaaaaagca ccgactcggt gccactttt caagttgata acggactagc cttattttaa      60
cttgctattt ctagctctaa aactcacctg ggccagggag ggaggtgttt cgtccttcc     120 acaag                                                                125

<210> SEQ ID NO 332
<211> LENGTH: 125
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic primer"

<400> SEQUENCE: 332
aaaaaaagca ccgactcggt gccactttt caagttgata acggactagc cttattttaa      60
cttgctattt ctagctctaa aacgttctgg aaccacacct tcaggtgttt cgtccttttcc    120 acaag                                                                125

<210> SEQ ID NO 333
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 333
aaaaaaagca ccgactcggt gccactttt caagttgata acggactagc cttattttaa      60
cttgctattt ctagctctaa aacgggaggg aggggcacag atgggtgttt cgtccttttcc   120 acaag                                                                125

<210> SEQ ID NO 334
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 334
aaaaaaagca ccgactcggt gccactttt caagttgata acggactagc cttattttaa      60
cttgctattt ctagctctaa aacgggccag ggagggaggg gcaggtgttt cgtccttttcc   120 acaag                                                                125

<210> SEQ ID NO 335
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 335
aaaaaaagca ccgactcggt gccactttt caagttgata acggactagc cttattttaa      60
cttgctattt ctagctctaa aacgttctgg aaccacacct tcaggtgttt cgtccttttcc   120 acaag                                                                125

<210> SEQ ID NO 336
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 336
aaaaaaagca ccgactcggt gccactttt caagttgata acggactagc cttattttaa      60
```
cttgctattt ctagctctaa aacaggtgaa ggtgtggttc cagggtgttt cgtcctttcc    120
acaag    125

<210> SEQ ID NO 337
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 337
aaaaaaagca ccgactcggt gccactttt caagttgata acggactagc cttattttaa    60
cttgctattt ctagctctaa aacgaaccgg aggacaaagt acaggtgttt cgtcctttcc    120
acaag    125

<210> SEQ ID NO 338
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 338
aaaaaaagca ccgactcggt gccactttt caagttgata acggactagc cttattttaa    60
cttgctattt ctagctctaa aaccaaaccc acgagggcag agtggtgttt cgtcctttcc    120
acaag    125

<210> SEQ ID NO 339
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 339
aaaaaaagca ccgactcggt gccactttt caagttgata acggactagc cttattttaa    60
cttgctattt ctagctctaa aacgagtttc tcatctgtgc cccggtgttt cgtcctttcc    120
acaag    125

<210> SEQ ID NO 340
<211> LENGTH: 684
<212> TYPE: DNA
<213> ORGANISM: Homo sapiens
<220> FEATURE:
<221> NAME/KEY: CDS
<222> LOCATION: (1)..(123)
<220> FEATURE:
<221> NAME/KEY: CDS
<222> LOCATION: (127)..(159)
<220> FEATURE:
<221> NAME/KEY: CDS
<222> LOCATION: (163)..(399)
<220> FEATURE:
<221> NAME/KEY: CDS
<222> LOCATION: (403)..(684)

<400> SEQUENCE: 340 aaa acc acc ctt ctc tct ggc cca ctg tgt cct ctt cct gcc ctg cca    48

```
Lys Thr Thr Leu Leu Ser Gly Pro Leu Cys Pro Leu Pro Ala Leu Pro
1               5                   10                  15 tcc cct tct gtg aat gtt aga ccc atg gga gca gct ggt cag agg gga      96
Ser Pro Ser Val Asn Val Arg Pro Met Gly Ala Ala Gly Gln Arg Gly
                20                  25                  30 ccc cgg cct ggg gcc cct aac cct atg tag cct cag tct tcc cat cag     144
Pro Arg Pro Gly Ala Pro Asn Pro Met     Pro Gln Ser Ser His Gln
            35                  40                      45 gct ctc agc tca gcc tga gtg ttg agg ccc cag tgg ctg ctc tgg ggg     192
Ala Leu Ser Ser Ala     Val Leu Arg Pro Gln Trp Leu Leu Trp Gly
                50                  55                  60 cct cct gag ttt ctc atc tgt gcc cct ccc tcc ctg gcc cag gtg aag     240
Pro Pro Glu Phe Leu Ile Cys Ala Pro Pro Ser Leu Ala Gln Val Lys
                65                  70                  75 gtg tgg ttc cag aac cgg agg aca aag tac aaa cgg cag aag ctg gag     288
Val Trp Phe Gln Asn Arg Arg Thr Lys Tyr Lys Arg Gln Lys Leu Glu
            80                  85                  90 gag gaa ggg cct gag tcc gag cag aag aag aag ggc tcc cat cac atc     336
Glu Glu Gly Pro Glu Ser Glu Gln Lys Lys Lys Gly Ser His His Ile
95                  100                 105                 110 aac cgg tgg cgc att gcc acg aag cag gcc aat ggg gag gac atc gat     384
Asn Arg Trp Arg Ile Ala Thr Lys Gln Ala Asn Gly Glu Asp Ile Asp
                115                 120                 125 gtc acc tcc aat gac tag ggt ggg caa cca caa acc cac gag ggc aga     432
Val Thr Ser Asn Asp     Gly Gly Gln Pro Gln Thr His Glu Gly Arg
                130                 135                 140 gtg ctg ctt gct gct ggc cag gcc cct gcg tgg gcc caa gct gga ctc     480
Val Leu Leu Ala Ala Gly Gln Ala Pro Ala Trp Ala Gln Ala Gly Leu
                145                 150                 155 tgg cca ctc cct ggc cag gct ttg ggg agg cct gga gtc atg gcc cca     528
Trp Pro Leu Pro Gly Gln Ala Leu Gly Arg Pro Gly Val Met Ala Pro
            160                 165                 170 cag ggc ttg aag ccc ggg gcc gcc att gac aga ggg aca agc aat ggg     576
Gln Gly Leu Lys Pro Gly Ala Ala Ile Asp Arg Gly Thr Ser Asn Gly
            175                 180                 185 ctg gct gag gcc tgg gac cac ttg gcc ttc tcc tcg gag agc ctg cct     624
Leu Ala Glu Ala Trp Asp His Leu Ala Phe Ser Ser Glu Ser Leu Pro
190                 195                 200                 205 gcc tgg gcg ggc ccg ccc gcc acc gca gcc tcc cag ctg ctc tcc gtg     672
Ala Trp Ala Gly Pro Pro Ala Thr Ala Ala Ser Gln Leu Leu Ser Val
                210                 215                 220 tct cca atc tcc                                                     684
Ser Pro Ile Ser
            225

<210> SEQ ID NO 341
<211> LENGTH: 41
<212> TYPE: PRT
<213> ORGANISM: Homo sapiens

<400> SEQUENCE: 341

Lys Thr Thr Leu Leu Ser Gly Pro Leu Cys Pro Leu Pro Ala Leu Pro
1               5                   10                  15

Ser Pro Ser Val Asn Val Arg Pro Met Gly Ala Ala Gly Gln Arg Gly
                20                  25                  30

Pro Arg Pro Gly Ala Pro Asn Pro Met
            35                  40

<210> SEQ ID NO 342
<211> LENGTH: 11
```

```
<212> TYPE: PRT
<213> ORGANISM: Homo sapiens

<400> SEQUENCE: 342

Pro Gln Ser Ser His Gln Ala Leu Ser Ser Ala
1               5                   10

<210> SEQ ID NO 343
<211> LENGTH: 79
<212> TYPE: PRT
<213> ORGANISM: Homo sapiens

<400> SEQUENCE: 343

Val Leu Arg Pro Gln Trp Leu Leu Trp Gly Pro Pro Glu Phe Leu Ile
1               5                   10                  15

Cys Ala Pro Pro Ser Leu Ala Gln Val Lys Val Trp Phe Gln Asn Arg
                20                  25                  30

Arg Thr Lys Tyr Lys Arg Gln Lys Leu Glu Glu Glu Gly Pro Glu Ser
            35                  40                  45

Glu Gln Lys Lys Lys Gly Ser His His Ile Asn Arg Trp Arg Ile Ala
        50                  55                  60

Thr Lys Gln Ala Asn Gly Glu Asp Ile Asp Val Thr Ser Asn Asp
65                  70                  75

<210> SEQ ID NO 344
<211> LENGTH: 94
<212> TYPE: PRT
<213> ORGANISM: Homo sapiens

<400> SEQUENCE: 344

Gly Gly Gln Pro Gln Thr His Glu Gly Arg Val Leu Leu Ala Ala Gly
1               5                   10                  15

Gln Ala Pro Ala Trp Ala Gln Ala Gly Leu Trp Pro Leu Pro Gly Gln
                20                  25                  30

Ala Leu Gly Arg Pro Gly Val Met Ala Pro Gln Gly Leu Lys Pro Gly
            35                  40                  45

Ala Ala Ile Asp Arg Gly Thr Ser Asn Gly Leu Ala Glu Ala Trp Asp
        50                  55                  60

His Leu Ala Phe Ser Ser Glu Ser Leu Pro Ala Trp Ala Gly Pro Pro
65                  70                  75                  80

Ala Thr Ala Ala Ser Gln Leu Leu Ser Val Ser Pro Ile Ser
                85                  90

<210> SEQ ID NO 345
<211> LENGTH: 57
<212> TYPE: DNA
<213> ORGANISM: Homo sapiens

<400> SEQUENCE: 345
aagctggagg aggaagggcc tgagtccgag cagaagaaga agggctccca tcacatc      57

<210> SEQ ID NO 346
<211> LENGTH: 28
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 346
```

```
gaguccgagc agaagaagaa guuuuaga                                       28
```

```
<210> SEQ ID NO 347
<211> LENGTH: 38
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 347
ggaagggccu gaguccgagc agaagaagaa guuuuaga                            38
```

```
<210> SEQ ID NO 348
<211> LENGTH: 38
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 348
ggccuccaag gaguccgagc agaagaagaa guuuuaga                            38
```

```
<210> SEQ ID NO 349
<211> LENGTH: 77
<212> TYPE: DNA
<213> ORGANISM: Homo sapiens

<400> SEQUENCE: 349
agaagaaggg ctcccatcac atcaaccggt ggcgcattgc cacgaagcag gccaatgggg    60
aggacatcga tgtcacc                                                   77
```

```
<210> SEQ ID NO 350
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 350
aaaaaaaaaa aaaaaaaaaa aaaaaaaaaa aaaaaaaaaa aaaaaaaaaa aaaaaaaaaa    60
aaaaaaaaaa aaaaaaaaaa aaaaaaaaaa aaaaaaaaaa aaaaaaaaaa aaaaaaaaaa    120
```

```
<210> SEQ ID NO 351
<211> LENGTH: 30
<212> TYPE: DNA
<213> ORGANISM: Homo sapiens

<400> SEQUENCE: 351
agaagaaggg ctcccatcat cgatgtcacc                                     30
```

```
<210> SEQ ID NO 352
<211> LENGTH: 41
<212> TYPE: DNA
<213> ORGANISM: Homo sapiens

<400> SEQUENCE: 352
agaagaaggg ctcccatcac agggaggaca tcgatgtcac c                        41
```

```
<210> SEQ ID NO 353
<211> LENGTH: 41
<212> TYPE: DNA
<213> ORGANISM: Homo sapiens

<400> SEQUENCE: 353
agaagaaggg ctcccatcac atcaaccggt gggatgtcac c                 41

<210> SEQ ID NO 354
<211> LENGTH: 69
<212> TYPE: DNA
<213> ORGANISM: Homo sapiens

<400> SEQUENCE: 354
agaagaaggg ctcccatcac atcaaccggt ggcgcattgc cacgaagcag gccaatgatc   60
gatgtcacc                                                          69

<210> SEQ ID NO 355
<211> LENGTH: 72
<212> TYPE: DNA
<213> ORGANISM: Homo sapiens

<400> SEQUENCE: 355
agaagaaggg ctcccatcac atcaaccggt ggcgccacga agcaggccaa tggggaggac   60
atcgatgtca cc                                                      72

<210> SEQ ID NO 356
<211> LENGTH: 74
<212> TYPE: DNA
<213> ORGANISM: Homo sapiens

<400> SEQUENCE: 356
agaagaaggg ctcccatctc aaccggtggc gcattgccac gaagcaggcc aatggggagg   60
acatcgatgt cacc                                                    74

<210> SEQ ID NO 357
<211> LENGTH: 74
<212> TYPE: DNA
<213> ORGANISM: Homo sapiens

<400> SEQUENCE: 357
agaagaaggg ctcccatcac atcaaccggt ggcgcattgc cacgaagcag gccggggagg   60
acatcgatgt cacc                                                    74

<210> SEQ ID NO 358
<211> LENGTH: 71
<212> TYPE: DNA
<213> ORGANISM: Homo sapiens

<400> SEQUENCE: 358
accggaggac aaagtacaaa cggcagaagc tggaggagga agggcctgag tccgagcaga   60
agaagaaggg c                                                       71

<210> SEQ ID NO 359
<211> LENGTH: 23
<212> TYPE: DNA
<213> ORGANISM: Homo sapiens

<400> SEQUENCE: 359
gaggccgagc agaagaaaga cgg                                          23
```

```
<210> SEQ ID NO 360
<211> LENGTH: 23
<212> TYPE: DNA
<213> ORGANISM: Homo sapiens

<400> SEQUENCE: 360
aagtctgagc acaagaagaa tgg                                           23

<210> SEQ ID NO 361
<211> LENGTH: 23
<212> TYPE: DNA
<213> ORGANISM: Homo sapiens

<400> SEQUENCE: 361
gagtcctagc aggagaagaa gag                                           23

<210> SEQ ID NO 362
<211> LENGTH: 23
<212> TYPE: DNA
<213> ORGANISM: Homo sapiens

<400> SEQUENCE: 362
gagtctaagc agaagaagaa gag                                           23

<210> SEQ ID NO 363
<211> LENGTH: 23
<212> TYPE: DNA
<213> ORGANISM: Homo sapiens

<400> SEQUENCE: 363
gagttagagc agaagaagaa agg                                           23

<210> SEQ ID NO 364
<211> LENGTH: 64
<212> TYPE: DNA
<213> ORGANISM: Homo sapiens

<400> SEQUENCE: 364
ccaatgggga ggacatcgat gtcacctcca atgactaggg tgggcaacca caaacccacg   60
aggg                                                                64

<210> SEQ ID NO 365
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 365
ccctcgtggg tttgtggttg cccaccgcta gcaagcttgt cattggaggt gacatcgatg   60
tcct                                                                64

<210> SEQ ID NO 366
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: CDS
```

```
<222> LOCATION: (1)..(63)

<400> SEQUENCE: 366 att gcc acg aag cag gcc aat ggg gag gac atc gat gtc acc tcc aat    48
Ile Ala Thr Lys Gln Ala Asn Gly Glu Asp Ile Asp Val Thr Ser Asn
1               5                   10                  15 gac tac tac cca tac                                                63
Asp Tyr Tyr Pro Tyr
            20

<210> SEQ ID NO 367
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 367

Ile Ala Thr Lys Gln Ala Asn Gly Glu Asp Ile Asp Val Thr Ser Asn
1               5                   10                  15

Asp Tyr Tyr Pro Tyr
            20

<210> SEQ ID NO 368
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 368
ggacctgtaa agcaggccaa tggggaggac atcgatgtca cctccaatga ctagggtggg    60
caa                                                                 63

<210> SEQ ID NO 369
<211> LENGTH: 70
<212> TYPE: DNA
<213> ORGANISM: Mus musculus

<400> SEQUENCE: 369
gatgacccca ccttgcctga aggttggaca cgaaagctta aacaaaggaa gtctggccga    60
tctgctggaa                                                          70

<210> SEQ ID NO 370
<211> LENGTH: 59
<212> TYPE: DNA
<213> ORGANISM: Mus musculus

<400> SEQUENCE: 370
gatgacccca ccttgcctga aggttggaca cgaaagctta aacaaaggat ctgctggaa     59

<210> SEQ ID NO 371
<211> LENGTH: 56
<212> TYPE: DNA
<213> ORGANISM: Mus musculus

<400> SEQUENCE: 371
gatgacccct gcctgaagg ttggacacga agcttaaac aaaggatctg ctggaa         56
```

```
<210> SEQ ID NO 372
<211> LENGTH: 54
<212> TYPE: DNA
<213> ORGANISM: Mus musculus

<400> SEQUENCE: 372
gatgacccca cctgaaggtt ggacacgaaa gcttaaacaa aggatctgct ggaa         54

<210> SEQ ID NO 373
<211> LENGTH: 44
<212> TYPE: DNA
<213> ORGANISM: Mus musculus

<400> SEQUENCE: 373
gatgacccca ccttgcctga aggtgtctgg ccgatctgct ggaa                    44

<210> SEQ ID NO 374
<211> LENGTH: 65
<212> TYPE: DNA
<213> ORGANISM: Mus musculus

<400> SEQUENCE: 374
gatgacccca cctgaaggtt ggacacgaaa gcttaaacaa aggaagtctg gccgatctgc   60
tggaa                                                               65

<210> SEQ ID NO 375
<211> LENGTH: 64
<212> TYPE: DNA
<213> ORGANISM: Mus musculus

<400> SEQUENCE: 375
gatgacccac ctgaaggttg gacacgaaag cttaaacaaa ggaagtctgg ccgatctgct   60
ggaa                                                                64

<210> SEQ ID NO 376
<211> LENGTH: 67
<212> TYPE: DNA
<213> ORGANISM: Mus musculus

<400> SEQUENCE: 376
gatgacccct tgcctgaagg ttggacacga aagcttaaac aaaggaagtc tggccgatct   60
gctggaa                                                             67

<210> SEQ ID NO 377
<211> LENGTH: 67
<212> TYPE: DNA
<213> ORGANISM: Mus musculus

<400> SEQUENCE: 377
gatgacccca tgcctgaagg ttggacacga aagcttaaac aaaggaagtc tggccgatct   60
gctggaa                                                             67

<210> SEQ ID NO 378
<211> LENGTH: 67
<212> TYPE: DNA
<213> ORGANISM: Mus musculus

<400> SEQUENCE: 378
gatgacccct tgcctgaagg ttggacacga aagcttaaac aaaggaagtc tggccgatct   60
gctggaa                                                             67
```

<210> SEQ ID NO 379
<211> LENGTH: 67
<212> TYPE: DNA
<213> ORGANISM: Mus musculus

<400> SEQUENCE: 379
gatgacccca ccttgcctga aggttggaca cgaaagctta aacaaaggtc tggccgatct    60
gctggaa    67

<210> SEQ ID NO 380
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 380
tgcgccaccg gttgatgtga tgg    23

<210> SEQ ID NO 381
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 381
actctgccct cgtgggtttg tgg    23

<210> SEQ ID NO 382
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 382
caaacggcag aagctggagg agg    23

<210> SEQ ID NO 383
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 383
aggccccagt ggctgctctg ggg    23

<210> SEQ ID NO 384
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 384
tgaaggtgtg gttccagaac cgg                                          23

<210> SEQ ID NO 385
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 385
gccgtttgta ctttgtcctc cgg                                          23

<210> SEQ ID NO 386
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 386
tcacctgggc cagggaggga ggg                                          23

<210> SEQ ID NO 387
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 387
ggggcacaga tgagaaactc agg                                          23

<210> SEQ ID NO 388
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 388
tcacctgggc cagggaggga ggg                                          23

<210> SEQ ID NO 389
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 389
ggggcacaca tgagaaactc agg                                          23

<210> SEQ ID NO 390
<211> LENGTH: 23
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 390
atctggtcag aatatgataa agg                                          23

<210> SEQ ID NO 391
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 391
gtcactgtac tgatgtgaat tgg                                          23

<210> SEQ ID NO 392
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 392
catctgaagg ccagcagcat tgg                                          23

<210> SEQ ID NO 393
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 393
tgataaggca gaaacctgtt tgg                                          23

<210> SEQ ID NO 394
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 394
gaagataagt gaggtttaaa agg                                          23

<210> SEQ ID NO 395
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 395
gtatcatttg acatatctaa tgg                                          23

```
<210> SEQ ID NO 396
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 396
cagcatggaa tgaaaatgac cgg                                            23

<210> SEQ ID NO 397
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 397
gcagcatgga atgaaaatga cgg                                            23

<210> SEQ ID NO 398
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 398
gtgcaagccg aacagatgaa agg                                            23

<210> SEQ ID NO 399
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 399
ggagtatcag aaatgactat tgg                                            23

<210> SEQ ID NO 400
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 400
ggtcactgta ctgatgtgaa tgg                                            23

<210> SEQ ID NO 401
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 401
tcactgtact gatgtgaatg ggg                                      23

<210> SEQ ID NO 402
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 402
gttccttaaa taagaacttt agg                                      23

<210> SEQ ID NO 403
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 403
tcctacaaga agataagtga agg                                      23

<210> SEQ ID NO 404
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 404
tatcatttga catatctaat tgg                                      23

<210> SEQ ID NO 405
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 405
aacttttcta actacaaaca agg                                      23

<210> SEQ ID NO 406
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 406
ccaacaccaa ccagaacttg ggg                                      23

<210> SEQ ID NO 407
<211> LENGTH: 23
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 407
acagcaatgc caatgctggg ggg                                              23

<210> SEQ ID NO 408
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 408
gtggaaatca tctttctcgt tgg                                              23

<210> SEQ ID NO 409
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 409
tctgctgcct gacacggcca agg                                              23

<210> SEQ ID NO 410
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 410
cgagctctgc tgcctgacac cgg                                              23

<210> SEQ ID NO 411
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 411
tccttgatgg ccacctcgtc cgg                                              23

<210> SEQ ID NO 412
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 412
atgacagcaa tgccaatgct tgg                                              23
```

<210> SEQ ID NO 413
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 413
agcaatgcca atgctgggggg ggg                                          23

<210> SEQ ID NO 414
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 414
gccaacacca accagaactt tgg                                           23

<210> SEQ ID NO 415
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 415
ggagaacagc actccgctct tgg                                           23

<210> SEQ ID NO 416
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 416
tgacagcaat gccaatgctg ggg                                           23

<210> SEQ ID NO 417
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 417
ccggccaaga ccttgaagcc agg                                           23

<210> SEQ ID NO 418
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 418
tattacagaa tgagagactg tgg                                         23

<210> SEQ ID NO 419
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 419
aaaagaccta aacaaaagaa tgg                                         23

<210> SEQ ID NO 420
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 420
tcagagcttc ctgacaccca tgg                                         23

<210> SEQ ID NO 421
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 421
gagaacagca ctccgctctg ggg                                         23

<210> SEQ ID NO 422
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 422
ctgcctgaca cggccaggac cgg                                         23

<210> SEQ ID NO 423
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 423
gagtccgagc agaagaagaa ggg                                         23

<210> SEQ ID NO 424
<211> LENGTH: 23
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 424
cacgaagcag gccaatgggg agg                                           23

<210> SEQ ID NO 425
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 425
ggagcccttc ttcttctgct cgg                                           23

<210> SEQ ID NO 426
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 426
ggcagagtgc tgcttgctgc tgg                                           23

<210> SEQ ID NO 427
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 427
ttgccacgaa gcaggccaat ggg                                           23

<210> SEQ ID NO 428
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 428
aggtgtggtt ccagaaccgg agg                                           23

<210> SEQ ID NO 429
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 429
cggcagaagc tggaggagga agg                                           23
```

<210> SEQ ID NO 430
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 430
agggctccca tcacatcaac cgg                          23

<210> SEQ ID NO 431
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 431
tgagtccgag cagaagaaga agg                          23

<210> SEQ ID NO 432
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 432
tcacctccaa tgactagggt ggg                          23

<210> SEQ ID NO 433
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 433
aacctcactt atcttcttgt agg                          23

<210> SEQ ID NO 434
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 434
ctcacttatc ttcttgtagg agg                          23

<210> SEQ ID NO 435
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 435
ccatgctgct ggccttcaga tgg        23

<210> SEQ ID NO 436
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 436
gccaaacata agtgaccaac agg        23

<210> SEQ ID NO 437
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 437
tgtcaaatga tacaaacatt agg        23

<210> SEQ ID NO 438
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 438
gctgctggcc ttcagatggc tgg        23

<210> SEQ ID NO 439
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 439
tcagcaacct ctaactaacc agg        23

<210> SEQ ID NO 440
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 440
tcattttcat tccatgctgc tgg        23

<210> SEQ ID NO 441
<211> LENGTH: 23

```
-continued

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 441
catgcaaacc ttcatctgtt cgg                                          23

<210> SEQ ID NO 442
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 442
ctggtagatg gagttgggtt tgg                                          23

<210> SEQ ID NO 443
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 443
agtgctgttc tcccaagttc tgg                                          23

<210> SEQ ID NO 444
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 444
ggcattgctg tcatcctcgt ggg                                          23

<210> SEQ ID NO 445
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 445
tcccaagttc tggttggtgt tgg                                          23

<210> SEQ ID NO 446
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 446
```
ttggccgtcc tggccgtgtc agg                                    23

<210> SEQ ID NO 447
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 447
ttccgacgag gtggccatca agg                                    23

<210> SEQ ID NO 448
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 448
tggcattgct gtcatcctcg tgg                                    23

<210> SEQ ID NO 449
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 449
cctcgtgggc acttccgacg agg                                    23

<210> SEQ ID NO 450
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 450
ctggttgtag gatttgagtt agg                                    23

<210> SEQ ID NO 451
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 451
ttatttctga agaatattaa agg                                    23

<210> SEQ ID NO 452
<211> LENGTH: 23
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 452
tgtgtgagga taaaagagtt ggg                                               23

<210> SEQ ID NO 453
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 453
aatacctagt tacaggcatt tgg                                               23

<210> SEQ ID NO 454
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 454
cagaagagcc cccccagcat tgg                                               23

<210> SEQ ID NO 455
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 455
cgtgggcact tccgacgagg tgg                                               23

<210> SEQ ID NO 456
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 456
tgatttccac catctctccg tgg                                               23

<210> SEQ ID NO 457
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 457
tgaccggaag atccaggggg tgg                                               23

<210> SEQ ID NO 458
```

```
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 458
ggaagggcct gagtccgagc agaagaagag gg                              32

<210> SEQ ID NO 459
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 459
ggcctccaag gagtccgagc agaagaagaa ggg                             33

<210> SEQ ID NO 460
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 460
gacatcgatg tcctccccat tgg                                        23

<210> SEQ ID NO 461
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 461
gtcacctcca atgactaggg tgg                                        23

<210> SEQ ID NO 462
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 462
gggcaaccac aaacccacga ggg                                        23

<210> SEQ ID NO 463
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 463
```
caagcagcac tctgccctcg tgg                                                    23

<210> SEQ ID NO 464
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 464
ttcttcttct gctcggactc agg                                                    23

<210> SEQ ID NO 465
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 465
ctccccattg gcctgcttcg agg                                                    23

<210> SEQ ID NO 466
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 466
gaacttacct ggttagttag agg                                                    23

<210> SEQ ID NO 467
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 467
ggtgatgatg ctctttgggt cgg                                                    23

<210> SEQ ID NO 468
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 468
tctgtgatct catgtctgac cgg                                                    23

<210> SEQ ID NO 469
<211> LENGTH: 23
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 469
cagcaatgcc aatgctgggg ggg                                              23

<210> SEQ ID NO 470
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 470
tttctcgtgg gcatccttga tgg                                              23

<210> SEQ ID NO 471
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 471
ggagaacagc actccgctct ggg                                              23

<210> SEQ ID NO 472
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 472
ctggttggtg ttggccgtcc tgg                                              23

<210> SEQ ID NO 473
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 473
gtccaacctt caggcaaggt ggg                                              23

<210> SEQ ID NO 474
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 474
gcgctgtttg ggggaagccg agg                                              23

```
<210> SEQ ID NO 475
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 475
gggtgggggg agtttgctcc tgg                                           23

<210> SEQ ID NO 476
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 476
gaccccctcc accccgcctc cgg                                           23

<210> SEQ ID NO 477
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 477
aagcttaaac aaaggaagtc tgg                                           23

<210> SEQ ID NO 478
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 478
ggctccatta tccgtgaccg ggg                                           23

<210> SEQ ID NO 479
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 479 tccctctttageccagagccg ggg                                           23

<210> SEQ ID NO 480
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 480 gaaactttc gtccaacttc tgg                                              23
```

OPTIMIZED CRISPR-CAS DOUBLE NICKASE SYSTEMS, METHODS AND COMPOSITIONS FOR SEQUENCE MANIPULATION

RELATED APPLICATIONS AND INCORPORATION BY REFERENCE

This application is a Continuation of U.S. patent application Ser. No. 14/972,523 filed on Dec. 17, 2015, which is a Continuation-In-Part of International Application Number PCT/US2014/041803 filed on Jun. 10, 2014 which published as PCT Publication Number WO2014/204725 on Dec. 12, 2014. Priority is claimed from U.S. provisional patent applications 61/836,123, filed Jun. 17, 2013, 61/847,537, filed Jul. 17, 2013, 61/862,355, filed Aug. 5, 2013, 61/871,301, filed Aug. 28, 2013, and 61/915,383, filed Dec. 12, 2013.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

STATEMENT AS TO FEDERALLY SPONSORED RESEARCH

This invention was made with government support under grant no. MH100706 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Dec. 14, 2015, is named 44790172022_SL.txt and is 253,354 bytes in size.

FIELD OF THE INVENTION

The present invention generally relates to the delivery, engineering and optimization of systems, methods and compositions used for the control of gene expression involving sequence targeting, such as genome perturbation or gene-editing, that relate to Clustered Regularly Interspaced Short Palindromic Repeats (CRISPR) and components thereof.

BACKGROUND OF THE INVENTION

Recent advances in genome sequencing techniques and analysis methods have significantly accelerated the ability to catalog and map genetic factors associated with a diverse range of biological functions and diseases. Precise genome targeting technologies are needed to enable systematic reverse engineering of causal genetic variations by allowing selective perturbation of individual genetic elements, as well as to advance synthetic biology, biotechnological, and medical applications. Although genome-editing techniques such as designer zinc fingers, transcription activator-like effectors (TALEs), or homing meganucleases are available for producing targeted genome perturbations, there remains a need for new genome engineering technologies that are affordable, easy to set up, scalable, and amenable to targeting multiple positions within the eukaryotic genome.

SUMMARY OF THE INVENTION

The CRISPR-Cas system does not require the generation of customized proteins to target specific sequences but rather a single Cas enzyme can be programmed by a short RNA molecule to recognize a specific DNA target. Adding the CRISPR-Cas system to the repertoire of genome sequencing techniques and analysis methods may significantly simplify the methodology and accelerate the ability to catalog and map genetic factors associated with a diverse range of biological functions and diseases. To utilize the CRISPR-Cas system effectively for genome editing without deleterious effects, it is critical to understand aspects of engineering and optimization of these genome engineering tools, which are aspects of the claimed invention.

There exists a pressing need for alternative and robust systems and techniques for sequence targeting with a wide array of applications. Aspects of this invention address this need and provides related advantages. An exemplary CRISPR complex comprises a CRISPR enzyme complexed with a guide sequence hybridized to a target sequence within the target polynucleotide. The guide sequence is linked to a tracr mate sequence, which in turn hybridizes to a tracr sequence.

In one aspect, the invention provides methods for using one or more elements of a CRISPR system. The CRISPR complex of the invention provides an effective means for modifying a target polynucleotide. The CRISPR complex of the invention has a wide variety of utilities including modifying (e.g., deleting, inserting, translocating, inactivating, activating) a target polynucleotide in a multiplicity of cell types. In one aspect, the cell is a eukaryotic cell. In one aspect, the cell is a prokaryotic cell. As such the CRISPR complex of the invention has a broad spectrum of applications in, e.g., gene or genome editing, gene therapy, drug discovery, drug screening, disease diagnosis, and prognosis. An exemplary CRISPR complex comprises a CRISPR enzyme complexed with a guide sequence hybridized to a target sequence within the target polynucleotide. In one aspect, the guide sequence is linked to a tracr mate sequence, which in turn hybridizes to a tracr sequence. In one aspect, the CRISPR enzyme is a nickase.

Aspects of the invention relate to Cas9 enzymes having improved target specificity in a CRISPR-Cas9 system, having guide RNAs with optimal activity, with Cas9 enzymes that are smaller in length than wild-type Cas9 enzymes (and nucleic acid molecules coding therefor), and chimeric Cas9 enzymes, as well as methods of improving the target specificity of a Cas9 enzyme or of designing a CRISPR-Cas9 system comprising designing or preparing guide RNAs having optimal activity and/or selecting or preparing a Cas9 enzyme having a smaller size or length than wild-type Cas9 whereby packaging a nucleic acid coding such construct into a delivery vector is advantageous as there is less coding therefor in the delivery vector than for wild-type Cas9, and/or generating chimeric Cas9 enzymes.

Also provided are uses of the present sequences, vectors, enzymes or systems, in medicine. Also provided are uses of the same in gene or genome editing.

In an additional aspect of the invention, a Cas9 enzyme may comprise one or more mutations and may be used as a generic DNA binding protein with or without fusion to a functional domain. The mutations may be artificially introduced mutations or gain- or loss-of-function mutations. The mutations may include but are not limited to mutations in one of the catalytic domains (e.g., at residues D10 and H840). Further mutations have been characterized and may be used in the inventive constructs. In one aspect of the invention, the mutated Cas9 enzyme may be fused to a protein domain, e.g., such as a transcriptional activation domain. In one aspect, the transcriptional activation domain may be VP64. Other aspects of the invention relate to the mutated Cas 9 enzyme being fused to domains which include but are not limited to a transcriptional repressor, a recombinase, a transposase, a histone remodeler, a DNA methyltransferase, a cryptochrome, a light inducible/controllable domain or a chemically inducible/controllable domain.

In a further embodiment, the invention provides for methods to generate mutant tracrRNA and direct repeat sequences or mutant chimeric guide sequences that allow for enhancing performance of these RNAs in cells. Aspects of the invention also provide for selection of said sequences.

Aspects of the invention also provide for methods of simplifying the cloning and delivery of components of the CRISPR complex. In the preferred embodiment of the invention, a suitable promoter, such as the U6 promoter, is amplified with a DNA oligo and positioned contiguous to and upstream of a sequence encoding the guide RNA. The resulting PCR product can then be transfected into cells to drive expression of the guide RNA. Aspects of the invention also relate to the guide RNA being transcribed in vitro or ordered from a synthesis company and directly transfected.

In one aspect, the invention provides for methods to improve activity by using a more active polymerase. In one aspect, a T7 promoter may be inserted contiguous to and upstream of a sequence encoding a guide RNA. In a preferred embodiment, the expression of guide RNAs under the control of the T7 promoter is driven by the expression of the T7 polymerase in the cell. In an advantageous embodiment, the cell is a eukaryotic cell. In a preferred embodiment the eukaryotic cell is a human cell. In a more preferred embodiment the human cell is a patient specific cell.

In one aspect, the invention provides for methods of reducing the toxicity of Cas enzymes. In certain aspects, the Cas enzyme is any Cas9 as described herein, for instance any naturally-occurring bacterial Cas9 as well as any chimaeras, mutants, homologs or orthologs. In one aspect, the Cas enzyme is a nickase. In one embodiment, the Cas9 is delivered into the cell in the form of mRNA. This allows for the transient expression of the enzyme thereby reducing toxicity. In another embodiment, the Cas9 is delivered into the cell in the nucleotide construct that encodes and expresses the Cas9 enzyme. In another embodiment, the invention also provides for methods of expressing Cas9 under the control of an inducible promoter the constructs used therein.

In another aspect, the invention provides for methods of improving the in vivo applications of the CRISPR-Cas system. In the preferred embodiment, the Cas enzyme is wildtype Cas9 or any of the modified versions described herein, including any naturally-occurring bacterial Cas9 as well as any chimaeras, mutants, homologs or orthologs. In one aspect, the Cas enzyme is a nickase. An advantageous aspect of the invention provides for the selection of Cas9 homologs that are easily packaged into viral vectors for delivery. Cas9 orthologs typically share the general organization of 3-4 RuvC domains and a HNH domain. The 5' most RuvC domain cleaves the non-complementary strand, and the HNH domain cleaves the complementary strand. All notations are in reference to the guide sequence.

The catalytic residue in the 5' RuvC domain is identified through homology comparison of the Cas9 of interest with other Cas9 orthologs (from *S. pyogenes* type II CRISPR locus, *S. thermophilus* CRISPR locus 1, *S. thermophilus* CRISPR locus 3, and *Franciscilla novicida* type II CRISPR locus), and the conserved Asp residue is mutated to alanine to convert Cas9 into a complementary-strand nicking enzyme. Similarly, the conserved His and Asn residues in the HNH domains are mutated to Alanine to convert Cas9 into a non-complementary-strand nicking enzyme.

In some embodiments, the CRISPR enzyme is a type I or III CRISPR enzyme, preferably a type II CRISPR enzyme. This type II CRISPR enzyme may be any Cas enzyme. A Cas enzyme may be identified Cas9 as this can refer to the general class of enzymes that share homology to the biggest nuclease with multiple nuclease domains from the type II CRISPR system. Most preferably, the Cas9 enzyme is from, or is derived from, spCas9 or saCas9. By derived, Applicants mean that the derived enzyme is largely based, in the sense of having a high degree of sequence homology with, a wildtype enzyme, but that it has been mutated (modified) in some way as described herein It will be appreciated that the terms Cas and CRISPR enzyme are generally used herein interchangeably, unless otherwise apparent. As mentioned above, many of the residue numberings used herein refer to the Cas9 enzyme from the type II CRISPR locus in *Streptococcus pyogenes* (annotated alternatively as SpCas9 or spCas9). However, it will be appreciated that this invention includes many more Cas9s from other species of microbes, such as SpCas9 derived from *S. pyogenes*, SaCas9 derived from *S. aureus*, St1Cas9 derived from *S. thermophilus* and so forth. Further examples are provided herein.

An example of a codon optimized sequence, in this instance optimized for humans (i.e. being optimized for expression in humans) is provided herein, see the SaCas9 human codon optimized sequence. Whilst this is preferred, it will be appreciated that other examples are possible and codon optimization for a host species other than human, or for codon optimization for specific organs such as the brain, is known.

In further embodiments, the invention provides for methods of enhancing the function of Cas9 by generating chimeric Cas9 proteins. These methods may comprise fusing N-terminal fragments of one Cas9 homolog with C-terminal fragments of another Cas9 homolog. These methods also allow for the selection of new properties displayed by the chimeric proteins.

It will be appreciated that in the present methods, where the organism is an animal or a plant, the modification may occur ex vivo or in vitro, for instance in a cell culture and in some instances not in vivo. In other embodiments, it may occur in vivo.

In one aspect, the invention provides a method of modifying an organism or a non-human organism by manipulation of a target sequence in a genomic locus of interest comprising:

delivering a non-naturally occurring or engineered composition comprising:

A)—I. a CRISPR-Cas system chimeric RNA (chiRNA) polynucleotide sequence, wherein the polynucleotide sequence comprises:
  (a) a guide sequence capable of hybridizing to a target sequence in a eukaryotic cell,
  (b) a tracr mate sequence, and
  (c) a tracr sequence, and
II. a polynucleotide sequence encoding a CRISPR enzyme comprising at least one or more nuclear localization sequences,
wherein (a), (b) and (c) are arranged in a 5' to 3' orientation, wherein when transcribed, the tracr mate sequence hybridizes to the tracr sequence and the guide sequence directs sequence-specific binding of a CRISPR complex to the target sequence, and
wherein the CRISPR complex comprises the CRISPR enzyme complexed with (1) the guide sequence that is hybridizable to the target sequence, and (2) the tracr mate sequence that is hybridized to the tracr sequence and the polynucleotide sequence encoding a CRISPR enzyme is DNA or RNA,
or
(B) I. polynucleotides comprising:
  (a) a guide sequence capable of hybridizing to a target sequence in a prokaryotic cell, and
  (b) at least one or more tracr mate sequences,
II. a polynucleotide sequence encoding a CRISPR enzyme, and
III. a polynucleotide sequence comprising a tracr sequence, wherein when transcribed, the tracr mate sequence hybridizes to the tracr sequence and the guide sequence directs sequence-specific binding of a CRISPR complex to the target sequence, and
wherein the CRISPR complex comprises the CRISPR enzyme complexed with (1) the guide sequence that is hybridizable to the target sequence, and (2) the tracr mate sequence that is hybridized to the tracr sequence and the polynucleotide sequence encoding a CRISPR enzyme is DNA or RNA.

Any or all of the polynucleotide sequence encoding a CRISPR enzyme, guide sequence, tracr mate sequence or tracr sequence may be RNA, DNA or a combination of RNA and DNA. In one aspect, the polynucleotides comprising the sequence encoding a CRISPR enzyme, the guide sequence, tracr mate sequence or tracr sequence are RNA. In one aspect, the polynucleotides comprising the sequence encoding a CRISPR enzyme, the guide sequence, tracr mate sequence or tracr sequence are DNA. In one aspect, the polynucleotides are a mixture of DNA and RNA, wherein some of the polynucleotides comprising the sequence encoding one or more of the CRISPR enzyme, the guide sequence, tracr mate sequence or tracr sequence are DNA and some of the polynucleotides are RNA. In one aspect, the polynucleotide comprising the sequence encoding the CRISPR enzyme is a DNA and the guide sequence, tracr mate sequence or tracr sequence are RNA. The one or more polynucleotides comprising the sequence encoding a CRISPR enzyme, the guide sequence, tracr mate sequence or tracr sequence may be delivered via nanoparticles, exosomes, microvesicles, or a gene-gun.

It will be appreciated that where reference is made to a polynucleotide, where that polynucleotide is RNA and is said to 'comprise' a feature such as a tracr mate sequence, the RNA sequence includes the feature. Where the polynucleotide is DNA and is said to comprise a feature such a tracr mate sequence, the DNA sequence is or can be transcribed into the RNA that comprises the feature at issue. Where the feature is a protein, such as the CRISPR enzyme, the DNA or RNA sequence referred to is, or can be, translated (and in the case of DNA transcribed first). Furthermore, in cases where an RNA encoding the CRISPR enzyme is provided to a cell, it is understood that the RNA is capable of being translated by the cell into which it is delivered.

Accordingly, in certain embodiments the invention provides a method of modifying an organism, including a prokaryotic organism or a eukaryotic organism such as a plant or an animal, e.g., a mammal including human or a non-human mammal or organism, by manipulation of a target sequence in a genomic locus of interest comprising delivering a non-naturally occurring or engineered composition comprising a viral or plasmid vector system comprising one or more viral or plasmid vectors operably encoding a composition for expression thereof, wherein the composition comprises:

(A) a non-naturally occurring or engineered composition comprising a vector system comprising one or more vectors comprising I. a first regulatory element operably linked to a CRISPR-Cas system chimeric RNA (chiRNA) polynucleotide sequence, wherein the polynucleotide sequence comprises (a) a guide sequence capable of hybridizing to a target sequence in a eukaryotic cell, (b) a tracr mate sequence, and (c) a tracr sequence, and II. a second regulatory element operably linked to an enzyme-coding sequence encoding a CRISPR enzyme comprising zero or at least one or more nuclear localization sequences (or optionally at least one or more nuclear localization sequences as some embodiments can involve no NLS), wherein (a), (b) and (c) are arranged in a 5' to 3' orientation, wherein components I and II are located on the same or different vectors of the system, wherein when transcribed, the tracr mate sequence hybridizes to the tracr sequence and the guide sequence directs sequence-specific binding of a CRISPR complex to the target sequence, and wherein the hybridizable complex comprises the CRISPR enzyme complexed with (1) the guide sequence that is hybridizable to the target sequence, and (2) the tracr mate sequence that is hybridized to the tracr sequence, or (B) a non-naturally occurring or engineered composition comprising a vector system comprising one or more vectors comprising I. a first regulatory element operably linked to (a) a guide sequence capable of hybridizing to a target sequence in a prokaryotic cell, and (b) at least one or more tracr mate sequences, II. a second regulatory element operably linked to an enzyme-coding sequence encoding a CRISPR enzyme, and III. a third regulatory element operably linked to a tracr sequence, wherein components I, II and III are located on the same or different vectors of the system, wherein when transcribed, the tracr mate sequence hybridizes to the tracr sequence and the guide sequence directs sequence-specific binding of a CRISPR complex to the target sequence, and wherein the CRISPR complex comprises the CRISPR enzyme complexed with (1) the guide sequence that is hybridizable to the target sequence, and (2) the tracr mate sequence that is hybridized to the tracr sequence. In one aspect, the CRISPR enzyme comprises one or more mutations in one of the catalytic domains. In one aspect, the CRISPR enzyme is a nickase.

Preferably, the vector is a viral vector, such as a lenti- or baculo- or preferably adeno-viral/adeno-associated viral vectors, but other means of delivery are known (such as yeast systems, microvesicles, gene guns/means of attaching vectors to gold nanoparticles) and are provided. In some embodiments, one or more of the viral or plasmid vectors may be delivered via nanoparticles, exosomes, microvesicles, or a gene-gun.

By manipulation of a target sequence, Applicants also mean the epigenetic manipulation of a target sequence. This may be of the chromatin state of a target sequence, such as by modification of the methylation state of the target sequence (i.e. addition or removal of methylation or methylation patterns or CpG islands), histone modification, increasing or reducing accessibility to the target sequence, or by promoting or reducing 3D folding.

It will be appreciated that where reference is made to a method of modifying an organism, including a prokaryotic organism or a eukaryotic organism such as a plant or an animal, e.g., a mammal including human or a non-human mammal or organism) by manipulation of a target sequence in a genomic locus of interest, this may apply to the organism (or mammal) as a whole or just a single cell or population of cells from that organism (if the organism is multicellular). In the case of humans, for instance, Applicants envisage, inter alia, a single cell or a population of cells and these may preferably be modified ex vivo and then re-introduced. In this case, a biopsy or other tissue or biological fluid sample may be necessary. Stem cells are also particularly preferred in this regard. But, of course, in vivo embodiments are also envisaged.

In certain embodiments the invention provides a method of treating or inhibiting a condition caused by a defect in a target sequence in a genomic locus of interest in a subject (e.g., mammal or human) or a non-human subject (e.g., mammal) in need thereof comprising modifying the human subject or a non-human subject by manipulation of the target sequence and wherein the condition is susceptible to treatment or inhibition by manipulation of the target sequence comprising providing treatment comprising: delivering a non-naturally occurring or engineered composition comprising an AAV vector system comprising one or more AAV vectors comprising operably encoding a composition for expression thereof, wherein the target sequence is manipulated by the composition when expressed, wherein the composition comprises:

(A) a non-naturally occurring or engineered composition comprising a vector system comprising one or more vectors comprising I. a first regulatory element operably linked to a CRISPR-Cas system chimeric RNA (chiRNA) polynucleotide sequence, wherein the polynucleotide sequence comprises (a) a guide sequence capable of hybridizing to a target sequence in a eukaryotic cell, (b) a tracr mate sequence, and (c) a tracr sequence, and II. a second regulatory element operably linked to an enzyme-coding sequence encoding a CRISPR enzyme comprising zero or at least one or more nuclear localization sequences (or optionally at least one or more nuclear localization sequences as some embodiments can involve no NLS) wherein (a), (b) and (c) are arranged in a 5' to 3' orientation, wherein components I and II are located on the same or different vectors of the system, wherein when transcribed, the tracr mate sequence hybridizes to the tracr sequence and the guide sequence directs sequence-specific binding of a CRISPR complex to the target sequence, and wherein the CRISPR complex comprises the CRISPR enzyme complexed with (1) the guide sequence that is hybridizable to the target sequence, and (2) the tracr mate sequence that is hybridized to the tracr sequence, or (B) a non-naturally occurring or engineered composition comprising a vector system comprising one or more vectors comprising I. a first regulatory element operably linked to (a) a guide sequence capable of hybridizing to a target sequence in a prokaryotic cell, and (b) at least one or more tracr mate sequences, II. a second regulatory element operably linked to an enzyme-coding sequence encoding a CRISPR enzyme, and III. a third regulatory element operably linked to a tracr sequence, wherein components I, II and III are located on the same or different vectors of the system, wherein when transcribed, the tracr mate sequence hybridizes to the tracr sequence and the guide sequence directs sequence-specific binding of a CRISPR complex to the target sequence, and wherein the CRISPR complex comprises the CRISPR enzyme complexed with (1) the guide sequence that is hybridizable to the target sequence, and (2) the tracr mate sequence that is hybridized to the tracr sequence.

Some methods of the invention can include inducing expression. In some methods of the invention the organism or subject is a eukaryote, including e.g., a plant or an animal (including mammal, including human) or a non-human eukaryote or a non-human animal or a non-human mammal. In some methods of the invention the organism or subject is a plant. In some methods of the invention the organism or subject is a mammal or a non-human mammal. In some methods of the invention the organism or subject is algae. In some methods of the invention the viral vector is an AAV. In some methods of the invention the viral vector is a lentivirus-derived vector. In some methods of the invention the viral vector is an *Agrobacterium* Ti or Ri plasmid for use in plants. In some methods of the invention the CRISPR enzyme is a Cas9. In some methods of the invention the CRISPR enzyme comprises one or more mutations in one of the catalytic domains. In some methods of the invention the CRISPR enzyme is a Cas9 nickase. In some methods of the invention the expression of the guide sequence is under the control of a T7 promoter that is driven by the expression of T7 polymerase. In some methods of the invention the expression of the guide sequence is under the control of a U6 promoter.

By manipulation of a target sequence, Applicants mean the alteration of the target sequence, which may include the epigenetic manipulation of a target sequence. This epigenetic manipulation may be of the chromatin state of a target sequence, such as by modification of the methylation state of the target sequence (i.e., addition or removal of methylation or methylation patterns or CpG islands), histone modification, increasing or reducing accessibility to the target sequence, or by promoting or reducing 3D folding.

It will be appreciated that where reference is made to a method of modifying an organism or a non-human organism by manipulation of a target sequence in a genomic locus of interest, this may apply to the organism as a whole or just a single cell or population of cells from that organism (if the organism is multicellular). In the case of humans, for instance, Applicants envisage, inter alia, a single cell or a population of cells and these may preferably be modified ex vivo and then re-introduced. In this case, a biopsy or other tissue or biological fluid sample may be necessary. Stem cells are also particularly preferred in this regard. But, of course, in vivo embodiments are also envisaged.

In certain embodiments the invention provides a method of treating or inhibiting a condition caused by a defect in a target sequence in a genomic locus of interest in a subject or a non-human subject in need thereof comprising modifying the subject or a non-human subject by manipulation of the target sequence and wherein the condition is susceptible to treatment or inhibition by manipulation of the target sequence comprising providing treatment comprising: delivering a non-naturally occurring or engineered composition comprising a vector system comprising one or more vectors comprising operably encoding a composition for expression thereof, wherein the target sequence is manipulated by the composition when expressed, wherein the composition comprises:

(A) a non-naturally occurring or engineered composition comprising a vector system comprising one or more vectors comprising I. a first regulatory element operably linked to a CRISPR-Cas system chimeric RNA (chiRNA) polynucleotide sequence, wherein the chiRNA polynucleotide sequence comprises (a) a guide sequence capable of hybridizing to a target sequence in a eukaryotic cell, (b) a tracr mate sequence, and (c) a tracr sequence, and II. a second regulatory element operably linked to an enzyme-coding sequence encoding a CRISPR enzyme comprising zero or at least one or more nuclear localization sequences (or optionally at least one or more nuclear localization sequences as some embodiments can involve no NLS) wherein (a), (b) and (c) are arranged in a 5' to 3' orientation, wherein components I and II are located on the same or different vectors of the system, wherein when transcribed, the tracr mate sequence hybridizes to the tracr sequence and the guide sequence directs sequence-specific binding of a CRISPR complex to the target sequence, and wherein the CRISPR complex comprises the CRISPR enzyme complexed with (1) the guide sequence that is hybridizable to the target sequence, and (2) the tracr mate sequence that is hybridized to the tracr sequence, or (B) a non-naturally occurring or engineered composition comprising a vector system comprising one or more vectors comprising I. a first regulatory element operably linked to (a) a guide sequence capable of hybridizing to a target sequence in a prokaryotic cell, and (b) at least one or more tracr mate sequences, II. a second regulatory element operably linked to an enzyme-coding sequence encoding a CRISPR enzyme, and III. a third regulatory element operably linked to a tracr sequence, wherein components I, II and III are located on the same or different vectors of the system, wherein when transcribed, the tracr mate sequence hybridizes to the tracr sequence and the guide sequence directs sequence-specific binding of a CRISPR complex to the target sequence, and wherein the CRISPR complex comprises the CRISPR enzyme complexed with (1) the guide sequence that is hybridizable to the target sequence, and (2) the tracr mate sequence that is hybridized to the tracr sequence. In an embodiment for use in a eukaryotic cell, the vector system comprises a viral vector system, e.g., an AAV vector or AAV vector system or a lentivirus-derived vector system or a tobacco mosaic virus-derived system.

Some methods of the invention can include inducing expression. In some methods of the invention the organism or subject is a eukaryote, including e.g., a plant or an animal (including mammal, including human) or a non-human eukaryote or a non-human animal. In some methods of the invention the organism or subject is a plant. In some methods of the invention the organism or subject is a mammal or a non-human mammal. In some methods of the invention the organism or subject is algae. In some methods of the invention the viral vector is an AAV. In some methods of the invention the viral vector is a lentiviral vector. In some methods of the invention the viral vector is a tobacco mosaic virus vector. In some methods of the invention the CRISPR enzyme is a Cas9. In some methods of the invention the CRISPR enzyme comprises one or more mutations in one of the catalytic domains. In some methods of the invention the CRISPR enzyme is a Cas9 nickase. In some methods of the invention the expression of the guide sequence is under the control of the T7 promoter is driven by the expression of T7 polymerase. In some methods of the invention the expression of the guide sequence is under the control of a U6 promoter.

The invention in some embodiments comprehends a method of delivering a CRISPR enzyme comprising delivering to a cell mRNA encoding the CRISPR enzyme. In some of these methods the CRISPR enzyme is a Cas9.

The invention in some embodiments comprehends a method of preparing the AAV vector of the invention comprising transfecting one or more plasmid(s) containing or consisting essentially of nucleic acid molecule(s) coding for the AAV into AAV-infectable cells, and supplying AAV rep and/or cap obligatory for replication and packaging of the AAV. In some embodiments the AAV rep and/or cap obligatory for replication and packaging of the AAV are supplied by transfecting the cells with helper plasmid(s) or helper virus(es). In some embodiments the helper virus is a poxvirus, adenovirus, herpesvirus or baculovirus. In some embodiments the poxvirus is a vaccinia virus. In some embodiments the cells are mammalian cells. And in some embodiments the cells are insect cells and the helper virus is baculovirus.

In plants, pathogens are often host-specific. For example, *Fusarium oxysporum* f. sp. *lycopersici* causes tomato wilt but attacks only tomato, and *F. oxysporum* f. *dianthii Puccinia graminis* f. sp. *tritici* attacks only wheat. Plants have existing and induced defenses to resist most pathogens. Mutations and recombination events across plant generations lead to genetic variability that gives rise to susceptibility, especially as pathogens reproduce with more frequency than plants. In plants there can be non-host resistance, e.g., the host and pathogen are incompatible. There can also be Horizontal Resistance, e.g., partial resistance against all races of a pathogen, typically controlled by many genes and Vertical Resistance, e.g., complete resistance to some races of a pathogen but not to other races, typically controlled by a few genes. In a Gene-for-Gene level, plants and pathogens evolve together, and the genetic changes in one balance changes in other. Accordingly, using Natural Variability, breeders combine most useful genes for Yield, Quality, Uniformity, Hardiness, Resistance. The sources of resistance genes include native or foreign Varieties, Heirloom Varieties, Wild Plant Relatives, and Induced Mutations, e.g., treating plant material with mutagenic agents. Using the present invention, plant breeders are provided with a new tool to induce mutations. Accordingly, one skilled in the art can analyze the genome of sources of resistance genes, and in Varieties having desired characteristics or traits employ the present invention to induce the rise of resistance genes, with more precision than previous mutagenic agents and hence accelerate and improve plant breeding programs.

The invention further comprehends a composition of the invention or a CRISPR enzyme thereof (including or alternatively mRNA encoding the CRISPR enzyme) for use in medicine. In some embodiments the invention comprehends a composition according to the invention or a CRISPR enzyme thereof (including or alternatively mRNA encoding the CRISPR enzyme) for use in a method according to the invention. In some embodiments the invention provides for the use of a composition of the invention or a CRISPR enzyme thereof (including or alternatively mRNA encoding the CRISPR enzyme) in ex vivo gene or genome editing. In certain embodiments the invention comprehends use of a composition of the invention or a CRISPR enzyme thereof (including or alternatively mRNA encoding the CRISPR enzyme) in the manufacture of a medicament for ex vivo gene or genome editing or for use in a method according of the invention. In some methods of the invention the CRISPR enzyme comprises one or more mutations in one of the catalytic domains. In some methods of the invention the CRISPR enzyme is a Cas9 nickase. The invention comprehends in some embodiments a composition of the invention or a CRISPR enzyme thereof (including or alternatively mRNA encoding the CRISPR enzyme), wherein the target sequence is flanked at its 3' end by a 5'-motif termed a proto-spacer adjacent motif (PAM), especially where the Cas9 is (or is derived from) *S. pyogenes* or *S. aureus* Cas9. For example, a suitable PAM is 5'-NRG or 5'-NNGRR (where N is any Nucleotide) for SpCas9 or SaCas9 enzymes (or derived enzymes), respectively, as mentioned below.

It will be appreciated that SpCas9 or SaCas9 are those from or derived from *S. pyogenes* or *S. aureus* Cas9.

Aspects of the invention comprehend improving the specificity of a CRISPR enzyme, e.g. Cas9, mediated gene targeting and reducing the likelihood of off-target modification by the CRISPR enzyme, e.g. Cas9. The invention in some embodiments comprehends a method of modifying an organism or a non-human organism by minimizing off-target modifications by manipulation of a first and a second target sequence on opposite strands of a DNA duplex in a genomic locus of interest in a cell, said method comprising delivering a non-naturally occurring or engineered composition comprising:

I. a first CRISPR-Cas system chimeric RNA (chiRNA) polynucleotide sequence, wherein the first polynucleotide sequence comprises:
  (a) a first guide sequence capable of hybridizing to the first target sequence,
  (b) a first tracr mate sequence, and
  (c) a first tracr sequence,
II. a second CRISPR-Cas system chiRNA polynucleotide sequence, wherein the second polynucleotide sequence comprises:
  (a) a second guide sequence capable of hybridizing to the second target sequence,
  (b) a second tracr mate sequence, and
  (c) a second tracr sequence, and
III. a polynucleotide sequence encoding a CRISPR enzyme comprising zero or at least one or more nuclear localization sequences and comprising one or more mutations in the CRISPR enzyme,
wherein (a), (b) and (c) of I. and II. are arranged in a 5' to 3' orientation, wherein when transcribed, the first and the second tracr mate sequence hybridize to the first and second tracr sequence respectively and the first and the second guide sequence directs sequence-specific binding of a first and a second CRISPR complex to the first and second target sequences respectively, wherein the first CRISPR complex comprises the CRISPR enzyme complexed with (1) the first guide sequence that is hybridizable to the first target sequence, and (2) the first tracr mate sequence that is hybridized to the first tracr sequence, wherein the second CRISPR complex comprises the CRISPR enzyme complexed with (1) the second guide sequence that is hybridizable to the second target sequence, and (2) the second tracr mate sequence that is hybridized to the second tracr sequence,
wherein the polynucleotide sequence encoding a CRISPR enzyme is DNA or RNA, and wherein the first guide sequence directs cleavage of one strand of the DNA duplex near the first target sequence and the second guide sequence directs cleavage of opposite strand of the DNA duplex near the second target sequence, thereby inducing a break in the DNA, thereby modifying the organism or the non-human organism by minimizing off-target modifications. In one aspect, the first nick and the second nick in the DNA is offset relative to each other by at least one base pair of the duplex. In one aspect, the first nick and the second nick are offset relative to each other so that the resulting DNA break has a 3' overhang. In one aspect, the first nick and the second nick are offset relative to each other so that the resulting DNA break has a 5' overhang. In one aspect, the first nick and the second nick are positioned relative to each other such that the overhang is at least 1 nt, at least 10 nt, at least 15 nt, at least 26 nt, at least 30 nt, at least 50 nt or more that at least 50 nt. Additional aspects of the invention comprising the resulting offset double nicked DNA strand can be appreciated by one skilled in the art, and exemplary uses of the double nick system are provided herein.

In some methods of the invention any or all of the polynucleotide sequences encoding the CRISPR enzyme, the first and the second guide sequence, the first and the second tracr mate sequence or the first and the second tracr sequence, is/are RNA. In further embodiments of the invention the polynucleotides comprising the sequence encoding the CRISPR enzyme, the first and the second guide sequence, the first and the second tracr mate sequence or the first and the second tracr sequence, is/are RNA and are delivered via nanoparticles, exosomes, microvesicles, or a gene-gun. In certain embodiments of the invention, the first and second tracr mate sequence share 100% identity and/or the first and second tracr sequence share 100% identity. In preferred embodiments of the invention the CRISPR enzyme is a Cas9 enzyme, e.g. SpCas9. In an aspect of the invention the CRISPR enzyme comprises one or more mutations in one of the catalytic domains, wherein the one or more mutations is selected from the group consisting of D10A, E762A, and D986A in the RuvC domain or the one or more mutations is selected from the group consisting of H840A, N854A and N863A in the HNH domain. In a highly preferred embodiment the CRISPR enzyme has the D10A mutation or the H840A mutation.

In preferred methods of the invention the first guide sequence directing cleavage of one strand of the DNA duplex near the first target sequence and the second guide sequence directing cleavage of the opposite strand near the second target sequence results in a 5' overhang. In embodiments of the invention the 5' overhang is at most 200 base pairs, preferably at most 100 base pairs, or more preferably at most 50 base pairs. In embodiments of the invention the 5' overhang is at least 26 base pairs, preferably at least 30 base pairs or more preferably 34-50 base pairs or 1-34 base pairs. In other preferred methods of the invention the first guide sequence directing cleavage of one strand of the DNA duplex near the first target sequence and the second guide sequence directing cleavage of other strand near the second target sequence results in a blunt cut or a 3' overhang. In embodiments of the invention the 3' overhang is at most 150, 100 or 25 base pairs or at least 15, 10 or 1 base pairs. In preferred embodiments the 3' overhang is 1-100 basepairs.

The invention in some embodiments comprehends a method of modifying an organism or a non-human organism by minimizing off-target modifications by manipulation of a first and a second target sequence on opposite strands of a DNA duplex in a genomic locus of interest in a cell, the method comprising delivering a non-naturally occurring or engineered composition comprising a vector system comprising one or more vectors comprising I. a first regulatory element operably linked to
   (a) a first guide sequence capable of hybridizing to the first target sequence, and
   (b) at least one or more tracr mate sequences,
II. a second regulatory element operably linked to
   (a) a second guide sequence capable of hybridizing to the second target sequence, and
   (b) at least one or more tracr mate sequences,
III. a third regulatory element operably linked to an enzyme-coding sequence encoding a CRISPR enzyme, and
IV. a fourth regulatory element operably linked to a tracr sequence,
wherein components I, II, III and IV are located on the same or different vectors of the system, and
when transcribed, the tracr mate sequence hybridizes to the tracr sequence and the first and the second guide sequence directs sequence-specific binding of a first and a second CRISPR complex to the first and second target sequences respectively, wherein the first CRISPR complex comprises the CRISPR enzyme complexed with (1) the first guide sequence that is hybridizable to the first target sequence, and (2) the tracr mate sequence that is hybridized to the tracr sequence, wherein the second CRISPR complex comprises the CRISPR enzyme complexed with (1) the second guide sequence that is hybridizable to the second target sequence, and (2) the tracr mate sequence that is hybridized to the tracr sequence, wherein the polynucleotide sequence encoding a CRISPR enzyme is DNA or RNA, and wherein the first guide sequence directs cleavage of one strand of the DNA duplex near the first target sequence and the second guide sequence directs cleavage of other strand near the second target sequence inducing a double strand break, thereby modifying the organism or the non-human organism by minimizing off-target modifications.

In some methods of the invention any or all of the polynucleotide sequence encoding the CRISPR enzyme, the first and the second guide sequence, the first and the second tracr mate sequence or the first and the second tracr sequence, is/are RNA. In further embodiments of the invention the first and second tracr mate sequence share 100% identity and/or the first and second tracr sequence share 100% identity. In preferred embodiments of the invention the CRISPR enzyme is a Cas9 enzyme, e.g. SpCas9. In an aspect of the invention the CRISPR enzyme comprises one or more mutations in one of the catalytic domains, wherein the one or more mutations is selected from the group consisting of D10A, E762A, and D986A in the RuvC domain or the one or more mutations is selected from the group consisting of H840A, N854A and N863A in the HNH domain. In a highly preferred embodiment the CRISPR enzyme has the D10A mutation or the H840A mutation. As CRISPR enzymes or Cas proteins may still promote residual NHEJ activity with either the D10A or the H840A mutations, through out the application the invention comprehends the generation of even more precise nickases that further reduces NHEJ activity by introducing multiple mutations in the CRISPR enzyme or the Cas protein. A better version of the D10A nickaske may include the mutations D10A, E762A and D986A (or some subset of these) and a better version of the H840A nickases may include the mutations H840A, N854A and N863A (or some subset of these).

In a further embodiment of the invention, one or more of the viral vectors are delivered via nanoparticles, exosomes, microvesicles, or a gene-gun.

In preferred methods of the invention the first guide sequence directing cleavage of one strand of the DNA duplex near the first target sequence and the second guide sequence directing cleavage of other strand near the second target sequence results in a 5' overhang. In embodiments of the invention the 5' overhang is at most 200 base pairs, preferably at most 100 base pairs, or more preferably at most 50 base pairs. In embodiments of the invention the 5' overhang is at least 26 base pairs, preferably at least 30 base pairs or more preferably 34-50 base pairs or 1-34 base pairs. In other preferred methods of the invention the first guide sequence directing cleavage of one strand of the DNA duplex near the first target sequence and the second guide sequence directing cleavage of other strand near the second target sequence results in a blunt cut or a 3' overhang. In embodiments of the invention the 3' overhang is at most 150, 100 or 25 base pairs or at least 15, 10 or 1 base pairs. In preferred embodiments the 3' overhang is 1-100 basepairs.

The invention in some embodiments comprehends a method of modifying a genomic locus of interest by minimizing off-target modifications by introducing into a cell containing and expressing a double stranded DNA molecule encoding the gene product an engineered, non-naturally occurring CRISPR-Cas system comprising a Cas protein having one or more mutations and two guide RNAs that target a first strand and a second strand of the DNA molecule respectively, whereby the guide RNAs target the DNA molecule encoding the gene product and the Cas protein nicks each of the first strand and the second strand of the DNA molecule encoding the gene product, whereby expression of the gene product is altered; and, wherein the Cas protein and the two guide RNAs do not naturally occur together.

In preferred methods of the invention the Cas protein nicking each of the first strand and the second strand of the DNA molecule encoding the gene product results in a 5' overhang. In embodiments of the invention the 5' overhang is at most 200 base pairs, preferably at most 100 base pairs, or more preferably at most 50 base pairs. In embodiments of the invention the 5' overhang is at least 26 base pairs, preferably at least 30 base pairs or more preferably 34-50 base pairs or 1-34 base pairs. In other preferred methods of the invention the Cas protein nicking each of the first strand and the second strand of the DNA molecule encoding the gene product results in a 3' overhang, wherein the 3' overhang is 1-100 base pairs.

Embodiments of the invention also comprehend the guide RNAs comprising a guide sequence fused to a tracr mate sequence and a tracr sequence. In an aspect of the invention the Cas protein is codon optimized for expression in a eukaryotic cell, wherein it may be a mammalian cell or a human cell. In further embodiments of the invention the Cas protein is a type II CRISPR-Cas protein, e.g. a Cas 9 protein. In a highly preferred embodiment the Cas protein is a Cas9 protein, e.g. SpCas9. In aspects of the invention the Cas protein has one or more mutations in one of the catalytic domains, wherein the one or more mutations is selected from the group consisting of D10A, E762A, and D986A in the RuvC domain or the one or more mutations is selected from the group consisting of H840A, N854A and N863A in the HNH domain. In a highly preferred embodiment the Cas protein has the D10A mutation or the H840A mutation.

Aspects of the invention relate to the expression of the gene product being decreased or a template polynucleotide being further introduced into the DNA molecule encoding the gene product or an intervening sequence being excised precisely by allowing the two 5' overhangs to reanneal and ligate or the activity or function of the gene product being altered or the expression of the gene product being increased. In an embodiment of the invention, the gene product is a protein.

The invention also comprehends an engineered, non-naturally occurring CRISPR-Cas system comprising a Cas protein having one or more mutations and two guide RNAs that target a first strand and a second strand respectively of a double stranded DNA molecule encoding a gene product in a cell, whereby the guide RNAs target the DNA molecule encoding the gene product and the Cas protein nicks each of the first strand and the second strand of the DNA molecule encoding the gene product, whereby expression of the gene product is altered; and, wherein the Cas protein and the two guide RNAs do not naturally occur together.

In aspects of the invention the guide RNAs may comprise a guide sequence fused to a tracr mate sequence and a tracr sequence. In an embodiment of the invention the Cas protein is a type II CRISPR-Cas protein. In an aspect of the invention the Cas protein is codon optimized for expression in a eukaryotic cell, wherein it may be a mammalian cell or a human cell. In further embodiments of the invention the Cas protein is a type II CRISPR-Cas protein, e.g. a Cas 9 protein. In a highly preferred embodiment the Cas protein is a Cas9 protein, e.g. SpCas9. In aspects of the invention the Cas protein has one or more mutations in one of the catalytic domains, wherein the one or more mutations is selected from the group consisting of D10A, E762A, and D986A in the RuvC domain or the one or more mutations is selected from the group consisting of H840A, N854A and N863A in the HNH domain. In a highly preferred embodiment the Cas protein has the D10A mutation or the H840A mutation.

Aspects of the invention relate to the expression of the gene product being decreased or a template polynucleotide being further introduced into the DNA molecule encoding the gene product or an intervening sequence being excised precisely by allowing the two 5' or 3' overhangs to reanneal and ligate or the activity or function of the gene product being altered or the expression of the gene product being increased. In an embodiment of the invention, the gene product is a protein.

The invention also comprehends an engineered, non-naturally occurring vector system comprising one or more vectors comprising:
   a) a first regulatory element operably linked to each of two CRISPR-Cas system guide RNAs that target a first strand and a second strand respectively of a double stranded DNA molecule encoding a gene product,
   b) a second regulatory element operably linked to a Cas protein,
   wherein components (a) and (b) are located on same or different vectors of the system, whereby the guide RNAs target the DNA molecule encoding the gene product and the Cas protein nicks each of the first strand and the second strand of the DNA molecule encoding the gene product, whereby expression of the gene product is altered; and, wherein the Cas protein and the two guide RNAs do not naturally occur together.

In aspects of the invention the guide RNAs may comprise a guide sequence fused to a tracr mate sequence and a tracr sequence. In an embodiment of the invention the Cas protein is a type II CRISPR-Cas protein. In an aspect of the invention the Cas protein is codon optimized for expression in a eukaryotic cell, wherein it may be a mammalian cell or a human cell. In further embodiments of the invention the Cas protein is a type II CRISPR-Cas protein, e.g. a Cas 9 protein. In a highly preferred embodiment the Cas protein is a Cas9 protein, e.g. SpCas9. In aspects of the invention the Cas protein has one or more mutations in one of the catalytic domains, wherein the one or more mutations is selected from the group consisting of D10A, E762A, and D986A in the RuvC domain or the one or more mutations is selected from the group consisting of H840A, N854A and N863A in the HNH domain. In a highly preferred embodiment the Cas protein has the D10A mutation or the H840A mutation.

Aspects of the invention relate to the expression of the gene product being decreased or a template polynucleotide being further introduced into the DNA molecule encoding the gene product or an intervening sequence being excised precisely by allowing the two 5' or 3' overhangs to reanneal and ligate or the activity or function of the gene product being altered or the expression of the gene product being increased. In an embodiment of the invention, the gene product is a protein. In preferred embodiments of the invention the vectors of the system are viral vectors. In a further embodiment, the vectors of the system are delivered via nanoparticles, exosomes, microvesicles, or a gene-gun.

Aspects of the invention provide for methods of modifying an organism comprising a first and a second target sequence on opposite strands of a DNA duplex in a genomic locus of interest in a cell by promoting homology directed repair wherein the method may comprise delivering a non-naturally occurring or engineered composition comprising:
I. a first CRISPR-Cas system chimeric RNA (chiRNA) polynucleotide sequence, wherein the first polynucleotide sequence comprises:
(a) a first guide sequence capable of hybridizing to the first target sequence,
(b) a first tracr mate sequence, and
(c) a first tracr sequence,
II. a second CRISPR-Cas system chiRNA polynucleotide sequence, wherein the second polynucleotide sequence comprises:
(a) a second guide sequence capable of hybridizing to the second target sequence,
(b) a second tracr mate sequence, and
(c) a second tracr sequence, and
III. a polynucleotide sequence encoding a CRISPR enzyme comprising at least one or more nuclear localization sequences and comprising one or more mutations,
IV. a repair template comprising a synthesized or engineered single-stranded oligonucleotide,
   wherein (a), (b) and (c) are arranged in a 5' to 3' orientation, wherein when transcribed, the first and the second tracr mate sequence hybridize to the first and second tracr sequence respectively and the first and the second guide sequence directs sequence-specific binding of a first and a second CRISPR complex to the first and second target sequences respectively, wherein the first CRISPR complex comprises the CRISPR enzyme complexed with (1) the first guide sequence that is hybridizable to the first target sequence, and (2) the first tracr mate sequence that is hybridized to the first tracr sequence, wherein the second CRISPR complex comprises the CRISPR enzyme complexed with (1) the second guide sequence that is hybridizable to the second target sequence, and (2) the second tracr mate sequence that is hybridized to the second tracr sequence, wherein the polynucleotide sequence encoding a CRISPR enzyme is DNA or RNA, wherein the first guide sequence directs cleavage of one strand of the DNA duplex near the first target sequence and the second guide sequence directs cleavage of other strand near the second target sequence inducing a double strand break, and wherein the repair template is introduced into the DNA duplex by homologous recombination, whereby the organism is modified.

In embodiments of the invention the repair template may further comprise a restriction endonuclease restriction site.

In further embodiments, the first guide sequence directing cleavage of one strand of the DNA duplex near the first target sequence and the second guide sequence directing cleavage of other strand near the second target sequence results in a 5' or 3' overhang. In preferred embodiments of the invention, the 5' overhang is 1-200 base pairs or the 3' overhang is 1-100 base pairs. In other aspects, any or all of the polynucleotide sequence encoding the CRISPR enzyme, the first and the second guide sequence, the first and the second tracr mate sequence or the first and the second tracr sequence, is/are RNA. In yet further aspects the polynucleotides comprising the sequence encoding the CRISPR enzyme, the first and the second guide sequence, the first and the second tracr mate sequence or the first and the second tracr sequence, is/are RNA and are delivered via nanoparticles, exosomes, microvesicles, or a gene-gun. In further embodiments of the invention the first and second tracr mate sequence share 100% identity and/or the first and second tracr sequence share 100% identity. In preferred embodiments of the invention the CRISPR enzyme is a Cas9 enzyme, e.g. SpCas9. In an aspect of the invention the CRISPR enzyme comprises one or more mutations in one of the catalytic domains, wherein the one or more mutations is selected from the group consisting of D10A, E762A, and D986A in the RuvC domain or the one or more mutations is selected from the group consisting of H840A, N854A and N863A in the HNH domain. In a highly preferred embodiment the CRISPR enzyme has the D10A mutation or the H840A mutation.

Aspects of the invention also provide for methods of modifying an organism comprising a first and a second target sequence on opposite strands of a DNA duplex in a genomic locus of interest in a cell by facilitating non homologous end joining (NHEJ) mediated ligation comprising delivering a non-naturally occurring or engineered composition comprising:
I. a first CRISPR-Cas system chimeric RNA (chiRNA) polynucleotide sequence, wherein the first polynucleotide sequence comprises:
(a) a first guide sequence capable of hybridizing to the first target sequence,
(b) a first tracr mate sequence, and
(c) a first tracr sequence,
II. a second CRISPR-Cas system chiRNA polynucleotide sequence, wherein the second polynucleotide sequence comprises:
(a) a second guide sequence capable of hybridizing to the second target sequence,
(b) a second tracr mate sequence, and
(c) a second tracr sequence, and
III. a polynucleotide sequence encoding a CRISPR enzyme comprising at least one or more nuclear localization sequences and comprising one or more mutations,
IV. a repair template comprising a first set of overhangs, wherein (a), (b) and (c) are arranged in a 5' to 3' orientation, wherein when transcribed, the first and the second tracr mate sequence hybridize to the first and second tracr sequence respectively and the first and the second guide sequence directs sequence-specific binding of a first and a second CRISPR complex to the first and second target sequences respectively, wherein the first CRISPR complex comprises the CRISPR enzyme complexed with (1) the first guide sequence that is hybridizable to the first target sequence, and (2) the first tracr mate sequence that is hybridized to the first tracr sequence, wherein the second CRISPR complex comprises the CRISPR enzyme complexed with (1) the second guide sequence that is hybridizable to the second target sequence, and (2) the second tracr mate sequence that is hybridized to the second tracr sequence, wherein the polynucleotide sequence encoding a CRISPR enzyme is DNA or RNA, wherein the first guide sequence directs cleavage of one strand of the DNA duplex near the first target sequence and the second guide sequence directs cleavage of other strand near the second target sequence inducing a double strand break with a second set of overhangs, wherein the first set of overhangs is compatible with and matches the second set of overhangs, and wherein the repair template is introduced into the DNA duplex by ligation, whereby the organism is modified.

In some embodiments of the invention the repair template is a synthesized or engineered double-stranded oligonucleotide duplex or in other embodiments the repair template is generated from a piece of DNA that is introduced into the cell and is enzymatically processed. This enzymatic processing may be carried out by endogenous enzymes or by enzymes (e.g. restriction endonucelases, nucleases or a pair of nickases) that have been introduced into the cell so the compatible overhangs are generated on the repair template.

In further embodiments, the first guide sequence directing cleavage of one strand of the DNA duplex near the first target sequence and the second guide sequence directing cleavage of other strand near the second target sequence results in a 5' or 3' overhang. In preferred embodiments of the invention, the 5' overhang is 1-200 base pairs or the 3' overhang is 1-100 base pairs. In other aspects, any or all of the polynucleotide sequence encoding the CRISPR enzyme, the first and the second guide sequence, the first and the second tracr mate sequence or the first and the second tracr sequence, is/are RNA. In yet further aspects the polynucleotides comprising the sequence encoding the CRISPR enzyme, the first and the second guide sequence, the first and the second tracr mate sequence or the first and the second tracr sequence, is/are RNA and are delivered via nanoparticles, exosomes, microvesicles, or a gene-gun. In further embodiments of the invention the first and second tracr mate sequence share 100% identity and/or the first and second tracr sequence share 100% identity. In preferred embodiments of the invention the CRISPR enzyme is a Cas9 enzyme, e.g. SpCas9. In an aspect of the invention the CRISPR enzyme comprises one or more mutations in one of the catalytic domains, wherein the one or more mutations is selected from the group consisting of D10A, E762A, and D986A in the RuvC domain or the one or more mutations is selected from the group consisting of H840A, N854A and N863A in the HNH domain. In a highly preferred embodiment the CRISPR enzyme has the D10A mutation or the H840A mutation.

In one aspect, the invention provides a method of modifying a target polynucleotide in a eukaryotic cell. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence. In some embodiments, said cleavage comprises cleaving one or two strands at the location of the target sequence by said CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expressed from a gene comprising the target sequence. In some embodiments, the method further comprises delivering one or more vectors to said eukaryotic cell, wherein the one or more vectors drive expression of one or more of: the CRISPR enzyme, the guide sequence linked to the tracr mate sequence, and the tracr sequence. In some embodiments, said vectors are delivered to the eukaryotic cell in a subject. In some embodiments, said modifying takes place in said eukaryotic cell in a cell culture. In some embodiments, the method further comprises isolating said eukaryotic cell from a subject prior to said modifying. In some embodiments, the method further comprises returning said eukaryotic cell and/or cells derived therefrom to said subject.

In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized to a target sequence within said polynucleotide, wherein said guide sequence is linked to a tracr mate sequence which in turn hybridizes to a tracr sequence. In some embodiments, the method further comprises delivering one or more vectors to said eukaryotic cells, wherein the one or more vectors drive expression of one or more of: the CRISPR enzyme, the guide sequence linked to the tracr mate sequence, and the tracr sequence.

In one aspect, the invention provides a method of generating a model eukaryotic cell comprising a mutated disease gene. In some embodiments, a disease gene is any gene associated an increase in the risk of having or developing a disease. In some embodiments, the method comprises (a) introducing one or more vectors into a eukaryotic cell, wherein the one or more vectors drive expression of one or more of: a CRISPR enzyme, a guide sequence linked to a tracr mate sequence, and a tracr sequence; and (b) allowing a CRISPR complex to bind to a target polynucleotide to effect cleavage of the target polynucleotide within said disease gene, wherein the CRISPR complex comprises the CRISPR enzyme complexed with (1) the guide sequence that is hybridizable to the target sequence within the target polynucleotide, and (2) the tracr mate sequence that is hybridized to the tracr sequence, thereby generating a model eukaryotic cell comprising a mutated disease gene. In some embodiments, said cleavage comprises cleaving one or two strands at the location of the target sequence by said CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expression from a gene comprising the target sequence.

In one aspect the invention provides for a method of selecting one or more prokaryotic cell(s) by introducing one or more mutations in a gene in the one or more prokaryotic cell (s), the method comprising: introducing one or more vectors into the prokaryotic cell (s), wherein the one or more vectors drive expression of one or more of: a CRISPR enzyme, a guide sequence linked to a tracr mate sequence, a tracr sequence, and an editing template; wherein the editing template comprises the one or more mutations that abolish CRISPR enzyme cleavage; allowing homologous recombination of the editing template with the target polynucleotide in the cell(s) to be selected; allowing a CRISPR complex to bind to a target polynucleotide to effect cleavage of the target polynucleotide within said gene, wherein the CRISPR complex comprises the CRISPR enzyme complexed with (1) the guide sequence that is hybridizable to the target sequence within the target polynucleotide, and (2) the tracr mate sequence that is hybridized to the tracr sequence, wherein binding of the CRISPR complex to the target polynucleotide induces cell death, thereby allowing one or more prokaryotic cell(s) in which one or more mutations have been introduced to be selected. In a preferred embodiment, the CRISPR enzyme is Cas9. In another aspect of the invention the cell to be selected may be a eukaryotic cell. Aspects of the invention allow for selection of specific cells without requiring a selection marker or a two-step process that may include a counter-selection system.

In one aspect, the invention provides for methods of modifying a target polynucleotide in a eukaryotic cell. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence.

In other embodiments, this invention provides a method of modifying expression of a polynucleotide in a eukaryotic cell. The method comprises increasing or decreasing expression of a target polynucleotide by using a CRISPR complex that binds to the polynucleotide.

Where desired, to effect the modification of the expression in a cell, one or more vectors comprising a tracr sequence, a guide sequence linked to the tracr mate sequence, a sequence encoding a CRISPR enzyme is delivered to a cell. In some methods, the one or more vectors comprises a regulatory element operably linked to an enzyme-coding sequence encoding said CRISPR enzyme comprising a nuclear localization sequence; and a regulatory element operably linked to a tracr mate sequence and one or more insertion sites for inserting a guide sequence upstream of the tracr mate sequence. When expressed, the guide sequence directs sequence-specific binding of a CRISPR complex to a target sequence in a cell. Typically, the CRISPR complex comprises a CRISPR enzyme complexed with (1) the guide sequence that is hybridizable to the target sequence, and (2) the tracr mate sequence that is hybridized to the tracr sequence.

In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein is not produced.

In certain embodiments, the CRISPR enzyme comprises one or more mutations D10A, E762A, H840A, N854A, N863A or D986A and/or the one or more mutations is in a RuvC1 or HNH domain of the CRISPR enzyme or is a mutation as otherwise as discussed herein. In some embodiments, the CRISPR enzyme has one or more mutations in a catalytic domain, wherein when transcribed, the tracr mate sequence hybridizes to the tracr sequence and the guide sequence directs sequence-specific binding of a CRISPR complex to the target sequence, and wherein the enzyme further comprises a functional domain. In some embodiments, the mutated Cas9 enzyme may be fused to a protein domain, e.g., such as a transcriptional activation domain. In one aspect, a transcriptional activation domain is VP64. In some embodiments, a transcription repression domains is KRAB. In some embodiments, a transcription repression domain is SID, or concatemers of SID (i.e. SID4x). In some embodiments, an epigenetic modifying enzyme is provided. In some embodiments, an activation domain is provided, which may be the P65 activation domain.

In some embodiments, the CRISPR enzyme is a type I or III CRISPR enzyme, preferably a type II CRISPR enzyme. This type II CRISPR enzyme may be any Cas enzyme. A Cas enzyme may be identified Cas9 as this can refer to the general class of enzymes that share homology to the biggest nuclease with multiple nuclease domains from the type II CRISPR system. Most preferably, the Cas9 enzyme is from, or is derived from, spCas9 or saCas9. By derived, Applicants mean that the derived enzyme is largely based, in the sense of having a high degree of sequence homology with, a wildtype enzyme, but that it has been mutated (modified) in some way as described herein.

The invention also provides a method of modifying a DNA duplex at a locus of interest in a cell, the method comprising delivering to the cell:
 I. a first polynucleotide comprising:
   (a) a first guide sequence capable of hybridizing to a first target sequence,
   (b) a first tracr mate sequence, and
   (c) a first tracr sequence;
 II. a second polynucleotide comprising:
   (a) a second guide sequence capable of hybridizing to a second target sequence,
   (b) a second tracr mate sequence, and
   (c) a second tracr sequence;
 and
 III. a third polynucleotide comprising a sequence encoding a CRISPR enzyme and one or more nuclear localization sequences
wherein (a), (b) and (c) in said first and second polynucleotides are arranged in a 5' to 3' orientation;
wherein the first target sequence is on a first strand of the DNA duplex and the second target sequence is on the opposite strand of the DNA duplex, and when the first and second guide sequences are hybridized to said target sequences in the duplex, the 5' ends of the first polynucleotide and the second polynucleotide are offset relative to each other by at least one base pair of the duplex;
wherein when transcribed, the first and the second tracr mate sequences hybridize to the first and second tracr sequences, respectively, and the first and the second guide sequences direct sequence-specific binding of a first and a second CRISPR complex to the first and second target sequences respectively,
wherein the first CRISPR complex comprises the CRISPR enzyme complexed with (1) the first guide sequence that is hybridizable to the first target sequence, and (2) the first tracr mate sequence that is hybridized to the first tracr sequence,
wherein the second CRISPR complex comprises the CRISPR enzyme complexed with (1) the second guide sequence that is hybridizable to the second target sequence, and (2) the second tracr mate sequence that is hybridized to the second tracr sequence,
and wherein said first strand of the DNA duplex is cleaved near said first target sequence, and said opposite strand of the DNA duplex is cleaved near said second target sequence, resulting in a double strand break with a 5' overhang or a 3' overhang.

The invention also provides a method of modifying a DNA duplex at a locus of interest in a cell, the method comprising delivering to the cell a vector system comprising one or more vectors comprising:
 I. a first polynucleotide sequence comprising a regulatory element operably linked to
   (a) a first guide sequence capable of hybridizing to a first target sequence, and
   (b) at least one or more tracr mate sequences,
 II. a second polynucleotide sequence comprising a second regulatory element operably linked to
   (a) a second guide sequence capable of hybridizing to a second target sequence, and
   (b) at least one or more tracr mate sequences,
 III. a third polynucleotide sequence comprising a third regulatory element operably linked to a sequence encoding a CRISPR enzyme, and
 IV. a fourth polynucleotide sequence comprising a fourth regulatory element operably linked to a tracr sequence,
wherein components I, II, III and IV are located on the same or different vectors of the system
wherein the first target sequence is on a first strand of the DNA duplex and the second target sequence is on the opposite strand of the DNA duplex, and when the first and second guide sequences are hybridized to said target sequences in the duplex, the 5' ends of the first polynucleotide and the second polynucleotide are offset relative to each other by at least one base pair of the duplex;
wherein when transcribed, the first and the second tracr mate sequences hybridize to a tracr sequence, and the first and the second guide sequences direct sequence-specific binding of a first and a second CRISPR complex to the first and second target sequences respectively,
wherein the first CRISPR complex comprises the CRISPR enzyme complexed with (1) the first guide sequence that is hybridizable to the first target sequence, and (2) the first tracr mate sequence that is hybridized to a tracr sequence,
wherein the second CRISPR complex comprises the CRISPR enzyme complexed with (1) the second guide sequence that is hybridizable to the second target sequence, and (2) the second tracr mate sequence that is hybridized to a tracr sequence,
and wherein said first strand of the DNA duplex is cleaved near said first target sequence, and said opposite strand of the DNA duplex is cleaved near said second target sequence, resulting in a double strand break with a 5' overhang or a 3' overhang.

In methods of the invention, the CRISPR enzyme advantageously is a nickase enzyme, optionally a Cas9 enzyme comprising at least one mutation in a catalytic domain. For instance, there can be at least one mutation is in the RuvC domain and optionally is selected from the group consisting of D10A, E762A and D986A, or is in the HNH domain and optionally is selected from the group consisting of H840A, N854A and N863A. In inventive methods, advantageously the offset between the 5' ends of the first polynucleotide and the second polynucleotide can be greater than −8 bp or −278 to +58 bp or −200 to +200 bp or up to or over 100 bp or −4 to 20 bp or +23 bp or +16 or +20 or +16 to +20 bp or −3 to +18 bp; and it being understood that where appropriate one may use the term nucleotide or nt for bp. Advantageously, in inventive methods the cleavage of said first strand and of said opposite strand of the DNA duplex occurs 3' to a PAM (Protospacer adjacent motif) on each strand, and wherein said PAM on said first strand is separated from said PAM on said opposite strand by from 30 to 150 base pairs. In inventive methods, the overhang can be at most 200 bases, at most 100 bases, or at most 50 bases; e.g., the overhang can be at least 1 base, at least 10 bases, at least 15 bases, at least 26 bases or at least 30 bases; or, the overhang can be between 34 and 50 bases or between 1 and 34 bases. Advantageously in inventive methods, any or all of the polynucleotide sequence encoding the CRISPR enzyme, the first and the second guide sequence, the first and the second tracr mate sequence or the first and the second tracr sequence, is/are RNA, and optionally wherein any or all of I, II and III are delivered via nanoparticles, exosomes, microvesicles, or a gene-gun. In inventive methods advantageously the first and second tracr mate sequence can share 100% identity and/or the first and second tracr sequence share 100% identity. For instance, each of I, II and III can be provided in a vector, optionally wherein each is provided in the same or a different vector. The locus of interest in inventive methods can comprises a gene and wherein said method results in a change in the expression of said gene, or in a change in the activity or function of the gene product. For instance, the gene product can be a protein, and/or wherein said change in expression, activity or function is a reduction in said expression, activity or function. Inventive methods can further comprise: (a) delivering to the cell a double-stranded oligodeoxynucleotide (dsODN) comprising overhangs complimentary to the overhangs created by said double strand break, wherein said dsODN is integrated into the locus of interest; or —(b) delivering to the cell a single-stranded oligodeoxynucleotide (ssODN), wherein said ssODN acts as a template for homology directed repair of said double strand break. Inventive methods can be for the prevention or treatment of disease in an individual, optionally wherein said disease is caused by a defect in said locus of interest. Inventive methods can be conducted in vivo in the individual or ex vivo on a cell taken from the individual, optionally wherein said cell is returned to the individual.

The invention also provides a kit or composition comprising:
I. a first polynucleotide comprising:
   (a) a first guide sequence capable of hybridizing to a first target sequence,
   (b) a first tracr mate sequence, and
   (c) a first tracr sequence;
II. a second polynucleotide comprising:
   (a) a second guide sequence capable of hybridizing to a second target sequence,
   (b) a second tracr mate sequence, and
   (c) a second tracr sequence;
and
III. a third polynucleotide comprising a sequence encoding a CRISPR enzyme and one or more nuclear localization sequences wherein (a), (b) and (c) in said first and second polynucleotides are arranged in a 5' to 3' orientation;
wherein the first target sequence is on a first strand of a DNA duplex and the second target sequence is on the opposite strand of the DNA duplex, and when the first and second guide sequences are hybridized to said target sequences in the duplex, the 5' ends of the first polynucleotide and the second polynucleotide are offset relative to each other by at least one base pair of the duplex,
and optionally wherein each of I, II and III is provided in the same or a different vector.

The invention also provides use of a kit or composition according of the invention in a method of the invention. The invention also provides use of a kit or composition of the invention in the manufacture of a medicament, optionally wherein said medicament is for the prevention or treatment of a disease caused by a defect in said locus of interest.

It will be appreciated that the terms Cas and CRISPR enzyme are generally used herein interchangeably, unless otherwise apparent. As mentioned above, many of the residue numberings used herein refer to the Cas9 enzyme from the type II CRISPR locus in *Streptococcus pyogenes*. However, it will be appreciated that this invention includes many more Cas9s from other species of microbes, such as SpCas9, SaCa9, St1Cas9 and so forth.

An example of a codon optimized sequence, in this instance optimized for humans (i.e. being optimized for expression in humans), is provided herein, see the SaCas9 human codon optimized sequence. Whilst this is preferred, it will be appreciated that other examples are possible and codon optimization for a host species other than human, or for codon optimization for specific organs such as the brain, is known.

In one aspect, delivery is in the form of a vector. In one aspect the vector may be a viral vector, such as a lenti- or baculo- or preferably adeno-viral/adeno-associated viral vectors, but other means of delivery are known (such as yeast systems, microvesicles, gene guns/means of attaching vectors to gold nanoparticles) and are provided. A vector may mean not only a viral or yeast system (for instance, where the nucleic acids of interest may be operably linked to and under the control (in terms of expression, such as to ultimately provide a processed RNA) a promoter), but also direct delivery of nucleic acids into a host cell. While in herein methods the vector may be a viral vector and this is advantageously an AAV, other viral vectors as herein discussed can be employed. For example, baculoviruses may be used for expression in insect cells. These insect cells may, in turn be useful for producing large quantities of further vectors, such as AAV vectors adapted for delivery of the present invention. Also envisaged is a method of delivering the present CRISPR enzyme comprising delivering to a cell mRNA encoding the CRISPR enzyme. It will be appreciated that the CRISPR enzyme is truncated, comprised of less than one thousand amino acids or less than four thousand amino acids, is a nuclease or nickase, is codon-optimized comprises one or more mutations, and/or comprises a chimeric CRISPR enzyme, or the other options as herein discussed. AAV viral vectors are preferred.

In certain embodiments, the target sequence is flanked or followed, at its 3' end, by a PAM suitable for the CRISPR enzyme, typically a Cas and in particular a Cas9.

For example, a suitable PAM is 5'-NRG or 5'-NNGRR for SpCas9 or SaCas9 enzymes (or derived enzymes), respectively.

It will be appreciated that SpCas9 or SaCas9 are those from or derived from *S. pyogenes* or *S. aureus* Cas9.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2C discloses SEQ ID NOS 255 and 256, respectively, in order of appearance. FIG. 2E discloses SEQ ID NOS 257-259, respectively, in order of appearance. FIG. 2F discloses SEQ ID NOS 260-264, respectively, in order of appearance.

Figure 4A:
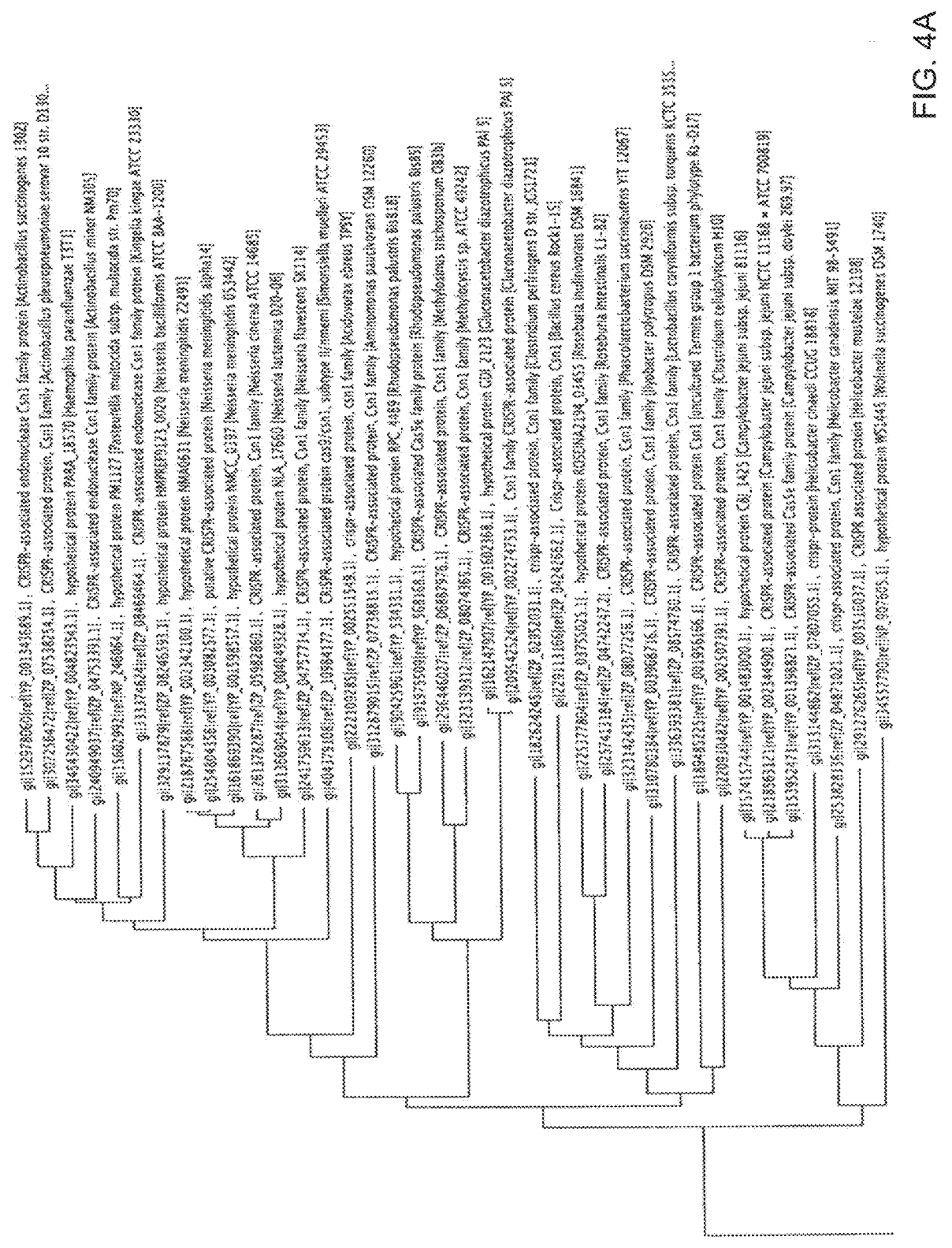
Figure 4D:
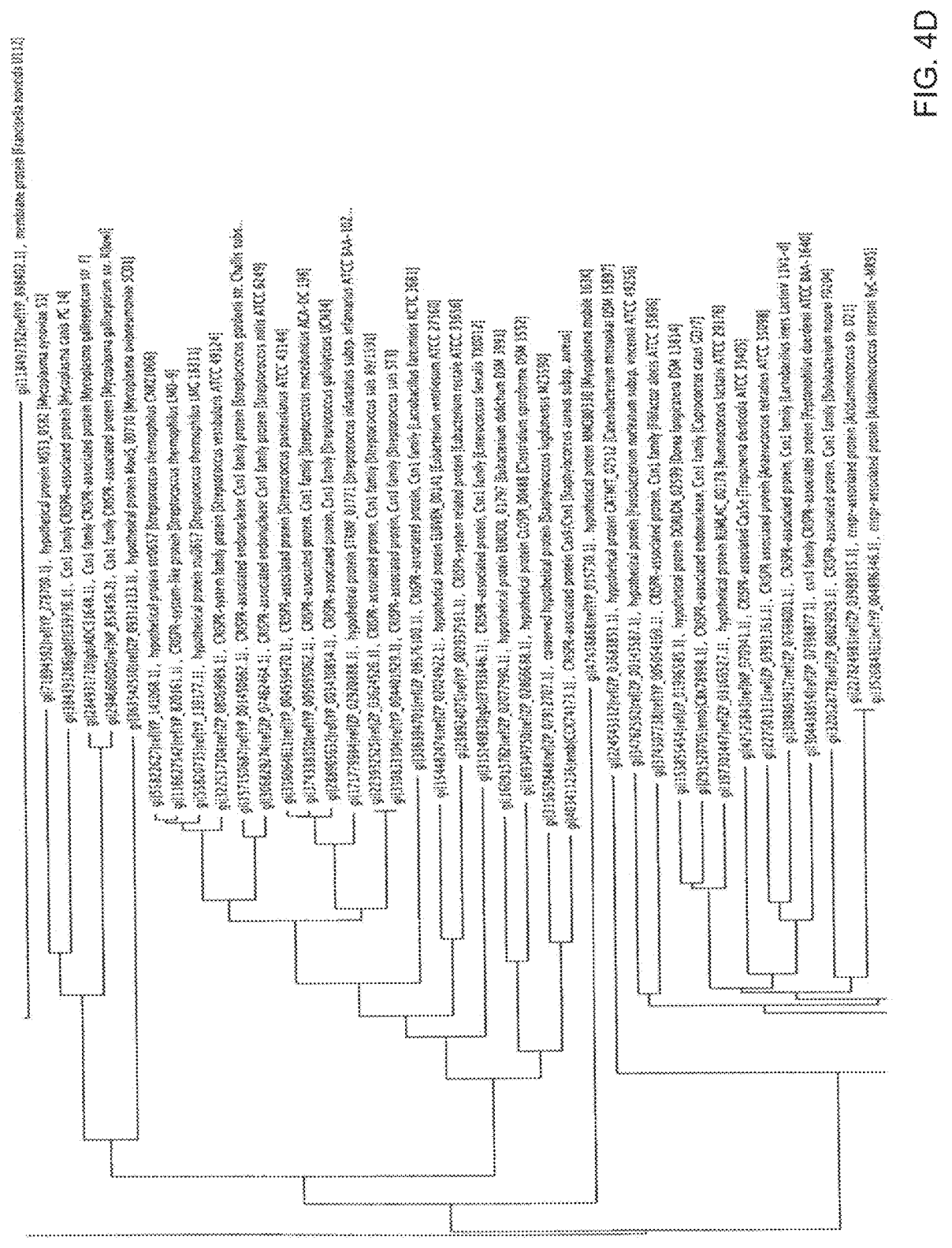

FIG. 4A-F shows the linear phylogenetic analysis revealing five families of Cas9s, including three groups of large Cas9s (1400 amino acids) and two of small Cas9s (1100 amino acids).

Figure 6H:
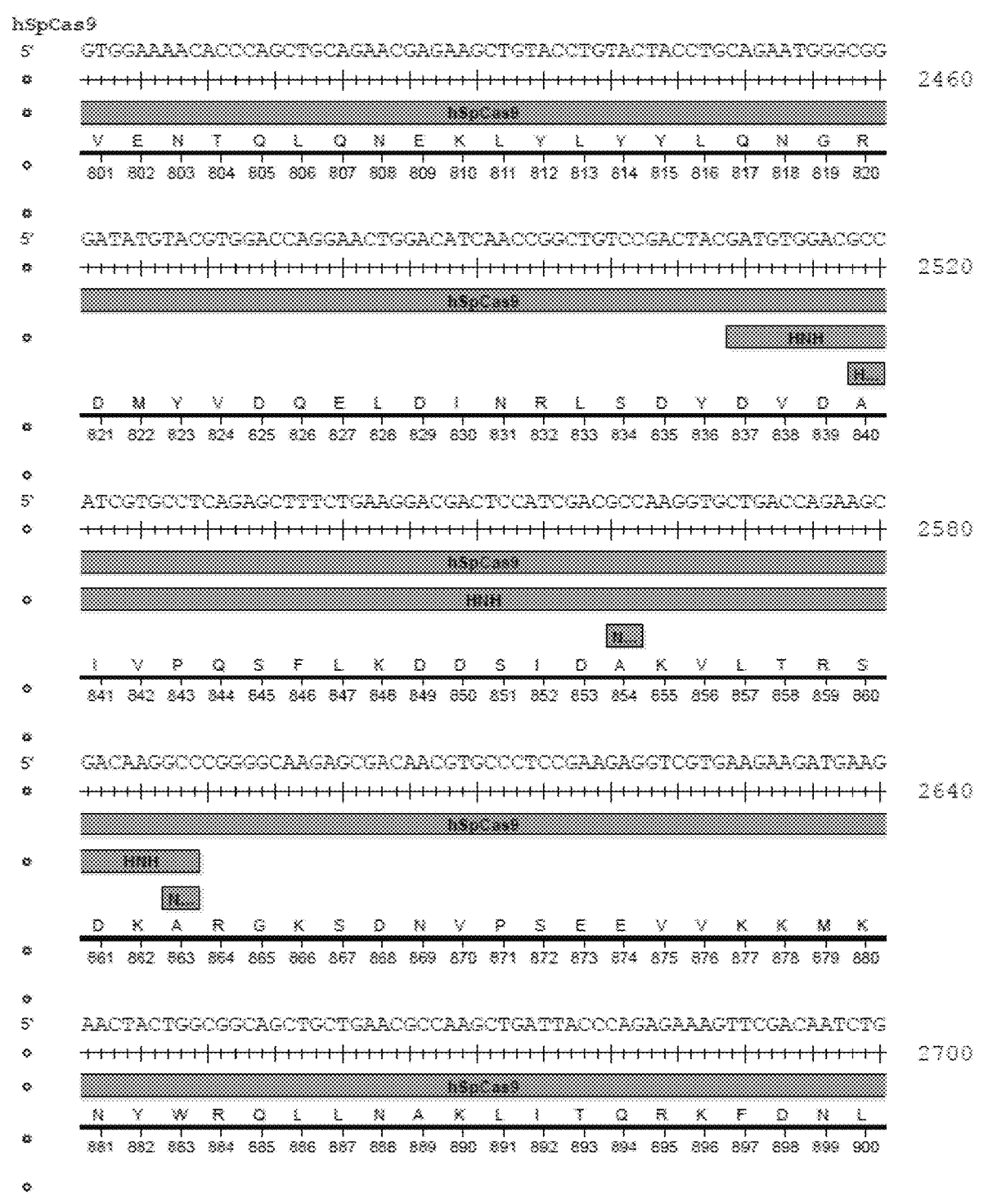
Figure 6I:
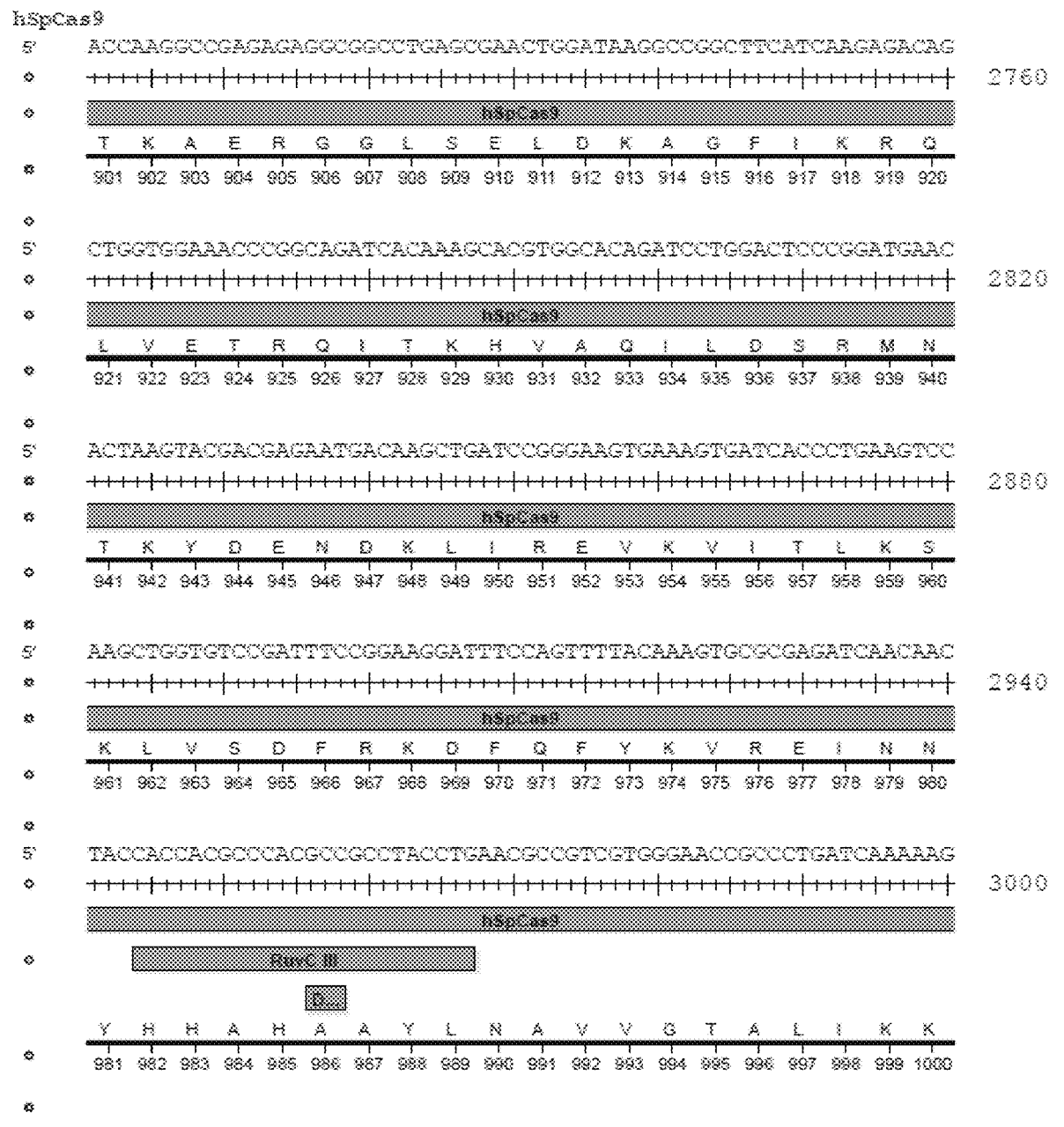

FIG. 6A-M shows sequences where the mutation points are located within the SpCas9 gene. FIG. 6A-M discloses the nucleotide sequence as SEQ ID NO: 265 and the amino acid sequence as SEQ ID NO: 266.

FIG. 9 shows delivery and in vivo mouse brain Cas9 expression data.

FIG. 12B discloses SEQ ID NOS 267-269, 267, 270, and 269, respectively, in order of appearance. (c) Example of the effect of ssODNs on HDR in the EMX1 locus is shown using both wild-type Cas9 and Cas9 nickase (D10A). Each ssODN contains homology arms of 90 bp flanking a 12-bp insertion of two restriction sites.

FIG. 13A-C shows the repair strategy for Cystic Fibrosis delta F508 mutation. FIG. 13A discloses the nucleotide sequence as SEQ ID NO: 271 and the amino acid sequence as SEQ ID NO: 272. FIG. 13B discloses SEQ ID NO: 273. FIG. 13C discloses the nucleotide sequence as SEQ ID NO: 274 and the amino acid sequence as SEQ ID NO: 275.

FIG. 24 shows expression of SpCas9 and SaCas9 in cortical primary neurons in culture 7 days after transduction. Representative Western blot of HA-tagged SpCas9 and SaCas9 versions under the control of different promoters and with bgh or short polyA (spA) sequences. Tubulin is loading control.

FIG. 33 discloses SEQ ID NOS 276-292, respectively, in order of appearance.

FIG. 34 shows a list of U6 reverse primer sequences used to generate U6-guide RNA expression cassettes. Each primer needs to be paired with the U6 forward primer "gcactgagggcctatttcccatgattc" (SEQ ID NO: 1) to generate amplicons containing U6 and the desired guide RNA. FIG. 34 discloses SEQ ID NOS 293-339 and 295, respectively, in order of appearance.

FIG. 35 discloses the nucleotide sequence as SEQ ID NO: 340 and the amino acid sequences as 341-344, respectively, in order of appearance.

FIG. 36 shows on (right) a gel image indicating the formation of indels at the target site when variable 5′ overhangs are present after cleavage by the Cas9 nickase targeted by different pairs of guide RNAs. on (left) a table indicating the lane numbers of the gel on the right and various parameters including identifying the guide RNA pairs used and the length of the 5' overhang present following cleavage by the Cas9 nickase.

FIG. 37 discloses the nucleotide sequence as SEQ ID NO: 340 and the amino acid sequences as 341-344, respectively, in order of appearance.

FIG. 38A discloses SEQ ID NOS 345-348, respectively, in order of appearance. (B) SURVEYOR assay gel showing comparable modification of target 1 by sgRNAs bearing 20- and 30-nt long guide sequences. (C) Northern blot showing that extended sgRNAs are largely reverted to 20-nt guide-length sgRNAs in HEK 293FT cells.

FIG. 39C discloses SEQ ID NOS 349-357, respectively, in order of appearance.

FIG. 40A discloses SEQ ID NOS 358-363, respectively, in order of appearance. (B) On-target modification rate by Cas9n and a pair of sgRNAs is comparable to those mediated by wildtype Cas9 and single sgRNAs (left panel). Cas9-sgRNA 1 complexes generate significant off-target mutagenesis, while no off-target locus modification is detected with Cas9n (right panel). (C) Five off-target loci of sgRNA 1 are examined for indel modifications by deep sequencing of transfected HEK 293FT cells. (n=3, error bars show mean±s.e.m.) (D) Specificity comparison of Cas9n with double nicking and wild-type Cas9 with sgRNA 1 alone at the off-target sites. Specificity ratio is calculated as on-target/off-target modification rates. (n=3; error bars show mean±s.e.m.) (E, F) Double nicking minimizes off-target modification at two additional human VEGFA loci while maintaining high specificity (on/off target modification ratio; n=3, error bars show mean±s.e.m.).

FIG. 41A discloses SEQ ID NOS 364-365, respectively, in order of appearance. (B) Restriction digest assay gel showing successful insertion of HindIII cleavage sites by double nicking-mediated HDR in HEK 293FT cells. Upper bands are unmodified template; lower bands are HindIII cleavage product. (C) Double nicking promotes HDR in the HUES62 human embryonic stem cell line. HDR frequencies are determined by deep sequencing. (n=3; error bars show mean±s.e.m.). (D) HDR efficiency depends on the configuration of Cas9 or Cas9n-mediated nicks. HDR is facilitated when a nick occurs near the center of the ssODN homology arm (HDR insertion site) leading to a 5'-resulting overhang. Nicking configurations are annotated with position and strand (red arrows) and length of overhang (black lines) (left panel). The distance (bp) of each nick from the HDR insertion site is indicated at the end of the black lines in italics, and the positions of the sgRNAs are illustrated in bold on the schematic of the EMX1 locus. HDR efficiency mediated by double nicking with paired sgRNAs (top panel) or single sgRNAs with either Cas9 or Cas9n are shown (bottom panel, FIG. 45; n=3, error bars show mean±s.e.m.).

FIG. 42A discloses SEQ ID NOS 366-368, respectively, in order of appearance. (B) Co-delivery of four sgRNAs with Cas9n generate long-range genomic deletions in the DYRK1A locus (from 0.5 kb up to 6 kb). Deletion was detected using primers (Table S6) spanning the target region.

FIG. 43A discloses SEQ ID NOS 369-379, respectively, in order of appearance. (B) Efficient blastocyst modification is achieved at multiple concentrations of sgRNAs (1.5 to 50 ng/uL) and wildtype Cas9 or Cas9n (ng/uL to 100 ng/uL).

FIG. 44A-F shows a list of sgRNA pairs used with Cas9 nickase (D10A) to identify the optimal target site spacing for double nicking across multiple genes, related to FIG. 39. N.D.: not detected. N.T.: not tested. Left sgRNA target site guide sequences. EMX1 disclosed as SEQ ID NOS 380, 381, 381, 382, 383, 384, 385, 385, 386, 380, 380, 387, 387, 386, 386, 385, 387, 386, 387, 386, 388, 389, 386, and 387. DYRK1A disclosed as SEQ ID NOS 390, 391, 392, 391, 393, 394, 395, 396, 397, 390, 398, 399, 400, 401, 402, 403, 392, 394, 394, 404, 403 and 405. GRIN2B disclosed as SEQ ID NOS 406, 407, 408, 409, 410, 411, 412, 413, 414, 415, 412, 416, 417, 418, 419, 413, 420, 412, 413, 421, 414, 422, 421 and 422. MeCP2 disclosed as SEQ ID NOS 473 and 474. VEGFA disclosed as SEQ ID NOS 475 and 476. Right sgRNA target site guide sequences. EMX1 disclosed as SEQ ID NOS 383, 423, 424, 425, 387, 385, 426, 382, 384, 427, 424, 384, 428, 382, 429, 430, 382, 431, 430, 427, 432, 432, 426 and 426. DYRK1A disclosed as SEQ ID NOS 433, 433, 434, 435, 436, 433, 437, 435, 438, 439, 440, 399, 436, 436, 437, 441, 436, 440, 435, 440, 436 and 440. GRIN2B disclosed as SEQ ID NOS 442, 443, 444, 445, 446, 447, 448, 448, 446, 445, 449, 449, 450, 451, 452, 449, 453, 447, 447, 454, 455, 456, 456 and 457. MeCP2 disclosed as SEQ ID NOS 477 and 478. VEGFA disclosed as SEQ ID NOS 479 and 480. All sequences identified in order of appearance.

FIG. 45A-D shows a list of sgRNAs used in Example 31. Related to FIG. 39. Guide sequences. EMX1 disclosed as SEQ ID NOS 423, 458, 459, 383, 387, 388, 384, 428, 385, 382, 429, 431, 425, 430, 380, 427, 424, 432, 426, 460, 461, 462, 381, 463, 464, 465 and 461. DYRK1A disclosed as SEQ ID NOS 466, 399, 400, 436, 402, 437, 390, 391, 392, 393, 394, 395, 396, 397, 398, 401, 403, 404, 405, 433, 434, 435, 438, 439, 440, 441, 418, 451, 419, 452, 417, 450, 420 and 453. GRIN2B disclosed as SEQ ID NOS 467, 468, 469, 449, 470, 456, 471, 472, 406, 407, 408, 409, 410, 411, 412, 413, 414, 416, 421, 422, 442, 443, 444, 445, 446, 447, 448, 454, 455 and 457. MeCP2 disclosed as SEQ ID NOS 473, 477, 474 and 478. VEGFA disclosed as SEQ ID NOS 475, 479, 476 and 480. All sequences identified in order of appearance.

DETAILED DESCRIPTION OF THE INVENTION

Figure 1:
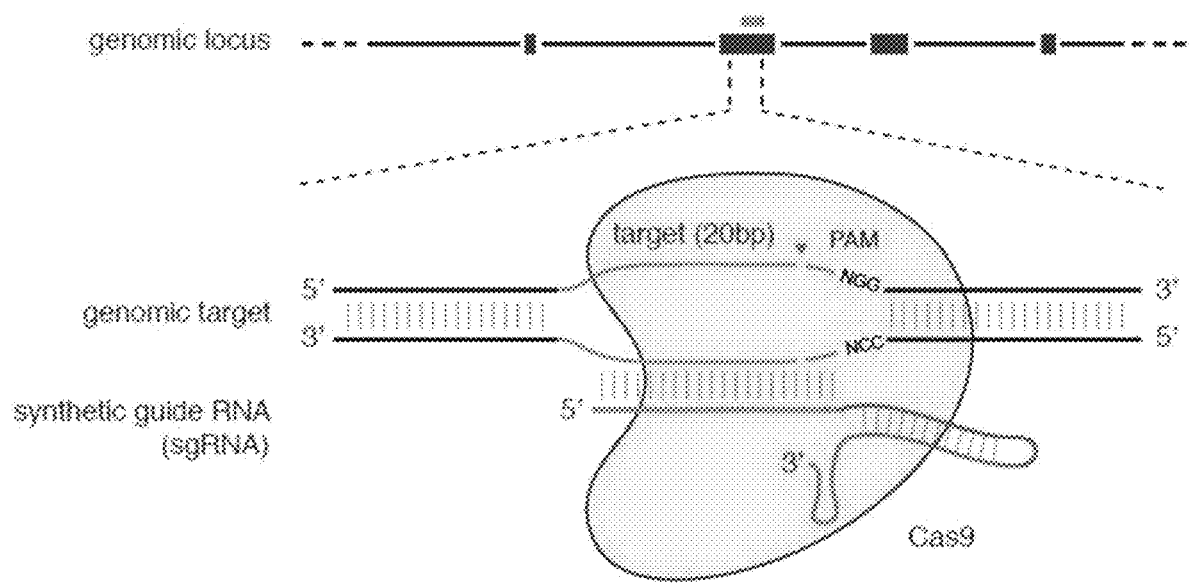
FIG. 1 shows a schematic model of the CRISPR system. The Cas9 nuclease from *Streptococcus pyogenes* (yellow) is targeted to genomic DNA by a synthetic guide RNA (sgRNA) consisting of a 20-nt guide sequence (blue) and a scaffold (red). The guide sequence base-pairs with the DNA target (blue), directly upstream of a requisite 5'-NGG protospacer adjacent motif (PAM; magenta), and Cas9 mediates a double-stranded break (DSB) ~3 bp upstream of the PAM (red triangle).

With respect to general information on CRISPR-Cas Systems: Reference is made to U.S. provisional applications 61/758,468; 61/802,174; 61/806,375; 61/814,263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent applications 61/836,123, 61/847,537, 61/862,355 and 61/871,301, filed on Jun. 17, 2013; Jul. 17, 2013, Aug. 5, 2013 and Aug. 28, 2013 respectively. Reference is further made to U.S. provisional patent applications 61/736,527 and 61/748,427 filed on Dec. 12, 2012 and Jan. 2, 2013, respectively. Reference is additionally made to U.S. provisional patent application 61/791,409, filed on Mar. 15, 2013. Reference is also made to U.S. provisional patent application 61/799,800, filed Mar. 15, 2013. Reference is also made to U.S. provisional patent applications 61/835,931, 61/835,936, 61/836,127, 61/836,101, 61/836,123, 61/836,080, and 61/835,973 each filed Jun. 17, 2013. Each of these applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these applications and the appln cited documents) are incorporated herein by reference to the same extent as if each individual document was specifically and individually indicated to be incorporated by reference.

Also with respect to general information on CRISPR-Cas Systems, mention is made of:

*Multiplex genome engineering using CRISPR/Cas systems*. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

*RNA-guided editing of bacterial genomes using CRISPR-Cas systems*. Jiang W., Bikard D., Cox D., Zhang F, Marraffini L A. Nat Biotechnol March; 31(3):233-9 (2013);

*One-Step Generation of Mice Carrying Mutations in Multiple Genes by CRISPR/Cas-Mediated Genome Engineering*. Wang H., Yang H., Shivalila C S., Dawlaty M M., Cheng A W., Zhang F., Jaenisch R. Cell May 9; 153(4):910-8 (2013);

*Optical control of mammalian endogenous transcription and epigenetic states*. Konermann S, Brigham M D, Trevino A E, Hsu P D, Heidenreich M, Cong L, Platt R J, Scott D A, Church G M, Zhang F. Nature. 2013 Aug. 22; 500(7463):472-6. doi: 10.1038/Nature 12466. Epub 2013 Aug. 23;

*Double Nicking by RNA-Guided CRISPR Cas9 for Enhanced Genome Editing Specificity*. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5. (2013);

*DNA targeting specificity of RNA-guided Cas9 nucleases*. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

*Genome engineering using the CRISPR-Cas9 system*. Ran, F A., Hsu, P D., Wright, J., Agarwala, V., Scott, D A., Zhang, F. Nature Protocols November; 8(11):2281-308. (2013);

*Genome-Scale CRISPR-Cas9 Knockout Screening in Human Cells*. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013). [Epub ahead of print];

*Crystal structure of cas9 in complex with guide RNA and target DNA*. Nishimasu, H., Ran, F A., Hsu, P D., Konermann, S., Shehata, S I., Dohmae, N., Ishitani, R., Zhang, F., Nureki, O. Cell February 27. (2014). 156(5):935-49;

*Genome-wide binding of the CRISPR endonuclease Cas9 in mammalian cells*. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. (2014) April 20. doi: 10.1038/nbt.2889, and

*Development and Applications of CRISPR-Cas9 for Genome Engineering*, Hsu et al, Cell 157, 1262-1278 (Jun. 5, 2014) (Hsu 2014), each of which is incorporated herein by reference, and discussed briefly below:

Cong et al. engineered type II CRISPR/Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR/Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of Streptococcus pneumoniae and Escherichia coli. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in S. pneumoniae, nearly 100% of cells that were recovered using the described approach contained the desired mutation, and in E. coli, 65% that were recovered contained the mutation.

Konermann et al. addressed the need in the art for versatile and robust technologies that enable optical and chemical modulation of DNA-binding domains based CRISPR Cas9 enzyme and also Transcriptional Activator Like Effectors As discussed in the present specification, the Cas9 nuclease from the microbial CRISPR-Cas system is targeted to specific genomic loci by a 20 nt guide sequence, which can tolerate certain mismatches to the DNA target and thereby promote undesired off-target mutagenesis. To address this, Ran et al. described an approach that combined a Cas9 nickase mutant with paired guide RNAs to introduce targeted double-strand breaks. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knock-out (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of Streptococcus pyogenes Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from Streptococcus pyogenes loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Hsu 2014 is a review article that discusses generally CRISPR-Cas9 history from yogurt to genome editing, including genetic screening of cells, that is in the information, data and findings of the applications in the lineage of this specification filed prior to Jun. 5, 2014. The general teachings of Hsu 2014 do not involve the specific models, animals of the instant specification.

The invention relates to the engineering and optimization of systems, methods and compositions used for the control of gene expression involving sequence targeting, such as genome perturbation or gene-editing, that relate to the CRISPR-Cas system and components thereof. In advantageous embodiments, the Cas enzyme is Cas9.

An advantage of the present methods is that the CRISPR system avoids off-target binding and its resulting side effects. This is achieved using systems arranged to have a high degree of sequence specificity for the target DNA.

Cas9 optimization may be used to enhance function or to develop new functions, one can generate chimeric Cas9 proteins. Examples that the Applicants have generated are provided in Example 6. Chimeric Cas9 proteins can be made by combining fragments from different Cas9 homologs. For example, two example chimeric Cas9 proteins from the Cas9s described herein. For example, Applicants fused the N-term of St1Cas9 (fragment from this protein is in bold) with C-term of SpCas9. The benefit of making chimeric Cas9s include any or all of:

reduced toxicity;
improved expression in eukaryotic cells;
enhanced specificity;
reduced molecular weight of protein, make protein smaller by combining the smallest domains from different Cas9 homologs; and/or
altering the PAM sequence requirement.

The Cas9 may be used as a generic DNA binding protein. For example, and as shown in Example 7, Applicants used Cas9 as a generic DNA binding protein by mutating the two catalytic domains (D10 and H840) responsible for cleaving both strands of the DNA target. In order to upregulate gene transcription at a target locus Applicants fused the transcriptional activation domain (VP64) to Cas9. Other transcriptional activation domains are known. As shown in Example 11, transcriptional activation is possible. As also shown in Example 11, gene repression (in this case of the beta-catenin gene) is possible using a Cas9 repressor (DNA-binding domain) that binds to the target gene sequence, thus repressing its activity.

Figure 7A:
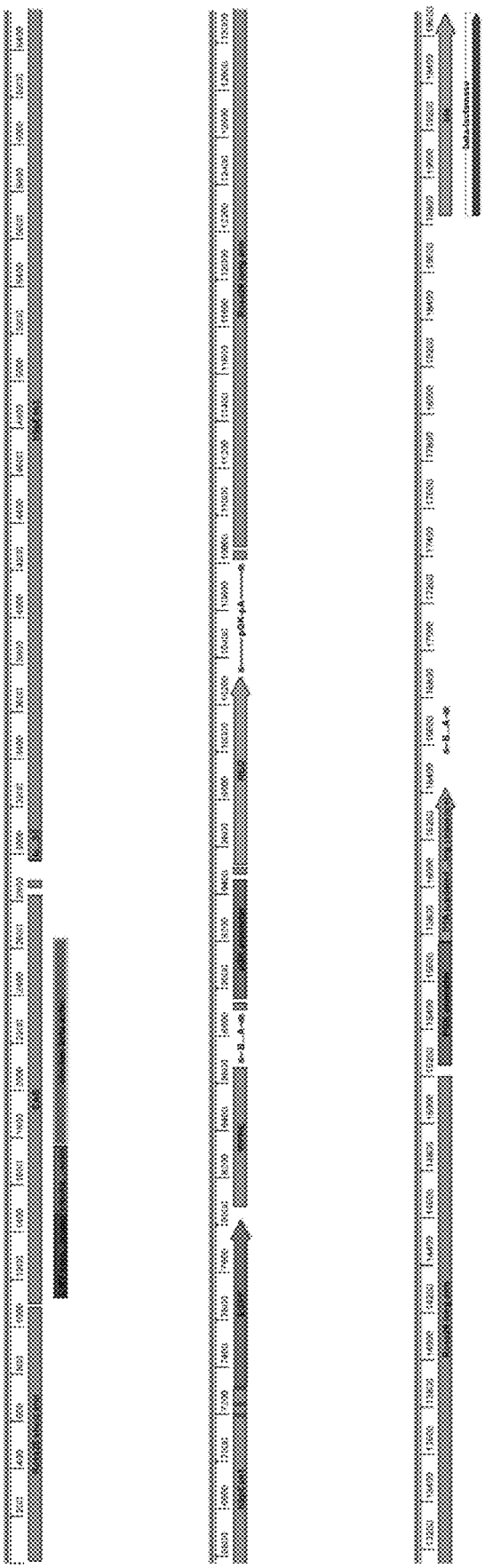
FIG. 7A shows the Conditional Cas9, Rosa26 targeting vector map.
Figure 7B:
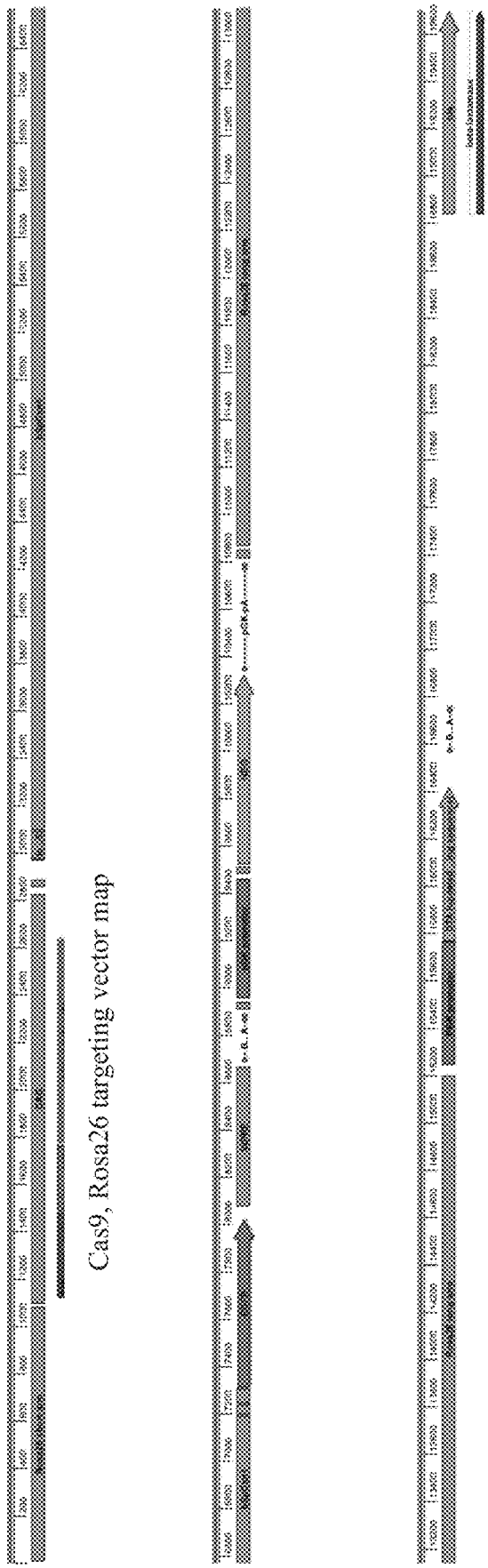
FIG. 7B shows the Constitutive Cas9, Rosa26 targeting vector map.
Figure 8:
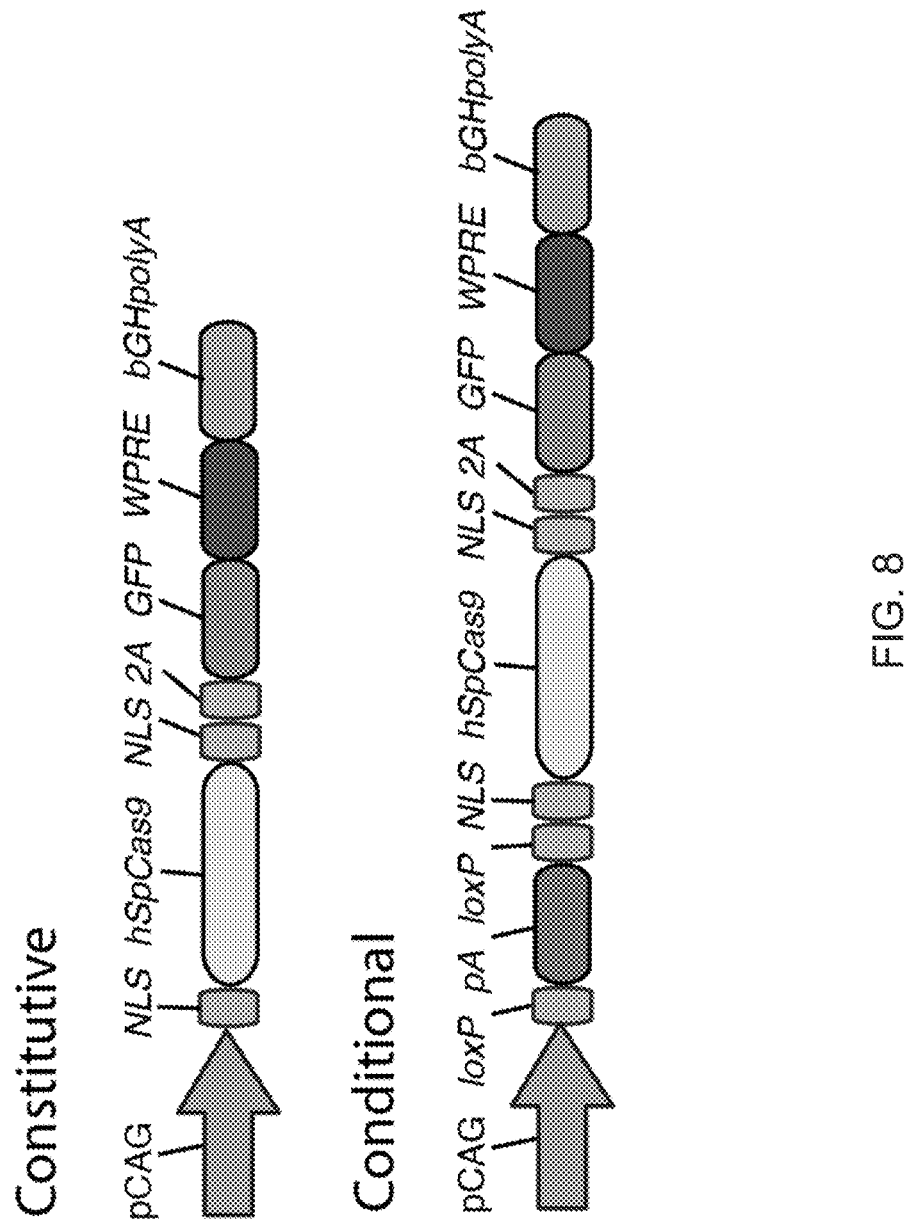
FIG. 8 shows a schematic of the important elements in the Constitutive and Conditional Cas9 constructs.

Transgenic animals are also provided. Preferred examples include animals comprising Cas9, in terms of polynucleotides encoding Cas9 or the protein itself. Mice, rats and rabbits are preferred. To generate transgenic mice with the constructs, as exemplified herein one may inject pure, linear DNA into the pronucleus of a zygote from a pseudo pregnant female, e.g. a CB56 female. Founders may then be identified are identified, genotyped, and backcrossed to CB57 mice. The constructs may then be cloned and optionally verified, for instance by Sanger sequencing. Knock outs are envisaged where for instance one or more genes are knocked out in a model. However, are knockins are also envisaged (alone or in combination). An example Knock in Cas9 mouse was generated and this is exemplified, but Cas9 knockins are preferred. To generate a Cas9 knock in mice one may target the same constitutive and conditional constructs to the Rosa26 locus, as described herein (FIGS. 7A-B and 8). That the CRISPR-Cas system is able to be employed in generating transgenic mice is also provided in the manuscript "One-step generation of mice carrying mutations in multiple genes by CRISPR/Cas-mediated genome engineering." by Wang et al. Cell. 2013 May 9; 153(4):910-8. doi: 10.1016/j.cell.2013.04.025. Epub 2013 May 2, incorporated by reference in its entirety, wherein it is demonstrated that CRISPR/Cas mediated gene editing allows for the simultaneous disruption of five genes in mouse embryonic stem cells with high efficiency.

Utility of the conditional Cas9 mouse: Applicants have shown in 293 cells that the Cas9 conditional expression construct can be activated by co-expression with Cre. Applicants also show that the correctly targeted R1 mESCs can have active Cas9 when Cre is expressed. Because Cas9 is followed by the P2A peptide cleavage sequence and then EGFP Applicants identify successful expression by observing EGFP. Applicants have shown Cas9 activation in mESCs. This same concept is what makes the conditional Cas9 mouse so useful. Applicants may cross their conditional Cas9 mouse with a mouse that ubiquitously expresses Cre (ACTB-Cre line) and may arrive at a mouse that expresses Cas9 in every cell. It should only take the delivery of chimeric RNA to induce genome editing in embryonic or adult mice. Interestingly, if the conditional Cas9 mouse is crossed with a mouse expressing Cre under a tissue specific promoter, there should only be Cas9 in the tissues that also express Cre. This approach may be used to edit the genome in only precise tissues by delivering chimeric RNA to the same tissue.

As mentioned above, transgenic animals are also provided, as are transgenic plants, especially crops and algae. The transgenic may be useful in applications outside of providing a disease model. These may include food of feed production through expression of, for instance, higher protein, carbohydrate, nutrient or vitamins levels than would normally be seen in the wildtype. In this regard, transgenic plants, especially pulses and tubers, and animals, especially mammals such as livestock (cows, sheep, goats and pigs), but also poultry and edible insects, are preferred.

Transgenic algae or other plants such as rape may be particularly useful in the production of vegetable oils or biofuels such as alcohols (especially methanol and ethanol), for instance. These may be engineered to express or over-express high levels of oil or alcohols for use in the oil or biofuel industries.

In terms of in vivo delivery, AAV is advantageous over other viral vectors for a couple of reasons:

Low toxicity (this may be due to the purification method not requiring ultra centrifugation of cell particles that can activate the immune response)

Low probability of causing insertional mutagenesis because it doesn't integrate into the host genome.

AAV has a packaging limit of 4.5 or 4.75 Kb. This means that Cas9 as well as a promoter and transcription terminator have to be all fit into the same viral vector. Constructs larger than 4.5 or 4.75 Kb will lead to significantly reduced virus production. SpCas9 is quite large, the gene itself is over 4.1 Kb, which makes it difficult for packing into AAV. Therefore embodiments of the invention include utilizing homologs of Cas9 that are shorter. For example:

| Species | Cas9 Size |
|---|---|
| Corynebacter diphtheriae | 3252 |
| Eubacterium ventriosum | 3321 |
| Streptococcus pasteurianus | 3390 |
| Lactobacillus farciminis | 3378 |
| Sphaerochaeta globus | 3537 |
| Azospirillum B510 | 3504 |
| Gluconacetobacter diazotrophicus | 3150 |
| Neisseria cinerea | 3246 |
| Roseburia intestinalis | 3420 |
| Parvibaculum lavamentivorans | 3111 |
| Staphylococcus aureus | 3159 |
| Nitratifractor salsuginis DSM 16511 | 3396 |
| Campylobacter lari CF89-12 | 3009 |
| Streptococcus thermophilus LMD-9 | 3396 |

These species are therefore, in general, preferred Cas9 species. Applicants have shown delivery and in vivo mouse brain Cas9 expression data.

Two ways to package Cas9 coding nucleic acid molecules, e.g., DNA, into viral vectors to mediate genome modification in vivo are preferred:

To achieve NHEJ-mediated gene knockout:
Single virus vector:
  Vector containing two or more expression cassettes:
  Promoter-Cas9 coding nucleic acid molecule-terminator
  Prom oter-gRNA1-terminator
  Promoter-gRNA2-terminator
  Promoter-gRNA(N)-terminator (up to size limit of vector)
Double virus vector:
  Vector 1 containing one expression cassette for driving the expression of Cas9
  Promoter-Cas9 coding nucleic acid molecule-terminator
  Vector 2 containing one more expression cassettes for driving the expression of one or more guideRNAs
  Prom oter-gRNA1-terminator
  Promoter-gRNA(N)-terminator (up to size limit of vector)
To mediate homology-directed repair.
In addition to the single and double virus vector approaches described above, an additional vector is used to deliver a homology-direct repair template.

Promoter used to drive Cas9 coding nucleic acid molecule expression can include:
  AAV ITR can serve as a promoter: this is advantageous for eliminating the need for an additional promoter element (which can take up space in the vector). The additional space freed up can be used to drive the expression of additional elements (gRNA, etc). Also, ITR activity is relatively weaker, so can be used to reduce toxicity due to over expression of Cas9.
  For ubiquitous expression, can use promoters: CMV, CAG, CBh, PGK, SV40, Ferritin heavy or light chains, etc.
  For brain expression, can use promoters: Synapsin1 for all neurons, CaMKIIalpha for excitatory neurons, GAD67 or GAD65 or VGAT for GABAergic neurons, etc.
  For liver expression, can use Albumin promoter
  For lung expression, can use SP-B
  For endothelial cells, can use ICAM
  For hematopoietic cells can use IFNbeta or CD45
  For Osteoblasts can use OG-2
Promoter used to drive guide RNA can include:
  Pol III promoters such as U6 or H1
  Use of Pol II promoter and intronic cassettes to express gRNA.

As to AAV, the AAV can be AAV1, AAV2, AAV5 or any combination thereof. One can select the AAV of the AAV with regard to the cells to be targeted; e.g., one can select AAV serotypes 1, 2, 5 or a hybrid or capsid AAV1, AAV2, AAV5 or any combination thereof for targeting brain or neuronal cells; and one can select AAV4 for targeting cardiac tissue. AAV8 is useful for delivery to the liver. The above promoters and vectors are preferred individually.

RNA delivery is also a useful method of in vivo delivery. FIG. 9 shows delivery and in vivo mouse brain Cas9 expression data. It is possible to deliver Cas9 and gRNA (and, for instance, HR repair template) into cells using liposomes or nanoparticles. Thus delivery of the CRISPR enzyme, such as a Cas9 and/or delivery of the RNAs of the invention may be in RNA form and via microvesicles, liposomes or nanoparticles. For example, Cas9 mRNA and gRNA can be packaged into liposomal particles for delivery in vivo. Liposomal transfection reagents such as Invivofectamine from Life Technologies and other reagents on the market can effectively deliver RNA molecules into the liver.

Enhancing NHEJ or HR efficiency is also helpful for delivery. It is preferred that NHEJ efficiency is enhanced by co-expressing end-processing enzymes such as Trex2 (Dumitrache et al. Genetics. 2011 August; 188(4): 787-797). It is preferred that HR efficiency is increased by transiently inhibiting NHEJ machineries such as Ku70 and Ku86. HR efficiency can also be increased by co-expressing prokaryotic or eukaryotic homologous recombination enzymes such as RecBCD, RecA.

Various means of delivery are described herein, and further discussed in this section.

Viral delivery: The CRISPR enzyme, for instance a Cas9, and/or any of the present RNAs, for instance a guide RNA, can be delivered using adeno associated virus (AAV), lentivirus, adenovirus or other viral vector types, or combinations thereof. Cas9 and one or more guide RNAs can be packaged into one or more viral vectors. In some embodiments, the viral vector is delivered to the tissue of interest by, for example, an intramuscular injection, while other times the viral delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector chose, the target cell, organism, or tissue, the general condition of the subject to be treated, the degree of transformation/modification sought, the administration route, the administration mode, the type of transformation/modification sought, etc.

Such a dosage may further contain, for example, a carrier (water, saline, ethanol, glycerol, lactose, sucrose, calcium phosphate, gelatin, dextran, agar, pectin, peanut oil, sesame oil, etc.), a diluent, a pharmaceutically-acceptable carrier (e.g., phosphate-buffered saline), a pharmaceutically-acceptable excipient, an adjuvant to enhance antigenicity, an immunostimulatory compound or molecule, and/or other compounds known in the art. The adjuvant herein may contain a suspension of minerals (alum, aluminum hydroxide, aluminum phosphate) on which antigen is adsorbed; or water-in-oil emulsion in which antigen solution is emulsified in oil (MF-59, Freund's incomplete adjuvant), sometimes with the inclusion of killed mycobacteria (Freund's complete adjuvant) to further enhance antigenicity (inhibits degradation of antigen and/or causes influx of macrophages). Adjuvants also include immunostimulatory molecules, such as cytokines, costimulatory molecules, and for example, immunostimulatory DNA or RNA molecules, such as CpG oligonucleotides. Such a dosage formulation is readily ascertainable by one skilled in the art. The dosage may further contain one or more pharmaceutically acceptable salts such as, for example, a mineral acid salt such as a hydrochloride, a hydrobromide, a phosphate, a sulfate, etc.; and the salts of organic acids such as acetates, propionates, malonates, benzoates, etc. Additionally, auxiliary substances, such as wetting or emulsifying agents, pH buffering substances, gels or gelling materials, flavorings, colorants, microspheres, polymers, suspension agents, etc. may also be present herein. In addition, one or more other conventional pharmaceutical ingredients, such as preservatives, humectants, suspending agents, surfactants, antioxidants, anticaking agents, fillers, chelating agents, coating agents, chemical stabilizers, etc. may also be present, especially if the dosage form is a reconstitutable form. Suitable exemplary ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin, albumin and a combination thereof. A thorough discussion of pharmaceutically acceptable excipients is available in REMINGTON'S PHARMACEUTICAL SCIENCES (Mack Pub. Co., N.J. 1991) which is incorporated by reference herein.

In an embodiment herein the delivery is via an adenovirus, which may be at a single booster dose containing at least $1\times10^5$ particles (also referred to as particle units, pu) of adenoviral vector. In an embodiment herein, the dose preferably is at least about $1\times10^6$ particles (for example, about $1\times10^6$-$1\times10^{12}$ particles), more preferably at least about $1\times10^7$ particles, more preferably at least about $1\times10^8$ particles (e.g., about $1\times10^8$-$1\times10^{11}$ particles or about $1\times10^8$-$1\times10^{12}$ particles), and most preferably at least about $1\times10^9$ particles (e.g., about $1*\times10^9$-$1\times10^{10}$ particles or about $1\times10^9$-$1\times10^{12}$ particles), or even at least about $1\times10^{10}$ particles (e.g., about $1\times10^{10}$-$1\times10^{12}$ particles) of the adenoviral vector. Alternatively, the dose comprises no more than about $1\times10^{14}$ particles, preferably no more than about $1\times10^{13}$ particles, even more preferably no more than about $1\times10^{12}$ particles, even more preferably no more than about $1\times10^{11}$ particles, and most preferably no more than about $1\times10^{10}$ particles (e.g., no more than about $1\times10^9$ articles). Thus, the dose may contain a single dose of adenoviral vector with, for example, about $1\times10^6$ particle units (pu), about $2\times10^6$ pu, about $4\times10^6$ pu, about $1\times10^7$ pu, about $2\times10^7$ pu, about $4\times10^7$ pu, about $1\times10^8$ pu, about $2\times10^8$ pu, about $4\times10^8$ pu, about $1\times10^9$ pu, about $2\times10^9$ pu, about $4\times10^9$ pu, about $1\times10^{10}$ pu, about $2\times10^{10}$ pu, about $4\times10^{10}$ pu, about $1\times10^{11}$ pu, about $2\times10^{11}$ pu, about $4\times10^{11}$ pu, about $1\times10^{12}$ pu, about $2\times10^{12}$ pu, or about $4\times10^{12}$ pu of adenoviral vector. See, for example, the adenoviral vectors in U.S. Pat. No. 8,454,972 B2 to Nabel, et. al., granted on Jun. 4, 2013; incorporated by reference herein, and the dosages at col 29, lines 36-58 thereof. In an embodiment herein, the adenovirus is delivered via multiple doses.

In an embodiment herein, the delivery is via an AAV. A therapeutically effective dosage for in vivo delivery of the AAV to a human is believed to be in the range of from about 20 to about 50 ml of saline solution containing from about $1\times10^{10}$ to about $1\times10^{10}$ functional AAV/ml solution. The dosage may be adjusted to balance the therapeutic benefit against any side effects. In an embodiment herein, the AAV dose is generally in the range of concentrations of from about $1\times10^5$ to $1\times10^{50}$ genomes AAV, from about $1\times10^8$ to $1\times10^{20}$ genomes AAV, from about $1\times10^{10}$ to about $1\times10^{16}$ genomes, or about $1\times10^{11}$ to about $1\times10^{16}$ genomes AAV. A human dosage may be about $1\times10^{13}$ genomes AAV. Such concentrations may be delivered in from about 0.001 ml to about 100 ml, about 0.05 to about 50 ml, or about 10 to about 25 ml of a carrier solution. Other effective dosages can be readily established by one of ordinary skill in the art through routine trials establishing dose response curves. See, for example, U.S. Pat. No. 8,404,658 B2 to Hajjar, et al., granted on Mar. 26, 2013, at col. 27, lines 45-60.

In an embodiment herein the delivery is via a plasmid. In such plasmid compositions, the dosage should be a sufficient amount of plasmid to elicit a response. For instance, suitable quantities of plasmid DNA in plasmid compositions can be from about 0.1 to about 2 mg, or from about 1 µg to about 10 µg.

The doses herein are based on an average 70 kg individual. The frequency of administration is within the ambit of the medical or veterinary practitioner (e.g., physician, veterinarian), or scientist skilled in the art.

Cas9 and one or more guide RNA can be delivered using adeno associated virus (AAV), lentivirus, adenovirus or other plasmid or viral vector types, using formulations and doses from, for example, U.S. Pat. No. 8,454,972 (formulations, doses for adenovirus), U.S. Pat. No. 8,404,658 (formulations, doses for AAV) and U.S. Pat. No. 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus. For plasmid delivery, the route of administration, formulation and dose can be as in U.S. Pat. No. 5,846,946 and as in clinical studies involving plasmids. Doses may be based on or extrapolated to an average 70 kg individual, and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed.

The viral vectors can be injected into the tissue of interest. For cell-type specific genome modification, the expression of Cas9 can be driven by a cell-type specific promoter. For example, liver-specific expression might use the Albumin promoter and neuron-specific expression might use the Synapsin I promoter.

RNA delivery: The CRISPR enzyme, for instance a Cas9, and/or any of the present RNAs, for instance a guide RNA, can also be delivered in the form of RNA. Cas9 mRNA can be generated using in vitro transcription. For example, Cas9 mRNA can be synthesized using a PCR cassette containing the following elements: T7_promoter-kozak sequence (GCCACC)-Cas9-3' UTR from beta globin-polyA tail (a string of 120 or more adenines (SEQ ID NO: 350)). The cassette can be used for transcription by T7 polymerase. Guide RNAs can also be transcribed using in vitro transcription from a cassette containing T7 promoter-GG-guide RNA sequence.

To enhance expression and reduce toxicity, the CRISPR enzyme and/or guide RNA can be modified using pseudo-U or 5-Methyl-C.

CRISPR enzyme mRNA and guide RNA may be delivered simultaneously using nanoparticles or lipid envelopes.

For example, Su X, Fricke J, Kavanagh D G, Irvine D J ("In vitro and in vivo mRNA delivery using lipid-enveloped pH-responsive polymer nanoparticles" Mol Pharm. 2011 Jun. 6; 8(3):774-87. doi: 10.1021/mp100390w. Epub 2011 Apr. 1) describes biodegradable core-shell structured nanoparticles with a poly(β-amino ester) (PBAE) core enveloped by a phospholipid bilayer shell. These were developed for in vivo mRNA delivery. The pH-responsive PBAE component was chosen to promote endosome disruption, while the lipid surface layer was selected to minimize toxicity of the polycation core. Such are, therefore, preferred for delivering RNA of the present invention.

Furthermore, Michael S D Kormann et al. ("Expression of therapeutic proteins after delivery of chemically modified mRNA in mice: Nature Biotechnology, Volume:29, Pages: 154-157 (2011) Published online 9 Jan. 2011) describes the use of lipid envelopes to deliver RNA. Use of lipid envelopes is also preferred in the present invention.

mRNA delivery methods are especially promising for liver delivery currently.

CRISPR enzyme mRNA and guide RNA might also be delivered separately. CRISPR enzyme mRNA can be delivered prior to the guide RNA to give time for CRISPR enzyme to be expressed. CRISPR enzyme mRNA might be administered 1-12 hours (preferably around 2-6 hours) prior to the administration of guide RNA.

Alternatively, CRISPR enzyme mRNA and guide RNA can be administered together. Advantageously, a second booster dose of guide RNA can be administered 1-12 hours (preferably around 2-6 hours) after the initial administration of CRISPR enzyme mRNA+guide RNA.

Additional administrations of CRISPR enzyme mRNA and/or guide RNA might be useful to achieve the most efficient levels of genome modification.

For minimization of toxicity and off-target effect, it will be important to control the concentration of CRISPR enzyme mRNA and guide RNA delivered. Optimal concentrations of CRISPR enzyme mRNA and guide RNA can be determined by testing different concentrations in a cellular or animal model and using deep sequencing the analyze the extent of modification at potential off-target genomic loci. For example, for the guide sequence targeting 5'-GAGTCCGAGCAGAAGAAGAA-3' (SEQ ID NO: 2) in the EMX1 gene of the human genome, deep sequencing can be used to assess the level of modification at the following two off-target loci, 1:5'-GAGTCCTAGCAGGAGAAGAA-3' (SEQ ID NO: 3) and 2:5'-GAGTCTAAGCAGAAGAAGAA-3' (SEQ ID NO: 4). The concentration that gives the highest level of on-target modification while minimizing the level of off-target modification should be chosen for in vivo delivery.

Alternatively, to minimize the level of toxicity and off-target effect, CRISPR enzyme nickase mRNA (for example S. pyogenes Cas9 with either a D10A or a H840A mutation) can be delivered with a pair of guide RNAs targeting a site of interest. The two guide RNAs need to be spaced as follows. Guide sequences in red (single underline) and blue (double underline) respectively (these examples are based on the PAM requirement for Streptococcus pyogenes Cas9.

| Overhang length (bp) | Guide RNA design (guide sequence and PAM color coded) |
|---|---|
| 14 | 5'-NNNNNNNNNNNNNNNNNNNNCCNNNNNNNNNNNNNNNNNNNNGGNNNNNNNNNNNNNNNN-3' (SEQ ID NO: 5) <br> 3'-NNNNNNNNNNNNNNNNNNNNNNNNGGNNNNNNNNNNNNNNNNNNNNNCCNNNNNNNNNNNNNNNN-5' (SEQ ID NO: 6) |
| 13 | 5'-NNNNNNNNNNNNNNNNNNNNNCCNNNNNNNNNNNNNNNNNNNNGGNNNNNNNNNNNNNNNN-3' (SEQ ID NO: 7) <br> 3'-NNNNNNNNNNNNNNNNNNNNNNNGGNNNNNNNNNNNNNNNNNNNNCCNNNNNNNNNNNNNNNN-5' (SEQ ID NO: 8) |
| 12 | 5'-NNNNNNNNNNNNNNNNNNNNNNCNNNNNNNNNNNNNNNNNNNNGGNNNNNNNNNNNNNNNN-3' (SEQ ID NO: 9) <br> 3'-NNNNNNNNNNNNNNNNNNNNNNGGNNNNNNNNNNNNNNNNNNNNNCCNNNNNNNNNNNNNNNN-5' (SEQ ID NO: 10) |
| 11 | 5'-NNNNNNNNNNNNNNNNNNNNNNNCCNNNNNNNNNNNNNNNNNNNGGNNNNNNNNNNNNNNNN-3' (SEQ ID NO: 11) <br> 3'-NNNNNNNNNNNNNNNNNNNNNNNGGNNNNNNNNNNNNNNNNNNCCNNNNNNNNNNNNNNNN-5' (SEQ ID NO: 12) |
| 10 | 5'-NNNNNNNNNNNNNNNNNNNNNNNNCCNNNNNNNNNNNNNNNNNNGGNNNNNNNNNNNNNNNN-3' (SEQ ID NO: 13) <br> 3'-NNNNNNNNNNNNNNNNNNNNNNGGNNNNNNNNNNNNNNNNNNNNCCNNNNNNNNNNNNNNNN-5' (SEQ ID NO: 14) |
| 9 | 5'-NNNNNNNNNNNNNNNNNNNNNNNNNCCNNNNNNNNNNNNNNNNNNGGNNNNNNNNNNNNNNNN-3' (SEQ ID NO: 15) <br> 3'-NNNNNNNNNNNNNNNNNNNNNNNGGNNNNNNNNNNNNNNNNNNNCCNNNNNNNNNNNNNNNN-5' (SEQ ID NO: 16) |
| 8 | 5'-NNNNNNNNNNNNNNNNNNNNNNNNNNCCNNNNNNNNNNNNNNNNGGNNNNNNNNNNNNNNNN-3' (SEQ ID NO: 17) <br> 3'-NNNNNNNNNNNNNNNNNNNNNNNNGGNNNNNNNNNNNNNNNNNCCNNNNNNNNNNNNNNNN-5' (SEQ ID NO: 18) |
| 7 | 5'-NNNNNNNNNNNNNNNNNNNNNNNNNNNCCNNNNNNNNNNNNNNNGGNNNNNNNNNNNNNNNN-3' (SEQ ID NO: 19) <br> 3'-NNNNNNNNNNNNNNNNNNNNNNNNNGGNNNNNNNNNNNNNNNNCCNNNNNNNNNNNNNNNN-5' (SEQ ID NO: 20) |

-continued

| Overhang length (bp) | Guide RNA design (guide sequence and PAM color coded) |
|---|---|
| 6 | 5'-NNNNNNNNNNNNNNNNNNNNNNCCNNNNNNNNNNNNNNGGNNNNNNNNNNNNNNNNNNNNN-3' (SEQ ID NO: 21)<br>3'-NNNNNNNNNNNNNNNNNNNNNNGGNNNNNNNNNNNNNNCCNNNNNNNNNNNNNNNNNNNNN-5' (SEQ ID NO: 22) |
| 5 | 5'-NNNNNNNNNNNNNNNNNNNNNNNCCNNNNNNNNNNNNNNGGNNNNNNNNNNNNNNNNNNNNN-3' (SEQ ID NO: 23)<br>3'-NNNNNNNNNNNNNNNNNNNNNNNGGNNNNNNNNNNNNNNCCNNNNNNNNNNNNNNNNNNNNN-5' (SEQ ID NO: 24) |
| 4 | 5'-NNNNNNNNNNNNNNNNNNNNNNNNCCNNNNNNNNNNNNNNGGNNNNNNNNNNNNNNNNNNNNN-3' (SEQ ID NO: 25)<br>3'-NNNNNNNNNNNNNNNNNNNNNNNNGGNNNNNNNNNNNNNNCCNNNNNNNNNNNNNNNNNNNNN-5' (SEQ ID NO: 26) |
| 3 | 5'-NNNNNNNNNNNNNNNNNNNNNNNNNCCNNNNNNNNNNNNNNGGNNNNNNNNNNNNNNNNNNNNN-3' (SEQ ID NO: 27)<br>3'-NNNNNNNNNNNNNNNNNNNNNNNNNGGNNNNNNNNNNNNNNCCNNNNNNNNNNNNNNNNNNNNN-5' (SEQ ID NO: 28) |
| 2 | 5'-NNNNNNNNNNNNNNNNNNNNNNNNNNCCNNNNNNNNNNNNNGGNNNNNNNNNNNNNNNNNNNNN-3' (SEQ ID NO: 29)<br>3'-NNNNNNNNNNNNNNNNNNNNNNNNNNGGNNNNNNNNNNNNNCCNNNNNNNNNNNNNNNNNNNNN-5' (SEQ ID NO: 30) |
| 1 | 5'-NNNNNNNNNNNNNNNNNNNNNNNNNNNCCNNNNNNNNNNNNGGNNNNNNNNNNNNNNNNNNNNN-3' (SEQ ID NO: 31)<br>3'-NNNNNNNNNNNNNNNNNNNNNNNNNNNGGNNNNNNNNNNNCCNNNNNNNNNNNNNNNNNNNNN-5' (SEQ ID NO: 32) |
| blunt | 5'-NNNNNNNNNNNNNNNNNNNNNNNNNNNNCCNNNNNNNNNNGGNNNNNNNNNNNNNNNNNNNNN-3' (SEQ ID NO: 33)<br>3'-NNNNNNNNNNNNNNNNNNNNNNNNNNNNGGNNNNNNNNCCNNNNNNNNNNNNNNNNNNNNN-5' (SEQ ID NO: 34) |
| 1 | 5'-NNNNNNNNNNNNNNNNNNNNNNNNNNNNNCCNNNNNNNNNGGNNNNNNNNNNNNNNNNNNNNN-3' (SEQ ID NO: 35)<br>3'-NNNNNNNNNNNNNNNNNNNNNNNNNNNNNGGNNNNNNNCCNNNNNNNNNNNNNNNNNNNNN-5' (SEQ ID NO: 36) |
| 2 | 5'-NNNNNNNNNNNNNNNNNNNNNNNNNNNNNNCCNNNNNNNGGNNNNNNNNNNNNNNNNNNNNN-3' (SEQ ID NO: 37)<br>3'-NNNNNNNNNNNNNNNNNNNNNNNNNNNNNNGGNNNNNNCCNNNNNNNNNNNNNNNNNNNNN-5' (SEQ ID NO: 38) |
| 3 | 5'-NNNNNNNNNNNNNNNNNNNNNNNNNNNNNNNCCNNNNNNGGNNNNNNNNNNNNNNNNNNNNN-3' (SEQ ID NO: 39)<br>3'-NNNNNNNNNNNNNNNNNNNNNNNNNNNNNNNGGNNNNNCCNNNNNNNNNNNNNNNNNNNNN-5' (SEQ ID NO: 40) |
| 4 | 5'-NNNNNNNNNNNNNNNNNNNNNNNNNNNNNNNNCCNNNNGGNNNNNNNNNNNNNNNNNNNNN-3' (SEQ ID NO: 41)<br>3'-NNNNNNNNNNNNNNNNNNNNNNNNNNNNNNNNGGNNNNCCNNNNNNNNNNNNNNNNNNNNN-5' (SEQ ID NO: 42) |
| 5 | 5'-NNNNNNNNNNNNNNNNNNNNNNNNNNNNNNNNNCCNNGGNNNNNNNNNNNNNNNNNNNNN-3' (SEQ ID NO: 43)<br>3'-NNNNNNNNNNNNNNNNNNNNNNNNNNNNNNNNNGGNNCCNNNNNNNNNNNNNNNNNNNNN-5' (SEQ ID NO: 44) |
| 6 | 5'-NNNNNNNNNNNNNNNNNNNNNNNNNNNNNNNNNNCCNNGGNNNNNNNNNNNNNNNNNNNNN-3' (SEQ ID NO: 45)<br>3'-NNNNNNNNNNNNNNNNNNNNNNNNNNNNNNNNNNGGNNCCNNNNNNNNNNNNNNNNNNNNN-5' (SEQ ID NO: 46) |
| 7 | 5'-NNNNNNNNNNNNNNNNNNNNNNNNNNNNNNNNNNNCCNGGNNNNNNNNNNNNNNNNNNNNN-3' (SEQ ID NO: 47)<br>3'-NNNNNNNNNNNNNNNNNNNNNNNNNNNNNNNNNNNGGNCCNNNNNNNNNNNNNNNNNNNNN-5' (SEQ ID NO: 48) |
| 8 | 5'-NNNNNNNNNNNNNNNNNNNNNNNNNNNNNNNNNNNNCCGGNNNNNNNNNNNNNNNNNNNNN-3' (SEQ ID NO: 49)<br>3'-NNNNNNNNNNNNNNNNNNNNNNNNNNNNNNNNNNNNGGCCNNNNNNNNNNNNNNNNNNNNN-5' (SEQ ID NO: 50) |

| Overhang length (bp) | Guide RNA design (guide sequence and PAM color coded) |
|---|---|
| 12 | 5'-NNNNNNNNNNNNNNNNNNNNNGGNNNNNNNNNNNNNNNNNNNNNNNNNNNNNNNNN-3'<br>(SEQ ID NO: 51)<br>3'-NNNNNNNNNNNNNNNNNNNNNNNNNCCGGNNNNNNNNNNNNNNNNNNNNNNNNNNNNN-5'<br>(SEQ ID NO: 52) |
| 13 | 5'-NNNNNNNNNNNNNNNNNNNNNNCGGNNNNNNNNNNNNNNNNNNNNNNNNNNNNNNNN-3'<br>(SEQ ID NO: 53)<br>3'-NNNNNNNNNNNNNNNNNNNNNNNNNCCNGGNNNNNNNNNNNNNNNNNNNNNNNNNNNNN-5'<br>(SEQ ID NO: 54) |
| 14 | 5'-NNNNNNNNNNNNNNNNNNNNNNCGGNNNNNNNNNNNNNNNNNNNNNNNNNNNNNNNN-3'<br>(SEQ ID NO: 53)<br>3'-NNNNNNNNNNNNNNNNNNNNNNNNNCCNNGGNNNNNNNNNNNNNNNNNNNNNNNNNNNN-5'<br>(SEQ ID NO: 55) |
| 15 | 5'-NNNNNNNNNNNNNNNNNNNNNNCGGNNNNNNNNNNNNNNNNNNNNNNNNNNNNNNNN-3'<br>(SEQ ID NO: 53)<br>3'-NNNNNNNNNNNNNNNNNNNNNNNNNCCNNNGGNNNNNNNNNNNNNNNNNNNNNNNNNNN-5'<br>(SEQ ID NO: 56) |
| 16 | 5'-NNNNNNNNNNNNNNNNNNNNNNCGGNNNNNNNNNNNNNNNNNNNNNNNNNNNNNNNN-3'<br>(SEQ ID NO: 53)<br>3'-NNNNNNNNNNNNNNNNNNNNNNNNNCCNNNNGGNNNNNNNNNNNNNNNNNNNNNNNNNN-5'<br>(SEQ ID NO: 57) |
| 17 | 5'-NNNNNNNNNNNNNNNNNNNNNNCGGNNNNNNNNNNNNNNNNNNNNNNNNNNNNNNNN-3'<br>(SEQ ID NO: 53)<br>3'-NNNNNNNNNNNNNNNNNNNNNNNNNCCNNNNNGGNNNNNNNNNNNNNNNNNNNNNNNNN-5'<br>(SEQ ID NO: 58) |

Further interrogation of the system have given Applicants evidence of the 5' overhang (see, e.g., Ran et al., Cell. 2013 Sep. 12; 154(6):1380-9 and U.S. Provisional Patent Application Ser. No. 61/871,301 filed Aug. 28, 2013). Applicants have further identified parameters that relate to efficient cleavage by the Cas9 nickase mutant when combined with two guide RNAs and these parameters include but are not limited to the length of the 5' overhang. In embodiments of the invention the 5' overhang is at most 200 base pairs, preferably at most 100 base pairs, or more preferably at most 50 base pairs. In embodiments of the invention the 5' overhang is at least 26 base pairs, preferably at least 30 base pairs or more preferably 34-50 base pairs or 1-34 base pairs. In other preferred methods of the invention the first guide sequence directing cleavage of one strand of the DNA duplex near the first target sequence and the second guide sequence directing cleavage of other strand near the second target sequence results in a blunt cut or a 3' overhang. In embodiments of the invention the 3' overhang is at most 150, 100 or 25 base pairs or at least 15, 10 or 1 base pairs. In preferred embodiments the 3' overhang is 1-100 basepairs.

Aspects of the invention relate to the expression of the gene product being decreased or a template polynucleotide being further introduced into the DNA molecule encoding the gene product or an intervening sequence being excised precisely by allowing the two 5' overhangs to reanneal and ligate or the activity or function of the gene product being altered or the expression of the gene product being increased. In an embodiment of the invention, the gene product is a protein.

Only sgRNA pairs creating 5' overhangs with less than 8 bp overlap between the guide sequences (offset greater than −8 bp) were able to mediate detectable indel formation. Importantly, each guide used in these assays is able to efficiently induce indels when paired with wildtype Cas9, indicating that the relative positions of the guide pairs are the most important parameters in predicting double nicking activity.

Since Cas9n and Cas9H840A nick opposite strands of DNA, substitution of Cas9n with Cas9H840A with a given sgRNA pair should result in the inversion of the overhang type. For example, a pair of sgRNAs that will generate a 5' overhang with Cas9n should in principle generate the corresponding 3' overhang instead. Therefore, sgRNA pairs that lead to the generation of a 3' overhang with Cas9n might be used with Cas9H840A to generate a 5' overhang. Unexpectedly, Applicants tested Cas9H840A with a set of sgRNA pairs designed to generate both 5' and 3' overhangs (offset range from −278 to +58 bp), but were unable to observe indel formation. Further work may be needed to identify the necessary design rules for sgRNA pairing to allow double nicking by Cas9H840A.

Additional delivery options for the brain include encapsulation of CRISPR enzyme and guide RNA in the form of either DNA or RNA into liposomes and conjugating to molecular Trojan horses for trans-blood brain barrier (BBB) delivery. Molecular Trojan horses have been shown to be effective for delivery of B-gal expression vectors into the brain of non-human primates. The same approach can be used to delivery vectors containing CRISPR enzyme and guide RNA. For instance, Xia C F and Boado R J, Pardridge W M ("Antibody-mediated targeting of siRNA via the human insulin receptor using avidin-biotin technology." Mol Pharm. 2009 May-June; 6(3):747-51. doi: 10.1021/mp800194) describes how delivery of short interfering RNA (siRNA) to cells in culture, and in vivo, is possible with combined use of a receptor-specific monoclonal antibody (mAb) and avidin-biotin technology. The authors also report that because the bond between the targeting mAb and the siRNA is stable with avidin-biotin technology, and RNAi effects at distant sites such as brain are observed in vivo following an intravenous administration of the targeted siRNA.

Zhang Y, Schlachetzki F, Pardridge W M. ("Global non-viral gene transfer to the primate brain following intravenous administration." Mol Ther. 2003 January; 7(1):11-8) describe how expression plasmids encoding reporters such as luciferase were encapsulated in the interior of an "artificial virus" comprised of an 85 nm pegylated immunoliposome, which was targeted to the rhesus monkey brain in vivo with a monoclonal antibody (MAb) to the human insulin receptor (HIR). The HIRMAb enables the liposome carrying the exogenous gene to undergo transcytosis across the blood-brain barrier and endocytosis across the neuronal plasma membrane following intravenous injection. The level of luciferase gene expression in the brain was 50-fold higher in the rhesus monkey as compared to the rat. Widespread neuronal expression of the beta-galactosidase gene in primate brain was demonstrated by both histochemistry and confocal microscopy. The authors indicate that this approach makes feasible reversible adult transgenics in 24 hours. Accordingly, the use of immunoliposome is preferred. These may be used in conjunction with antibodies to target specific tissues or cell surface proteins.

Other means of delivery or RNA are also preferred, such as via nanoparticles (Cho, S., Goldberg, M., Son, S., Xu, Q., Yang, F., Mei, Y., Bogatyrev, S., Langer, R. and Anderson, D., Lipid-like nanoparticles for small interfering RNA delivery to endothelial cells, Advanced Functional Materials, 19: 3112-3118, 2010) or exosomes (Schroeder, A., Levins, C., Cortez, C., Langer, R., and Anderson, D., Lipid-based nanotherapeutics for siRNA delivery, Journal of Internal Medicine, 267: 9-21, 2010, PMID: 20059641). Indeed, exozomes have been shown to be particularly useful in delivery siRNA, a system with some parallels to the CRISPR system. For instance, El-Andaloussi S, et al. ("Exosome-mediated delivery of siRNA in vitro and in vivo." Nat Protoc. 2012 December; 7(12):2112-26. doi: 10.1038/nprot.2012.131. Epub 2012 Nov. 15) describe how exosomes are promising tools for drug delivery across different biological barriers and can be harnessed for delivery of siRNA in vitro and in vivo. Their approach is to generate targeted exosomes through transfection of an expression vector, comprising an exosomal protein fused with a peptide ligand. The exosomes are then purify and characterized from transfected cell supernatant, then siRNA is loaded into the exosomes.

Targeted deletion of genes is preferred. Examples are exemplified in Example 12. Preferred are, therefore, genes involved in cholesterol biosynthesis, fatty acid biosynthesis, and other metabolic disorders, genes encoding mis-folded proteins involved in amyloid and other diseases, oncogenes leading to cellular transformation, latent viral genes, and genes leading to dominant-negative disorders, amongst other disorders. As exemplified here, Applicants prefer gene delivery of a CRISPR-Cas system to the liver, brain, ocular, epithelial, hematopoetic, or another tissue of a subject or a patient in need thereof, suffering from metabolic disorders, amyloidosis and protein-aggregation related diseases, cellular transformation arising from genetic mutations and translocations, dominant negative effects of gene mutations, latent viral infections, and other related symptoms, using either viral or nanoparticle delivery system.

Therapeutic applications of the CRISPR-Cas system include Glaucoma, Amyloidosis, and Huntington's disease. These are exemplified in Example 14 and the features described therein are preferred alone or in combination.

As an example, chronic infection by HIV-1 may be treated or prevented. In order to accomplish this, one may generate CRISPR-Cas guide RNAs that target the vast majority of the HIV-1 genome while taking into account HIV-1 strain variants for maximal coverage and effectiveness. One may accomplish delivery of the CRISPR-Cas system by conventional adenoviral or lentiviral-mediated infection of the host immune system. Depending on approach, host immune cells could be a) isolated, transduced with CRISPR-Cas, selected, and re-introduced in to the host or b) transduced in vivo by systemic delivery of the CRISPR-Cas system. The first approach allows for generation of a resistant immune population whereas the second is more likely to target latent viral reservoirs within the host. This is discussed in more detail in the Examples section.

It is also envisaged that the present invention generates a gene knockout cell library. Each cell may have a single gene knocked out. This is exemplified in Example 17.

One may make a library of ES cells where each cell has a single gene knocked out, and the entire library of ES cells will have every single gene knocked out. This library is useful for the screening of gene function in cellular processes as well as diseases. To make this cell library, one may integrate Cas9 driven by an inducible promoter (e.g. doxycycline inducible promoter) into the ES cell. In addition, one may integrate a single guide RNA targeting a specific gene in the ES cell. To make the ES cell library, one may simply mix ES cells with a library of genes encoding guide RNAs targeting each gene in the human genome. One may first introduce a single BxB1 attB site into the AAVS1 locus of the human ES cell. Then one may use the BxB1 integrase to facilitate the integration of individual guide RNA genes into the BxB1 attB site in AAVS1 locus. To facilitate integration, each guide RNA gene may be contained on a plasmid that carries of a single attP site. This way BxB1 will recombine the attB site in the genome with the attP site on the guide RNA containing plasmid. To generate the cell library, one may take the library of cells that have single guide RNAs integrated and induce Cas9 expression. After induction, Cas9 mediates double strand break at sites specified by the guide RNA.

Chronic administration of protein therapeutics may elicit unacceptable immune responses to the specific protein. The immunogenicity of protein drugs can be ascribed to a few immunodominant helper T lymphocyte (HTL) epitopes. Reducing the MHC binding affinity of these HTL epitopes contained within these proteins can generate drugs with lower immunogenicity (Tangri S, et al. ("Rationally engineered therapeutic proteins with reduced immunogenicity" J Immunol. 2005 Mar. 15; 174(6):3187-96.) In the present invention, the immunogenicity of the CRISPR enzyme in particular may be reduced following the approach first set out in Tangri et al with respect to erythropoietin and subsequently developed. Accordingly, directed evolution or rational design may be used to reduce the immunogenicity of the CRISPR enzyme (for instance a Cas9) in the host species (human or other species).

In Example 28, Applicants used 3 guideRNAs of interest and able to visualize efficient DNA cleavage in vivo occurring only in a small subset of cells. Essentially, what Applicants have shown here is targeted in vivo cleavage. In particular, this provides proof of concept that specific targeting in higher organisms such as mammals can also be achieved. It also highlights multiplex aspect in that multiple guide sequences (i.e. separate targets) can be used simultaneously (in the sense of co-delivery). In other words, Applicants used a multiple approach, with several different sequences targeted at the same time, but independently.

A suitable example of a protocol for producing AAV, a preferred vector of the invention is provided in Example 29.

Trinucleotide repeat disorders are preferred conditions to be treated. These are also exemplified herein.

According to another aspect, a method of gene therapy for the treatment of a subject having a mutation in the CFTR gene is provided and comprises administering a therapeutically effective amount of a CRISPR-Cas gene therapy particle, optionally via a biocompatible pharmaceutical carrier, to the cells of a subject. Preferably, the target DNA comprises the mutation deltaF508. In general, it is of preferred that the mutation is repaired to the wildtype. In this case, the mutation is a deletion of the three nucleotides that comprise the codon for phenylalanine (F) at position 508. Accordingly, repair in this instance requires reintroduction of the missing codon into the mutant.

To implement this Gene Repair Strategy, it is preferred that an adenovirus/AAV vector system is introduced into the host cell, cells or patient. Preferably, the system comprises a Cas9 (or Cas9 nickase) and the guide RNA along with a adenovirus/AAV vector system comprising the homology repair template containing the F508 residue. This may be introduced into the subject via one of the methods of delivery discussed earlier. The CRISPR-Cas system may be guided by the CFTRdelta 508 chimeric guide RNA. It targets a specific site of the CFTR genomic locus to be nicked or cleaved. After cleavage, the repair template is inserted into the cleavage site via homologous recombination correcting the deletion that results in cystic fibrosis or causes cystic fibrosis related symptoms. This strategy to direct delivery and provide systemic introduction of CRISPR systems with appropriate guide RNAs can be employed to target genetic mutations to edit or otherwise manipulate genes that cause metabolic, liver, kidney and protein diseases and disorders such as those in Table B.

For an example of CFTRdelta508 chimeric guide RNA, see Example which demonstrates gene transfer or gene delivery of a CRISPR-Cas system in airways of subject or a patient in need thereof, suffering from cystic fibrosis or from cystic fibrosis (CF) related symptoms, using adeno-associated virus (AAV) particles. In particular, they exemplify a repair strategy for Cystic Fibrosis delta F508 mutation. This type of strategy should apply across all organisms. With particular reference to CF, suitable patients may include: Human, non-primate human, canine, feline, bovine, equine and other domestic animals. In this instance, Applicants utilized a CRISPR-Cas system comprising a Cas9 enzyme to target deltaF508 or other CFTR-inducing mutations.

The treated subjects in this instance receive pharmaceutically effective amount of aerosolized AAV vector system per lung endobronchially delivered while spontaneously breathing. As such, aerosolized delivery is preferred for AAV delivery in general. An adenovirus or an AAV particle may be used for delivery. Suitable gene constructs, each operably linked to one or more regulatory sequences, may be cloned into the delivery vector. In this instance, the following constructs are provided as examples: Cbh or EF1a promoter for Cas9, U6 or H1 promoter for chimeric guide RNA): A preferred arrangement is to use a CFTRdelta508 targeting chimeric guide, a repair template for deltaF508 mutation and a codon optimized Cas9 enzyme (preferred Cas9s are those with nuclease or nickase activity) with optionally one or more nuclear localization signal or sequence(s) (NLS(s)), e.g., two (2) NLSs. Constructs without NLS are also envisaged.

In order to identify the Cas9 target site, Applicants analyzed the human CFTR genomic locus and identified the Cas9 target site. Preferably, in general and in this CF case, the PAM may contain a NGG or a NNAGAAW motif.

Accordingly, in the case of CF, the present method comprises manipulation of a target sequence in a genomic locus of interest comprising delivering a non-naturally occurring or engineered composition comprising a viral vector system comprising one or more viral vectors operably encoding a composition for expression thereof, wherein the composition comprises:

a non-naturally occurring or engineered composition comprising a vector system comprising one or more vectors comprising I. a first regulatory element operably linked to a CRISPR-Cas system chimeric RNA (chiRNA) polynucleotide sequence, wherein the polynucleotide sequence comprises (a) a guide sequence capable of hybridizing to the CF target sequence in a suitable mammalian cell, (b) a tracr mate sequence, and (c) a tracr sequence, and II. a second regulatory element operably linked to an enzyme-coding sequence encoding a CRISPR enzyme comprising at least one or more nuclear localization sequences, wherein (a), (b) and (c) are arranged in a 5' to 3' orientation, wherein components I and II are located on the same or different vectors of the system, wherein when transcribed, the tracr mate sequence hybridizes to the tracr sequence and the guide sequence directs sequence-specific binding of a CRISPR complex to the target sequence, and wherein the CRISPR complex comprises the CRISPR enzyme complexed with (1) the guide sequence that is hybridizable to the target sequence, and (2) the tracr mate sequence that is hybridized to the tracr sequence. In respect of CF, preferred target DNA sequences comprise the CFTRdelta508 mutation. A preferred PAM is described above. A preferred CRISPR enzyme is any Cas (described herein, but particularly that described in Example 16).

Alternatives to CF include any genetic disorder and examples of these are well known. Another preferred method or use of the invention is for correcting defects in the EMP2A and EMP2B genes that have been identified to be associated with Lafora disease.

In some embodiments, a "guide sequence" may be distinct from "guide RNA". A guide sequence may refer to an approx. 20 bp sequence, within the guide RNA, that specifies the target site.

In some embodiments, the Cas9 is (or is derived from) the SpCas9. In such embodiments, preferred mutations are at any or all or positions 10, 762, 840, 854, 863 and/or 986 of SpCas9 or corresponding positions in other Cas9s (which may be ascertained for instance by standard sequence comparison tools. In particular, any or all of the following mutations are preferred in SpCas9: D10A, E762A, H840A, N854A, N863A and/or D986A; as well as conservative substitution for any of the replacement amino acids is also envisaged. The same (or conservative substitutions of these mutations) at corresponding positions in other Cas9s are also preferred. Particularly preferred are D10 and H840 in SpCas9. However, in other Cas9s, residues corresponding to SpCas9 D10 and H840 are also preferred. These are advantageous as they provide nickase activity.

It will be readily apparent that a host of other diseases can be treated in a similar fashion. Some examples of genetic diseases caused by mutations are provided herein, but many more are known. The above strategy can be applied to these diseases.

The invention uses nucleic acids to bind target DNA sequences. This is advantageous as nucleic acids are much easier and cheaper to produce and the specificity can be varied according to the length of the stretch where homology is sought. Complex 3-D positioning of multiple fingers, for example is not required.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein the term "wild type" is a term of the art understood by skilled persons and means the typical form of an organism, strain, gene or characteristic as it occurs in nature as distinguished from mutant or variant forms.

As used herein the term "variant" should be taken to mean the exhibition of qualities that have a pattern that deviates from what occurs in nature.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

"Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y. Where reference is made to a polynucleotide sequence, then complementary or partially complementary sequences are also envisaged. These are preferably capable of hybridising to the reference sequence under highly stringent conditions. Generally, in order to maximize the hybridization rate, relatively low-stringency hybridization conditions are selected: about 20 to 25° C. lower than the thermal melting point ($T_m$). The $T_m$ is the temperature at which 50% of specific target sequence hybridizes to a perfectly complementary probe in solution at a defined ionic strength and pH. Generally, in order to require at least about 85% nucleotide complementarity of hybridized sequences, highly stringent washing conditions are selected to be about 5 to 15° C. lower than the $T_m$. In order to require at least about 70% nucleotide complementarity of hybridized sequences, moderately-stringent washing conditions are selected to be about 15 to 30° C. lower than the $T_m$. Highly permissive (very low stringency) washing conditions may be as low as 50° C. below the $T_m$, allowing a high level of mis-matching between hybridized sequences. Those skilled in the art will recognize that other physical and chemical parameters in the hybridization and wash stages can also be altered to affect the outcome of a detectable hybridization signal from a specific level of homology between target and probe sequences. Preferred highly stringent conditions comprise incubation in 50% formamide, 5×SSC, and 1% SDS at 42° C., or incubation in 5×SSC and 1% SDS at 65° C., with wash in 0.2×SSC and 0.1% SDS at 65° C.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

As used herein, the term "genomic locus" or "locus" (plural loci) is the specific location of a gene or DNA sequence on a chromosome. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

As used herein, "expression of a genomic locus" or "gene expression" is the process by which information from a gene is used in the synthesis of a functional gene product. The products of gene expression are often proteins, but in non-protein coding genes such as rRNA genes or tRNA genes, the product is functional RNA. The process of gene expression is used by all known life—eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context. As used herein, "expression" also refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

As used herein, the term "domain" or "protein domain" refers to a part of a protein sequence that may exist and function independently of the rest of the protein chain.

As described in aspects of the invention, sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the dTALEs described herein have sequences that are at least 95% identical or share identity to the capping region amino acid sequences provided herein.

Sequence homologies may be generated by any of a number of computer programs known in the art, for example BLAST or FASTA, etc. A suitable computer program for carrying out such an alignment is the GCG Wisconsin Bestfit package (University of Wisconsin, U.S.A; Devereux et al., 1984, Nucleic Acids Research 12:387). Examples of other software than may perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

Percentage (%) sequence homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity.

However, these more complex methods assign "gap penalties" to each gap that occurs in the alignment so that, for the same number of identical amino acids, a sequence alignment with as few gaps as possible—reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension.

Calculation of maximum % homology therefore first requires the production of an optimal alignment, taking into consideration gap penalties. A suitable computer program for carrying out such an alignment is the GCG Wisconsin Bestfit package (Devereux et al., 1984 Nuc. Acids Research 12 p 387). Examples of other software than may perform sequence comparisons include, but are not limited to, the BLAST package (see Ausubel et al., 1999 *Short Protocols in Molecular Biology*, 4$^{th}$ Ed. —Chapter 18), FASTA (Altschul et al., 1990 *J. Mol. Biol.* 403-410) and the GENEWORKS suite of comparison tools. Both BLAST and FASTA are available for offline and online searching (see Ausubel et al., 1999, *Short Protocols in Molecular Biology*, pages 7-58 to 7-60). However, for some applications, it is preferred to use the GCG Bestfit program. A new tool, called BLAST 2 Sequences is also available for comparing protein and nucleotide sequences (see *FEMS Microbiol Lett.* 1999 174 (2): 247-50; *FEMS Microbiol Lett.* 1999 177(1): 187-8 and the website of the National Center for Biotechnology information at the website of the National Institutes for Health).

Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), Gene 73(1), 237-244). Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids may be grouped together based on the properties of their side chains alone. However, it is more useful to include mutation data as well. The sets of amino acids thus derived are likely to be conserved for structural reasons. These sets may be described in the form of a Venn diagram (Livingstone C. D. and Barton G. J. (1993) "Protein sequence alignments: a strategy for the hierarchical analysis of residue conservation" Comput. Appl. Biosci. 9: 745-756) (Taylor W. R. (1986) "The classification of amino acid conservation" J. Theor. Biol. 119; 205-218). Conservative substitutions may be made, for example according to the table below which describes a generally accepted Venn diagram grouping of amino acids.

| | Set | Sub-set | |
|---|---|---|---|
| Hydrophobic | F W Y H K M I L V A G C | Aromatic | F W Y H |
| | | Aliphatic | I L V |
| Polar | W Y H K R E D C S T N Q | Charged | H K R E D |
| | | Positively charged | H K R |
| | | Negatively charged | E D |
| Small | V C A G S P T N D | Tiny | A G S |

Embodiments of the invention include sequences (both polynucleotide or polypeptide) which may comprise homologous substitution (substitution and replacement are both used herein to mean the interchange of an existing amino acid residue or nucleotide, with an alternative residue or nucleotide) that may occur i.e., like-for-like substitution in the case of amino acids such as basic for basic, acidic for acidic, polar for polar, etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as 0), pyriylalanine, thienylalanine, naphthylalanine and phenylglycine.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, which involves the presence of one or more amino acid residues in peptoid form, may be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

In one aspect, the invention provides for vectors that are used in the engineering and optimization of CRISPR-Cas systems.

A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety.

Aspects of the invention relate to bicistronic vectors for chimeric RNA and Cas9. Bicistronic expression vectors for chimeric RNA and Cas9 are preferred. In general and particularly in this embodiment Cas9 is preferably driven by the CBh promoter. The chimeric RNA may preferably be driven by a U6 promoter. Ideally the two are combined. The chimeric guide RNA typically consists of a 20 bp guide sequence (Ns) and this may be joined to the tracr sequence (running from the first "U" of the lower strand to the end of the transcript). The tracr sequence may be truncated at various positions as indicated. The guide and tracr sequences are separated by the tracr-mate sequence, which may be GUUUUAGAGCUA (SEQ ID NO: 59). This may be followed by the loop sequence GAAA as shown. Both of these are preferred examples. Applicants have demonstrated Cas9-mediated indels at the human EMX1 and PVALB loci by SURVEYOR assays. ChiRNAs are indicated by their "+n" designation, and crRNA refers to a hybrid RNA where guide and tracr sequences are expressed as separate transcripts. Throughout this application, chimeric RNA may also be called single guide, or synthetic guide RNA (sgRNA). The loop is preferably GAAA, but it is not limited to this sequence or indeed to being only 4 bp in length. Indeed, preferred loop forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG.

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol I promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). With regards to regulatory sequences, mention is made of U.S. patent application Ser. No. 10/491,026, the contents of which are incorporated by reference herein in their entirety. With regards to promoters, mention is made of PCT publication WO 2011/028929 and U.S. application Ser. No. 12/511,940, the contents of which are incorporated by reference herein in their entirety.

Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) Gene 69:301-315) and pET 11d (Studier et al., GENE EXPRESSION TECHNOLOGY: METHODS IN ENZYMOLOGY 185, Academic Press, San Diego, Calif. (1990) 60-89).

In some embodiments, a vector is a yeast expression vector. Examples of vectors for expression in yeast *Saccharomyces cerivisae* include pYepSec1 (Baldari, et al., 1987. *EMBO J.* 6: 229-234), pMFa (Kuijan and Herskowitz, 1982. *Cell* 30: 933-943), pJRY88 (Schultz et al., 1987. *Gene* 54: 113-123), pYES2 (Invitrogen Corporation, San Diego, Calif.), and picZ (InVitrogen Corp, San Diego, Calif.).

In some embodiments, a vector drives protein expression in insect cells using baculovirus expression vectors. Baculovirus vectors available for expression of proteins in cultured insect cells (e.g., SF9 cells) include the pAc series (Smith, et al., 1983. *Mol. Cell. Biol.* 3: 2156-2165) and the pVL series (Lucklow and Summers, 1989. *Virology* 170: 31-39).

In some embodiments, a vector is capable of driving expression of one or more sequences in mammalian cells using a mammalian expression vector. Examples of mammalian expression vectors include pCDM8 (Seed, 1987. *Nature* 329: 840) and pMT2PC (Kaufman, et al., 1987. *EMBO J.* 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268-277), lymphoid-specific promoters (Calame and Eaton, 1988. *Adv. Immunol.* 43: 235-275), in particular promoters of T cell receptors (Winoto and Baltimore, 1989. *EMBO J.* 8: 729-733) and immunoglobulins (Baneiji, et al., 1983. *Cell* 33: 729-740; Queen and Baltimore, 1983. *Cell* 33: 741-748), neuron-specific promoters (e.g., the neurofilament promoter; Byrne and Ruddle, 1989. *Proc. Natl. Acad. Sci. USA* 86: 5473-5477), pancreas-specific promoters (Edlund, et al., 1985. *Science* 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. *Science* 249: 374-379) and the α-fetoprotein promoter (Campes and Tilghman, 1989. *Genes Dev.* 3: 537-546). With regards to these prokaryotic and eukaryotic vectors, mention is made of U.S. Pat. No. 6,750,059, the contents of which are incorporated by reference herein in their entirety. Other embodiments of the invention may relate to the use of viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety.

In some embodiments, a regulatory element is operably linked to one or more elements of a CRISPR system so as to drive expression of the one or more elements of the CRISPR system. In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al., J. Bacteriol., 169:5429-5433 [1987]; and Nakata et al., J. Bacteriol., 171:3553-3556 [1989]), and associated genes. Similar interspersed SSRs have been identified in *Haloferax mediterranei, Streptococcus pyogenes, Anabaena*, and *Mycobacterium tuberculosis* (See, Groenen et al., Mol. Microbiol., 10:1057-1065 [1993]; Hoe et al., Emerg. Infect. Dis., 5:254-263 [1999]; Masepohl et al., Biochim. Biophys. Acta 1307:26-30 [1996]; and Mojica et al., Mol. Microbiol., 17:85-93 [1995]). The CRISPR loci typically differ from other SSRs by the structure of the repeats, which have been termed short regularly spaced repeats (SRSRs) (Janssen et al., OMICS J. Integ. Biol., 6:23-33 [2002]; and Mojica et al., Mol. Microbiol., 36:244-246 [2000]). In general, the repeats are short elements that occur in clusters that are regularly spaced by unique intervening sequences with a substantially constant length (Mojica et al., [2000], supra). Although the repeat sequences are highly conserved between strains, the number of interspersed repeats and the sequences of the spacer regions typically differ from strain to strain (van Embden et al., J. Bacteriol., 182:2393-2401 [2000]). CRISPR loci have been identified in more than 40 prokaryotes (See e.g., Jansen et al., Mol. Microbiol., 43:1565-1575 [2002]; and Mojica et al., [2005]) including, but not limited to *Aeropyrum, Pyrobaculum, Sulfolobus, Archaeoglobus, Halocarcula, Methanobacterium, Methanococcus, Methanosarcina, Methanopyrus, Pyrococcus, Picrophilus, Thermoplasma, Corynebacterium, Mycobacterium, Streptomyces, Aquifex, Porphyromonas, Chlorobium, Thermus, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthomonas, Yersinia, Treponema*, and *Thermotoga*.

In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. In embodiments of the invention the terms guide sequence and guide RNA are used interchangeably. In some embodiments, one or more elements of a CRISPR system is derived from a type I, type II, or type III CRISPR system. In some embodiments, one or more elements of a CRISPR system is derived from a particular organism comprising an endogenous CRISPR system, such as *Streptococcus pyogenes*. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell.

In some embodiments, direct repeats may be identified in silico by searching for repetitive motifs that fulfill any or all of the following criteria:

1. found in a 2 Kb window of genomic sequence flanking the type II CRISPR locus;
2. span from 20 to 50 bp; and
3. interspaced by 20 to 50 bp.

In some embodiments, 2 of these criteria may be used, for instance 1 and 2, 2 and 3, or 1 and 3. In some embodiments, all 3 criteria may be used.

In some embodiments, candidate tracrRNA may be subsequently predicted by sequences that fulfill any or all of the following criteria:

1. sequence homology to direct repeats (motif search in Geneious with up to 18-bp mismatches);
2. presence of a predicted Rho-independent transcriptional terminator in direction of transcription; and
3. stable hairpin secondary structure between tracrRNA and direct repeat.

In some embodiments, 2 of these criteria may be used, for instance 1 and 2, 2 and 3, or 1 and 3. In some embodiments, all 3 criteria may be used.

In some embodiments, chimeric synthetic guide RNAs (sgRNAs) designs may incorporate at least 12 bp of duplex structure between the direct repeat and tracrRNA.

In preferred embodiments of the invention, the CRISPR system is a type II CRISPR system and the Cas enzyme is Cas9, which catalyzes DNA cleavage. Enzymatic action by Cas9 derived from *Streptococcus pyogenes* or any closely related Cas9 generates double stranded breaks at target site sequences which hybridize to 20 nucleotides of the guide sequence and that have a protospacer-adjacent motif (PAM) sequence (examples include NGG/NRG or a PAM that can be determined as described herein) following the 20 nucleotides of the target sequence. CRISPR activity through Cas9 for site-specific DNA recognition and cleavage is defined by the guide sequence, the tracr sequence that hybridizes in part to the guide sequence and the PAM sequence. More aspects of the CRISPR system are described in Karginov and Hannon, The CRISPR system: small RNA-guided defense in bacteria and archaea, Mole Cell 2010, Jan. 15; 37(1): 7.

Figure 2A:
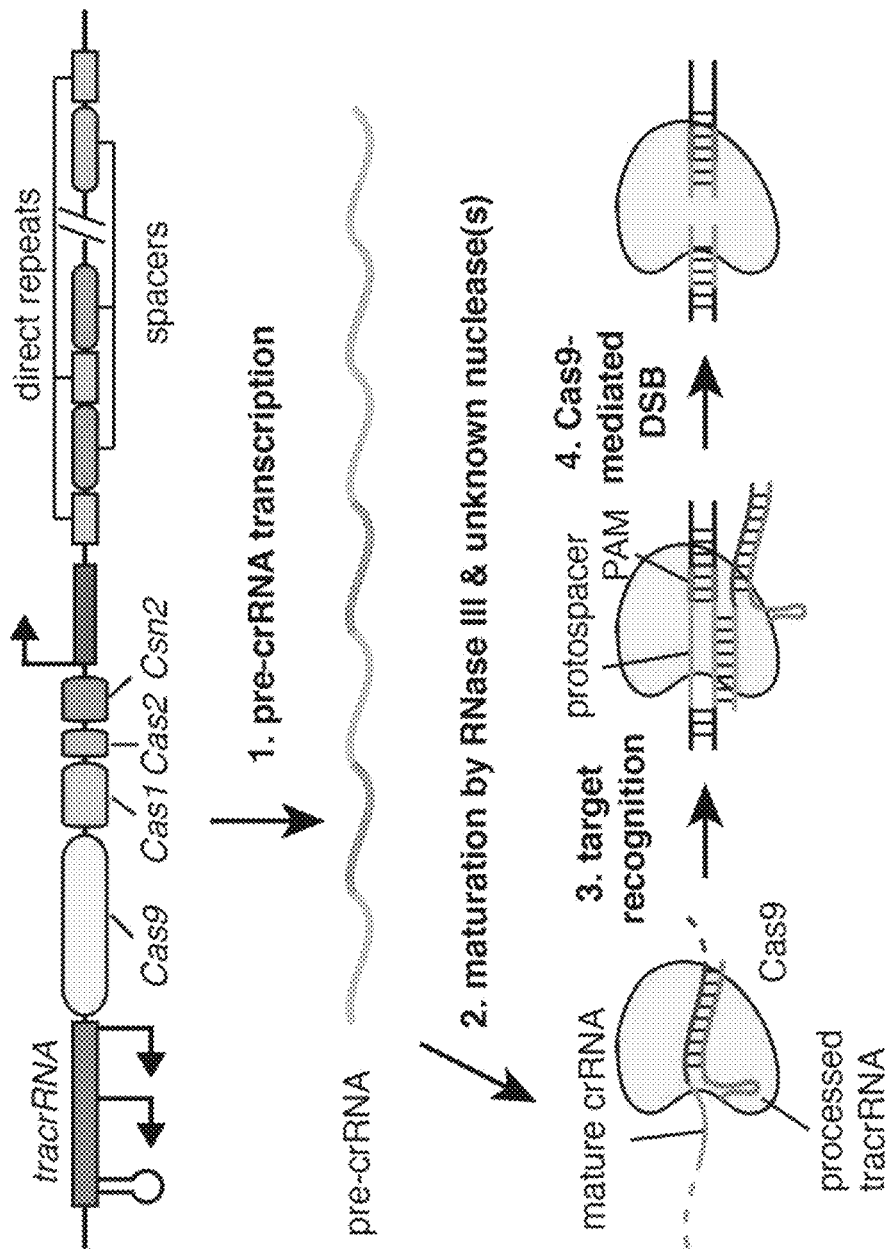
FIG. 2A-F shows a schematic representation assay carried out to evaluate the cleavage specificity of Cas9 form *Streptococcus pyogenes*. Single base pair mismatches between the guide RNA sequence and the target DNA are mapped against cleavage efficiency in %.
Figure 2B:
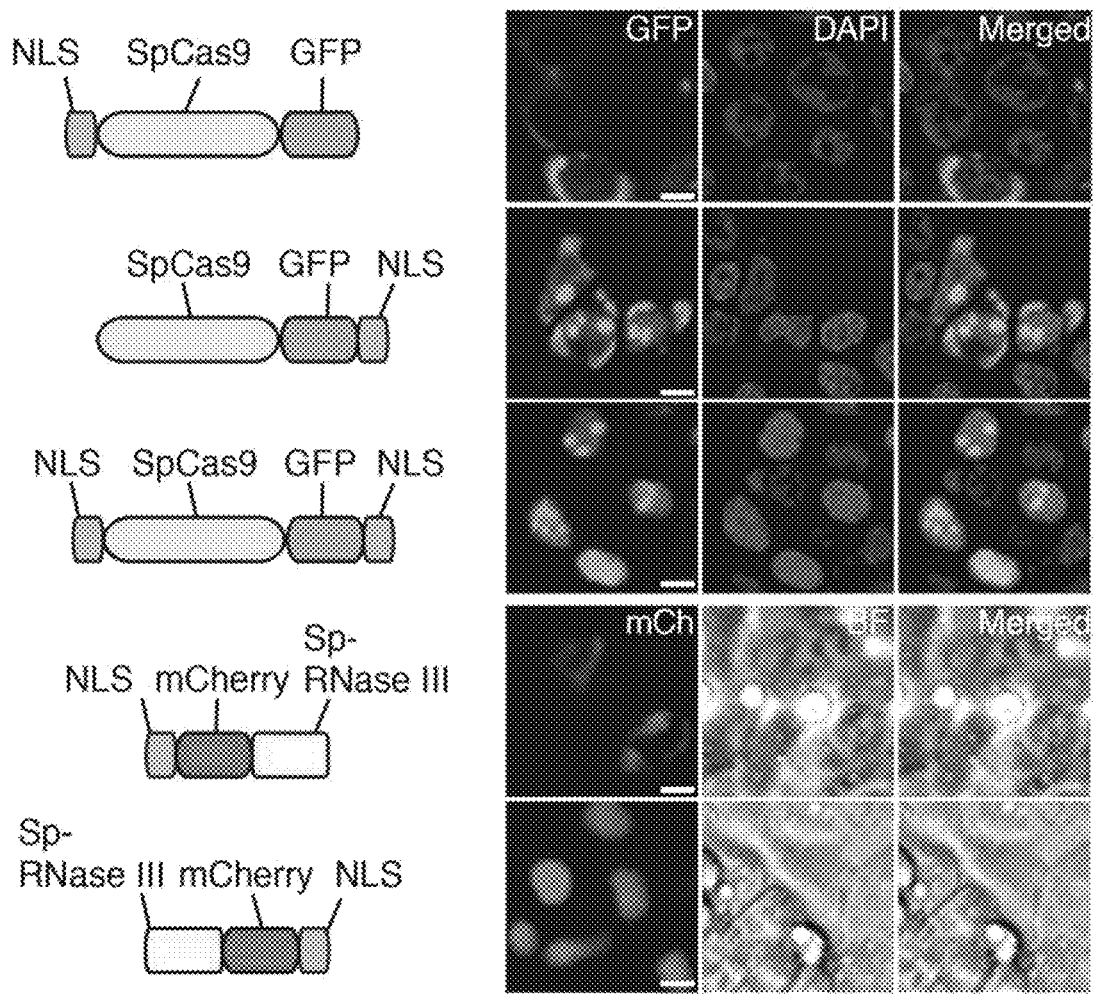
Figure 2C:
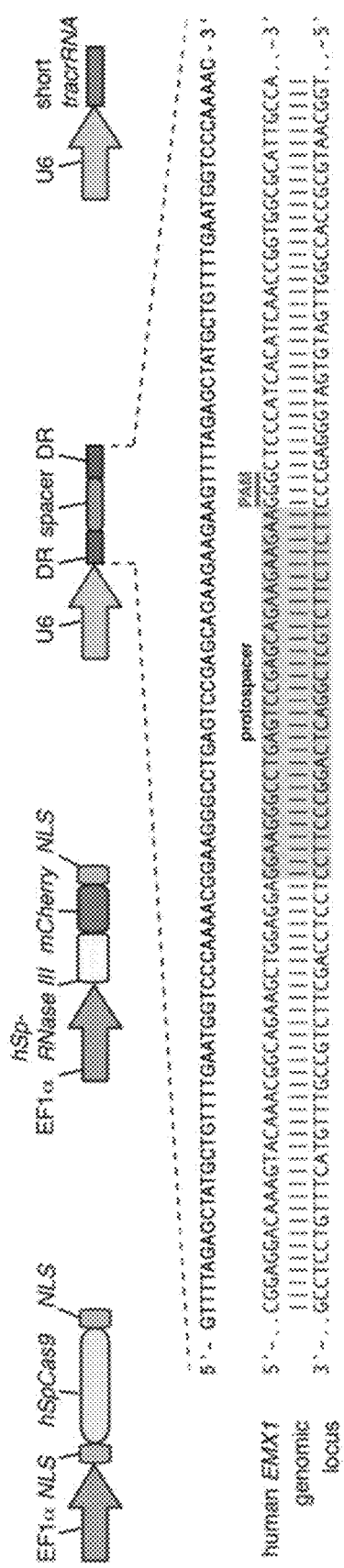
Figure 2D:
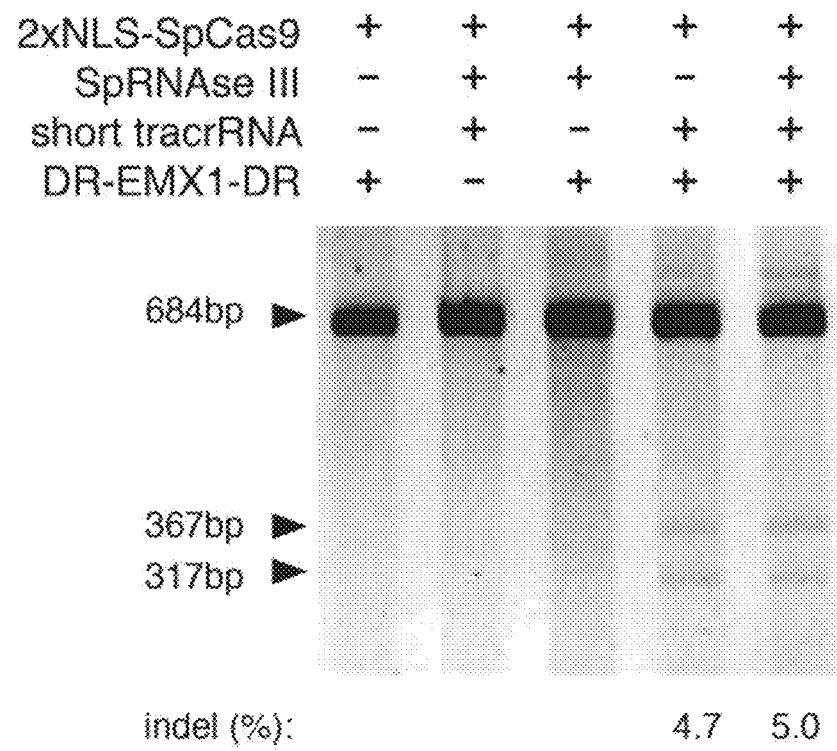
Figures 2E, 2F:
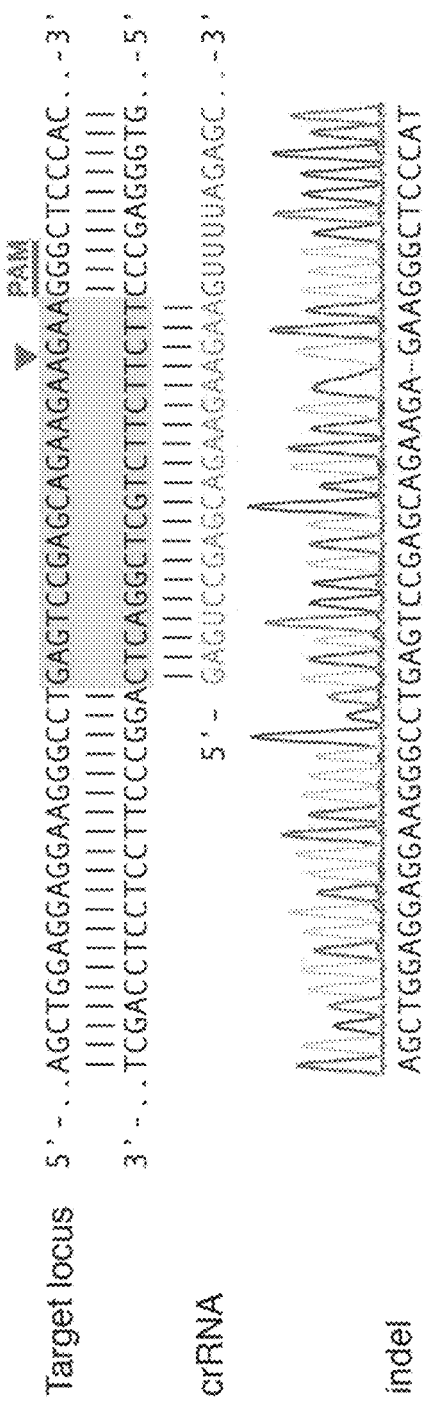
Figure 3A:
FIG. 3A-D is a circular phylogenetic tree of Cas genes
Figure 3B:
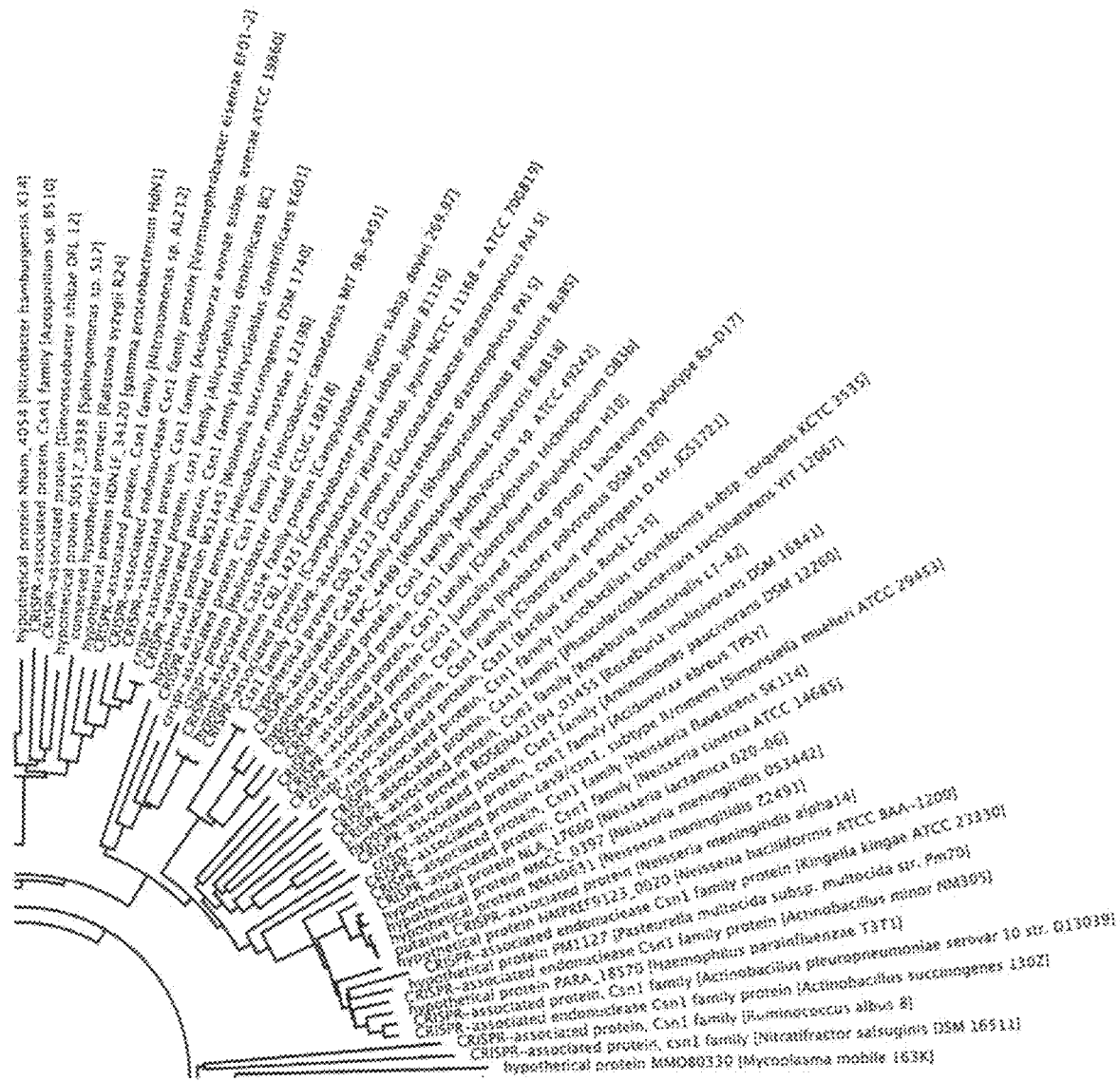
Figure 3C:
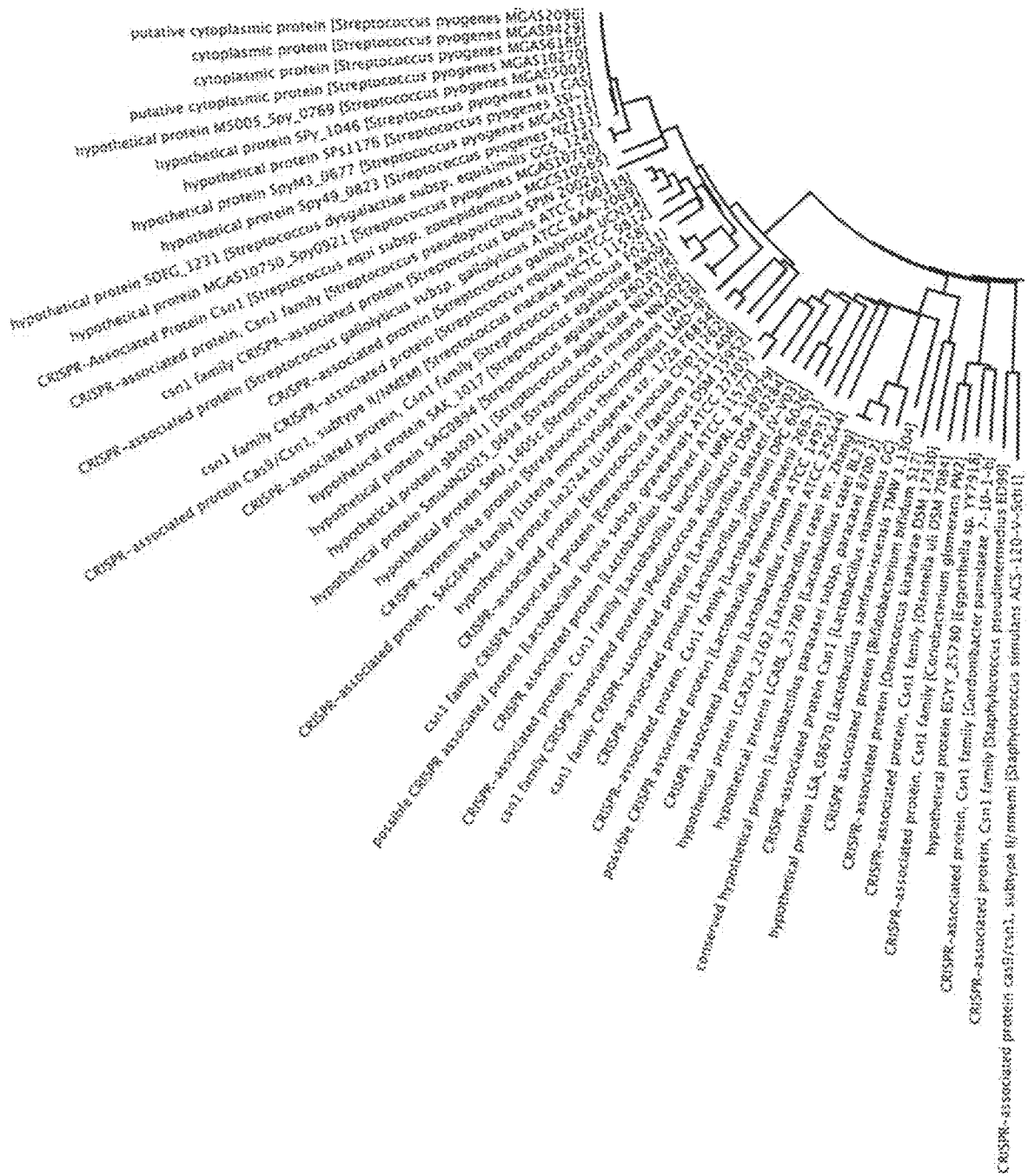
Figure 3D:
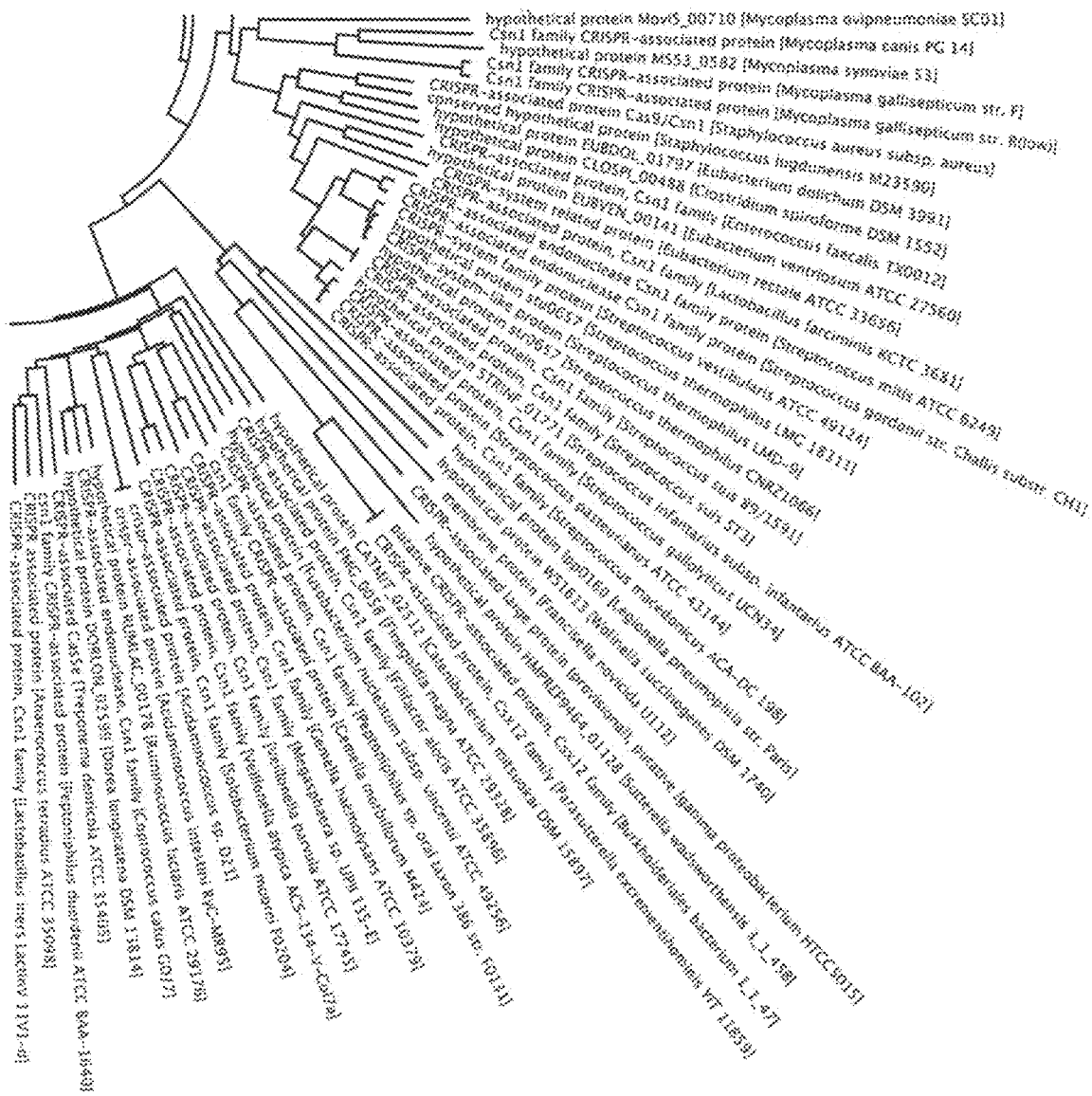
Figure 4B:
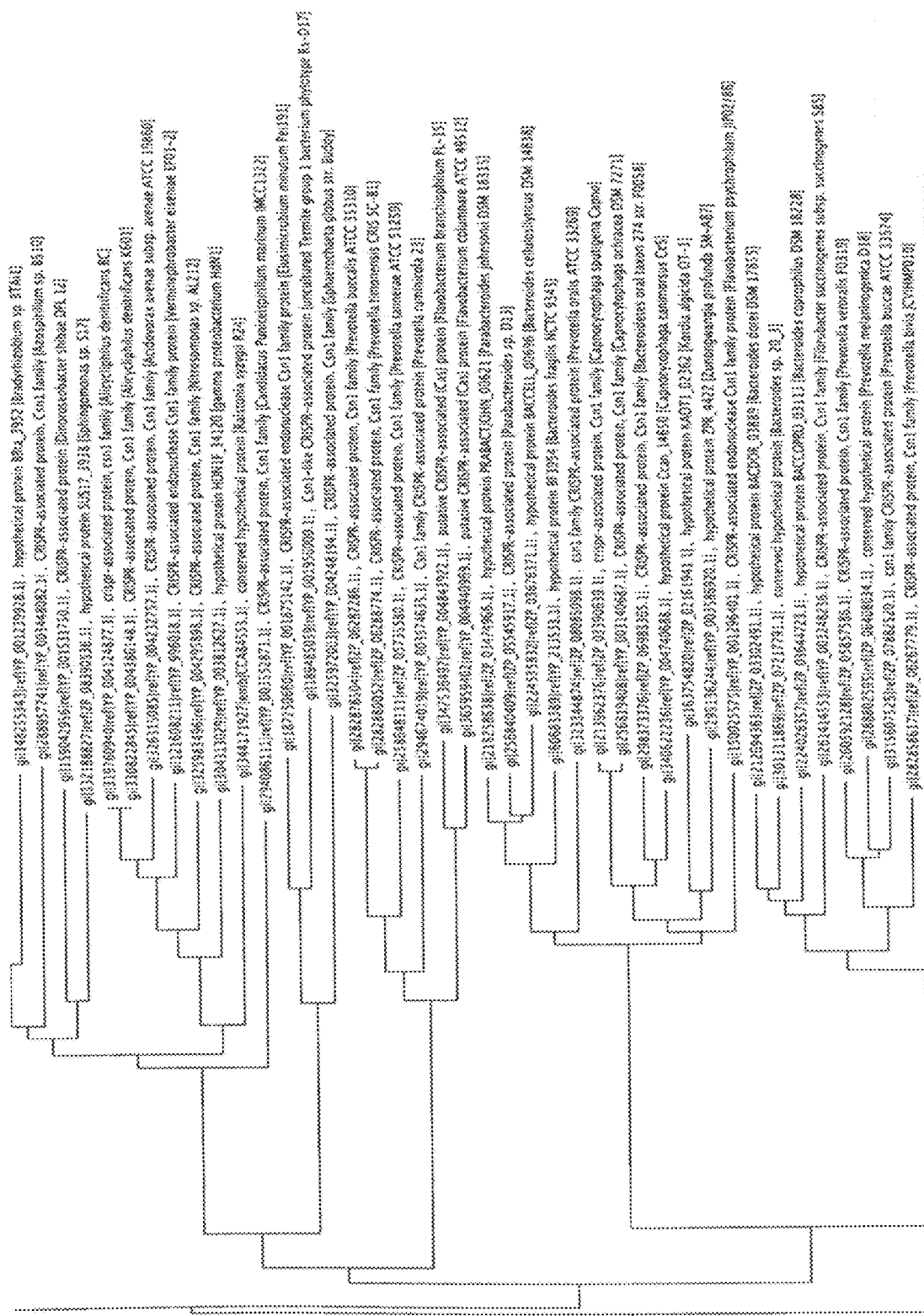
Figure 4C:
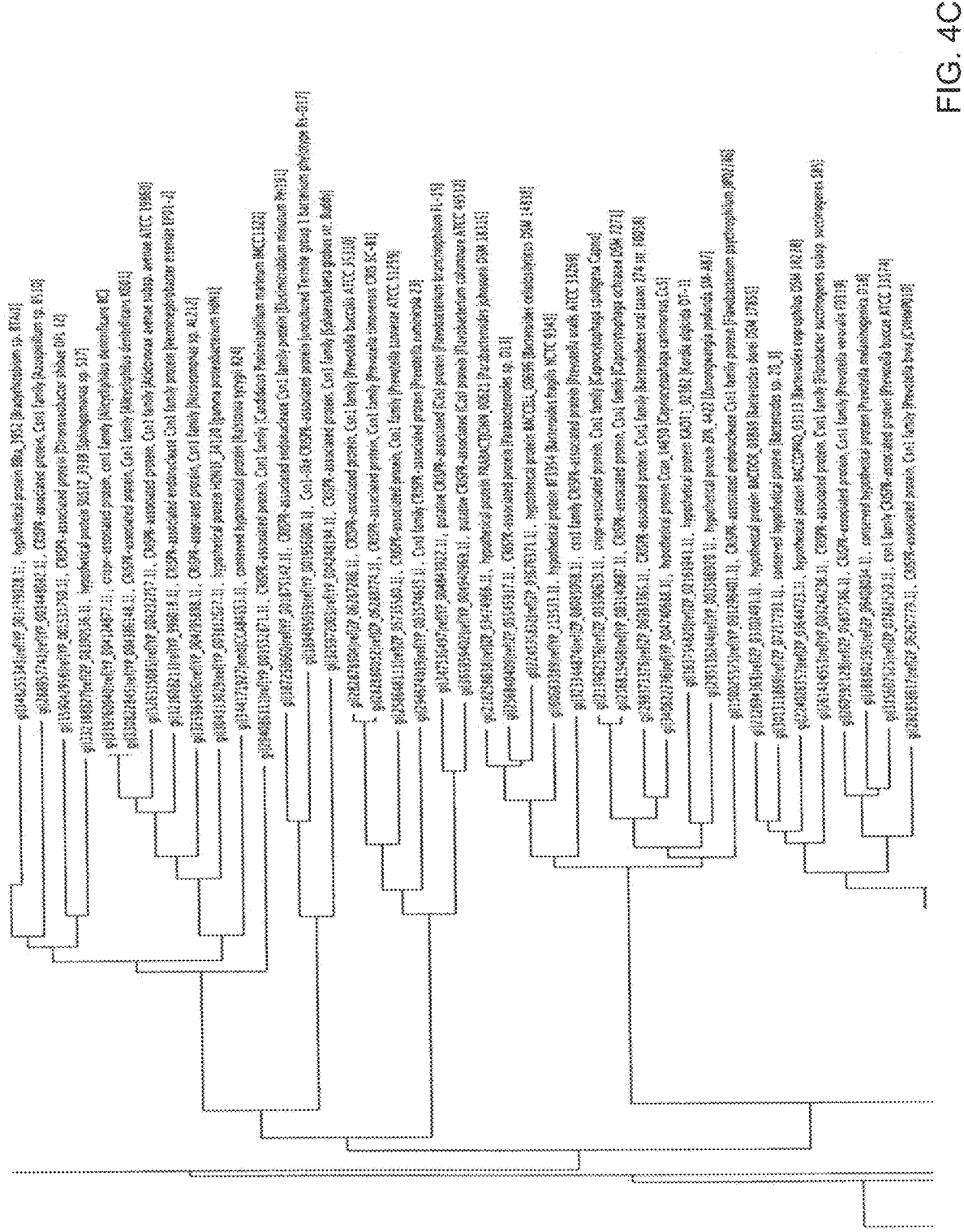
Figure 4E:
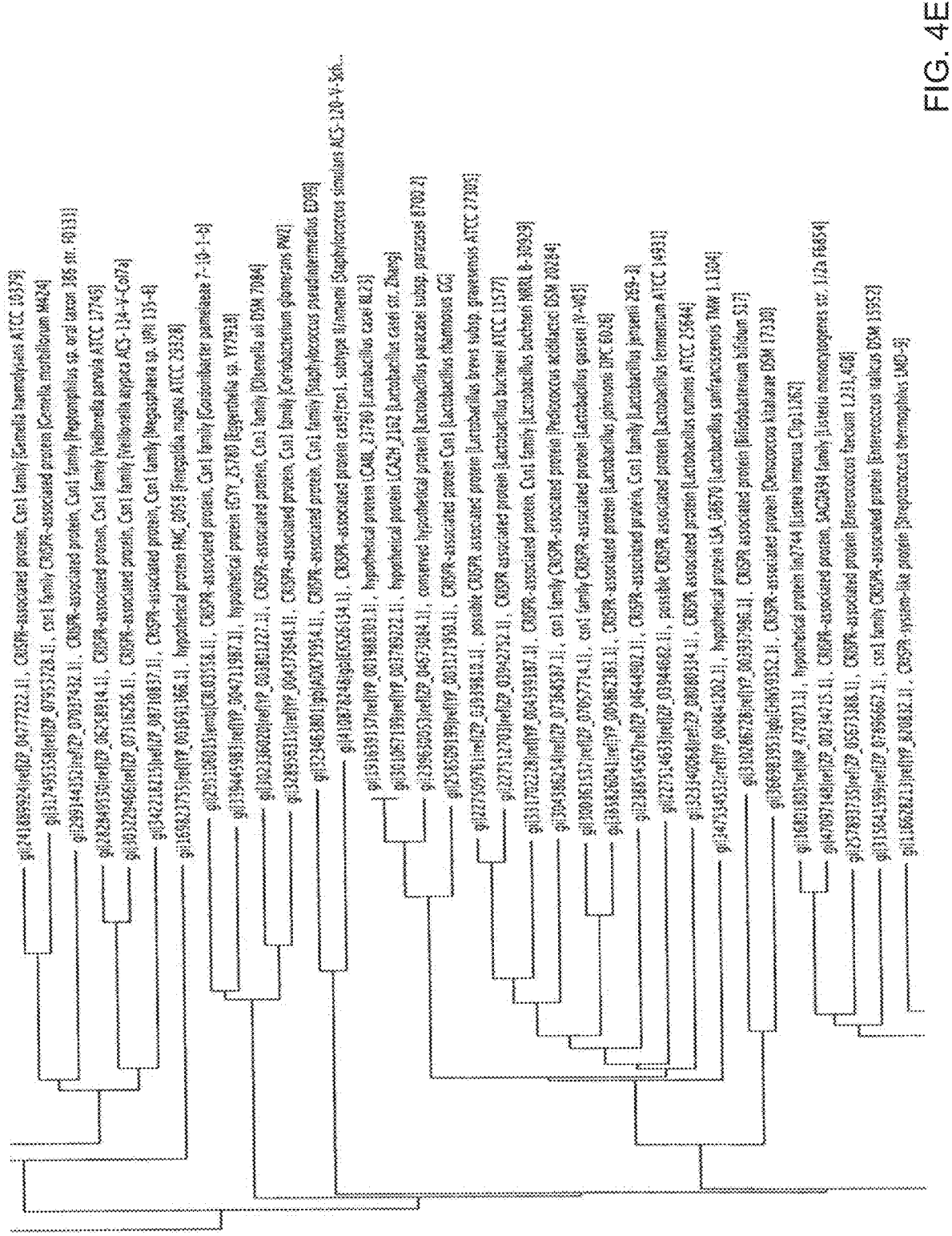
Figure 4F:
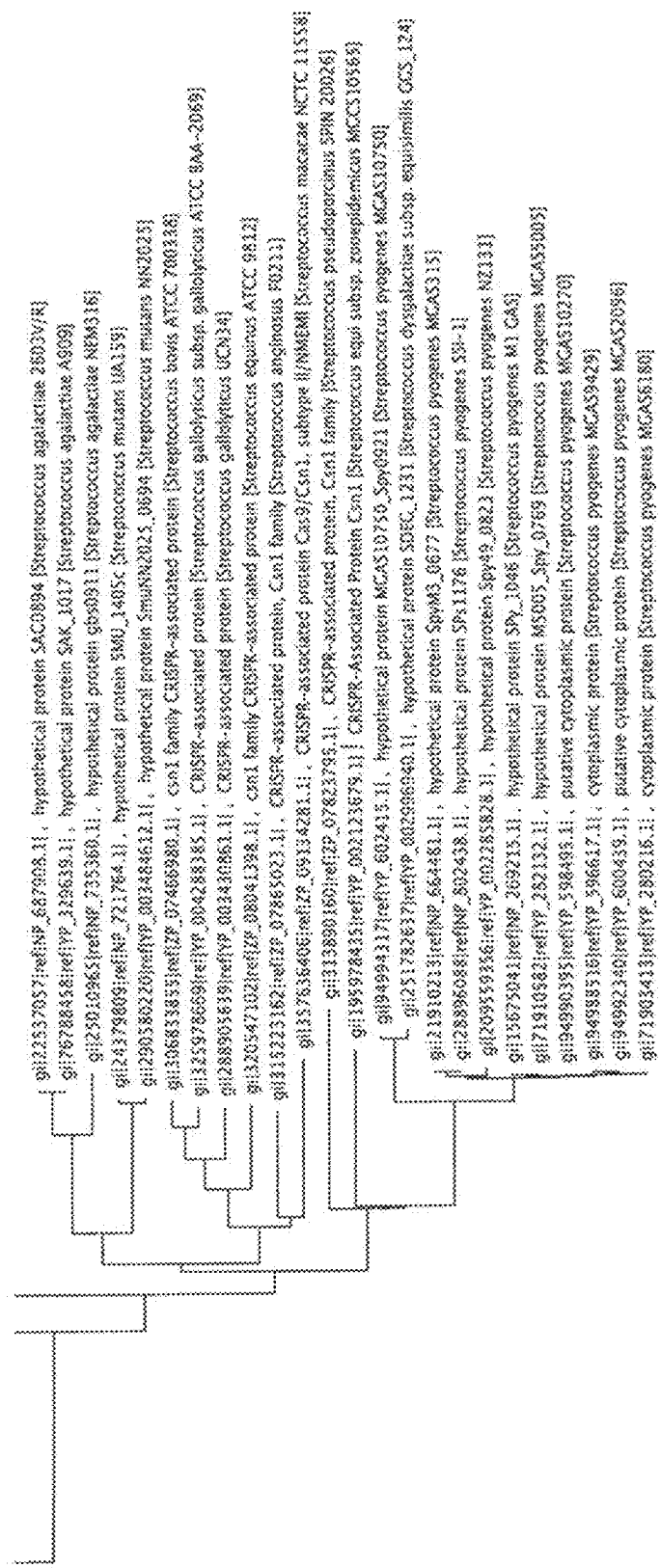

The type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) is generated in four sequential steps (FIG. 2A). First, two non-coding RNAs, the pre-crRNA array and tracrRNA, are transcribed from the CRISPR locus. Second, tracrRNA hybridizes to the direct repeats of pre-crRNA, which is then processed into mature crRNAs containing individual spacer sequences. Third, the mature crRNA:tracrRNA complex directs Cas9 to the DNA target consisting of the protospacer and the corresponding PAM via heteroduplex formation between the spacer region of the crRNA and the protospacer DNA. Finally, Cas9 mediates cleavage of target DNA upstream of PAM to create a DSB within the protospacer (FIG. 2A). FIG. 2B demonstrates the nuclear localization of the codon optimized Cas9. To promote precise transcriptional initiation, the RNA polymerase III-based U6 promoter was selected to drive the expression of tracrRNA (FIG. 2C). Similarly, a U6 promoter-based construct was developed to express a pre-crRNA array consisting of a single spacer flanked by two direct repeats (DRs, also encompassed by the term "tracr-mate sequences"; FIG. 2C). The initial spacer was designed to target a 33-base-pair (bp) target site (30-bp protospacer plus a 3-bp CRISPR motif (PAM) sequence satisfying the NGG recognition motif of Cas9) in the human EMX1 locus (FIG. 2C), a key gene in the development of the cerebral cortex.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence. In some embodiments, one or more vectors driving expression of one or more elements of a CRISPR system are introduced into a host cell such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g. each in a different intron, two or more in at least one intron, or all in a single intron). In some embodiments, the CRISPR enzyme, guide sequence, tracr mate sequence, and tracr sequence are operably linked to and expressed from the same promoter.

In some embodiments, a vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell.

In some embodiments, a vector comprises a regulatory element operably linked to an enzyme-coding sequence encoding a CRISPR enzyme, such as a Cas protein. Non-limiting examples of Cas proteins include Cas1, Cas1B, Cas2, Cas3, Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In some embodiments, the unmodified CRISPR enzyme has DNA cleavage activity, such as Cas9. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. As a further example, two or more catalytic domains of Cas9 (RuvC I, RuvC II, and RuvC III or the HNH domain) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is less than about 25%, 10%, 5%, 1%, 0.1%, 0.01%, or lower with respect to its non-mutated form.

An aspartate-to-alanine substitution (D10A) in the RuvC I catalytic domain of SpCas9 was engineered to convert the nuclease into a nickase (SpCas9n) (see e.g. Sapranauskas et al., 2011, Nucleic Acis Research, 39: 9275; Gasiunas et al., 2012, Proc. Natl. Acad. Sci. USA, 109:E2579), such that nicked genomic DNA undergoes the high-fidelity homology-directed repair (HDR). Surveyor assay confirmed that SpCas9n does not generate indels at the EMX1 protospacer target. Co-expression of EMX1-targeting chimeric crRNA (having the tracrRNA component as well) with SpCas9 produced indels in the target site, whereas co-expression with SpCas9n did not (n=3). Moreover, sequencing of 327 amplicons did not detect any indels induced by SpCas9n. The same locus was selected to test CRISPR-mediated HR by co-transfecting HEK 293FT cells with the chimeric RNA targeting EMX1, hSpCas9 or hSpCas9n, as well as a HR template to introduce a pair of restriction sites (HindIII and NheI) near the protospacer.

Preferred orthologs are described herein. A Cas enzyme may be identified Cas9 as this can refer to the general class of enzymes that share homology to the biggest nuclease with multiple nuclease domains from the type II CRISPR system. Most preferably, the Cas9 enzyme is from, or is derived from, spCas9 or saCas9. By derived, Applicants mean that the derived enzyme is largely based, in the sense of having a high degree of sequence homology with, a wildtype enzyme, but that it has been mutated (modified) in some way as described herein.

It will be appreciated that the terms Cas and CRISPR enzyme are generally used herein interchangeably, unless otherwise apparent. As mentioned above, many of the residue numberings used herein refer to the Cas9 enzyme from the type II CRISPR locus in *Streptococcus pyogenes*. However, it will be appreciated that this invention includes many more Cas9s from other species of microbes, such as SpCas9, SaCa9, St1Cas9 and so forth.

An example of a codon optimized sequence, in this instance optimized for humans (i.e. being optimized for expression in humans) is provided herein, see the SaCas9 human codon optimized sequence. Whilst this is preferred, it will be appreciated that other examples are possible and codon optimization for a host species other than human, or for codon optimization for specific organs such as the brain, is known.

In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded.

In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/ (visited Jul. 9, 2002), and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a CRISPR enzyme correspond to the most frequently used codon for a particular amino acid.

In some embodiments, a vector encodes a CRISPR enzyme comprising one or more nuclear localization sequences (NLSs), such as about or more than about 1, 2, 3, 4, 5, 6, 7, 8, 9, 10, or more NLSs. In some embodiments, the CRISPR enzyme comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. one or more NLS at the amino-terminus and one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the CRISPR enzyme comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 60); the NLS from nucleoplasmin (e.g. the nucleoplasmin bipartite NLS with the sequence KRPAATKKAGQAKKKK (SEQ ID NO: 61)); the c-myc NLS having the amino acid sequence PAAKRVKLD (SEQ ID NO: 62) or RQRRNELKRSP (SEQ ID NO: 63); the hRNPA1 M9 NLS having the sequence NQSSNFGPMKGGNFGGRSSGPYGGGGQYFAK-PRNQGGY (SEQ ID NO: 64); the sequence RMRIZFKNKGKDTAELRRRRVEVSVELRKAKKD-EQILKRRNV (SEQ ID NO: 65) of the IBB domain from importin-alpha; the sequences VSRKRPRP (SEQ ID NO: 66) and PPKKARED (SEQ ID NO: 67) of the myoma T protein; the sequence PQPKKKPL (SEQ ID NO: 68) of human p53; the sequence SALIKKKKKMAP (SEQ ID NO: 69) of mouse c-abl IV; the sequences DRLRR (SEQ ID NO: 70) and PKQKKRK (SEQ ID NO: 71) of the influenza virus NS1; the sequence RKLKKKIKKL (SEQ ID NO: 72) of the Hepatitis virus delta antigen; the sequence REKKKFLKRR (SEQ ID NO: 73) of the mouse Mx1 protein; the sequence KRKGDEVDGVDEVAKKKSKK (SEQ ID NO: 74) of the human poly(ADP-ribose) polymerase; and the sequence RKCLQAGMNLEARKTKK (SEQ ID NO: 75) of the steroid hormone receptors (human) glucocorticoid.

In general, the one or more NLSs are of sufficient strength to drive accumulation of the CRISPR enzyme in a detectable amount in the nucleus of a eukaryotic cell. In general, strength of nuclear localization activity may derive from the number of NLSs in the CRISPR enzyme, the particular NLS(s) used, or a combination of these factors. Detection of accumulation in the nucleus may be performed by any suitable technique. For example, a detectable marker may be fused to the CRISPR enzyme, such that location within a cell may be visualized, such as in combination with a means for detecting the location of the nucleus (e.g. a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or CRISPR enzyme activity), as compared to a control no exposed to the CRISPR enzyme or complex, or exposed to a CRISPR enzyme lacking the one or more NLSs.

In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies; available at www.novocraft.com), ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

A guide sequence may be selected to target any target sequence. In some embodiments, the target sequence is a sequence within a genome of a cell. Exemplary target sequences include those that are unique in the target genome. For example, for the *S. pyogenes* Cas9, a unique target sequence in a genome may include a Cas9 target site of the form MMMMMMMMNNNNNNNNNNNNXGG where NNNNNNNNNNNNXGG (N is A, G, T, or C; and X can be anything) has a single occurrence in the genome. A unique target sequence in a genome may include an *S. pyogenes* Cas9 target site of the form MMMMMMMMNNNNNNNNNNNNXGG where NNNNNNNNNNNNXGG (N is A, G, T, or C; and X can be anything) has a single occurrence in the genome. For the *S. thermophilus* CRISPR1 Cas9, a unique target sequence in a genome may include a Cas9 target site of the form MMMMMMMMNNNNNNNNNNNNXXAGAAW (SEQ ID NO: 76) where NNNNNNNNNNNNXXAGAAW (SEQ ID NO: 77) (N is A, G, T, or C; X can be anything; and W is A or T) has a single occurrence in the genome. A unique target sequence in a genome may include an *S. thermophilus* CRISPR1 Cas9 target site of the form MMMMMMMMNNNNNNNNNNNNXXAGAAW (SEQ ID NO: 78) where NNNNNNNNNNNNXXAGAAW (SEQ ID NO: 79) (N is A, G, T, or C; X can be anything; and W is A or T) has a single occurrence in the genome. For the *S. pyogenes* Cas9, a unique target sequence in a genome may include a Cas9 target site of the form MMMMMMMMNNNNNNNNNNNNXGGXG where NNNNNNNNNNNNXGGXG (N is A, G, T, or C; and X can be anything) has a single occurrence in the genome. A unique target sequence in a genome may include an *S. pyogenes* Cas9 target site of the form MMMMMMMMNNNNNNNNNNNNXGGXG where NNNNNNNNNNNNXGGXG (N is A, G, T, or C; and X can be anything) has a single occurrence in the genome. In each of these sequences "M" may be A, G, T, or C, and need not be considered in identifying a sequence as unique.

In some embodiments, a guide sequence is selected to reduce the degree secondary structure within the guide sequence. In some embodiments, about or less than about 75%, 50%, 40%, 30%, 25%, 20%, 15%, 10%, 5%, 1%, or fewer of the nucleotides of the guide sequence participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, *Cell* 106(1): 23-24; and PA Carr and GM Church, 2009, *Nature Biotechnology* 27(12): 1151-62).

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop corresponds to the tracr mate sequence, and the portion of the sequence 3' of the loop corresponds to the tracr sequence Further non-limiting examples of single polynucleotides comprising a guide sequence, a tracr mate sequence, and a tracr sequence are as follows (listed 5' to 3'), where "N" represents a base of a guide sequence, the first block of lower case letters represent the tracr mate sequence, and the second block of lower case letters represent the tracr sequence, and the final poly-T sequence represents the transcription terminator:

(1)
(SEQ ID NO: 80)
NNNNNNNNNNNNNNNNNNNNgttttt gtactctcaagatttaGAAAtaaa
tcttgcagaagctacaaagataaggcttcatgccgaaatcaacaccctgt
cattttatggcagggtgttttcgttatttaaTTTTTT;

(2)
(SEQ ID NO: 81)
NNNNNNNNNNNNNNNNNNNNgttttt gtactctcaGAAAtgcagaagcta
caaagataaggcttcatgccgaaatcaacaccctgtcattttatggcagg
gtgttttcgttatttaaTTTTTT;

(3)
(SEQ ID NO: 82)
NNNNNNNNNNNNNNNNNNNNgttttt gtactctcaGAAAtgcagaagcta
caaagataaggcttcatgccgaaatcaacaccctgtcattttatggcagg
gtgtTTTTTT;

(4)
(SEQ ID NO: 83)
NNNNNNNNNNNNNNNNNNNNgttttagagctaGAAAtagcaagttaaaat
aaggctagtccgttatcaacttgaaaaagtggcaccgagtcggtgcTTTT
TT;

(5)
(SEQ ID NO: 84)
NNNNNNNNNNNNNNNNNNNNgttttagagctaGAAATAGcaagttaaaat
aaggctagtccgttatcaacttgaaaaagtGTTTTTTT;
and (6)
(SEQ ID NO: 85)
NNNNNNNNNNNNNNNNNNNNgttttagagctagAAATAGcaagttaaaat
aaggctagtccgttatcaTTTTTTTT.

In some embodiments, sequences (1) to (3) are used in combination with Cas9 from *S. thermophilus* CRISPR1. In some embodiments, sequences (4) to (6) are used in combination with Cas9 from *S. pyogenes*. In some embodiments, the tracr sequence is a separate transcript from a transcript comprising the tracr mate sequence.

In some embodiments, a recombination template is also provided. A recombination template may be a component of another vector as described herein, contained in a separate vector, or provided as a separate polynucleotide. In some embodiments, a recombination template is designed to serve as a template in homologous recombination, such as within or near a target sequence nicked or cleaved by a CRISPR enzyme as a part of a CRISPR complex. A template polynucleotide may be of any suitable length, such as about or more than about 10, 15, 20, 25, 50, 75, 100, 150, 200, 500, 1000, or more nucleotides in length. In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

In some embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions. Additional domains that may form part of a fusion protein comprising a CRISPR enzyme are described in US20110059502, incorporated herein by reference. In some embodiments, a tagged CRISPR enzyme is used to identify the location of a target sequence.

In some embodiments, a CRISPR enzyme may form a component of an inducible system. The inducible nature of the system would allow for spatiotemporal control of gene editing or gene expression using a form of energy. The form of energy may include but is not limited to electromagnetic radiation, sound energy, chemical energy and thermal energy. Examples of inducible system include tetracycline inducible promoters (Tet-On or Tet-Off), small molecule two-hybrid transcription activations systems (FKBP, ABA, etc), or light inducible systems (Phytochrome, LOV domains, or cryptochrome). In one embodiment, the CRISPR enzyme may be a part of a Light Inducible Transcriptional Effector (LITE) to direct changes in transcriptional activity in a sequence-specific manner. The components of a light may include a CRISPR enzyme, a light-responsive cytochrome heterodimer (e.g. from *Arabidopsis thaliana*), and a transcriptional activation/repression domain. Further examples of inducible DNA binding proteins and methods for their use are provided in U.S. 61/736,465 and U.S. 61/721,283, which is hereby incorporated by reference in its entirety.

In some aspects, the invention provides methods comprising delivering one or more polynucleotides, such as or one or more vectors as described herein, one or more transcripts thereof, and/or one or proteins transcribed therefrom, to a host cell. In some aspects, the invention further provides cells produced by such methods, and animals comprising or produced from such cells. In some embodiments, a CRISPR enzyme in combination with (and optionally complexed with) a guide sequence is delivered to a cell. Conventional viral and non-viral based gene transfer methods can be used to introduce nucleic acids in mammalian cells or target tissues. Such methods can be used to administer nucleic acids encoding components of a CRISPR system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256:808-813 (1992); Nabel & Felgner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Bohm (eds) (1995); and Yu et al., Gene Therapy 1:13-26 (1994).

Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Virol. 66:2731-2739 (1992); Johann et al., J. Virol. 66:1635-1640 (1992); Sommnerfelt et al., Virol. 176:58-59 (1990); Wilson et al., J. Virol. 63:2374-2378 (1989); Miller et al., J. Virol. 65:2220-2224 (1991); PCT/US94/05700).

In applications where transient expression is preferred, adenoviral based systems may be used. Adenoviral based vectors are capable of very high transduction efficiency in many cell types and do not require cell division. With such vectors, high titer and levels of expression have been obtained. This vector can be produced in large quantities in a relatively simple system.

Adeno-associated virus ("AAV") vectors may also be used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989).

Packaging cells are typically used to form virus particles that are capable of infecting a host cell. Such cells include 293 cells, which package adenovirus, and w2 cells or PA317 cells, which package retrovirus. Viral vectors used in gene therapy are usually generated by producer a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line may also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

Accordingly, AAV is considered an ideal candidate for use as a transducing vector. Such AAV transducing vectors can comprise sufficient cis-acting functions to replicate in the presence of adenovirus or herpesvirus or poxvirus (e.g., vaccinia virus) helper functions provided in trans. Recombinant AAV (rAAV) can be used to carry exogenous genes into cells of a variety of lineages. In these vectors, the AAV cap and/or rep genes are deleted from the viral genome and replaced with a DNA segment of choice. Current AAV vectors may accommodate up to 4300 bases of inserted DNA.

There are a number of ways to produce rAAV, and the invention provides rAAV and methods for preparing rAAV. For example, plasmid(s) containing or consisting essentially of the desired viral construct are transfected into AAV-infected cells. In addition, a second or additional helper plasmid is cotransfected into these cells to provide the AAV rep and/or cap genes which are obligatory for replication and packaging of the recombinant viral construct. Under these conditions, the rep and/or cap proteins of AAV act in trans to stimulate replication and packaging of the rAAV construct. Two to Three days after transfection, rAAV is harvested. Traditionally rAAV is harvested from the cells along with adenovirus. The contaminating adenovirus is then inactivated by heat treatment. In the instant invention, rAAV is advantageously harvested not from the cells themselves, but from cell supernatant. Accordingly, in an initial aspect the invention provides for preparing rAAV, and in addition to the foregoing, rAAV can be prepared by a method that comprises or consists essentially of: infecting susceptible cells with a rAAV containing exogenous DNA including DNA for expression, and helper virus (e.g., adenovirus, herpesvirus, poxvirus such as vaccinia virus) wherein the rAAV lacks functioning cap and/or rep (and the helper virus (e.g., adenovirus, herpesvirus, poxvirus such as vaccinia virus) provides the cap and/or rev function that the rAAV lacks); or infecting susceptible cells with a rAAV containing exogenous DNA including DNA for expression, wherein the recombinant lacks functioning cap and/or rep, and transfecting said cells with a plasmid supplying cap and/or rep function that the rAAV lacks; or infecting susceptible cells with a rAAV containing exogenous DNA including DNA for expression, wherein the recombinant lacks functioning cap and/or rep, wherein said cells supply cap and/or rep function that the recombinant lacks; or transfecting the susceptible cells with an AAV lacking functioning cap and/or rep and plasmids for inserting exogenous DNA into the recombinant so that the exogenous DNA is expressed by the recombinant and for supplying rep and/or cap functions whereby transfection results in an rAAV containing the exogenous DNA including DNA for expression that lacks functioning cap and/or rep.

The rAAV can be from an AAV as herein described, and advantageously can be an rAAV1, rAAV2, AAV5 or rAAV having hybrid or capsid which may comprise AAV1, AAV2, AAV5 or any combination thereof. One can select the AAV of the rAAV with regard to the cells to be targeted by the rAAV; e.g., one can select AAV serotypes 1, 2, 5 or a hybrid or capsid AAV1, AAV2, AAV5 or any combination thereof for targeting brain or neuronal cells; and one can select AAV4 for targeting cardiac tissue.

In addition to 293 cells, other cells that can be used in the practice of the invention and the relative infectivity of certain AAV serotypes in vitro as to these cells (see Grimm, D. et al, J. Virol. 82: 5887-5911 (2008)) are as follows:

| Cell Line | AAV-1 | AAV-2 | AAV-3 | AAV-4 | AAV-5 | AAV-6 | AAV-8 | AAV-9 |
|---|---|---|---|---|---|---|---|---|
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |
| HeLa | 3 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND |

The invention provides rAAV that contains or consists essentially of an exogenous nucleic acid molecule encoding a CRISPR (Clustered Regularly Interspaced Short Palindromic Repeats) system, e.g., a plurality of cassettes comprising or consisting a first cassette comprising or consisting essentially of a promoter, a nucleic acid molecule encoding a CRISPR-associated (Cas) protein (putative nuclease or helicase proteins), e.g., Cas9 and a terminator, and a two, or more, advantageously up to the packaging size limit of the vector, e.g., in total (including the first cassette) five, cassettes comprising or consisting essentially of a promoter, nucleic acid molecule encoding guide RNA (gRNA) and a terminator (e.g., each cassette schematically represented as Promoter-gRNA1-terminator, Promoter-gRNA2-terminator Promoter-gRNA(N)-terminator (where N is a number that can be inserted that is at an upper limit of the packaging size limit of the vector), or two or more individual rAAVs, each containing one or more than one cassette of a CRISPR system, e.g., a first rAAV containing the first cassette comprising or consisting essentially of a promoter, a nucleic acid molecule encoding Cas, e.g., Cas9 and a terminator, and a second rAAV containing a plurality, four, cassettes comprising or consisting essentially of a promoter, nucleic acid molecule encoding guide RNA (gRNA) and a terminator (e.g., each cassette schematically represented as Promoter-gRNA1-terminator, Promoter-gRNA2-terminator . . . Promoter-gRNA(N)-terminator (where N is a number that can be inserted that is at an upper limit of the packaging size limit of the vector). As rAAV is a DNA virus, the nucleic acid molecules in the herein discussion concerning AAV or rAAV are advantageously DNA. The promoter is in some embodiments advantageously human Synapsin I promoter (hSyn).

Additional methods for the delivery of nucleic acids to cells are known to those skilled in the art. See, for example, US20030087817, incorporated herein by reference.

In some embodiments, a host cell is transiently or non-transiently transfected with one or more vectors described herein. In some embodiments, a cell is transfected as it naturally occurs in a subject. In some embodiments, a cell that is transfected is taken from a subject. In some embodiments, the cell is derived from cells taken from a subject, such as a cell line. A wide variety of cell lines for tissue culture are known in the art. Examples of cell lines include, but are not limited to, C8161, CCRF-CEM, MOLT, mIMCD-3, NHDF, HeLa-S3, Huh1, Huh4, Huh7, HUVEC, HASMC, HEKn, HEKa, MiaPaCell, Panc1, PC-3, TF1, CTLL-2, C1R, Rat6, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRCS, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr−/−, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepa1c1c7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)). In some embodiments, a cell transfected with one or more vectors described herein is used to establish a new cell line comprising one or more vector-derived sequences. In some embodiments, a cell transiently transfected with the components of a CRISPR system as described herein (such as by transient transfection of one or more vectors, or transfection with RNA), and modified through the activity of a CRISPR complex, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

In some embodiments, one or more vectors described herein are used to produce a non-human transgenic animal or transgenic plant. In some embodiments, the transgenic animal is a mammal, such as a mouse, rat, or rabbit. Methods for producing transgenic plants and animals are known in the art, and generally begin with a method of cell transfection, such as described herein.

With recent advances in crop genomics, the ability to use CRISPR-Cas systems to perform efficient and cost effective gene editing and manipulation will allow the rapid selection and comparison of single and and multiplexed genetic manipulations to transform such genomes for improved production and enhanced traits. In this regard reference is made to US patents and publications: U.S. Pat. No. 6,603,061—*Agrobacterium*-Mediated Plant Transformation Method; U.S. Pat. No. 7,868,149—Plant Genome Sequences and Uses Thereof and US 2009/0100536—Transgenic Plants with Enhanced Agronomic Traits, all the contents and disclosure of each of which are herein incorporated by reference in their entirety. In the practice of the invention, the contents and disclosure of Morrell et al "Crop genomics: advances and applications" Nat Rev Genet. 2011 Dec. 29; 13(2):85-96 are also herein incorporated by reference in their entirety. In an advantageous embodiment of the invention, the CRISPR/Cas9 system is used to engineer microalgae. That the CRISPR-Cas system is able to be employed in plant systems is also provided in the manuscript "Efficient Genome Editing in Plants using a CRISPR/Cas System", by Feng et al. Cell Res. 2013 Aug. 20. doi: 10.1038/cr.2013.114. [Epub ahead of print], incorporated by reference in its entirety, wherein it is demonstrated that engineered CRISPR/Cas complexes may be used to create double strand breaks at specific sites of the plant genome to achieve targeted genome modifications in both dicot and monocot plants. Accordingly, reference herein to animal cells may also apply, mutatis mutandis, to plant cells unless otherwise apparent.

In one aspect, the invention provides for methods of modifying a target polynucleotide in a eukaryotic cell, which may be in vivo, ex vivo or in vitro. In some embodiments, the method comprises sampling a cell or population of cells from a human or non-human animal or plant (including micro-algae), and modifying the cell or cells. Culturing may occur at any stage ex vivo. The cell or cells may even be re-introduced into the non-human animal or plant (including micro-algae). For re-introduced cells it is particularly preferred that the cells are stem cells.

In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence.

In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized to a target sequence within said polynucleotide, wherein said guide sequence is linked to a tracr mate sequence which in turn hybridizes to a tracr sequence. Similar considerations and conditions apply as above for methods of modifying a target polynucleotide. In fact, these sampling, culturing and re-introduction options apply across the aspects of the present invention.

Indeed, in any aspect of the invention, the CRISPR complex may comprise a CRISPR enzyme complexed with a guide sequence hybridized to a target sequence, wherein said guide sequence may be linked to a tracr mate sequence which in turn may hybridize to a tracr sequence. Similar considerations and conditions apply as above for methods of modifying a target polynucleotide.

In one aspect, the invention provides kits containing any one or more of the elements disclosed in the above methods and compositions. Elements may be provided individually or in combinations, and may be provided in any suitable container, such as a vial, a bottle, or a tube. In some embodiments, the kit includes instructions in one or more languages, for example in more than one language.

In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more oligonucleotides corresponding to a guide sequence for insertion into a vector so as to operably link the guide sequence and a regulatory element. In some embodiments, the kit comprises a homologous recombination template polynucleotide.

In one aspect, the invention provides methods for using one or more elements of a CRISPR system. The CRISPR complex of the invention provides an effective means for modifying a target polynucleotide. The CRISPR complex of the invention has a wide variety of utility including modifying (e.g., deleting, inserting, translocating, inactivating, activating) a target polynucleotide in a multiplicity of cell types. As such the CRISPR complex of the invention has a broad spectrum of applications in, e.g., gene therapy, drug screening, disease diagnosis, and prognosis. An exemplary CRISPR complex comprises a CRISPR enzyme complexed with a guide sequence hybridized to a target sequence within the target polynucleotide. The guide sequence is linked to a tracr mate sequence, which in turn hybridizes to a tracr sequence.

In one embodiment, this invention provides a method of cleaving a target polynucleotide. The method comprises modifying a target polynucleotide using a CRISPR complex that binds to the target polynucleotide and effect cleavage of said target polynucleotide. Typically, the CRISPR complex of the invention, when introduced into a cell, creates a break (e.g., a single or a double strand break) in the genome sequence. For example, the method can be used to cleave a disease gene in a cell.

Figure 11:
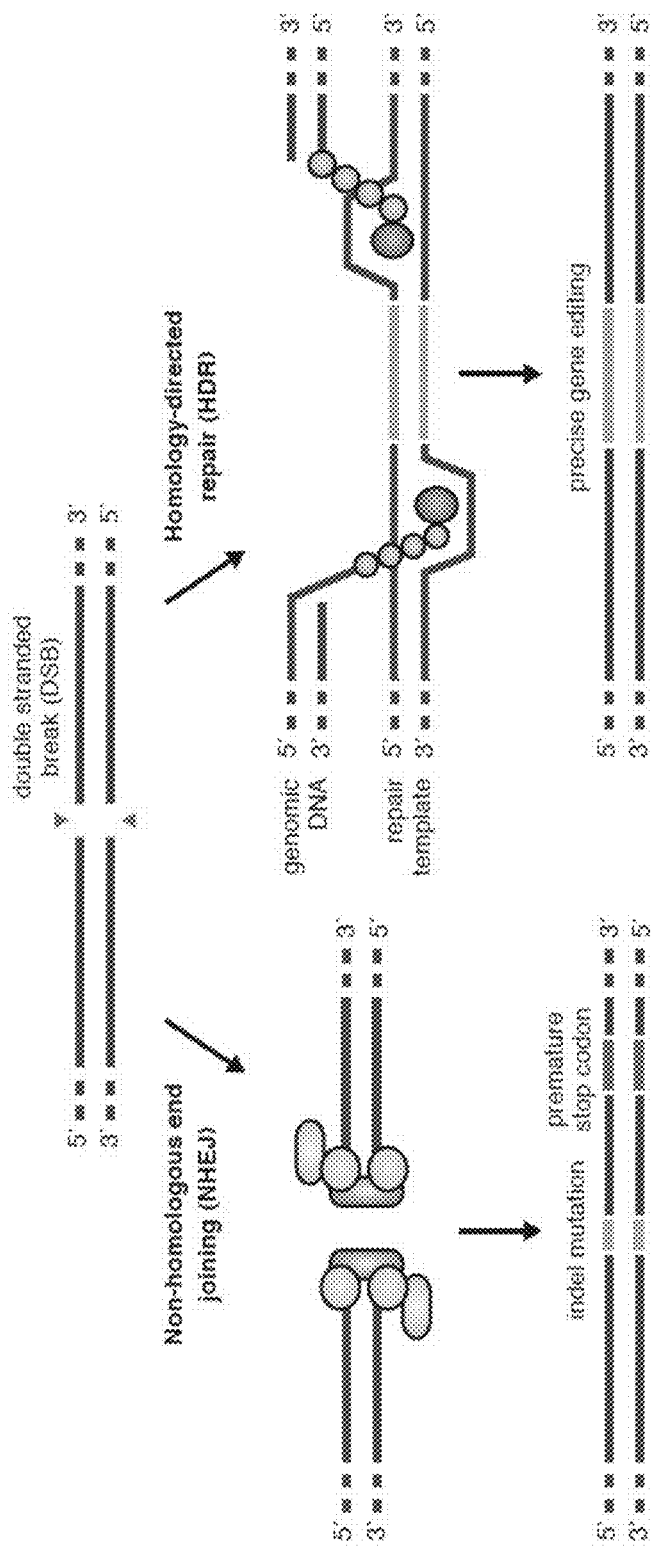
FIG. 11 shows how DNA double-strand break (DSB) repair promotes gene editing. In the error-prone non-homologous end joining (NHEJ) pathway, the ends of a DSB are processed by endogenous DNA repair machineries and rejoined together, which can result in random insertion/deletion (indel) mutations at the site of junction. Indel mutations occurring within the coding region of a gene can result in frame-shift and a premature stop codon, leading to gene knockout. Alternatively, a repair template in the form of a plasmid or single-stranded oligodeoxynucleotides (ssODN) can be supplied to leverage the homology-directed repair (HDR) pathway, which allows high fidelity and precise editing.

The break created by the CRISPR complex can be repaired by a repair processes such as the error prone non-homologous end joining (NHEJ) pathway or the high fidelity homology-directed repair (HDR) (FIG. 11). During these repair process, an exogenous polynucleotide template can be introduced into the genome sequence. In some methods, the HDR process is used modify genome sequence. For example, an exogenous polynucleotide template comprising a sequence to be integrated flanked by an upstream sequence and a downstream sequence is introduced into a cell. The upstream and downstream sequences share sequence similarity with either side of the site of integration in the chromosome.

Where desired, a donor polynucleotide can be DNA, e.g., a DNA plasmid, a bacterial artificial chromosome (BAC), a yeast artificial chromosome (YAC), a viral vector, a linear piece of DNA, a PCR fragment, a naked nucleic acid, or a nucleic acid complexed with a delivery vehicle such as a liposome or poloxamer.

The exogenous polynucleotide template comprises a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control sequence or sequences. Alternatively, the sequence to be integrated may provide a regulatory function.

The upstream and downstream sequences in the exogenous polynucleotide template are selected to promote recombination between the chromosomal sequence of interest and the donor polynucleotide. The upstream sequence is a nucleic acid sequence that shares sequence similarity with the genome sequence upstream of the targeted site for integration. Similarly, the downstream sequence is a nucleic acid sequence that shares sequence similarity with the chromosomal sequence downstream of the targeted site of integration. The upstream and downstream sequences in the exogenous polynucleotide template can have 75%, 80%, 85%, 90%, 95%, or 100% sequence identity with the targeted genome sequence. Preferably, the upstream and downstream sequences in the exogenous polynucleotide template have about 95%, 96%, 97%, 98%, 99%, or 100% sequence identity with the targeted genome sequence. In some methods, the upstream and downstream sequences in the exogenous polynucleotide template have about 99% or 100% sequence identity with the targeted genome sequence.

An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000 bp.

In some methods, the exogenous polynucleotide template may further comprise a marker. Such a marker may make it easy to screen for targeted integrations. Examples of suitable markers include restriction sites, fluorescent proteins, or selectable markers. The exogenous polynucleotide template of the invention can be constructed using recombinant techniques (see, for example, Sambrook et al., 2001 and Ausubel et al., 1996).

In an exemplary method for modifying a target polynucleotide by integrating an exogenous polynucleotide template, a double stranded break is introduced into the genome sequence by the CRISPR complex, the break is repaired via homologous recombination an exogenous polynucleotide template such that the template is integrated into the genome. The presence of a double-stranded break facilitates integration of the template.

In other embodiments, this invention provides a method of modifying expression of a polynucleotide in a eukaryotic cell. The method comprises increasing or decreasing expression of a target polynucleotide by using a CRISPR complex that binds to the polynucleotide.

In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein is not produced.

In some methods, a control sequence can be inactivated such that it no longer functions as a control sequence. As used herein, "control sequence" refers to any nucleic acid sequence that effects the transcription, translation, or accessibility of a nucleic acid sequence. Examples of a control sequence include, a promoter, a transcription terminator, and an enhancer are control sequences.

The inactivated target sequence may include a deletion mutation (i.e., deletion of one or more nucleotides), an insertion mutation (i.e., insertion of one or more nucleotides), or a nonsense mutation (i.e., substitution of a single nucleotide for another nucleotide such that a stop codon is introduced). In some methods, the inactivation of a target sequence results in "knock-out" of the target sequence.

A method of the invention may be used to create a plant, an animal or cell that may be used as a disease model. As used herein, "disease" refers to a disease, disorder, or indication in a subject. For example, a method of the invention may be used to create an animal or cell that comprises a modification in one or more nucleic acid sequences associated with a disease, or a plant, animal or cell in which the expression of one or more nucleic acid sequences associated with a disease are altered. Such a nucleic acid sequence may encode a disease associated protein sequence or may be a disease associated control sequence. Accordingly, it is understood that in embodiments of the invention, a plant, subject, patient, organism or cell can be a non-human subject, patient, organism or cell. Thus, the invention provides a plant, animal or cell, produced by the present methods, or a progeny thereof. The progeny may be a clone of the produced plant or animal, or may result from sexual reproduction by crossing with other individuals of the same species to introgress further desirable traits into their offspring. The cell may be in vivo or ex vivo in the cases of multicellular organisms, particularly animals or plants. In the instance where the cell is in cultured, a cell line may be established if appropriate culturing conditions are met and preferably if the cell is suitably adapted for this purpose (for instance a stem cell). Bacterial cell lines produced by the invention are also envisaged. Hence, cell lines are also envisaged.

In some methods, the disease model can be used to study the effects of mutations on the animal or cell and development and/or progression of the disease using measures commonly used in the study of the disease. Alternatively, such a disease model is useful for studying the effect of a pharmaceutically active compound on the disease.

In some methods, the disease model can be used to assess the efficacy of a potential gene therapy strategy. That is, a disease-associated gene or polynucleotide can be modified such that the disease development and/or progression is inhibited or reduced. In particular, the method comprises modifying a disease-associated gene or polynucleotide such that an altered protein is produced and, as a result, the animal or cell has an altered response. Accordingly, in some methods, a genetically modified animal may be compared with an animal predisposed to development of the disease such that the effect of the gene therapy event may be assessed.

In another embodiment, this invention provides a method of developing a biologically active agent that modulates a cell signaling event associated with a disease gene. The method comprises contacting a test compound with a cell comprising one or more vectors that drive expression of one or more of a CRISPR enzyme, a guide sequence linked to a tracr mate sequence, and a tracr sequence; and detecting a change in a readout that is indicative of a reduction or an augmentation of a cell signaling event associated with, e.g., a mutation in a disease gene contained in the cell.

A cell model or animal model can be constructed in combination with the method of the invention for screening a cellular function change. Such a model may be used to study the effects of a genome sequence modified by the CRISPR complex of the invention on a cellular function of interest. For example, a cellular function model may be used to study the effect of a modified genome sequence on intracellular signaling or extracellular signaling. Alternatively, a cellular function model may be used to study the effects of a modified genome sequence on sensory perception. In some such models, one or more genome sequences associated with a signaling biochemical pathway in the model are modified.

Several disease models have been specifically investigated. These include de novo autism risk genes CHD8, KATNAL2, and SCN2A; and the syndromic autism (Angelman Syndrome) gene UBE3A. These genes and resulting autism models are of course preferred, but serve to show the broad applicability of the invention across genes and corresponding models.

An altered expression of one or more genome sequences associated with a signaling biochemical pathway can be determined by assaying for a difference in the mRNA levels of the corresponding genes between the test model cell and a control cell, when they are contacted with a candidate agent. Alternatively, the differential expression of the sequences associated with a signaling biochemical pathway is determined by detecting a difference in the level of the encoded polypeptide or gene product.

To assay for an agent-induced alteration in the level of mRNA transcripts or corresponding polynucleotides, nucleic acid contained in a sample is first extracted according to standard methods in the art. For instance, mRNA can be isolated using various lytic enzymes or chemical solutions according to the procedures set forth in Sambrook et al. (1989), or extracted by nucleic-acid-binding resins following the accompanying instructions provided by the manufacturers. The mRNA contained in the extracted nucleic acid sample is then detected by amplification procedures or conventional hybridization assays (e.g. Northern blot analysis) according to methods widely known in the art or based on the methods exemplified herein.

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of E. coli DNA polymerase, and reverse transcriptase. A preferred amplification method is PCR. In particular, the isolated RNA can be subjected to a reverse transcription assay that is coupled with a quantitative polymerase chain reaction (RT-PCR) in order to quantify the expression level of a sequence associated with a signaling biochemical pathway.

Detection of the gene expression level can be conducted in real time in an amplification assay. In one aspect, the amplified products can be directly visualized with fluorescent DNA-binding agents including but not limited to DNA intercalators and DNA groove binders. Because the amount of the intercalators incorporated into the double-stranded DNA molecules is typically proportional to the amount of the amplified DNA products, one can conveniently determine the amount of the amplified products by quantifying the fluorescence of the intercalated dye using conventional optical systems in the art. DNA-binding dye suitable for this application include SYBR green, SYBR blue, DAPI, propidium iodine, Hoeste, SYBR gold, ethidium bromide, acridines, proflavine, acridine orange, acriflavine, fluorocoumanin, ellipticine, daunomycin, chloroquine, distamycin D, chromomycin, homidium, mithramycin, ruthenium polypyridyls, anthramycin, and the like.

In another aspect, other fluorescent labels such as sequence specific probes can be employed in the amplification reaction to facilitate the detection and quantification of the amplified products. Probe-based quantitative amplification relies on the sequence-specific detection of a desired amplified product. It utilizes fluorescent, target-specific probes (e.g., TaqMan® probes) resulting in increased specificity and sensitivity. Methods for performing probe-based quantitative amplification are well established in the art and are taught in U.S. Pat. No. 5,210,015.

In yet another aspect, conventional hybridization assays using hybridization probes that share sequence homology with sequences associated with a signaling biochemical pathway can be performed. Typically, probes are allowed to form stable complexes with the sequences associated with a signaling biochemical pathway contained within the biological sample derived from the test subject in a hybridization reaction. It will be appreciated by one of skill in the art that where antisense is used as the probe nucleic acid, the target polynucleotides provided in the sample are chosen to be complementary to sequences of the antisense nucleic acids. Conversely, where the nucleotide probe is a sense nucleic acid, the target polynucleotide is selected to be complementary to sequences of the sense nucleic acid.

Hybridization can be performed under conditions of various stringency. Suitable hybridization conditions for the practice of the present invention are such that the recognition interaction between the probe and sequences associated with a signaling biochemical pathway is both sufficiently specific and sufficiently stable. Conditions that increase the stringency of a hybridization reaction are widely known and published in the art. See, for example, (Sambrook, et al., (1989); Nonradioactive In Situ Hybridization Application Manual, Boehringer Mannheim, second edition). The hybridization assay can be formed using probes immobilized on any solid support, including but are not limited to nitrocellulose, glass, silicon, and a variety of gene arrays. A preferred hybridization assay is conducted on high-density gene chips as described in U.S. Pat. No. 5,445,934.

For a convenient detection of the probe-target complexes formed during the hybridization assay, the nucleotide probes are conjugated to a detectable label. Detectable labels suitable for use in the present invention include any composition detectable by photochemical, biochemical, spectroscopic, immunochemical, electrical, optical or chemical means. A wide variety of appropriate detectable labels are known in the art, which include fluorescent or chemiluminescent labels, radioactive isotope labels, enzymatic or other ligands. In preferred embodiments, one will likely desire to employ a fluorescent label or an enzyme tag, such as digoxigenin, ß-galactosidase, urease, alkaline phosphatase or peroxidase, avidin/biotin complex.

The detection methods used to detect or quantify the hybridization intensity will typically depend upon the label selected above. For example, radiolabels may be detected using photographic film or a phosphoimager. Fluorescent markers may be detected and quantified using a photodetector to detect emitted light. Enzymatic labels are typically detected by providing the enzyme with a substrate and measuring the reaction product produced by the action of the enzyme on the substrate; and finally colorimetric labels are detected by simply visualizing the colored label.

An agent-induced change in expression of sequences associated with a signaling biochemical pathway can also be determined by examining the corresponding gene products. Determining the protein level typically involves a) contacting the protein contained in a biological sample with an agent that specifically bind to a protein associated with a signaling biochemical pathway; and (b) identifying any agent:protein complex so formed. In one aspect of this embodiment, the agent that specifically binds a protein associated with a signaling biochemical pathway is an antibody, preferably a monoclonal antibody.

The reaction is performed by contacting the agent with a sample of the proteins associated with a signaling biochemical pathway derived from the test samples under conditions that will allow a complex to form between the agent and the proteins associated with a signaling biochemical pathway. The formation of the complex can be detected directly or indirectly according to standard procedures in the art. In the direct detection method, the agents are supplied with a detectable label and unreacted agents may be removed from the complex; the amount of remaining label thereby indicating the amount of complex formed. For such method, it is preferable to select labels that remain attached to the agents even during stringent washing conditions. It is preferable that the label does not interfere with the binding reaction. In the alternative, an indirect detection procedure may use an agent that contains a label introduced either chemically or enzymatically. A desirable label generally does not interfere with binding or the stability of the resulting agent:polypeptide complex. However, the label is typically designed to be accessible to an antibody for an effective binding and hence generating a detectable signal.

A wide variety of labels suitable for detecting protein levels are known in the art. Non-limiting examples include radioisotopes, enzymes, colloidal metals, fluorescent compounds, bioluminescent compounds, and chemiluminescent compounds.

The amount of agent:polypeptide complexes formed during the binding reaction can be quantified by standard quantitative assays. As illustrated above, the formation of agent:polypeptide complex can be measured directly by the amount of label remained at the site of binding. In an alternative, the protein associated with a signaling biochemical pathway is tested for its ability to compete with a labeled analog for binding sites on the specific agent. In this competitive assay, the amount of label captured is inversely proportional to the amount of protein sequences associated with a signaling biochemical pathway present in a test sample.

A number of techniques for protein analysis based on the general principles outlined above are available in the art. They include but are not limited to radioimmunoassays, ELISA (enzyme linked immunoradiometric assays), "sandwich" immunoassays, immunoradiometric assays, in situ immunoassays (using e.g., colloidal gold, enzyme or radioisotope labels), western blot analysis, immunoprecipitation assays, immunofluorescent assays, and SDS-PAGE.

Antibodies that specifically recognize or bind to proteins associated with a signaling biochemical pathway are preferable for conducting the aforementioned protein analyses. Where desired, antibodies that recognize a specific type of post-translational modifications (e.g., signaling biochemical pathway inducible modifications) can be used. Post-translational modifications include but are not limited to glycosylation, lipidation, acetylation, and phosphorylation. These antibodies may be purchased from commercial vendors. For example, anti-phosphotyrosine antibodies that specifically recognize tyrosine-phosphorylated proteins are available from a number of vendors including Invitrogen and Perkin Elmer. Anti-phosphotyrosine antibodies are particularly useful in detecting proteins that are differentially phosphorylated on their tyrosine residues in response to an ER stress. Such proteins include but are not limited to eukaryotic translation initiation factor 2 alpha (eIF-2α). Alternatively, these antibodies can be generated using conventional polyclonal or monoclonal antibody technologies by immunizing a host animal or an antibody-producing cell with a target protein that exhibits the desired post-translational modification.

In practicing the subject method, it may be desirable to discern the expression pattern of an protein associated with a signaling biochemical pathway in different bodily tissue, in different cell types, and/or in different subcellular structures. These studies can be performed with the use of tissue-specific, cell-specific or subcellular structure specific antibodies capable of binding to protein markers that are preferentially expressed in certain tissues, cell types, or subcellular structures.

An altered expression of a gene associated with a signaling biochemical pathway can also be determined by examining a change in activity of the gene product relative to a control cell. The assay for an agent-induced change in the activity of a protein associated with a signaling biochemical pathway will dependent on the biological activity and/or the signal transduction pathway that is under investigation. For example, where the protein is a kinase, a change in its ability to phosphorylate the downstream substrate(s) can be determined by a variety of assays known in the art. Representative assays include but are not limited to immunoblotting and immunoprecipitation with antibodies such as anti-phosphotyrosine antibodies that recognize phosphorylated proteins. In addition, kinase activity can be detected by high throughput chemiluminescent assays such as AlphaScreen™ (available from Perkin Elmer) and eTag™ assay (Chan-Hui, et al. (2003) Clinical Immunology 111: 162-174).

Where the protein associated with a signaling biochemical pathway is part of a signaling cascade leading to a fluctuation of intracellular pH condition, pH sensitive molecules such as fluorescent pH dyes can be used as the reporter molecules. In another example where the protein associated with a signaling biochemical pathway is an ion channel, fluctuations in membrane potential and/or intracellular ion concentration can be monitored. A number of commercial kits and high-throughput devices are particularly suited for a rapid and robust screening for modulators of ion channels. Representative instruments include FLIP® (Molecular Devices, Inc.) and VIPR (Aurora Biosciences). These instruments are capable of detecting reactions in over 1000 sample wells of a microplate simultaneously, and providing real-time measurement and functional data within a second or even a minisecond.

In practicing any of the methods disclosed herein, a suitable vector can be introduced to a cell or an embryo via one or more methods known in the art, including without limitation, microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, proprietary agent-enhanced uptake of nucleic acids, and delivery via liposomes, immunoliposomes, virosomes, or artificial virions. In some methods, the vector is introduced into an embryo by microinjection. The vector or vectors may be microinjected into the nucleus or the cytoplasm of the embryo. In some methods, the vector or vectors may be introduced into a cell by nucleofection.

The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA).

Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA).

The target polynucleotide of a CRISPR complex may include a number of disease-associated genes and polynucleotides as well as signaling biochemical pathway-associated genes and polynucleotides as listed in U.S. provisional patent applications 61/736,527 and 61/748,427, both entitled SYSTEMS METHODS AND COMPOSITIONS FOR SEQUENCE MANIPULATION filed on Dec. 12, 2012 and Jan. 2, 2013, respectively, the contents of all of which are herein incorporated by reference in their entirety.

Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

Examples of disease-associated genes and polynucleotides are listed in Tables A and B. Disease specific information is available from McKusick-Nathans Institute of Genetic Medicine, Johns Hopkins University (Baltimore, Md.) and National Center for Biotechnology Information, National Library of Medicine (Bethesda, Md.), available on the World Wide Web. Examples of signaling biochemical pathway-associated genes and polynucleotides are listed in Table C.

Mutations in these genes and pathways can result in production of improper proteins or proteins in improper amounts which affect function. Further examples of genes, diseases and proteins are hereby incorporated by reference from U.S. Provisional applications 61/736,527 filed on Dec. 12, 2012 and 61/748,427 filed on Jan. 2, 2013. Such genes, proteins and pathways may be the target polynucleotide of a CRISPR complex.

TABLE A

| DISEASE/ DISORDERS | GENE(S) |
|---|---|
| Neoplasia | PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; Apc |
| Age-related Macular Degeneration | Abcr; Ccl2; Cc2; cp (ceruloplasmin); Timp3; cathepsinD; Vldlr; Ccr2 |
| Schizophrenia | Neuregulin1 (Nrg1); Erb4 (receptor for Neuregulin); Complexinl (Cp1x1); Tph1 Tryptophan hydroxylase; Tph2 Tryptophan hydroxylase 2; Neurexin 1; GSK3; GSK3a; GSK3b |
| Disorders | 5-HTT (Slc6a4); COMT; DRD (Drdla); SLC6A3; DAOA; DTNBP1; Dao (Dao1) |
| Trinucleotide Repeat Disorders | HTT (Huntington's Dx); SBMA/SMAX1/AR (Kennedy's Dx); FWX25 (Friedrich's Ataxia); ATX3 (Machado-Joseph's Dx); ATXN1 and ATXN2 (spinocerebellar ataxias); DNIPK (myotonic dystrophy); Atrophin-1 and Atn1 (DRPLA Dx); CBP (Creb-BP- global instability); VLDLR (Alzheimer's); Atxn7; Atxn10 |
| Fragile X Syndrome | FMR2; FXR1; FXR2; mGLUR5 |
| Secretase Related Disorders | APH-1 (alpha and beta); Presenilin (Psen1); nicastrin (Ncstn); PEN-2 |
| Others | Nos1 ; Parp1; Nat1 ; Nat2 |
| Prion-related disorders | Prp |
| ALS | SOD1; ALS2; STEX; FUS; TARDBP; VEGF (VEGF-a; VEGF-b; VEGF-c) |
| Drug addiction | Prkce (alcohol); Drd2; Drd4; ABAT (alcohol); GRIA2; Grm5; Grinl; Htr1b; Grin2a; Drd3; Pdyn; Grial (alcohol) |
| Autism | Mecp2; BZRAP1; MDGA2; Sema5A; Neurexin 1; Fragile X (FMR2 (AFF2); FXR1; FXR2; Mglur5) |

TABLE A-continued

| DISEASE/DISORDERS | GENE(S) |
|---|---|
| Alzheimer's Disease | E1; CHIP; UCH; UBB; Tau; LRP; PICALM; Clusterin; PS1; SORL1; CR1; Vldlr; Uba1; Uba3; CHIP28 (Aqp1, Aquaporin 1); Uchl1; Uchl3; APP |
| Inflammation | IL-10; IL-1 (IL-1a; IL-1b); IL-13; IL-17 (IL-17a (CTLA8); IL-17b; IL-17c; IL-17d; IL-17f); II-23; Cx3cr1; ptpn22; TNFa; NOD2/CARD15 for IBD; IL-6; IL-12 (IL-12a; IL-12b); CTLA4; Cx3cl1 |
| Parkinson's Disease | x-Synuclein; DJ-1; LRRK2; Parkin; PINK1 |

TABLE B

| | |
|---|---|
| Blood and coagulation diseases and disorders | Anemia (CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT); Bare lymphocyte syndrome (TAPBP, TPSN, TAP2, ABCB3, PSF2, RING11, MHC2TA, C2TA, RFX5, RFXAP, RFX5), Bleeding disorders (TBXA2R, P2RX1, P2X1); Factor H and factor H-like 1 (HF1, CFH, HUS); Factor V and factor VIII (MCFD2); Factor VII deficiency (F7); Factor X deficiency (F10); Factor XI deficiency (F11); Factor XII deficiency (F12, HAF); Factor XIIIA deficiency (F13A1, F13A); Factor XIIIB deficiency (F13B); Fanconi anemia (FANCA, FACA, FA1, FA, FAA, FAAP95, FAAP90, F1134064, FANCB, FANCC, FACC, BRCA2, FANCD1, FANCD2, FANCD, FACD, FAD, FANCE, FACE, FANCF, XRCC9, FANCG, BRIP1, BACH1, FANCJ, PHF9, FANCL, FANCM, KIAA1596); Hemophagocytic lymphohistiocytosis disorders (PRF1, HPLH2, UNC13D, MUNC13-4, HPLH3, HLH3, FHL3); Hemophilia A (F8, F8C, HEMA); Hemophilia B (F9, HEMB), Hemorrhagic disorders (PI, ATT, F5); Leukocyde deficiencies and disorders (ITGB2, CD18, LCAMB, LAD, EIF2B1, EIF2BA, EIF2B2, EIF2B3, EIF2B5, LVWM, CACH, CLE, EIF2B4); Sickle cell anemia (HBB); Thalassemia (HBA2, HBB, HBD, LCRB, HBA1). |
| Cell dysregulation and oncology diseases and disorders | B-cell non-Hodgkin lymphoma (BCL7A, BCL7); Leukemia (TAL1, TCL5, SCL, TAL2, FLT3, NBS1, NBS, ZNFN1A1, IK1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, CEBP, CHIC2, BTL, FLT3, KIT, PBT, LPP, NPM1, NUP214, D9546E, CAN, CAIN, RUNX1, CBFA2, AML1, WHSC1L1, NSD3, FLT3, AF1Q, NPM1, NUMA1, ZNF145, PLZF, PML, MYL, STAT5B, AF10, CALM, CLTH, ARL11, ARLTS1, P2RX7, P2X7, BCR, CML, PHL, ALL, GRAF, NF1, VRNF, WSS, NFNS, PTPN11, PTP2C, SHP2, NS1, BCL2, CCND1, PRAD1, BCL1, TCRA, GATA1, GF1, ERYF1, NFE1, ABL1, NQO1, DIA4, NMOR1, NUP214, D9546E, CAN, CAIN). |
| Inflammation and immune related diseases and disorders | AIDS (KIR3DL1, NKAT3, NKB1, AMB11, KIR3D51, IFNG, CXCL12, SDF1); Autoimmune lymphoproliferative syndrome (TNFRSF6, APT1, FAS, CD95, ALPS1A); Combined immunodeficiency, (IL2RG, SCIDX1, SCIDX, IMD4); HIV-1 (CCL5, SCYA5, D17S136E, TCP228), HIV susceptibility or infection (IL10, CS1F, CMKBR2, CCR2, CMKBR5, CCCKR5 (CCR5)); Immunodeficiencies (CD3E, CD3G, AICDA, AID, HIGM2, TNFRSF5, CD40, UNG, DGU, HIGM4, TNFSF5, CD40LG, HIGM1, IGM, FOXP3, IPEX, AIID, XPID, PIDX, TNFRSF14B, TACI); Inflammation (IL-10, IL-1 (IL-1a, IL-1b), IL-13, IL-17 (IL-17a (CTLA8), IL-17b, IL-17c, IL-17d, IL-17f), II-23, Cx3cr1, ptpn22, TNFa, NOD2/CARD15 for IBD, IL-6, IL-12 (IL-12a, IL-12b), CTLA4, Cx3cl1); Severe combined immunodeficiencies (SCIDs)(JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4). |
| Metabolic, liver, kidney and protein diseases and disorders | Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRH1A, NAIC, TEX292, KIAA1988); Cystic fibrosis (CFTR, ABCC7, CF, MRP7); Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma, 142330 (TCF1, HNF1A, MODY3), Hepatic failure, early onset, and neurologic disorder (SCOD1, SCO1), Hepatic lipase deficiency (LIPC), Hepatoblastoma, cancer and carcinomas (CTNNB1, PDGFRL, PDGRL, PRLTS, AXIN1, AXIN, CTNNB1, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63). |
| Muscular/Skeletal diseases and disorders | Becker muscular dystrophy (DMD, BMD, MYF6), Duchenne Muscular Dystrophy (DMD, BMD); Emery-Dreifuss muscular dystrophy (LMNA, LMN1, EMD2, FPLD, CMD1A, HGPS, LGMD1B, LMNA, LMN1, EMD2, FPLD, CMD1A); Facioscapulohumeral muscular dystrophy (FSHMD1A, FSHD1A); Muscular dystrophy (FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, |

TABLE B-continued

| | |
|---|---|
| | LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1); Osteopetrosis (LRP5, BMND1, LRP7, LR3, OPPG, VBCH2, CLCN7, CLC7, OPTA2, OSTM1, GL, TCIRG1, TIRC7, OC116, OPTB1); Muscular atrophy (VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1). |
| Neurological and neuronal diseases and disorders | ALS (SOD1, ALS2, STEX, FUS, TARDBP, VEGF (VEGF-a, VEGF-b, VEGF-c); Alzheimer disease (APP, AAA, CVAP, AD1, APOE, AD2, PSEN2, AD4, STM2, APBB2, FE65L1, NOS3, PLAU, URK, ACE, DCP1, ACE1, MPO, PACIP1, PAXIP1L, PTIP, A2M, BLMH, BMH, PSEN1, AD3); Autism (Mecp2, BZRAP1, MDGA2, Sema5A, Neurexin 1, GLO1, MECP2, RTT, PPMX, MRX16, MRX79, NLGN3, NLGN4, KIAA1260, AUTSX2); Fragile X Syndrome (FMR2, FXR1, FXR2, mGLUR5); Huntington's disease and disease like disorders (HD, IT15, PRNP, PRIP, JPH3, JP3, HDL2, TBP, SCA17); Parkinson disease (NR4A2, NURR1, NOT, TINUR, SNCAIP, TBP, SCA17, SNCA, NACP, PARK1, PARK4, DJ1, PARK7, LRRK2, PARK8, PINK1, PARK6, UCHL1, PARKS, SNCA, NACP, PARK1, PARK4, PRKN, PARK2, PDJ, DBH, NDUFV2); Rett syndrome (MECP2, RTT, PPMX, MRX16, MRX79, CDKL5, STK9, MECP2, RTT, PPMX, MRX16, MRX79, x-Synuclein, DJ-1); Schizophrenia (Neuregulin1 (Nrg1), Erb4 (receptor for Neuregulin), Complexinl (Cp1x1), Tph1 Tryptophan hydroxylase, Tph2, Tryptophan hydroxylase 2, Neurexin 1, GSK3, GSK3a, GSK3b, 5-HTT (Slc6a4), COMT, DRD (Drd1a), SLC6A3, DAOA, DTNBP1, Dao (Dao1)); Secretase Related Disorders (APH-1 (alpha and beta), Presenilin (Psen1), nicastrin, (Ncstn), PEN-2, Nos1, Parpl, Nat1, Nat2); Trinucleotide Repeat Disorders (HTT (Huntington's Dx), SBMA/SMAX1/AR (Kennedy's Dx), FWX25 (Friedrich's Ataxia), ATX3 (Machado- Joseph's Dx), ATXN1 and ATXN2 (spinocerebellar ataxias), DMPK (myotonic dystrophy), Atrophin-1 and Atn1 (DRPLA Dx), CBP (Creb-BP-global instability), VLDLR (Alzheimer's), Atxn7, Atxn10). |
| Occular diseases and disorders | Age-related macular degeneration (Abcr, Ccl2, Cc2, cp (ceruloplasmin), Timp3, cathepsinD, Vldlr, Ccr2); Cataract (CRYAA, CRYA1, CRYBB2, CRYB2, PITX3, BFSP2, CP49, CP47, CRYAA, CRYA1, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQP0, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT1); Corneal clouding and dystrophy (APOA1, TGFBI, CSD2, CDGG1, CSD, BIGH3, CDG2, TACSTD2, TROP2, M1S1, VSX1, RINX, PPCD, PPD, KTCN, COL8A2, FECD, PPCD2, PIP5K3, CFD); Cornea plana congenital (KERA, CNA2); Glaucoma (MYOC, TIGR, GLC1A, JOAG, GPOA, OPTN, GLC1E, FIP2, HYPL, NRP, CYP1B1, GLC3A, OPA1, NTG, NPG, CYP1B1, GLC3A); Leber congenital amaurosis (CRB1, RP12, CRX, CORD2, CRD, RPGRIP1, LCA6, CORD9, RPE65, RP20, AIPL1, LCA4, GUCY2D, GUC2D, LCA1, CORD6, RDH12, LCA3); Macular dystrophy (ELOVL4, ADMD, STGD2, STGD3, RDS, RP7, PRPH2, PRPH, AVMD, AOFMD, VMD2). |

TABLE C

| CELLULAR FUNCTION | GENES |
|---|---|
| PI3K/AKT Signaling | PRKCE; ITGAM; ITGA5; IRAK1; PRKAA2; EIF2AK2; PTEN; EIF4E; PRKCZ; GRK6; MAPK1; TSC1; PLK1; AKT2; IKBKB; PIK3CA; CDK8; CDKN1B; NFKB2; BCL2; PIK3CB; PPP2R1A; MAPK8; BCL2L1; MAPK3; TSC2; ITGA1; KRAS; EIF4EBP1; RELA; PRKCD; NOS3; PRKAA1; MAPK9; CDK2; PPP2CA; PIM1; ITGB7; YWHAZ; ILK; TP53; RAF1; IKBKG; RELB; DYRK1A; CDKN1A; ITGB1; MAP2K2; JAK1; AKT1; JAK2; PIK3R1; CHUK; PDPK1; PPP2R5C; CTNNB1; MAP2K1; NFKB1; PAK3; ITGB3; CCND1; GSK3A; FRAP1; SFN; ITGA2; TTK; CSNK1A1; BRAF; GSK3B; AKT3; FOXO1; SGK; HSP90AA1; RPS6KB1 |
| ERK/MAPK Signaling | PRKCE; ITGAM; ITGA5; HSPB1; IRAK1; PRKAA2; EIF2AK2; RAC1; RAP1A; TLN1; EIF4E; ELK1; GRK6; MAPK1; RAC2; PLK1; AKT2; PIK3CA; CDK8; CREB1; PRKCI; PTK2; FOS; RPS6KA4; PIK3CB; PPP2R1A; PIK3C3; MAPK8; MAPK3; ITGA1; ETS1; KRAS; MYCN; EIF4EBP1; PPARG; PRKCD; PRKAA1; MAPK9; SRC; CDK2; PPP2CA; PIM1; PIK3C2A; ITGB7; YWHAZ; |

TABLE C-continued

| CELLULAR FUNCTION | GENES |
|---|---|
| | PPP1CC; KSR1; PXN; RAF1; FYN; DYRK1A; ITGB1; MAP2K2; PAK4; PIK3R1; STAT3; PPP2R5C; MAP2K1; PAK3; ITGB3; ESR1; ITGA2; MYC; TTK; CSNK1A1; CRKL; BRAF; ATF4; PRKCA; SRF; STAT1; SGK |
| Glucocorticoid Receptor Signaling | RAC1; TAF4B; EP300; SMAD2; TRAF6; PCAF; ELK1; MAPK1; SMAD3; AKT2; IKBKB; NCOR2; UBE2I; PIK3CA; CREB1; FOS; HSPA5; NFKB2; BCL2; MAP3K14; STAT5B; PIK3CB; PIK3C3; MAPK8; BCL2L1; MAPK3; TSC22D3; MAPK10; NRIP1; KRAS; MAPK13; RELA; STAT5A; MAPK9; NOS2A; PBX1; NR3C1; PIK3C2A; CDKN1C; TRAF2; SERPINE1; NCOA3; MAPK14; TNF; RAF1; IKBKG; MAP3K7; CREBBP; CDKN1A; MAP2K2; JAK1; IL8; NCOA2; AKT1; JAK2; PIK3R1; CHUK; STAT3; MAP2K1; NFKB1; TGFBR1; ESR1; SMAD4; CEBPB; JUN; AR; AKT3; CCL2; MNIP1; STAT1; IL6; HSP90AA1 |
| Axonal Guidance Signaling | PRKCE; ITGAM; ROCK1; ITGA5; CXCR4; ADAM12; IGF1; RAC1; RAP1A; EIF4E; PRKCZ; NRP1; NTRK2; ARHGEF7; SMO; ROCK2; MAPK1; PGF; RAC2; PTPN11; GNAS; AKT2; PIK3CA; ERBB2; PRKCI; PTK2; CFL1; GNAQ; PIK3CB; CXCL12; PIK3C3; WNT11; PRKD1; GNB2L1; ABL1; MAPK3; ITGA1; KRAS; RHOA; PRKCD; PIK3C2A; ITGB7; GLI2; PXN; VASP; RAF1; FYN; ITGB1; MAP2K2; PAK4; ADAM17; AKT1; PIK3R1; GLI1; WNT5A; ADAM10; MAP2K1; PAK3; ITGB3; CDC42; VEGFA; ITGA2; EPHA8; CRKL; RND1; GSK3B; AKT3; PRKCA |
| Ephrin Receptor Signaling | PRKCE; ITGAM; ROCK1; ITGA5; CXCR4; IRAK1; PRKAA2; EIF2AK2; RAC1; RAP1A; GRK6; ROCK2; MAPK1; PGF; RAC2; PTPN11; GNAS; PLK1; AKT2; DOK1; CDK8; CREB1; PTK2; CFL1; GNAQ; MAP3K14; CXCL12; MAPK8; GNB2L1; ABL1; MAPK3; ITGA1; KRAS; RHOA; PRKCD; PRKAA1; MAPK9; SRC; CDK2; PIM1; ITGB7; PXN; RAF1; FYN; DYRK1A; ITGB1; MAP2K2; PAK4; AKT1; JAK2; STAT3; ADAM10; MAP2K1; PAK3; ITGB3; CDC42; VEGFA; ITGA2; EPHA8; TTK; CSNK1A1; CRKL; BRAF; PTPN13; ATF4; AKT3; SGK |
| Actin Cytoskeleton Signaling | ACTN4; PRKCE; ITGAM; ROCK1; ITGA5; IRAK1; PRKAA2; EIF2AK2; RAC1; INS; ARHGEF 7; GRK6; ROCK2; MAPK1; RAC2; PLK1; AKT2; PIK3CA; CDK8; PTK2; CFL1; PIK3CB; MYH9; DIAPH1; PIK3C3; MAPK8; F2R; MAPK3; SLC9A1; ITGAl; KRAS; RHOA; PRKCD; PRKAA1; MAPK9; CDK2; PIM1; PIK3C2A; ITGB7; PPP1CC; PXN; VIL2; RAF1; GSN; DYRK1A; ITGB1; MAP2K2; PAK4; PIP5K1A; PIK3R1; MAP2K1; PAK3; ITGB3; CDC42; APC; ITGA2; TTK; CSNK1A1; CRKL; BRAF; VAV3; SGK |
| Huntington's Disease Signaling | PRKCE; IGF1; EP300; RCOR1; PRKCZ; HDAC4; TGM2; MAPK1; CAPNS1; AKT2; EGFR; NCOR2; SP1; CAPN2; PIK3CA; HDAC5; CREB1; PRKCI; HSPA5; REST; GNAQ; PIK3CB; PIK3C3; MAPK8; IGF1R; PRKD1; GNB2L1; BCL2L1; CAPN1; MAPK3; CASP8; HDAC2; HDAC7A; PRKCD; HDAC11; MAPK9; HDAC9; PIK3C2A; HDAC3; TP53; CASP9; CREBBP; AKT1; PIK3R1; PDPK1; CASP1; APAF1; FRAP1; CASP2; JUN; BAX; ATF4; AKT3; PRKCA; CLTC; SGK; HDAC6; CASP3 |
| Apoptosis Signaling | PRKCE; ROCK1; BID; IRAK1; PRKAA2; EIF2AK2; BAK1; BIRC4; GRK6; MAPK1; CAPNS1; PLK1; AKT2; IKBKB; CAPN2; CDK8; FAS; NFKB2; BCL2; MAP3K14; MAPK8; BCL2L1; CAPN1; MAPK3; CASP8; KRAS; RELA; PRKCD; PRKAA1; MAPK9; CDK2; PIM1; TP53; TNF; RAF1; IKBKG; RELB; CASP9; DYRK1A; MAP2K2; CHUK; APAF1; MAP2K1; NFKB1; PAK3; LMNA; CASP2; BIRC2; TTK; CSNK1A1; BRAF; BAX; PRKCA; SGK; CASP3; BIRC3; PARP1 |
| B Cell Receptor Signaling | RAC1; PTEN; LYN; ELK1; MAPK1; RAC2; PTPN11; AKT2; IKBKB; PIK3CA; CREB1; SYK; NFKB2; CAMK2A; MAP3K14; PIK3CB; PIK3C3; MAPK8; BCL2L1; ABL1; MAPK3; ETS1; KRAS; MAPK13; RELA; PTPN6; MAPK9; EGR1; PIK3C2A; BTK; MAPK14; RAF1; IKBKG; RELB; MAP3K7; MAP2K2; AKT1; PIK3R1; CHUK; MAP2K1; NFKB1; CDC42; GSK3A; FRAP1; BCL6; BCL10; JUN; GSK3B; ATF4; AKT3; VAV3; RPS6KB1 |

TABLE C-continued

| CELLULAR FUNCTION | GENES |
|---|---|
| Leukocyte Extravasation Signaling | ACTN4; CD44; PRKCE; ITGAM; ROCK1; CXCR4; CYBA; RAC1; RAP1A; PRKCZ; ROCK2; RAC2; PTPN11; MMP14; PIK3CA; PRKCI; PTK2; PIK3CB; CXCL12; PIK3C3; MAPK8; PRKD1; ABL1; MAPK10; CYBB; MAPK13; RHOA; PRKCD; MAPK9; SRC; PIK3C2A; BTK; MAPK14; NOX1; PXN; VIL2; VASP; ITGB1; MAP2K2; CTNND1; PIK3R1; CTNNB1; CLDN1; CDC42; F11R; ITK; CRKL; VAV3; CTTN; PRKCA; MMP1; MMP9 |
| Integrin Signaling | ACTN4; ITGAM; ROCK1; ITGA5; RAC1; PTEN; RAP1A; TLN1; ARHGEF7; MAPK1; RAC2; CAPNS1; AKT2; CAPN2; PIK3CA; PTK2; PIK3CB; PIK3C3; MAPK8; CAV1; CAPN1; ABL1; MAPK3; ITGA1; KRAS; RHOA; SRC; PIK3C2A; ITGB7; PPP1CC; ILK; PXN; VASP; RAF1; FYN; ITGB1; MAP2K2; PAK4; AKT1; PIK3R1; TNK2; MAP2K1; PAK3; ITGB3; CDC42; RND3; ITGA2; CRKL; BRAF; GSK3B; AKT3 |
| Acute Phase Response Signaling | IRAK1; SOD2; MYD88; TRAF6; ELK1; MAPK1; PTPN11; AKT2; IKBKB; PIK3CA; FOS; NFKB2; MAP3K14; PIK3CB; MAPK8; RIPK1; MAPK3; IL6ST; KRAS; MAPK13; IL6R; RELA; SOCS1; MAPK9; FTL; NR3C1; TRAF2; SERPINE1; MAPK14; TNF; RAF1; PDK1; IKBKG; RELB; MAP3K7; MAP2K2; AKT1; JAK2; PIK3R1; CHUK; STAT3; MAP2K1; NFKB1; FRAP1; CEBPB; JUN; AKT3; IL1R1; IL6 |
| PTEN Signaling | ITGAM; ITGA5; RAC1; PTEN; PRKCZ; BCL2L11; MAPK1; RAC2; AKT2; EGFR; IKBKB; CBL; PIK3CA; CDKN1B; PTK2; NFKB2; BCL2; PIK3CB; BCL2L1; MAPK3; ITGA1; KRAS; ITGB7; ILK; PDGFRB; INSR; RAF1; IKBKG; CASP9; CDKN1A; ITGB1; MAP2K2; AKT1; PIK3R1; CHUK; PDGFRA; PDPK1; MAP2K1; NFKB1; ITGB3; CDC42; CCND1; GSK3A; ITGA2; GSK3B; AKT3; FOXO1; CASP3; RPS6KB1 |
| p53 Signaling | PTEN; EP300; BBC3; PCAF; FASN; BRCA1; GADD45A; BIRC5; AKT2; PIK3CA; CHEK1; TP53INP1; BCL2; PIK3CB; PIK3C3; MAPK8; THBS1; ATR; BCL2L1; E2F1; PMAIP1; CHEK2; TNFRSF10B ; TP73; RB1; HDAC 9; CDK2; PIK3C2A; MAPK14; TP53; LRDD; CDKN1A; HIPK2; AKT1; PIK3R1; RRM2B; APAF1; CTNNB1; SIRT1; CCND1; PRKDC; ATM; SFN; CDKN2A; JUN; SNAI2; GSK3B; BAX; AKT3 |
| Aryl Hydrocarbon Receptor Signaling | HSPB1; EP300; FASN; TGM2; RXRA; MAPK1; NQO1; NCOR2; SP1; ARNT; CDKN1B; FOS; CHEK1; SMARCA4; NFKB2; MAPK8; ALDH1A1; ATR; E2F1; MAPK3; NRIP1; CHEK2; RELA; TP73; GSTP1; RB1; SRC; CDK2; AHR; NFE2L2; NCOA3; TP53; TNF; CDKN1A; NCOA2; APAF1; NFKB1; CCND1; ATM; ESR1; CDKN2A; MYC; JUN; ESR2; BAX; IL6; CYP1B1; HSP90AA1 |
| Xenobiotic Metabolism Signaling | PRKCE; EP300; PRKCZ; RXRA; MAPK1; NQO1; NCOR2; PIK3CA; ARNT; PRKCI; NFKB2; CAMK2A; PIK3CB; PPP2R1A; PIK3C3; MAPK8; PRKD1; ALDH1A1; MAPK3; NRIP1; KRAS; MAPK13; PRKCD; GSTP1; MAPK9; NOS2A; ABCB1; AHR; PPP2CA; FTL; NFE2L2; PIK3C2A; PPARGC1A; MAPK14; TNF; RAF1; CREBBP; MAP2K2; PIK3R1; PPP2R5C; MAP2K1; NFKB1; KEAP1; PRKCA; EIF2AK3; IL6; CYP1B1; HSP90AA1 |
| SAPK/JNK Signaling | PRKCE; IRAK1; PRKAA2; EIF2AK2; RAC1; ELK1; GRK6; MAPK1; GADD45A; RAC2; PLK1; AKT2; PIK3CA; FADD; CDK8; PIK3CB; PIK3C3; MAPK8; RIPK1; GNB2L1; IRS1; MAPK3; MAPK10; DAXX; KRAS; PRKCD; PRKAA1; MAPK9; CDK2; PIM1; PIK3C2A; TRAF2; TP53; LCK; MAP3K7; DYRK1A; MAP2K2; PIK3R1; MAP2K1; PAK3; CDC42; JUN; TTK; CSNK1A1; CRKL; BRAF; SGK |
| PPAr/RXR Signaling | PRKAA2; EP300; INS; SMAD2; TRAF6; PPARA; FASN; RXRA; MAPK1; SMAD3; GNAS; IKBKB; NCOR2; ABCA1; GNAQ; NFKB2; MAP3K14; STAT5B; MAPK8; IRS1; MAPK3; KRAS; RELA; PRKAA1; PPARGC1A; NCOA3; MAPK14; INSR; RAF1; IKBKG; RELB; MAP3K7; CREBBP; MAP2K2; JAK2; CHUK; MAP2K1; NFKB1; TGFBR1; SMAD4; JUN; IL1R1; PRKCA; IL6; HSP90AA1; ADIPOQ |
| NF-KB Signaling | IRAK1; EIF2AK2; EP300; INS; MYD88; PRKCZ; TRAF6; TBK1; AKT2; EGFR; IKBKB; PIK3CA; BTRC; NFKB2; MAP3K14; PIK3CB; PIK3C3; MAPK8; RIPK1; HDAC2; KRAS; RELA; PIK3C2A; TRAF2; TLR4; PDGFRB; TNF; |

TABLE C-continued

| CELLULAR FUNCTION | GENES |
|---|---|
| | INSR; LCK; IKBKG; RELB; MAP3K7; CREBBP; AKT1; PIK3R1; CHUK; PDGFRA; NFKB1; TLR2; BCL10; GSK3B; AKT3; TNFAIP3; IL1R1 |
| Neuregulin Signaling | ERBB4; PRKCE; ITGAM; ITGA5; PTEN; PRKCZ; ELK1; MAPK1; PTPN11; AKT2; EGFR; ERBB2; PRKCI; CDKN1B; STAT5B; PRKD1; MAPK3; ITGA1; KRAS; PRKCD; STAT5A; SRC; ITGB7; RAF1; ITGB1; MAP2K2; ADAM17; AKT1; PIK3R1; PDPK1; MAP2K1; ITGB3; EREG; FRAP1; PSEN1; ITGA2; MYC; NRG1; CRKL; AKT3; PRKCA; HSP90AA1; RPS6KB1 |
| Wnt & Beta catenin Signaling | CD44; EP300; LRP6; DVL3; CSNK1E; GJA1; SMO; AKT2; PIN1; CDH1; BTRC; GNAQ; MARK2; PPP2R1A; WNT11; SRC; DKK1; PPP2CA; S0X6; SFRP2; ILK; LEF1; 50X9; TP53; MAP3K7; CREBBP; TCF7L2; AKT1; PPP2R5C; WNT5A; LRP5; CTNNB1; TGFBR1; CCND1; GSK3A; DVL1; APC; CDKN2A; MYC; CSNK1A1; GSK3B; AKT3; SOX2 |
| Insulin Receptor Signaling | PTEN; INS; EIF4E; PTPN1; PRKCZ; MAPK1; TSC1; PTPN11; AKT2; CBL; PIK3CA; PRKCI; PIK3CB; PIK3C3; MAPK8; IRS1; MAPK3; TSC2; KRAS; EIF4EBP1; SLC2A4; PIK3C2A; PPP1CC; INSR; RAF1; FYN; MAP2K2; JAK1; AKT1; JAK2; PIK3R1; PDPK1; MAP2K1; GSK3A; FRAP1; CRKL; GSK3B; AKT3; FOX01; SGK; RPS6KB1 |
| IL-6 Signaling | HSPB1; TRAF6; MAPKAPK2; ELK1; MAPK1; PTPN11; IKBKB; FOS; NFKB2; MAP3K14; MAPK8; MAPK3; MAPK10; IL6ST; KRAS; MAPK13; IL6R; RELA; SOCS1; MAPK9; ABCB1; TRAF2; MAPK14; TNF; RAF1; IKBKG; RELB; MAP3K7; MAP2K2; IL8; JAK2; CHUK; STAT3; MAP2K1; NFKB1; CEBPB; JUN; IL1R1; SRF; IL6 |
| Hepatic Cholestasis | PRKCE; IRAK1; INS; MYD88; PRKCZ; TRAF6; PPARA; RXRA; IKBKB; PRKCI; NFKB2; MAP3K14; MAPK8; PRKD1; MAPK10; RELA; PRKCD; MAPK9; ABCB1; TRAF2; TLR4; TNF; INSR; IKBKG; RELB; MAP3K7; IL8; CHUK; NR1H2; TJP2; NFKB1; ESR1; SREBF1; FGFR4; JUN; IL1R1; PRKCA; IL6 |
| IGF-1 Signaling | IGF1; PRKCZ; ELK1; MAPK1; PTPN11; NEDD4; AKT2; PIK3CA; PRKCI; PTK2; FOS; PIK3CB; PIK3C3; MAPK8; IGF1R; IRS1; MAPK3; IGFBP7; KRAS; PIK3C2A; YWHAZ; PXN; RAF1; CASP9; MAP2K2; AKT1; PIK3R1; PDPK1; MAP2K1; IGFBP2; SFN; JUN; CYR61; AKT3; FOXO1; SRF; CTGF; RPS6KB1 |
| NRF2-mediated Oxidative Stress Response | PRKCE; EP300; SOD2; PRKCZ; MAPK1; SQSTM1; NQO1; PIK3CA; PRKCI; FOS; PIK3CB; PIK3C3; MAPK8; PRKD1; MAPK3; KRAS; PRKCD; GSTP1; MAPK9; FTL; NFE2L2; PIK3C2A; MAPK14; RAF1; MAP3K7; CREBBP; MAP2K2; AKT1; PIK3R1; MAP2K1; PPM; JUN; KEAP1; GSK3B; ATF4; PRKCA; EIF2AK3; HSP9OAA1 |
| Hepatic Fibrosis/ Hepatic Stellate Cell Activation | EDN1; IGF1; KDR; FLT1; SMAD2; FGFR1; MET; PGF; SMAD3; EGFR; FAS; CSF1; NFKB2; BCL2; MYH9; IGF1R; IL6R; RELA; TLR4; PDGFRB; TNF; RELB; IL8; PDGFRA; NFKB1; TGFBR1; SMAD4; VEGFA; BAX; IL1R1; CCL2; HGF; MMP1; STAT1; IL6; CTGF; MIMP9 |
| PPAR Signaling | EP300; INS; TRAF6; PPARA; RXRA; MAPK1; IKBKB; NCOR2; FOS; NFKB2; MAP3K14; STAT5B; MAPK3; NRIP1; KRAS; PPARG; RELA; STAT5A; TRAF2; PPARGC1A; PDGFRB; TNF; INSR; RAF1; IKBKG; RELB; MAP3K7; CREBBP; MAP2K2; CHUK; PDGFRA; MAP2K1; NFKB1; JUN; IL1R1; HSP90AA1 |
| Fc Epsilon RI Signaling | PRKCE; RAC1; PRKCZ; LYN; MAPK1; RAC2; PTPN11; AKT2; PIK3CA; SYK; PRKCI; PIK3CB; PIK3C3; MAPK8; PRKD1; MAPK3; MAPK10; KRAS; MAPK13; PRKCD; MAPK9; PIK3C2A; BTK; MAPK14; TNF; RAF1; FYN; MAP2K2; AKT1; PIK3R1; PDPK1; MAP2K1; AKT3; VAV3; PRKCA |
| G-Protein Coupled Receptor Signaling | PRKCE; RAP1A; RGS16; MAPK1; GNAS; AKT2; IKBKB; PIK3CA; CREB1; GNAQ; NFKB2; CAMK2A; PIK3CB; PIK3C3; MAPK3; KRAS; RELA; SRC; PIK3C2A; RAF1; IKBKG; RELB; FYN; MAP2K2; AKT1; PIK3R1; CHUK; PDPK1; STAT3; MAP2K1; NFKB1; BRAF; ATF4; AKT3; PRKCA |
| Inositol Phosphate Metabolism | PRKCE; IRAK1; PRKAA2; EIF2AK2; PTEN; GRK6; MAPK1; PLK1; AKT2; PIK3CA; CDK8; PIK3CB; PIK3C3; MAPK8; MAPK3; PRKCD; PRKAA1; MAPK9; CDK2; PIM1; PIK3C2A; DYRK1A; MAP2K2; PIP5K1A; PIK3R1; MAP2K1; PAK3; ATM; TTK; CSNK1A1; BRAF; SGK |

TABLE C-continued

| CELLULAR FUNCTION | GENES |
|---|---|
| PDGF Signaling | EIF2AK2; ELK1; ABL2; MAPK1; PIK3CA; FOS; PIK3CB; PIK3C3; MAPK8; CAV1; ABL1; MAPK3; KRAS; SRC; PIK3C2A; PDGFRB; RAF1; MAP2K2; JAK1; JAK2; PIK3R1; PDGFRA; STAT3; SPHK1; MAP2K1; MYC; JUN; CRKL; PRKCA; SRF; STAT1; SPHK2 |
| VEGF Signaling | ACTN4; ROCK1; KDR; FLT1; ROCK2; MAPK1; PGF; AKT2; PIK3CA; ARNT; PTK2; BCL2; PIK3CB; PIK3C3; BCL2L1; MAPK3; KRAS; HIF1A; NOS3; PIK3C2A; PXN; RAF1; MAP2K2; ELAVL1; AKT1; PIK3R1; MAP2K1; SFN; VEGFA; AKT3; FOXO1; PRKCA |
| Natural Killer Cell Signaling | PRKCE; RAC1; PRKCZ; MAPK1; RAC2; PTPN11; KIR2DL3; AKT2; PIK3CA; SYK; PRKCI; PIK3CB; PIK3C3; PRKD1; MAPK3; KRAS; PRKCD; PTPN6; PIK3C2A; LCK; RAF1; FYN; MAP2K2; PAK4; AKT1; PIK3R1; MAP2K1; PAK3; AKT3; VAV3; PRKCA |
| Cell Cycle: G1/S Checkpoint Regulation | HDAC4; SMAD3; SUV39H1; HDAC5; CDKN1B; BTRC; ATR; ABL1; E2F1; HDAC2; HDAC7A; RB1; HDAC11; HDAC9; CDK2; E2F2; HDAC3; TP53; CDKN1A; CCND1; E2F4; ATM; RBL2; SMAD4; CDKN2A; MYC; NRG1; GSK3B; RBL1; HDAC6 |
| T Cell Receptor Signaling | RAC1; ELK1; MAPK1; IKBKB; CBL; PIK3CA; FOS; NFKB2; PIK3CB; PIK3C3; MAPK8; MAPK3; KRAS; RELA; PIK3C2A; BTK; LCK; RAF1; IKBKG; RELB; FYN; MAP2K2; PIK3R1; CHUK; MAP2K1; NFKB1; ITK; BCL10; JUN; VAV3 |
| Death Receptor Signaling | CRADD; HSPB1; BID; BIRC4; TBK1; IKBKB; FADD; FAS; NFKB2; BCL2; MAP3K14; MAPK8; RIPK1; CASP8; DAXX; TNFRSF10B; RELA; TRAF2; TNF; IKBKG; RELB; CASP9; CHUK; APAF1; NFKB1; CASP2; BIRC2; CASP3; BIRC3 |
| FGF Signaling | RAC1; FGFR1; MET; MAPKAPK2; MAPK1; PTPN11; AKT2; PIK3CA; CREB1; PIK3CB; PIK3C3; MAPK8; MAPK3; MAPK13; PTPN6; PIK3C2A; MAPK14; RAF1; AKT1; PIK3R1; STAT3; MAP2K1; FGFR4; CRKL; ATF4; AKT3; PRKCA; HGF |
| GM-CSF Signaling | LYN; ELK1; MAPK1; PTPN11; AKT2; PIK3CA; CAMK2A; STAT5B; PIK3CB; PIK3C3; GNB2L1; BCL2L1; MAPK3; ETS1; KRAS; RUNX1; PIM1; PIK3C2A; RAF1; MAP2K2; AKT1; JAK2; PIK3R1; STAT3; MAP2K1; CCND1; AKT3; STAT1 |
| Amyotrophic Lateral Sclerosis Signaling | BID; IGF1; RAC1; BIRC4; PGF; CAPNS1; CAPN2; PIK3CA; BCL2; PIK3CB; PIK3C3; BCL2L1; CAPN1; PIK3C2A; TP53; CASP9; PIK3R1; RAB5A; CASP1; APAF1; VEGFA; BIRC2; BAX; AKT3; CASP3; BIRC3 |
| JAK/Stat Signaling | PTPN1; MAPK1; PTPN11; AKT2; PIK3CA; STAT5B; PIK3CB; PIK3C3; MAPK3; KRAS; SOCS1; STAT5A; PTPN6; PIK3C2A; RAF1; CDKN1A; MAP2K2; JAK1; AKT1; JAK2; PIK3R1; STAT3; MAP2K 1; FRAP1; AKT3; STAT1 |
| Nicotinate and Nicotinamide Metabolism | PRKCE; IRAK1; PRKAA2; EIF2AK2; GRK6; MAPK1; PLK1; AKT2; CDK8; MAPK8; MAPK3; PRKCD; PRKAA1; PBEF1; MAPK9; CDK2; PIM1; DYRK1A; MAP2K2; MAP2K1; PAK3; NT5E; TTK; CSNK1A1; BRAF; SGK |
| Chemokine Signaling | CXCR4; ROCK2; MAPK1; PTK2; FOS; CFL1; GNAQ; CAMK2A; CXCL12; MAPK8; MAPK3; KRAS; MAPK13; RHOA; CCR3; SRC; PPP1CC; MAPK14; NOX1; RAF1; MAP2K2; MAP2K1; JUN; CCL2; PRKCA |
| IL-2 Signaling | ELK1; MAPK1; PTPN11; AKT2; PIK3CA; SYK; FOS; STAT5B; PIK3CB; PIK3C3; MAPK8; MAPK3; KRAS; SOCS1; STAT5A; PIK3C2A; LCK; RAF1; MAP2K2; JAK1; AKT1; PIK3R1; MAP2K1; JUN; AKT3 |
| Synaptic Long Term Depression | PRKCE; IGF1; PRKCZ; PRDX6; LYN; MAPK1; GNAS; PRKCI; GNAQ; PPP2R1A; IGF1R; PRKD1; MAPK3; KRAS; GRN; PRKCD; NO53; NOS2A; PPP2CA; YWHAZ; RAF1; MAP2K2; PPP2R5C; MAP2K1; PRKCA |
| Estrogen Receptor Signaling | TAF4B; EP300; CARM1; PCAF; MAPK1; NCOR2; SMARCA4; MAPK3; NRIP1; KRAS; SRC; NR3C1; HDAC3; PPARGC1A; RBM9; NCOA3; RAF1; CREBBP; MAP2K2; NCOA2; MAP2K1; PRKDC; ESR1; ESR2 |
| Protein Ubiquitination Pathway | TRAF6; SMURF1; BIRC4; BRCA1; UCHL1; NEDD4; CBL; UBE2I; BTRC; HSPA5; USP7; USP10; FBW7; USP9X; STUB1; USP22; B2M; BIRC2; PARK2; USP8; USP1; VHL; HSP90AA1; BIRC3 |
| IL-10 Signaling | TRAF6; CCR1; ELK1; IKBKB; SP1; FOS; NFKB2; MAP3K14; MAPK8; MAPK13; RELA; MAPK14; TNF; IKBKG; RELB; MAP3K7; JAK1; CHUK; STAT3; NFKB1; JUN; IL1R1; IL6 |

TABLE C-continued

| CELLULAR FUNCTION | GENES |
|---|---|
| VDR/RXR Activation | PRKCE; EP300; PRKCZ; RXRA; GADD45A; HES1; NCOR2; SP1; PRKCI; CDKN1B; PRKD1; PRKCD; RUNX2; KLF4; YY1; NCOA3; CDKN1A; NCOA2; SPP1; LRP5; CEBPB; FOXO1; PRKCA |
| TGF-beta Signaling | EP300; SMAD2; SMURF1; MAPK1; SMAD3; SMAD1; FOS; MAPK8; MAPK3; KRAS; MAPK9; RUNX2; SERPINE1; RAF1; MAP3K7; CREBBP; MAP2K2; MAP2K1; TGFBR1; SMAD4; JUN; SMAD5 |
| Toll-like Receptor Signaling | IRAK1; EIF2AK2; MYD88; TRAF6; PPARA; ELK1; IKBKB; FOS; NFKB2; MAP3K14; MAPK8; MAPK13; RELA; TLR4; MAPK14; IKBKG; RELB; MAP3K7; CHUK; NFKB1; TLR2; JUN |
| p38 MAPK Signaling | HSPB1; IRAK1; TRAF6; MAPKAPK2; ELK1; FADD; FAS; CREB1; DDIT3; RPS6KA4; DAXX; MAPK13; TRAF2; MAPK14; TNF; MAP3K7; TGFBR1; MYC; ATF4; IL1R1; SRF; STAT1 |
| Neurotrophin/ TRK Signaling | NTRK2; MAPK1; PTPN11; PIK3CA; CREB1; FOS; PIK3CB; PIK3C3; MAPK8; MAPK3; KRAS; PIK3C2A; RAF1; MAP2K2; AKT1; PIK3R1; PDPK1; MAP2K1; CDC42; JUN; ATF4 |
| FXR/RXR Activation | INS; PPARA; FASN; RXRA; AKT2; SDC1; MAPK8; APOB; MAPK10; PPARG; MTTP; MAPK9; PPARGC1A; TNF; CREBBP; AKT1; SREBF1; FGFR4; AKT3; FOXO1 |
| Synaptic Long Term Potentiation | PRKCE; RAP1A; EP300; PRKCZ; MAPK1; CREB1; PRKCI; GNAQ; CAMK2A; PRKD1; MAPK3; KRAS; PRKCD; PPP1CC; RAF1; CREBBP; MAP2K2; MAP2K1; ATF4; PRKCA |
| Calcium Signaling | RAP1A; EP300; HDAC4; MAPK1; HDAC5; CREB1; CAMK2A; MYH9; MAPK3; HDAC2; HDAC7A; HDAC11; HDAC9; HDAC3; CREBBP; CALR; CAMKK2; ATF4; HDAC6 |
| EGF Signaling | ELK1; MAPK1; EGFR; PIK3CA; FOS; PIK3CB; PIK3C3; MAPK8; MAPK3; PIK3C2A; RAF1; JAK1; PIK3R1; STAT3; MAP2K1; JUN; PRKCA; SRF; STAT1 |
| Hypoxia Signaling in the Cardiovascular System | EDN1; PTEN; EP300; NQO1; UBE2I; CREB1; ARNT; HIF1A; SLC2A4; NOS3; TP53; LDHA; AKT1; ATM; VEGFA; JUN; ATF4; VHL; HSP90AA1 |
| LPS/IL-1 Mediated Inhibition of RXR Function | IRAK1; MYD88; TRAF6; PPARA; RXRA; ABCA1; MAPK8; ALDH1A1; GSTP1; MAPK9; ABCB1; TRAF2; TLR4; TNF; MAP3K7; NR1H2; SREBF1; JUN; IL1R1 |
| LXR/RXR Activation | FASN; RXRA; NCOR2; ABCA1; NFKB2; IRF3; RELA; NOS2A; TLR4; TNF; RELB; LDLR; NR1H2; NFKB1; SREBF1; IL1R1; CCL2; IL6; MMP9 |
| Amyloid Processing | PRKCE; CSNK1E; MAPK1; CAPNS1; AKT2; CAPN2; CAPN1; MAPK3; MAPK13; MAPT; MAPK14; AKT1; PSEN1; CSNK1A1; GSK3B; AKT3; APP |
| IL-4 Signaling | AKT2; PIK3CA; PIK3CB; PIK3C3; IRS1; KRAS; SOCS1; PTPN6; NR3C1; PIK3C2A; JAK1; AKT1; JAK2; PIK3R1; FRAP1; AKT3; RPS6KB1 |
| Cell Cycle: G2/MDNA Damage Checkpoint Regulation | EP300; PCAF; BRCA1; GADD45A; PLK1; BTRC; CHEK1; ATR; CHEK2; YWHAZ; TP53; CDKN1A; PRKDC; ATM; SFN; CDKN2A |
| Nitric Oxide Signaling in the Cardiovascular System | KDR; FLT1; PGF; AKT2; PIK3CA; PIK3CB; PIK3C3; CAV1; PRKCD; N053; PIK3C2A; AKT1; PIK3R1; VEGFA; AKT3; HSP90AA1 |
| Purine Metabolism | NME2; SMARCA4; MYH9; RRM2; ADAR; EIF2AK4; PKM2; ENTPD1; RAD51; RRM2B; TJP2; RAD51C; NT5E; POLD1; NME1 |
| cAMP-mediated Signaling | RAP1A; MAPK1; GNAS; CREB1; CAMK2A; MAPK3; SRC; RAF1; MAP2K2; STAT3; MAP2K1; BRAF; ATF4 |
| Mitochondrial Dysfunction | SOD2; MAPK8; CASP8; MAPK10; MAPK9; CASP9; PARK7; PSEN1; PARK2; APP; CASP3 |
| Notch Signaling | HES1; JAG1; NUMB; NOTCH4; ADAM17; NOTCH2; PSEN1; NOTCH3; NOTCH1; DLL4 |
| Endoplasmic Reticulum Stress Pathway | HSPA5; MAPK8; XBP1; TRAF2; ATF6; CASP9; ATF4; EIF2AK3; CASP3 |

TABLE C-continued

| CELLULAR FUNCTION | GENES |
|---|---|
| Pyrimidine Metabolism | NME2; AICDA; RRM2; EIF2AK4; ENTPD1; RRM2B; NT5E; POLD1; NME1 |
| Parkinson's Signaling | UCHL1; MAPK8; MAPK13; MAPK14; CASP9; PARK7; PARK2; CASP3 |
| Cardiac & Beta Adrenergic Signaling | GNAS; GNAQ; PPP2R1A; GNB2L1; PPP2CA; PPP1CC; PPP2R5C |
| Glycolysis/Gluconeogenesis | HK2; GCK; GPI; ALDH1A1; PKM2; LDHA; HK1 |
| Interferon Signaling | IRF1; SOCS1; JAK1; JAK2; IFITM1; STAT1; IFIT3 |
| Sonic Hedgehog Signaling | ARRB2; SMO; GLI2; DYRK1A; GLI1; GSK3B; DYRK1B |
| Glycerophospholipid Metabolism | PLD1; GRN; GPAM; YWHAZ; SPHK1; SPHK2 |
| Phospholipid Degradation | PRDX6; PLD1; GRN; YWHAZ; SPHK1; SPHK2 |
| Tryptophan Metabolism | SIAH2; PRMT5; NEDD4; ALDH1A1; CYP1B1; SIAH1 |
| Lysine Degradation | SUV39H1; EHMT2; NSD1; SETD7; PPP2R5C |
| Nucleotide Excision Repair Pathway | ERCC5; ERCC4; XPA; XPC; ERCC1 |
| Starch and Sucrose Metabolism | UCHL1; HK2; GCK; GPI; HK1 |
| Aminosugars Metabolism | NQO1; HK2; GCK; HK1 |
| Arachidonic Acid Metabolism | PRDX6; GRN; YWHAZ; CYP1B1 |
| Circadian Rhythm Signaling | CSNK1E; CREB1; ATF4; NR1D1 |
| Coagulation System | BDKRB1; F2R; SERPINE1; F3 |
| Dopamine Receptor Signaling | PPP2R1A; PPP2CA; PPP1CC; PPP2R5C |
| Glutathione Metabolism | IDH2; GSTP1; ANPEP; IDH1 |
| Glycerolipid Metabolism | ALDH1A1; GPAM; SPHK1; SPHK2 |
| Linoleic Acid Metabolism | PRDX6; GRN; YWHAZ; CYP1B1 |
| Methionine Metabolism | DNMT1; DNMT3B; AHCY; DNMT3A |
| Pyruvate Metabolism | GLO1; ALDH1A1; PKM2; LDHA |
| Arginine and Proline Metabolism | ALDH1A1; NOS3; NOS2A |
| Eicosanoid Signaling | PRDX6; GRN; YWHAZ |
| Fructose and Mannose Metabolism | HK2; GCK; HK1 |
| Galactose Metabolism | HK2; GCK; HK1 |
| Stilbene, Coumarine and Lignin Biosynthesis | PRDX6; PRDX1; TYR |
| Antigen Presentation Pathway | CALR; B2M |
| Biosynthesis of Steroids | NQO1; DHCR7 |
| Butanoate Metabolism | ALDH1A1; NLGN1 |
| Citrate Cycle | IDH2; IDH1 |
| Fatty Acid Metabolism | ALDH1A1 ; CYP1B1 |

TABLE C-continued

| CELLULAR FUNCTION | GENES |
| --- | --- |
| Glycerophospholipid Metabolism | PRDX6; CHKA |
| Histidine Metabolism | PRMT5; ALDH1A1 |
| Inositol Metabolism | ERO1L; APEX1 |
| Metabolism of Xenobiotics by Cytochrome p450 | GSTP1; CYP1B1 |
| Methane Metabolism | PRDX6; PRDX1 |
| Phenylalanine Metabolism | PRDX6; PRDX1 |
| Propanoate Metabolism | ALDH1A1; LDHA |
| Selenoamino Acid Metabolism | PRMT5; AHCY |
| Sphingolipid Metabolism | SPHK1; SPHK2 |
| Aminophosphonate Metabolism | PRMT5 |
| Androgen and Estrogen Metabolism | PRMT5 |
| Ascorbate and Aldarate Metabolism | ALDH1A1 |
| Bile Acid Biosynthesis | ALDH1A1 |
| Cysteine Metabolism | LDHA |
| Fatty Acid Biosynthesis | FASN |
| Glutamate Receptor Signaling | GNB2L1 |
| NRF2-mediated Oxidative Stress Response | PRDX1 |
| Pentose Phosphate Pathway | GPI |
| Pentose and Glucuronate Interconversions | UCHL1 |
| Retinol Metabolism | ALDH1A1 |
| Riboflavin Metabolism | TYR |
| Tyrosine Metabolism | PRMT5, TYR |
| Ubiquinone Biosynthesis | PRMT5 |
| Valine, Leucine and Isoleucine Degradation | ALDH1A1 |
| Glycine, Serine and Threonine Metabolism | CHKA |
| Lysine Degradation | ALDH1A1 |
| Pain/Taste | TRPM5; TRPA1 |
| Pain | TRPM7; TRPC5; TRPC6; TRPC1; Cnr1; cnr2; Grk2; Trpa1; Pomc; Cgrp; Crf; Pka; Era; Nr2b; TRPM5; Prkaca; Prkacb; Prkar1a; Prkar2a |
| Mitochondrial Function | AIF; CytC; SMAC (Diablo); Aifm-1; Aifm-2 |
| Developmental Neurology | BMP-4; Chordin (Chrd); Noggin (Nog); WNT (Wnt2; Wnt2b; Wnt3a; Wnt4; Wnt5a; Wnt6; Wnt7b; Wnt8b; Wnt9a; Wnt9b; Wnt10a; Wnt10b; Wnt16); beta-catenin; Dkk-1; Frizzled related proteins; Otx-2; Gbx2; FGF-8; Reelin; Dab1; unc-86 (Pou4f1 or Brn3a); Numb; Reln |

Embodiments of the invention also relate to methods and compositions related to knocking out genes, amplifying genes and repairing particular mutations associated with DNA repeat instability and neurological disorders (Robert D. Wells, Tetsuo Ashizawa, Genetic Instabilities and Neurological Diseases, Second Edition, Academic Press, Oct. 13, 2011—Medical). Specific aspects of tandem repeat sequences have been found to be responsible for more than twenty human diseases (New insights into repeat instability: role of RNA.DNA hybrids. McIvor E I, Polak U, Napierala M. RNA Biol. 2010 September-October; 7(5):551-8). The CRISPR-Cas system may be harnessed to correct these defects of genomic instability.

A further aspect of the invention relates to utilizing the CRISPR-Cas system for correcting defects in the EMP2A and EMP2B genes that have been identified to be associated with Lafora disease. Lafora disease is an autosomal recessive condition which is characterized by progressive myoclonus epilepsy which may start as epileptic seizures in adolescence. A few cases of the disease may be caused by mutations in genes yet to be identified. The disease causes seizures, muscle spasms, difficulty walking, dementia, and eventually death. There is currently no therapy that has proven effective against disease progression. Other genetic abnormalities associated with epilepsy may also be targeted by the CRISPR-Cas system and the underlying genetics is further described in Genetics of Epilepsy and Genetic Epilepsies, edited by Giuliano Avanzini, Jeffrey L. Noebels, Mariani Foundation Paediatric Neurology:20; 2009).

In yet another aspect of the invention, the CRISPR-Cas system may be used to correct ocular defects that arise from several genetic mutations further described in Genetic Diseases of the Eye, Second Edition, edited by Elias I. Traboulsi, Oxford University Press, 2012.

Several further aspects of the invention relate to correcting defects associated with a wide range of genetic diseases which are further described on the website of the National Institutes of Health under the topic subsection Genetic Disorders (website at health.nih.gov/topic/GeneticDisorders). The genetic brain diseases may include but are not limited to Adrenoleukodystrophy, Agenesis of the Corpus Callosum, Aicardi Syndrome, Alpers' Disease, Alzheimer's Disease, Barth Syndrome, Batten Disease, CADASIL, Cerebellar Degeneration, Fabry's Disease, Gerstmann-Straussler-Scheinker Disease, Huntington's Disease and other Triplet Repeat Disorders, Leigh's Disease, Lesch-Nyhan Syndrome, Menkes Disease, Mitochondrial Myopathies and NINDS Colpocephaly. These diseases are further described on the website of the National Institutes of Health under the subsection Genetic Brain Disorders.

In some embodiments, the condition may be neoplasia. In some embodiments, where the condition is neoplasia, the genes to be targeted are any of those listed in Table A (in this case PTEN and so forth). In some embodiments, the condition may be Age-related Macular Degeneration. In some embodiments, the condition may be a Schizophrenic Disorder. In some embodiments, the condition may be a Trinucleotide Repeat Disorder. In some embodiments, the condition may be Fragile X Syndrome. In some embodiments, the condition may be a Secretase Related Disorder. In some embodiments, the condition may be a Prion—related disorder. In some embodiments, the condition may be ALS. In some embodiments, the condition may be a drug addiction. In some embodiments, the condition may be Autism. In some embodiments, the condition may be Alzheimer's Disease. In some embodiments, the condition may be inflammation. In some embodiments, the condition may be Parkinson's Disease.

Examples of proteins associated with Parkinson's disease include but are not limited to α-synuclein, DJ-1, LRRK2, PINK1, Parkin, UCHL1, Synphilin-1, and NURR1.

Examples of addiction-related proteins may include ABAT for example.

Examples of inflammation-related proteins may include the monocyte chemoattractant protein-1 (MCP1) encoded by the Ccr2 gene, the C-C chemokine receptor type 5 (CCR5) encoded by the Ccr5 gene, the IgG receptor IIB (FCGR2b, also termed CD32) encoded by the Fcgr2b gene, or the Fc epsilon R1g (FCER1g) protein encoded by the Fcer1g gene, for example.

Examples of cardiovascular diseases associated proteins may include IL1B (interleukin 1, beta), XDH (xanthine dehydrogenase), TP53 (tumor protein p53), PTGIS (prostaglandin I2 (prostacyclin) synthase), MB (myoglobin), IL4 (interleukin 4), ANGPT1 (angiopoietin 1), ABCG8 (ATP-binding cassette, sub-family G (WHITE), member 8), or CTSK (cathepsin K), for example.

Examples of Alzheimer's disease associated proteins may include the very low density lipoprotein receptor protein (VLDLR) encoded by the VLDLR gene, the ubiquitin-like modifier activating enzyme 1 (UBA1) encoded by the UBA1 gene, or the NEDD8-activating enzyme E1 catalytic subunit protein (UBE1C) encoded by the UBA3 gene, for example.

Examples of proteins associated Autism Spectrum Disorder may include the benzodiazapine receptor (peripheral) associated protein 1 (BZRAP1) encoded by the BZRAP1 gene, the AF4/FMR2 family member 2 protein (AFF2) encoded by the AFF2 gene (also termed MFR2), the fragile X mental retardation autosomal homolog 1 protein (FXR1) encoded by the FXR1 gene, or the fragile X mental retardation autosomal homolog 2 protein (FXR2) encoded by the FXR2 gene, for example.

Examples of proteins associated Macular Degeneration may include the ATP-binding cassette, sub-family A (ABC1) member 4 protein (ABCA4) encoded by the ABCR gene, the apolipoprotein E protein (APOE) encoded by the APOE gene, or the chemokine (C-C motif) Ligand 2 protein (CCL2) encoded by the CCL2 gene, for example.

Examples of proteins associated Schizophrenia may include NRG1, ErbB4, CPLX1, TPH1, TPH2, NRXN1, GSK3A, BDNF, DISC1, GSK3B, and combinations thereof.

Examples of proteins involved in tumor suppression may include ATM (ataxia telangiectasia mutated), ATR (ataxia telangiectasia and Rad3 related), EGFR (epidermal growth factor receptor), ERBB2 (v-erb-b2 erythroblastic leukemia viral oncogene homolog 2), ERBB3 (v-erb-b2 erythroblastic leukemia viral oncogene homolog 3), ERBB4 (v-erb-b2 erythroblastic leukemia viral oncogene homolog 4), Notch 1, Notch2, Notch 3, or Notch 4, for example.

Examples of proteins associated with a secretase disorder may include PSENEN (presenilin enhancer 2 homolog (C. elegans)), CTSB (cathepsin B), PSEN1 (presenilin 1), APP (amyloid beta (A4) precursor protein), APH1B (anterior pharynx defective 1 homolog B (C. elegans)), PSEN2 (presenilin 2 (Alzheimer disease 4)), or BACE1 (beta-site APP-cleaving enzyme 1), for example.

Examples of proteins associated with Amyotrophic Lateral Sclerosis may include SOD1 (superoxide dismutase 1), ALS2 (amyotrophic lateral sclerosis 2), FUS (fused in sarcoma), TARDBP (TAR DNA binding protein), VAGFA (vascular endothelial growth factor A), VAGFB (vascular endothelial growth factor B), and VAGFC (vascular endothelial growth factor C), and any combination thereof.

Examples of proteins associated with prion diseases may include SOD1 (superoxide dismutase 1), ALS2 (amyotrophic lateral sclerosis 2), FUS (fused in sarcoma), TARDBP (TAR DNA binding protein), VAGFA (vascular endothelial growth factor A), VAGFB (vascular endothelial growth factor B), and VAGFC (vascular endothelial growth factor C), and any combination thereof.

Examples of proteins related to neurodegenerative conditions in prion disorders may include A2M (Alpha-2-Macroglobulin), AATF (Apoptosis antagonizing transcription factor), ACPP (Acid phosphatase prostate), ACTA2 (Actin alpha 2 smooth muscle aorta), ADAM22 (ADAM metallopeptidase domain), ADORA3 (Adenosine A3 receptor), or ADRA1D (Alpha-1D adrenergic receptor for Alpha-1D adrenoreceptor), for example.

Examples of proteins associated with Immunodeficiency may include A2M [alpha-2-macroglobulin]; AANAT [arylalkylamine N-acetyltransferase]; ABCA1 [ATP-binding cassette, sub-family A (ABC1), member 1]; ABCA2 [ATP-binding cassette, sub-family A (ABC1), member 2]; or ABCA3 [ATP-binding cassette, sub-family A (ABC1), member 3]; for example.

Examples of proteins associated with Trinucleotide Repeat Disorders include AR (androgen receptor), FMR1 (fragile X mental retardation 1), HTT (huntingtin), or DMPK (dystrophia myotonica-protein kinase), FXN (frataxin), ATXN2 (ataxin 2), for example.

Examples of proteins associated with Neurotransmission Disorders include SST (somatostatin), NOS1 (nitric oxide synthase 1 (neuronal)), ADRA2A (adrenergic, alpha-2A-, receptor), ADRA2C (adrenergic, alpha-2C-, receptor), TACR1 (tachykinin receptor 1), or HTR2c (5-hydroxytryptamine (serotonin) receptor 2C), for example.

Examples of neurodevelopmental-associated sequences include A2BP1 [ataxin 2-binding protein 1], AADAT [aminoadipate aminotransferase], AANAT [arylalkylamine N-acetyltransferase], ABAT [4-aminobutyrate aminotransferase], ABCA1 [ATP-binding cassette, sub-family A (ABC1), member 1], or ABCA13 [ATP-binding cassette, sub-family A (ABC1), member 13], for example.

Further examples of preferred conditions treatable with the present system include may be selected from: Aicardi-Goutières Syndrome; Alexander Disease; Allan-Herndon-Dudley Syndrome; POLG-Related Disorders; Alpha-Mannosidosis (Type II and III); Alström Syndrome; Angelman; Syndrome; Ataxia-Telangiectasia; Neuronal Ceroid-Lipofuscinoses; Beta-Thalassemia; Bilateral Optic Atrophy and (Infantile) Optic Atrophy Type 1; Retinoblastoma (bilateral); Canavan Disease; Cerebrooculofacioskeletal Syndrome 1 [COFS1]; Cerebrotendinous Xanthomatosis; Cornelia de Lange Syndrome; MAPT-Related Disorders; Genetic Prion Diseases; Dravet Syndrome; Early-Onset Familial Alzheimer Disease; Friedreich Ataxia [FRDA]; Fryns Syndrome; Fucosidosis; Fukuyama Congenital Muscular Dystrophy; Galactosialidosis; Gaucher Disease; Organic Acidemias; Hemophagocytic Lymphohistiocytosis; Hutchinson-Gilford Progeria Syndrome; Mucolipidosis II; Infantile Free Sialic Acid Storage Disease; PLA2G6-Associated Neurodegeneration; Jervell and Lange-Nielsen Syndrome; Junctional Epidermolysis Bullosa; Huntington Disease; Krabbe Disease (Infantile); Mitochondrial DNA-Associated Leigh Syndrome and NARP; Lesch-Nyhan Syndrome; LIS1-Associated Lissencephaly; Lowe Syndrome; Maple Syrup Urine Disease; MECP2 Duplication Syndrome; ATP7A-Related Copper Transport Disorders; LAMA2-Related Muscular Dystrophy; Arylsulfatase A Deficiency; Mucopolysaccharidosis Types I, II or III; Peroxisome Biogenesis Disorders, Zellweger Syndrome Spectrum; Neurodegeneration with Brain Iron Accumulation Disorders; Acid Sphingomyelinase Deficiency; Niemann-Pick Disease Type C; Glycine Encephalopathy; ARX-Related Disorders; Urea Cycle Disorders; COL1A1/2-Related Osteogenesis Imperfecta; Mitochondrial DNA Deletion Syndromes; PLP1-Related Disorders; Perry Syndrome; Phelan-McDermid Syndrome; Glycogen Storage Disease Type II (Pompe Disease) (Infantile); MAPT-Related Disorders; MECP2-Related Disorders; Rhizomelic Chondrodysplasia Punctata Type 1; Roberts Syndrome; Sandhoff Disease; Schindler Disease—Type 1; Adenosine Deaminase Deficiency; Smith-Lemli-Opitz Syndrome; Spinal Muscular Atrophy; Infantile-Onset Spinocerebellar Ataxia; Hexosaminidase A Deficiency; Thanatophoric Dysplasia Type 1; Collagen Type VI-Related Disorders; Usher Syndrome Type I; Congenital Muscular Dystrophy; Wolf-Hirschhorn Syndrome; Lysosomal Acid Lipase Deficiency; and Xeroderma Pigmentosum.

As will be apparent, it is envisaged that the present system can be used to target any polynucleotide sequence of interest. Some examples of conditions or diseases that might be usefully treated using the present system are included in the Tables above and examples of genes currently associated with those conditions are also provided there. However, the genes exemplified are not exhaustive.

For example, "wild type StCas9" refers to wild type Cas9 from S thermophilus, the protein sequence of which is given in the SwissProt database under accession number G3ECR1. Similarly, S pyogenes Cas9 is included in SwissProt under accession number Q99ZW2.

The ability to use CRISPR-Cas systems to perform efficient and cost effective gene editing and manipulation will allow the rapid selection and comparison of single and multiplexed genetic manipulations to transform such genomes for improved production and enhanced traits. In this regard reference is made to US patents and publications: U.S. Pat. No. 6,603,061—Agrobacterium-Mediated Plant Transformation Method; U.S. Pat. No. 7,868,149—Plant Genome Sequences and Uses Thereof and US 2009/0100536—Transgenic Plants with Enhanced Agronomic Traits, all the contents and disclosure of each of which are herein incorporated by reference in their entirety. In the practice of the invention, the contents and disclosure of Morrell et al "Crop genomics:advances and applications" Nat Rev Genet. 2011 Dec. 29; 13(2):85-96 are also herein incorporated by reference in their entirety.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Methodological Improvement to Simplify Cloning and Delivery

Rather than encoding the U6-promoter and guide RNA on a plasmid, Applicants amplified the U6 promoter with a DNA oligo to add on the guide RNA. The resulting PCR product may be transfected into cells to drive expression of the guide RNA.

Example primer pair that allows the generation a PCR product consisting of U6-promoter::guideRNA targeting human Emx1 locus:

Forward Primer: AAACTCTAGAgagggcctatttccatgattc (SEQ ID NO: 86)

Reverse Primer (carrying the guide RNA, which is underlined):

```
                                        (SEQ ID NO: 87)
acctctagAAAAAAAGCACCGACTCGGTGCCACTTTTTCAAGTTGATAAC

GGACTAGCCTTATTTTAACTTGCTATGCTGTTTTGTTTCCAAAACAGCAT

AGCTCTAAAACCCCTAGTCATTGGAGGTGACGGTGTTTCGTCCTTTCCAC aag
```

Example 2: Methodological Improvement to Improve Activity

Rather than use pol3 promoters, in particular RNA polymerase III (e.g. U6 or H1 promoters), to express guide RNAs in eukaryotic cells, Applicants express the T7 polymerase in eukaryotic cells to drive expression of guide RNAs using the T7 promoter.

One example of this system may involve introduction of three pieces of DNA:
1. expression vector for Cas9
2. expression vector for T7 polymerase
3. expression vector containing guideRNA fused to the T7 promoter

Example 3: Methodological Improvement to Reduce Toxicity of Cas9: Delivery of Cas9 in the Form of mRNA Delivery of Cas9 in the form of mRNA enables transient expression of Cas9 in cells, to reduce toxicity. For example, humanized SpCas9 may be amplified using the following primer pair:

Forward Primer (to add on T7 promoter for in vitro transcription):

```
                                        (SEQ ID NO: 88)
TAATACGACTCACTATAGGAAGTGCGCCACCATGGCCCCAAAGAAGAAGC
GG

Reverse Primer (to add on polyA tail):
                                        (SEQ ID NO: 89)
GGTTTTTTTTTTTTTTTTTTTTTTTTTTTTTTttcttaCTTTTTCTTTTT
TGCCTGGCCG
```

Applicants transfect the Cas9 mRNA into cells with either guide RNA in the form of RNA or DNA cassettes to drive guide RNA expression in eukaryotic cells.

Example 4: Methodological Improvement to Reduce Toxicity of Cas9: Use of an Inducible Promoter Applicants transiently turn on Cas9 expression only when it is needed for carrying out genome modification. Examples of inducible system include tetracycline inducible promoters (Tet-On or Tet-Off), small molecule two-hybrid transcription activations systems (FKBP, ABA, etc), or light inducible systems (Phytochrome, LOV domains, or cryptochrome).

Example 5: Improvement of the Cas9 System for In Vivo Application

Figure 5:
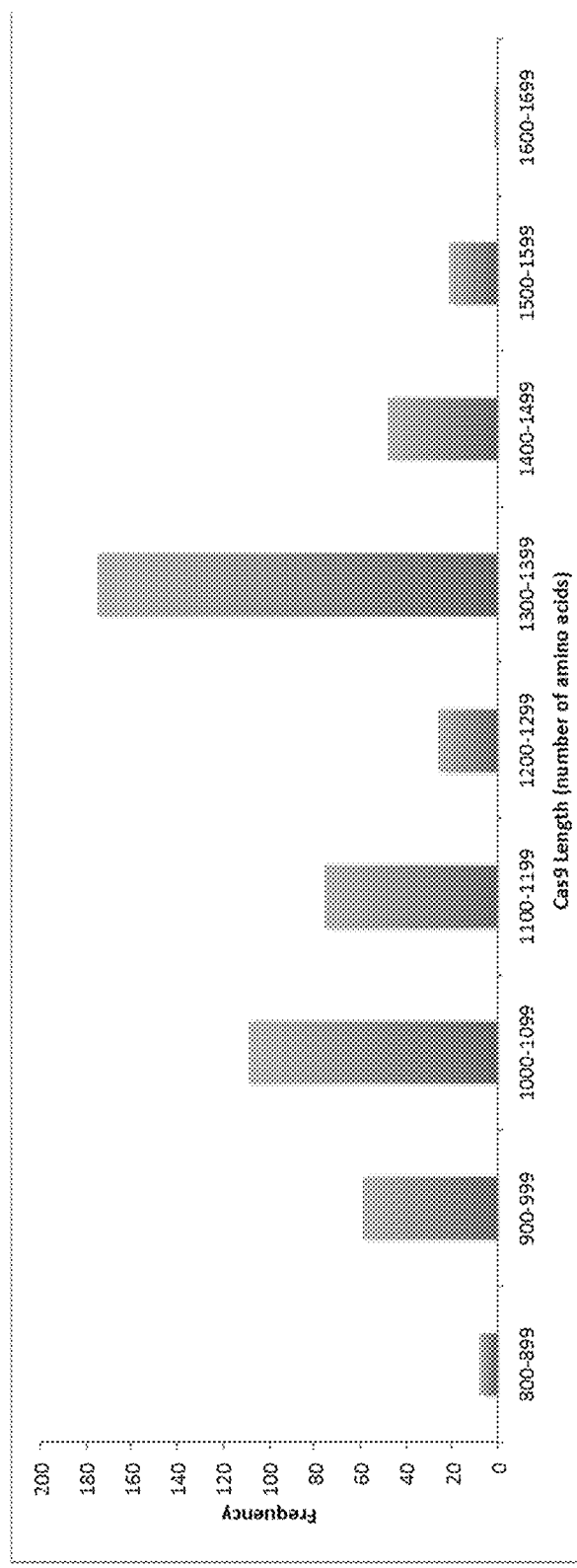
FIG. 5 shows a graph representing the length distribution of Cas9 orthologs.
Figure 6A:
Figure 6M:

Applicants conducted a Metagenomic search for a Cas9 with small molecular weight. Most Cas9 homologs are fairly large. For example the SpCas9 is around 1368aa long, which is too large to be easily packaged into viral vectors for delivery. A graph representing the length distribution of Cas9 homologs is generated from sequences deposited in GenBank (FIG. 5). Some of the sequences may have been mis-annotated and therefore the exact frequency for each length may not necessarily be accurate. Nevertheless it provides a glimpse at distribution of Cas9 proteins and suggest that there are shorter Cas9 homologs.

Through computational analysis, Applicants found that in the bacterial strain *Campylobacter*, there are two Cas9 proteins with less than 1000 amino acids. The sequence for one Cas9 from *Campylobacter jejuni* is presented below. At this length, CjCas9 can be easily packaged into AAV, lentiviruses, Adenoviruses, and other viral vectors for robust delivery into primary cells and in vivo in animal models. In a preferred embodiment of the invention, the Cas9 protein from *S. aureus* is used.

```
>Campylobacter jejuni Cas9 (CjCas9)
                                        (SEQ ID NO: 90)
MARILAFDIGISSIGWAFSENDELKDCGVRIFTKVENPKTGESLALPRRL

ARSARKRLARRKARLNHLKHLIANEFKLNYEDYQSFDESLAKAYKGSLIS

PYELRFRALNELLSKQDFARVILHIAKRRGYDDIKNSDDKEKGAILKAIK

QNEEKLANYQSVGEYLYKEYFQKFKENSKEFTNVRNKKESYERCIAQSFL

KDELKLIFKKQREFGFSFSKKFEEEVLSVAFYKRALKDFSHLVGNCSFFT

DEKRAPKNSPLAFMFVALTRIINLLNNLKNTEGILYTKDDLNALLNEVLK

NGTLTYKQTKKLLGLSDDYEFKGEKGTYFIEFKKYKEFIKALGEHNLSQD

DLNEIAKDITLIKDEIKLKKALAKYDLNQNQIDSLSKLEFKDHLNISFKA

LKLVTPLMLEGKKYDEACNELNLKVAINEDKKDFLPAFNETYYKDEVTNP

VVLRAIKEYRKVLNALLKKYGKVHKINIELAREVGKNHSQRAKIEKEQNE

NYKAKKDAELECEKLGLKINSKNILKLRLFKEQKEFCAYSGEKIKISDLQ

DEKMLEIDHIYPYSRSFDDSYMNKVLVFTKQNQEKLNQTPFEAFGNDSAK

WQKIEVLAKNLPTKKQKRILDKNYKDKEQKNFKDRNLNDTRYIARLVLNY

TKDYLDFLPLSDDENTKLNDTQKGSKVHVEAKSGMLTSALRHTWGFSAKD

RNNHLHHAIDAVIIAYANNSIVKAFSDFKKEQESNSAELYAKKISELDYK

NKRKFFEPFSGFRQKVLDKIDEIFVSKPERKKPSGALHEETFRKEEEFYQ

SYGGKEGVLKALELGKIRKVNGKIVKNGDMFRVDIFKHKKTNKFYAVPIY

TMDFALKVLPNKAVARSKKGEIKDWILMDENYEFCFSLYKDSLILIQTKD

MQEPEFVYYNAFTSSTVSLIVSKHDNKFETLSKNQKILFKNANEKEVIAK

SIGIQNLKVFEKYIVSALGEVTKAEFRQREDFKK.
```

The putative tracrRNA element for this CjCas9 is:

(SEQ ID NO: 91)
TATAATCTCATAAGAAATTTAAAAAGGGACTAAAATAAAGAGTTTGCG
GGACTCTGCGGGGTTACAATCCCCTAAAACCGCTTTTAAAATT

The Direct Repeat sequence is:

(SEQ ID NO: 92)
ATTTTACCATAAAGAAATTTAAAAAGGGACTAAAAC

An example of a chimeric guideRNA for CjCas9 is:

(SEQ ID NO: 93)
NNNNNNNNNNNNNNNNNNNNNGUUUUAGUCCCGAAAGGGACUAAAAU
AAAGAGUUUGCGGGACUCUGCGGGGUUACAAUCCCCUAAAACCGCUUUU

Example 6: Cas9 Optimization

For enhanced function or to develop new functions, Applicants generate chimeric Cas9 proteins by combining fragments from different Cas9 homologs. For example, two example chimeric Cas9 proteins:

For example, Applicants fused the N-term of St1Cas9 (fragment from this protein is in bold) with C-term of SpCas9 (fragment from this protein is underlined).

>St1(N)Sp(C)Cas9
(SEQ ID NO: 94)
MSDLVLGLDIGIGSVGVGILNKVTGEIIHKNSRIFPAAQAENNLVRRTN

RQGRRLARRKKEIRRVRLNRLFEESGLITDFTKISINLNPYQLRVKGLTD

ELSNEELFIALKNMVKHRGISYLDDASDDGNSSVGDYAQIVKENSKQLET

KTPGQIQLERYQTYGQLRGDFTVEKDGKKHRLINVFPTSAYRSEALRILQ

TQQEFNPQITDEFINRYLEILTGKRKYYHGPGNEKSRTDYGRYRTSGETL

DNIFGILIGKCTFYPDEFRAAKASYTAQEFNLLNDLNNLTVPTETKKLSK

EQKNQIINYVKNEKAMGPAKLFKYIAKLLSCDVADIKGYRIDKSGKAEIH

TFEAYRKMKTLETLDIEQMDRETLDKLAYVLTLNTEREGIQEALEHEFAD

GSFSQKQVDELVQFRKANSSIFGKGWHNFSVKLMMELIPELYETSEEQMT

ILTRLGKQKTTSSSNKTKYIDEKLLTEEIYNPVVAKSVRQAIKIVNAAIK

EYGDFDNIVIEMARENQTTQKGQKNSRERMKRIEEGIKELGSQILKEHPV

ENTQLQNEKLYLYYLQNGRDMYVDQELDINRLSDYDVDHIVPQSFLKDDS

IDNKVLTRSDKNRGKSDNVPSEEVVKKMKNYWRQLLNAKLITQRKFDNLT

KAERGGLSELDKAGFIKRQLVETRQITKHVAQILDSRMNTKYDENDKLIR

EVKVITLKSKLVSDFRKDFQFYKVREINNYHHAHDAYLNAVVGTALIKKY

PKLESEFVYGDYKVYDVRKMIAKSEQEIGKATAKYFFYSNIMNFFKTEIT

LANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEK

GKSKKLKSVKELLGITIMERSSFEKNPIDFLEAKGYKEVKKDLIIKLPKY

SLFELENGRKRMLASAGELQKGNELALPSKYVNFLYLASHYEKLKGSPED

NEQKQLFVEQHKHYLDEIIEQISEFSKRVILADANLDKVLSAYNKHRDKP

IREQAENIIHLFTLTNLGAPAAFKYFDTTIDRKRYTSTKEVLDATLIHQS

ITGLYETRIDLSQLGGD

>Sp(N)St1(C)Cas9
(SEQ ID NO: 95)
MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARETNEDDEKKAIQKIQKANKDEKDAAMLKAANQYNG

KAELPHSVFHGHKQLATKIRLWHQQGERCLYTGKTISIHDLINNSNQFEV

DHILPLSITFDDSLANKVLVYATANQEKGQRTPYQALDSMDDAWSFRELK

AFVRESKTLSNKKKEYLLTEEDISKFDVRKKFIERNLVDTRYASRVVLNA

LQEHFRAHKIDTKVSVVRGQFTSQLRRHWGIEKTRDTYHHHAVDALHAAS

SQLNLWKKQKNTLVSYSEDQLLDIETGELISDDEYKESVFKAPYQHFVDT

LKSKEFEDSILFSYQVDSKFNRKISDATIYATRQAKVGKDKADETYVLGK

IKDIYTQDGYDAFMKIYKKDKSKFLMYRHDPQTFEKVIEPILENYPNKQI

NEKGKEVPCNPFLKYKEEHGYIRKYSKKGNGPEIKSLKYYDSKLGNHIDI

TPKDSNNKVVLQSVSPWRADVYFNKTTGKYEILGLKYADLQFEKGTGTYK

ISQEKYNDIKKKEGVDSDSEFKFTLYKNDLLLVKDTETKEQQLFRFLSRT

MPKQKHYVELKPYDKQKFEGGEALIKVLGNVANSGQCKKGLGKSNISIYK

VRTDVLGNQHIIKNEGDKPKLDF

The benefit of making chimeric Cas9 include:
reduce toxicity
improve expression in eukaryotic cells
enhance specificity
reduce molecular weight of protein, make protein smaller by combining the smallest domains from different Cas9 homologs.
Altering the PAM sequence requirement Example 7: Utilization of Cas9 as a Generic DNA Binding Protein Applicants used Cas9 as a generic DNA binding protein by mutating the two catalytic domains (D10 and H840)

responsible for cleaving both strands of the DNA target. In order to upregulate gene transcription at a target locus Applicants fused the transcriptional activation domain (VP64) to Cas9. Applicants hypothesized that it would be important to see strong nuclear localization of the Cas9-VP64 fusion protein because transcription factor activation strength is a function of time spent at the target. Therefore, Applicants cloned a set of Cas9-VP64-GFP constructs, transfected them into 293 cells and assessed their localization under a fluorescent microscope 12 hours post-transfection.

The same constructs were cloned as a 2A-GFP rather than a direct fusion in order to functionally test the constructs without a bulky GFP present to interfere. Applicants elected to target the Sox2 locus with the Cas9 transactivator because it could be useful for cellular reprogram and the locus has already been validated as a target for TALE-TF mediated transcriptional activation. For the Sox2 locus Applicants chose eight targets near the transcriptional start site (TSS). Each target was 20 bp long with a neighboring NGG protospacer adjacent motif (PAM). Each Cas9-VP64 construct was co-transfected with each PCR generated chimeric crispr RNA (chiRNA) in 293 cells. 72 hours post transfection the transcriptional activation was assessed using RT-qPCR.

To further optimize the transcriptional activator, Applicants titrated the ratio of chiRNA (Sox2.1 and Sox2.5) to Cas9 (NLS-VP64-NLS-hSpCas9-NLS-VP64-NLS), transfected into 293 cells, and quantified using RT-qPCR. These results indicate that Cas9 can be used as a generic DNA binding domain to upregulate gene transcription at a target locus.

Applicants designed a second generation of constructs. (see list below).

--- pLenti-EF1a-GFP-2A-6xHis-NLS-VP64-NLS-hSpCsn1(D10A, H840A)-NLS ("6xHis" disclosed as SEQ ID NO: 96)
pLenti-EF1a-GFP-2A-6xHis-NLS-VP64-NLS-hSpCsn1(D10A, H840A) ("6xHis" disclosed as SEQ ID NO: 96)
pLenti-EF1a-GFP-2A-6xHis-NLS-VP64-NLS-NLS-hSpCsn1(D10A, H840A) ("6xHis" disclosed as SEQ ID NO: 96)
pLenti-EF1a-GFP-2A-6xHis-NLS-hSpCsn1 (D10A, H840A)-NLS ("6xHis" disclosed as SEQ ID NO: 96)
pLenti-EF1a-GFP-2A-6xHis-NLS-hSpCsn1 (D10A, H840A) ("6xHis" disclosed as SEQ ID NO: 96)
pLenti-EF1a-GFP-2A-6xHis-NLS-NLS-hSpCsn1(D10A, H840A) ("6xHis" disclosed as SEQ ID NO: 96)

---

Applicants use these constructs to assess transcriptional activation (VP64 fused constructs) and repression (Cas9 only) by RT-qPCR. Applicants assess the cellular localization of each construct using anti-His antibody, nuclease activity using a Surveyor nuclease assay, and DNA binding affinity using a gel shift assay. In a preferred embodiment of the invention, the gel shift assay is an EMSA gel shift assay.

Example 8: Cas9 Transgenic and Knock in Mice

To generate a mouse that expresses the Cas9 nuclease Applicants submit two general strategies, transgenic and knock in. These strategies may be applied to generate any other model organism of interest, for e.g. Rat. For each of the general strategies Applicants made a constitutively active Cas9 and a Cas9 that is conditionally expressed (Cre recombinase dependent). The constitutively active Cas9 nuclease is expressed in the following context: pCAG-NLS-Cas9-NLS-P2A-EGFP-WPRE-bGHpolyA. pCAG is the promoter, NLS is a nuclear localization signal, P2A is the peptide cleavage sequence, EGFP is enhanced green fluorescent protein, WPRE is the woodchuck hepatitis virus posttranscriptional regulatory element, and bGHpolyA is the bovine growth hormone poly-A signal sequence (FIGS. 7A-B). The conditional version has one additional stop cassette element, loxP-SV40 polyA x3-loxP, after the promoter and before NLS-Cas9-NLS (i.e. pCAG-loxP-SV40polyAx3-loxP-NLS-Cas9-NLS-P2A-EGFP-WPRE-bGHpolyA). The important expression elements can be visualized as in FIG. 8. The constitutive construct should be expressed in all cell types throughout development, whereas, the conditional construct will only allow Cas9 expression when the same cell is expressing the Cre recombinase. This latter version will allow for tissue specific expression of Cas9 when Cre is under the expression of a tissue specific promoter. Moreover, Cas9 expression could be induced in adult mice by putting Cre under the expression of an inducible promoter such as the TET on or off system.

Validation of Cas9 constructs: Each plasmid was functionally validated in three ways: 1) transient transfection in 293 cells followed by confirmation of GFP expression; 2) transient transfection in 293 cells followed by immunofluorescence using an antibody recognizing the P2A sequence; and 3) transient transfection followed by Surveyor nuclease assay. The 293 cells may be 293FT or 293 T cells depending on the cells that are of interest. In a preferred embodiment the cells are 293FT cells. The results of the Surveyor were run out on the top and bottom row of the gel for the conditional and constitutive constructs, respectively. Each was tested in the presence and absence of chimeric RNA targeted to the hEMX1 locus (chimeric RNA hEMX1.1). The results indicate that the construct can successfully target the hEMX1 locus only in the presence of chimeric RNA (and Cre in the conditional case). The gel was quantified and the results are presented as average cutting efficiency and standard deviation for three samples.

Transgenic Cas9 mouse: To generate transgenic mice with constructs, Applicants inject pure, linear DNA into the pronucleus of a zygote from a pseudo pregnant CB56 female. Founders are identified, genotyped, and backcrossed to CB57 mice. The constructs were successfully cloned and verified by Sanger sequencing.

Knock in Cas9 mouse: To generate Cas9 knock in mice Applicants target the same constitutive and conditional constructs to the Rosa26 locus. Applicants did this by cloning each into a Rosa26 targeting vector with the following elements: Rosa26 short homology arm—constitutive/conditional Cas9 expression cassette—pPGK-Neo-Rosa26 long homology arm—pPGK-DTA. pPGK is the promoter for the positive selection marker Neo, which confers resistance to neomycin, a 1 kb short arm, a 4.3 kb long arm, and a negative selection diphtheria toxin (DTA) driven by PGK.

The two constructs were electroporated into R1 mESCs and allowed to grow for 2 days before neomycin selection was applied. Individual colonies that had survived by days 5-7 were picked and grown in individual wells. 5-7 days later the colonies were harvested, half were frozen and the other half were used for genotyping. Genotyping was done by genomic PCR, where one primer annealed within the donor plasmid (AttpF) and the other outside of the short homology arm (Rosa26-R) Of the 22 colonies harvested for the conditional case, 7 were positive (Left). Of the 27 colonies harvested for the constitutive case, zero were positive (Right). It is likely that Cas9 causes some level of toxicity in the mESC and for this reason there were no positive clones. To test this Applicants introduced a Cre expression plasmid into correctly targeted conditional Cas9 cells and found very low toxicity after many days in culture. The reduced copy number of Cas9 in correctly targeted conditional Cas9 cells (1-2 copies per cell) is enough to allow stable expression and relatively no cytotoxicity. Moreover, this data indicates that the Cas9 copy number determines toxicity. After electroporation each cell should get several copies of Cas9 and this is likely why no positive colonies were found in the case of the constitutive Cas9 construct. This provides strong evidence that utilizing a conditional, Cre-dependent strategy should show reduced toxicity. Applicants inject correctly targeted cells into a blastocyst and implant into a female mouse. Chimerics are identified and backcrossed. Founders are identified and genotyped.

Utility of the conditional Cas9 mouse: Applicants have shown in 293 cells that the Cas9 conditional expression construct can be activated by co-expression with Cre. Applicants also show that the correctly targeted R1 mESCs can have active Cas9 when Cre is expressed. Because Cas9 is followed by the P2A peptide cleavage sequence and then EGFP Applicants identify successful expression by observing EGFP. This same concept is what makes the conditional Cas9 mouse so useful. Applicants may cross their conditional Cas9 mouse with a mouse that ubiquitously expresses Cre (ACTB-Cre line) and may arrive at a mouse that expresses Cas9 in every cell. It should only take the delivery of chimeric RNA to induce genome editing in embryonic or adult mice. Interestingly, if the conditional Cas9 mouse is crossed with a mouse expressing Cre under a tissue specific promoter, there should only be Cas9 in the tissues that also express Cre. This approach may be used to edit the genome in only precise tissues by delivering chimeric RNA to the same tissue.

Example 9: Cas9 Diversity and Chimeric RNAs

The CRISPR-Cas system is an adaptive immune mechanism against invading exogenous DNA employed by diverse species across bacteria and archaea. The type II CRISPR-Cas system consists of a set of genes encoding proteins responsible for the "acquisition" of foreign DNA into the CRISPR locus, as well as a set of genes encoding the "execution" of the DNA cleavage mechanism; these include the DNA nuclease (Cas9), a non-coding transactivating cr-RNA (tracrRNA), and an array of foreign DNA-derived spacers flanked by direct repeats (crRNAs). Upon maturation by Cas9, the tracrRNA and crRNA duplex guide the Cas9 nuclease to a target DNA sequence specified by the spacer guide sequences, and mediates double-stranded breaks in the DNA near a short sequence motif in the target DNA that is required for cleavage and specific to each CRISPR-Cas system. The type II CRISPR-Cas systems are found throughout the bacterial kingdom and highly diverse in in Cas9 protein sequence and size, tracrRNA and crRNA direct repeat sequence, genome organization of these elements, and the motif requirement for target cleavage. One species may have multiple distinct CRISPR-Cas systems.

Applicants evaluated 207 putative Cas9s from bacterial species identified based on sequence homology to known Cas9s and structures orthologous to known subdomains, including the HNH endonuclease domain and the RuvC endonuclease domains [information from the Eugene Koonin and Kira Makarova]. Phylogenetic analysis based on the protein sequence conservation of this set revealed five families of Cas9s, including three groups of large Cas9s (~1400 amino acids) and two of small Cas9s (~1100 amino acids) (FIGS. 3 and 4A-F).

Applicants have also optimized Cas9 guide RNA using in vitro methods.

Example 10: Cas9 Mutations

In this example, Applicants show that the following mutations can convert SpCas9 into a nicking enzyme: D10A, E762A, H840A, N854A, N863A, D986A.

Applicants provide sequences showing where the mutation points are located within the SpCas9 gene (FIG. 6A-M). Applicants also show that the nickases are still able to mediate homologous recombination. Furthermore, Applicants show that SpCas9 with these mutations (individually) do not induce double strand break.

Cas9 orthologs all share the general organization of 3-4 RuvC domains and a HNH domain. The 5' most RuvC domain cleaves the non-complementary strand, and the HNH domain cleaves the complementary strand. All notations are in reference to the guide sequence.

The catalytic residue in the 5' RuvC domain is identified through homology comparison of the Cas9 of interest with other Cas9 orthologs (from *S. pyogenes* type II CRISPR locus, *S. thermophilus* CRISPR locus 1, *S. thermophilus* CRISPR locus 3, and *Franciscilla novicida* type II CRISPR locus), and the conserved Asp residue is mutated to alanine to convert Cas9 into a complementary-strand nicking enzyme. Similarly, the conserved His and Asn residues in the HNH domains are mutated to Alanine to convert Cas9 into a non-complementary-strand nicking enzyme.

Example 11: Cas9 Transcriptional Activation and Cas9 Repressor

Cas9 Transcriptional Activation

A second generation of constructs have been designed and are in the pipeline to be tested (Table 1). These constructs will be used to assess transcriptional activation (VP64 fused constructs) and repression (Cas9 only) by RT-qPCR. Applicants will also assess the cellular localization of each construct using anti-His antibody, nuclease activity using a Surveyor nuclease assay, and DNA binding affinity using a gel shift assay.

Cas Repressor

It has been shown previously that dCas9 can be used as a generic DNA binding domain to repress gene expression. Applicants report an improved dCas9 design as well as dCas9 fusions to the repressor domains KRAB and SID4×. From the plasmid library created for modulating transcription using Cas9 in Table 1, the following repressor plasmids were functionally characterized by qPCR: pXRP27, pXRP28, pXRP29, pXRP48, pXRP49, pXRP50, pXRP51, pXRP52, pXRP53, pXRP56, pXRP58, pXRP59, pXRP61, and pXRP62.

Each dCas9 repressor plasmid was co-transfected with two guide RNAs targeted to the coding strand of the beta-catenin gene. RNA was isolated 72 hours after transfection and gene expression was quantified by RT-qPCR. The endogenous control gene was GAPDH. Two validated shRNAs were used as positive controls. Negative controls were certain plasmids transfected without gRNA, these are denoted as "pXRP ## control". The plasmids pXRP28, pXRP29, pXRP48, and pXRP49 could repress the beta-catenin gene when using the specified targeting strategy. These plasmids correspond to dCas9 without a functional domain (pXRP28 and pXRP28) and dCas9 fused to SID4× (pXRP48 and pXRP49).

Further work investigates: repeating the above experiment, targeting different genes, utilizing other gRNAs to determine the optimal targeting position, and multiplexed repression.

TABLE 1

(Table 1 discloses GGGGS$_3$ as SEQ ID NO: 97, EAAAK$_3$ as SEQ ID NO: 98 and "GGGGGS$_3$" as SEQ ID NO: 99)

pXRP024-pLenti2-EF1a-VP64-NLS-FLAG-Linker-dCas9-NLS-gLuc-2A-GFP-WPRE
pXRP025-pLenti2-EF1a-VP64-NLS-GGGGS$_3$Linker-dCas9-NLS-gLuc-2A-GFP-WPRE
pXRP026-pLenti2-EF1a-VP64-NLS-EAAAK$_3$Linker-dCas9-NLS-gLuc-2A-GFP-WPRE
pXRP027-pLenti2-EF1a-NLS-FLAG-Linker-dCas9-NLS-gLuc-2A-GFP-WPRE
pXRP028-pLenti2-EF1a-NLS-GGGGS$_3$Linker-dCas9-NLS-gLuc-2A-GFP-WPRE
pXRP029-pLenti2-EF1a-NLS-EAAAK$_3$Linker-dCas9-NLS-gLuc-2A-GFP-WPRE
pXRP030-pLenti2-pSV40-VP64-NLS-FLAG-Linker-dCas9-NLS-gLuc-2A-GFP-WPRE
pXRP031-pLenti2-pPGK-VP64-NLS-FLAG-Linker-dCas9-NLS-gLuc-2A-GFP-WPRE
pXRP032-pLenti2-LTR-VP64-NLS-FLAG-Linker-dCas9-NLS-gLuc-2A-GFP-WPRE
pXRP033-pLenti2-pSV40-VP64-NLS-GGGGS$_3$Linker-dCas9-NLS-gLuc-2A-GFP-WPRE
pXRP034-pLenti2-pPGK-VP64-NLS-GGGGS$_3$Linker-dCas9-NLS-gLuc-2A-GFP-WPRE
pXRP035-pLenti2-LTR-VP64-NLS-GGGGS$_3$Linker-dCas9-NLS-gLuc-2A-GFP-WPRE
pXRP036-pLenti2-pSV40-VP64-NLS-EAAAK$_3$Linker-dCas9-NLS-gLuc-2A-GFP-WPRE
pXRP037-pLenti2-pPGK-VP64-NLS-EAAAK$_3$Linker-dCas9-NLS-gLuc-2A-GFP-WPRE
pXRP038-pLenti2-LTR-VP64-NLS-EAAAK$_3$Linker-dCas9-NLS-gLuc-2A-GFP-WPRE
pXRP048-pLenti2-EF1a-SID4x-NLS-FLAG-Linker-dCas9-NLS-gLuc-2A-GFP-WPRE
pXRP049-pLenti2-EF1a-SID4X-NLS-GGGGS$_3$Linker-dCas9-NLS-gLuc-2A-GFP-WPRE
pXRP050-pLenti2-EF1a-SID4X-NLS-EAAAK$_3$Linker-dCas9-NLS-gLuc-2A-GFP-WPRE
pXRP051-pLenti2-EF1a-KRAB-NLS-FLAG-Linker-dCas9-NLS-gLuc-2A-GFP-WPRE
pXRP052-pLenti2-EF1a-KRAB-NILS-GGGGS$_3$Linker-dCas9-NLS-gLuc-2A-GFP-WPRE
pXRP053-pLenti2-EF1a-KRAB-NLS-EAAAK$_3$Linker-dCas9-NLS-gLuc-2A-GFP-WPRE
pXRP054-pLenti2-EF1a-dCas9-Linker-FLAG-NLS-VP64-gLuc-2A-GFP-WPRE
pXRP055-pLenti2-EF1a-dCas9-Linker-FLAG-NLS-SID4X-gLuc-2A-GFP-WPRE
pXRP056-pLenti2-EF1a-dCas9-Linker-FLAG-NLS-KRAB-gLuc-2A-GFP-WPRE
pXRP057-pLenti2-EF1a-dCas9-GGGGGS$_3$-NLS-VP64-gLuc-2A-GFP-WPRE
pXRP058-pLenti2-EF1a-dCas9-GGGGGS$_3$-NLS-SID4X-gLuc-2A-GFP-WPRE
pXRP059-pLenti2-EF1a-dCas9-GGGGGS$_3$-NLS-KRAB-gLuc-2A-GFP-WPRE
pXRP060-pLenti2-EF1a-dCas9-EAAAK$_3$-NLS-VP64-gLuc-2A-GFP-WPRE
pXRP061-pLenti2-EF1a-dCas9-EAAAK$_3$-NLS-SID4X-gLuc-2A-GFP-WPRE
pXRP062-pLenti2-EF1a-dCas9-EAAAK$_3$-NLS-KRAB-gLuc-2A-GFP-WPRE
pXRP024-pLenti2-EF1a-VP64-NLS-FLAG-Linker-Cas9-NLS-gLuc-2A-GFP-WPRE
pXRP025-pLenti2-EF1a-VP64-NLS-GGGGS$_3$Linker-Cas9-NLS-gLuc-2A-GFP-WPRE
pXRP026-pLenti2-EF1a-VP64-NLS-EAAAK$_3$Linker-Cas9-NLS-gLuc-2A-GFP-WPRE
pXRP027-pLenti2-EF1a-NLS-FLAG-Linker-Cas9-NLS-gLuc-2A-GFP-WPRE
pXRP028-pLenti2-EF1a-NLS-GGGGS$_3$Linker-Cas9-NLS-gLuc-2A-GFP-WPRE
pXRP029-pLenti2-EF1a-NLS-EAAAK$_3$Linker-Cas9-NLS-gLuc-2A-GFP-WPRE
pXRP030-pLenti2-pSV40-VP64-NLS-FLAG-Linker-Cas9-NLS-gLuc-2A-GFP-WPRE
pXRP031-pLenti2-pPGK-VP64-NLS-FLAG-Linker-Cas9-NLS-gLuc-2A-GFP-WPRE
pXRP032-pLenti2-LTR-VP64-NLS-FLAG-Linker-Cas9-NLS-gLuc-2A-GFP-WPRE
pXRP033-pLenti2-pSV40-VP64-NLS-GGGGS$_3$Linker-Cas9-NLS-gLuc-2A-GFP-WPRE
pXRP034-pLenti2-pPGK-VP64-NLS-GGGGS$_3$Linker-Cas9-NLS-gLuc-2A-GFP-WPRE
pXRP035-pLenti2-LTR-VP64-NLS-GGGGS$_3$Linker-Cas9-NLS-gLuc-2A-GFP-WPRE
pXRP036-pLenti2-pSV40-VP64-NLS-EAAAK$_3$Linker-Cas9-NLS-gLuc-2A-GFP-WPRE
pXRP037-pLenti2-pPGK-VP64-NLS-EAAAK$_3$Linker-Cas9-NLS-gLuc-2A-GFP-WPRE
pXRP038-pLenti2-LTR-VP64-NLS-EAAAK$_3$Linker-Cas9-NLS-gLuc-2A-GFP-WPRE
pXRP048-pLenti2-EF1a-SID4x-NLS-FLAG-Linker-Cas9-NLS-gLuc-2A-GFP-WPRE
pXRP049-pLenti2-EF1a-SID4X-NLS-GGGGS$_3$Linker-Cas9-NLS-gLuc-2A-GFP-WPRE
pXRP050-pLenti2-EF1a-SID4X-NLS-EAAAK$_3$Linker-Cas9-NLS-gLuc-2A-GFP-WPRE
pXRP051-pLenti2-EF1a-KRAB-NLS-FLAG-Linker-Cas9-NLS-gLuc-2A-GFP-WPRE
pXRP052-pLenti2-EF1a-KRAB-NLS-GGGGS$_3$Linker-Cas9-NLS-gLuc-2A-GFP-WPRE
pXRP053-pLenti2-EF1a-KRAB-NLS-EAAAK$_3$Linker-Cas9-NLS-gLuc-2A-GFP-WPRE
pXRP054-pLenti2-EF1a-Cas9-Linker-FLAG-NLS-VP64-gLuc-2A-GFP-WPRE
pXRP055-pLenti2-EF1a-Cas9-Linker-FLAG-NLS-SID4X-gLuc-2A-GFP-WPRE
pXRP056-pLenti2-EF1a-Cas9-Linker-FLAG-NLS-KRAB-gLuc-2A-GFP-WPRE
pXRP057-pLenti2-EF1a-Cas9-GGGGGS$_3$-NLS-VP64-gLuc-2A-GFP-WPRE
pXRP058-pLenti2-EF1a-Cas9-GGGGGS$_3$-NLS-SID4X-gLuc-2A-GFP-WPRE
pXRP059-pLenti2-EF1a-Cas9-GGGGGS$_3$-NLS-KRAB-gLuc-2A-GFP-WPRE
pXRP060-pLenti2-EF1a-Cas9-EAAAK$_3$-NLS-VP64-gLuc-2A-GFP-WPRE
pXRP061-pLenti2-EF1a-Cas9-EAAAK$_3$-NLS-SID4X-gLuc-2A-GFP-WPRE
pXRP062-pLenti2-EF1a-Cas9-EAAAK$_3$-NLS-KRAB-gLuc-2A-GFP-WPRE Example 12: Targeted Deletion of Genes Involved in Cholesterol Biosynthesis, Fatty Acid Biosynthesis, and Other Metabolic Disorders, Genes Encoding Mis-Folded Proteins Involved in Amyloid and Other Diseases, Oncogenes Leading to Cellular Transformation, Latent Viral Genes, and Genes Leading to Dominant-Negative Disorders, Amongst Other Disorders Applicants demonstrate gene delivery of a CRISPR-Cas system in the liver, brain, ocular, epithelial, hematopoetic, or another tissue of a subject or a patient in need thereof, suffering from metabolic disorders, amyloidosis and protein-aggregation related diseases, cellular transformation arising from genetic mutations and translocations, dominant negative effects of gene mutations, latent viral infections, and other related symptoms, using either viral or nanoparticle delivery system.

Study Design: Subjects or patients in need thereof suffering from metabolic disorders, amyloidosis and protein aggregation related disease which include but are not limited to human, non-primate human, canine, feline, bovine, equine, other domestic animals and related mammals. The CRISPR-Cas system is guided by a chimeric guide RNA and targets a specific site of the human genomic loci to be cleaved. After cleavage and non-homologous end-joining mediated repair, frame-shift mutation results in knock out of genes.

Applicants select guide-RNAs targeting genes involved in above-mentioned disorders to be specific to endogenous loci with minimal off-target activity. Two or more guide RNAs may be encoded into a single CRISPR array to induce simultaneous double-stranded breaks in DNA leading to micro-deletions of affected genes or chromosomal regions.

Identification and Design of Gene Targets

For each candidate disease gene, Applicants select DNA sequences of interest include protein-coding exons, sequences including and flanking known dominant negative mutation sites, sequences including and flanking pathological repetitive sequences. For gene-knockout approaches, early coding exons closest to the start codon offer best options for achieving complete knockout and minimize possibility of truncated protein products retaining partial function.

Applicants analyze sequences of interest for all possible targetable 20-bp sequences immediately 5' to a NGG motif (for SpCas9 system) or a NNAGAAW (for St1Cas9 system). Applicants choose sequences for unique, single RNA-guided Cas9 recognition in the genome to minimize off-target effects based on computational algorithm to determine specificity.

Cloning of Guide Sequences into a Delivery System

Guide sequences are synthesized as double-stranded 20-24 bp oligonucleotides. After 5'-phosphorylation treatment of oligos and annealing to form duplexes, oligos are ligated into suitable vector depending on the delivery method:

Virus-Based Delivery Methods

AAV-based vectors (PX260, 330, 334, 335) have been described elsewhere

Lentiviral-based vectors use a similar cloning strategy of directly ligating guide sequences into a single vector carrying a U6 promoter-driven chimeric RNA scaffold and a EF1a promoter-driven Cas9 or Cas9 nickase.

Virus production is described elsewhere.

Nanoparticle-Based RNA Delivery Methods

1. Guide sequences are synthesized as an oligonucleotide duplex encoding T7 promoter—guide sequence—chimeric RNA. A T7 promoter is added 5' of Cas9 by PCR method.

2. T7-driven Cas9 and guide-chimeric RNAs are transcribed in vitro, and Cas9 mRNA is further capped and A-tailed using commercial kits. RNA products are purified per kit instructions.

Hydrodynamic Tail Vein Delivery Methods (for Mouse)

Guide sequences are cloned into AAV plasmids as described above and elsewhere in this application.

In Vitro Validation on Cell Lines

Transfection

1. DNA Plasmid Transfection

Plasmids carrying guide sequences are transfected into human embryonic kidney (HEK293T) or human embryonic stem (hES) cells, other relevant cell types using lipid-, chemical-, or electroporation-based methods. For a 24-well transfection of HEK293T cells (~260,000 cells), 500 ng of total DNA is transfected into each single well using Lipofectamine 2000. For a 12-well transfection of hES cells, 1 ug of total DNA is transfected into a single well using Fugene HD.

2. RNA Transfection

Figure 10:
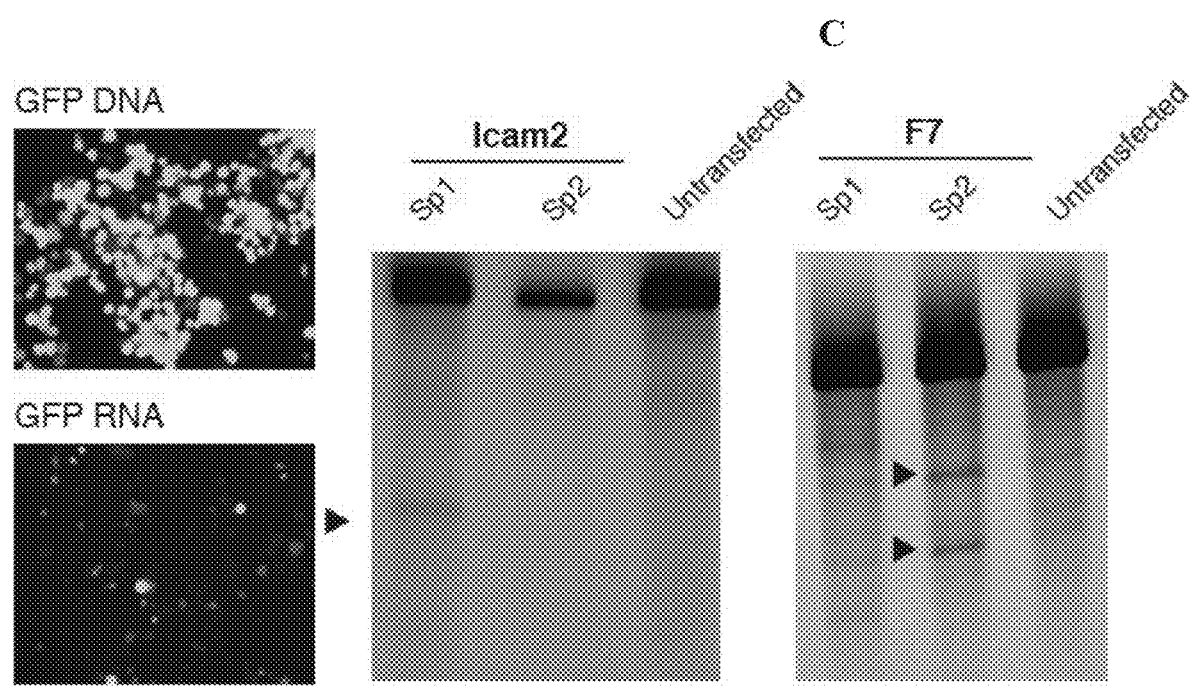
FIG. 10 shows RNA delivery of Cas9 and chimeric RNA into cells (A) Delivery of a GFP reporter as either DNA or mRNA into Neuro-2A cells. (B) Delivery of Cas9 and chimeric RNA against the Icam2 gene as RNA results in cutting for one of two spacers tested. (C) Delivery of Cas9 and chimeric RNA against the F7 gene as RNA results in cutting for one of two spacers tested.

Purified RNA described above is used for transfection into HEK293T cells. 1-2 ug of RNA may be transfected into ~260,000 using Lipofectamine 2000 per manufacturer's instruction. RNA delivery of Cas9 and chimeric RNA is shown in FIG. 10.

Assay of Indel Formation In Vitro

Cells are harvested 72-hours post-transfection and assayed for indel formation as an indication of double-stranded breaks.

Briefly, genomic region around target sequence is PCR amplified (~400-600 bp amplicon size) using high-fidelity polymerase. Products are purified, normalized to equal concentration, and slowly annealed from 95° C. to 4° C. to allow formation of DNA heteroduplexes. Post annealing, the Cel-I enzyme is used to cleave heteroduplexes, and resulting products are separated on a polyacrylamide gel and indel efficiency calculated.

In Vivo Proof of Principle in Animal

Delivery Mechanisms

AAV or Lentivirus production is described elsewhere.

Nanoparticle formulation: RNA mixed into nanoparticle formulation

Hydrodynamic tail vein injections with DNA plasmids in mice are conducted using a commercial kit Cas9 and guide sequences are delivered as virus, nanoparticle-coated RNA mixture, or DNA plasmids, and injected into subject animals. A parallel set of control animals is injected with sterile saline, Cas9 and GFP, or guide sequence and GFP alone.

Three weeks after injection, animals are tested for amelioration of symptoms and sacrificed. Relevant organ systems analyzed for indel formation. Phenotypic assays include blood levels of HDL, LDL, lipids, Assay for Indel Formation DNA is extracted from tissue using commercial kits; indel assay will be performed as described for in vitro demonstration.

Therapeutic applications of the CRISPR-Cas system are amenable for achieving tissue-specific and temporally controlled targeted deletion of candidate disease genes. Examples include genes involved in cholesterol and fatty acid metabolism, amyloid diseases, dominant negative diseases, latent viral infections, among other disorders.

Examples of a Single Guide-RNA to Introduce Targeted Indels at a Gene Locus

| Disease | GENE | SPACER | PAM | SEQ ID NO: | Mechanism | References |
|---|---|---|---|---|---|---|
| Hypercholesterolemia | HMG-CR | GCCAAATTGGACGACCCTCG | CGG | 100 | Knockout | Fluvastatin: a review of its pharmacology and use in the management of hypercholesterolaemia. (Plosker GL et al. Drugs 1996, 51(3):433-459) |
| Hypercholesterolemia | SQLE | CGAGGAGACCCCCGTTTCGG | TGG | 101 | Knockout | Potential role of nonstatin cholesterol lowering agents (Trapani et al. IUBMB Life, Volume 63, Issue 11, pages 964-971, November 2011) |
| Hyperlipidemia | DGAT1 | CCCGCCGCCGCCGTGGCTCG | AGG | 102 | Knockout | DGAT1 inhibitors as anti-obesity and anti-diabetic agents. (Birch AM et al. Current Opinion in Drug Discovery & Development |
| Leukemia | BCR-ABL | TGAGCTCTACGAGATCCACA | AGG | 103 | Knockout | Killing of leukemic cells with a BCR/ABL fusion gene by RNA interference (RNAi). (Fuchs et al. Oncogene 2002, 21(37):5716-5724) |

Examples of a Pair of Guide-RNA to Introduce Chromosomal Microdeletion at a Gene Locus

| Disease | GENE | SPACER | PAM | SEQ ID NO: | Mechanism | References |
|---|---|---|---|---|---|---|
| Hyperlipidemia | PLIN2 guide1 | CTCAAAATTCATACCGGTTG | TGG | 104 | Microdeletion | Perilipin-2 Null Mice are Protected Against Diet-Induced Obesity, Adipose Inflammation and Fatty Liver Disease (McManaman JL et al. The Journal of Lipid Research, jlr.M035063. First Published on Feb. 12, 2013) |
| Hyperlipidemia | PLIN2 guide2 | CGTTAAACAACAACCGGACT | TGG | 105 | Microdeletion | |
| Hyperlipidemia | SREBP guide1 | TTCACCCCGCGGCGCTGAAT | ggg | 106 | Microdeletion | Inhibition of SREBP by a Small Molecule, Betulin, Improves Hyperlipidemia and Insulin Resistance and Reduces Atherosclerotic Plaques (Tang J et al. Cell Metabolism, Volume 13, Issue 1, 44-56, 5 Jan. 2011) |
| Hyperlipidemia | SREBP guide2 | ACCACTACCAGTCCGTCCAC | agg | 107 | Microdeletion | |

Example 13: Targeted Integration of Repair for
Genes Carrying Disease-Causing Mutations;
Reconstitution of Enzyme Deficiencies and Other
Related Diseases Study Design
I. Identification and design of gene targets
Described in Example 16
II. Cloning of guide sequences and repair templates into a delivery system
Described above in Example 16
Applicants clone DNA repair templates to include homology arms with diseased allele as well a wild-type repair template
III. In vitro validation on cell lines
a. Transfection is described above in Example 16; Cas9, guide RNAs, and repair template are co-transfected into relevant cell types.
b. Assay for repair in vitro
i. Applicants harvest cells 72-hours post-transfection and assay for repair
ii. Briefly, Applicants amplify genomic region around repair template PCR using high-fidelity polymerase. Applicants sequence products for decreased incidence of mutant allele.
IV. In vivo proof of principle in animal
a. Delivery mechanisms are described above Examples 16 and 29.
b. Assay for repair in vivo
i. Applicants perform the repair assay as described in the in vitro demonstration.
V. Therapeutic applications
The CRISPR-Cas system is amenable for achieving tissue-specific and temporally controlled targeted deletion of candidate disease genes. Examples include genes involved in cholesterol and fatty acid metabolism, amyloid diseases, dominant negative diseases, latent viral infections, among other disorders.
Example of one single missense mutation with repair template:

| Disease | GENE | SPACER | PAM |
|---|---|---|---|
| Familial amyloid polyneuropathy | TTR | AGCCTTTCTGAACACATGCA (SEQ ID NO: 108) | CGG |

Mechanism References
Transthyretin mutations in health and disease (Joao et al. Human Mutation, V30M repair Volume 5, Issue 3, pages 191-196, 1995)

| V30M allele | CCTGCCATCAATGTGGCCATGCATGTGTTCAGAAAGGCT (SEQ ID NO: 109) |
|---|---|
| WT allele | CCTGCCATCAATGTGGCCGTGCATGTGTTCAGAAAGGCT (SEQ ID NO: 110) |

Example 14: Therapeutic Application of the
CRISPR-Cas System in Glaucoma, Amyloidosis,
and Huntington's Disease Glaucoma: Applicants design guide RNAs to target the first exon of the mycilin (MYOC) gene. Applicants use adenovirus vectors (Ad5) to package both Cas9 as well as a guide RNA targeting the MYOC gene. Applicants inject adenoviral vectors into the trabecular meshwork where cells have been implicated in the pathophysiology of glaucoma. Applicants initially test this out in mouse models carrying the mutated MYOC gene to see whether they improve visual acuity and decrease pressure in the eyes. Therapeutic application in humans employ a similar strategy.

Amyloidosis: Applicants design guide RNAs to target the first exon of the transthyretin (TTR) gene in the liver. Applicants use AAV8 to package Cas9 as well as guide RNA targeting the first exon of the TTR gene. AAV8 has been shown to have efficient targeting of the liver and will be administered intravenously. Cas9 can be driven either using liver specific promoters such as the albumin promoter, or using a constitutive promoter. A pol3 promoter drives the guide RNA.

Alternatively, Applicants utilize hydrodynamic delivery of plasmid DNA to knockout the TTR gene. Applicants deliver a plasmid encoding Cas9 and the guideRNA targeting Exon1 of TTR.

As a further alternative approach, Applicants administer a combination of RNA (mRNA for Cas9, and guide RNA). RNA can be packaged using liposomes such as Invivofectamine from Life Technologies and delivered intravenously. To reduce RNA-induced immunogenicity, increase the level of Cas9 expression and guide RNA stability, Applicants modify the Cas9 mRNA using 5' capping. Applicants also incorporate modified RNA nucleotides into Cas9 mRNA and guide RNA to increase their stability and reduce immunogenicity (e.g. activation of TLR). To increase efficiency, Applicants administer multiple doses of the virus, DNA, or RNA.

Huntington's Disease: Applicants design guide RNA based on allele specific mutations in the HTT gene of patients. For example, in a patient who is heterozygous for HTT with expanded CAG repeat, Applicants identify nucleotide sequences unique to the mutant HTT allele and use it to design guideRNA. Applicants ensure that the mutant base is located within the last 9 bp of the guide RNA (which Applicants have ascertained has the ability to discriminate between single DNA base mismatches between the target size and the guide RNA).

Applicants package the mutant HTT allele specific guide RNA and Cas9 into AAV9 and deliver into the striatum of Huntington's patients. Virus is injected into the striatum stereotactically via a craniotomy. AAV9 is known to transduce neurons efficiently. Applicants drive Cas9 using a neuron specific promoter such as human Synapsin I.

Example 15: Therapeutic Application of the
CRISPR-Cas System in HIV

Chronic viral infection is a source of significant morbidity and mortality. While there exists for many of these viruses conventional antiviral therapies that effectively target various aspects of viral replication, current therapeutic modalities are usually non-curative in nature due to "viral latency." By its nature, viral latency is characterized by a dormant phase in the viral life cycle without active viral production. During this period, the virus is largely able to evade both immune surveillance and conventional therapeutics allowing for it to establish long-standing viral reservoirs within the host from which subsequent re-activation can permit continued propagation and transmission of virus. Key to viral latency is the ability to stably maintain the viral genome, accomplished either through episomal or proviral latency, which stores the viral genome in the cytoplasm or integrates it into the host genome, respectively. In the absence of effective vaccinations which would prevent primary infection, chronic viral infections characterized by latent reservoirs and episodes of lytic activity can have significant consequences: human papilloma virus (HPV) can result in cervical cancer, hepatitis C virus (HCV) predisposes to hepatocellular carcinoma, and human immunodeficiency virus eventually destroys the host immune system resulting in susceptibility to opportunistic infections. As such, these infections require life-long use of currently available antiviral therapeutics. Further complicating matters is the high mutability of many of these viral genomes which lead to the evolution of resistant strains for which there exists no effective therapy.

The CRISPR-Cas system is a bacterial adaptive immune system able to induce double-stranded DNA breaks (DSB) in a multiplex-able, sequence-specific manner and has been recently re-constituted within mammalian cell systems. It has been shown that targeting DNA with one or numerous guide-RNAs can result in both indels and deletions of the intervening sequences, respectively. As such, this new technology represents a means by which targeted and multiplexed DNA mutagenesis can be accomplished within a single cell with high efficiency and specificity. Consequently, delivery of the CRISPR-Cas system directed against viral DNA sequences could allow for targeted disruption and deletion of latent viral genomes even in the absence of ongoing viral production.

As an example, chronic infection by HIV-1 represents a global health issue with 33 million individuals infected and an annual incidence of 2.6 million infections. The use of the multimodal highly active antiretroviral therapy (HAART), which simultaneously targets multiple aspects of viral replication, has allowed HIV infection to be largely managed as a chronic, not terminal, illness. Without treatment, progression of HIV to AIDS occurs usually within 9-10 years resulting in depletion of the host immune system and occurrence of opportunistic infections usually leading to death soon thereafter. Secondary to viral latency, discontinuation of HAART invariably leads to viral rebound. Moreover, even temporary disruptions in therapy can select for resistant strains of HIV uncontrollable by available means. Additionally, the costs of HAART therapy are significant: within the US $10,000-15,0000 per person per year. As such, treatment approaches directly targeting the HIV genome rather than the process of viral replication represents a means by which eradication of latent reservoirs could allow for a curative therapeutic option.

Development and delivery of an HIV-1 targeted CRISPR-Cas system represents a unique approach differentiable from existing means of targeted DNA mutagenesis, i.e. ZFN and TALENs, with numerous therapeutic implications. Targeted disruption and deletion of the HIV-1 genome by CRISPR-mediated DSB and indels in conjunction with HAART could allow for simultaneous prevention of active viral production as well as depletion of latent viral reservoirs within the host.

Once integrated within the host immune system, the CRISPR-Cas system allows for generation of a HIV-1 resistant sub-population that, even in the absence of complete viral eradication, could allow for maintenance and re-constitution of host immune activity. This could potentially prevent primary infection by disruption of the viral genome preventing viral production and integration, representing a means to "vaccination". Multiplexed nature of the CRISPR-Cas system allows targeting of multiple aspects of the genome simultaneously within individual cells.

As in HAART, viral escape by mutagenesis is minimized by requiring acquisition of multiple adaptive mutations concurrently. Multiple strains of HIV-1 can be targeted simultaneously which minimizes the chance of super-infection and prevents subsequent creation of new recombinants strains. Nucleotide, rather than protein, mediated sequence-specificity of the CRISPR-Cas system allows for rapid generation of therapeutics without need for significantly altering delivery mechanism.

In order to accomplish this, Applicants generate CRISPR-Cas guide RNAs that target the vast majority of the HIV-1 genome while taking into account HIV-1 strain variants for maximal coverage and effectiveness. Sequence analyses of genomic conservation between HIV-1 subtypes and variants should allow for targeting of flanking conserved regions of the genome with the aims of deleting intervening viral sequences or induction of frame-shift mutations which would disrupt viral gene functions.

Applicants accomplish delivery of the CRISPR-Cas system by conventional adenoviral or lentiviral-mediated infection of the host immune system. Depending on approach, host immune cells could be a) isolated, transduced with CRISPR-Cas, selected, and re-introduced in to the host or b) transduced in vivo by systemic delivery of the CRISPR-Cas system. The first approach allows for generation of a resistant immune population whereas the second is more likely to target latent viral reservoirs within the host.

| Examples of potential HIV-1 targeted spacers adapted from Mcintyre et al, which generated shRNAs against HIV-1 optimized for maximal coverage of HIV-1 variants. |
|---|
| CACTGCTTAAGCCTCGCTCG<u>AGG</u> (SEQ ID NO: 111) |
| TCACCAGCAATATTCGCTCG<u>AGG</u> (SEQ ID NO: 112) |
| CACCAGCAATATTCCGCTCG<u>AGG</u> (SEQ ID NO: 113) |
| TAGCAACAGACATACGCTCG<u>AGG</u> (SEQ ID NO: 114) |
| GGGCAGTAGTAATACGCTCG<u>AGG</u> (SEQ ID NO: 115) |
| <u>CCA</u>ATTCCCATACATTATTGTAC (SEQ ID NO: 116) |

Example 16: Targeted Correction of deltaF508 or Other Mutations in Cystic Fibrosis An aspect of the invention provides for a pharmaceutical composition that may comprise an CRISPR-Cas gene therapy particle and a biocompatible pharmaceutical carrier. According to another aspect, a method of gene therapy for the treatment of a subject having a mutation in the CFTR gene comprises administering a therapeutically effective amount of a CRISPR-Cas gene therapy particle to the cells of a subject.

This Example demonstrates gene transfer or gene delivery of a CRISPR-Cas system in airways of subject or a patient in need thereof, suffering from cystic fibrosis or from cystic fibrosis related symptoms, using adeno-associated virus (AAV) particles.

Study Design: Subjects or patients in need there of: Human, non-primate human, canine, feline, bovine, equine and other domestic animals, related. This study tests efficacy of gene transfer of a CRISPR-Cas system by a AAV vector. Applicants determine transgene levels sufficient for gene expression and utilize a CRISPR-Cas system comprising a Cas9 enzyme to target deltaF508 or other CFTR-inducing mutations.

The treated subjects receive pharmaceutically effective amount of aerosolized AAV vector system per lung endobronchially delivered while spontaneously breathing. The control subjects receive equivalent amount of a pseudotyped AAV vector system with an internal control gene. The vector system may be delivered along with a pharmaceutically acceptable or biocompatible pharmaceutical carrier. Three weeks or an appropriate time interval following vector administration, treated subjects are tested for amelioration of cystic fibrosis related symptoms.

Applicants use an adenovirus or an AAV particle.

Applicants clone the following gene constructs, each operably linked to one or more regulatory sequences (Cbh or EF1a promoter for Cas9, U6 or H1 promoter for chimeric guide RNA), into one or more adenovirus or AAV vectors or any other compatible vector: A CFTRdelta508 targeting chimeric guide RNA (FIG. 13B), a repair template for deltaF508 mutation (FIG. 13C) and a codon optimized Cas9 enzyme with optionally one or more nuclear localization signal or sequence(s) (NLS(s)), e.g., two (2) NLSs.

Identification of Cas9 Target Site

Applicants analyzed the human CFTR genomic locus and identified the Cas9 target site (FIG. 13A). (PAM may contain a NGG or a NNAGAAW motif).

Gene Repair Strategy

Applicants introduce an adenovirus/AAV vector system comprising a Cas9 (or Cas9 nickase) and the guide RNA along with a adenovirus/AAV vector system comprising the homology repair template containing the F508 residue into the subject via one of the methods of delivery discussed earlier. The CRISPR-Cas system is guided by the CFTRdelta 508 chimeric guide RNA and targets a specific site of the CFTR genomic locus to be nicked or cleaved. After cleavage, the repair template is inserted into the cleavage site via homologous recombination correcting the deletion that results in cystic fibrosis or causes cystic fibrosis related symptoms. This strategy to direct delivery and provide systemic introduction of CRISPR systems with appropriate guide RNAs can be employed to target genetic mutations to edit or otherwise manipulate genes that cause metabolic, liver, kidney and protein diseases and disorders such as those in Table B.

Example 17: Generation of Gene Knockout Cell Library

This example demonstrates how to generate a library of cells where each cell has a single gene knocked out:

Applicants make a library of ES cells where each cell has a single gene knocked out, and the entire library of ES cells will have every single gene knocked out. This library is useful for the screening of gene function in cellular processes as well as diseases.

To make this cell library, Applicants integrate Cas9 driven by an inducible promoter (e.g. doxycycline inducible promoter) into the ES cell. In addition, Applicants integrate a single guide RNA targeting a specific gene in the ES cell. To make the ES cell library, Applicants simply mix ES cells with a library of genes encoding guide RNAs targeting each gene in the human genome. Applicants first introduce a single BxB1 attB site into the AAVS1 locus of the human ES cell. Then Applicants use the BxB1 integrase to facilitate the integration of individual guide RNA genes into the BxB1 attB site in AAVS1 locus. To facilitate integration, each guide RNA gene is contained on a plasmid that carries of a single attP site. This way BxB1 will recombine the attB site in the genome with the attP site on the guide RNA containing plasmid.

To generate the cell library, Applicants take the library of cells that have single guide RNAs integrated and induce Cas9 expression. After induction, Cas9 mediates double strand break at sites specified by the guide RNA. To verify the diversity of this cell library, Applicants carry out whole exome sequencing to ensure that Applicants are able to observe mutations in every single targeted gene. This cell library can be used for a variety of applications, including who library-based screens, or can be sorted into individual cell clones to facilitate rapid generation of clonal cell lines with individual human genes knocked out.

Example 18: Engineering of Microalgae Using Cas9

Methods of Delivering Cas9

Method 1: Applicants deliver Cas9 and guide RNA using a vector that expresses Cas9 under the control of a constitutive promoter such as Hsp70A-Rbc S2 or Beta2-tubulin.

Method 2: Applicants deliver Cas9 and T7 polymerase using vectors that expresses Cas9 and T7 polymerase under the control of a constitutive promoter such as Hsp70A-Rbc S2 or Beta2-tubulin. Guide RNA will be delivered using a vector containing T7 promoter driving the guide RNA.

Method 3: Applicants deliver Cas9 mRNA and in vitro transcribed guide RNA to algae cells. RNA can be in vitro transcribed. Cas9 mRNA will consist of the coding region for Cas9 as well as 3'UTR from Cop1 to ensure stabilization of the Cas9 mRNA.

For Homologous recombination, Applicants provide an additional homology directed repair template.

Sequence for a cassette driving the expression of Cas9 under the control of beta-2 tubulin promoter, followed by the 3' UTR of Cop1.

(SEQ ID NO: 117)
TCTTTCTTGCGCTATGACACTTCCAGCAAAAGGTAGGGCGGGCTGCGA

GACGGCTTCCCGGCGCTGCATGCAACACCGATGATGCTTCGACCCCCCGA

AGCTCCTTCGGGGCTGCATGGGCGCTCCGATGCCGCTCCAGGGCGAGCGC

TGTTTAAATAGCCAGGCCCCCGATTGCAAAGACATTATAGCGAGCTACCA

AAGCCATATTCAAACACCTAGATCACTACCACTTCTACACAGGCCACTCG

AGCTTGTGATCGCACTCCGCTAAGGGGCGCCTCTTCCTCTTCGTTTCAG

TCACAACCCGCAAACATGTACCCATACGATGTTCCAGATTACGCTTCGCC

GAAGAAAAGCGCAAGGTCGAAGCGTCCGACAAGAAGTACAGCATCGGCC

TGGACATCGGCACCAACTCTGTGGGCTGGGCCGTGATCACCGACGAGTAC

AAGGTGCCCAGCAAGAAATTCAAGGTGCTGGGCAACACCGACCGGCACAG

CATCAAGAAGAACCTGATCGGAGCCCTGCTGTTCGACAGCGGCGAAACAG

CCGAGGCCACCCGGCTGAAGAGAACCGCCAGAAGAAGATACACCAGACGG

AAGAACCGGATCTGCTATCTGCAAGAGATCTTCAGCAACGAGATGGCCAA

GGTGGACGACAGCTTCTTCCACAGACTGGAAGAGTCCTTCCTGGTGGAAG

AGGATAAGAAGCACGAGCGGCACCCCATCTTCGGCAACATCGTGGACGAG

GTGGCCTACCACGAGAAGTACCCCACCATCTACCACCTGAGAAAGAAACT

-continued
```
GGTGGACAGCACCGACAAGGCCGACCTGCGGCTGATCTATCTGGCCCTGG
CCCACATGATCAAGTTCCGGGGCCACTTCCTGATCGAGGGCGACCTGAAC
CCCGACAACAGCGACGTGGACAAGCTGTTCATCCAGCTGGTGCAGACCTA
CAACCAGCTGTTCGAGGAAAACCCCATCAACGCCAGCGGCGTGGACGCCA
AGGCCATCCTGTCTGCCAGACTGAGCAAGAGCAGACGGCTGGAAAATCTG
ATCGCCCAGCTGCCCGGCGAGAAGAAGAATGGCCTGTTCGGCAACCTGAT
TGCCCTGAGCCTGGGCCTGACCCCCAACTTCAAGAGCAACTTCGACCTGG
CCGAGGATGCCAAACTGCAGCTGAGCAAGGACACCTACGACGACGACCTG
GACAACCTGCTGGCCCAGATCGGCGACCAGTACGCCGACCTGTTTCTGGC
CGCCAAGAACCTGTCCGACGCCATCCTGCTGAGCGACATCCTGAGAGTGA
ACACCGAGATCACCAAGGCCCCCCTGAGCGCCTCTATGATCAAGAGATAC
GACGAGCACCACCAGGACCTGACCCTGCTGAAAGCTCTCGTGCGGCAGCA
GCTGCCTGAGAAGTACAAAGAGATTTTCTTCGACCAGAGCAAGAACGGCT
ACGCCGGCTACATTGACGGCGGAGCCAGCCAGGAAGAGTTCTACAAGTTC
ATCAAGCCCATCCTGGAAAAGATGGACGGCACCGAGGAACTGCTCGTGAA
GCTGAACAGAGAGGACCTGCTGCGGAAGCAGCGGACCTTCGACAACGGCA
GCATCCCCCACCAGATCCACCTGGGAGAGCTGCACGCCATTCTGCGGCGG
CAGGAAGATTTTTACCCATTCCTGAAGGACAACCGGGAAAAGATCGAGAA
GATCCTGACCTTCCGCATCCCCTACTACGTGGGCCCTCTGGCCAGGGGAA
ACAGCAGATTCGCCTGGATGACCAGAAAGAGCGAGGAAACCATCACCCCC
TGGAACTTCGAGGAAGTGGTGGACAAGGGCGCTTCCGCCCAGAGCTTCAT
CGAGCGGATGACCAACTTCGATAAGAACCTGCCCAACGAGAAGGTGCTGC
CCAAGCACAGCCTGCTGTACGAGTACTTCACCGTGTATAACGAGCTGACC
AAAGTGAAATACGTGACCGAGGGAATGAGAAAGCCCGCCTTCCTGAGCGG
CGAGCAGAAAAAGGCCATCGTGGACCTGCTGTTCAAGACCAACCGGAAAG
TGACCGTGAAGCAGCTGAAAGAGGACTACTTCAAGAAAATCGAGTGCTTC
GACTCCGTGGAAATCTCCGGCGTGGAAGATCGGTTCAACGCCTCCCTGGG
CACATACCACGATCTGCTGAAAATTATCAAGGACAAGGACTTCCTGGACA
ATGAGGAAAACGAGGACATTCTGGAAGATATCGTGCTGACCCTGACACTG
TTTGAGGACAGAGAGATGATCGAGGAACGGCTGAAAACCTATGCCCACCT
GTTCGACGACAAAGTGATGAAGCAGCTGAAGCGGCGGAGATACACCGGCT
GGGGCAGGCTGAGCCGGAAGCTGATCAACGGCATCCGGGACAAGCAGTCC
GGCAAGACAATCCTGGATTTCCTGAAGTCCGACGGCTTCGCCAACAGAAA
CTTCATGCAGCTGATCCACGACGACAGCCTGACCTTTAAAGAGGACATCC
AGAAAGCCCAGGTGTCCGGCCAGGGCGATAGCCTGCACGAGCACATTGCC
AATCTGGCCGGCAGCCCCGCCATTAAGAAGGGCATCCTGCAGACAGTGAA
GGTGGTGGACGAGCTCGTGAAAGTGATGGGCCGGCACAAGCCCGAGAACA
TCGTGATCGAAATGGCCAGAGAGAACCAGACCACCCAGAAGGGACAGAAG
AACAGCCGCGAGAGAATGAAGCGGATCGAAGAGGGCATCAAAGAGCTGGG
CAGCCAGATCCTGAAAGAACACCCCGTGGAAAACACCCAGCTGCAGAACG
AGAAGCTGTACCTGTACTACCTGCAGAATGGGCGGGATATGTACGTGGAC
CAGGAACTGGACATCAACCGGCTGTCCGACTACGATGTGGACCATATCGT
GCCTCAGAGCTTTCTGAAGGACGACTCCATCGACAACAAGGTGCTGACCA
GAAGCGACAAGAACCGGGGCAAGAGCGACAACGTGCCCTCCGAAGAGGTC
GTGAAGAAGATGAAGAACTACTGGCGGCAGCTGCTGAACGCCAAGCTGAT
TACCCAGAGAAAGTTCGACAATCTGACCAAGGCCGAGAGAGGCGGCCTGA
GCGAACTGGATAAGGCCGGCTTCATCAAGAGACAGCTGGTGGAAACCCGG
CAGATCACAAAGCACGTGGCACAGATCCTGGACTCCCGGATGAACACTAA
GTACGACGAGAATGACAAGCTGATCCGGGAAGTGAAAGTGATCACCCTGA
AGTCCAAGCTGGTGTCCGATTTCCGGAAGGATTTCCAGTTTTACAAAGTG
CGCGAGATCAACAACTACCACCACGCCCACGACGCCTACCTGAACGCCGT
CGTGGGAACCGCCCTGATCAAAAAGTACCCTAAGCTGGAAAGCGAGTTCG
TGTACGGCGACTACAAGGTGTACGACGTGCGGAAGATGATCGCCAAGAGC
GAGCAGGAAATCGGCAAGGCTACCGCCAAGTACTTCTTCTACAGCAACAT
CATGAACTTTTTCAAGACCGAGATTACCCTGGCCAACGGCGAGATCCGGA
AGCGGCCTCTGATCGAGACAAACGGCGAAACCGGGGAGATCGTGTGGGAT
AAGGGCCGGGATTTTGCCACCGTGCGGAAAGTGCTGAGCATGCCCCAAGT
GAATATCGTGAAAAAGACCGAGGTGCAGACAGGCGGCTTCAGCAAAGAGT
CTATCCTGCCCAAGAGGAACAGCGATAAGCTGATCGCCAGAAAGAAGGAC
TGGGACCCTAAGAAGTACGGCGGCTTCGACAGCCCCACCGTGGCCTATTC
TGTGCTGGTGGTGGCCAAAGTGGAAAAGGGCAAGTCCAAGAAACTGAAGA
GTGTGAAAGAGCTGCTGGGGATCACCATCATGGAAAGAAGCAGCTTCGAG
AAGAATCCCATCGACTTTCTGGAAGCCAAGGGCTACAAAGAAGTGAAAAA
GGACCTGATCATCAAGCTGCCTAAGTACTCCCTGTTCGAGCTGGAAAACG
GCCGGAAGAGAATGCTGGCCTCTGCCGGCGAACTGCAGAAGGGAAACGAA
CTGGCCCTGCCCTCCAAATATGTGAACTTCCTGTACCTGGCCAGCCACTA
TGAGAAGCTGAAGGGCTCCCCCGAGGATAATGAGCAGAAACAGCTGTTTG
TGGAACAGCACAAGCACTACCTGGACGAGATCATCGAGCAGATCAGCGAG
TTCTCCAAGAGAGTGATCCTGGCCGACGCTAATCTGGACAAAGTGCTGTC
CGCCTACAACAAGCACCGGGATAAGCCCATCAGAGAGCAGGCCGAGAATA
TCATCCACCTGTTTACCCTGACCAATCTGGGAGCCCCTGCCGCCTTCAAG
TACTTTGACACCACCATCGACCGGAAGAGGTACACCAGCACCAAAGAGGT
GCTGGACGCCACCCTGATCCACCAGAGCATCACCGGCCTGTACGAGACAC
GGATCGACCTGTCTCAGCTGGGAGGCGACAGCCCCAAGAAGAAGAGAAAG
GTGGAGGCCAGCTAAGGATCCGGCAAGACTGGCCCCGCTTGGCAACGCAA
CAGTGAGCCCTCCCTAGTGTGTTTGGGGATGTGACTATGTATTCGTGTG
TTGGCCAACGGGTCAACCCGAACAGATTGATACCCGCCTTGGCATTTCCT
GTCAGAATGTAACGTCAGTTGATGGTACT
```

Sequence for a cassette driving the expression of T7 polymerase under the control of beta-2 tubulin promoter, followed by the 3′ UTR of Cop1:

(SEQ ID NO: 118)
```
TCTTTCTTGCGCTATGACACTTCCAGCAAAAGGTAGGGCGGGCTGCGA
GACGGCTTCCCGGCGCTGCATGCAACACCGATGATGCTTCGACCCCCG
AAGCTCCTTCGGGGCTGCATGGGCGCTCCGATGCCGCTCCAGGGCGAGC
GCTGTTTAAATAGCCAGGCCCCCGATTGCAAAGACATTATAGCGAGCTA
CCAAAGCCATATTCAAACACCTAGATCACTACCACTTCTACACAGGCCA
CTCGAGCTTGTGATCGCACTCCGCTAAGGGGGCGCCTCTTCCTCTTCGT
TTCAGTCACAACCCGCAAAcatgcctaagaagaagaggaaggttaacac
gattaacatcgctaagaacgacttctctgacatcgaactggctgctatc
ccgttcaacactctggctgaccattacggtgagcgtttagctcgcgaac
agttggcccttgagcatgagtcttacgagatgggtgaagcacgcttccg
caagatgtttgagcgtcaacttaaagctggtgaggttgcggataacgct
gccgccaagcctctcatcactaccctactccctaagatgattgcacgca
tcaacgactggtttgaggaagtgaaagctaagcgcggcaagcgcccgac
agccttccagttcctgcaagaaatcaagccggaagccgtagcgtacatc
accattaagaccactctggcttgcctaaccagtgctgacaatacaaccg
ttcaggctgtagcaagcgcaatcggtcgggccattgaggacgaggctcg
cttcggtcgtatccgtgaccttgaagctaagcacttcaagaaaaacgtt
gaggaacaactcaacaagcgcgtagggcacgtctacaagaaagcattta
tgcaagttgtcgaggctgacatgctctctaagggtctactcggtggcga
ggcgtggtcttcgtggcataaggaagactctattcatgtaggagtacgc
tgcatcgagatgctcattgagtcaaccggaatggttagcttacaccgcc
aaaatgctggcgtagtaggtcaagactctgagactatcgaactcgcacc
tgaatacgctgaggctatcgcaacccgtgcaggtgcgctggctggcatc
tctccgatgttccaaccttgcgtagttcctcctaagccgtggactggca
ttactggtggtggctattgggctaacggtcgtcgtcctctggcgctggt
gcgtactcacagtaagaaagcactgatgcgctacgaagacgtttacatg
cctgaggtgtacaaagcgattaacattgcgcaaaacaccgcatggaaaa
tcaacaagaaagtcctagcggtcgccaacgtaatcaccaagtggaagca
ttgtccggtcgaggacatccctgcgattgagcgtgaagaactcccgatg
aaaccggaagacatcgacatgaatcctgaggctctcaccgcgtggaaac
gtgctgccgctgctgtgtaccgcaaggacaaggctcgcaagtctcgccg
tatcagccttgagttcatgcttgagcaagccaataagtttgctaaccat
aaggccatctggttcccttacaacatggactggcgcggtcgtgtttacg
ctgtgtcaatgttcaacccgcaaggtaacgatatgaccaaaggactgct
tacgctggcgaaaggtaaaccaatcggtaaggaaggttactactggctg
aaaatccacggtgcaaactgtgcgggtgtcgacaaggttccgttccctg
agcgcatcaagttcattgaggaaaaccacgagaacatcatggcttgcgc
taagtctccactggagaacacttggtgggctgagcaagattctccgttc
tgatccttgcgttctgattgagtacgctggggtacagcaccacgcctg
agctataactgaccatccgctggcgtttgacgggtcttgctctggcatc
```
```
cagcacttctccgcgatgctccgagatgaggtaggtggtcgcgcggtta
acttgcttcctagtgaaaccgttcaggacatctacgggattgttgctaa
gaaagtcaacgagattctacaagcagacgcaatcaatgggaccgataac
gaagtagttaccgtgaccgatgagaacactggtgaaatactgagaaagt
caagagggcactaaggcactggctggtcaatggctggcttacggtgtta
ctcgcagtgtgactaagcgttcagtcatgacgctggcttacgggtccaa
agagttcggatccgtcaacaagtgctggaagataccattcagccagcta
ttgattccggcaagggtagatgttcactcagccgaatcaggctgctgga
tacatggctaagctgatttgggaatctgtgagcgtgacggtggtagagc
ggttgaagcaatgaactggcttaagtagagctaagagaggctgctgagg
tcaaagataagaagactggagagattatcgcaagcgttgcgctgtgcat
tgggtaactcctgatggtttccctgtgtggcaggaatacaagaagccta
ttcagacgcgcttgaacctgatgttcctcggtcagttccgcttacagcc
taccattaacaccaacaaagatagcgagattgatgcacacaaacaggag
taggtatcgctcctaactttgtacacagccaagacggtagccaccttcg
taagactgtagtgtgggcacacgagaagtacggaatcgaatatttgcac
tgattcacgactccttcggtacgattccggctgacgctgcgaacctgtt
caaagcagtgcgcgaaactatggttgacacatatgagtatgtgatgtac
tggctgatttctacgaccagttcgctgaccagttgcacgagtacaattg
gacaaaatgccagcacttccggctaaaggtaacttgaacctccgtgaca
tcttagagtcggacttcgcgttcgcgtaaGGATCCGGCAAGACTGGCCC
CGCTTGGCAACGCAACAGTGAGCCCCTCCCTAGTGTGTTTGGGGATGTG
ACTATGTATTCGTGTGTTGGCCAACGGGTCAACCCGAACAGATTGATAC
CCGCCTTGGCATTTCCTGTCAGAATGTAACGTCAGTTGATGGTACT
```

Sequence of guide RNA driven by the T7 promoter (T7 promoter, Ns represent targeting sequence):

(SEQ ID NO: 119)
```
gaaatTAATACGACTCACTATANNNNNNNNNNNNNNNNNNNNNNNNNgttttaga
gctaGAAAtagcaagttaaaataaggctagtccgttatcaacttgaaaaa
gtggcaccgagtcggtgatttttt
```

Gene Delivery:

*Chlamydomonas reinhardtii* strain CC-124 and CC-125 from the *Chlamydomonas* Resource Center will be used for electroporation. Electroporation protocol follows standard recommended protocol from the GeneArt *Chlamydomonas* Engineering kit.

Also, Applicants generate a line of *Chlamydomonas reinhardtii* that expresses Cas9 constitutively. This can be done by using pChlamy1 (linearized using PvuI) and selecting for hygromycin resistant colonies. Sequence for pChlamy1 containing Cas9 is below. In this way to achieve gene knockout one simply needs to deliver RNA for the guideRNA. For homologous recombination Applicants deliver guideRNA as well as a linearized homologous recombination template.

pChlamy1-Cas9:

(SEQ ID NO: 120)
TGCGGTATTTCACACCGCATCAGGTGGCACTTTTCGGGGAAATGTGC

GCGGAACCCCTATTTGTTTATTTTTCTAAATACATTCAAATATGTATCCG

CTCATGAGATTATCAAAAAGGATCTTCACCTAGATCCTTTTAAATTAAAA

ATGAAGTTTTAAATCAATCTAAAGTATATATGAGTAAACTTGGTCTGACA

GTTACCAATGCTTAATCAGTGAGGCACCTATCTCAGCGATCTGTCTATTT

CGTTCATCCATAGTTGCCTGACTCCCCGTCGTGTAGATAACTACGATACG

GGAGGGCTTACCATCTGGCCCCAGTGCTGCAATGATACCGCGAGACCCAC

GCTCACCGGCTCCAGATTTATCAGCAATAAACCAGCCAGCGGAAGGGCC

GAGCGCAGAAGTGGTCCTGCAACTTTATCCGCCTCCATCCAGTCTATTAA

TTGTTGCCGGGAAGCTAGAGTAAGTAGTTCGCCAGTTAATAGTTTGCGCA

ACGTTGTTGCCATTGCTACAGGCATCGTGGTGTCACGCTCGTCGTTTGGT

ATGGCTTCATTCAGCTCCGGTTCCCAACGATCAAGGCGAGTTACATGATC

CCCCATGTTGTGCAAAAAAGCGGTTAGCTCCTTCGGTCCTCCGATCGTTG

TCAGAAGTAAGTTGGCCGCAGTGTTATCACTCATGGTTATGGCAGCACTG

CATAATTCTCTTACTGTCATGCCATCCGTAAGATGCTTTTCTGTGACTGG

TGAGTACTCAACCAAGTCATTCTGAGAATAGTGTATGCGGCGACCGAGTT

GCTCTTGCCCGGCGTCAATACGGGATAATACCGCGCCACATAGCAGAACT

TTAAAAGTGCTCATCATTGGAAAACGTTCTTCGGGGCGAAAACTCTCAAG

GATCTTACCGCTGTTGAGATCCAGTTCGATGTAACCCACTCGTGCACCCA

ACTGATCTTCAGCATCTTTTACTTTCACCAGCGTTTCTGGGTGAGCAAAA

ACAGGAAGGCAAAATGCCGCAAAAAAGGGAATAAGGGCGACACGGAAATG

TTGAATACTCATACTCTTCCTTTTTCAATATTATTGAAGCATTTATCAGG

GTTATTGTCTCATGACCAAAATCCCTTAACGTGAGTTTTCGTTCCACTGA

GCGTCAGACCCCGTAGAAAAGATCAAAGGATCTTCTTGAGATCCTTTTTT

TCTGCGCGTAATCTGCTGCTTGCAAACAAAAAAACCACCGCTACCAGCGG

TGGTTTGTTTGCCGGATCAAGAGCTACCAACTCTTTTTCCGAAGGTAACT

GGCTTCAGCAGAGCGCAGATACCAAATACTGTTCTTCTAGTGTAGCCGTA

GTTAGGCCACCACTTCAAGAACTCTGTAGCACCGCCTACATACCTCGCTC

TGCTAATCCTGTTACCAGTGGCTGTTGCCAGTGGCGATAAGTCGTGTCTT

ACCGGGTTGGACTCAAGACGATAGTTACCGGATAAGGCGCAGCGGTCGGG

CTGAACGGGGGGTTCGTGCACACAGCCCAGCTTGGAGCGAACGACCTACA

CCGAACTGAGATACCTACAGCGTGAGCTATGAGAAAGCGCCACGCTTCCC

GAAGGGAGAAAGGCGGACAGGTATCCGGTAAGCGGCAGGGTCGGAACAGG

AGAGCGCACGAGGGAGCTTCCAGGGGGAAACGCCTGGTATCTTTATAGTC

CTGTCGGGTTTCGCCACCTCTGACTTGAGCGTCGATTTTTGTGATGCTCG

TCAGGGGGGCGGAGCCTATGGAAAAACGCCAGCAACGCGGCCTTTTTACG

GTTCCTGGCCTTTTGCTGGCCTTTTGCTCACATGTTCTTTCCTGCGTTAT

CCCCTGATTCTGTGGATAACCGTATTACCGCCTTTGAGTGAGCTGATACC

GCTCGCCGCAGCCGAACGACCGAGCGCAGCGAGTCAGTGAGCGAGGAAGC

GGTCGCTGAGGCTTGACATGATTGGTGCGTATGTTTGTATGAAGCTACAG

GACTGATTTGGCGGGCTATGAGGGCGGGGGAAGCTCTGGAAGGGCCGCGA

TGGGGCGCGCGGCGTCCAGAAGGCGCCATACGGCCCGCTGGCGGCACCCA

TCCGGTATAAAAGCCCGCGACCCCGAACGGTGACCTCCACTTTCAGCGAC

AAACGAGCACTTATACATACGCGACTATTCTGCCGCTATACATAACCACT

CAGCTAGCTTAAGATCCCATCAAGCTTGCATGCCGGGCGCGCCAGAAGGA

GCGCAGCCAAACCAGGATGATGTTTGATGGGGTATTTGAGCACTTGCAAC

CCTTATCCGGAAGCCCCCTGGCCCACAAAGGCTAGGCGCCAATGCAAGCA

GTTCGCATGCAGCCCCTGGAGCGGTGCCCTCCTGATAAACCGGCCAGGGG

GCCTATGTTCTTTACTTTTTTACAAGAGAAGTCACTCAACATCTTAAAAT

GGCCAGGTGAGTCGACGAGCAAGCCCGGCGGATCAGGCAGCGTGCTTGCA

GATTTGACTTGCAACGCCCGCATTGTGTCGACGAAGGCTTTTGGCTCCTC

TGTCGCTGTCTCAAGCAGCATCTAACCCTGCGTCGCCGTTTCCATTTGCA

GGAGATTCGAGGTACCATGTACCCATACGATGTTCCAGATTACGCTTCGC

CGAAGAAAAAGCGCAAGGTCGAAGCGTCCGACAAGAAGTACAGCATCGGC

CTGGACATCGGCACCAACTCTGTGGGCTGGGCCGTGATCACCGACGAGTA

CAAGGTGCCCAGCAAGAAATTCAAGGTGCTGGGCAACACCGACCGGCACA

GCATCAAGAAGAACCTGATCGGAGCCCTGCTGTTCGACAGCGGCGAAACA

GCCGAGGCCACCCGGCTGAAGAGAACCGCCAGAAGAAGATACACCAGACG

GAAGAACCGGATCTGCTATCTGCAAGAGATCTTCAGCAACGAGATGGCCA

AGGTGGACGACAGCTTCTTCCACAGACTGGAAGAGTCCTTCCTGGTGGAA

GAGGATAAGAAGCACGAGCGGCACCCCATCTTCGGCAACATCGTGGACGA

GGTGGCCTACCACGAGAAGTACCCCACCATCTACCACCTGAGAAAGAAAC

TGGTGGACAGCACCGACAAGGCCGACCTGCGGCTGATCTATCTGGCCCTG

GCCCACATGATCAAGTTCCGGGGCCACTTCCTGATCGAGGGCGACCTGAA

CCCCGACAACAGCGACGTGGACAAGCTGTTCATCCAGCTGGTGCAGACCT

ACAACCAGCTGTTCGAGGAAAACCCCATCAACGCCAGCGGCGTGGACGCC

AAGGCCATCCTGTCTGCCAGACTGAGCAAGAGCAGACGGCTGGAAAATCT

GATCGCCCAGCTGCCCGGCGAGAAGAAGAATGGCCTGTTCGGCAACCTGA

TTGCCCTGAGCCTGGGCCTGACCCCCAACTTCAAGAGCAACTTCGACCTG

GCCGAGGATGCCAAACTGCAGCTGAGCAAGGACACCTACGACGACGACCT

GGACAACCTGCTGGCCCAGATCGGCGACCAGTACGCCGACCTGTTTCTGG

CCGCCAAGAACCTGTCCGACGCCATCCTGCTGAGCGACATCCTGAGAGTG

AACACCGAGATCACCAAGGCCCCCCTGAGCGCCTCTATGATCAAGAGATA

CGACGAGCACCACCAGGACCTGACCCTGCTGAAAGCTCTCGTGCGGCAGC

AGCTGCCTGAGAAGTACAAAGAGATTTTCTTCGACCAGAGCAAGAACGGC

TACGCCGGCTACATTGACGGCGGAGCCAGCCAGGAAGAGTTCTACAAGTT

CATCAAGCCCATCCTGGAAAAGATGGACGGCACCGAGGAACTGCTCGTGA

AGCTGAACAGAGAGGACCTGCTGCGGAAGCAGCGGACCTTCGACAACGGC

AGCATCCCCCACCAGATCCACCTGGGAGAGCTGCACGCCATTCTGCGGCG

GCAGGAAGATTTTTACCCATTCCTGAAGGACAACCGGGAAAAGATCGAGA

```
AGATCCTGACCTTCCGCATCCCCTACTACGTGGGCCCTCTGGCCAGGGGA
AACAGCAGATTCGCCTGGATGACCAGAAAGAGCGAGGAAACCATCACCCC
CTGGAACTTCGAGGAAGTGGTGGACAAGGGCGCTTCCGCCCAGAGCTTCA
TCGAGCGGATGACCAACTTCGATAAGAACCTGCCCAACGAGAAGGTGCTG
CCCAAGCACAGCCTGCTGTACGAGTACTTCACCGTGTATAACGAGCTGAC
CAAAGTGAAATACGTGACCGAGGGAATGAGAAAGCCCGCCTTCCTGAGCG
GCGAGCAGAAAAAGGCCATCGTGGACCTGCTGTTCAAGACCAACCGGAAA
GTGACCGTGAAGCAGCTGAAAGAGGACTACTTCAAGAAAATCGAGTGCTT
CGACTCCGTGGAAATCTCCGGCGTGGAAGATCGGTTCAACGCCTCCCTGG
GCACATACCACGATCTGCTGAAAATTATCAAGGACAAGGACTTCCTGGAC
AATGAGGAAAACGAGGACATTCTGGAAGATATCGTGCTGACCCTGACACT
GTTTGAGGACAGAGAGATGATCGAGGAACGGCTGAAAACCTATGCCCACC
TGTTCGACGACAAAGTGATGAAGCAGCTGAAGCGGCGGAGATACACCGGC
TGGGGCAGGCTGAGCCGGAAGCTGATCAACGGCATCCGGGACAAGCAGTC
CGGCAAGACAATCCTGGATTTCCTGAAGTCCGACGGCTTCGCCAACAGAA
ACTTCATGCAGCTGATCCACGACGACAGCCTGACCTTTAAAGAGGACATC
CAGAAAGCCCAGGTGTCCGGCCAGGGCGATAGCCTGCACGAGCACATTGC
CAATCTGGCCGGCAGCCCCGCCATTAAGAAGGGCATCCTGCAGACAGTGA
AGGTGGTGGACGAGCTCGTGAAAGTGATGGGCCGGCACAAGCCCGAGAAC
ATCGTGATCGAAATGGCCAGAGAGAACCAGACCACCCAGAAGGGACAGAA
GAACAGCCGCGAGAGAATGAAGCGGATCGAAGAGGGCATCAAAGAGCTGG
GCAGCCAGATCCTGAAAGAACACCCCGTGGAAAACACCCAGCTGCAGAAC
GAGAAGCTGTACCTGTACTACCTGCAGAATGGGCGGGATATGTACGTGGA
CCAGGAACTGGACATCAACCGGCTGTCCGACTACGATGTGGACCATATCG
TGCCTCAGAGCTTTCTGAAGGACGACTCCATCGACAACAAGGTGCTGACC
AGAAGCGACAAGAACCGGGGCAAGAGCGACAACGTGCCCTCCGAAGAGGT
CGTGAAGAAGATGAAGAACTACTGGCGGCAGCTGCTGAACGCCAAGCTGA
TTACCCAGAGAAAGTTCGACAATCTGACCAAGGCCGAGAGAGGCGGCCTG
AGCGAACTGGATAAGGCCGGCTTCATCAAGAGACAGCTGGTGGAAACCCG
GCAGATCACAAAGCACGTGGCACAGATCCTGGACTCCCGGATGAACACTA
AGTACGACGAGAATGACAAGCTGATCCGGGAAGTGAAAGTGATCACCCTG
AAGTCCAAGCTGGTGTCCGATTTCCGGAAGGATTTCCAGTTTTACAAAGT
GCGCGAGATCAACAACTACCACCACGCCCACGACGCCTACCTGAACGCCG
TCGTGGGAACCGCCCTGATCAAAAAGTACCCTAAGCTGGAAAGCGAGTTC
GTGTACGGCGACTACAAGGTGTACGACGTGCGGAAGATGATCGCCAAGAG
CGAGCAGGAAATCGGCAAGGCTACCGCCAAGTACTTCTTCTACAGCAACA
TCATGAACTTTTTCAAGACCGAGATTACCCTGGCCAACGGCGAGATCCGG
AAGCGGCCTCTGATCGAGACAAACGGCGAAACCGGGGAGATCGTGTGGGA
TAAGGGCCGGGATTTTGCCACCGTGCGGAAAGTGCTGAGCATGCCCCAAG
TGAATATCGTGAAAAAGACCGAGGTGCAGACAGGCGGCTTCAGCAAAGAG
TCTATCCTGCCCAAGAGGAACAGCGATAAGCTGATCGCCAGAAAGAAGGA
CTGGGACCCTAAGAAGTACGGCGGCTTCGACAGCCCCACCGTGGCCTATT
CTGTGCTGGTGGTGGCCAAAGTGGAAAAGGGCAAGTCCAAGAAACTGAAG
AGTGTGAAAGAGCTGCTGGGGATCACCATCATGGAAAGAAGCAGCTTCGA
GAAGAATCCCATCGACTTTCTGGAAGCCAAGGGCTACAAAGAAGTGAAAA
AGGACCTGATCATCAAGCTGCCTAAGTACTCCCTGTTCGAGCTGGAAAAC
GGCCGGAAGAGAATGCTGGCCTCTGCCGGCGAACTGCAGAAGGGAAACGA
ACTGGCCCTGCCCTCCAAATATGTGAACTTCCTGTACCTGGCCAGCCACT
ATGAGAAGCTGAAGGGCTCCCCCGAGGATAATGAGCAGAAACAGCTGTTT
GTGGAACAGCACAAGCACTACCTGGACGAGATCATCGAGCAGATCAGCGA
GTTCTCCAAGAGAGTGATCCTGGCCGACGCTAATCTGGACAAAGTGCTGT
CCGCCTACAACAAGCACCGGGATAAGCCCATCAGAGAGCAGGCCGAGAAT
ATCATCCACCTGTTTACCCTGACCAATCTGGGAGCCCCTGCCGCCTTCAA
GTACTTTGACACCACCATCGACCGGAAGAGGTACACCAGCACCAAAGAGG
TGCTGGACGCCACCCTGATCCACCAGAGCATCACCGGCCTGTACGAGACA
CGGATCGACCTGTCTCAGCTGGGAGGCGACAGCCCCAAGAAGAAGAGAAA
GGTGGAGGCCAGCTAACATATGATTCGAATGTCTTTCTTGCGCTATGACA
CTTCCAGCAAAAGGTAGGGCGGGCTGCGAGACGGCTTCCCGGCGCTGCAT
GCAACACCGATGATGCTTCGACCCCCGAAGCTCCTTCGGGGCTGCATGG
GCGCTCCGATGCCGCTCCAGGGCGAGCGCTGTTTAAATAGCCAGGCCCCC
GATTGCAAAGACATTATAGCGAGCTACCAAAGCCATATTCAAACACCTAG
ATCACTACCACTTCTACACAGGCCACTCGAGCTTGTGATCGCACTCCGCT
AAGGGGGCGCCTCTTCCTCTTCGTTTCAGTCACAACCCGCAAACATGACA
CAAGAATCCCTGTTACTTCTCGACCGTATTGATTCGGATGATTCCTACGC
GAGCCTGCGGAACGACCAGGAATTCTGGGAGGTGAGTCGACGAGCAAGCC
CGGCGGATCAGGCAGCGTGCTTGCAGATTTGACTTGCAACGCCCGCATTG
TGTCGACGAAGGCTTTTGGCTCCTCTGTCGCTGTCTCAAGCAGCATCTAA
CCCTGCGTCGCCGTTTCCATTTGCAGCCGCTGGCCCGCCGAGCCCTGGAG
GAGCTCGGGCTGCCGGTGCCGCCGGTGCTGCGGGTGCCCGGCGAGAGCAC
CAACCCCGTACTGGTCGGCGAGCCCGGCCCGGTGATCAAGCTGTTCGGCG
AGCACTGGTGCGGTCCGGAGAGCCTCGCGTCGGAGTCGGAGGCGTACGCG
GTCCTGGCGGACGCCCCGGTGCCGGTGCCCCGCCTCCTCGGCCGCGGCGA
GCTGCGGCCCGGCACCGGAGCCTGGCCGTGGCCCTACCTGGTGATGAGCC
GGATGACCGGCACCACCTGGCGGTCCGCGATGGACGGCACGACCGACCGG
AACGCGCTGCTCGCCCTGGCCCGCGAACTCGGCCGGGTGCTCGGCCGGCT
GCACAGGGTGCCGCTGACCGGGAACACCGTGCTCACCCCCCATTCCGAGG
TCTTCCCGGAACTGCTGCGGGAACGCCGCGCGGCGACCGTCGAGGACCAC
CGCGGGTGGGCTACCTCTCGCCCCGGCTGCTGGACCGCCTGGAGGACTG
GCTGCCGGACGTGGACACGCTGCTGGCCGGCCGCGAACCCCGGTTCGTCC
ACGGCGACCTGCACGGGACCAACATCTTCGTGGACCTGGCCGCGACCGAG
GTCACCGGGATCGTCGACTTCACCGACGTCTATGCGGGAGACTCCCGCTA
```

```
                       -continued
CAGCCTGGTGCAACTGCATCTCAACGCCTTCCGGGGCGACCGCGAGATCC

TGGCCGCGCTGCTCGACGGGGCGCAGTGGAAGCGGACCGAGGACTTCGCC

CGCGAACTGCTCGCCTTCACCTTCCTGCACGACTTCGAGGTGTTCGAGGA

GACCCCGCTGGATCTCTCCGGCTTCACCGATCCGGAGGAACTGGCGCAGT

TCCTCTGGGGGCCGCCGGACACCGCCCCGGCGCCTGATAAGGATCCGGC

AAGACTGGCCCCGCTTGGCAACGCAACAGTGAGCCCCTCCCTAGTGTGTT

TGGGGATGTGACTATGTATTCGTGTGTTGGCCAACGGGTCAACCCGAACA

GATTGATACCCGCCTTGGCATTTCCTGTCAGAATGTAACGTCAGTTGATG

GTACT
```

For all modified *Chlamydomonas reinhardtii* cells, Applicants use PCR, SURVEYOR nuclease assay, and DNA sequencing to verify successful modification.

Example 19: Use of Cas9 to Target a Variety of Disease Types

Diseases that involve mutations in protein coding sequence:

Dominant disorders may be targeted by inactivating the dominant negative allele. Applicants use Cas9 to target a unique sequence in the dominant negative allele and introduce a mutation via NHEJ. The NHEJ-induced indel may be able to introduce a frame-shift mutation in the dominant negative allele and eliminate the dominant negative protein. This may work if the gene is haplo-sufficient (e.g. MYOC mutation induced glaucoma and Huntington's disease).

Recessive disorders may be targeted by repairing the disease mutation in both alleles. For dividing cells, Applicants use Cas9 to introduce double strand breaks near the mutation site and increase the rate of homologous recombination using an exogenous recombination template. For dividing cells, this may be achieved using multiplexed nickase activity to catalyze the replacement of the mutant sequence in both alleles via NHEJ-mediated ligation of an exogenous DNA fragment carrying complementary overhangs.

Applicants also use Cas9 to introduce protective mutations (e.g. inactivation of CCR5 to prevent HIV infection, inactivation of PCSK9 for cholesterol reduction, or introduction of the A673T into APP to reduce the likelihood of Alzheimer's disease).

Diseases that Involve Non-Coding Sequences

Applicants use Cas9 to disrupt non-coding sequences in the promoter region, to alter transcription factor binding sites and alter enhancer or repressor elements. For example, Cas9 may be used to excise out the Klf1 enhancer EHS1 in hematopoietic stem cells to reduce BCL11a levels and reactivate fetal globin gene expression in differentiated erythrocytes Applicants also use Cas9 to disrupt functional motifs in the 5' or 3' untranslated regions. For example, for the treatment of myotonic dystrophy, Cas9 may be used to remove CTG repeat expansions in the DMPK gene.

Example 20: Multiplexed Nickase

Aspects of optimization and the teachings of Cas9 detailed in this application may also be used to generate Cas9 nickases. Applicants use Cas9 nickases in combination with pairs of guide RNAs to generate DNA double strand breaks with defined overhangs. When two pairs of guide RNAs are used, it is possible to excise an intervening DNA fragment. If an exogenous piece of DNA is cleaved by the two pairs of guide RNAs to generate compatible overhangs with the genomic DNA, then the exogenous DNA fragment may be ligated into the genomic DNA to replace the excised fragment. For example, this may be used to remove trinucleotide repeat expansion in the huntintin (HTT) gene to treat Huntington's Disease.

If an exogenous DNA that bears fewer number of CAG repeats is provided, then it may be able to generate a fragment of DNA that bears the same overhangs and can be ligated into the HTT genomic locus and replace the excised fragment (fragments below disclosed as SEQ ID NOS 121-128, respectively, in order of appearance).

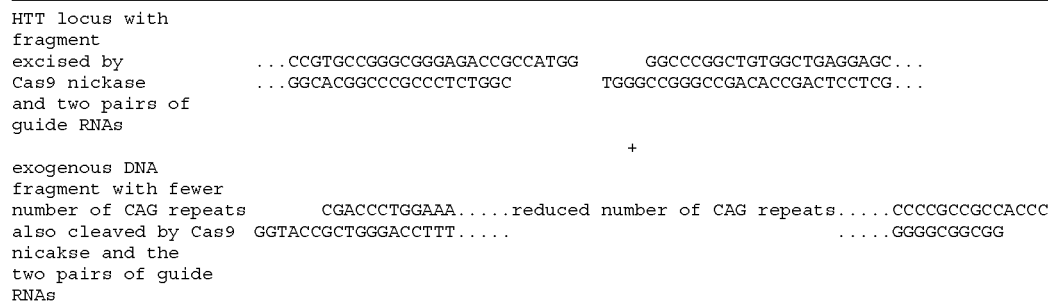

The ligation of the exogenous DNA fragment into the genome does not require homologous recombination machineries and therefore this method may be used in post-mitotic cells such as neurons.

Example 21: Delivery of CRISPR System

Cas9 and its chimeric guide RNA, or combination of tracrRNA and crRNA, can be delivered either as DNA or RNA. Delivery of Cas9 and guide RNA both as RNA (normal or containing base or backbone modifications) molecules can be used to reduce the amount of time that Cas9 protein persist in the cell. This may reduce the level of off-target cleavage activity in the target cell. Since delivery of Cas9 as mRNA takes time to be translated into protein, it might be advantageous to deliver the guide RNA several hours following the delivery of Cas9 mRNA, to maximize the level of guide RNA available for interaction with Cas9 protein.

In situations where guide RNA amount is limiting, it may be desirable to introduce Cas9 as mRNA and guide RNA in the form of a DNA expression cassette with a promoter driving the expression of the guide RNA. This way the amount of guide RNA available will be amplified via transcription.

A variety of delivery systems can be introduced to introduce Cas9 (DNA or RNA) and guide RNA (DNA or RNA) into the host cell. These include the use of liposomes, viral vectors, electroporation, nanoparticles, nanowires (Shalek et al., Nano Letters, 2012), exosomes. Molecular trojan horses liposomes (Pardridge et al., Cold Spring Harb Protoc; 2010; doi:10.1101/pdb.prot5407) may be used to deliver Cas9 and guide RNA across the blood brain barrier.

Example 22: Cas9 Orthologs

Applicants analyzed Cas9 orthologs (FIGS. 3 and 4A-F) to identify the relevant PAM sequences and the corresponding chimeric guide RNAs. This expanded set of PAMs may provide broader targeting across the genome and also significantly increases the number of unique target sites and provides potential for identifying novel Cas9s with increased levels of specificity in the genome. Applicants determined the PAM for *Staphylococcus aureus* sp. *Aureus* Cas9 to be NNGRR *Staphylococcus aureus* sp. *Aureus* Cas9 is also known as SaCas9.

The specificity of Cas9 orthologs can be evaluated by testing the ability of each Cas9 to tolerate mismatches between the guide RNA and its DNA target. For example, the specificity of SpCas9 has been characterized by testing the effect of mutations in the guide RNA on cleavage efficiency. Libraries of guide RNAs were made with single or multiple mismatches between the guide sequence and the target DNA. Based on these findings, target sites for SpCas9 can be selected based on the following guidelines:

To maximize SpCas9 specificity for editing a particular gene, one should choose a target site within the locus of interest such that potential 'off-target' genomic sequences abide by the following four constraints: First and foremost, they should not be followed by a PAM with either 5'-NGG or NAG sequences. Second, their global sequence similarity to the target sequence should be minimized. Third, a maximal number of mismatches should lie within the PAM-proximal region of the off-target site. Finally, a maximal number of mismatches should be consecutive or spaced less than four bases apart.

Similar methods can be used to evaluate the specificity of other Cas9 orthologs and to establish criteria for the selection of specific target sites within the genomes of target species.

Example 23: Therapeutic Strategies for Trinucleotide Repeat Disorders

As previously mentioned in the application, the target polynucleotide of a CRISPR complex may include a number of disease-associated genes and polynucleotides and some of these disease associated gene may belong to a set of genetic disorders referred to as Trinucleotide repeat disorders (referred to as also trinucleotide repeat expansion disorders, triplet repeat expansion disorders or codon reiteration disorders).

These diseases are caused by mutations in which the trinucleotide repeats of certain genes exceed the normal, stable threshold which may usually differ in a gene. The discovery of more repeat expansion disorders has allowed for the classification of these disorders into a number of categories based on underlying similar characteristics. Huntington's disease (HD) and the spinocerebellar ataxias that are caused by a CAG repeat expansion in protein-coding portions of specific genes are included in Category I. Diseases or disorders with expansions that tend to make them phenotypically diverse and include expansions are usually small in magnitude and also found in exons of genes are included in Category II. Category III includes disorders or diseases which are characterized by much larger repeat expansions than either Category I or II and are generally located outside protein coding regions. Examples of Category III diseases or disorders include but are not limited to Fragile X syndrome, myotonic dystrophy, two of the spinocerebellar ataxias, juvenile myoclonic epilepsy, and Friedreich's ataxia.

Figure 14A:
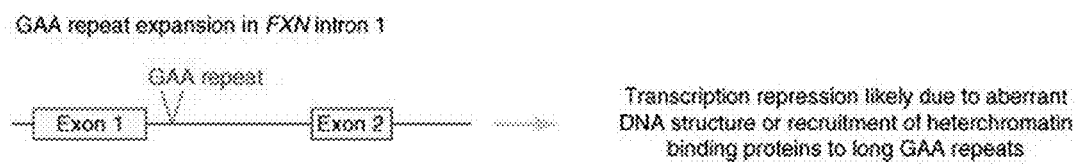
FIG. 14A-B shows a schematic of the GAA repeat expansion in FXN intron 1 and (b) shows a schematic of the strategy adopted to excise the GAA expansion region using the CRISPR/Cas system.

Similar therapeutic strategies, like the one mentioned for Friedreich's ataxia below may be adopted to address other trinucleotide repeat or expansion disorders as well. For example, another triple repeat disease that can be treated using almost identical strategy is dystrophia myotonica 1 (DM1), where there is an expanded CTG motif in the 3' UTR. In Friedreich's ataxia, the disease results from expansion of GAA trinucleotides in the first intron of frataxin (FXN). One therapeutic strategy using CRISPR is to excise the GAA repeat from the first intron. The expanded. GAA repeat is thought to affect the DNA structure and leads to recruit the formation of heterochromatin which turn off the frataxin gene (FIG. 14A).

Competitive Advantage over other therapeutic strategies are listed below:

siRNA knockdown is not applicable in this case, as disease is due to reduced expression of frataxin. Viral gene therapy is currently being explored. HSV-1 based vectors were used to deliver the frataxin gene in animal models and have shown therapeutic effect. However, long term efficacy of virus-based frataxin delivery suffer from several problems: First, it is difficult to regulate the expression of frataxin to match natural levels in health individuals, and second, long term over expression of frataxin leads to cell death.

Nucleases may be used to excise the GAA repeat to restore healthy genotype, but Zinc Finger Nuclease and TALEN strategies require delivery of two pairs of high efficacy nucleases, which is difficult for both delivery as well as nuclease engineering (efficient excision of genomic DNA by ZFN or TALEN is difficult to achieve).

In contrast to above strategies, the CRISPR-Cas system has clear advantages. The Cas9 enzyme is more efficient and more multiplexible, by which it is meant that one or more targets can be set at the same time. So far, efficient excision of genomic DNA>30% by Cas9 in human cells and may be as high as 30%, and may be improved in the future. Furthermore, with regard to certain trinucleotide repeat disorders like Huntington's disease (HD), trinucleotide repeats in the coding region may be addressed if there are differences between the two alleles. Specifically, if a HD patient is heterozygous for mutant HTT and there are nucleotide differences such as SNPs between the wt and mutant HTT alleles, then Cas9 may be used to specifically target the mutant HTT allele. ZFN or TALENs will not have the ability to distinguish two alleles based on single base differences.

Figure 14B:
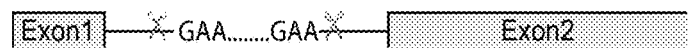

In adopting a strategy using the CRISPR-Cas 9 enzyme to address Friedreich's ataxia, Applicants design a number of guide RNAs targeting sites flanking the GAA expansion and the most efficient and specific ones are chosen (FIG. 14B).

Applicants deliver a combination of guide RNAs targeting the intron 1 of FXN along with Cas9 to mediate excision of the GAA expansion region. AAV9 may be used to mediate efficient delivery of Cas9 and in the spinal cord.

If the Alu element adjacent to the GAA expansion is considered important, there may be constraints to the number of sites that can be targeted but Applicants may adopt strategies to avoid disrupting it.

Alternative Strategies:

Rather than modifying the genome using Cas9, Applicants may also directly activate the FXN gene using Cas9 (nuclease activity deficient)-based DNA binding domain to target a transcription activation domain to the FXN gene. Applicants may have to address the robustness of the Cas9-mediated artificial transcription activation to ensure that it is robust enough as compared to other methods (Tremblay et al., Transcription Activator-Like Effector Proteins Induce the Expression of the Frataxin Gene; Human Gene Therapy, August 2012, 23(8): 883-890.)

Example 24: Strategies for Minimizing Off-Target Cleavage Using Cas9 Nickase

As previously mentioned in the application, Cas9 may be mutated to mediate single strand cleavage via one or more of the following mutations: D10A, E762A, and H840A.

To mediate gene knockout via NHEJ, Applicants use a nickase version of Cas9 along with two guide RNAs. Off-target nicking by each individual guide RNA may be primarily repaired without mutation, double strand breaks (which can lead to mutations via NHEJ) only occur when the target sites are adjacent to each other. Since double strand breaks introduced by double nicking are not blunt, co-expression of end-processing enzymes such as TREX1 will increase the level of NHEJ activity.

The following list of targets in tabular form are for genes involved in the following diseases:

Lafora's Disease—target GSY1 or PPP1R3C (PTG) to reduce glycogen in neurons.

Hypercholesterolemia—target PCSK9

Target sequences are listed in pairs (L and R) with different number of nucleotides in the spacer (0 to 3 bp). Each spacer may also be used by itself with the wild type Cas9 to introduce double strand break at the target locus.

| Gene | Label | Sequence | SEQ ID NO |
|---|---|---|---|
| GYS1 (human) | GGCC-L | ACCCTTGTTAGCCACCTCCC | (SEQ ID NO: 129) |
| | GGCC-R | GAACGCAGTGCTCTTCGAAG | (SEQ ID NO: 130) |
| | GGNCC-L | CTCACGCCCTGCTCCGTGTA | (SEQ ID NO: 131) |
| | GGNCC-R | GGCGACAACTACTTCCTGGT | (SEQ ID NO: 132) |
| | GGNNCC-L | CTCACGCCCTGCTCCGTGTA | (SEQ ID NO: 133) |
| | GGNNCC-R | GGGCGACAACTACTTCCTGG | (SEQ ID NO: 134) |
| | GGNNNCC-L | CCTCTTCAGGGCCGGGGTGG | (SEQ ID NO: 135) |
| | GGNNNCC-R | GAGGACCCAGGTGGAACTGC | (SEQ ID NO: 136) |
| PCSK9 (human) | GGCC-L | TCAGCTCCAGGCGGTCCTGG | (SEQ ID NO: 137) |
| | GGCC-R | AGCAGCAGCAGCAGTGGCAG | (SEQ ID NO: 138) |
| | GGNCC-L | TGGGCACCGTCAGCTCCAGG | (SEQ ID NO: 139) |
| | GGNCC-R | CAGCAGTGGCAGCGGCCACC | (SEQ ID NO: 140) |
| | GGNNCC-L | ACCTCTCCCCTGGCCCTCAT | (SEQ ID NO: 141) |
| | GGNNCC-R | CCAGGACCGCCTGGAGCTGA | (SEQ ID NO: 142) |
| | GGNNNCC-L | CCGTCAGCTCCAGGCGGTCC | (SEQ ID NO: 143) |
| | GGNNNCC-R | AGCAGCAGCAGCAGTGGCAG | (SEQ ID NO: 144) |
| PPP1R3C (PTG) (human) | GGCC-L | ATGTGCCAAGCAAAGCCTCA | (SEQ ID NO: 145) |
| | GGCC-R | TTCGGTCATGCCCGTGGATG | (SEQ ID NO: 146) |
| | GGNCC-L | GTCGTTGAAATTCATCGTAC | (SEQ ID NO: 147) |
| | GGNCC-R | ACCACCTGTGAAGAGTTTCC | (SEQ ID NO: 148) |
| | GGNNCC-L | CGTCGTTGAAATTCATCGTA | (SEQ ID NO: 149) |
| | GGNNCC-R | ACCACCTGTGAAGAGTTTCC | (SEQ ID NO: 150) |
| Gys1 (mouse) | GGCC-L | GAACGCAGTGCTTTTCGAGG | (SEQ ID NO: 151) |
| | GGCC-R | ACCCTTGTTGGCCACCTCCC | (SEQ ID NO: 152) |
| | GGNCC-L | GGTGACAACTACTATCTGGT | (SEQ ID NO: 153) |
| | GGNCC-R | CTCACACCCTGCTCCGTGTA | (SEQ ID NO: 154) |
| | GGNNCC-L | GGGTGACAACTACTATCTGG | (SEQ ID NO: 155) |
| | GGNNCC-R | CTCACACCCTGCTCCGTGTA | (SEQ ID NO: 156) |
| | GGNNNCC-L | CGAGAACGCAGTGCTTTTCG | (SEQ ID NO: 157) |
| | GGNNNCC-R | ACCCTTGTTGGCCACCTCCC | (SEQ ID NO: 158) |
| PPP1R3C (PTG) (mouse) | GGCC-L | ATGAGCCAAGCAAATCCTCA | (SEQ ID NO: 159) |
| | GGCC-R | TTCCGTCATGCCCGTGGACA | (SEQ ID NO: 160) |
| | GGNCC-L | CTTCGTTGAAAACCATTGTA | (SEQ ID NO: 161) |
| | GGNCC-R | CCACCTCTGAAGAGTTTCCT | (SEQ ID NO: 162) |
| | GGNNCC-L | CTTCGTTGAAAACCATTGTA | (SEQ ID NO: 163) |
| | GGNNCC-R | ACCACCTCTGAAGAGTTTCC | (SEQ ID NO: 164) |
| | GGNNNCC-L | CTTCCACTCACTCTGCGATT | (SEQ ID NO: 165) |
| | GGNNNCC-R | ACCATGTCTCAGTGTCAAGC | (SEQ ID NO: 166) |
| PCSK9 (mouse) | GGCC-L | GGCGGCAACAGCGGCAACAG | (SEQ ID NO: 167) |
| | GGCC-R | ACTGCTCTGCGTGGCTGCGG | (SEQ ID NO: 168) |
| | GGNNCC-L | CCGCAGCCACGCAGAGCAGT | (SEQ ID NO: 169) |
| | GGNNCC-R | GCACCTCTCCTCGCCCCGAT | (SEQ ID NO: 170) |

Alternative strategies for improving stability of guide RNA and increasing specificity 1. Nucleotides in the 5' of the guide RNA may be linked via thiolester linkages rather than phosphoester linkage like in natural RNA. Thiolester linkage may prevent the guide RNA from being digested by endogenous RNA degradation machinery.
2. Nucleotides in the guide sequence (5' 20 bp) of the guide RNA can use bridged nucleic acids (BNA) as the bases to improve the binding specificity.

Example 25: CRISPR-Cas for Rapid, Multiplex Genome Editing

Aspects of the invention relate to protocols and methods by which efficiency and specificity of gene modification may be tested within 3-4 days after target design, and modified clonal cell lines may be derived within 2-3 weeks.

Programmable nucleases are powerful technologies for mediating genome alteration with high precision. The RNA-guided Cas9 nuclease from the microbial CRISPR adaptive immune system can be used to facilitate efficient genome editing in eukaryotic cells by simply specifying a 20-nt targeting sequence in its guide RNA. Applicants describe a set of protocols for applying Cas9 to facilitate efficient genome editing in mammalian cells and generate cell lines for downstream functional studies. Beginning with target design, efficient and specific gene modification can be achieved within 3-4 days, and modified clonal cell lines can be derived within 2-3 weeks.

The ability to engineer biological systems and organisms holds enormous potential for applications across basic science, medicine, and biotechnology. Programmable sequence-specific endonucleases that facilitate precise editing of endogenous genomic loci are now enabling systematic interrogation of genetic elements and causal genetic variations in a broad range of species, including those that have not been genetically tractable previously. A number of genome editing technologies have emerged in recent years, including zinc finger nucleases (ZFNs), transcription activator-like effector nucleases (TALENs), and the RNA-guided CRISPR-Cas nuclease system. The first two technologies use a common strategy of tethering endonuclease catalytic domains to modular DNA-binding proteins for inducing targeted DNA double stranded breaks (DSB) at specific genomic loci. By contrast, Cas9 is a nuclease guided by small RNAs through Watson-Crick base-pairing with target DNA, presenting a system that is easy to design, efficient, and well-suited for high-throughput and multiplexed gene editing for a variety of cell types and organisms. Here Applicants describe a set of protocols for applying the recently developed Cas9 nuclease to facilitate efficient genome editing in mammalian cells and generate cell lines for downstream functional studies.

Like ZFNs and TALENs, Cas9 promotes genome editing by stimulating DSB at the target genomic loci. Upon cleavage by Cas9, the target locus undergoes one of two major pathways for DNA damage repair, the error-prone non-homologous end joining (NHEJ) or the high-fidelity homology directed repair (HDR) pathway. Both pathways may be utilized to achieve the desired editing outcome.

NHEJ: In the absence of a repair template, the NHEJ process re-ligates DSBs, which may leave a scar in the form of indel mutations. This process can be harnessed to achieve gene knockouts, as indels occurring within a coding exon may lead to frameshift mutations and a premature stop codon. Multiple DSBs may also be exploited to mediate larger deletions in the genome.

HDR: Homology directed repair is an alternate major DNA repair pathway to NHEJ. Although HDR typically occurs at lower frequencies than NHEJ, it may be harnessed to generate precise, defined modifications at a target locus in the presence of an exogenously introduced repair template. The repair template may be either in the form of double stranded DNA, designed similarly to conventional DNA targeting constructs with homology arms flanking the insertion sequence, or single-stranded DNA oligonucleotides (ssODNs). The latter provides an effective and simple method for making small edits in the genome, such as the introduction of single nucleotide mutations for probing causal genetic variations. Unlike NHEJ, HDR is generally active only in dividing cells and its efficiency varies depending on the cell type and state.

Overview of CRISPR: The CRISPR-Cas system, by contrast, is at minimum a two-component system consisting of the Cas9 nuclease and a short guide RNA. Re-targeting of Cas9 to different loci or simultaneous editing of multiple genes simply requires cloning a different 20-bp oligonucleotide. Although specificity of the Cas9 nuclease has yet to be thoroughly elucidated, the simple Watson-Crick base-pairing of the CRISPR-Cas system is likely more predictable than that of ZFN or TALEN domains.

The type II CRISPR-Cas (clustered regularly interspaced short palindromic repeats) is a bacterial adaptive immune system that uses Cas9, to cleave foreign genetic elements. Cas9 is guided by a pair of non-coding RNAs, a variable crRNA and a required auxiliary tracrRNA. The crRNA contains a 20-nt guide sequence determines specificity by locating the target DNA via Watson-Crick base-pairing. In the native bacterial system, multiple crRNAs are co-transcribed to direct Cas9 against various targets. In the CRISPR-Cas system derived from *Streptococcus pyogenes*, the target DNA must immediately precede a 5'-NGG/NRG protospacer adjacent motif (PAM), which can vary for other CRISPR systems.

CRISPR-Cas is reconstituted in mammalian cells through the heterologous expression of human codon-optimized Cas9 and the requisite RNA components. Furthermore, the crRNA and tracrRNA can be fused to create a chimeric, synthetic guide RNA (sgRNA). Cas9 can thus be re-directed toward any target of interest by altering the 20-nt guide sequence within the sgRNA.

Given its ease of implementation and multiplex capability, Cas9 has been used to generate engineered eukaryotic cells carrying specific mutations via both NHEJ and HDR. In addition, direct injection of sgRNA and mRNA encoding Cas9 into embryos has enabled the rapid generation of transgenic mice with multiple modified alleles; these results hold promise for editing organisms that are otherwise genetically intractable.

A mutant Cas9 carrying a disruption in one of its catalytic domains has been engineered to nick rather than cleave DNA, allowing for single-stranded breaks and preferential repair through HDR, potentially ameliorating unwanted indel mutations from off-target DSBs. Additionally, a Cas9 mutant with both DNA-cleaving catalytic residues mutated has been adapted to enable transcriptional regulation in *E. coli*, demonstrating the potential of functionalizing Cas9 for diverse applications. Certain aspects of the invention relate to the construction and application of Cas9 for multiplexed editing of human cells.

Applicants have provided a human codon-optimized, nuclear localization sequence-flanked Cas9 to facilitate eukaryotic gene editing. Applicants describe considerations for designing the 20-nt guide sequence, protocols for rapid construction and functional validation of sgRNAs, and finally use of the Cas9 nuclease to mediate both NHEJ- and HDR-based genome modifications in human embryonic kidney (HEK-293FT) and human stem cell (HUES9) lines. This protocol can likewise be applied to other cell types and organisms.

Target selection for sgRNA: There are two main considerations in the selection of the 20-nt guide sequence for gene targeting: 1) the target sequence should precede the 5'-NGG PAM for *S. pyogenes* Cas9, and 2) guide sequences should be chosen to minimize off-target activity. Applicants provided an online Cas9 targeting design tool that takes an input sequence of interest and identifies suitable target sites. To experimentally assess off-target modifications for each sgRNA, Applicants also provide computationally predicted off-target sites for each intended target, ranked according to Applicants' quantitative specificity analysis on the effects of base-pairing mismatch identity, position, and distribution.

The detailed information on computationally predicted off-target sites is as follows:

Considerations for Off-target Cleavage Activities: Similar to other nucleases, Cas9 can cleave off-target DNA targets in the genome at reduced frequencies. The extent to which a given guide sequence exhibit off-target activity depends on a combination of factors including enzyme concentration, thermodynamics of the specific guide sequence employed, and the abundance of similar sequences in the target genome. For routine application of Cas9, it is important to consider ways to minimize the degree of off-target cleavage and also to be able to detect the presence of off-target cleavage.

Minimizing off-target activity: For application in cell lines, Applicants recommend following two steps to reduce the degree of off-target genome modification. First, using our online CRISPR target selection tool, it is possible to computationally assess the likelihood of a given guide sequence to have off-target sites. These analyses are performed through an exhaustive search in the genome for off-target sequences that are similar sequences as the guide sequence. Comprehensive experimental investigation of the effect of mismatching bases between the sgRNA and its target DNA revealed that mismatch tolerance is 1) position dependent—the 8-14 bp on the 3' end of the guide sequence are less tolerant of mismatches than the 5' bases, 2) quantity dependent—in general more than 3 mismatches are not tolerated, 3) guide sequence dependent—some guide sequences are less tolerant of mismatches than others, and 4) concentration dependent—off-target cleavage is highly sensitive to the amount of transfected DNA. The Applicants' target site analysis web tool (available at the website genome-engineering.org/tools) integrates these criteria to provide predictions for likely off-target sites in the target genome. Second, Applicants recommend titrating the amount of Cas9 and sgRNA expression plasmid to minimize off-target activity.

Detection of off-target activities: Using Applicants' CRISPR targeting web tool, it is possible to generate a list of most likely off-target sites as well as primers performing SURVEYOR or sequencing analysis of those sites. For isogenic clones generated using Cas9, Applicants strongly recommend sequencing these candidate off-target sites to check for any undesired mutations. It is worth noting that there may be off target modifications in sites that are not included in the predicted candidate list and full genome sequence should be performed to completely verify the absence of off-target sites. Furthermore, in multiplex assays where several DSBs are induced within the same genome, there may be low rates of translocation events and can be evaluated using a variety of techniques such as deep sequencing.

The online tool provides the sequences for all oligos and primers necessary for 1) preparing the sgRNA constructs, 2) assaying target modification efficiency, and 3) assessing cleavage at potential off-target sites. It is worth noting that because the U6 RNA polymerase III promoter used to express the sgRNA prefers a guanine (G) nucleotide as the first base of its transcript, an extra G is appended at the 5' of the sgRNA where the 20-nt guide sequence does not begin with G.

Approaches for sgRNA construction and delivery: Depending on the desired application, sgRNAs may be delivered as either 1) PCR amplicons containing an expression cassette or 2) sgRNA-expressing plasmids. PCR-based sgRNA delivery appends the custom sgRNA sequence onto the reverse PCR primer used to amplify a U6 promoter template. The resulting amplicon may be co-transfected with a plasmid containing Cas9 (PX165). This method is optimal for rapid screening of multiple candidate sgRNAs, as cell transfections for functional testing can be performed mere hours after obtaining the sgRNA-encoding primers. Because this simple method obviates the need for plasmid-based cloning and sequence verification, it is well suited for testing or co-transfecting a large number of sgRNAs for generating large knockout libraries or other scale-sensitive applications. Note that the sgRNA-encoding primers are over 100-bp, compared to the ~20-bp oligos required for plasmid-based sgRNA delivery.

Construction of an expression plasmid for sgRNA is also simple and rapid, involving a single cloning step with a pair of partially complementary oligonucleotides. After annealing the oligo pairs, the resulting guide sequences may be inserted into a plasmid bearing both Cas9 and an invariant scaffold bearing the remainder of the sgRNA sequence (PX330). The transfection plasmids may also be modified to enable virus production for in vivo delivery.

In addition to PCR and plasmid-based delivery methods, both Cas9 and sgRNA can be introduced into cells as RNA.

Design of repair template: Traditionally, targeted DNA modifications have required use of plasmid-based donor repair templates that contain homology arms flanking the site of alteration. The homology arms on each side can vary in length, but are typically longer than 500 bp. This method can be used to generate large modifications, including insertion of reporter genes such as fluorescent proteins or antibiotic resistance markers. The design and construction of targeting plasmids has been described elsewhere.

More recently, single-stranded DNA oligonucleotides (ssODNs) have been used in place of targeting plasmids for short modifications within a defined locus without cloning. To achieve high HDR efficiencies, ssODNs contain flanking sequences of at least 40 bp on each side that are homologous to the target region, and can be oriented in either the sense or antisense direction relative to the target locus.

Functional Testing

SURVEYOR nuclease assay: Applicants detected indel mutations either by the SURVEYOR nuclease assay (or PCR amplicon sequencing. Applicants online CRISPR target design tool provides recommended primers for both approaches. However, SURVEYOR or sequencing primers may also be designed manually to amplify the region of interest from genomic DNA and to avoid non-specific amplicons using NCBI Primer-BLAST. SURVEYOR primers should be designed to amplify 300-400 bp (for a 600-800 bp total amplicon) on either side of the Cas9 target for allowing clear visualization of cleavage bands by gel electrophoresis. To prevent excessive primer dimer formation, SURVEYOR primers should be designed to be typically under 25-nt long with melting temperatures of ~60° C. Applicants recommend testing each pair of candidate primers for specific PCR amplicons as well as for the absence of non-specific cleavage during the SURVEYOR nuclease digestion process.

Plasmid- or ssODN-mediated HDR: HDR can be detected via PCR-amplification and sequencing of the modified region. PCR primers for this purpose should anneal outside the region spanned by the homology arms to avoid false detection of residual repair template (HDR Fwd and Rev, FIG. 12). For ssODN-mediated HDR, SURVEYOR PCR primers can be used.

Detection of indels or HDR by sequencing: Applicants detected targeted genome modifications by either Sanger or next-generation deep sequencing (NGS). For the former, genomic DNA from modified region can be amplified using either SURVEYOR or HDR primers. Amplicons should be subcloned into a plasmid such as pUC19 for transformation; individual colonies can be sequenced to reveal clonal genotype.

Applicants designed next-generation sequencing (NGS) primers for shorter amplicons, typically in the 100-200 bp size range. For detecting NHEJ mutations, it is important to design primers with at least 10-20 bp between the priming regions and the Cas9 target site to allow detection of longer indels. Applicants provide guidelines for a two-step PCR method to attach barcoded adapters for multiplex deep sequencing. Applicants recommend the Illumina platform, due to its generally low levels of false positive indels. Off-target analysis (described previously) can then be performed through read alignment programs such as ClustalW, Geneious, or simple sequence analysis scripts.

Materials and Reagents
sgRNA Preparation:
UltraPure DNaseRNase-free distilled water (Life Technologies, cat. no. 10977-023)
Herculase II fusion polymerase (Agilent Technologies, cat. no. 600679)
CRITICAL. Standard Taq polymerase, which lacks 3'-5' exonuclease proofreading activity, has lower fidelity and can lead to amplification errors. Herculase II is a high-fidelity polymerase (equivalent fidelity to Pfu) that produces high yields of PCR product with minimal optimization. Other high-fidelity polymerases may be substituted.
Herculase II reaction buffer (5×; Agilent Technologies, included with polymerase)
dNTP solution mix (25 mM each; Enzymatics, cat. no. N205L)
MgCl2 (25 mM; ThermoScientific, cat. no. R0971)
QIAquick gel extraction kit (Qiagen, cat. no. 28704)
QIAprep spin miniprep kit (Qiagen, cat. no. 27106)
UltraPure TBE buffer (10×; Life Technologies, cat. no. 15581-028)
SeaKem LE agarose (Lonza, cat. no. 50004)
SYBR Safe DNA stain (10,000×; Life Technologies, cat. no. 533102)
1-kb Plus DNA ladder (Life Technologies, cat. no. 10787-018)
TrackIt CyanOrange loading buffer (Life Technologies, cat. no. 10482-028)
FastDigest BbsI (BpiI) (Fermentas/ThermoScientific, cat. no. FD1014)
Fermentas Tango Buffer (Fermentas/ThermoScientific, cat. no. BY5)
DL-dithiothreitol (DTT; Fermentas/ThermoScientific, cat. no. R0862)
T7 DNA ligase (Enzymatics, cat. no. L602L)
Critical:Do not substitute the more commonly used T4 ligase. T7 ligase has 1,000-fold higher activity on the sticky ends than on the blunt ends and higher overall activity than commercially available concentrated T4 ligases.
T7 2× Rapid Ligation Buffer (included with T7 DNA ligase, Enzymatics, cat. no. L602L)
T4 Polynucleotide Kinase (New England Biolabs, cat. no M0201S)
T4 DNA Ligase Reaction Buffer (10×; New England Biolabs, cat. no B0202S)
Adenosine 5'-triphosphate (10 mM; New England Biolabs, cat. no. P0756S)
PlasmidSafe ATP-dependent DNase (Epicentre, cat. no. E3101K)
One Shot Stbl3 chemically competent *Escherichia coli* (*E. coli*) (Life Technologies, cat. no. C7373-03)
SOC medium (New England Biolabs, cat. no. B9020S)
LB medium (Sigma, cat. no. L3022)
LB agar medium (Sigma, cat. no. L2897)
Ampicillin, sterile filtered (100 mg ml-1; Sigma, cat. no. A5354)
Mammalian Cell Culture:
HEK293FT cells (Life Technologies, cat. no. R700-07)
Dulbecco's minimum Eagle's medium (DMEM, 1×, high glucose; Life Technologies, cat. no. 10313-039)
Dulbecco's minimum Eagle's medium (DMEM, 1×, high glucose, no phenol red; Life Technologies, cat. no. 31053-028)
Dulbecco's phosphate-buffered saline (DPBS, 1×; Life Technologies, cat. no. 14190-250)
Fetal bovine serum, qualified and heat inactivated (Life Technologies, cat. no. 10438-034)
Opti-MEM I reduced-serum medium (FBS; Life Technologies, cat. no. 11058-021)
Penicillin-streptomycin (100×; Life Technologies, cat. no. 15140-163)
TrypLE™ Express (1×, no Phenol Red; Life Technologies, cat. no. 12604-013)
Lipofectamine 2000 transfection reagent (Life Technologies, cat. no. 11668027)
Amaxa SF Cell Line 4D-Nucleofector® X Kit S (32 RCT; Lonza, cat. no V4XC-2032)
HUES 9 cell line (HARVARD STEM CELL SCIENCE)
Geltrex LDEV-Free Reduced Growth Factor Basement Membrane Matrix (Life Technologies, cat. no. A1413201)
mTeSR1 medium (Stemcell Technologies, cat. no. 05850)
Accutase cell detachment solution (Stemcell Technologies, cat. no. 07920)
ROCK Inhibitor (Y-27632; Millipore, cat. no. SCM075)
Amaxa P3 Primary Cell 4D-Nucleofector® X Kit S (32 RCT; Lonza cat. no. V4XP-3032)
Genotyping Analysis:
QuickExtract DNA extraction solution (Epicentre, cat. no. QE09050)
PCR primers for SURVEYOR, RFLP analysis, or sequencing (see Primer table)
Herculase II fusion polymerase (Agilent Technologies, cat. no. 600679)
CRITICAL. As Surveyor assay is sensitive to single-base mismatches, it is particularly important to use a high-fidelity polymerase. Other high-fidelity polymerases may be substituted.

Herculase II reaction buffer (5×; Agilent Technologies, included with polymerase)

dNTP solution mix (25 mM each; Enzymatics, cat. no. N205L)

QIAquick gel extraction kit (Qiagen, cat. no. 28704)

Taq Buffer (10×; Genscript, cat. no. B0005)

SURVEYOR mutation detection kit for standard gel electrophoresis (Transgenomic, cat. no. 706025)

UltraPure TBE buffer (10×; Life Technologies, cat. no. 15581-028)

SeaKem LE agarose (Lonza, cat. no. 50004)

4-20% TBE Gels 1.0 mm, 15 Well (Life Technologies, cat. no. EC62255BOX) Novex® Hi-Density TBE Sample Buffer (5×; Life Technologies, cat. no. LC6678)

SYBR Gold Nucleic Acid Gel Stain (10,000×; Life Technologies, cat. no. S-11494)

1-kb Plus DNA ladder (Life Technologies, cat. no. 10787-018)

TrackIt CyanOrange loading buffer (Life Technologies, cat. no. 10482-028)

FastDigest HindIII (Fermentas/ThermoScientific, cat. no. FD0504)

Equipment

Filtered sterile pipette tips (Corning)

Standard 1.5 ml microcentrifuge tubes (Eppendorf, cat. no. 0030 125.150)

Axygen 96-well PCR plates (VWR, cat. no. PCR-96M2-HSC)

Axygen 8-Strip PCR tubes (Fischer Scientific, cat. no. 14-222-250)

Falcon tubes, polypropylene, 15 ml (BD Falcon, cat. no. 352097)

Falcon tubes, polypropylene, 50 nil (BD Falcon, cat. no. 352070)

Round-bottom Tube with cell strainer cap, 5 ml (BD Falcon, cat. no. 352235)

Petri dishes (60 mm×15 mm; BD Biosciences, cat. no. 351007)

Tissue culture plate (24 well; BD Falcon, cat. no. 353047)

Tissue culture plate (96 well, flat bottom; BD Falcon, cat. no. 353075)

Tissue culture dish (100 mm; BD Falcon, 3530.03)

96-well thermocycler with programmable temperature stepping functionality (Applied Biosystems Veriti, cat. no. 4375786).

Desktop microcentrifuges 5424, 5804 (Eppendorf)

Gel electrophoresis system (PowerPac basic power supply, Bio-Rad, cat. no. 164-5050, and Sub-Cell GT System gel tray, Bio-Rad, cat. no. 170-4401)

Novex XCell SureLock Mini-Cell (Life Technologies, cat. no. EI0001)

Digital gel imaging system (GelDoc EZ, Bio-Rad, cat. no. 170-8270, and blue sample tray, Bio-Rad, cat. no. 170-8273)

Blue light transilluminator and orange filter goggles (SafeImager 2.0; Invitrogen, cat. no. G6600)

Gel quantification software (Bio-Rad, ImageLab, included with GelDoc EZ, or open-source ImageJ from the National Institutes of Health, available at the website rsbweb.nih.gov/ij/) UV spectrophotometer (NanoDrop 2000c, Thermo Scientific)

Reagent Setup

Tris-borate EDTA (TBE) electrophoresis solution Dilute TBE buffer in distilled water to 1× working solution for casting agarose gels and for use as a buffer for gel electrophoresis. Buffer may be stored at room temperature (18-22° C.) for at least 1 year.

ATP, 10 mM Divide 10 mM ATP into 50-μl aliquots and store at −20° C. for up to 1 year; avoid repeated freeze-thaw cycles.

DTT, 10 mM Prepare 10 mM DTT solution in distilled water and store in 20-μl aliquots at −70° C. for up to 2 years; for each reaction, use a new aliquot, as DTT is easily oxidized.

D10 culture medium For culture of HEK293FT cells, prepare D10 culture medium by supplementing DMEM with 1× GlutaMAX and 10% (vol/vol) fetal bovine serum. As indicated in the protocol, this medium can also be supplemented with 1× penicillin-streptomycin. D10 medium can be made in advance and stored at 4° C. for up to 1 month.

mTeSR1 culture medium For culture of human embryonic stem cells, prepare mTeSR1 medium by supplementing the 5× supplement (included with mTeSR1 basal medium), and 100 ug/ml Normocin.

Procedure

Design of targeting components and use of the online tool•Timing 1 d

1| Input target genomic DNA sequence. Applicants provide an online Cas9 targeting design tool that takes an input sequence of interest, identifies and ranks suitable target sites, and computationally predicts off-target sites for each intended target. Alternatively, one can manually select guide sequence by identifying the 20-bp sequence directly upstream of any 5'-NGG.

2| Order necessary oligos and primers as specified by the online tool. If the site is chosen manually, the oligos and primers should be designed.

Preparation of sgRNA expression construct

3| To generate the sgRNA expression construct, either the PCR- or plasmid-based protocol can be used.

(A) Via PCR amplification•Timing 2 h (i) Applicants prepare diluted U6 PCR template. Applicants recommend using PX330 as a PCR template, but any U6-containing plasmid may likewise be used as the PCR template. Applicants diluted template with ddH$_2$O to a concentration of 10 ng/ul. Note that if a plasmid or cassette already containing an U6-driven sgRNA is used as a template, a gel extraction needs to be performed to ensure that the product contains only the intended sgRNA and no trace sgRNA carryover from template.

(ii) Applicants prepared diluted PCR oligos. U6-Fwd and U6-sgRNA-Rev primers are diluted to a final concentration of 10 uM in ddH$_2$O (add 10 ul of 100 uM primer to 90 ul ddH$_2$O).

(iii) U6-sgRNA PCR reaction. Applicants set up the following reaction for each U6-sgRNA-Rev primer and mastermix as needed:

| Component: | Amount (ul) | Final concentration |
| --- | --- | --- |
| Herculase II PCR buffer, 5X | 10 | 1X |
| dNTP, 100 mM (25 mM each) | 0.5 | 1 mM |
| U6 template (PX330) | 1 | 0.2 ng/ul |
| U6-Fwd primer | 1 | 0.2 uM |
| U6-sgRNA-Rev primer (variable) | 1 | 0.2 uM |
| Herculase II Fusion polymerase | 0.5 | |
| Distilled water | 36 | |
| Total | 50 | |

(iv) Applicants performed PCR reaction on the reactions from step (iii) using the following cycling conditions:

| Cycle number | Denature | Anneal | Extend |
|---|---|---|---|
| 1 | 95° C., 2 m | | |
| 2-31 | 95° C., 20 s | 60° C., 20 s | 72° C., 20 s |
| 32 | | | 72° C., 3 m |

(v) After the reaction is completed, Applicants ran the product on a gel to verify successful, single-band amplification. Cast a 2% (wt/vol) agarose gel in 1×TBE buffer with 1× SYBR Safe dye. Run 5 ul of the PCR product in the gel at 15 V cm-1 for 20-30 min. Successful amplicons should yield one single 370-bp product and the template should be invisible. It should not be necessary to gel extract the PCR amplicon.

(vi) Applicants purified the PCR product using the QIAquick PCR purification kit according to the manufacturer's directions. Elute the DNA in 35 ul of Buffer EB or water. Purified PCR products may be stored at 4° C. or −20° C.

(B) Cloning sgRNA into Cas9-containing bicistronic expression vector•Timing 3 d (i) Prepare the sgRNA oligo inserts. Applicants resuspended the top and bottom strands of oligos for each sgRNA design to a final concentration of 100 uM. Phosphorylate and anneal the oligo as follows:

| | |
|---|---|
| Oligo 1 (100 uM) | 1 ul |
| Oligo 2 (100 uM) | 1 ul |
| T4 Ligation Buffer, 10X | 1 ul |
| T4 PNK | 1 ul |
| ddH$_2$O | 6 ul |
| Total | 10 ul |

(ii) Anneal in a thermocycler using the following parameters:

37° C. for 30 m
95° C. for 5 m
Ramp down to 25° C. at 5° C. per m (iii) Applicants diluted phosphorylated and annealed oligos 1:200 by add 1 ul of oligo to 199 ul room temperature ddH$_2$O.

(iv) Clone sgRNA oligo into PX330. Applicants set up Golden Gate reaction for each sgRNA. Applicants recommend also setting up a no-insert, PX330 only negative control.

| | |
|---|---|
| PX330 (100 ng) | x ul |
| Diluted oligo duplex from step (iii) | 2 ul |
| Tango Buffer, 10X | 2 ul |
| DTT, 10 mM | 1 ul |
| ATP, 10 mM | 1 ul |
| FastDigest BbsI | 1 ul |
| T7 Ligase | 0.5 ul |
| ddH$_2$O | x ul |
| Total | 20 ul |

(v) Incubate the Golden Gate reaction for a total of 1 h:

| Cycle number | Condition |
|---|---|
| 1-6 | 37° C. for 5 m, 21° C. for 5 m |

(vi) Applicants treated Golden Gate reaction with PlasmidSafe exonuclease to digest any residual linearized DNA. This step is optional but highly recommended.

| | |
|---|---|
| Golden Gate reaction from step 4 | 11 ul |
| 10X PlasmidSafe Buffer | 1.5 ul |
| ATP, 10 mM | 1.5 ul |
| PlasmidSafe exonuclease | 1 ul |
| Total | 15 ul |

(vii) Applicants incubated the PlasmidSafe reaction at 37° C. for 30 min, followed by inactivation at 70° C. for 30 min. Pause point: after completion, the reaction may be frozen and continued later. The circular DNA should be stable for at least 1 week.

(viii) Transformation. Applicants transformed the PlasmidSafe-treated plasmid into a competent E. coli strain, according to the protocol supplied with the cells. Applicants recommend Stbl3 for quick transformation. Briefly, Applicants added 5 ul of the product from step (vii) into 20 ul of ice-cold chemically competent Stbl3 cells. This is then incubated on ice for 10 m, heat shocked at 42° C. for 30 s, returned immediately to ice for 2 m, 100 ul of SOC medium is added, and this is plated onto an LB plate containing 100 ug/ml ampicillin with incubation overnight at 37° C.

(ix) Day 2: Applicants inspected plates for colony growth. Typically, there are no colonies on the negative control plates (ligation of BbsI-digested PX330 only, no annealed sgRNA oligo), and tens to hundreds of colonies on the PX330-sgRNA cloning plates.

(x) From each plate, Applicants picked 2-3 colonies to check correct insertion of sgRNA. Applicants used a sterile pipette tip to inoculate a single colony into a 3 ml culture of LB medium with 100 ug/ml ampicillin. Incubate and shake at 37° C. overnight.

(xi) Day 3: Applicants isolated plasmid DNA from overnight cultures using a QiAprep Spin miniprep kit according to the manufacturer's instructions.

(xii) Sequence validate CRISPR plasmid. Applicants verified the sequence of each colony by sequencing from the U6 promoter using the U6-Fwd primer. Optional: sequence the Cas9 gene using primers listed in the following Primer table.

| Primer | Sequence (5' to 3') | Purpose |
|---|---|---|
| U6-For | GAGGGCCTATTTCCCATGATTCC (SEQ ID NO: 171) | Amplify U6-sgRNA |
| U6-Rev | AAAAAAAGCACCGACTCGGTGCCACTTTTTCAAGTTGAT AACGGACTAGCCTTATTTTAACTTGCTATTTCTAG CTCTAAAACNNNNNNNNNNNNNNNNNNNNCCGGTGTTTC GTCCTTTCCACAAG (SEQ ID NO: 172) | Amplify U6-sgRNA; N is reverse complement of target |

| Primer | Sequence (5' to 3') | Purpose |
|---|---|---|
| sgRNA-top | CACCGNNNNNNNNNNNNNNNNNNNN (SEQ ID NO: 173) | Clone sgRNA into PX330 |
| sgRNA-bottom | AAACNNNNNNNNNNNNNNNNNNNNC (SEQ ID NO: 174) | Clone sgRNA into PX330 |
| U6-EMX1-Rev | AAAAAAAGCACCGACTCGGTGCCACTTTTTCAAGTTGAT AACGGACTAGCCTTATTTTAACTTGCTATTTCTAG CTCTAAAACCCCTAGTCATTGGAGGTGACCGGTGTTTCG TCCTTTC CACAAG (SEQ ID NO: 175) | Amplify U6-EMX1 sgRNA |
| EMX1-top | CACCGTCACCTCCAATGACTAGGG (SEQ ID NO: 176) | Clone EMX1 sgRNA into PX330 |
| EMX1-bottom | AAACCCCTAGTCATTGGAGGTGAC (SEQ ID NO: 177) | Clone EMX1 sgRNA into PX330 |
| ssODN-sense | CAGAAGAAGAAGGGCTCCCATCACATCAACCGGTGGCG CATTGCCACGAAGCAGGCCAATGGGGAGGACATC GATGTCACCTCCAATGAC<u>AAGCTTGCTAGC</u>GGTGGGCAA CCACAAACCCACGAGGGCAGAGTGCTGCTTGCTG CTGGCCAGGCCCCTGCGTGGGCCCAAGCTGGACTCTGGC CACTCCCT (SEQ ID NO: 178) | EMX1 HDR (sense; insertion underlined) |
| ssODN-antisense | AGGGAGTGGCCAGAGTCCAGCTTGGGCCCACGCAGGGG CCTGGCCAGCAGCAAGCAGCACTCTGCCCTCGTG GGTTTGTGGTTGCCCACC<u>GCTAGCAAGCTT</u>GTCATTGGA GGTGACATCGATGTCCTCCCCATTGGCCTGCTTCG TGGCAATGCGCCACCGGTTGATGTGATGGGAGCCCTTCT TCTTCTG (SEQ ID NO: 179) | EMX1 HDR (antisense; insertion underlined) |
| EMX1-SURV-F | CCATCCCCTTCTGTGAATGT (SEQ ID NO: 180) | EMX1 SURVEYOR assay PCR, sequencing |
| EMX1-SURV-R | GGAGATTGGAGACACGGAGA (SEQ ID NO: 181) | EMX1 SURVEYOR assay PCR, sequencing |
| EMX1-HDR-F | GGCTCCCTGGGTTCAAAGTA (SEQ ID NO: 182) | EMX1 RFLP analysis PCR, sequencing |
| EMX1-HDR-R | AGAGGGGTCTGGATGTCGTAA (SEQ ID NO: 183) | EMX1 RFLP analysis PCR, sequencing |
| pUC19-F | CGCCAGGGTTTTCCCAGTCACGAC (SEQ ID NO: 184) | pUC19 multiple cloning site F primer, for Sanger sequencing |

Applicants referenced the sequencing results against the PX330 cloning vector sequence to check that the 20 bp guide sequence was inserted between the U6 promoter and the remainder of the sgRNA scaffold. Details and sequence of the PX330 map in GenBank vector map format (*.gb file) can be found at the website crispr.genome-engineering.org.

(Optional) Design of ssODN Template•Timing 3 d Planning Ahead

3| Design and order ssODN. Either the sense or antisense ssODN can be purchased directly from supplier. Applicants recommend designing homology arms of at least 40 bp on either side and 90 bp for optimal HDR efficiency. In Applicants' experience, antisense oligos have slightly higher modification efficiencies.

4| Applicants resuspended and diluted ssODN ultramers to a final concentration of 10 uM. Do not combine or anneal the sense and antisense ssODNs. Store at −20° C.

5| Note for HDR applications, Applicants recommend cloning sgRNA into the PX330 plasmid.

Functional Validation of sgRNAs: Cell Culture and Transfections•Timing 3-4 d

The CRISPR-Cas system has been used in a number of mammalian cell lines. Conditions may vary for each cell line. The protocols below details transfection conditions for HEK239FT cells. Note for ssODN-mediated HDR transfections, the Amaxa SF Cell Line Nucleofector Kit is used for optimal delivery of ssODNs. This is described in the next section.

7| HEK293FT maintenance. Cells are maintained according to the manufacturer's recommendations. Briefly, Applicants cultured cells in D10 medium (GlutaMax DMEM supplemented with 10% Fetal Bovine Serum), at 37° C. and 5% CO2.

8| To passage, Applicants removed medium and rinsed once by gently adding DPBS to side of vessel, so as not to dislodge cells. Applicants added 2 ml of TrypLE to a T75 flask and incubated for 5 m at 37° C. 10 ml of warm D10 medium is added to inactivate and transferred to a 50 ml Falcon tube. Applicants dissociated cells by triturating gently, and re-seeded new flasks as necessary. Applicants typically passage cells every 2-3 d at a split ratio of 1:4 or 1:8, never allowing cells to reach more than 70% confluency. Cell lines are restarted upon reaching passage number 15.

9| Prepare cells for transfection. Applicants plated well-dissociated cells onto 24-well plates in D10 medium without antibiotics 16-24 h before transfection at a seeding density of $1.3 \times 10^5$ cells per well and a seeding volume of 500 ul. Scale up or down according to the manufacturer's manual as needed. It is suggested to not plate more cells than recommended density as doing so may reduce transfection efficiency.

10| On the day of transfection, cells are optimal at 70-90% confluency. Cells may be transfected with Lipofectamine 2000 or Amaxa SF Cell Line Nucleofector Kit according to the manufacturers' protocols.

(A) For sgRNAs cloned into PX330, Applicants transfected 500 ng of sequence-verified CRISPR plasmid; if transfecting more than one plasmid, mix at equimolar ratio and no more than 500 ng total.

(B) For sgRNA amplified by PCR, Applicants mixed the following:

| PX165 (Cas9 only) | 200 ng |
| sgRNA amplicon (each) | 40 ng |
| pUC19 | fill up total DNA to 500 ng |

Applicants recommend transfecting in technical triplicates for reliable quantification and including transfection controls (e.g. GFP plasmid) to monitor transfection efficiency. In addition, PX330 cloning plasmid and/or sgRNA amplicon may be transfected alone as a negative control for downstream functional assays.

11| Applicants added Lipofectamine complex to cells gently as HEK293FT cells may detach easily from plate easily and result in lower transfection efficiency.

12| Applicants checked cells 24 h after transfection for efficiency by estimating the fraction of fluorescent cells in the control (e.g., GFP) transfection using a fluorescence microscope. Typically cells are more than 70% transfected.

13| Applicants supplemented the culture medium with an additional 500 ul of warm D10 medium. Add D10 very slowly to the side of the well and do not use cold medium, as cells can detach easily.

14| Cells are incubated for a total of 48-72 h post-transfection before harvested for indel analysis. Indel efficiency does not increase noticeably after 48 h.

(Optional) Co-Transfection of CRISPR Plasmids and ssODNs or Targeting Plasmids for HR•Timing 3-4 d 15| Linearize targeting plasmid. Targeting vector is linearized if possible by cutting once at a restriction site in the vector backbone near one of the homology arms or at the distal end of either homology arm.

16| Applicants ran a small amount of the linearized plasmid alongside uncut plasmid on a 0.8-1% agarose gel to check successful linearization. Linearized plasmid should run above the supercoiled plasmid.

17| Applicants purified linearized plasmid with the QIAQuick PCR Purification kit.

18| Prepare cells for transfection. Applicants cultured HEK293FT in T75 or T225 flasks. Sufficient cell count before day of transfection is planned for. For the Amaxa strip-cuvette format, $2 \times 10^6$ cells are used per transfection.

19| Prepare plates for transfection. Applicants added 1 ml of warm D10 medium into each well of a 12 well plate. Plates are placed into the incubator to keep medium warm.

20| Nucleofection. Applicants transfected HEK293FT cells according to the Amaxa SF Cell Line Nucleofector 4D Kit manufacturer's instructions, adapted in the steps below.

a. For ssODN and CRISPR cotransfection, pre-mix the following DNA in PCR tubes:

| pCRISPR plasmid (Cas9 + sgRNA) | 500 ng |
| ssODN template (10 uM) | 1 ul | b. For HDR targeting plasmid and CRISPR cotransfection, pre-mix the following DNA in PCR tubes:

| CRISPR plasmid (Cas9 + sgRNA) | 500 ng |
| Linearized targeting plasmid | 500 ng |

For transfection controls, see previous section. In addition, Applicants recommend transfecting ssODN or targeting plasmid alone as a negative control.

21| Dissociate to single cells. Applicants removed medium and rinsed once gently with DPBS, taking care not to dislodge cells. 2 ml of TrypLE is added to a T75 flask and incubated for 5 m at 37° C. 10 ml of warm D10 medium is added to inactivate and triturated gently in a 50 ml Falcon tube. It is recommended that cells are triturated gently and dissociated to single cells. Large clumps will reduce transfection efficiency. Applicants took a 10 ul aliquot from the suspension and diluted into 90 ul of D10 medium for counting. Applicants counted cells and calculated the number of cells and volume of suspension needed for transfection. Applicants typically transfected $2 \times 10^5$ cells per condition using the Amaxa Nucleocuvette strips, and recommend calculating for 20% more cells than required to adjust for volume loss in subsequent pipetting steps. The volume needed is transferred into a new Falcon tube.

23| Applicants spun down the new tube at 200×g for 5 m. Applicants prepared the transfection solution by mixing the SF solution and 51 supplement as recommended by Amaxa. For Amaxa strip-cuvettes, a total of 20 ul of supplemented SF solution is needed per transfection. Likewise, Applicants recommend calculating for 20% more volume than required.

25| Applicants removed medium completely from pelleted cells from step 23 and gently resuspended in appropriate volume (20 ul per $2 \times 10^5$ cells) of 51-supplemented SF solution. Do not leave cells in SF solution for extended period of time.

26| 20 ul of resuspended cells is pipetted into each DNA pre-mix from step 20. Pipette gently to mix and transfer to Nucleocuvette strip chamber. This is repeated for each transfection condition.

Electroporate cells using the Nucleofector 4D program recommended by Amaxa, CM-130.

28| Applicants gently and slowly pipetted 100 ul of warm D10 medium into each Nucleocuvette strip chamber, and transferred all volume into the pre-warmed plate from step 19. CRITICAL. Cells are very fragile at this stage and harsh pipetting can cause cell death. Incubate for 24 h. At this point, transfection efficiency can be estimated from fraction of fluorescent cells in positive transfection control. Nucleofection typically results in greater than 70-80% transfection efficiency. Applicants slowly added 1 ml warm D10 medium to each well without dislodging the cells. Incubate cells for a total of 72 h.

Human Embryonic Stem Cell (HUES 9) Culture and Transfection•Timing 3-4 d

Maintaining hESC (HUES9) line. Applicants routinely maintain HUES9 cell line in feeder-free conditions with mTesR1 medium. Applicants prepared mTeSR1 medium by adding the 5× supplement included with basal medium and 100 ug/ml Normocin. Applicants prepared a 10 ml aliquot of mTeSR1 medium supplemented further with 10 uM Rock Inhibitor. Coat tissue culture plate. Dilute cold GelTrex 1:100 in cold DMEM and coat the entire surface of a 100 mm tissue culture plate.

Place plate in incubator for at least 30 m at 37° C. Thaw out a vial of cells at 37° C. in a 15 ml Falcon tube, add 5 ml of mTeSR1 medium, and pellet at 200×g for 5 m. Aspirate off GelTrex coating and seed ~1×106 cells with 10 ml mTeSR1 medium containing Rock Inhibitor. Change to normal mTeSR1 medium 24 h after transfection and re-feed daily. Passaging cells. Re-feed cells with fresh mTeSR1 medium daily and passage before reaching 70% confluency. Aspirate off mTeSR1 medium and wash cells once with DPBS. Dissociate cells by adding 2 ml Accutase and incubating at 37° C. for 3-5 m. Add 10 ml mTeSR1 medium to detached cells, transfer to 15 ml Falcon tube and resuspend gently. Re-plate onto GelTrex-coated plates in mTeSR1 medium with 10 uM Rock Inhibitor. Change to normal mTeSR1 medium 24 h after plating.

Transfection. Applicants recommend culturing cells for at least 1 week post-thaw before transfecting using the Amaxa P3 Primary Cell 4-D Nucleofector Kit (Lonza). Re-feed log-phase growing cells with fresh medium 2 h before transfection. Dissociate to single cells or small clusters of no more than 10 cells with accutase and gentle resuspension. Count the number of cells needed for nucleofection and spin down at 200×g for 5 m. Remove medium completely and resuspend in recommended volume of S1-supplemented P3 nucleofection solution. Gently plate electroporated cells into coated plates in presence of 1× Rock Inhibitor.

Check transfection success and re-feed daily with regular mTeSR1 medium beginning 24 h after nucleofection. Typically, Applicants observe greater than 70% transfection efficiency with Amaxa Nucleofection. Harvest DNA. 48-72 h post transfection, dissociate cells using accutase and inactivate by adding 5× volume of mTeSR1. Spin cells down at 200×g for 5 m. Pelleted cells can be directed processed for DNA extraction with QuickExtract solution. It is recommended to not mechanically dissociate cells without accutase. It is recommended to not spin cells down without inactivating accutase or above the recommended speed; doing so may cause cells to lyse.

Isolation of Clonal Cell Lines by FACS. Timing•2-3 h Hands-on; 2-3 Weeks Expansion Clonal isolation may be performed 24 h post-transfection by FACS or by serial dilution.

54| Prepare FACS buffer. Cells that do not need sorting using colored fluorescence may be sorted in regular D10 medium supplemented with 1× penicillin/streptinomycin. If colored fluorescence sorting is also required, a phenol-free DMEM or DPBS is substituted for normal DMEM. Supplement with 1× penicillin/streptinomycin and filter through a 0.22 um Steriflip filter.

55| Prepare 96 well plates. Applicants added 100 ul of D10 media supplemented with 1× penicillin/streptinomycin per well and prepared the number of plates as needed for the desired number of clones.

56| Prepare cells for FACS. Applicants dissociated cells by aspirating the medium completely and adding 100 ul TrypLE per well of a 24-well plate. Incubate for 5 m and add 400 ul warm D10 media.

57| Resuspended cells are transferred into a 15 ml Falcon tube and gently triturated 20 times. Recommended to check under the microscope to ensure dissociation to single cells.

58| Spin down cells at 200×g for 5 minutes.

59| Applicants aspirated the media, and resuspended the cells in 200 ul of FACS media.

60| Cells are filtered through a 35 um mesh filter into labeled FACS tubes. Applicants recommend using the BD Falcon 12×75 mm Tube with Cell Strainer cap. Place cells on ice until sorting.

61| Applicants sorted single cells into 96-well plates prepared from step 55. Applicants recommend that in one single designated well on each plate, sort 100 cells as a positive control.

NOTE. The remainder of the cells may be kept and used for genotyping at the population level to gauge overall modification efficiency.

62| Applicants returned cells into the incubator and allowed them to expand for 2-3 weeks. 100 ul of warm D10 medium is added 5 d post sorting. Change 100 ul of medium every 3-5 d as necessary.

63| Colonies are inspected for "clonal" appearance 1 week post sorting: rounded colonies radiating from a central point. Mark off wells that are empty or may have been seeded with doublets or multiplets.

64| When cells are more than 60% confluent, Applicants prepared a set of replica plates for passaging. 100 ul of D10 medium is added to each well in the replica plates. Applicants dissociated cells directly by pipetting up and down vigorously 20 times. 20% of the resuspended volume was plated into the prepared replica plates to keep the clonal lines. Change the medium every 2-3 d thereafter and passage accordingly.

65| Use the remainder 80% of cells for DNA isolation and genotyping.

Optional: Isolation of Clonal Cell Lines by Dilution. Timing•2-3 h Hands-on; 2-3 Weeks Expansion 66| Applicants dissociated cells from 24-well plates as described above. Make sure to dissociate to single cells. A cell strainer can be used to prevent clumping of cells.

67| The number of cells are counted in each condition. Serially dilute each condition in D10 medium to a final concentration of 0.5 cells per 100 ul. For each 96 well plate, Applicants recommend diluting to a final count of 60 cells in 12 ml of D10. Accurate count of cell number is recommended for appropriate clonal dilution. Cells may be recounted at an intermediate serial dilution stage to ensure accuracy.

68| Multichannel pipette was used to pipette 100 ul of diluted cells to each well of a 96 well plate.

NOTE. The remainder of the cells may be kept and used for genotyping at the population level to gauge overall modification efficiency.

69| Applicants inspected colonies for "clonal" appearance ~1 week post plating: rounded colonies radiating from a central point. Mark off wells that may have seeded with doublets or multiplets.

70| Applicants returned cells to the incubator and allowed them to expand for 2-3 weeks. Re-feed cells as needed as detailed in previous section.

SURVEYOR Assay for CRISPR Cleavage Efficiency. Timing•5-6 h

Before assaying cleavage efficiency of transfected cells, Applicants recommend testing each new SURVEYOR primer on negative (untransfected) control samples through the step of SURVEYOR nuclease digestion using the protocol described below. Occasionally, even single-band clean SURVEYOR PCR products can yield non-specific SURVEYOR nuclease cleavage bands and potentially interfere with accurate indel analysis.

71| Harvest cells for DNA. Dissociate cells and spin down at 200×g for 5 m. NOTE. Replica plate at this stage as needed to keep transfected cell lines.

72| Aspirate the supernatant completely.

73| Applicants used QuickExtract DNA extraction solution according to the manufacturer's instructions. Applicants typically used 50 ul of the solution for each well of a 24 well plate and 10 ul for a 96 well plate.

74| Applicants normalized extracted DNA to a final concentration of 100-200 ng/ul with ddH$_2$O. Pause point: Extracted DNA may be stored at −20° C. for several months.

75| Set up the SURVEYOR PCR. Master mix the following using SURVEYOR primers provided by Applicants online/computer algorithm tool:

| Component: | Amount (ul) | Final concentration |
|---|---|---|
| Herculase II PCR buffer, 5X | 10 | 1X |
| dNTP, 100 mM (25 mM each) | 1 | 1 mM |
| SURVEYOR Fwd primer (10 uM) | 1 | 0.2 uM |
| SURVEYOR Rev primer (10 uM) | 1 | 0.2 uM |
| Herculase II Fusion polymerase | 1 | |
| MgCl$_2$ (25 mM) | 2 | 1 mM |
| Distilled water | 33 | |
| Total | 49 (for each reaction) | |

76| Applicants added 100-200 ng of normalized genomic DNA template from step 74 for each reaction.

77| PCR reaction was performed using the following cycling conditions, for no more than 30 amplification cycles:

| Cycle number | Denature | Anneal | Extend |
|---|---|---|---|
| 1 | 95° C., 2 min | | |
| 2-31 | 95° C., 20 s | 60° C., 20 s | 72° C., 30 s |
| 32 | | | 72° C., 3 min |

78| Applicants ran 2-5 ul of PCR product on a 1% gel to check for single-band product. Although these PCR conditions are designed to work with most pairs of SURVEYOR primers, some primers may need additional optimization by adjusting the template concentration, MgCl$_2$ concentration, and/or the annealing temperature.

79| Applicants purified the PCR reactions using the QIAQuick PCR purification kit and normalized eluant to 20 ng/ul. Pause point: Purified PCR product may be stored at −20° C.

80| DNA heteroduplex formation. The annealing reaction was set up as follows:

| | |
|---|---|
| Taq PCR buffer, 10X | 2 ul |
| Normalized DNA (20 ng/ul) | 18 ul |
| Total volume | 20 ul |

81| Anneal the reaction using the following conditions:

| Cycle number | Condition |
|---|---|
| 1 | 95° C., 10 mn |
| 2 | 95° C.-85° C., −2° C./s |
| 3 | 85° C., 1 min |
| 4 | 85° C.-75° C., −0.3° C./s |
| 5 | 75° C., 1 min |
| 6 | 75° C.-65° C., −0.3° C./s |
| 7 | 65° C., 1 min |
| 8 | 65° C.-55° C., −0.3° C./s |
| 9 | 55° C., 1 min |
| 10 | 55° C.-45° C., −0.3° C./s |
| 11 | 45° C., 1 min |
| 12 | 45° C.-35° C., −0.3° C./s |
| 13 | 35° C., 1 min |
| 14 | 35° C.-25° C., −0.3° C./s |
| 15 | 25° C., 1 min |

82| SURVEYOR nuclease S digestion. Applicants prepared master-mix and added the following components on ice to annealed heteroduplexes from step 81 for a total final volume of 25 ul:

| Component | Amount (ul) | Final Concentration |
|---|---|---|
| MgCl$_2$ solution, 0.15M | 2.5 | 15 mM |
| ddH$_2$O | 0.5 | |
| SURVEYOR nuclease S | 1 | 1X |
| SURVEYOR enhancer S | 1 | 1X |
| Total | 5 | |

83| Vortex well and spin down. Incubate the reaction at 42° C. for 1 h.

84| Optional: 2 ul of the Stop Solution from the SURVEYOR kit may be added. Pause point. The digested product may be stored at −20° C. for analysis at a later time.

85| Visualize the SURVEYOR reaction. SURVEYOR nuclease digestion products may be visualized on a 2% agarose gel. For better resolution, products may be run on a 4-20% gradient Polyacrylamide TBE gel. Applicants loaded 10 ul of product with the recommended loading buffer and ran the gel according to manufacturer's instructions. Typically, Applicants run until the bromophenol blue dye has migrated to the bottom of the gel. Include DNA ladder and negative controls on the same gel.

86| Applicants stained the gel with 1×SYBR Gold dye diluted in TBE. The gel was gently rocked for 15 m.

87| Applicants imaged the gel using a quantitative imaging system without overexposing the bands. The negative controls should have only one band corresponding to the size of the PCR product, but may have occasionally nonspecific cleavage bands of other sizes. These will not interfere with analysis if they are different in size from target cleavage bands. The sum of target cleavage band sizes, provided by Applicants online/computer algorithm tool, should be equal to the size of the PCR product.

88| Estimate the cleavage intensity. Applicants quantified the integrated intensity of each band using ImageJ or other gel quantification software.

89| For each lane, Applicants calculated the fraction of the PCR product cleaved ($f_{cut}$) using the following formula: $f_{cut}=(b+c)/(a+b+c)$, where a is the integrated intensity of the undigested PCR product and b and c are the integrated intensities of each cleavage product. 90| Cleavage efficiency may be estimated using the following formula, based on the binomial probability distribution of duplex formation:

91| indel (%)=100×(1−$\sqrt{(1-f_{cut})}$)

Sanger Sequencing for Assessing CRISPR Cleavage Efficiency. Timing•3 d

Initial steps are identical to Steps 71-79 of the SURVEYOR assay. Note: SURVEYOR primers may be used for Sanger sequencing if appropriate restriction sites are appended to the Forward and Reverse primers. For cloning into the recommended pUC19 backbone, EcoRI may be used for the Fwd primer and HindIII for the Rev primer.

92| Amplicon digestion. Set up the digestion reaction as follows:

| Component | Amount (ul) |
| --- | --- |
| Fast Digest buffer, 10X | 3 |
| FastDigest EcoRI | 1 |
| FastDigest HindIII | 1 |
| Normalized DNA (20 ng/ul) | 10 |
| ddH$_2$O | 15 |
| Total volume | 30 |

93| pUC19 backbone digestion. Set up the digestion reaction as follows:

| Component | Amount (ul) |
| --- | --- |
| Fast Digest buffer, 10X | 3 |
| FastDigest EcoRI | 1 |
| FastDigest HindIII | 1 |
| FastAP Alkaline Phosphatase | 1 |
| pUC19 vector (200 ng/ul) | 5 |
| ddH$_2$O | 20 |
| Total volume | 30 |

94| Applicants purified the digestion reactions using the QIAQuick PCR purification kit. Pause point: Purified PCR product may be stored at −20° C.

95| Applicants ligated the digested pUC19 backbone and Sanger amplicons at a 1:3 vector:insert ratio as follows:

| Component | Amount (ul) |
| --- | --- |
| Digested pUC19 | x (50 ng) |
| Digested insert | x (1:3 vector:insert molar ratio) |
| T7 ligase | 1 |
| 2X Rapid Ligation Buffer | 10 |
| ddH$_2$O | x |
| Total volume | 20 |

96| Transformation. Applicants transformed the Plasmid-Safe-treated plasmid into a competent *E. coli* strain, according to the protocol supplied with the cells. Applicants recommend Stbl3 for quick transformation. Briefly, 5 ul of the product from step 95 is added into 20 ul of ice-cold chemically competent Stbl3 cells, incubated on ice for 10 m, heat shocked at 42° C. for 30 s, returned immediately to ice for 2 m, 100 ul of SOC medium is added, and plated onto an LB plate containing 100 ug/ml ampicillin. This is incubated overnight at 37° C.

97| Day 2: Applicants inspected plates for colony growth. Typically, there are no colonies on the negative control plates (ligation of EcoRI-HindIII digested pUC19 only, no Sanger amplicon insert), and tens to hundreds of colonies on the pUC19-Sanger amplicon cloning plates.

98| Day 3: Applicants isolated plasmid DNA from overnight cultures using a QIAprep Spin miniprep kit according to the manufacturer's instructions.

99| Sanger sequencing. Applicants verified the sequence of each colony by sequencing from the pUC19 backbone using the pUC19-For primer. Applicants referenced the sequencing results against the expected genomic DNA sequence to check for the presence of Cas9-induced NHEJ mutations. % editing efficiency=(# modified clones)/(# total clones). It is important to pick a reasonable number of clones (>24) to generate accurate modification efficiencies.

Genotyping for Microdeletion. Timing•2-3 d Hands on; 2-3 Weeks Expansion

100| Cells were transfected as described above with a pair of sgRNAs targeting the region to be deleted.

101| 24 h post-transfection, clonal lines are isolated by FACS or serial dilution as described above.

102| Cells are expanded for 2-3 weeks.

103| Applicants harvested DNA from clonal lines as described above using 10 ul QuickExtract solution and normalized genomic DNA with ddH$_2$O to a final concentration of 50-100 ng/ul.

104| PCR Amplify the modified region. The PCR reaction is set up as follows:

| Component: | Amount (ul) | Final concentration |
| --- | --- | --- |
| Herculase II PCR buffer, 5X | 10 | 1X |
| dNTP, 100 mM (25 mM each) | 1 | 1 mM |
| Out Fwd primer (10 uM) | 1 | 0.2 uM |
| Out Rev primer (10 uM) | 1 | 0.2 uM |
| Herculase II Fusion polymerase | 1 | |
| MgCl2 (25 mM) | 2 | 1 mM |
| ddH$_2$O | 32 | |
| Total | 48 (for each reaction) | |

Note: if deletion size is more than 1 kb, set up a parallel set of PCR reactions with In-Fwd and In-Rev primers to screen for the presence of the wt allele.

105| To screen for inversions, a PCR reaction is set up as follows:

| Component: | Amount (ul) | Final concentration |
| --- | --- | --- |
| Herculase II PCR buffer, 5X | 10 | 1X |
| dNTP, 100 mM (25 mM each) | 1 | 1 mM |
| Out Fwd or Out-Rev primer (10 uM) | 1 | 0.2 uM |
| In Fwd or In-Rev primer (10 uM) | 1 | 0.2 uM |
| Herculase II Fusion polymerase | 1 | |
| MgCl$_2$ (25 mM) | 2 | 1 mM |
| ddH$_2$O | 32 | |
| Total | 48 (for each reaction) | |

Note: primers are paired either as Out-Fwd+In Fwd, or Out-Rev+In-Rev.

106| Applicants added 100-200 ng of normalized genomic DNA template from step 103 for each reaction.

107| PCR reaction was performed using the following cycling conditions:

| Cycle number | Denature | Anneal | Extend |
|---|---|---|---|
| 1 | 95° C., 2 min | | |
| 2-31 | 95° C., 20 s | 60° C., 20 s | 72° C., 30 s |
| 32 | | | 72° C., 3 m |

108| Applicants run 2-5 ul of PCR product on a 1-2% gel to check for product. Although these PCR conditions are designed to work with most primers, some primers may need additional optimization by adjusting the template concentration, $MgCl_2$ concentration, and/or the annealing temperature.

Genotyping for Targeted Modifications Via HDR. Timing•2-3 d, 2-3 h Hands on

109| Applicants harvested DNA as described above using QuickExtract solution and normalized genomic DNA with TE to a final concentration of 100-200 ng/ul.

110| PCR Amplify the modified region. The PCR reaction is set up as follows:

| Component: | Amount (ul) | Final concentration |
|---|---|---|
| Herculase II PCR buffer, 5X | 10 | 1X |
| dNTP, 100 mM (25 mM each) | 1 | 1 mM |
| HDR Fwd primer (10 uM) | 1 | 0.2 uM |
| HDR Rev primer (10 uM) | 1 | 0.2 uM |
| Herculase II Fusion polymerase | 1 | |
| $MgCl_2$ (25 mM) | 2 | 1 mM |
| $ddH_2O$ | 33 | |
| Total | 49 (for each reaction) | |

111| Applicants added 100-200 ng of genomic DNA template from step 109 for each reaction and run the following program.

| Cycle number | Denature | Anneal | Extend |
|---|---|---|---|
| 1 | 95° C., 2 min | | |
| 2-31 | 95° C., 20 s | 60° C., 20 s | 72° C., 30-60 s per kb |
| 32 | | | 72° C., 3 min |

112| Applicants ran 5 ul of PCR product on a 0.8-1% gel to check for single-band product. Primers may need additional optimization by adjusting the template concentration, $MgCl_2$ concentration, and/or the annealing temperature.

113| Applicants purified the PCR reactions using the QIAQuick PCR purification kit.

114| In the HDR example, a HindIII restriction site is inserted into the EMX1 gene. These are detected by a restriction digest of the PCR amplicon:

| Component | Amount (ul) |
|---|---|
| Purified PCR amplicon (200-300 ng) | x |
| F.D. buffer, Green | 1 |
| HindIII | 0.5 |
| ddH2O | x |
| Total | 10 | i. The DNA is digested for 10 m at 37° C.:
ii. Applicants ran 10 ul of the digested product with loading dye on a 4-20% gradient polyacrylamide TBE gel until the xylene cyanol band had migrated to the bottom of the gel.
iii. Applicants stained the gel with 1×SYBR Gold dye while rocking for 15 m.
iv. The cleavage products are imaged and quantified as described above in the SURVEYOR assay section. HDR efficiency is estimated by the formula: $(b+c)/(a+b+c)$, where a is the integrated intensity for the undigested HDR PCR product, and b and c are the integrated intensities for the HindIII-cut fragments.

115| Alternatively, purified PCR amplicons from step 113 may be cloned and genotyped using Sanger sequencing or NGS.

Deep Sequencing and Off-Target Analysis•Timing 1-2 d

The online CRISPR target design tool generates candidate genomic off-target sites for each identified target site. Off-target analysis at these sites can be performed by SURVEYOR nuclease assay, Sanger sequencing, or next-generation deep sequencing. Given the likelihood of low or undetectable modification rates at many of these sites, Applicants recommend deep sequencing with the Illumina Miseq platform for high sensitivity and accuracy. Protocols will vary with sequencing platform; here, Applicants briefly describe a fusion PCR method for attaching sequencing adapters.

116| Design deep sequencing primers. Next-generation sequencing (NGS) primers are designed for shorter amplicons, typically in the 100-200 bp size range. Primers may be manually designed using NCBI Primer-Blast or generated with online CRISPR target design tools (website at genome-engineering.org/tools).

117| Harvest genomic DNA from Cas9-targeted cells. Normalize QuickExtract genomic DNA to 100-200 ng/ul with $ddH_2O$.

118| Initial library preparation PCR. Using the NGS primers from step 116, prepare the initial library preparation PCR

| Component: | Amount (ul) | Final concentration |
|---|---|---|
| Herculase II PCR buffer, 5X | 10 | 1X |
| dNTP, 100 mM (25 mM each) | 1 | 1 mM |
| NGS Fwd primer (10 uM) | 1 | 0.2 uM |
| NGS Rev primer (10 uM) | 1 | 0.2 uM |
| Herculase II Fusion polymerase | 1 | |
| MgCl2 (25 mM) | 2 | 1 mM |
| ddH2O | 33 | |
| Total | 49 (for each reaction) | |

119| Add 100-200 ng of normalized genomic DNA template for each reaction.

120| Perform PCR reaction using the following cycling conditions, for no more than 20 amplification cycles:

| Cycle number | Denature | Anneal | Extend |
|---|---|---|---|
| 1 | 95° C., 2 min | | |
| 2-21 | 95° C., 20 s | 60° C., 20 s | 72° C., 15 s |
| 22 | | | 72° C., 3 min |

121| Run 2-5 ul of PCR product on a 1% gel to check for single-band product. As with all genomic DNA PCRs, NGS primers may require additional optimization by adjusting the template concentration, $MgCl_2$ concentration, and/or the annealing temperature.

[22] Purify the PCR reactions using the QIAQuick PCR purification kit and normalize eluant to 20 ng/ul. Pause point: Purified PCR product may be stored at −20° C.

[23] Nextera XT DNA Sample Preparation Kit. Following the manufacturer's protocol, generate Miseq sequencing-ready libraries with unique barcodes for each sample.

[24] Analyze sequencing data. Off-target analysis may be performed through read alignment programs such as ClustalW, Geneious, or simple sequence analysis scripts.

Timing

Steps 1-2 Design and synthesis of sgRNA oligos and ssODNs: 1-5 d, variable depending on supplier Steps 3-5 Construction of CRISPR plasmid or PCR expression cassette: 2 h to 3 d Steps 6-53 Transfection into cell lines: 3 d (1 h hands-on time)

Steps 54-70 Optional derivation of clonal lines: 1-3 weeks, variable depending on cell type Steps 71-91 Functional validation of NHEJ via SURVEYOR: 5-6 h Steps 92-124 Genotyping via Sanger or next-gen deep sequencing: 2-3 d (3-4 h hands on time)

Addressing Situations Concerning Herein Examples there is some variability in the cleavage efficiency of a given sgRNA, and on rare occasions certain sgRNAs may not work for reasons yet unknown. Applicants recommend designing two sgRNAs for each locus, and testing their efficiencies in the intended cell type.

Example 26: NLSs

Cas9 Transcriptional Modulator: Applicants set out to turn the Cas9/gRNA CRISPR system into a generalized DNA binding system in which functions beyond DNA cleavage can be executed. For instance, by fusing functional domain(s) onto a catalytically inactive Cas9 Applicants have imparted novel functions, such as transcriptional activation/repression, methylation/demethylation, or chromatin modifications. To accomplish this goal Applicants made a catalytically inactive Cas9 mutant by changing two residues essential for nuclease activity, D10 and H840, to alanine. By mutating these two residues the nuclease activity of Cas9 is abolished while maintaining the ability to bind target DNA. The functional domains Applicants decided to focus on to test Applicants' hypothesis are the transcriptional activator VP64 and the transcriptional repressors SID and KRAB.

| Situation | Solution |
|---|---|
| No amplification of sgRNA | Titrate U6-template concentration |
| SURVEYOR or HDR PCR dirty or no amplification | Titrate MgCl2; normalize and titrate template concentration; annealing temp gradient; redesign primers |
| Unequal amplification of alleles in microdeletion PCRs | Set up separate PCRs to detect wildtype and deletion alleles; Redesign primers with similar sized amplicons |
| Colonies on negative control plate | Increase BbsI; increase Golden Gate reaction cycle number, cut PX330 separately with Antarctic Phosphate treatment |
| No sgRNA sequences or wrong sequences | Screen additional colonies |
| Low lipofectamine transfection efficiency | Check cell health and density; titrate DNA; add GFP transfection control |
| Low nucleofection transfection efficiency | Check cell health and density; titrate DNA; suspend to single cell |
| Clumps or no cells after FACS | Filter cells before FACS; dissociate to single cells; resuspend in appropriate density |
| Clumps or no cells in serial dilution | Recount cells; dissociate to single cells and filter through strainer; check serial dilution |
| High SURVEYOR background on negative sample | Redesign primers to prime from different locations |
| Dirty SURVEYOR result on gel | Purify PCR product; reduce input DNA; reduce 42° C. incubation to 30 m |
| No SURVEYOR cleavage | Purify and normalize PCR product; re-anneal with TaqB buffer; Redesign sgRNAs; sequence verify Cas9 on px330 backbone |
| Samples do not sink in TBE acrylamide gel | Supplement with MgCl2 to a final concentration of 15 mM or add loading buffer containing glycerol |

DISCUSSION

Figure 12A:
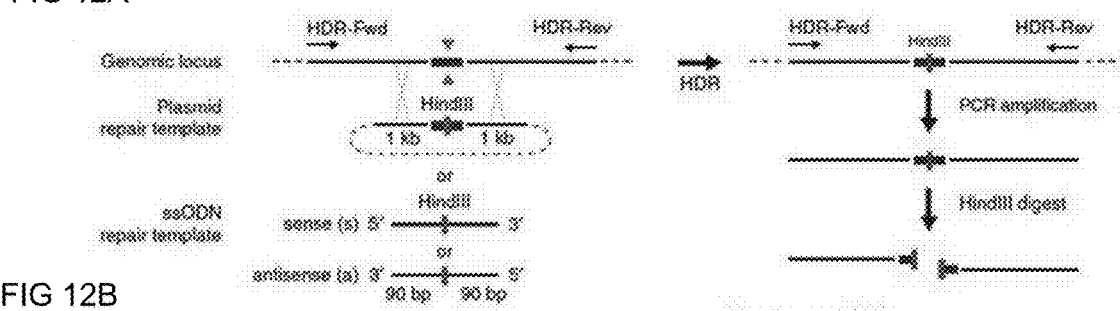
FIG. 12A-C shows anticipated results for HDR in HEK and HUES9 cells. (a) Either a targeting plasmid or an ssODN (sense or antisense) with homology arms can be used to edit the sequence at a target genomic locus cleaved by Cas9 (red triangle). To assay the efficiency of HDR, we introduced a HindIII site (red bar) into the target locus, which was PCR-amplified with primers that anneal outside of the region of homology. Digestion of the PCR product with HindIII reveals the occurrence of HDR events. (b) ssODNs, oriented in either the sense or the antisense (s or a) direction relative to the locus of interest, can be used in combination with Cas9 to achieve efficient HDR-mediated editing at the target locus. A minimal homology region of 40 bp, and preferably 90 bp, is recommended on either side of the modification (red bar).
Figure 12B:
Figure 12C:
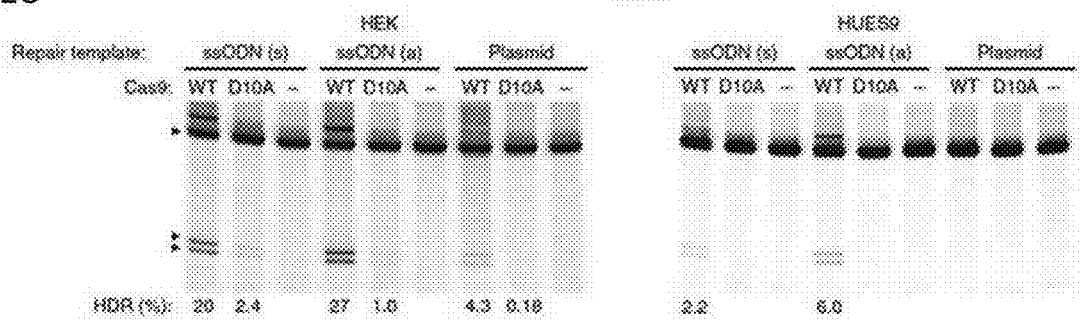

CRISPR-Cas may be easily multiplexed to facilitate simultaneous modification of several genes and mediate chromosomal microdeletions at high efficiencies. Applicants used two sgRNAs to demonstrate simultaneous targeting of the human GRIN2B and DYRK1A loci at efficiencies of up to 68% in HEK293FT cells. Likewise, a pair of sgRNAs may be used to mediate microdeletions, such as excision of an exon, which can be genotyped by PCR on a clonal level. Note that the precise location of exon junctions can vary. Applicants also demonstrated the use of ssODNs and targeting vector to mediate HDR with both wildtype and nickase mutant of Cas9 in HEK 293FT and HUES9 cells (FIG. 12). Note that Applicants have not been able to detect HDR in HUES9 cells using the Cas9 nickase, which may be due to low efficiency or a potential difference in repair activities in HUES9 cells. Although these values are typical, Cas9 Nuclear localization: Applicants hypothesized that the most effective Cas9 transcriptional modulator would be strongly localized to the nucleus where it would have its greatest influence on transcription. Moreover, any residual Cas9 in the cytoplasm could have unwanted effects. Applicants determined that wild-type Cas9 does not localize into the nucleus without including multiple nuclear localization signals (NLSs) (although a CRISPR system need not have one or more NLSs but advantageously has at least one or more NLS(s)). Because multiple NLS sequences were required it was reasoned that it is difficult to get Cas9 into the nucleus and any additional domain that is fused to Cas9 could disrupt the nuclear localization. Therefore, Applicants made four Cas9-VP64-GFP fusion constructs with different NLS sequences (pXRP02-pLenti2-EF1a-NLS-hSpCsn1(10A,840A)-NLS-VP64-EGFP, pXRP04-pLenti2-EF1a-NLS-hSpCsn1(10A,840A)-NLS-VP64-2A-EGFP-NLS, pXRP06-pLenti2-EF1a-NLS-EGFP-VP64-NLS-hSpCsn1

(10A,840A)-NLS, pXRP08-pLenti2-EF1a-NLS-VP64-NLS-hSpCsn1(10A,840A)-NLS-VP64-EGFP-NLS). These constructs were cloned into a lenti backbone under the expression of the human EF1α promoter. The WPRE element was also added for more robust protein expression. Each construct was transfected into HEK 293FT cells using Lipofectame 2000 and imaged 24 hours post-transfection. The best nuclear localization is obtained when the fusion proteins have NLS sequences on both the N- and C-term of the fusion protein. The highest observed nuclear localization occurred in the construct with four NLS elements.

To more robustly understand the influence of NLS elements on Cas9 Applicants made 16 Cas9-GFP fusions by adding the same alpha importin NLS sequence on either the N- or C-term looking at zero to three tandem repeats. Each construct was transfected into HEK 293FT cells using Lipofectame 2000 and imaged 24 hours post-transfection. Notably, the number of NLS elements does not directly correlate with the extent of nuclear localization. Adding an NLS on the C-term has a greater influence on nuclear localization than adding on the N-term.

Cas9 Transcriptional Activator: Applicants functionally tested the Cas9-VP64 protein by targeting the Sox2 locus and quantifying transcriptional activation by RT-qPCR. Eight DNA target sites were chosen to span the promoter of Sox2. Each construct was transfected into HEK 293FT cells using Lipofectame 2000 and 72 hours post-transfection total RNA was extracted from the cells. 1 ug of RNA was reverse transcribed into cDNA (qScript Supermix) in a 40 ul reaction. 2 ul of reaction product was added into a single 20 ul TaqMan assay qPCR reaction. Each experiment was performed in biological and technical triplicates. No RT control and no template control reactions showed no amplification. Constructs that do not show strong nuclear localization, pXRP02 and pXRP04, result in no activation. For the construct that did show strong nuclear localization, pXRP08, moderate activation was observed. Statistically significant activation was observed in the case of guide RNAs Sox2.4 and Sox2.5.

Example 27: In Vivo Mouse Data

Figure 15:
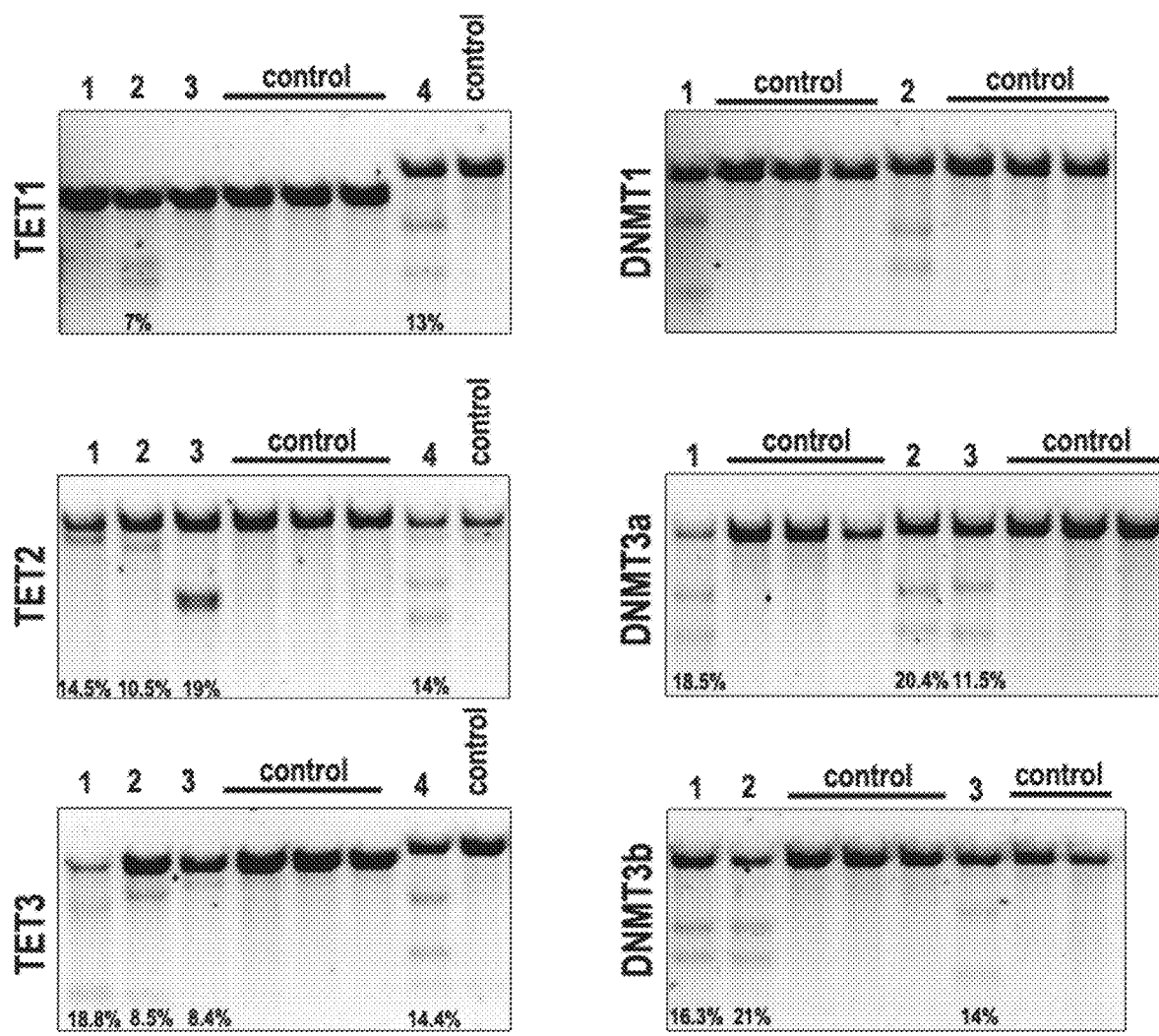
FIG. 15 shows a screen for efficient SpCas9 mediated targeting of Tet1-3 and Dnmt1, 3a and 3b gene loci. Surveyor assay on DNA from transfected N2A cells demonstrates efficient DNA cleavage by using different gRNAs.
Figure 16:
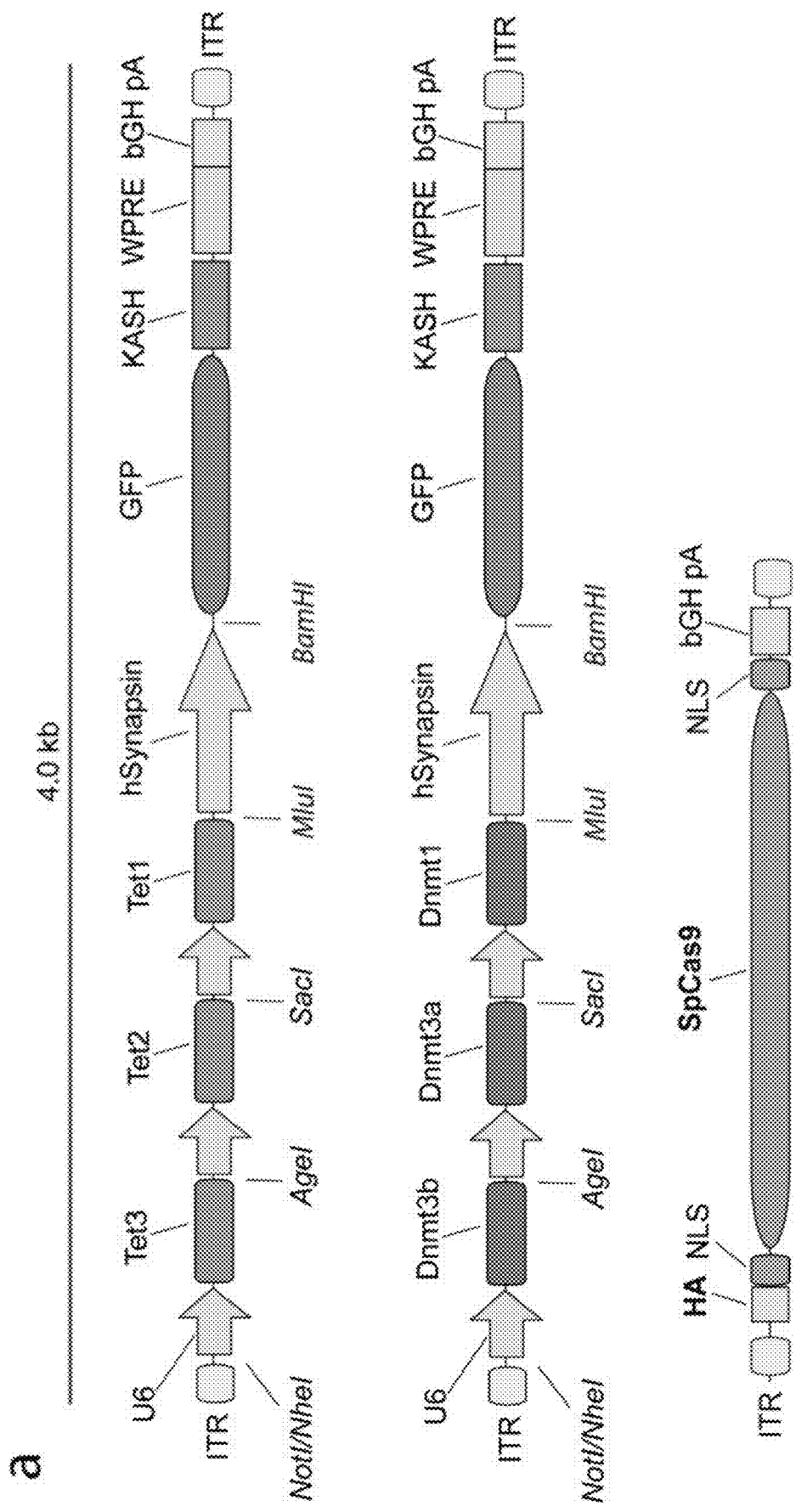
FIG. 16 shows a strategy of multiplex genome targeting using a 2-vector system in an AAV1/2 delivery system. Tet1-3 and Dnmt1, 3a and 3b gRNA under the control of the U6 promoter. GFP-KASH under the control of the human synapsin promoter. Restriction sides shows simple gRNA replacement strategy by subcloning. HA-tagged SpCas9 flanked by two nuclear localization signals (NLS) is shown. Both vectors are delivered into the brain by AAV1/2 virus in a 1:1 ratio.

Material and Reagents
Herculase II fusion polymerase (Agilent Technologies, cat. no. 600679)
10× NEBuffer 4 (NEB, cat. No. B7004S)
BsaI HF (NEB, cat. No. R3535S)
T7 DNA ligase (Enzymatics, cat. no. L602L)
Fast Digest buffer, 10× (ThermoScientific, cat. No. B64)
FastDigest NotI (ThermoScientific, cat. No. FD0594)
FastAP Alkaline Phosphatase (ThermoScientific, cat. No. EF0651)
Lipofectamine2000 (Life Technologies, cat. No. 11668-019)
Trypsin (Life Technologies, cat. No. 15400054)
Forceps #4 (Sigma, cat. No. Z168777-1EA)
Forceps #5 (Sigma, cat. No. F6521-1EA)
10× Hank's Balanced Salt Solution (Sigma, cat. No. H4641-500 ML)
Penicillin/Streptomycin solution (Life Technologies, cat. No. P4333)
Neurobasal (Life Technologies, cat. No. 21103049)
B27 Supplement (Life Technologies, cat. No. 17504044)
L-glutamine (Life Technologies, cat. No. 25030081)
Glutamate (Sigma, cat. No. RES5063G-A7)
β-mercaptoethanol (Sigma, cat. No. M6250-100 ML)
HA rabbit antibody (Cell Signaling, cat. No. 3724S)
LIVE/DEAD® Cell Imaging Kit (Life Technologies, cat. No. R37601)
30G World Precision Instrument syringe (World Precision Instruments, cat. No. NANOFIL)
Stereotaxic apparatus (Kopf Instruments)
UltraMicroPump3 (World Precision Instruments, cat. No. UMP3-4)
Sucrose (Sigma, cat. No. 57903)
Calcium chloride (Sigma, cat. No. C1016)
Magnesium acetate (Sigma, cat. No. M0631)
Tris-HCl (Sigma, cat. no T5941)
EDTA (Sigma, cat. No. E6758)
NP-40 (Sigma, cat. No. NP40)
Phenylmethanesulfonyl fluoride (Sigma, cat. No. 78830)
Magnesium chloride (Sigma, cat. No. M8266)
Potassium chloride (Sigma, cat. No. P9333)
β-glycerophosphate (Sigma, cat. No. G9422)
Glycerol (Sigma, cat. No. G9012)
Vybrant® DyeCycle™ Ruby Stain (Life technologies, cat. No. 54942)
FACS Aria Flu-act-cell sorter (Koch Institute of MIT, Cambridge US)
DNAeasy Blood & Tissue Kit (Qiagen, cat. No. 69504)
Procedure
Constructing gRNA Multiplexes for Using In Vivo in the Brain Applicants designed and PCR amplified single gRNAs targeting mouse TET and DNMT family members (as described herein) Targeting efficiency was assessed in N2a cell line (FIG. 15). To obtain simultaneous modification of several genes in vivo, efficient gRNA was multiplexed in AAV-packaging vector (FIG. 16). To facilitate further analysis of system efficiency applicants added to the system expression cassette consistent of GFP-KASH domain fusion protein under control of human Synapsin I promoter (FIG. 16). This modification allows for further analysis of system efficiency in neuronal population (more detail procedure in section Sorting nuclei and in vivo results).

All 4 parts of the system were PCR amplified using Herculase II Fusion polymerase using following primers:

1st U6 Fw:
(SEQ ID NO: 185)
gagggtctcgtccttgcggccgcgctagcgagggcctatttcccatgatt
c 1st gRNA Rv:
(SEQ ID NO: 186)
ctcggtctcggtAAAAAAgcaccgactcggtgccacttttcaagttgat
aacggactagcctttatttaacttgctaTTTCtagctctaaaacNNNNNN
NNNNNNNNNNNNNNNNNGGTGTTTCGTCCTTTCCAC 2nd U6 Fw:
(SEQ ID NO: 187)
gagggtctcTTTaccggtgagggcctatttcccatgattcc 2nd gRNA Rv:
(SEQ ID NO: 188)
ctcggtctcctcAAAAAAgcaccgactcggtgccacttttcaagttgat
aacggactagc cttattttaacttgctaTTTCtagctctaaaacNNNNN
NNNNNNNNNNNNNNNNGGTGTTTCGTCCTTTCCAC 3rd U6 Fw:
(SEQ ID NO: 189)
gagggtctcTTTgagctcgagggcctatttcccatgattc 3rd gRNA Rv:
(SEQ ID NO: 190)
ctcggtctcgcgtAAAAAAgcaccgactcggtgccacttttcaagttga
taacggactag cctttatttaacttgctaTTTCtagctctaaaacNNNN
NNNNNNNNNNNNNNNNGGTGTTTCGTCCTTTCCA -continued hSyn_GFP-kash Fw:
(SEQ ID NO: 191)
gagggtctcTTacgcgtgtgtctagac hSyn_GFP-kash Rv:
(SEQ ID NO: 192)
ctcggtctcAaggaCAGGGAAGGGAGCAGTGGTTCACGCCTGTAATCCCA
GCAATTTGGGA GGCCAAGGTGGGTAGATCACCTGAGATTAGGAGTTGC (NNNNNNNNNNNNNNNNNNNN is a reverse compliment targeted genomic sequence)

Applicants used Golden Gate strategy to assemble all parts (1:1 molecular ratio) of the system in a single step reaction:

| | | |
|---|---|---|
| 1$^{st}$ U6_gRNA | 18 ng | |
| 2$^{nd}$ U6_gRNA | 18 ng | |
| 3$^{rd}$ U6_gRNA | 18 ng | |
| Syn_GFP-kash | 100 ng | |
| 10x NEBuffer 4 | 1.0 µl | |
| 10x BSA | 1.0 µl | |
| 10 mM ATP | 1.0 µl | |
| BsaI HF | 0.75 µl | |
| T7 ligase | 0.25 µl | |
| ddH$_2$O | 10 µl | |
| Cycle number | Condition | |
| 1-50 | 37° C. for 5 m, 21° C. for 5 m | |

Golden Gate reaction product was PCR amplified using Herculase II fusion polymerase and following primers:

Fw
(SEQ ID NO: 193)
5'cctgtccttgcggccgcgctagcgagggcc

Rv
(SEQ ID NO: 194)
5'cacgcggccgcaaggacagggaagggagcag

PCR product was cloned into AAV backbone, between ITR sequences using NotI restriction sites:

| | |
|---|---|
| PCR product digestion: | |
| Fast Digest buffer, 10X | 3 µl |
| FastDigest NotI | 1 µl |
| DNA | 1 µg |
| ddH$_2$O | up to 30 µl |
| AAV backbone digestion: | |
| Fast Digest buffer, 10X | 3 µl |
| FastDigest NotI | 1 µl |
| FastAP Alkaline Phosphatase | 1 µl |
| AAV backbone | 1 µg |
| ddH$_2$O | up to 30 µl |

After 20 min incubation in 37° C. samples were purified using QIAQuick PCR purification kit. Standardized samples were ligated at a 1:3 vector:insert ratio as follows:

| | |
|---|---|
| Digested pUC19 | 50 ng |
| Digested insert | 1:3 vector:insert molar ratio |
| T7 ligase | 1 µl |
| 2X Rapid Ligation Buffer | 5 µl |
| ddH$_2$O | up to 10 µl |

After transformation of bacteria with ligation reaction product, applicants confirmed obtained clones with Sanger sequencing.

Figure 17:
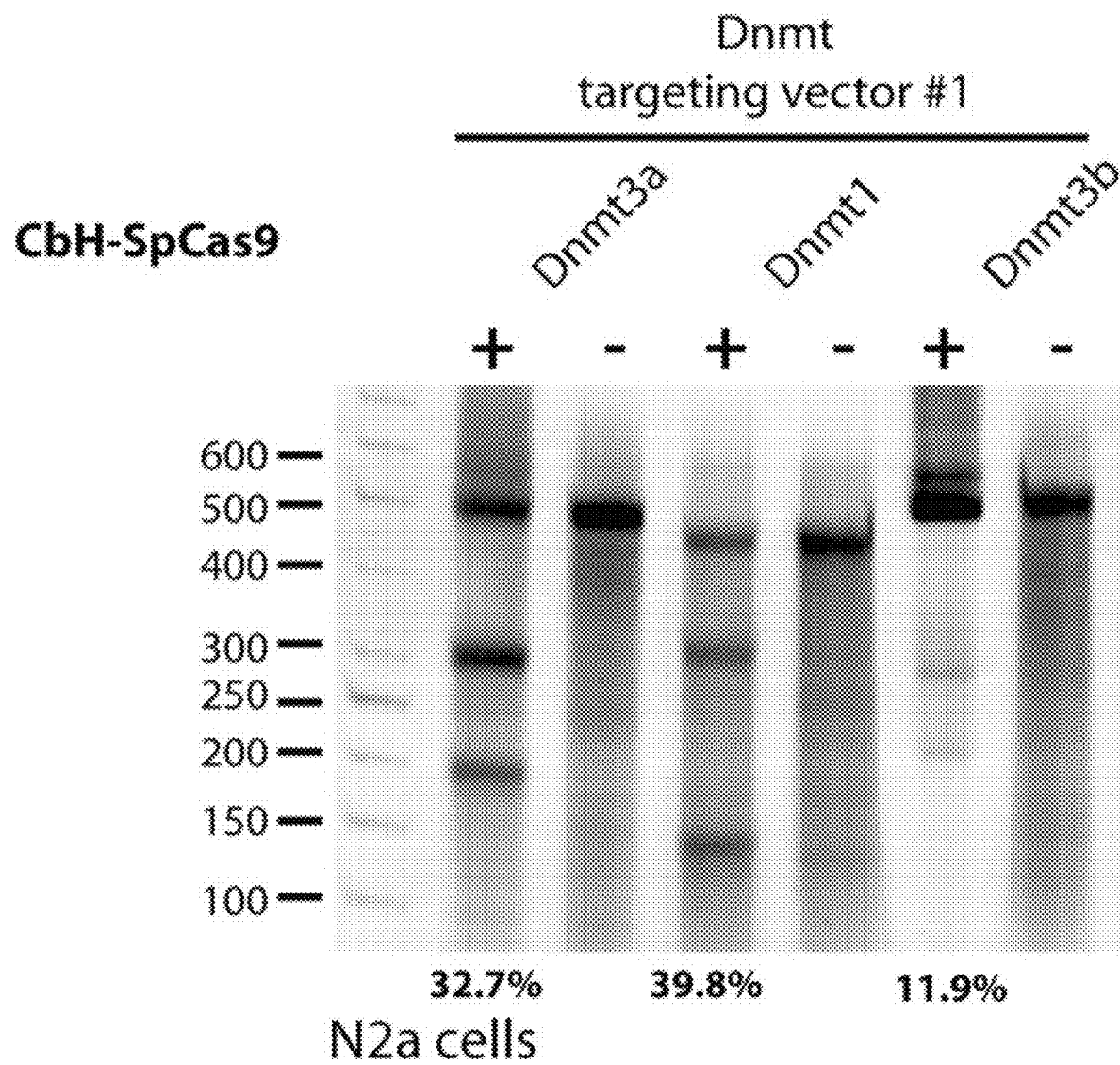
FIG. 17 shows verification of multiplex DNMT targeting vector #1 functionality using Surveyor assay. N2A cells were co-transfected with the DNMT targeting vector #1 (+) and the SpCas9 encoding vector for testing SpCas9 mediated cleavage of DNMTs genes family loci. gRNA only (−) is negative control. Cells were harvested for DNA purification and downstream processing 48 h after transfection.
Figure 18:
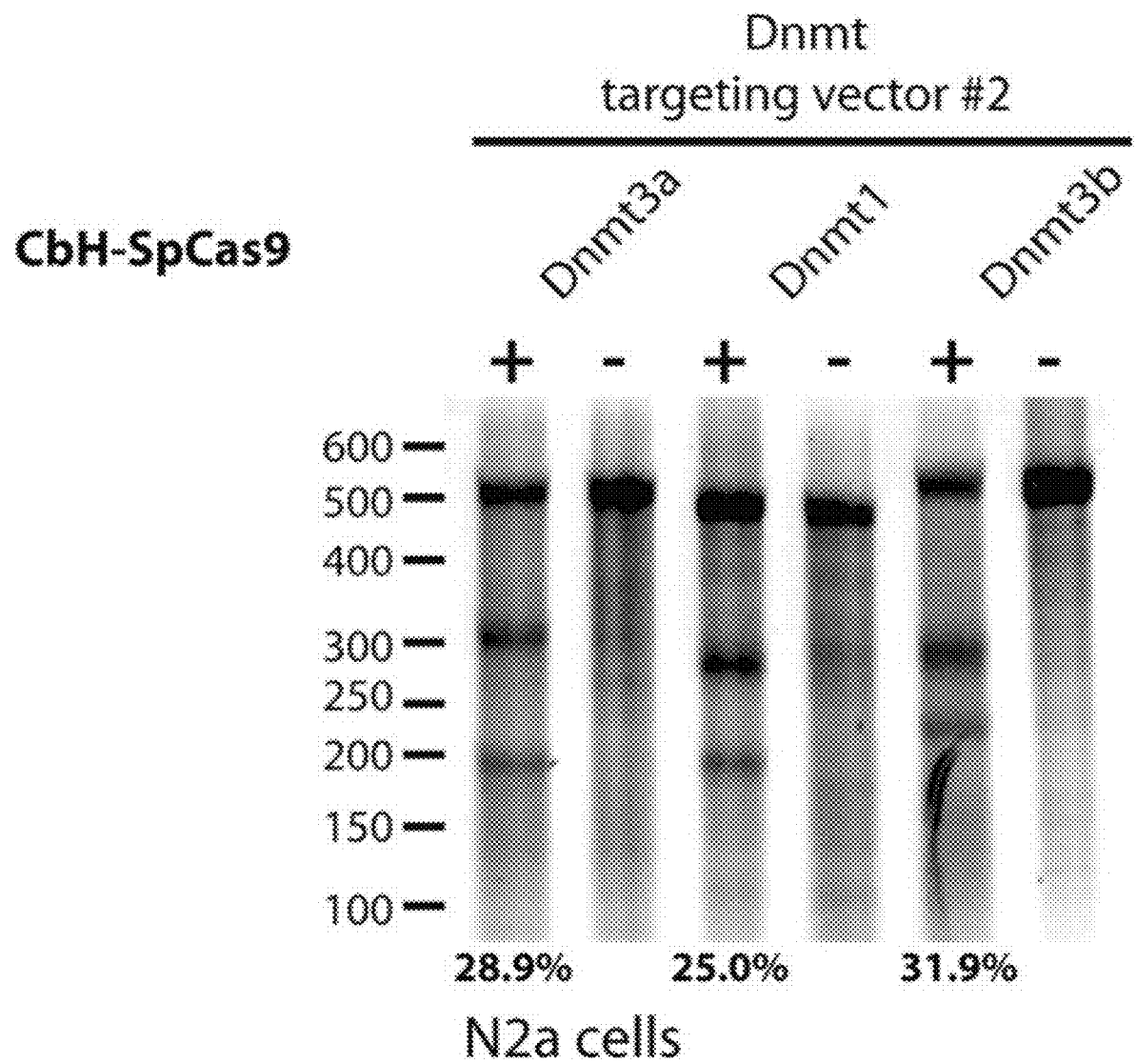
FIG. 18 shows verification of multiplex DNMT targeting vector #2 functionality using Surveyor assay. N2A cells were co-transfected with the DNMT targeting vector #1 (+) and the SpCas9 encoding vector for testing SpCas9 mediated cleavage of DNMTs genes family loci. gRNA only (−) is negative control. Cells were harvested for DNA purification and downstream processing 48 h after transfection.

Positive DNA clones were tested in N2a cells after co-transfection with Cas9 construct (FIGS. 17 and 18).

Design of New Cas9 Constructs for AAV Delivery

Figure 19:
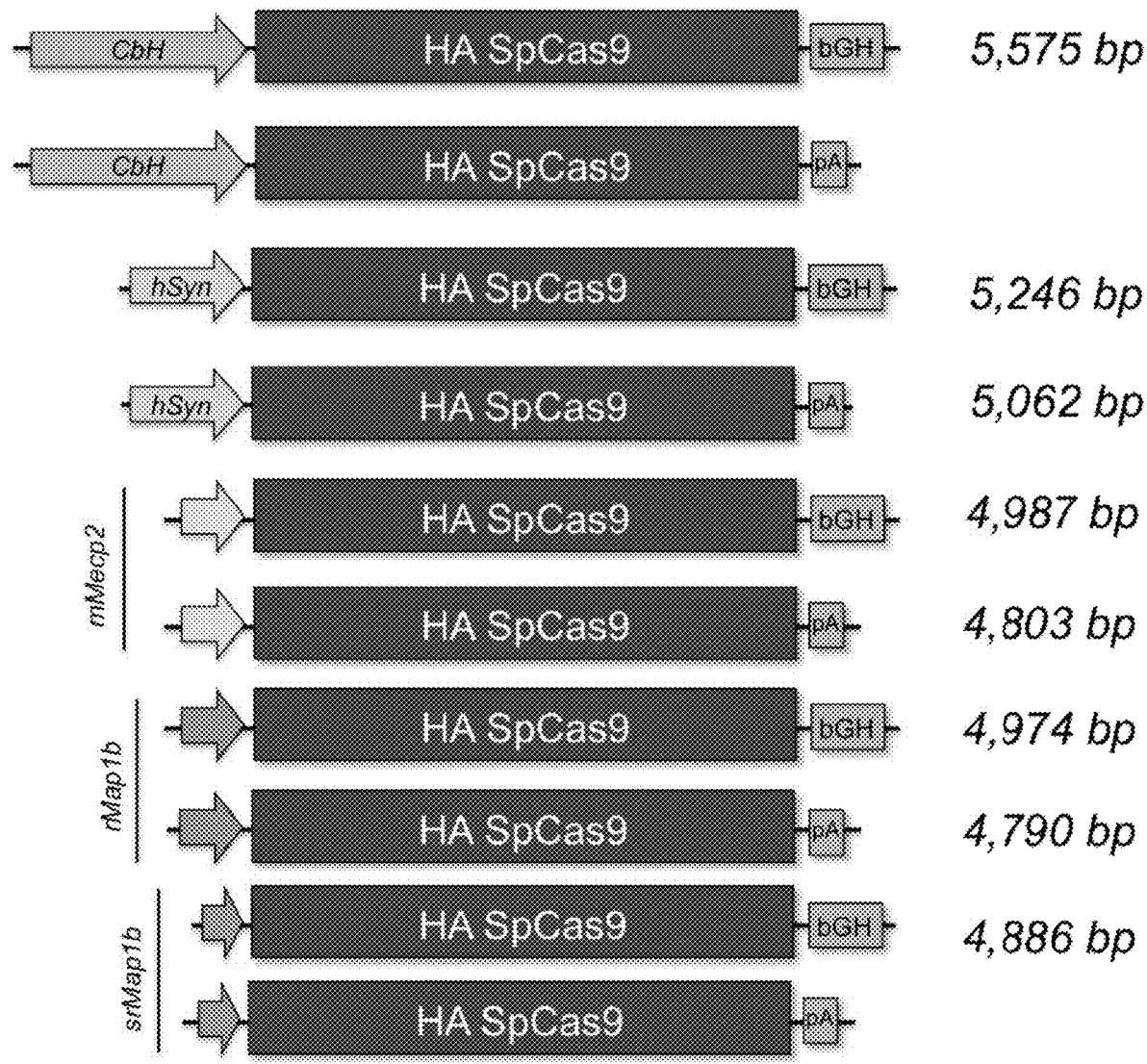
FIG. 19 shows schematic overview of short promoters and short polyA versions used for HA-SpCas9 expression in vivo. Sizes of the encoding region from L-ITR to R-ITR are shown on the right.
Figure 20:
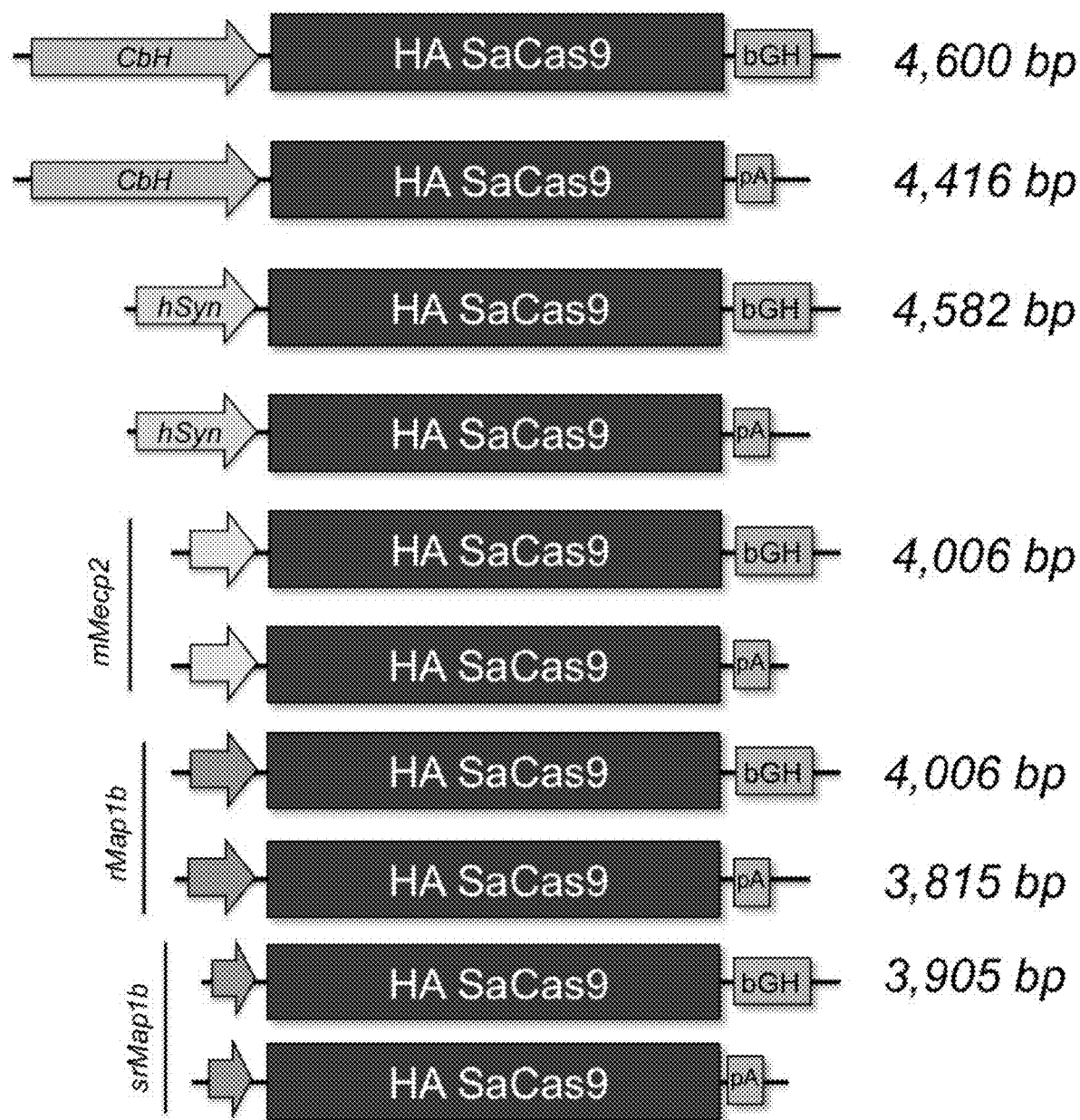
FIG. 20 shows schematic overview of short promoters and short polyA versions used for HA-SaCas9 expression in vivo. Sizes of the encoding region from L-ITR to R-ITR are shown on the right.
Figure 21:
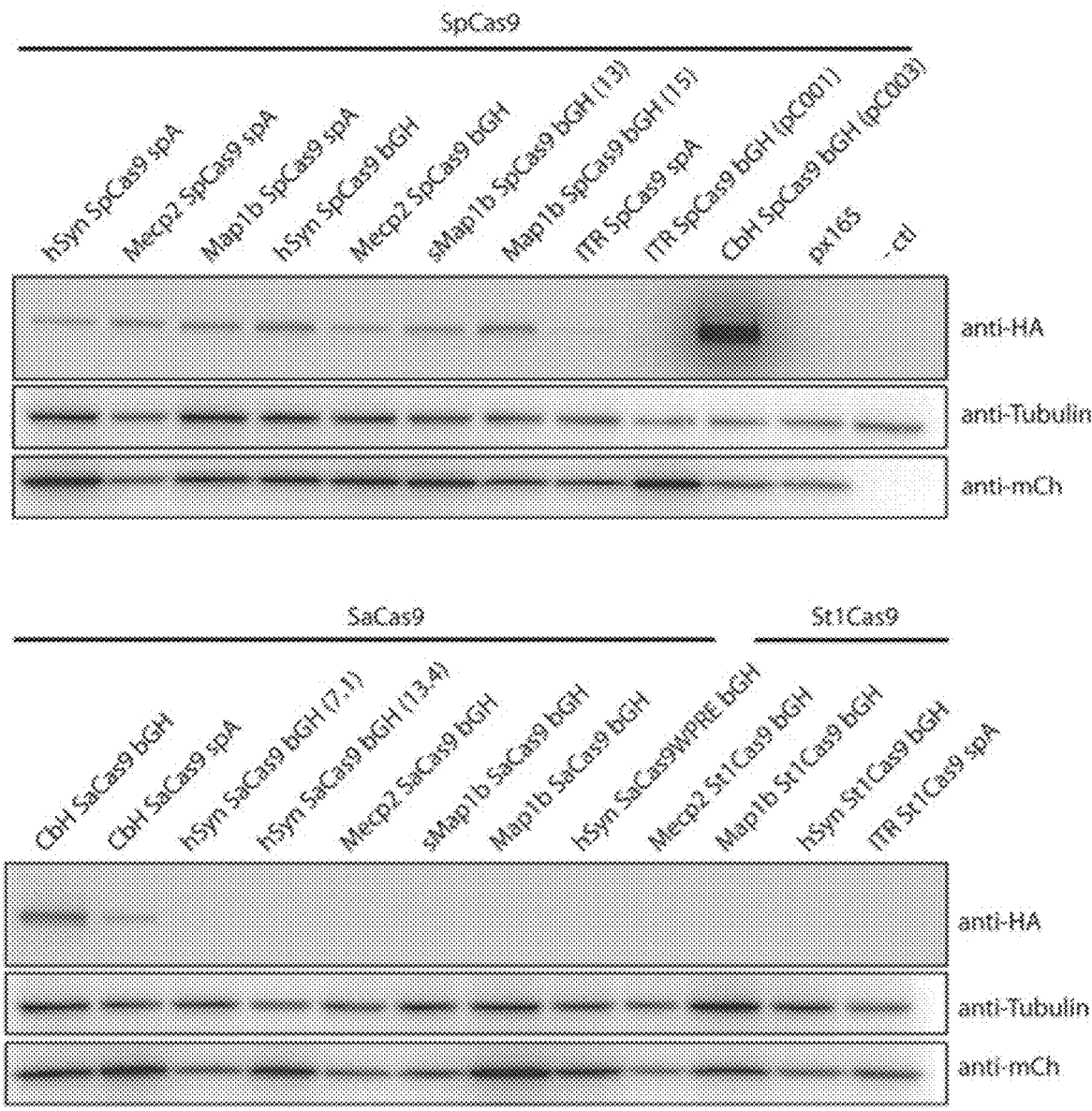
FIG. 21 shows expression of SpCas9 and SaCas9 in N2A cells. Representative Western blot of HA-tagged SpCas9 and SaCas9 versions under the control of different short promoters and with or short polyA (spA) sequences. Tubulin is loading control. mCherry (mCh) is a transfection control. Cells were harvested and further processed for Western blotting 48 h after transfection.
Figure 22:
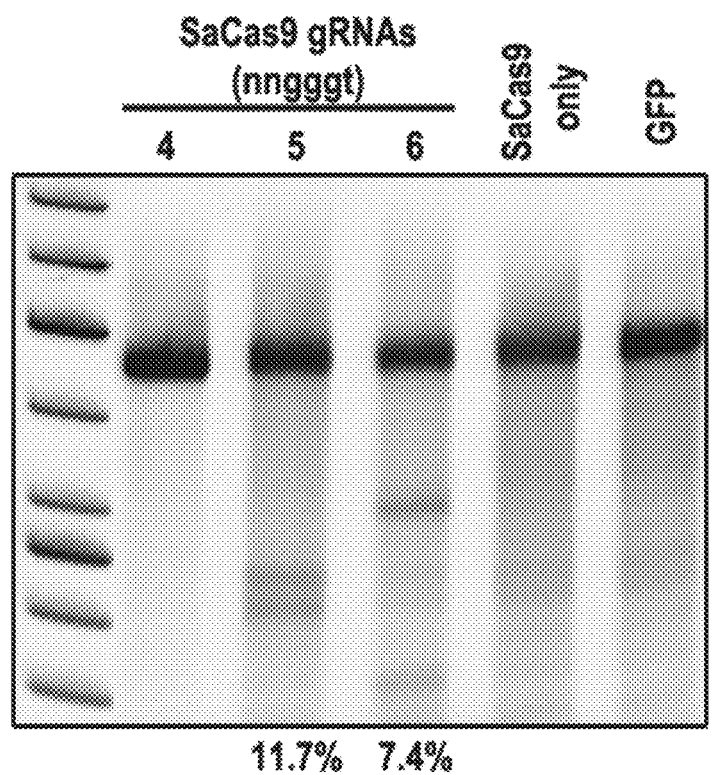
FIG. 22 shows screen for efficient SaCas9 mediated targeting of Tet3 gene locus. Surveyor assay on DNA from transfected N2A cells demonstrates efficient DNA cleavage by using different gRNAs with NNGGGT PUM sequence. GFP transfected cells and cells expressing only SaCas9 are controls.
Figure 23:
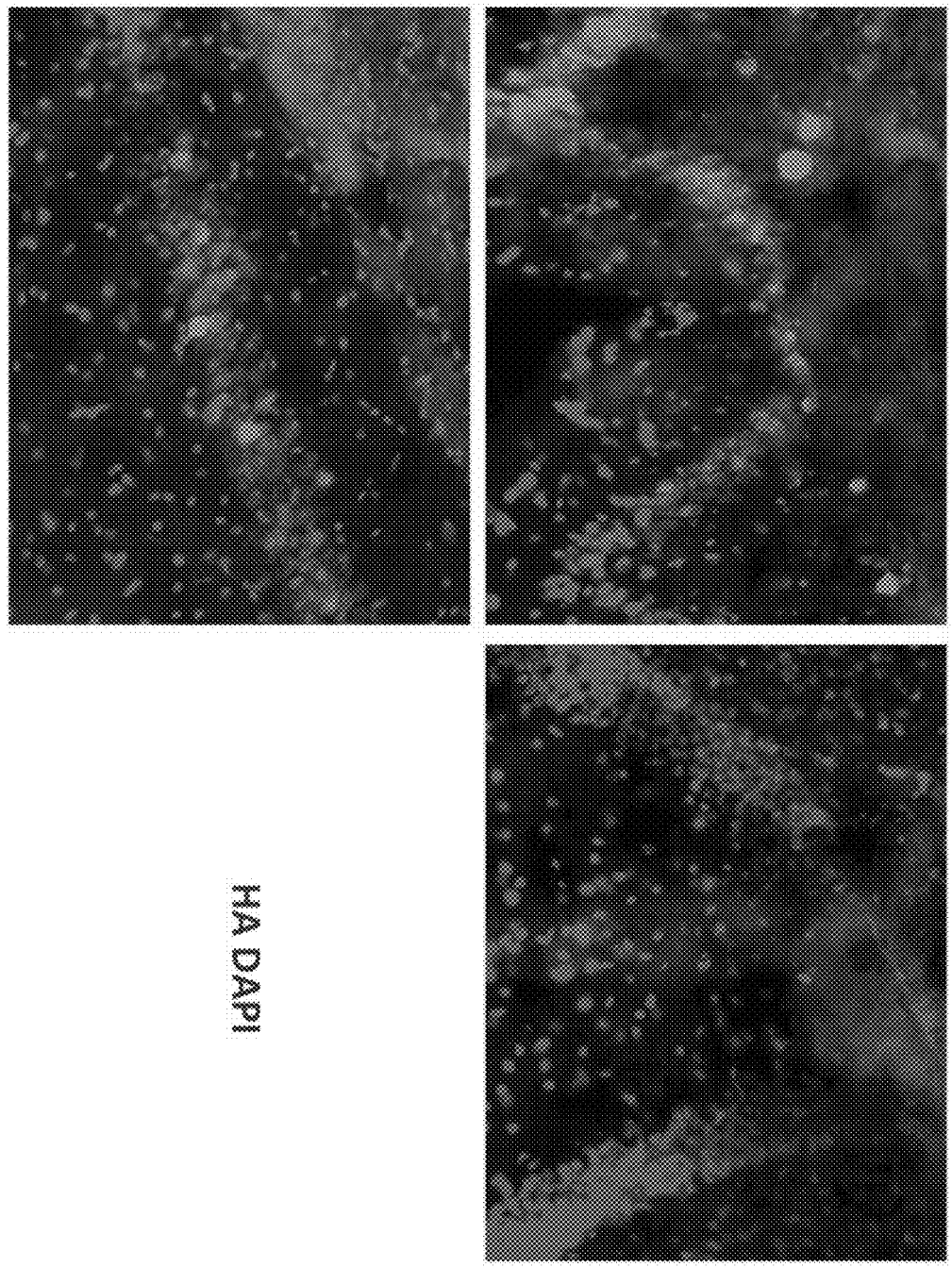
FIG. 23 shows expression of HA-SaCas9 in the mouse brain. Animals were injected into dentate gyri with virus driving expression of HA-SaCas9 under the control of human Synapsin promoter. Animals were sacrificed 2 weeks after surgery. HA tag was detected using rabbit monoclonal antibody C29F4 (Cell Signaling). Cell nuclei stained in blue with DAPI stain.

AAV delivery system despite its unique features has packing limitation—to successfully deliver expressing cassette in vivo it has to be in size<then 4.7 kb. To decrease the size of SpCas9 expressing cassette and facilitate delivery applicants tested several alteration: different promoters, shorter polyA signal and finally a smaller version of Cas9 from Staphylococcus aureus (SaCas9) (FIGS. 19 and 20). All tested promoters were previously tested and published to be active in neurons, including mouse Mecp2 (Gray et al., 2011), rat Map1b and truncated rat Map1b (Liu and Fischer, 1996). Alternative synthetic polyA sequence was previously shown to be functional as well (Levitt et al., 1989; Gray et al., 2011). All cloned constructs were expressed in N2a cells after transfection with Lipofectamine 2000, and tested with Western blotting method (FIG. 21).

Testing AAV Multiplex System in Primary Neurons

To confirm functionality of developed system in neurons, Applicants use primary neuronal cultures in vitro. Mouse cortical neurons was prepared according to the protocol published previously by Banker and Goslin (Banker and Goslin, 1988).

Neuronal cells are obtained from embryonic day 16. Embryos are extracted from the euthanized pregnant female and decapitated, and the heads are placed in ice-cold HBSS. The brains are then extracted from the skulls with forceps (#4 and #5) and transferred to another change of ice-cold HBSS. Further steps are performed with the aid of a stereoscopic microscope in a Petri dish filled with ice-cold HBSS and #5 forceps. The hemispheres are separated from each other and the brainstem and cleared of meninges. The hippocampi are then very carefully dissected and placed in a 15 ml conical tube filled with ice-cold HBSS. Cortices that remain after hippocampal dissection can be used for further cell isolation using an analogous protocol after removing the brain steam residuals and olfactory bulbs. Isolated hippocampi are washed three times with 10 ml ice-cold HBSS and dissociated by 15 min incubation with trypsin in HBSS (4 ml HBSS with the addition of 10 µl 2.5% trypsin per hippocampus) at 37° C. After trypsinization, the hippocampi are very carefully washed three times to remove any traces of trypsin with HBSS preheated to 37° C. and dissociated in warm HBSS. Applicants usually dissociate cells obtained from 10-12 embryos in 1 ml HBSS using 1 ml pipette tips and dilute dissociated cells up to 4 ml. Cells are plated at a density of 250 cells/mm2 and cultured at 37° C. and 5% CO2 for up to 3 week HBSS
435 ml H2O
50 ml 10× Hank's Balanced Salt Solution
16.5 ml 0.3M HEPES pH 7.3
5 ml penicillin-streptomycin solution
Filter (0.2 µm) and store 4° C.
Neuron Plating Medium (100 ml)
97 ml Neurobasal
2 ml B27 Supplement
1 ml penicillin-streptomycin solution
250 µl glutamine
125 µl glutamate Neurons are transduced with concentrated AAV1/2 virus or AAV1 virus from filtered medium of HEK293FT cells, between 4-7 days in culture and keep for at least one week in culture after transduction to allow for delivered gene expression.

AAV-Driven Expression of the System

Applicants confirmed expression of SpCas9 and SaCas9 in neuronal cultures after AAV delivery using Western blot method (FIG. 24). One week after transduction neurons were collected in NuPage SDS loading buffer with β-mercaptoethanol to desaturate proteins in 95° C. for 5 min. Samples were separated on SDS PAGE gel and transferred on PVDF membrane for WB protein detection. Cas9 proteins were detected with HA antibody.

Figure 32:
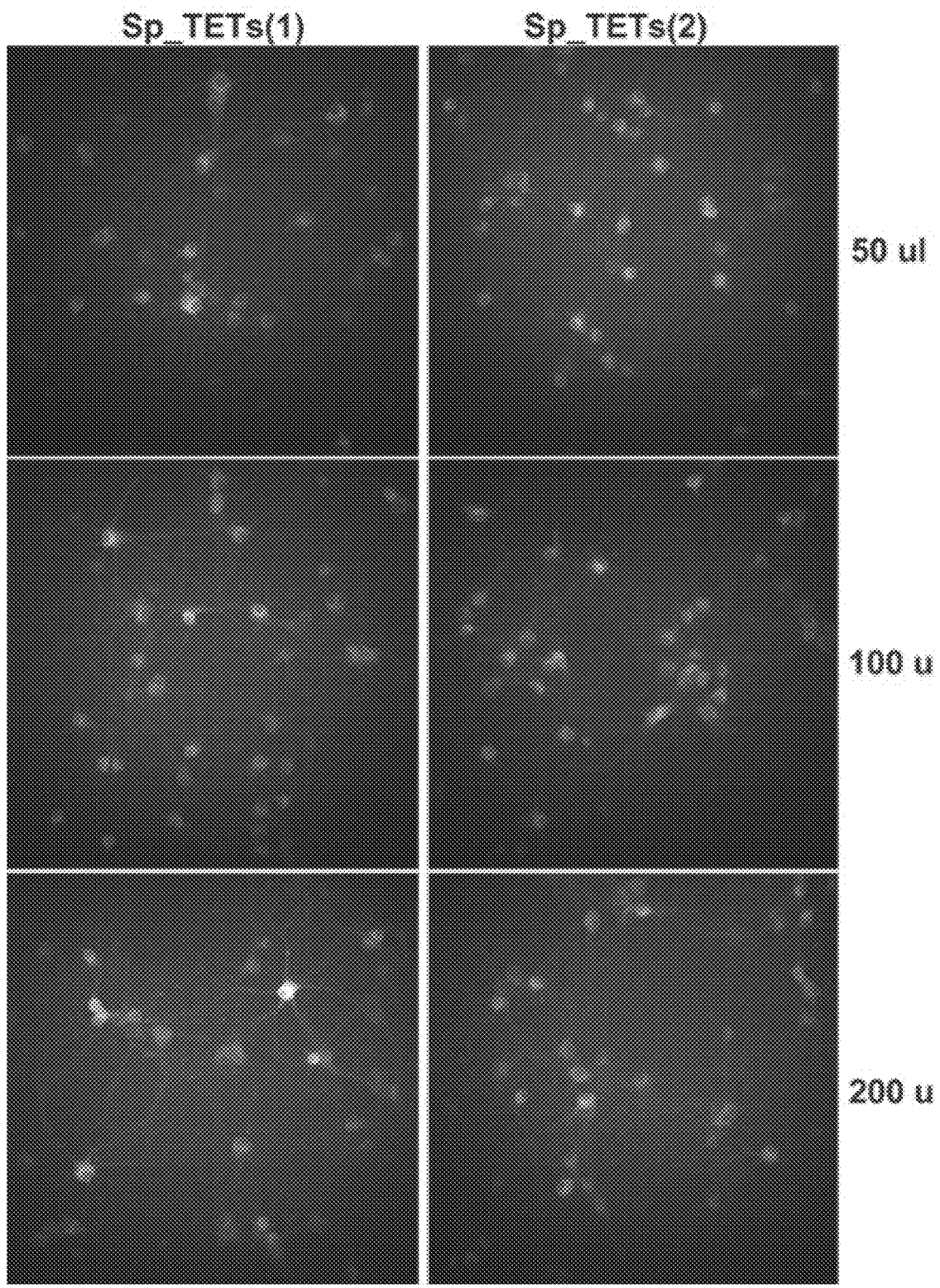
FIG. 32 shows GFP-KASH expression in cortical neurons in culture. Neurons were transduced with AAV1 virus carrying gRNA multiplex constructs targeting TET genes loci. The strongest signal localize around cells nuclei due to KASH domain localization.

Expression of Syn-GFP-kash from gRNA multiplex AAV was confirmed with fluorescent microscopy (FIG. 32).

Toxicity

Figure 25:
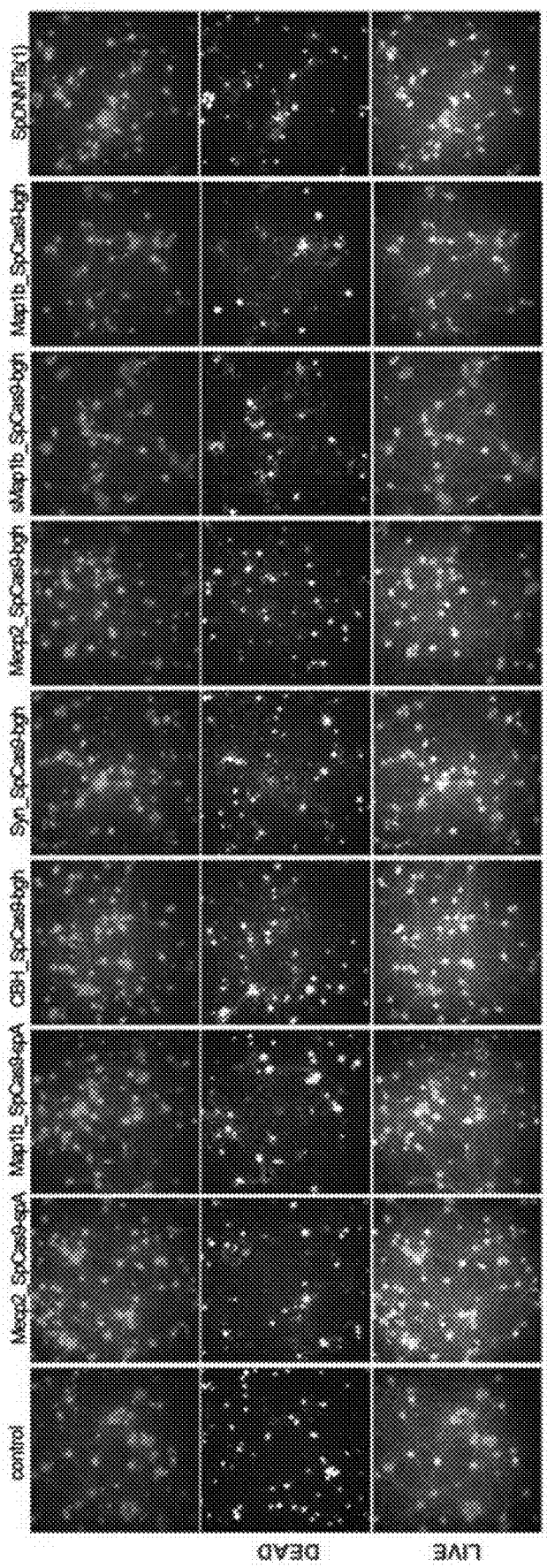
FIG. 25 shows LIVE/DEAD stain of primary cortical neurons 7 days after transduction with AAV1 particles carrying SpCas9 with different promoters and multiplex gRNAs constructs (example shown on the last panel for DNMTs). Neurons after AAV transduction were compared with control untransduced neurons. Red nuclei indicate permeabilized, dead cells (second line of panels). Live cells are marked in green color (third line of panels).
Figure 26:
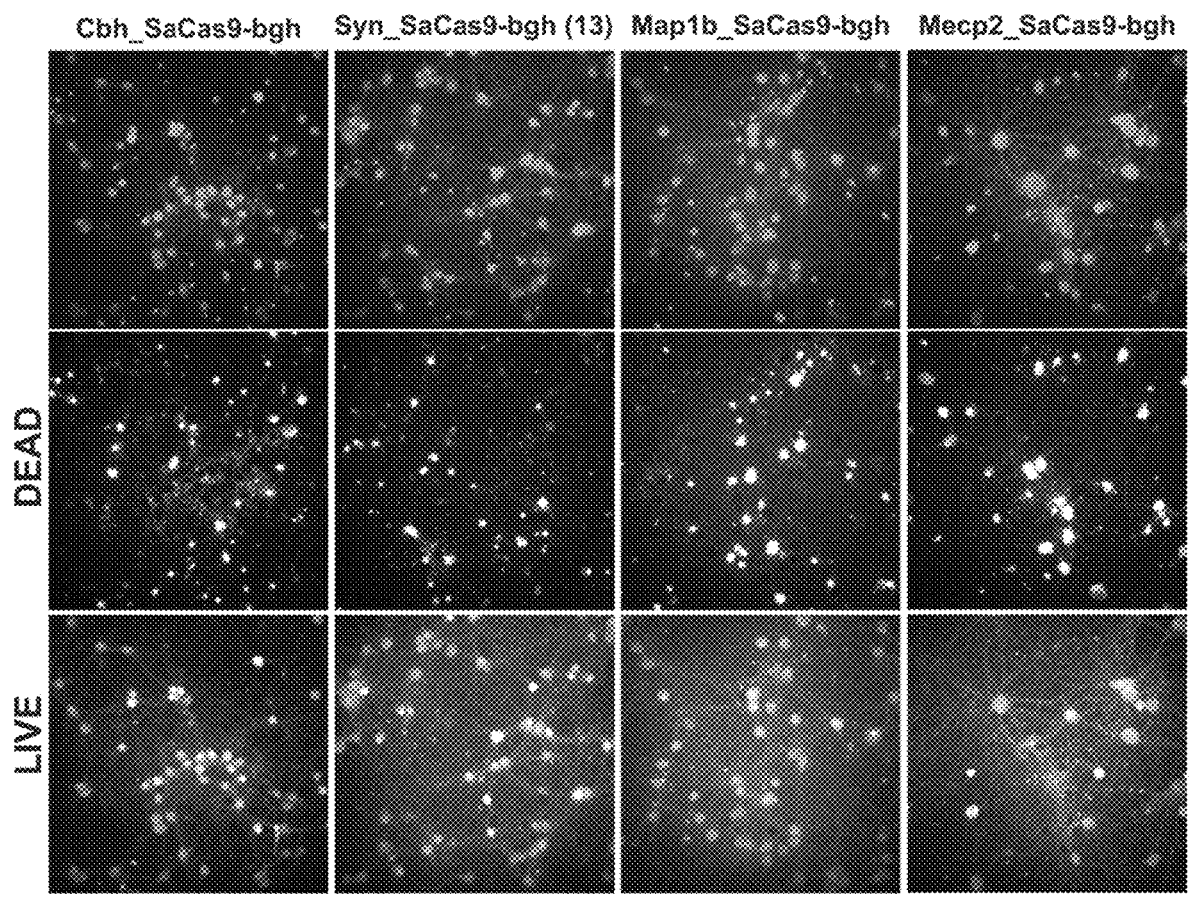
FIG. 26 shows LIVE/DEAD stain of primary cortical neurons 7 days after transduction with AAV1 particles carrying SaCas9 with different promoters. Red nuclei indicate permeabilized, dead cells (second line of panels). Live cells are marked in green color (third line of panels).
Figure 27:
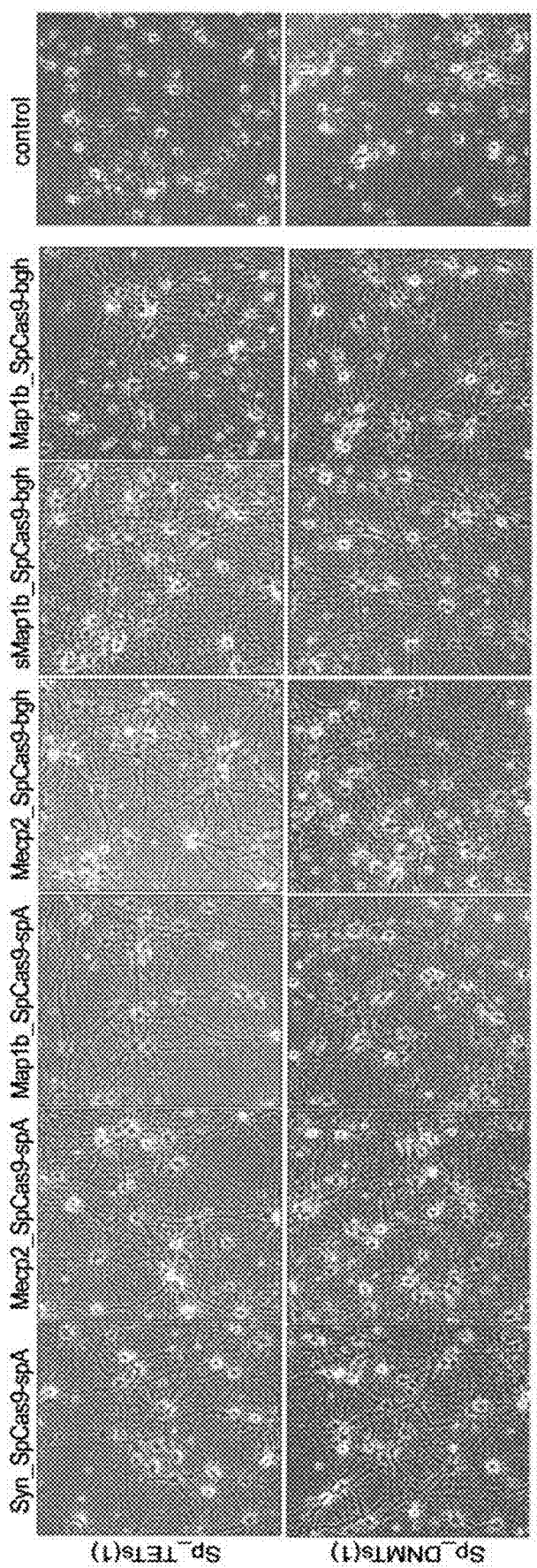
FIG. 27 shows comparison of morphology of neurons after transduction with AAV1 virus carrying SpCas9 and gRNA multiplexes for TETs and DNMTs genes loci. Neurons without transduction are shown as a control.
Figure 28:
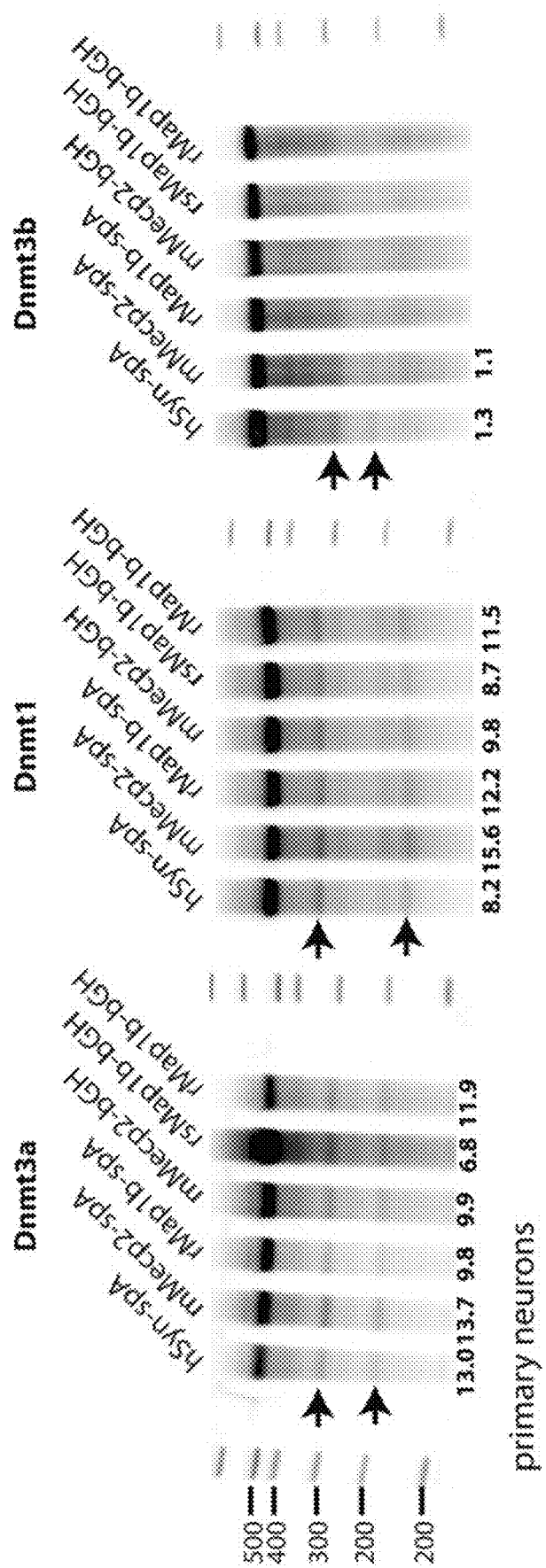
FIG. 28 shows verification of multiplex DNMT targeting vector #1 functionality using Surveyor assay in primary cortical neurons. Cells were co-transduced with the DNMT targeting vector #1 and the SpCas9 viruses with different promoters for testing SpCas9 mediated cleavage of DNMTs genes family loci.
Figure 29:
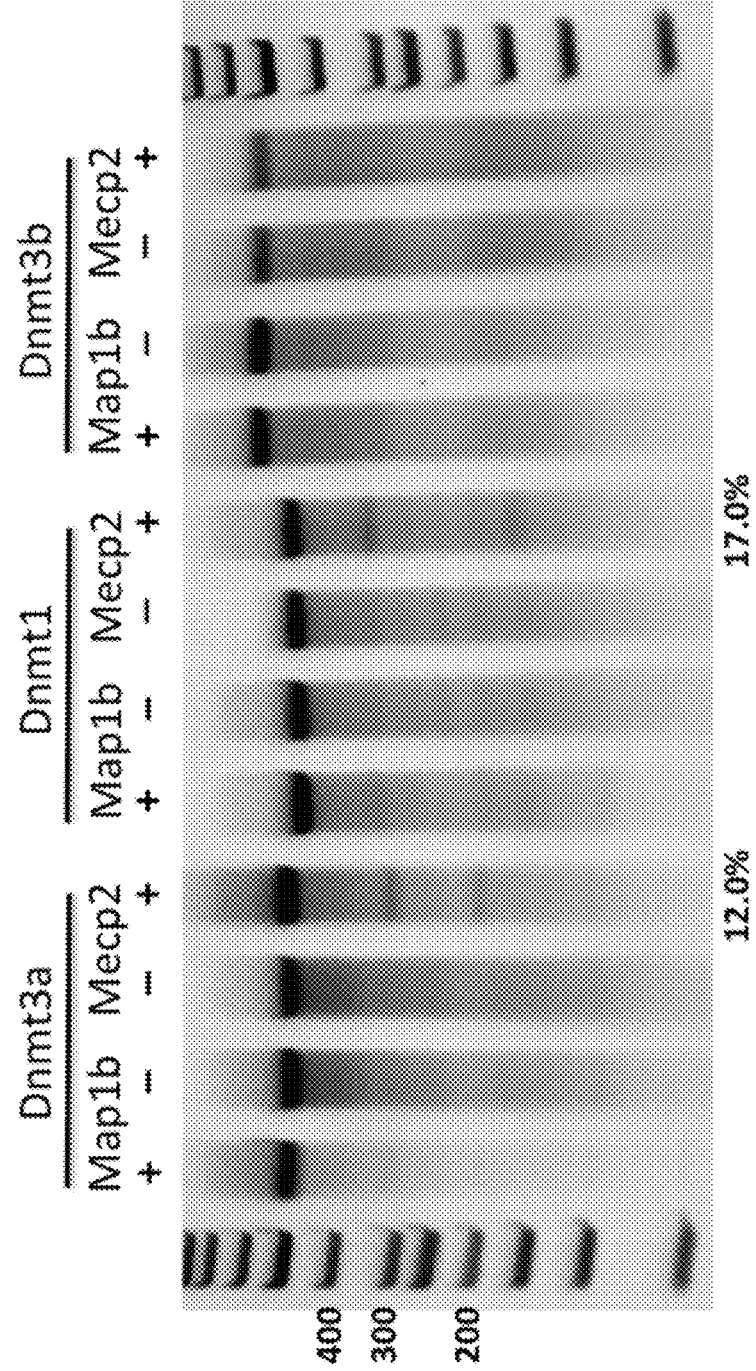
FIG. 29 shows in vivo efficiency of SpCas9 cleavage in the brain. Mice were injected with AAV1/2 virus carrying gRNA multiplex targeting DNMT family genes loci together with SpCas9 viruses under control of 2 different promoters: mouse Mecp2 and rat Map1b. Two weeks after injection brain tissue was extracted and nuclei were prepped and sorted using FACS, based on the GFP expression driven by Synapsin promoter from gRNA multiplex construct. After gDNA extraction Surveyor assay was run. + indicates GFP positive nuclei and − control, GFP-negative nuclei from the same animal. Numbers on the gel indicate assessed SpCas9 efficiency.
Figure 30:
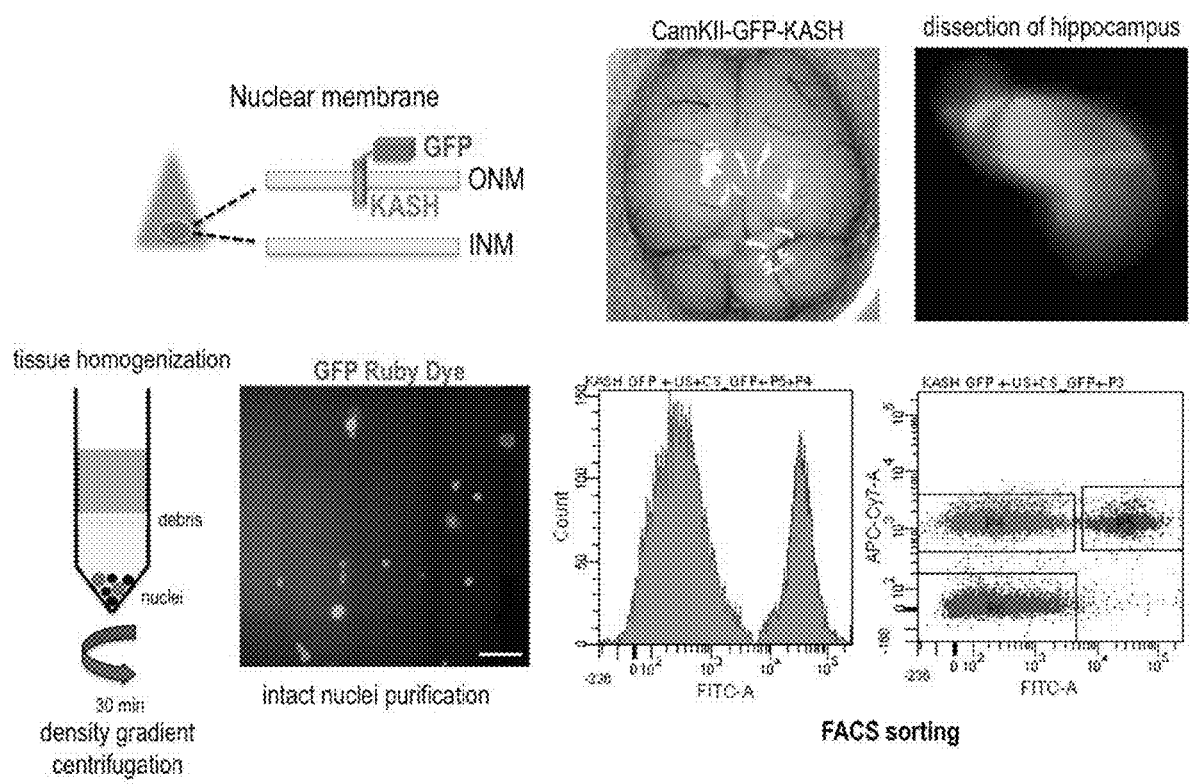
FIG. 30 shows purification of GFP-KASH labeled cell nuclei from hippocampal neurons. The outer nuclear membrane (ONM) of the cell nuclear membrane is tagged with a fusion of GFP and the KASH protein transmembrane domain. Strong GFP expression in the brain after one week of stereotactic surgery and AAV1/2 injection. Density gradient centrifugation step to purify cell nuclei from intact brain. Purified nuclei are shown. Chromatin stain by Vybrant® DyeCycle™ Ruby Stain is shown in red, GFP labeled nuclei are green. Representative FACS profile of GFP+ and GFP− cell nuclei (Magenta: Vybrant® DyeCycle™ Ruby Stain, Green: GFP).
Figure 31:
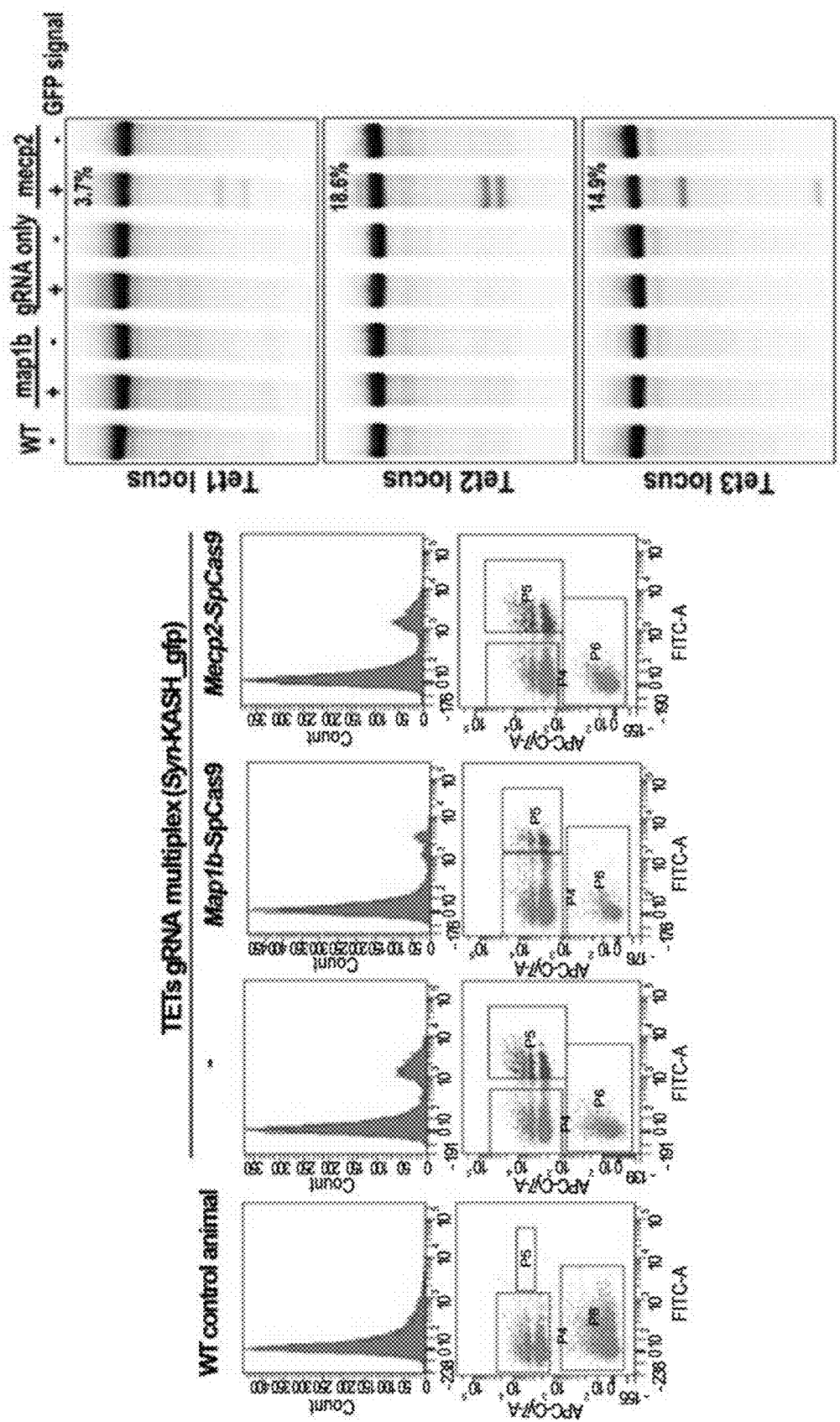
FIG. 31 shows efficiency of SpCas9 cleavage in the mouse brain. Mice were injected with AAV1/2 virus carrying gRNA multiplex targeting TET family genes loci together with SpCas9 viruses under control of 2 different promoters: mouse Mecp2 and rat Map1b. Three weeks after injection brain tissue was extracted, nuclei were prepped and sorted using FACS, based on the GFP expression driven by Synapsin promoter from gRNA multiplex construct. After gDNA extraction Surveyor assay was run. + indicates GFP positive nuclei and − control, GFP-negative nuclei from the same animal. Numbers on the gel indicate assessed SpCas9 efficiency.

To assess the toxicity of AAV with CRISPR system Applicants tested overall morphology of neurons one week after virus transduction (FIG. 27). Additionally, Applicants tested potential toxicity of designed system with the LIVE/DEAD® Cell Imaging Kit, which allows to distinguish live and dead cells in culture. It is based on the presence of intracellular esterase activity (as determined by the enzymatic conversion of the non-fluorescent calcein AM to the intensely green fluorescent calcein). On the other hand, the red, cell-impermeant component of the Kit enters cells with damaged membranes only and bind to DNA generating fluorescence in dead cells. Both fluorophores can be easily visualized in living cells with fluorescent microscopy. AAV-driven expression of Cas9 proteins and multiplex gRNA constructs in the primary cortical neurons was well tolerated and not toxic (FIGS. 25 and 26), what indicates that designed AAV system is suitable for in vivo tests.

Virus Production

Concentrated virus was produced according to the methods described in McClure et al., 2011. Supernatant virus production occurred in HEK293FT cells.

Brain Surgeries

For viral vector injections 10-15 week old male C57BL/6N mice were anesthetized with a Ketamine/Xylazine cocktail (Ketamine dose of 100 mg/kg and Xylazine dose of 10 mg/kg) by intraperitoneal injection. Intraperitonial administration of Buprenex was used as a pre-emptive analgesic (1 mg/kg). Animals were immobilized in a Kopf stereotaxic apparatus using intra-aural positioning studs and tooth bar to maintain an immobile skull. Using a hand-held drill, a hole (1-2 mm) at −3.0 mm posterior to Bregma and 3.5 mm lateral for injection in the CA1 region of the hippocampus was made. Using 30G World Precision Instrument syringe at a depth of 2.5 mm, the solution of AAV viral particles in a total volume of 1 ul was injected. The injection was monitored by a 'World Precision Instruments UltraMicroPump3' injection pump at a flow rate of 0.5 ul/min to prevent tissue damage. When the injection was complete, the injection needle was removed slowly, at a rate of 0.5 mm/min. After injection, the skin was sealed with 6-0 Ethilon sutures. Animals were postoperatively hydrated with 1 mL lactated Ringer's (subcutaneous) and housed in a temperature controlled (37° C.) environment until achieving an ambulatory recovery. 3 weeks after surgery animals were euthanized by deep anesthesia followed by tissue removal for nuclei sorting or with 4% paraformaldehyde perfusion for immunochemistry.

Sorting Nuclei and In Vivo Results

Applicants designed a method to specifically genetically tag the gRNA targeted neuronal cell nuclei with GFP for Fluorescent Activated Cell Sorting (FACS) of the labeled cell nuclei and downstream processing of DNA, RNA and nuclear proteins. To that purpose the applicants' multiplex targeting vector was designed to express both a fusion protein between GFP and the mouse nuclear membrane protein domain KASH (Starr D A, 2011, Current biology) and the 3 gRNAs to target specific gene loci of interest (FIG. 16). GFP-KASH was expressed under the control of the human Synapsin promoter to specifically label neurons. The amino acid of the fusion protein GFP-KASH was:

(SEQ ID NO: 195)
MVSKGEELFTGVVPILVELDGDVNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDFKEDGNILGHKLEYNYNSHN

VYIMADKQKNGIKVNFKIRHNIEDGSVQLADHYQQNTPIGDGPVLLPDNH

YLSTQSALSKDPNEKRDHMVLLEFVTAAGITLGMDELYKSGLRSREEEEE

TDSRMPHLDSPGSSQPRRSFLSRVIRAALPLQLLLLLLLLLACLLPASED

DYSCTQANNFARSFYPMLRYTNGPPPT

One week after AAV1/2 mediated delivery into the brain a robust expression of GFP-KASH was observed. For FACS and downstream processing of labeled nuclei, the hippocampi were dissected 3 weeks after surgery and processed for cell nuclei purification using a gradient centrifugation step. For that purpose the tissue was homogenized in 320 mM Sucrose, 5 mM CaCl, 3 mM Mg(Ac)2, 10 mM Tris pH 7.8, 0.1 mM EDTA, 0.1% NP40, 0.1 mM Phenylmethanesulfonyl fluoride (PMSF), 1 mM β-mercaptoethanol using 2 ml Dounce homogenizer (Sigma) The homogenisate was centrifuged on a 25% to 29% Optiprep® gradient according to the manufacture's protocol for 30 min at 3.500 rpm at 4° C. The nuclear pellet was resuspended in 340 mM Sucrose, 2 mM MgCl2, 25 mM KCl, 65 mM glycerophosphate, 5% glycerol, 0.1 mM PMSF, 1 mM β-mercaptoethanol and Vybrant® DyeCycle™ Ruby Stain (Life technologies) was added to label cell nuclei (offers near-infrared emission for DNA). The labeled and purified nuclei were sorted by FACS using an Aria Flu-act-cell sorter and BDFACS Diva software. The sorted GFP+ and GFP− nuclei were finally used to purify genomic DNA using DNAeasy Blood & Tissue Kit (Qiagen) for Surveyor assay analysis of the targeted genomic regions. The same approach can be easily used to purify nuclear RNA or protein from targeted cells for downstream processing. Due to the 2-vector system (FIG. 16) the applicants using in this approach efficient Cas9 mediated DNA cleavage was expected to occur only in a small subset of cells in the brain (cells which were co-infected with both the multiplex targeting vector and the Cas9 encoding vector). The method described here enables the applicants to specifically purify DNA, RNA and nuclear proteins from the cell population expressing the 3 gRNAs of interest and therefore are supposed to undergo Cas9 mediated DNA cleavage. By using this method the applicants were able to visualize efficient DNA cleavage in vivo occurring only in a small subset of cells.

Essentially, what Applicants have shown here is targeted in vivo cleavage. Furthermore, Applicants used a multiple approach, with several different sequences targeted at the same time, but independently. Presented system can be applied for studying brain pathologic conditions (gene knock out, e.g. Parkinson disease) and also open a field for further development of genome editing tools in the brain. By replacing nuclease activity with gene transcription regulators or epigenetic regulators it will be possible to answer whole spectrum of scientific question about role of gene regulation and epigenetic changes in the brain in not only in the pathologic conditions but also in physiological process as learning and memory formation. Finally, presented technology can be applied in more complex mammalian system as primates, what allows to overcome current technology limitations.

Example 28: Model Data

Several disease models have been specifically investigated. These include de novo autism risk genes CHD8, KATNAL2, and SCN2A; and the syndromic autism (Angelman Syndrome) gene UBE3A. These genes and resulting autism models are of course preferred, but show that the invention may be applied to any gene and therefore any model is possible.

Applicants have made these cells lines using Cas9 nuclease in human embryonic stem cells (hESCs). The lines were created by transient transfection of hESCs with Cbh-Cas9-2A-EGFP and pU6-sgRNA. Two sgRNAs are designed for each gene targeting most often the same exons in which patient nonsense (knock-out) mutations have been recently described from whole exome sequencing studies of autistic patients. The Cas9-2A-EGFP and pU6 plasmids were created specifically for this project.

Example 29: AAV Production System or Protocol

An AAV production system or protocol that was developed for, and works particularly well with, high through put screening uses is provided herein, but it has broader applicability in the present invention as well. Manipulating endogenous gene expression presents various challenges, as the rate of expression depends on many factors, including regulatory elements, mRNA processing, and transcript stability. To overcome this challenge, Applicants developed an adeno-associated virus (AAV)-based vector for the delivery. AAV has an ssDNA-based genome and is therefore less susceptible to recombination.

AAV1/2 (serotype AAV1/2, i.e., hybrid or mosaic AAV1/AAV2 capsid AAV) heparin purified concentrated virus protocol Media: D10+HEPES
500 ml bottle DMEM high glucose+Glutamax (GIBCO)
50 ml Hyclone FBS (heat-inactivated) (Thermo Fischer)
5.5 ml HEPES solution (1M, GIBCO)
Cells: low passage HEK293FT (passage<10 at time of virus production, thaw new cells of passage 2-4 for virus production, grow up for 3-5 passages)
Transfection Reagent: Polyethylenimine (PEI) "Max"
Dissolve 50 mg PEI "Max" in 50 ml sterile Ultrapure H2O
Adjust pH to 7.1
Filter with 0.22 um fliptop filter
Seal tube and wrap with parafilm
Freeze aliquots at −20° C. (for storage, can also be used immediately)
Cell Culture
Culture low passage HEK293FT in D10+HEPES
Passage everyday between 1:2 and 1:2.5
Advantageously do not allow cells to reach more than 85% confluency
For T75
Warm 10 ml HBSS (—Mg2+, —Ca2+, GIBCO)+1 ml TrypLE Express (GIBCO) per flask to 37° C. (Waterbath)
Aspirate media fully
Add 10 ml warm HBSS gently (to wash out media completely)
Add 1 ml TrypLE per Flask
Place flask in incubator (37° C.) for 1 min
Rock flask to detach cells
Add 9 ml D10+HEPES media (37° C.)
Pipette up and down 5 times to generate single cell suspension
Split at 1:2-1:2.5 (12 ml media for T75) ratio (if cells are growing more slowly, discard and thaw a new batch, they are not in optimal growth)
transfer to T225 as soon as enough cells are present (for ease of handling large amounts of cells)
AAV Production (5*15 cm Dish Scale Per Construct):
Plate 10 million cells in 21.5 ml media into a 15 cm dish
Incubate for 18-22 hours at 37° C.
Transfection is ideal at 80% confluence
Per Plate
Prewarm 22 ml media (D10+HEPES)
Prepare Tube with DNA Mixture (Use Endofree Maxiprep DNA):
5.2 ug vector of interest plasmid
4.35 ug AAV 1 serotype plasmid
4.35 ug AAV 2 serotype plasmid
10.4 ug pDF6 plasmid (adenovirus helper genes) □ Vortex to mix
Add 434 uL DMEM (no serum!)
Add 130 ul PEI solution
Vortex 5-10 seconds
Add DNA/DMEM/PEI mixture to prewarmed media
Vortex briefly to mix
Replace media in 15 cm dish with DNA/DMEM/PEI mixture
Return to 37° C. incubator
Incubate 48h before harvesting (make sure medium isn't turning too acidic)
Virus Harvest:
1. aspirate media carefully from 15 cm dish dishes (advantageously do not dislodge cells)
2. Add 25 ml RT DPBS (Invitrogen) to each plate and gently remove cells with a cell scraper. Collect suspension in 50 ml tubes.
3. Pellet cells at 800×g for 10 minutes.
4. Discard supernatant
Pause Point: Freeze Cell Pellet at −80 C if Desired
5. resuspend pellet in 150 mM NaCl, 20 mM Tris pH 8.0, use 10 ml per tissue culture plate.
6. Prepare a fresh solution of 10% sodium deoxycholate in dH2O. Add 1.25 ml of this per tissue culture plate for a final concentration of 0.5%. Add benzonase nuclease to a final concentration of 50 units per ml. Mix tube thoroughly.
7. Incubate at 37° C. for 1 hour (Waterbath).
8. Remove cellular debris by centrifuging at 3000×g for 15 mins. Transfer to fresh 50 ml tube and ensure all cell debris has been removed to prevent blocking of heparin columns.
Heparin Column Purification of AAV1/2:
1. Set up HiTrap heparin columns using a peristaltic pump so that solutions flow through the column at 1 ml per minute. It is important to ensure no air bubbles are introduced into the heparin column.
2. Equilibrate the column with 10 ml 150 mM NaCl, 20 mM Tris, pH 8.0 using the peristaltic pump.
3. Binding of virus: Apply 50 ml virus solution to column and allow to flow through.
4. Wash step 1: column with 20 ml 100 mM NaCl, 20 mM Tris, pH 8.0. (using the peristaltic pump)

5. Wash step 2: Using a 3 ml or 5 ml syringe continue to wash the column with 1 ml 200 mM NaCl, 20 mM Tris, pH 8.0, followed by 1 ml 300 mM NaCl, 20 mM Tris, pH 8.0. Discard the flow-through.
(prepare the syringes with different buffers during the 50 min flow through of virus solution above)
6. Elution Using 5 ml syringes and gentle pressure (flow rate of <1 ml/min) elute the virus from the column by applying:
1.5 ml 400 mM NaCl, 20 mM Tris, pH 8.0
3.0 ml 450 mM NaCl, 20 mM Tris, pH 8.0
1.5 ml 500 mM NaCl, 20 mM Tris, pH 8.0
Collect these in a 15 ml centrifuge tube.

Concentration of AAV1/2:
1. Concentration step 1: Concentrate the eluted virus using Amicon ultra 15 ml centrifugal filter units with a 100,000 molecular weight cutoff. Load column eluate into the concentrator and centrifuge at 2000×g for 2 minutes (at room temperature. Check concentrated volume—it should be approximately 500 µl. If necessary, centrifuge in 1 min intervals until correct volume is reached.
2. buffer exchange: Add 1 ml sterile DPBS to filter unit, centrifuge in 1 min intervals until correct volume (500 ul) is reached.
3. Concentration step 2: Add 500 ul concentrate to an Amicon Ultra 0.5 ml 100K filter unit. Centrifuge at 6000g for 2 min. Check concentrated volume—it should be approximately 100 µl. If necessary, centrifuge in 1 min intervals until correct volume is reached.
4. Recovery: Invert filter insert and insert into fresh collection tube. Centrifuge at 1000g for 2 min.
Aliquot and freeze at −80° C.
1 ul is typically required per injection site, small aliquots (e.g. 5 ul) are therefore recommended (avoid freeze-thaw of virus).
determine DNaseI-resistant GC particle titer using qPCR (see separate protocol)

Materials
Amicon Ultra, 0.5 ml, 100K; MILLIPORE; UFC510024
Amicon Ultra, 15 ml, 100K; MILLIPORE; UFC910024
Benzonase nuclease; Sigma-Aldrich, E1014
HiTrap Heparin cartridge; Sigma-Aldrich; 54836
Sodium deoxycholate; Sigma-Aldrich; D5670

AAV1 Supernatant Production Protocol
Media: D10+HEPES
500 ml bottle DMEM high glucose+Glutamax (Invitrogen)
50 ml Hyclone FBS (heat-inactivated) (Thermo Fischer)
5.5 ml HEPES solution (1M, GIBCO)
Cells: low passage HEK293FT (passage<10 at time of virus production)
Thaw new cells of passage 2-4 for virus production, grow up for 2-5 passages
Transfection reagent: Polyethylenimine (PEI) "Max"
Dissolve 50 mg PEI "Max" in 50 ml sterile Ultrapure H2O
Adjust pH to 7.1
Filter with 0.22 um fliptop filter
Seal tube and wrap with parafilm
Freeze aliquots at −20° C. (for storage, can also be used immediately)
Cell Culture
Culture low passage HEK293FT in D10+HEPES Passage everyday between 1:2 and 1:2.5
Advantageously do let cells reach more than 85% confluency
For T75
Warm 10 ml HBSS (—Mg2+, —Ca2+, GIBCO)+1 ml TrypLE Express (GIBCO) per flask to 37° C. (Waterbath)
Aspirate media fully
Add 10 ml warm HBSS gently (to wash out media completely)
Add 1 ml TrypLE per Flask
Place flask in incubator (37° C.) for 1 min
Rock flask to detach cells
Add 9 ml D10+HEPES media (37° C.)
Pipette up and down 5 times to generate single cell suspension
Split at 1:2-1:2.5 (12 ml media for T75) ratio (if cells are growing more slowly, discard and thaw a new batch, they are not in optimal growth)
transfer to T225 as soon as enough cells are present (for ease of handling large amounts of cells)
AAV production (single 15 cm dish scale)
Plate 10 million cells in 21.5 ml media into a 15 cm dish
Incubate for 18-22 hours at 37° C.
Transfection is ideal at 80% confluence per plate
Prewarm 22 ml media (D10+HEPES)
Prepare tube with DNA mixture (use endofree maxiprep DNA):
5.2 ug vector of interest plasmid
8.7 ug AAV 1 serotype plasmid
10.4 ug DF6 plasmid (adenovirus helper genes)
Vortex to mix
Add 434 uL DMEM (no serum!) Add 130 ul PEI solution
Vortex 5-10 seconds
Add DNA/DMEM/PEI mixture to prewarmed media
Vortex briefly to mix
Replace media in 15 cm dish with DNA/DMEM/PEI mixture
Return to 37° C. incubator
Incubate 48h before harvesting (advantageously monitor to ensure medium is not turning too acidic)
Virus Harvest:
Remove supernatant from 15 cm dish
Filter with 0.45 um filter (low protein binding) Aliquot and freeze at −80° C.
Transduction (primary neuron cultures in 24-well format, 5 DIV)
Replace complete neurobasal media in each well of neurons to be transduced with fresh
neurobasal (usually 400 ul out of 500 ul per well is replaced)
Thaw AAV supernatant in 37° C. waterbath
Let equilibrate in incubator for 30 min
Add 250 ul AAV supernatant to each well
Incubate 24h at 37° C.
Remove media/supernatant and replace with fresh complete neurobasal
Expression starts to be visible after 48h, saturates around 6-7 Days Post Infection
Constructs for pAAV plasmid with GOI should not exceed 4.8 kb including both ITRS.

Example of a human codon optimized sequence (i.e. being optimized for expression in humans) sequence: SaCas9 is provided below:

(SEQ ID NO: 196)
ACCGGTGCCACCATGTACCCATACGATGTTCCAGATTACGC

TTCGCCGAAGAAAAGCGCAAGGTCGAAGCGTCCATGAAAAGGAACTACA

TTCTGGGGCTGGACATCGGGATTACAAGCGTGGGGTATGGGATTATTGAC

TATGAAACAAGGGACGTGATCGACGCAGGCGTCAGACTGTTCAAGGAGGC

CAACGTGGAAAACAATGAGGGACGGAGAAGCAAGAGGGGAGCCAGGCGCC

-continued

```
TGAAACGACGGAGAAGGCACAGAATCCAGAGGGTGAAGAAACTGCTGTTC
GATTACAACCTGCTGACCGACCATTCTGAGCTGAGTGGAATTAATCCTTA
TGAAGCCAGGGTGAAAGGCCTGAGTCAGAAGCTGTCAGAGGAAGAGTTTT
CCGCAGCTCTGCTGCACCTGGCTAAGCGCCGAGGAGTGCATAACGTCAAT
GAGGTGGAAGAGGACACCGGCAACGAGCTGTCTACAAAGGAACAGATCTC
ACGCAATAGCAAAGCTCTGGAAGAGAAGTATGTCGCAGAGCTGCAGCTGG
AACGGCTGAAGAAAGATGGCGAGGTGAGAGGGTCAATTAATAGGTTCAAG
ACAAGCGACTACGTCAAAGAAGCCAAGCAGCTGCTGAAAGTGCAGAAGGC
TTACCACCAGCTGGATCAGAGCTTCATCGATACTTATATCGACCTGCTGG
AGACTCGGAGAACCTACTATGAGGGACCAGGAGAAGGGAGCCCCTTCGGA
TGGAAAGACATCAAGGAATGGTACGAGATGCTGATGGGACATTGCACCTA
TTTTCCAGAAGAGCTGAGAAGCGTCAAGTACGCTTATAACGCAGATCTGT
ACAACGCCCTGAATGACCTGAACAACCTGGTCATCACCAGGGATGAAAAC
GAGAAACTGGAATACTATGAGAAGTTCCAGATCATCGAAAACGTGTTTAA
GCAGAAGAAAAAGCCTACACTGAAACAGATTGCTAAGGAGATCCTGGTCA
ACGAAGAGGACATCAAGGGCTACCGGGTGACAAGCACTGGAAAACCAGAG
TTCACCAATCTGAAAGTGTATCACGATATTAAGGACATCACAGCACGGAA
AGAAATCATTGAGAACGCCGAACTGCTGGATCAGATTGCTAAGATCCTGA
CTATCTACCAGAGCTCCGAGGACATCCAGGAAGAGCTGACTAACCTGAAC
AGCGAGCTGACCCAGGAAGAGATCGAACAGATTAGTAATCTGAAGGGGTA
CACCGGAACACACAACCTGTCCCTGAAAGCTATCAATCTGATTCTGGATG
AGCTGTGGCATACAAACGACAATCAGATTGCAATCTTTAACCGGCTGAAG
CTGGTCCCAAAAAAGGTGGACCTGAGTCAGCAGAAAGAGATCCCAACCAC
ACTGGTGGACGATTTCATTCTGTCACCCGTGGTCAAGCGGAGCTTCATCC
AGAGCATCAAAGTGATCAACGCCATCATCAAGGAATACGGCCTGCCCAAT
GATATCATTATCGAGCTGGCTAGGGAGAAGAACAGCAAGGACGCACAGAA
GATGATCAATGAGATGCAGAAACGAAACCGGCAGACCAATGAACGCATTG
AAGAGATTATCCGAACTACCGGGAAAGAGAACGCAAAGTACCTGATTGAA
AAAATCAAGCTGCACGATATGCAGGAGGGAAAGTGTCTGTATTCTCTGGA
GGCCATCCCCCTGGAGGACCTGCTGAACAATCCATTCAACTACGAGGTCG
ATCATATTATCCCCAGAAGCGTGTCCTTCGACAATTCCTTTAACAACAAG
GTGCTGGTCAAGCAGGAAGAGAACTCTAAAAAGGGCAATAGGACTCCTTT
CCAGTACCTGTCTAGTTCAGATTCCAAGATCTCTTACGAAAACCTTTAAAA
AGCACATTCTGAATCTGGCCAAAGGAAAGGGCCGCATCAGCAAGACCAAA
AAGGAGTACCTGCTGGAAGAGCGGGACATCAACAGATTCTCCGTCCAGAA
GGATTTTATTAACCGGAATCTGGTGGACACAAGATACGCTACTCGCGGCC
TGATGAATCTGCTGCGATCCTATTTCCGGGTGAACAATCTGGATGTGAAA
GTCAAGTCCATCAACGGCGGGTTCACATCTTTTCTGAGGCGCAAATGGAA
GTTTAAAAAGGAGCGCAACAAAGGGTACAAGCACCATGCCGAAGATGCTC
TGATTATCGCAAATGCCGACTTCATCTTTAAGGAGTGGAAAAAGCTGGAC
AAAGCCAAGAAAGTGATGGAGAACCAGATGTTCGAAGAGAAGCAGGCCGA
ATCTATGCCCGAAATCGAGACAGAACAGGAGTACAAGGAGATTTTCATCA
CTCCTCACCAGATCAAGCATATCAAGGATTTCAAGGACTACAAGTACTCT
CACCGGGTGGATAAAAAGCCCAACAGAGAGCTGATCAATGACACCCTGTA
TAGTACAAGAAAAGACGATAAGGGGAATACCCTGATTGTGAACAATCTGA
ACGGACTGTACGACAAAGATAATGACAAGCTGAAAAAGCTGATCAACAAA
AGTCCCGAGAAGCTGCTGATGTACCACCATGATCCTCAGACATATCAGAA
ACTGAAGCTGATTATGGAGCAGTACGGCGACGAGAAGAACCCACTGTATA
AGTACTATGAAGAGACTGGGAACTACCTGACCAAGTATAGCAAAAAGGAT
AATGGCCCCGTGATCAAGAAGATCAAGTACTATGGGAACAAGCTGAATGC
CCATCTGGACATCACAGACGATTACCCTAACAGTCGCAACAAGGTGGTCA
AGCTGTCACTGAAGCCATACAGATTCGATGTCTATCTGGACAACGGCGTG
TATAAATTTGTGACTGTCAAGAATCTGGATGTCATCAAAAAGGAGAACTA
CTATGAAGTGAATAGCAAGTGCTACGAAGAGGCTAAAAAGCTGAAAAAGA
TTAGCAACCAGGCAGAGTTCATCGCCTCCTTTTACAACAACGACCTGATT
AAGATCAATGGCGAACTGTATAGGGTCATCGGGGTGAACAATGATCTGCT
GAACCGCATTGAAGTGAATATGATTGACATCACTTACCGAGAGTATCTGG
AAAACATGAATGATAAGCGCCCCCCTCGAATTATCAAAACAATTGCCTCT
AAGACTCAGAGTATCAAAAAGTACTCAACCGACATTCTGGGAAACCTGTA
TGAGGTGAAGAGCAAAAAGCACCCTCAGATTATCAAAAAGGGCTAAGAAT
TC
```

Example 30: Minimizing Off-Target Cleavage
Using Cas9 Nickase and Two Guide RNAs Cas9 is a RNA-guided DNA nuclease that may be targeted to specific locations in the genome with the help of a 20 bp RNA guide. However the guide sequence may tolerate some mismatches between the guide sequence and the DNA-target sequence. The flexibility is undesirable due to the potential for off-target cleavage, when the guide RNA targets Cas9 to a an off-target sequence that has a few bases different from the guide sequence. For all experimental applications (gene targeting, crop engineering, therapeutic applications, etc) it is important to be able to improve the specificity of Cas9 mediated gene targeting and reduce the likelihood of off-target modification by Cas9.

Applicants developed a method of using a Cas9 nickase mutant in combination with two guide RNAs to facilitate targeted double strand breaks in the genome without off-target modifications. The Cas9 nickase mutant may be generated from a Cas9 nuclease by disabling its cleavage activity so that instead of both strands of the DNA duplex being cleaved only one strand is cleaved. The Cas9 nickase may be generated by inducing mutations in one ore more domains of the Cas9 nuclease, e.g. Ruvc1 or HNH. These mutations may include but are not limited to mutations in a Cas9 catalytic domain, e.g in SpCas9 these mutations may be at positions D10 or H840. These mutations may include but are not limited to D10A, E762A, H840A, N854A, N863A or D986A in SpCas9 but nickases may be generated by inducing mutations at corresponding positions in other CRISPR enzymes or Cas9 orthologs. In a most preferred embodiment of the invention the Cas9 nickase mutant is a SpCas9 nickase with a D10A mutation.

The way this works is that each guide RNA in combination with Cas9 nickase would induce the targeted single strand break of a duplex DNA target. Since each guide RNA nicks one strand, the net result is a double strand break. The reason this method eliminates off-target mutations is because it is very unlikely to have an off-target site that has high degrees of similarity for both guide sequences (20 bp+2 bp (PAM)=22 bp specificity for each guide, and two guides means any off-target site will have to have close to 44 bp of homologous sequence). Although it is still likely that individual guides may have off-targets, but those off-targets will only be nicked, which is unlikely to be repaired by the mutagenic NHEJ process. Therefore the multiplexing of DNA double strand nicking provides a powerful way of introducing targeted DNA double strand breaks without off-target mutagenic effects.

Figure 33:
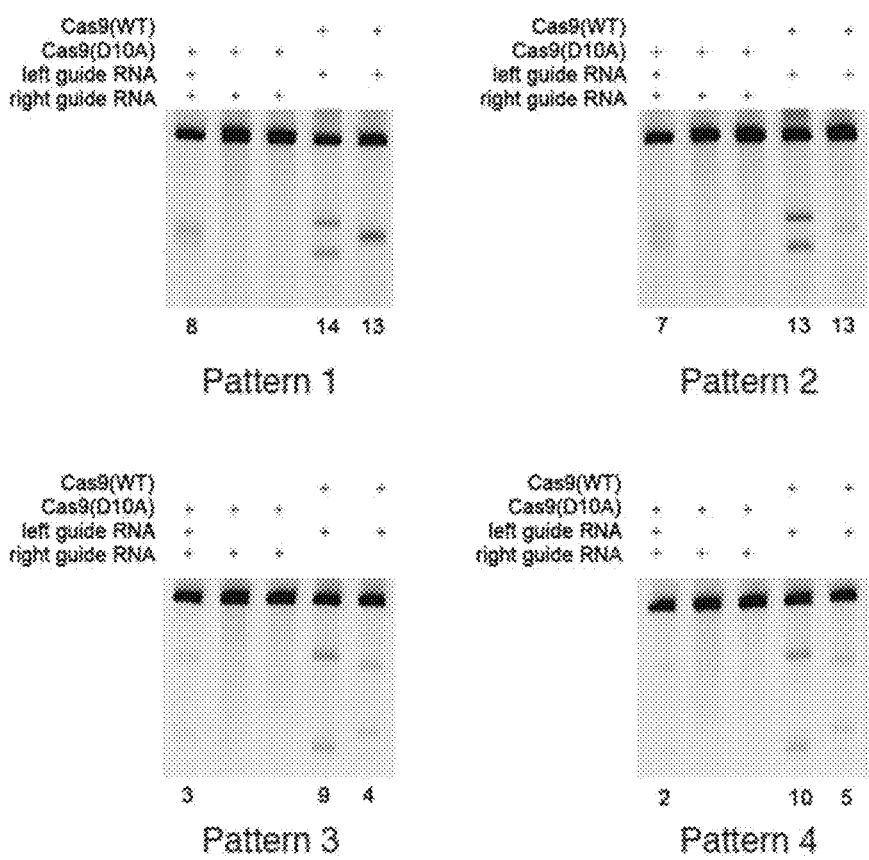
FIG. 33 shows (top) a list of spacing (as indicated by the pattern of arrangement for two PAM sequences) between pairs of guide RNAs. Only guide RNA pairs satisfying patterns 1, 2, 3, 4 exhibited indels when used with SpCas9 (D10A) nickase. (bottom) Gel images showing that combination of SpCas9(D10A) with pairs of guide RNA satisfying patterns 1, 2, 3, 4 led to the formation of indels in the target site.
Figure 34:
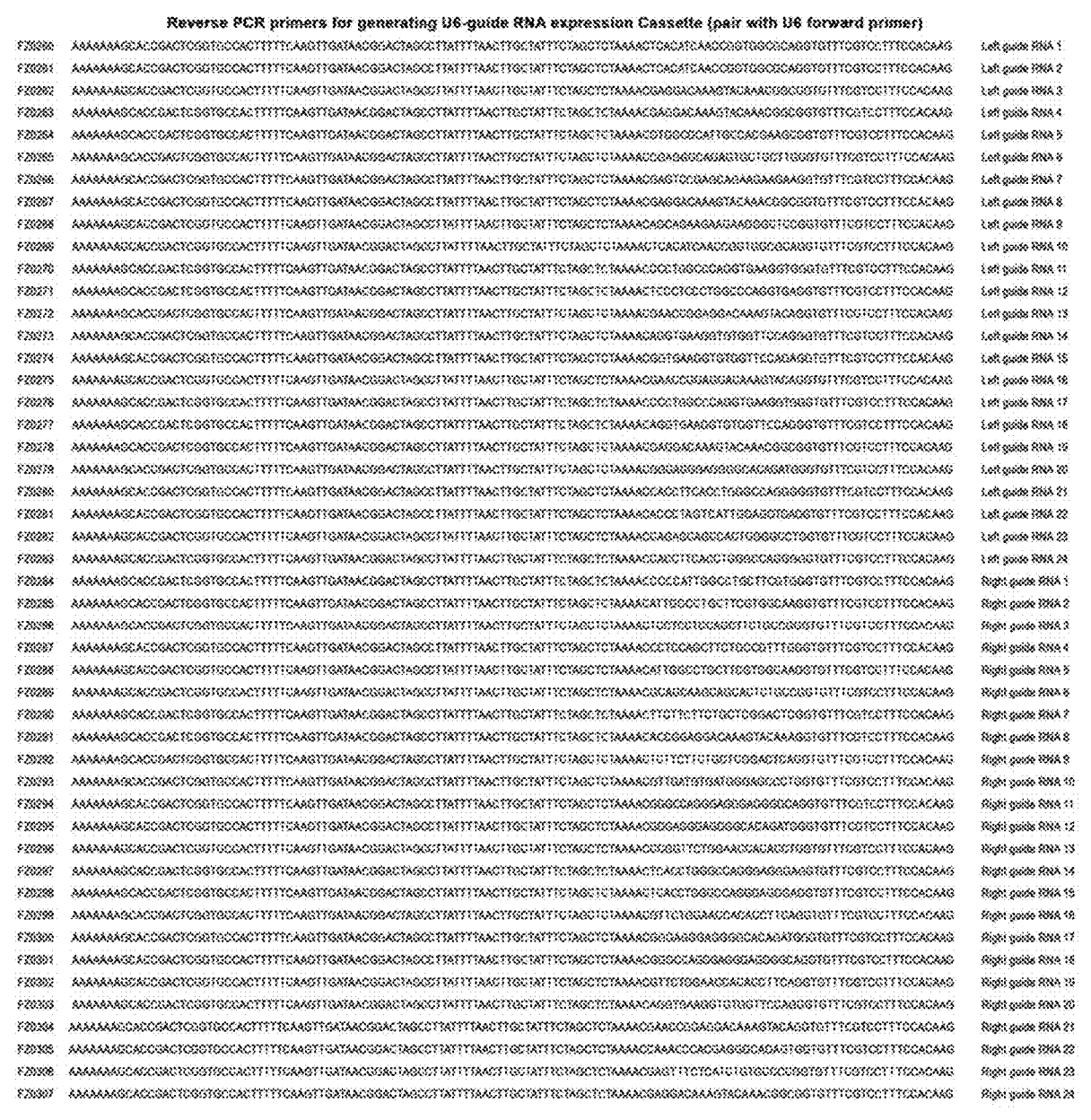
Figure 35:
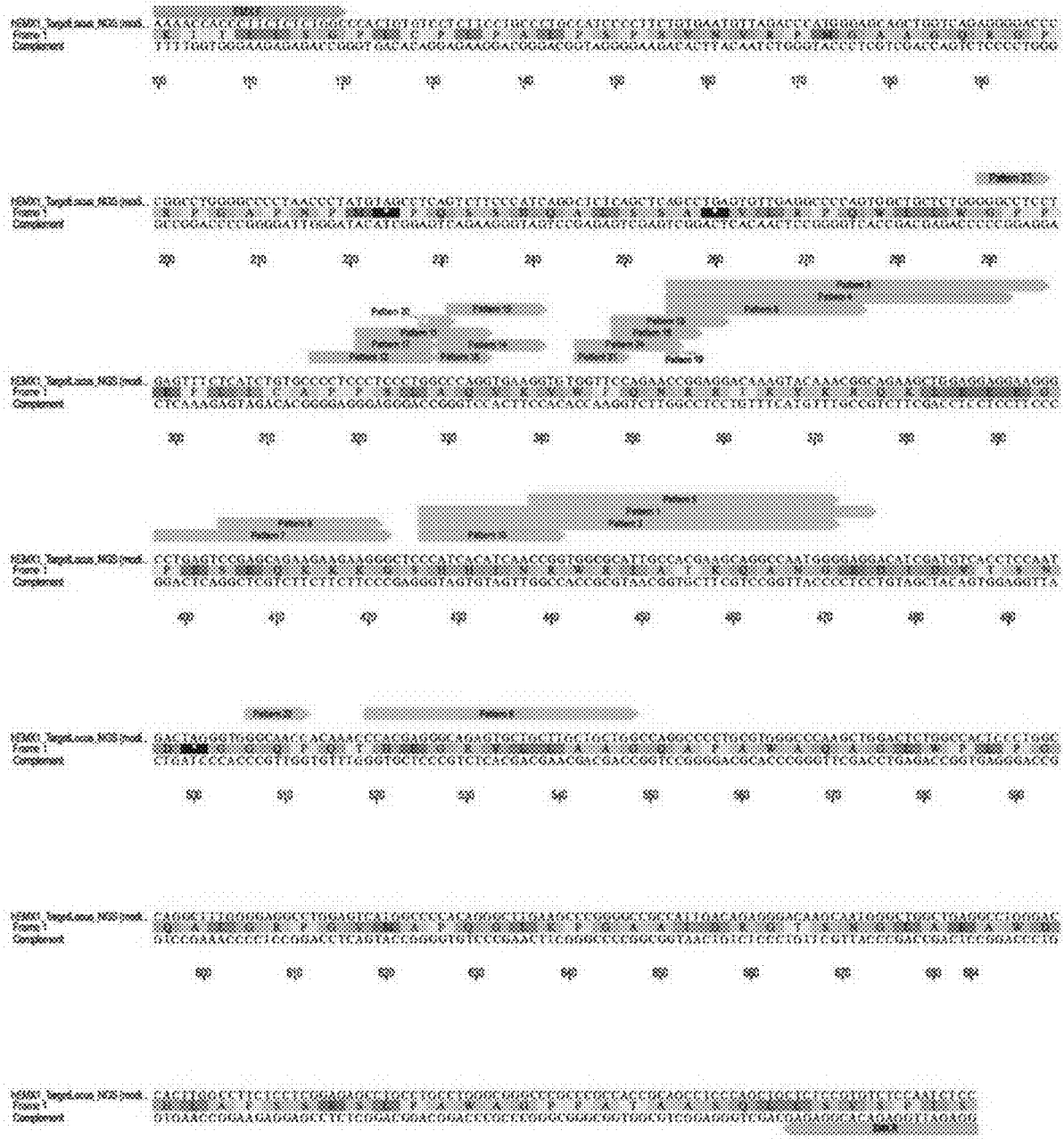
FIG. 35 shows a Genomic sequence map from the human Emx1 locus showing the locations of the 24 patterns listed in FIG. 33.

Applicants carried out experiments involving the co-transfection of HEK293FT cells with a plasmid encoding Cas9 (D10A) nickase as well as DNA expression cassettes for one or more guides. Applicants transfected cells using Lipofectamine 2000, and transfected cells were harvested 48 or 72 hours after transfections. Double nicking-induced NHEJ were detected using the SURVEYOR nuclease assay as described previously herein (FIGS. 33, 34 and 35).

Figure 37:
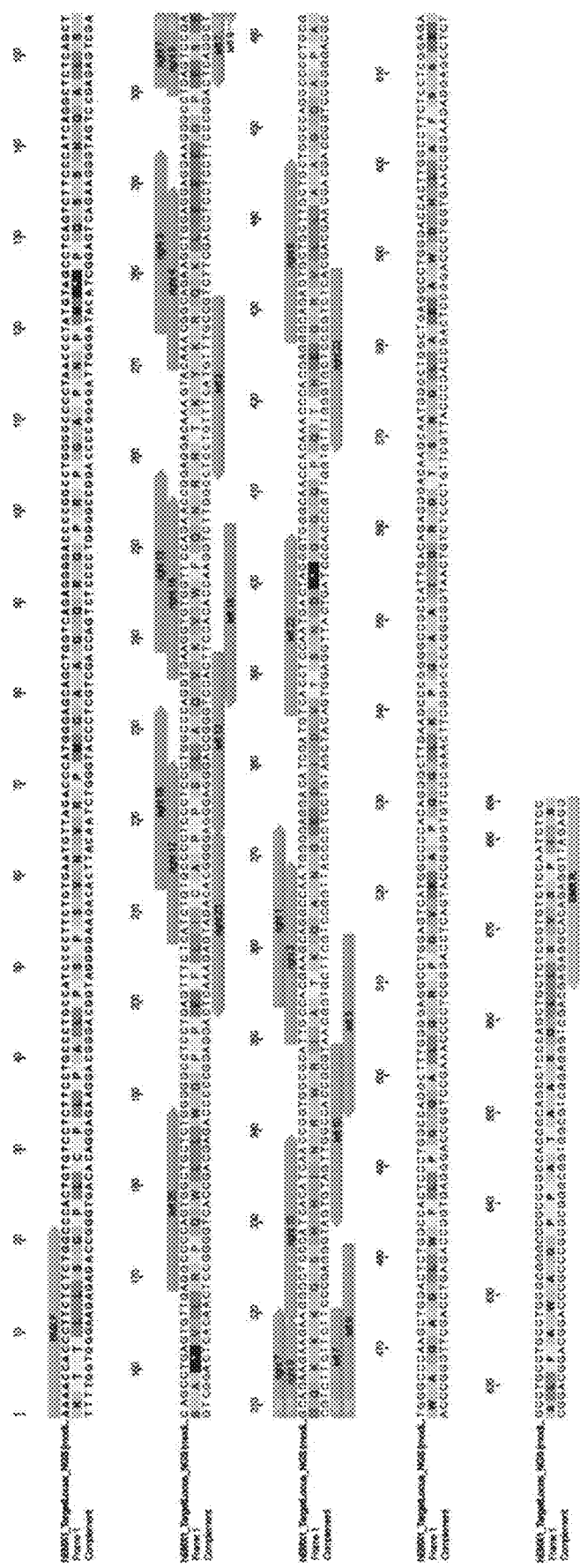
FIG. 37 shows a Genomic sequence map from the human Emx1 locus showing the locations of the different pairs of guide RNAs that result in the gel patterns of FIG. 36 (right) and which are further described in Example 30.

Applicants have further identified parameters that relate to efficient cleavage by the Cas9 nickase mutant when combined with two guide RNAs and these parameters include but are not limited to the length of the 5' overhang. Efficient cleavage is reported for 5' overhang of at least 26 base pairs. In a preferred embodiment of the invention, the 5' overhang is at least 30 base pairs and more preferably at least 34 base pairs. Overhangs of up to 200 base pairs may be acceptable for cleavage, while 5' overhangs less than 100 base pairs are preferred and 5' overhangs less than 50 base pairs are most preferred (FIGS. 36 and 37).

Example 31: Double Nicking by RNA-Guided CRISPR Cas9 for Enhanced Genome Editing Specificity Targeted genome editing technologies have enabled a broad range of research and medical applications. The Cas9 nuclease from the microbial CRISPR-Cas system is targeted to specific genomic loci by a 20-nt guide sequence, which can tolerate certain mismatches to the DNA target and thereby promote undesired off-target mutagenesis. As briefly described in Example 30, in this example Applicants further describe an approach that combines a Cas9 nickase mutant with paired guide RNAs to introduce targeted double-strand breaks. Since individual nicks in the genome are repaired with high fidelity, simultaneous nicking via appropriately offset guide RNAs is required for double stranded breaks and thus effectively extends the number of specifically recognized bases for target cleavage. Applicants demonstrated that using paired nicking can reduce off-target activity by 50-1,000 fold in cell lines and facilitate gene knockout in mouse zygotes without sacrificing on-target cleavage efficiency. This versatile strategy thus enables a wide variety of genome editing applications that require high specificity.

The ability to perturb the genome in a precise and targeted fashion is crucial for understanding genetic contributions to biology and disease. Genome engineering of cell lines or animal models has traditionally been accomplished through random mutagenesis or low-efficiency gene targeting. To facilitate genome editing, programmable sequence-specific DNA nuclease technologies have enabled targeted modification of endogenous genomic sequences with high efficiency, particularly in species that have proven genetically intractable. The RNA-guided Cas9 nucleases from the microbial CRISPR (clustered regularly interspaced short palindromic repeat)-Cas systems are robust and versatile tools for stimulating targeted double-stranded DNA breaks (DSBs) in eukaryotic cells, where the resulting cellular repair mechanisms—non-homologous end joining (NHEJ) or homology-directed repair (HDR) pathways—can be exploited to induce error-prone or defined alterations.

The Cas9 nuclease from Streptococcus pyogenes can be directed by a chimeric single guide RNA (sgRNA) to any genomic locus preceding a 5'-NGG protospacer-adjacent motif (PAM). A 20-nt guide sequence within the sgRNA directs Cas9 to the genomic target via Watson-Crick base pairing and can be easily programmed to target a desired genomic locus. Recent studies of Cas9 specificity have demonstrated that although each base within the 20-nt guide sequence contributes to overall specificity, multiple mismatches between the guide RNA and its complementary target DNA sequence can be tolerated depending on the quantity, position, and base identity of mismatches, leading to potential off-target DSBs and indel formation. These unwanted mutations can potentially limit the utility of Cas9 for genome editing applications that require high levels of precision, such as generation of isogenic cell lines for testing causal genetic variations or in vivo and ex vivo genome editing-based therapies.

To improve the specificity of Cas9-mediated genome editing, Applicants developed a novel strategy that combines the D10A mutant nickase version of Cas9 (Cas9n) with a pair of offset sgRNAs complementary to opposite strands of the target site. While nicking of both DNA strands by a pair of Cas9 nickases leads to site-specific DSBs and NHEJ, individual nicks are predominantly repaired by the high-fidelity base excision repair pathway (BER). A paired nickase strategy which may relate to the possibility for engineering a system to ameliorate off-target activity may be referred to in the Mali et al., 2013a paper titled CAS9 transcriptional activators for target specificity screening and paired nickases for cooperative genome engineering. In a manner analogous to dimeric zinc finger nucleases (ZFNs) and transcription activator-like effector nucleases (TALENs), where DNA cleavage requires synergistic interaction of two independent specificity-encoding DNA-binding modules directing FokI nuclease monomers, this double nicking strategy minimizes off-target mutagenesis by each individual Cas9n-sgRNA complex while maintaining on-target modification rates similar to those of wild type Cas9. Here Applicants define crucial parameters for the selection of sgRNA pairs that facilitate effective double nicking, compare the specificity of wildtype Cas9 and Cas9n with double nicking, and demonstrate a variety of experimental applications that can be achieved using double nicking in cells as well as in mouse zygotes.

Figure 38A:
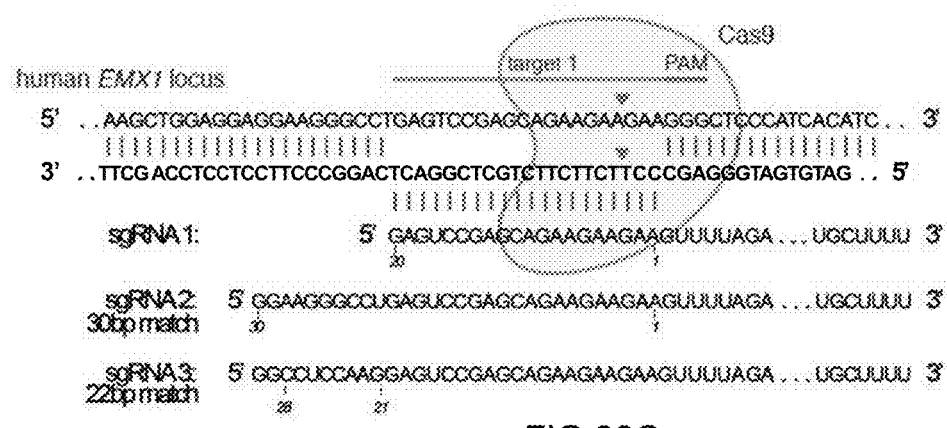
FIG. 38A-C shows the effect of guide sequence extension on Cas9 activity (A) Schematic showing Cas9 with matching or mismatching sgRNA sequences targeting a locus (target 1) within the human EMX1 gene.

Extension of guide sequence does not improve Cas9 targeting specificity: Cas9 targeting is facilitated by base-pairing between the 20-nt guide sequence within the sgRNA and the target DNA. Applicants reasoned that cleavage specificity might be improved by increasing the length of base-pairing between the guide RNA and its target locus. Applicants generated U6-driven expression cassettes to express three sgRNAs with 20-nt (sgRNA 1) or 30-nt guide sequences (sgRNAs 2 and 3) targeting a locus within the human EMX1 gene (FIG. 38A).

Figure 38B:
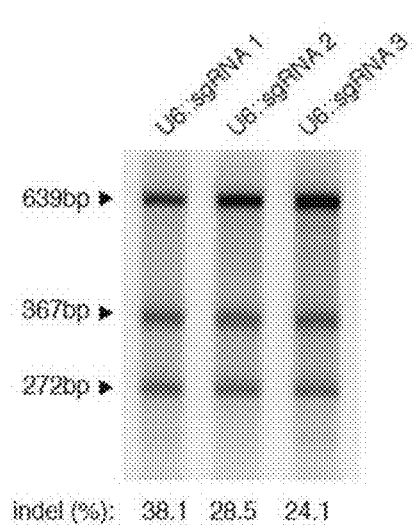
Figure 38C:
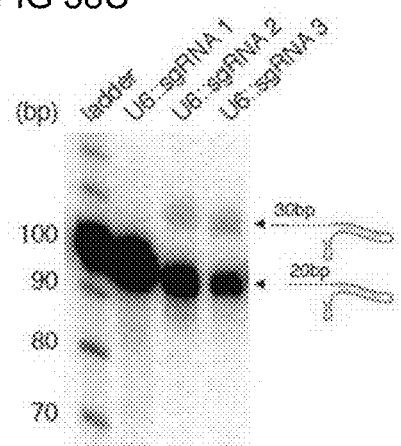

Applicants and others have previously shown that while single-base mismatches between the PAM-distal region of the guide sequence and target DNA are well-tolerated by Cas9, multiple mismatches in this region can significantly affect on-target activity. To determine whether additional PAM-distal bases (21-30) could influence overall targeting specificity, Applicants designed sgRNAs 2 and 3 to contain 10 additional bases consisting of either 10 perfectly matched or 8 mismatched bases (bases 21-28). Surprisingly, Applicants observed that these extended sgRNAs mediated similar levels of modification at the target locus in HEK 293FT cells regardless of whether the additional bases were complementary to the genomic target (FIG. 38B). Subsequent Northern blots revealed that the majority of both sgRNA 2 and 3 were processed to the same length as sgRNA 1, which contains the same 20-nt guide sequence without additional bases (FIG. 38C).

Figure 39A:
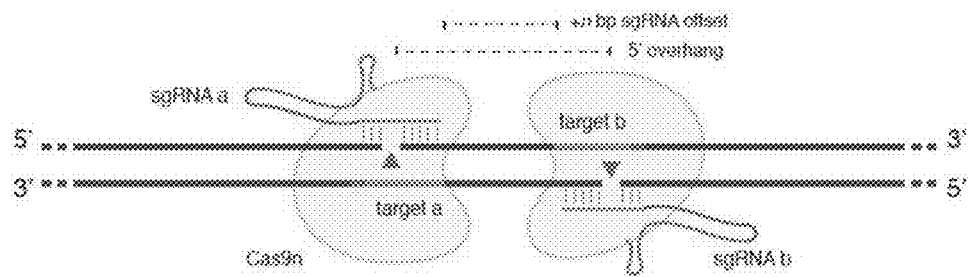
FIG. 39A-C shows that double nicking facilitates efficient genome editing in human cells (A) Schematic illustrating DNA double-stranded breaks using a pair of sgRNAs guiding Cas9 D10A nickases (Cas9n). The D10A mutation renders Cas9 able to cleave only the strand complementary to the sgRNA; a pair of sgRNA-Cas9n complexes can nick both strands simultaneously. sgRNA offset is defined as the distance between the PAM-distal (5') ends of the guide sequence of a given sgRNA pair; positive offset requires the sgRNA complementary to the top strand (sgRNA a) to be 5' of the sgRNA complementary to the bottom strand (sgRNA b), which always creates a 5'-overhang. (B) Efficiency of double nicking induced NHEJ as a function of the offset distance between two sgRNAs. Sequences for all sgRNAs used can be found in Table 51. (n=3; error bars show mean±s.e.m.) (C) Representative sequences of the human EMX1 locus targeted by Cas9n. sgRNA target sites and PAMs are indicated by blue and magenta bars respectively. Below, selected sequences showing representative indels. See also FIGS. 44 and 45.

Cas9 nickase generates efficient NHEJ with paired, offset guide RNAs: Given that extension of the guide sequence failed to improve Cas9 targeting specificity, Applicants sought an alternative strategy for increasing the overall base-pairing length between the guide sequence and its DNA target. Cas9 enzymes contain two conserved nuclease domains, HNH and RuvC, which cleave the DNA strand complementary and non-complementary to the guide RNA, respectively. Mutations of the catalytic residues (D10A in RuvC and H840A in HNH) convert Cas9 into DNA nickases. As single-strand nicks are preferentially repaired by the high-fidelity BER pathway, Applicants reasoned that two Cas9 nicking enzymes directed by a pair of sgRNAs targeting opposite strands of a target locus could mediate DSBs while minimizing off-target activity (FIG. 39A).

Figure 39B:
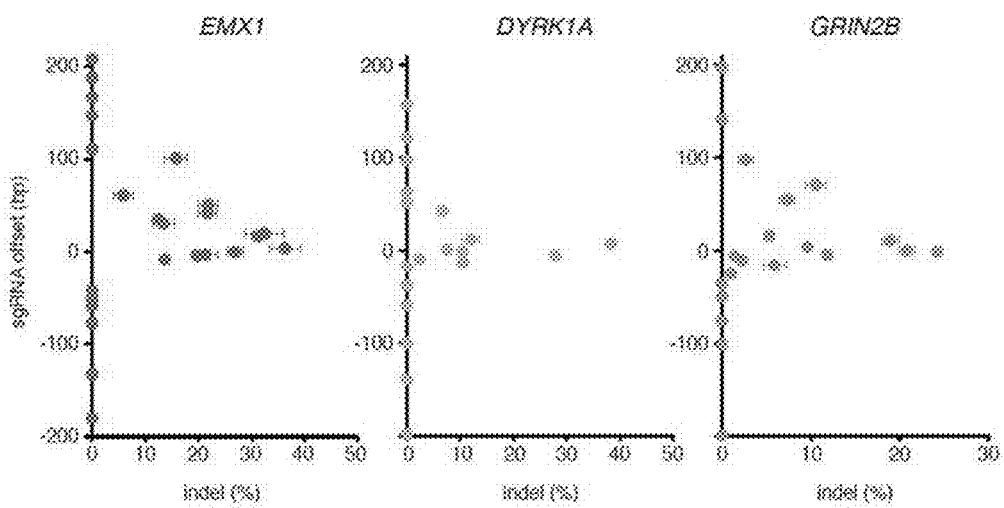
Figure 39C:
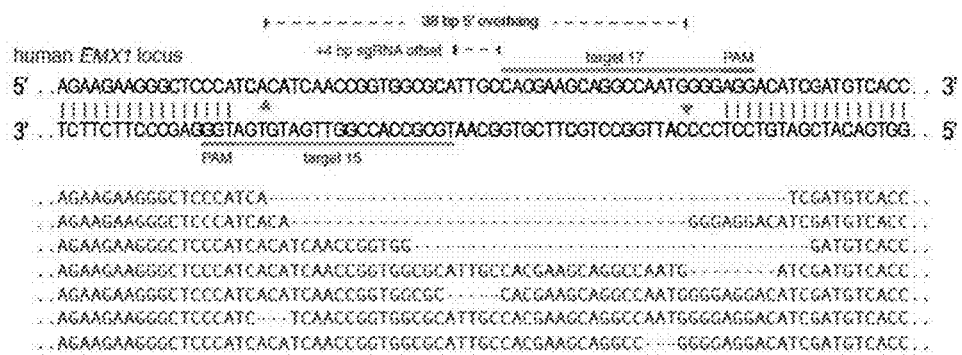

A number of factors may affect cooperative nicking leading to indel formation, including steric hindrance between two adjacent Cas9 molecules or Cas9-sgRNA complexes, overhang type, and sequence context; some of these may be characterized by testing multiple sgRNA pairs with distinct target sequences and offsets (the distance between the PAM-distal (5') ends of the guide sequence of a given sgRNA pair). To systematically assess how sgRNA offsets might affect subsequent repair and generation of indels, Applicants first designed sets of sgRNA pairs targeted against the human EMX1 genomic locus separated by a range of offset distances from approximately −200 to 200 bp to create both 5'- and 3'-overhang products (FIG. 39A, FIG. 44). Applicants then assessed the ability of each sgRNA pair, with the D10A Cas9 mutant (referred to as Cas9n; H840A Cas9 mutant is referred to as Cas9H840A), to generate indels in human HEK 293FT cells. Robust NHEJ (up to 40%) was observed for sgRNA pairs with offsets from −4 to 20 bp, with modest indels forming in pairs offset by up to 100-bp (FIG. 39B, left panel). Applicants subsequently recapitulated these findings by testing similarly offset sgRNA pairs at two other genomic loci, DYRK1A and GRIN2B (FIG. 39B, right panels). Notably, across all three loci examined, only sgRNA pairs creating 5' overhangs with less than 8 bp overlap between the guide sequences (offset greater than −8 bp) were able to mediate detectable indel formation (FIG. 39C). Importantly, each guide used in these assays is able to efficiently induce indels when paired with wildtype Cas9 (FIG. 44), indicating that the relative positions of the guide pairs are the most important parameters in predicting double nicking activity.

Since Cas9n and Cas9H840A nick opposite strands of DNA, substitution of Cas9n with Cas9H840A with a given sgRNA pair should result in the inversion of the overhang type. For example, a pair of sgRNAs that will generate a 5' overhang with Cas9n should in principle generate the corresponding 3' overhang instead. Therefore, sgRNA pairs that lead to the generation of a 3' overhang with Cas9n might be used with Cas9H840A to generate a 5' overhang. Unexpectedly, Applicants tested Cas9H840A with a set of sgRNA pairs designed to generate both 5' and 3' overhangs (offset range from ¬−278 to +58 bp), but were unable to observe indel formation. Further work may be needed to identify the necessary design rules for sgRNA pairing to allow double nicking by Cas9H840A.

Figure 40A:
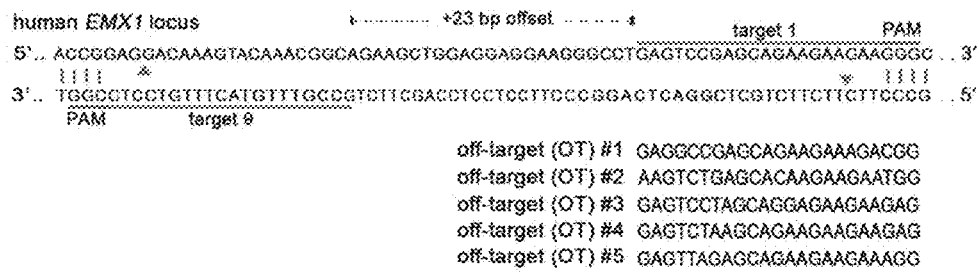
FIG. 40A-F shows that double nicking facilitates efficient genome editing in human cells (A) Schematic illustrating Cas9n double nicking (red arrows) the human EMX1 locus. Five off-target loci with sequence homology to EMX1 target 1 were selected to screen for Cas9n specificity.
Figure 40B:
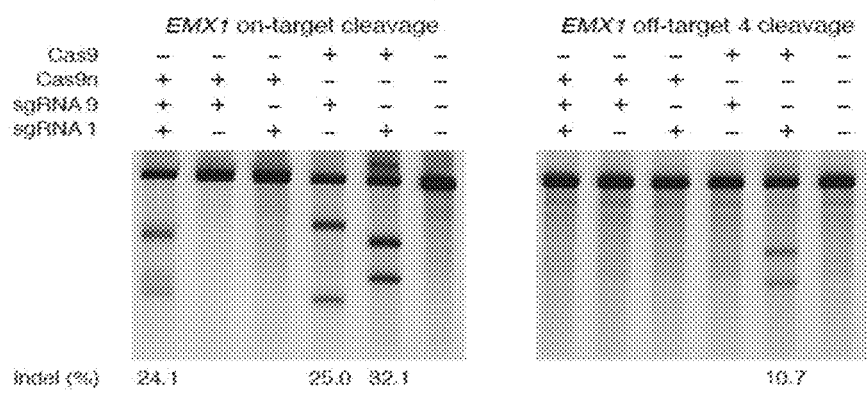

Double nicking mediates efficient genome editing with improved specificity: Having established that double nicking (DN) mediates high efficiency NHEJ at levels comparable to those induced by wildtype Cas9, Applicants next studied whether DN has improved specificity over wildtype Cas9 by measuring their off-target activities. Applicants co-delivered Cas9n with sgRNAs 1 and 9, spaced by a +23 bp offset, to target the human EMX1 locus in HEK 293FT cells (FIG. 40A). This DN configuration generated on-target indel levels similar to those generated by the wildtype Cas9 paired with each sgRNA alone (FIG. 40B, left panel). Strikingly, unlike with wildtype Cas9, DN did not generate detectable modification at a previously validated sgRNA 1 off-target site, OT-4, by SURVEYOR assay (FIG. 40B, right panel), suggesting that DN can potentially reduce the likelihood of off-target modifications.

Figure 40C:
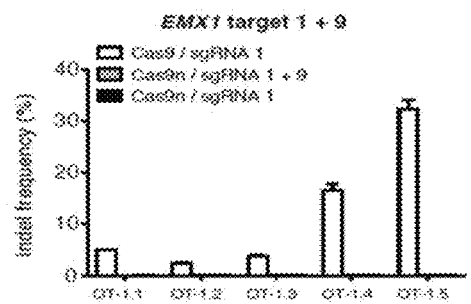
Figure 40D:
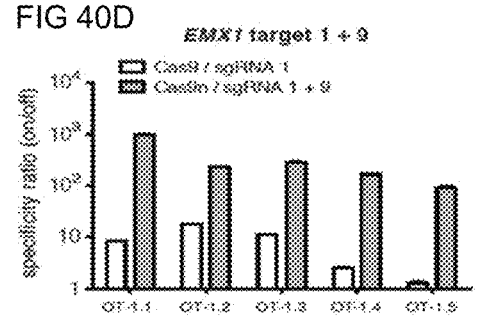
Figure 40E:
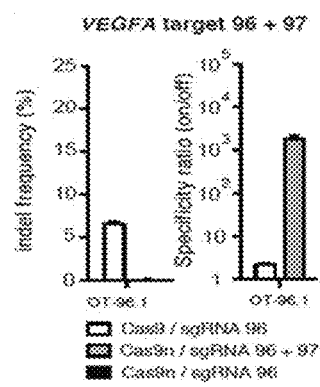
Figure 40F:
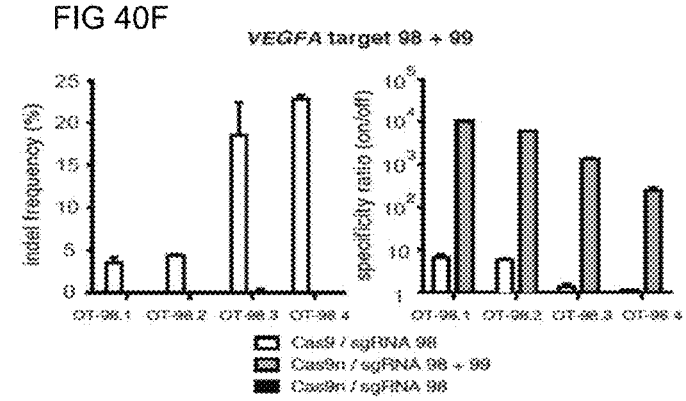

Using deep sequencing to assess modification at 5 different sgRNA 1 off-target loci (FIG. 40A), Applicants observed significant mutagenesis at all sites with wild type Cas9+ sgRNA 1 (FIG. 40C). In contrast, cleavage by Cas9n at 5 off-target sites tested was barely detectable above background sequencing error. Using the ratio of on- to off-target modification levels as a metric of specificity, Applicants found that Cas9n with a pair of sgRNAs was able to achieve over 100-fold greater specificity relative to wild type Cas9 with one of the sgRNAs (FIG. 40D). Applicants conducted additional off-target analysis by deep sequencing for two sgRNA pairs (offsets of +16 and +20 bp) targeting the VEGFA locus, with similar results (FIG. 40E). DN at these off-target loci (Table 4) was able to achieve 200 to over 1500-fold greater specificity than the wild-type Cas9 (FIG. 40F, FIG. 44). Taken together, these results demonstrate that Cas9-mediated double nicking minimizes off-target mutagenesis and is suitable for genome editing with increased specificity.

Figure 41A:
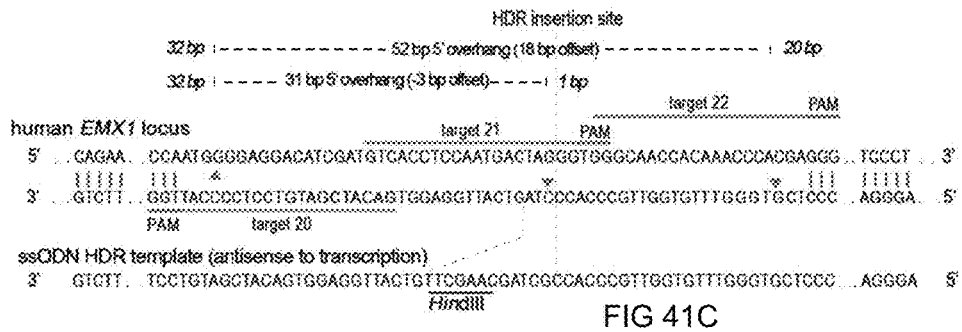
FIG. 41A-D shows that double nicking allows insertion into the genome via HDR in human cells (A) Schematic illustrating HDR mediated via a single stranded oligodeoxy-nucleotide (ssODN) template at a DSB created by a pair of Cas9n enzymes. A 12-nt sequence (red), including a HindIII restriction site, is inserted into the EMX1 locus at the position marked by the gray dashed lines; distances of Cas9n-mediated nicks from the HDR insertion site is indicated on top in italics.
Figure 41B:
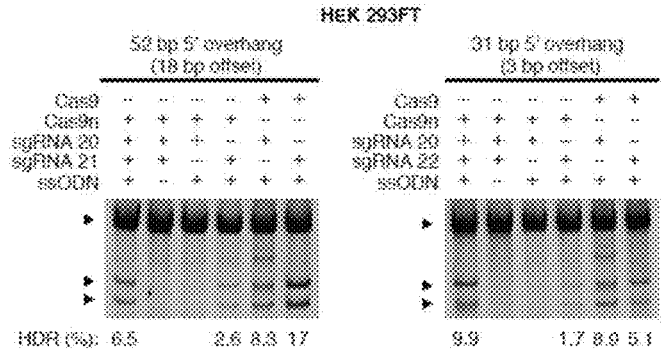
Figure 41C:
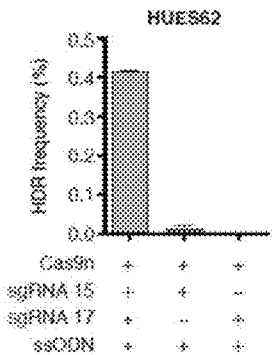

Double nicking facilitates high-efficiency homology directed repair, NHEJ-mediated DNA insertion, and genomic microdeletions: DSBs can stimulate homology directed repair (HDR) to enable highly precise editing of genomic target sites. To evaluate DN-induced HDR, Applicants targeted the human EMX1 locus with pairs of sgRNAs offset by −3 and +18 bp (generating 31- and 52-bp 5' overhangs), respectively, and introduced a single-stranded oligodeoxynucleotide (ssODN) bearing a HindIII restriction site as the HDR repair template (FIG. 41A). Each DN sgRNA pair successfully induced HDR at frequencies higher than those of single-guide Cas9n nickases and comparable to those of wild-type Cas9 (FIG. 41B). Furthermore, genome editing in embryonic stem cells or patient derived induced pluripotent stem cells represents a key opportunity for generating and studying new disease paradigms as well as developing new therapeutics. Since single nick approaches to inducing HDR in human embryonic stem cells (hESCs) have met with limited success, Applicants attempted DN in the HUES62 hES cell line and observed successful HDR (FIG. 41C).

Figure 41D:
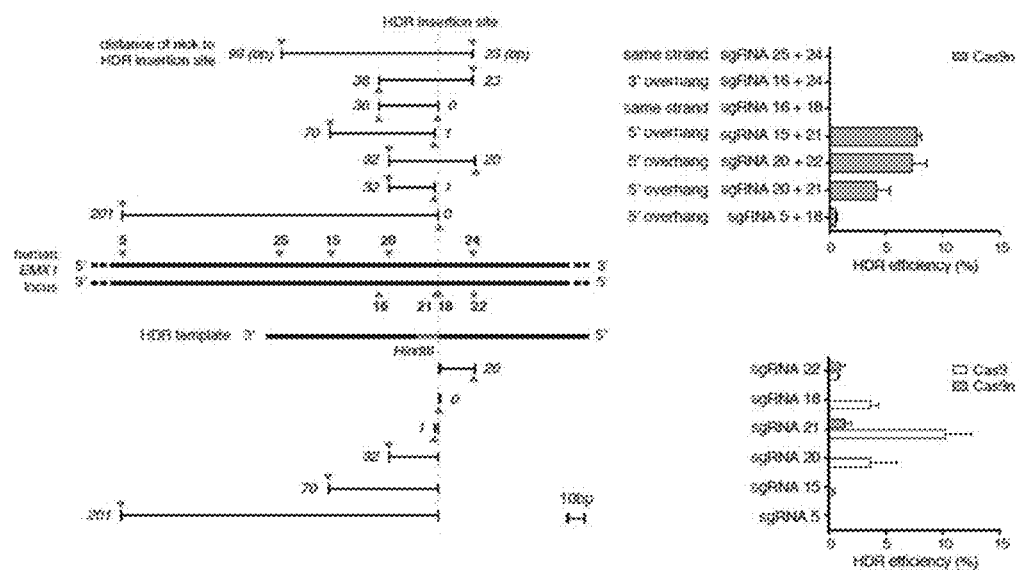

To further characterize how offset sgRNA spacing affects the efficiency of HDR, Applicants next tested in HEK 293FT cells a set of sgRNA pairs where the cleavage site of at least one sgRNA is situated near the site of recombination (overlapping with the HDR ssODN donor template arm). Applicants observed that sgRNA pairs generating 5' overhangs and having at least one nick occurring within 22 bp of the homology arm are able to induce HDR at levels comparable to those of wildtype Cas9-mediated HDR, and significantly greater than those of single Cas9n-sgRNA nicking. In contrast, Applicants did not observe HDR with sgRNA pairs that generated 3'-overhangs or double nicking of the same DNA strand (FIG. 41D).

Figure 42A:
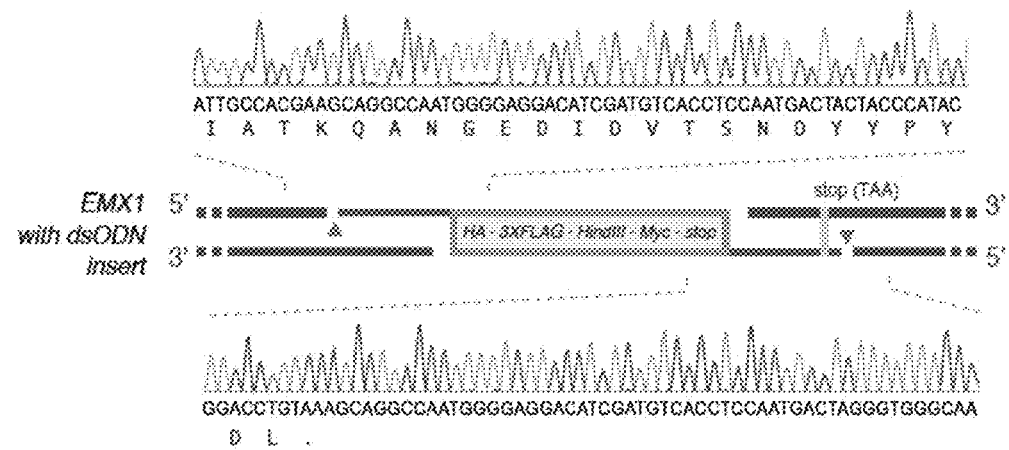
FIG. 42A-B shows that multiplexed nicking facilitates non-HR mediated gene integration and genomic deletions (A) Schematic showing insertion of a double-stranded oligodeoxynucleotide (dsODN) donor fragment bearing overhangs complementary to 5' overhangs created by Cas9 double nicking. The dsODN was designed to remove the native EMX1 stop codon and contains a HA tag, 3×FLAG tag, HindIII restriction site, Myc epitope tag, and a stop codon in frame, totaling 148 bp. Successful insertion was verified by Sanger sequencing as shown (1/37 clones screened). Amino acid translation of the modified locus is shown below the DNA sequence.

The ability to create defined overhangs could enable precise insertion of donor repair templates containing compatible overhangs via NHEJ-mediated ligation. To explore this alternative strategy for transgene insertion, Applicants targeted the EMX1 locus with Cas9n and an sgRNA pair designed to generate a 43 bp 5'-overhang near the stop codon, and supplied a double-stranded oligonucleotide (dsODN) duplex with matching overhangs (FIG. 42A). The annealed dsODN insert, containing multiple epitope tags and a restriction site, was successfully integrated into the target at a frequency of 3% (1/37 screened by Sanger sequencing of cloned amplicons). This ligation-based strategy thus illustrates an effective approach for inserting dsODNs encoding short modifications such as protein tags or recombination sites into an endogenous locus.

Figure 42B:
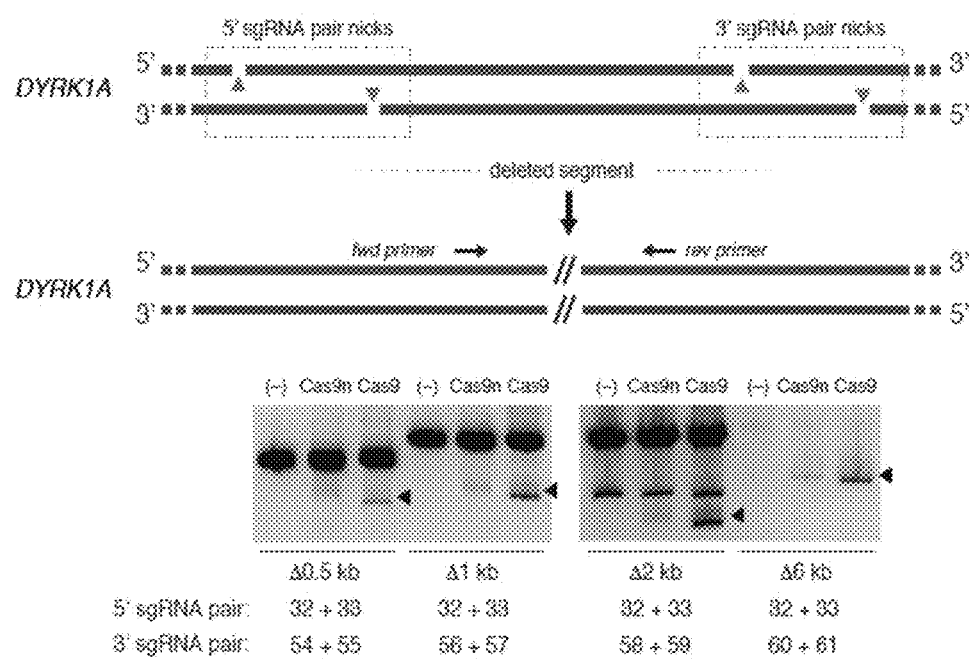

Additionally, Applicants targeted combinations of sgRNA pairs (4 sgRNAs per combination) to the DYRK1A locus in HEK 293FT cells to facilitate genomic microdeletions. Applicants generated a set of sgRNAs to mediate 0.5 kb, 1 kb, 2 kb, and 6 kb deletions (FIG. 42B, FIG. 45: sgRNAs 32, 33, 54-61) and verified successful multiplex nicking-mediated deletion over these ranges via PCR screen of predicted deletion sizes.

Figure 43A:
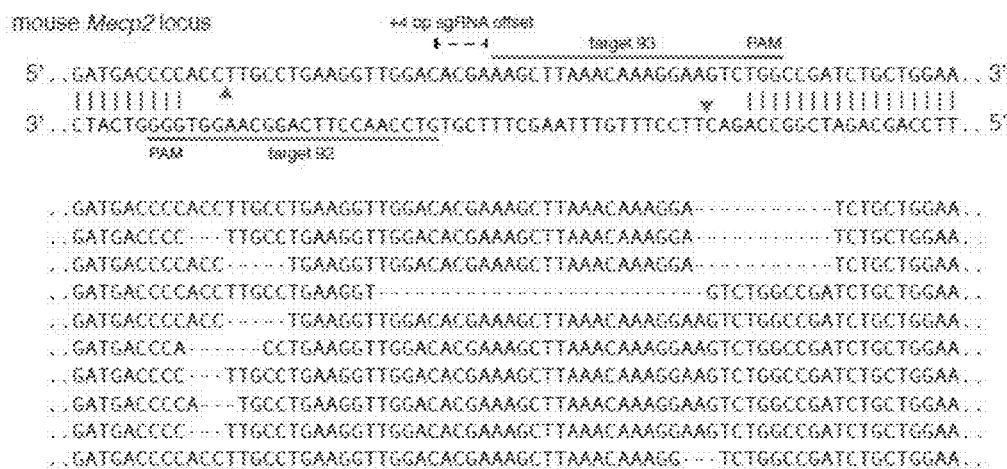
FIG. 43A-B shows that Cas9 double nicking mediates efficient indel formation in mouse embryos (A) Schematic illustrating Cas9n double nicking the mouse Mecp2 locus. Representative indels are shown for mouse blastocysts co-injected with in vitro transcribed Cas9n-encoding mRNA and sgRNA pairs matching targets 92 and 93.
Figure 43B:
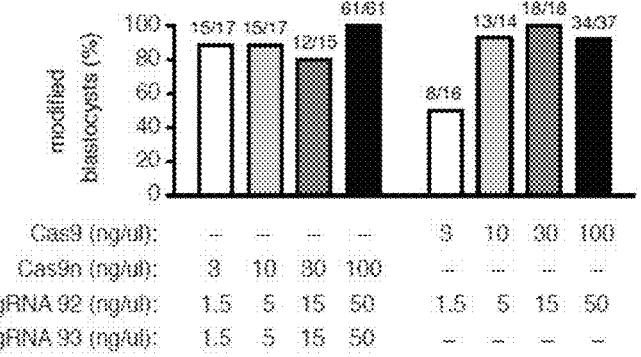

Double nicking enables efficient genome modification in mouse zygotes: Recent work demonstrated that co-delivery of wildtype Cas9 mRNA along with multiple sgRNAs can mediate single-step generation of transgenic mice carrying multiple allelic modifications. Given the ability to achieve genome modification in vivo using several sgRNAs at once, Applicants sought to assess the efficiency of multiple nicking by Cas9n in mouse zygotes. Cytoplasmic co-injection of wildtype Cas9 or Cas9n mRNA and sgRNAs into single-cell mouse zygotes allowed successful targeting of the Mecp2 locus (FIG. 43A). To identify the optimal concentration of Cas9n mRNA and sgRNA for efficient gene targeting, Applicants titrated Cas9 mRNA from 100 ng/uL to 3 ng/uL while maintaining the sgRNA levels at a 1:20 Cas9:sgRNA molar ratio. All concentrations tested for Cas9 double nicking mediated modifications in at least 80% of embryos screened, similar to levels achieved by wildtype Cas9 (FIG. 43B). Taken together, these results suggest a number of applications for double nicking-based genome editing.

Discussion: Given the permanent nature of genomic modifications, specificity is of paramount importance to sensitive applications such as studies aimed at linking specific genetic variants with biological processes or disease phenotypes and gene therapy. Applicants have explored strategies to improve the targeting specificity of Cas9. Although simply extending the guide sequence length of sgRNA failed to improve targeting specificity, combining two appropriately offset sgRNAs with Cas9n effectively generated indels while minimizing unwanted cleavage since individual off-target single-stranded nicks are repaired with high fidelity via base excision repair. Given that significant off-target mutagenesis has been previously reported for Cas9 nucleases in human cells, the DN approach could provide a generalizable solution for rapid and accurate genome editing. The characterization of spacing parameters governing successful Cas9 double nickase-mediated gene targeting reveals an effective offset window over 100-bp long, allowing for a high degree of flexibility in the selection of sgRNA pairs. Previous computational analyses have revealed an average targeting range of every 12-bp for the *Streptococcus pyogenes* Cas9 in the human genome based on the 5'-NGG PAM, which suggest that appropriate sgRNA pairs should be readily identifiable for most loci within the genome. Applicants have additionally demonstrated DN-mediated indel frequencies comparable to wild type Cas9 modification at multiple genes and loci in both human and mouse cells, confirming the reproducibility of this strategy for high-precision genome engineering (FIG. 44).

The Cas9 double nicking approach is in principle similar to ZFN and TALEN-based genome editing systems, where cooperation between two hemi-nuclease domains is required to achieve double-stranded break at the target site. Systematic studies of ZFN and TALEN systems have revealed that the targeting specificity of a given ZFN and TALEN pair can be highly dependent on the nuclease architecture (homo- or heterodimeric nucleases) or target sequence, and in some cases TALENs can be highly specific. Although the wildtype Cas9 system has been shown to exhibit high levels of off-target mutagenesis, the DN system is a promising solution and brings RNA-guided genome editing to similar specificity levels as ZFNs and TALENs.

Additionally, the ease and efficiency with which Cas9 can be targeted renders the DN system especially attractive. However, DNA targeting using DN will likely face similar off-target challenges as ZFNs and TALENs, where cooperative nicking at off-target sites might still occur, albeit at a significantly reduced likelihood. Given the extensive characterization of Cas9 specificity and sgRNA mutation analysis, as well as the NHEJ-mediating sgRNA offset range identified in this study, computational approaches may be used to evaluate the likely off-target sites for a given pair of sgRNAs. To facilitate sgRNA pair selection, Applicants developed an online web tool that identifies sgRNA combinations with optimal spacing for double nicking applications (available at the website genome-engineering.org).

Although Cas9n has been previously shown to facilitate HDR at on-target sites, its efficiency is substantially lower than that of wildtype Cas9. The double nicking strategy, by comparison, maintains high on-target efficiencies while reducing off-target modifications to background levels. Nevertheless, further characterizations of DN off-target activity, particularly via whole genome sequencing and targeted deep sequencing of cells or whole organisms generated using the DN approach, may be needed to evaluate the utility of Cas9n DN in biotechnological or clinical applications that require ultra-high precision genome editing. Additionally, Cas9n has been shown to induce low levels of indels at on-target sites for certain sgRNAs as indicated in the Mali et al. paper entitled "CAS9 transcriptional activators for target specificity screening and paired nickases for cooperative genome engineering" (2013), which may result from residual double-strand break activities and be circumvented by further structure-function studies of Cas9 catalytic activity. Overall, Cas9n-mediated multiplex nicking serves as a customizable platform for highly precise and efficient targeted genome engineering and promises to broaden the range of applications in biotechnology, basic science, and medicine.

Experimental Procedures

Cell culture and transfection: Human embryonic kidney (HEK) cell line 293FT (Life Technologies) or mouse Neuro 2a (Sigma-Aldrich) cell line was maintained in Dulbecco's modified Eagle's Medium (DMEM) supplemented with 10% fetal bovine serum (HyClone), 2 mM GlutaMAX (Life Technologies), 100 U/mL penicillin, and 100m/mL streptomycin at 37° C. with 5% CO2 incubation.

Cells were seeded onto 24-well plates (Corning) at a density of 120,000 cells/well, 24 hours prior to transfection. Cells were transfected using Lipofectamine 2000 (Life Technologies) at 80-90% confluency following the manufacturer's recommended protocol. A total of 500 ng Cas9 plasmid and 100 ng of U6-sgRNA PCR product was transfected.

Human embryonic stem cell line HUES62 (Harvard Stem Cell Institute core) was maintained in feeder-free conditions on GelTrex (Life Technologies) in mTesR medium (Stemcell Technologies) supplemented with 100 ug/ml Normocin (InvivoGen). HUES62 cells were transfected with Amaxa P3 Primary Cell 4-D Nucleofector Kit (Lonza) following the manufacturer's protocol.

SURVEYOR nuclease assay for genome modification: 293FT and HUES62 cells were transfected with DNA as described above. Cells were incubated at 37° C. for 72 hours post-transfection prior to genomic DNA extraction. Genomic DNA was extracted using the QuickExtract DNA Extraction Solution (Epicentre) following the manufacturer's protocol. Briefly, pelleted cells were resuspended in QuickExtract solution and incubated at 65° C. for 15 minutes, 68° C. for 15 minutes, and 98° C. for 10 minutes.

The genomic region flanking the CRISPR target site for each gene was PCR amplified (Table 2), and products were purified using QiaQuick Spin Column (Qiagen) following the manufacturer's protocol. 400 ng total of the purified PCR products were mixed with 2 µl 10× Taq DNA Polymerase PCR buffer (Enzymatics) and ultrapure water to a final volume of 20 µl, and subjected to a re-annealing process to enable heteroduplex formation: 95° C. for 10 min, 95° C. to 85° C. ramping at −2° C./s, 85° C. to 25° C. at −0.25° C./s, and 25° C. hold for 1 minute. After re-annealing, products were treated with SURVEYOR nuclease and SURVEYOR enhancer S (Transgenomics) following the manufacturer's recommended protocol, and analyzed on 4-20% Novex TBE poly-acrylamide gels (Life Technologies). Gels were stained with SYBR Gold DNA stain (Life Technologies) for 30 minutes and imaged with a Gel Doc gel imaging system (Bio-rad). Quantification was based on relative band intensities. Indel percentage was determined by the formula, $100 \times (1-(1-(b+c)/(a+b+c))^{1/2})$, where a is the integrated intensity of the undigested PCR product, and b and c are the integrated intensities of each cleavage product.

Northern blot analysis of tracrRNA expression in human cells Northern blots were performed as previously described in Cong et al., 2013. Briefly, RNAs were extracted using the mirPremier microRNA Isolation Kit (Sigma) and heated to 95° C. for 5 min before loading on 8% denaturing polyacrylamide gels (SequaGel, National Diagnostics). Afterwards, RNA was transferred to a pre-hybridized Hybond N+ membrane (GE Healthcare) and crosslinked with Stratagene UV Crosslinker (Stratagene). Probes were labeled with [gamma-32P] ATP (Perkin Elmer) with T4 polynucleotide kinase (New England Biolabs). After washing, membrane was exposed to phosphor screen for one hour and scanned with phosphorimager (Typhoon).

Deep sequencing to assess targeting specificity: HEK 293FT cells were plated and transfected as described above, 72 hours prior to genomic DNA extraction. The genomic region flanking the CRISPR target site for each gene was amplified (see Table 3 for primer sequences) by a fusion PCR method to attach the Illumina P5 adapters as well as unique sample-specific barcodes to the target. PCR products were purified using EconoSpin 96-well Filter Plates (Epoch Life Sciences) following the manufacturer's recommended protocol.

Barcoded and purified DNA samples were quantified by Qubit 2.0 Fluorometer (Life Technologies) and pooled in an equimolar ratio. Sequencing libraries were then sequenced with the Illumina MiSeq Personal Sequencer (Life Technologies).

Sequencing data analysis, indel detection, and homologous recombination detection: MiSeq reads were filtered by requiring an average Phred quality (Q score) of at least 30, as well as perfect sequence matches to barcodes and amplicon forward primers. Reads from on- and off-target loci were analyzed by performing Ratcliff-Obershelp string comparison, as implemented in the Python difflib module, against loci sequences that included 30 nucleotides upstream and downstream of the target site (a total of 80 bp). The resulting edit operations were parsed, and reads were counted as indels if insertion or deletion operations were found. Analyzed target regions were discarded if part of their alignment fell outside the MiSeq read itself or if more than 5 bases were uncalled.

Negative controls for each sample provided a gauge for the inclusion or exclusion of indels as putative cutting events. For quantification of homologous recombination, reads were first processed as in the indel detection workflow, and then checked for presence of homologous recombination template CCAGGCTTGG (SEQ ID NO: 197).

Microinjection into mouse zygotes: Cas9 mRNA and sgRNA templates were amplified with T7 promoter sequence-conjugated primers. After gel purification, Cas9 and Cas9n were transcribed with mMESSAGE mMACHINE T7 Ultra Kit (Life technologies). sgRNAs were transcribed with MEGAshortscript T7 Kit (Life technologies). RNAs were purified by MEGAclear Kit (Life technologies) and frozen at −80° C.

MII-stage oocytes were collected from 8-week old super-ovulated BDF1 females by injecting 7.5 I.U. of PMSG (Harbor, UCLA) and hCG (Millipore). They were transferred into HTF medium supplemented with 10 mg/ml bovine serum albumin (BSA; Sigma-Aldrich) and inseminated with capacitated sperm obtained from the caudal epididymides of adult C57BL/6 male mice. Six hours after fertilization, zygotes were injected with mRNAs and sgRNAs in M2 media (Millipore) using a Piezo impact-driven micromanipulator (Prime Tech Ltd., Ibaraki, Japan). The concentrations of Cas9 and Cas9n mRNAs and sgRNAs are described in the text and FIG. 6B. After microinjection, zygotes were cultured in KSOM (Millipore) in a humidified atmosphere of 5% CO2 and 95% air at 37° C.

Genome extraction from blastocyst embryos: Following in vitro culture of embryos for 6 days, the expanded blastocysts were washed with 0.01% BSA in PBS and individually collected into 0.2 mL tubes. Five microliters of genome extraction solution (50 mM Tris-HCl, pH 8.0, 0.5% Triton-X100, 1 mg/ml Proteinase K) were added and the samples were incubated in 65° C. for 3 hours followed by 95° C. for 10 min. Samples were then amplified for targeted deep sequencing as described above.

TABLE 2

Primers used for SURVEYOR assays. Related to Experimental Procedures.

| primer name | genomic target | primer sequence (5' to 3') | SEQ ID NO: |
|---|---|---|---|
| SUV901 | EMX1 | CCATCCCCTTCTGTGAATGT | 180 |
| SUV902 | EMX1 | GGAGATTGGAGACACGGAGA | 181 |
| DYRK1A-F | DYRK1A | GGAGCTGGTCTGTTGGAGAA | 198 |
| DYRK1A-R | DYRK1A | TCCCAATCCATAATCCCACGTT | 199 |
| GRIN2B-F | GRIN2B | CAGGAGGGCCAGGAGATTTG | 200 |
| GRIN2B-R | GRIN2B | TGAAATCGAGGATCTGGGCG | 201 |
| F1 | VEGFA | CAAAGGACCCCAGTCACTCC | 202 |
| R1 | VEGFA | GAGGAGGGAGCAGGAAAGTG | 203 |
| F2 | VEGFA | GACACTTCCCAAAGGACCCC | 204 |
| R2 | VEGFA | TGAGAGCCGTTCCCTCTTTG | 205 |
| F3 | VEGFA | GACAGGGGCAAAGTGAGTGA | 206 |
| R3 | VEGFA | TTCATGGTTTCGGAGGCCC | 207 |
| F4 | VEGFA | TGAGTGACCTGCTTTTGGGG | 208 |
| R4 | VEGFA | GTTCATGGTTTCGGAGGCCC | 209 |

TABLE 3

Primers used to generate amplicons for next-generation sequencing. Related to Experimental Procedures.

| primer name | primer sequence (5' to 3') | SEQ ID NO: |
|---|---|---|
| EMX1-F | GGAGGACAAAGTACAAACGGC | 210 |
| EMX1-R | ATCGATGTCCTCCCCATTGG | 211 |
| EMX1-HR-F | CCATCCCCTTCTGTGAATGT | 180 |
| EMX1-HR-R | GGAGATTGGAGACACGGAGA | 181 |
| EMX1-OT1.1-F | TGGGAGAGAGACCCCTTCTT | 212 |
| EMX1-OT1.1-R | TCCTGCTCTCACTTAGACTTTCTC | 213 |
| EMX1-OT1.2-F | GACATTCCTCCTGAGGGAAAA | 214 |
| EMX1-OT1.2-R | GATAAAATGTATTCCTTCTCACCATTC | 215 |
| EMX1-OT1.3-F | CCAGACTCAGTAAAGCCTGGA | 216 |
| EMX1-OT1.3-R | TGGCCCCAGTCTCTCTTCTA | 217 |
| EMX1-OT1.4-F | CACGGCCTTTGCAAATAGAG | 218 |
| EMX1-OT1.4-R | CATGACTTGGCCTTTGTAGGA | 219 |
| EMX1-OT1.5-F | TGGGGTTACAGAAAGAATAGGG | 220 |
| EMX1-OT1.5-R | TTCTGAGGGCTGCTACCTGT | 221 |
| VEGFA-F | TGAAGCAACTCCAGTCCCAA | 222 |
| VEGFA-R | CCCGGCTCTGGCTAAAGAG | 223 |
| VEGFA-OT96.1-F | TGGGTGTGCACATCTAAGGA | 224 |
| VEGFA-OT96.1-R | CCACTGAGTCAACTGTAAGCA | 225 |

TABLE 3-continued

Primers used to generate amplicons for next-generation sequencing.
Related to Experimental Procedures.

| primer name | primer sequence (5' to 3') | SEQ ID NO: |
|---|---|---|
| VEGFA-OT98.1-F | GCAGAGGAATATGTGACATGAGG | 226 |
| VEGFA-OT98.1-R | TACTCCCTGCTGTCCTCTCC | 227 |
| VEGFA-OT98.2-F | TTCCTGGCCAAGTCGATTCC | 228 |
| VEGFA-OT98.2-R | GGATACCAGCATGGGCTACC | 229 |
| VEGFA-OT98.3-F | ACTCTTGAGATTGGAACGGGA | 230 |
| VEGFA-OT98.3-R | CCACACTTATCTACGCCCCA | 231 |
| VEGFA-OT598.4-F | AGCCAGAAGAGAACATCCACG | 232 |
| VEGFA-OT98.4-R | AGTTGCTCTTTGTTGAGAGGGA | 233 |
| MECP2-F | TGACCGGGGACCTATGTATGA | 234 |
| MECP2-R | ACAAGACTTGCTCTTACTTACTTGA | 235 |

TABLE 4

VEGFA off-target site sequences. Related to Experimental Procedures.

| sgRNA | Off-target site | Off-target sequence (5' to 3') | SEQ ID NO: |
|---|---|---|---|
| 96 | OT-96.1 | GGATGGAGGGAGTTTGCTCCTGG | 236 |
| 98 | OT-98.1 | CGCCCTCCCCACCCCGCCTCCGG | 237 |
| 98 | OT-98.2 | TACCCCCACACCCCGCCTCTGG | 238 |
| 98 | OT-98.3 | GGGCCCCTCCACCCCGCCTCTGG | 239 |
| 98 | OT98.4 | CTACCCCTCCACCCCGCCTCGG | 240 |

TABLE 5

Primers used to screen for multiplex nicking induced microdeletion
in the EMX1 locus. Related to Experimental Procedures.

| Deletion size (kb) | Forward primer (5' to 3') | Reverse primer (5' to 3') |
|---|---|---|
| 0.5 | AGGTTGTTGCTGTTGCTTTACA (SEQ ID NO: 241) | AGCACGGTTAATTTGCATACATCT (SEQ ID NO: 243) |
| 1 | AGGTTGTTGCTGTTGCTTTACA (SEQ ID NO: 241) | TCCAGGCAGTTTTCTTCTGGT (SEQ ID NO: 244) |
| 2 | AGGTTGTTGCTGTTGCTTTACA (SEQ ID NO: 241) | CCAGAGAGCCAGCATTCCAA (SEQ ID NO: 245) |
| 6 | AGGTTTCACCTGGTTTGGGG (SEQ ID NO: 242) | AGGGCTCCCACTAGAAGAGG (SEQ ID NO: 246) |

All sequences are in the 5' to 3' direction. For U6 transcription, the string of underlined Ts serve as the transcriptional terminator.

>sgRNA containing +85 tracrRNA (*Streptococcus pyogenes* SF370)

(SEQ ID NO: 247)

gagggcctatttcccatgattccttcatatttgcatatacgatacaaggc tgttagagagataattggaattaatttgactgtaaacacaaagatattag tacaaaatacgtgacgtagaaagtaataatttatgggtagtttgcagttt taaaattatgttttaaaatggactatcatatgcttaccgtaacttgaaag tatttcgatttcttggattatatatcttgtggaaaggacgaaacaccNNN

NNNNNNNNNNNNNNNNNNNNgttttagagctagaaatagcaagttaaaataag gctagtccgttatcaacttgaaaaagtggcaccgagtcggtgcTTTTTTT (guide sequence is the bold stretch of upper case "N"s and the tracrRNA fragment is the sequence in bold before the string of underlined Ts)

>3xFLAG-NLS-SpCas9-NLS (SEQ ID NO: 248)

ATGGACTATAAGGACCACGACGGAGACTACAAGGATCATGATATTGATTACAAAGA

CGATGACGATAAGATGGCCCCAAAGAAGAAGCGGAAGGTCGGTATCCACGGAGTCC

CAGCAGCCGACAAGAAGTACAGCATCGGCCTGGACATCGGCACCAACTCTGTGGGCT

GGGCCGTGATCACCGACGAGTACAAGGTGCCCAGCAAGAAATTCAAGGTGCTGGGC

AACACCGACCGGCACAGCATCAAGAAGAACCTGATCGGAGCCCTGCTGTTCGACAGC

GGCGAAACAGCCGAGGCCACCCGGCTGAAGAGAACCGCCAGAAGAAGATACACCAG

ACGGAAGAACCGGATCTGCTATCTGCAAGAGATCTTCAGCAACGAGATGGCCAAGGT

GGACGACAGCTTCTTCCACAGACTGGAAGAGTCCTTCCTGGTGGAAGAGGATAAGAA

GCACGAGCGGCACCCCATCTTCGGCAACATCGTGGACGAGGTGGCCTACCACGAGAA

GTACCCCACCATCTACCACCTGAGAAAGAAACTGGTGGACAGCACCGACAAGGCCG

ACCTGCGGCTGATCTATCTGGCCCTGGCCCACATGATCAAGTTCCGGGGCCACTTCCT

GATCGAGGGCGACCTGAACCCCGACAACAGCGACGTGGACAAGCTGTTCATCCAGCT

GGTGCAGACCTACAACCAGCTGTTCGAGGAAAACCCCATCAACGCCAGCGGCGTGG

ACGCCAAGGCCATCCTGTCTGCCAGACTGAGCAAGAGCAGACGGCTGGAAAATCTG

ATCGCCCAGCTGCCCGGCGAGAAGAAGAATGGCCTGTTCGGCAACCTGATTGCCCTG

AGCCTGGGCCTGACCCCCAACTTCAAGAGCAACTTCGACCTGGCCGAGGATGCCAAA

CTGCAGCTGAGCAAGGACACCTACGACGACGACCTGGACAACCTGCTGGCCCAGATC

GGCGACCAGTACGCCGACCTGTTTCTGGCCGCCAAGAACCTGTCCGACGCCATCCTG

CTGAGCGACATCCTGAGAGTGAACACCGAGATCACCAAGGCCCCCCTGAGCGCCTCT

ATGATCAAGAGATACGACGAGCACCACCAGGACCTGACCCTGCTGAAAGCTCTCGTG

CGGCAGCAGCTGCCTGAGAAGTACAAAGAGATTTTCTTCGACCAGAGCAAGAACGG

CTACGCCGGCTACATTGACGGCGGAGCCAGCCAGGAAGAGTTCTACAAGTTCATCAA

GCCCATCCTGGAAAAGATGGACGGCACCGAGGAACTGCTCGTGAAGCTGAACAGAG

AGGACCTGCTGCGGAAGCAGCGGACCTTCGACAACGGCAGCATCCCCCACCAGATCC

ACCTGGGAGAGCTGCACGCCATTCTGCGGCGGCAGGAAGATTTTTACCCATTCCTGA

AGGACAACCGGGAAAAGATCGAGAAGATCCTGACCTTCCGCATCCCCTACTACGTGG

GCCCTCTGGCCAGGGGAAACAGCAGATTCGCCTGGATGACCAGAAAGAGCGAGGAA

ACCATCACCCCCTGGAACTTCGAGGAAGTGGTGGACAAGGGCGCTTCCGCCCAGAGC

TTCATCGAGCGGATGACCAACTTCGATAAGAACCTGCCCAACGAGAAGGTGCTGCCC

AAGCACAGCCTGCTGTACGAGTACTTCACCGTGTATAACGAGCTGACCAAAGTGAAA

TACGTGACCGAGGGAATGAGAAAGCCCGCCTTCCTGAGCGGCGAGCAGAAAAAGGC

CATCGTGGACCTGCTGTTCAAGACCAACCGGAAAGTGACCGTGAAGCAGCTGAAAG

-continued

```
AGGACTACTTCAAGAAAATCGAGTGCTTCGACTCCGTGGAAATCTCCGGCGTGGAAG
ATCGGTTCAACGCCTCCCTGGGCACATACCACGATCTGCTGAAAATTATCAAGGACA
AGGACTTCCTGGACAATGAGGAAAACGAGGACATTCTGGAAGATATCGTGCTGACCC
TGACACTGTTTGAGGACAGAGAGATGATCGAGGAACGGCTGAAAACCTATGCCCACC
TGTTCGACGACAAAGTGATGAAGCAGCTGAAGCGGCGGAGATACACCGGCTGGGGC
AGGCTGAGCCGGAAGCTGATCAACGGCATCCGGGACAAGCAGTCCGGCAAGACAAT
CCTGGATTTCCTGAAGTCCGACGGCTTCGCCAACAGAAACTTCATGCAGCTGATCCA
CGACGACAGCCTGACCTTTAAAGAGGACATCCAGAAAGCCCAGGTGTCCGGCCAGG
GCGATAGCCTGCACGAGCACATTGCCAATCTGGCCGGCAGCCCCGCCATTAAGAAGG
GCATCCTGCAGACAGTGAAGGTGGTGGACGAGCTCGTGAAAGTGATGGGCCGGCAC
AAGCCCGAGAACATCGTGATCGAAATGGCCAGAGAGAACCAGACCACCCAGAAGGG
ACAGAAGAACAGCCGCGAGAGAATGAAGCGGATCGAAGAGGGCATCAAAGAGCTG
GGCAGCCAGATCCTGAAAGAACACCCCGTGGAAAACACCCAGCTGCAGAACGAGAA
GCTGTACCTGTACTACCTGCAGAATGGGCGGGATATGTACGTGGACCAGGAACTGGA
CATCAACCGGCTGTCCGACTACGATGTGGACCATATCGTGCCTCAGAGCTTTCTGAA
GGACGACTCCATCGACAACAAGGTGCTGACCAGAAGCGACAAGAACCGGGGCAAGA
GCGACAACGTGCCCTCCGAAGAGGTCGTGAAGAAGATGAAGAACTACTGGCGGCAG
CTGCTGAACGCCAAGCTGATTACCCAGAGAAAGTTCGACAATCTGACCAAGGCCGAG
AGAGGCGGCCTGAGCGAACTGGATAAGGCCGGCTTCATCAAGAGACAGCTGGTGGA
AACCCGGCAGATCACAAAGCACGTGGCACAGATCCTGGACTCCCGGATGAACACTA
AGTACGACGAGAATGACAAGCTGATCCGGGAAGTGAAAGTGATCACCCTGAAGTCC
AAGCTGGTGTCCGATTTCCGGAAGGATTTCCAGTTTTACAAAGTGCGCGAGATCAAC
AACTACCACCACGCCCACGACGCCTACCTGAACGCCGTCGTGGGAACCGCCCTGATC
AAAAAGTACCCTAAGCTGGAAAGCGAGTTCGTGTACGGCGACTACAAGGTGTACGA
CGTGCGGAAGATGATCGCCAAGAGCGAGCAGGAAATCGGCAAGGCTACCGCCAAGT
ACTTCTTCTACAGCAACATCATGAACTTTTTCAAGACCGAGATTACCCTGGCCAACGG
CGAGATCCGGAAGCGGCCTCTGATCGAGACAAACGGCGAAACCGGGGAGATCGTGT
GGGATAAGGGCCGGGATTTTGCCACCGTGCGGAAAGTGCTGAGCATGCCCCAAGTGA
ATATCGTGAAAAAGACCGAGGTGCAGACAGGCGGCTTCAGCAAAGAGTCTATCCTGC
CCAAGAGGAACAGCGATAAGCTGATCGCCAGAAAGAAGGACTGGGACCCTAAGAAG
TACGGCGGCTTCGACAGCCCCACCGTGGCCTATTCTGTGCTGGTGGTGGCCAAAGTG
GAAAAGGGCAAGTCCAAGAAACTGAAGAGTGTGAAAGAGCTGCTGGGGATCACCAT
CATGGAAAGAAGCAGCTTCGAGAAGAATCCCATCGACTTTCTGGAAGCCAAGGGCTA
CAAAGAAGTGAAAAAGGACCTGATCATCAAGCTGCCTAAGTACTCCCTGTTCGAGCT
GGAAAACGGCCGGAAGAGAATGCTGGCCTCTGCCGGCGAACTGCAGAAGGGAAACG
AACTGGCCCTGCCCTCCAAATATGTGAACTTCCTGTACCTGGCCAGCCACTATGAGA
AGCTGAAGGGCTCCCCCGAGGATAATGAGCAGAAACAGCTGTTTGTGGAACAGCAC
AAGCACTACCTGGACGAGATCATCGAGCAGATCAGCGAGTTCTCCAAGAGAGTGATC
CTGGCCGACGCTAATCTGGACAAAGTGCTGTCCGCCTACAACAAGCACCGGGATAAG
CCCATCAGAGAGCAGGCCGAGAATATCATCCACCTGTTTACCCTGACCAATCTGGGA
```

-continued

GCCCCTGCCGCCTTCAAGTACTTTGACACCACCATCGACCGGAAGAGGTACACCAGC

ACCAAAGAGGTGCTGGACGCCACCCTGATCCACCAGAGCATCACCGGCCTGTACGAG

ACACGGATCGACCTGTCTCAGCTGGGAGGCGACAAGCGTCCTGCTGCTACTAAGAAA

GCTGGTCAAGCTAAGAAAAAGAAA

>3xFLAG-NLS-SpCas9n-NLS (the D10A nickase mutation is
highlighted in bold)

(SEQ ID NO: 249)

ATGGACTATAAGGACCACGACGGAGACTACAAGGATCATGATATTGATTACAAAGA

CGATGACGATAAGATGGCCCCAAAGAAGAAGCGGAAGGTCGGTATCCACGGAGTCC

CAGCAGCCGACAAGAAGTACAGCATCGGCCTGGCCATCGGCACCAACTCTGTGGGC

TGGGCCGTGATCACCGACGAGTACAAGGTGCCCAGCAAGAAATTCAAGGTGCTGGG

CAACACCGACCGGCACAGCATCAAGAAGAACCTGATCGGAGCCCTGCTGTTCGACAG

CGGCGAAACAGCCGAGGCCACCCGGCTGAAGAGAACCGCCAGAAGAAGATACACCA

GACGGAAGAACCGGATCTGCTATCTGCAAGAGATCTTCAGCAACGAGATGGCCAAG

GTGGACGACAGCTTCTTCCACAGACTGGAAGAGTCCTTCCTGGTGGAAGAGGATAAG

AAGCACGAGCGGCACCCCATCTTCGGCAACATCGTGGACGAGGTGGCCTACCACGAG

AAGTACCCCACCATCTACCACCTGAGAAAGAAACTGGTGGACAGCACCGACAAGGC

CGACCTGCGGCTGATCTATCTGGCCCTGGCCCACATGATCAAGTTCCGGGGCCACTTC

CTGATCGAGGGCGACCTGAACCCCGACAACAGCGACGTGGACAAGCTGTTCATCCAG

CTGGTGCAGACCTACAACCAGCTGTTCGAGGAAAACCCCATCAACGCCAGCGGCGTG

GACGCCAAGGCCATCCTGTCTGCCAGACTGAGCAAGAGCAGACGGCTGGAAAATCT

GATCGCCCAGCTGCCCGGCGAGAAGAAGAATGGCCTGTTCGGCAACCTGATTGCCCT

GAGCCTGGGCCTGACCCCCAACTTCAAGAGCAACTTCGACCTGGCCGAGGATGCCAA

ACTGCAGCTGAGCAAGGACACCTACGACGACGACCTGGACAACCTGCTGGCCCAGAT

CGGCGACCAGTACGCCGACCTGTTTCTGGCCGCCAAGAACCTGTCCGACGCCATCCT

GCTGAGCGACATCCTGAGAGTGAACACCGAGATCACCAAGGCCCCCCTGAGCGCCTC

TATGATCAAGAGATACGACGAGCACCACCAGGACCTGACCCTGCTGAAAGCTCTCGT

GCGGCAGCAGCTGCCTGAGAAGTACAAAGAGATTTTCTTCGACCAGAGCAAGAACG

GCTACGCCGGCTACATTGACGGCGGAGCCAGCCAGGAAGAGTTCTACAAGTTCATCA

AGCCCATCCTGGAAAAGATGGACGGCACCGAGGAACTGCTCGTGAAGCTGAACAGA

GAGGACCTGCTGCGGAAGCAGCGGACCTTCGACAACGGCAGCATCCCCCACCAGATC

CACCTGGGAGAGCTGCACGCCATTCTGCGGCGGCAGGAAGATTTTTACCCATTCCTG

AAGGACAACCGGGAAAAGATCGAGAAGATCCTGACCTTCCGCATCCCCTACTACGTG

GGCCCTCTGGCCAGGGGAAACAGCAGATTCGCCTGGATGACCAGAAAGAGCGAGGA

AACCATCACCCCCTGGAACTTCGAGGAAGTGGTGGACAAGGGCGCTTCCGCCCAGAG

CTTCATCGAGCGGATGACCAACTTCGATAAGAACCTGCCCAACGAGAAGGTGCTGCC

CAAGCACAGCCTGCTGTACGAGTACTTCACCGTGTATAACGAGCTGACCAAAGTGAA

ATACGTGACCGAGGGAATGAGAAAGCCCGCCTTCCTGAGCGGCGAGCAGAAAAAGG

CCATCGTGGACCTGCTGTTCAAGACCAACCGGAAAGTGACCGTGAAGCAGCTGAAAG

AGGACTACTTCAAGAAAATCGAGTGCTTCGACTCCGTGGAAATCTCCGGCGTGGAAG

ATCGGTTCAACGCCTCCCTGGGCACATACCACGATCTGCTGAAAATTATCAAGGACA

AGGACTTCCTGGACAATGAGGAAAACGAGGACATTCTGGAAGATATCGTGCTGACCC

-continued

```
TGACACTGTTTGAGGACAGAGAGATGATCGAGGAACGGCTGAAAACCTATGCCCACC
TGTTCGACGACAAAGTGATGAAGCAGCTGAAGCGGCGGAGATACACCGGCTGGGGC
AGGCTGAGCCGGAAGCTGATCAACGGCATCCGGGACAAGCAGTCCGGCAAGACAAT
CCTGGATTTCCTGAAGTCCGACGGCTTCGCCAACAGAAACTTCATGCAGCTGATCCA
CGACGACAGCCTGACCTTTAAAGAGGACATCCAGAAAGCCCAGGTGTCCGGCCAGG
GCGATAGCCTGCACGAGCACATTGCCAATCTGGCCGGCAGCCCCGCCATTAAGAAGG
GCATCCTGCAGACAGTGAAGGTGGTGGACGAGCTCGTGAAAGTGATGGGCCGGCAC
AAGCCCGAGAACATCGTGATCGAAATGGCCAGAGAGAACCAGACCACCCAGAAGGG
ACAGAAGAACAGCCGCGAGAGAATGAAGCGGATCGAAGAGGGCATCAAAGAGCTG
GGCAGCCAGATCCTGAAAGAACACCCCGTGGAAAACACCCAGCTGCAGAACGAGAA
GCTGTACCTGTACTACCTGCAGAATGGGCGGGATATGTACGTGGACCAGGAACTGGA
CATCAACCGGCTGTCCGACTACGATGTGGACCATATCGTGCCTCAGAGCTTTCTGAA
GGACGACTCCATCGACAACAAGGTGCTGACCAGAAGCGACAAGAACCGGGGCAAGA
GCGACAACGTGCCCTCCGAAGAGGTCGTGAAGAAGATGAAGAACTACTGGCGGCAG
CTGCTGAACGCCAAGCTGATTACCCAGAGAAAGTTCGACAATCTGACCAAGGCCGAG
AGAGGCGGCCTGAGCGAACTGGATAAGGCCGGCTTCATCAAGAGACAGCTGGTGGA
AACCCGGCAGATCACAAAGCACGTGGCACAGATCCTGGACTCCCGGATGAACACTA
AGTACGACGAGAATGACAAGCTGATCCGGGAAGTGAAAGTGATCACCCTGAAGTCC
AAGCTGGTGTCCGATTTCCGGAAGGATTTCCAGTTTTACAAAGTGCGCGAGATCAAC
AACTACCACCACGCCCACGACGCCTACCTGAACGCCGTCGTGGGAACCGCCCTGATC
AAAAAGTACCCTAAGCTGGAAAGCGAGTTCGTGTACGGCGACTACAAGGTGTACGA
CGTGCGGAAGATGATCGCCAAGAGCGAGCAGGAAATCGGCAAGGCTACCGCCAAGT
ACTTCTTCTACAGCAACATCATGAACTTTTTCAAGACCGAGATTACCCTGGCCAACGG
CGAGATCCGGAAGCGGCCTCTGATCGAGACAAACGGCGAAACCGGGGAGATCGTGT
GGGATAAGGGCCGGGATTTTGCCACCGTGCGGAAAGTGCTGAGCATGCCCCAAGTGA
ATATCGTGAAAAAGACCGAGGTGCAGACAGGCGGCTTCAGCAAAGAGTCTATCCTGC
CCAAGAGGAACAGCGATAAGCTGATCGCCAGAAAGAAGGACTGGGACCCTAAGAAG
TACGGCGGCTTCGACAGCCCCACCGTGGCCTATTCTGTGCTGGTGGTGGCCAAAGTG
GAAAAGGGCAAGTCCAAGAAACTGAAGAGTGTGAAAGAGCTGCTGGGGATCACCAT
CATGGAAAGAAGCAGCTTCGAGAAGAATCCCATCGACTTTCTGGAAGCCAAGGGCTA
CAAAGAAGTGAAAAAGGACCTGATCATCAAGCTGCCTAAGTACTCCCTGTTCGAGCT
GGAAAACGGCCGGAAGAGAATGCTGGCCTCTGCCGGCGAACTGCAGAAGGGAAACG
AACTGGCCCTGCCCTCCAAATATGTGAACTTCCTGTACCTGGCCAGCCACTATGAGA
AGCTGAAGGGCTCCCCCGAGGATAATGAGCAGAAACAGCTGTTTGTGGAACAGCAC
AAGCACTACCTGGACGAGATCATCGAGCAGATCAGCGAGTTCTCCAAGAGAGTGATC
CTGGCCGACGCTAATCTGGACAAAGTGCTGTCCGCCTACAACAAGCACCGGGATAAG
CCCATCAGAGAGCAGGCCGAGAATATCATCCACCTGTTTACCCTGACCAATCTGGGA
GCCCCTGCCGCCTTCAAGTACTTTGACACCACCATCGACCGGAAGAGGTACACCAGC
ACCAAAGAGGTGCTGGACGCCACCCTGATCCACCAGAGCATCACCGGCCTGTACGAG
ACACGGATCGACCTGTCTCAGCTGGGAGGCGACAAGCGTCCTGCTGCTACTAAGAAA
GCTGGTCAAGCTAAGAAAAGAAA
```

-continued

T7-SpCas9-NLS (T7 promoter is underlined)

(SEQ ID NO: 250)

GCCACCGGT<u>TAATACGACTCACTATA</u>GGGCCACCATGGACTATAAGGACCACGACGG

AGACTACAAGGATCATGATATTGATTACAAAGACGATGACGATAAGATGGCCCCAA

AGAAGAAGCGGAAGGTCGGTATCCACGGAGTCCCAGCAGCCGACAAGAAGTACAGC

ATCGGCCTGGACATCGGCACCAACTCTGTGGGCTGGGCCGTGATCACCGACGAGTAC

AAGGTGCCCAGCAAGAAATTCAAGGTGCTGGGCAACACCGACCGGCACAGCATCAA

GAAGAACCTGATCGGAGCCCTGCTGTTCGACAGCGGCGAAACAGCCGAGGCCACCC

GGCTGAAGAGAACCGCCAGAAGAAGATACACCAGACGGAAGAACCGGATCTGCTAT

CTGCAAGAGATCTTCAGCAACGAGATGGCCAAGGTGGACGACAGCTTCTTCCACAGA

CTGGAAGAGTCCTTCCTGGTGGAAGAGGATAAGAAGCACGAGCGGCACCCCATCTTC

GGCAACATCGTGGACGAGGTGGCCTACCACGAGAAGTACCCCACCATCTACCACCTG

AGAAAGAAACTGGTGGACAGCACCGACAAGGCCGACCTGCGGCTGATCTATCTGGC

CCTGGCCCACATGATCAAGTTCCGGGGCCACTTCCTGATCGAGGGCGACCTGAACCC

CGACAACAGCGACGTGGACAAGCTGTTCATCCAGCTGGTGCAGACCTACAACCAGCT

GTTCGAGGAAAACCCCATCAACGCCAGCGGCGTGGACGCCAAGGCCATCCTGTCTGC

CAGACTGAGCAAGAGCAGACGGCTGGAAAATCTGATCGCCCAGCTGCCCGGCGAGA

AGAAGAATGGCCTGTTCGGCAACCTGATTGCCCTGAGCCTGGGCCTGACCCCCAACT

TCAAGAGCAACTTCGACCTGGCCGAGGATGCCAAACTGCAGCTGAGCAAGGACACCT

ACGACGACGACCTGGACAACCTGCTGGCCCAGATCGGCGACCAGTACGCCGACCTGT

TTCTGGCCGCCAAGAACCTGTCCGACGCCATCCTGCTGAGCGACATCCTGAGAGTGA

ACACCGAGATCACCAAGGCCCCCCTGAGCGCCTCTATGATCAAGAGATACGACGAGC

ACCACCAGGACCTGACCCTGCTGAAAGCTCTCGTGCGGCAGCAGCTGCCTGAGAAGT

ACAAAGAGATTTTCTTCGACCAGAGCAAGAACGGCTACGCCGGCTACATTGACGGCG

GAGCCAGCCAGGAAGAGTTCTACAAGTTCATCAAGCCCATCCTGGAAAAGATGGAC

GGCACCGAGGAACTGCTCGTGAAGCTGAACAGAGAGGACCTGCTGCGGAAGCAGCG

GACCTTCGACAACGGCAGCATCCCCCACCAGATCCACCTGGGAGAGCTGCACGCCAT

TCTGCGGCGGCAGGAAGATTTTTACCCATTCCTGAAGGACAACCGGGAAAAGATCGA

GAAGATCCTGACCTTCCGCATCCCCTACTACGTGGGCCCTCTGGCCAGGGGAAACAG

CAGATTCGCCTGGATGACCAGAAAGAGCGAGGAAACCATCACCCCCTGGAACTTCGA

GGAAGTGGTGGACAAGGGCGCTTCCGCCCAGAGCTTCATCGAGCGGATGACCAACTT

CGATAAGAACCTGCCCAACGAGAAGGTGCTGCCCAAGCACAGCCTGCTGTACGAGTA

CTTCACCGTGTATAACGAGCTGACCAAAGTGAAATACGTGACCGAGGGAATGAGAA

AGCCCGCCTTCCTGAGCGGCGAGCAGAAAAAGGCCATCGTGGACCTGCTGTTCAAGA

CCAACCGGAAAGTGACCGTGAAGCAGCTGAAAGAGGACTACTTCAAGAAAATCGAG

TGCTTCGACTCCGTGGAAATCTCCGGCGTGGAAGATCGGTTCAACGCCTCCCTGGGC

ACATACCACGATCTGCTGAAAATTATCAAGGACAAGGACTTCCTGGACAATGAGGAA

AACGAGGACATTCTGGAAGATATCGTGCTGACCCTGACACTGTTTGAGGACAGAGAG

ATGATCGAGGAACGGCTGAAAACCTATGCCCACCTGTTCGACGACAAAGTGATGAAG

CAGCTGAAGCGGCGGAGATACACCGGCTGGGGCAGGCTGAGCCGGAAGCTGATCAA

CGGCATCCGGGACAAGCAGTCCGGCAAGACAATCCTGGATTTCCTGAAGTCCGACGG

-continued

```
CTTCGCCAACAGAAACTTCATGCAGCTGATCCACGACGACAGCCTGACCTTTAAAGA

GGACATCCAGAAAGCCCAGGTGTCCGGCCAGGGCGATAGCCTGCACGAGCACATTG

CCAATCTGGCCGGCAGCCCCGCCATTAAGAAGGGCATCCTGCAGACAGTGAAGGTGG

TGGACGAGCTCGTGAAAGTGATGGGCCGGCACAAGCCCGAGAACATCGTGATCGAA

ATGGCCAGAGAGAACCAGACCACCCAGAAGGGACAGAAGAACAGCCGCGAGAGAA

TGAAGCGGATCGAAGAGGGCATCAAAGAGCTGGGCAGCCAGATCCTGAAAGAACAC

CCCGTGGAAAACACCCAGCTGCAGAACGAGAAGCTGTACCTGTACTACCTGCAGAAT

GGGCGGGATATGTACGTGGACCAGGAACTGGACATCAACCGGCTGTCCGACTACGAT

GTGGACCATATCGTGCCTCAGAGCTTTCTGAAGGACGACTCCATCGACAACAAGGTG

CTGACCAGAAGCGACAAGAACCGGGGCAAGAGCGACAACGTGCCCTCCGAAGAGGT

CGTGAAGAAGATGAAGAACTACTGGCGGCAGCTGCTGAACGCCAAGCTGATTACCC

AGAGAAAGTTCGACAATCTGACCAAGGCCGAGAGAGGCGGCCTGAGCGAACTGGAT

AAGGCCGGCTTCATCAAGAGACAGCTGGTGGAAACCCGGCAGATCACAAAGCACGT

GGCACAGATCCTGGACTCCCGGATGAACACTAAGTACGACGAGAATGACAAGCTGA

TCCGGGAAGTGAAAGTGATCACCCTGAAGTCCAAGCTGGTGTCCGATTTCCGGAAGG

ATTTCCAGTTTTACAAAGTGCGCGAGATCAACAACTACCACCACGCCCACGACGCCT

ACCTGAACGCCGTCGTGGGAACCGCCCTGATCAAAAAGTACCCTAAGCTGGAAAGCG

AGTTCGTGTACGGCGACTACAAGGTGTACGACGTGCGGAAGATGATCGCCAAGAGC

GAGCAGGAAATCGGCAAGGCTACCGCCAAGTACTTCTTCTACAGCAACATCATGAAC

TTTTTCAAGACCGAGATTACCCTGGCCAACGGCGAGATCCGGAAGCGGCCTCTGATC

GAGACAAACGGCGAAACCGGGGAGATCGTGTGGGATAAGGGCCGGGATTTTGCCAC

CGTGCGGAAAGTGCTGAGCATGCCCCAAGTGAATATCGTGAAAAAGACCGAGGTGC

AGACAGGCGGCTTCAGCAAAGAGTCTATCCTGCCCAAGAGGAACAGCGATAAGCTG

ATCGCCAGAAAGAAGGACTGGGACCCTAAGAAGTACGGCGGCTTCGACAGCCCCAC

CGTGGCCTATTCTGTGCTGGTGGTGGCCAAAGTGGAAAAGGGCAAGTCCAAGAAACT

GAAGAGTGTGAAAGAGCTGCTGGGGATCACCATCATGGAAAGAAGCAGCTTCGAGA

AGAATCCCATCGACTTTCTGGAAGCCAAGGGCTACAAAGAAGTGAAAAAGGACCTG

ATCATCAAGCTGCCTAAGTACTCCCTGTTCGAGCTGGAAAACGGCCGGAAGAGAATG

CTGGCCTCTGCCGGCGAACTGCAGAAGGGAAACGAACTGGCCCTGCCCTCCAAATAT

GTGAACTTCCTGTACCTGGCCAGCCACTATGAGAAGCTGAAGGGCTCCCCCGAGGAT

AATGAGCAGAAACAGCTGTTTGTGGAACAGCACAAGCACTACCTGGACGAGATCATC

GAGCAGATCAGCGAGTTCTCCAAGAGAGTGATCCTGGCCGACGCTAATCTGGACAAA

GTGCTGTCCGCCTACAACAAGCACCGGGATAAGCCCATCAGAGAGCAGGCCGAGAA

TATCATCCACCTGTTTACCCTGACCAATCTGGGAGCCCCTGCCGCCTTCAAGTACTTT

GACACCACCATCGACCGGAAGAGGTACACCAGCACCAAAGAGGTGCTGGACGCCAC

CCTGATCCACCAGAGCATCACCGGCCTGTACGAGACACGGATCGACCTGTCTCAGCT

GGGAGGCGACAAAAGGCCGGCGGCCACGAAAAAGGCCGGCCAGGCAAAAAAGAAA

AAGTAAGAAAAAAAAAAAAAAAAAAAAAAAAAAAAAAAAACC
```

-continued

T7-SpCas9n-NLS (D10A nickase mutation is highlighted in bold; T7 promoter is underlined)

(SEQ ID NO: 251)

GCCACCGGT<u>TAATACGACTCACTATA</u>GGGCCACCATGGACTATAAGGACCACGACGG

AGACTACAAGGATCATGATATTGATTACAAAGACGATGACGATAAGATGGCCCCAA

AGAAGAAGCGGAAGGTCGGTATCCACGGAGTCCCAGCAGCCGACAAGAAGTACAGC

ATCGGCCTGGCCATCGGCACCAACTCTGTGGGCTGGGCCGTGATCACCGACGAGTAC

AAGGTGCCCAGCAAGAAATTCAAGGTGCTGGGCAACACCGACCGGCACAGCATCAA

GAAGAACCTGATCGGAGCCCTGCTGTTCGACAGCGGCGAAACAGCCGAGGCCACCC

GGCTGAAGAGAACCGCCAGAAGAAGATACACCAGACGGAAGAACCGGATCTGCTAT

CTGCAAGAGATCTTCAGCAACGAGATGGCCAAGGTGGACGACAGCTTCTTCCACAGA

CTGGAAGAGTCCTTCCTGGTGGAAGAGGATAAGAAGCACGAGCGGCACCCCATCTTC

GGCAACATCGTGGACGAGGTGGCCTACCACGAGAAGTACCCCACCATCTACCACCTG

AGAAAGAAACTGGTGGACAGCACCGACAAGGCCGACCTGCGGCTGATCTATCTGGC

CCTGGCCCACATGATCAAGTTCCGGGGCCACTTCCTGATCGAGGGCGACCTGAACCC

CGACAACAGCGACGTGGACAAGCTGTTCATCCAGCTGGTGCAGACCTACAACCAGCT

GTTCGAGGAAAACCCCATCAACGCCAGCGGCGTGGACGCCAAGGCCATCCTGTCTGC

CAGACTGAGCAAGAGCAGACGGCTGGAAAATCTGATCGCCCAGCTGCCCGGCGAGA

AGAAGAATGGCCTGTTCGGCAACCTGATTGCCCTGAGCCTGGGCCTGACCCCCAACT

TCAAGAGCAACTTCGACCTGGCCGAGGATGCCAAACTGCAGCTGAGCAAGGACACCT

ACGACGACGACCTGGACAACCTGCTGGCCCAGATCGGCGACCAGTACGCCGACCTGT

TTCTGGCCGCCAAGAACCTGTCCGACGCCATCCTGCTGAGCGACATCCTGAGAGTGA

ACACCGAGATCACCAAGGCCCCCCTGAGCGCCTCTATGATCAAGAGATACGACGAGC

ACCACCAGGACCTGACCCTGCTGAAAGCTCTCGTGCGGCAGCAGCTGCCTGAGAAGT

ACAAAGAGATTTTCTTCGACCAGAGCAAGAACGGCTACGCCGGCTACATTGACGGCG

GAGCCAGCCAGGAAGAGTTCTACAAGTTCATCAAGCCCATCCTGGAAAAGATGGAC

GGCACCGAGGAACTGCTCGTGAAGCTGAACAGAGAGGACCTGCTGCGGAAGCAGCG

GACCTTCGACAACGGCAGCATCCCCCACCAGATCCACCTGGGAGAGCTGCACGCCAT

TCTGCGGCGGCAGGAAGATTTTTACCCATTCCTGAAGGACAACCGGGAAAAGATCGA

GAAGATCCTGACCTTCCGCATCCCCTACTACGTGGGCCCTCTGGCCAGGGGAAACAG

CAGATTCGCCTGGATGACCAGAAAGAGCGAGGAAACCATCACCCCCTGGAACTTCGA

GGAAGTGGTGGACAAGGGCGCTTCCGCCCAGAGCTTCATCGAGCGGATGACCAACTT

CGATAAGAACCTGCCCAACGAGAAGGTGCTGCCCAAGCACAGCCTGCTGTACGAGTA

CTTCACCGTGTATAACGAGCTGACCAAAGTGAAATACGTGACCGAGGGAATGAGAA

AGCCCGCCTTCCTGAGCGGCGAGCAGAAAAAGGCCATCGTGGACCTGCTGTTCAAGA

CCAACCGGAAAGTGACCGTGAAGCAGCTGAAAGAGGACTACTTCAAGAAAATCGAG

TGCTTCGACTCCGTGGAAATCTCCGGCGTGGAAGATCGGTTCAACGCCTCCCTGGGC

ACATACCACGATCTGCTGAAAATTATCAAGGACAAGGACTTCCTGGACAATGAGGAA

AACGAGGACATTCTGGAAGATATCGTGCTGACCCTGACACTGTTTGAGGACAGAGAG

ATGATCGAGGAACGGCTGAAAACCTATGCCCACCTGTTCGACGACAAAGTGATGAAG

CAGCTGAAGCGGCGGAGATACACCGGCTGGGGCAGGCTGAGCCGGAAGCTGATCAA

CGGCATCCGGGACAAGCAGTCCGGCAAGACAATCCTGGATTTCCTGAAGTCCGACGG

-continued

```
CTTCGCCAACAGAAACTTCATGCAGCTGATCCACGACGACAGCCTGACCTTTAAAGA

GGACATCCAGAAAGCCCAGGTGTCCGGCCAGGGCGATAGCCTGCACGAGCACATTG

CCAATCTGGCCGGCAGCCCCGCCATTAAGAAGGGCATCCTGCAGACAGTGAAGGTGG

TGGACGAGCTCGTGAAAGTGATGGGCCGGCACAAGCCCGAGAACATCGTGATCGAA

ATGGCCAGAGAGAACCAGACCACCCAGAAGGGACAGAAGAACAGCCGCGAGAGAA

TGAAGCGGATCGAAGAGGGCATCAAAGAGCTGGGCAGCCAGATCCTGAAAGAACAC

CCCGTGGAAAACACCCAGCTGCAGAACGAGAAGCTGTACCTGTACTACCTGCAGAAT

GGGCGGGATATGTACGTGGACCAGGAACTGGACATCAACCGGCTGTCCGACTACGAT

GTGGACCATATCGTGCCTCAGAGCTTTCTGAAGGACGACTCCATCGACAACAAGGTG

CTGACCAGAAGCGACAAGAACCGGGGCAAGAGCGACAACGTGCCCTCCGAAGAGGT

CGTGAAGAAGATGAAGAACTACTGGCGGCAGCTGCTGAACGCCAAGCTGATTACCC

AGAGAAAGTTCGACAATCTGACCAAGGCCGAGAGAGGCGGCCTGAGCGAACTGGAT

AAGGCCGGCTTCATCAAGAGACAGCTGGTGGAAACCCGGCAGATCACAAAGCACGT

GGCACAGATCCTGGACTCCCGGATGAACACTAAGTACGACGAGAATGACAAGCTGA

TCCGGGAAGTGAAAGTGATCACCCTGAAGTCCAAGCTGGTGTCCGATTTCCGGAAGG

ATTTCCAGTTTTACAAAGTGCGCGAGATCAACAACTACCACCACGCCCACGACGCCT

ACCTGAACGCCGTCGTGGGAACCGCCCTGATCAAAAAGTACCCTAAGCTGGAAAGCG

AGTTCGTGTACGGCGACTACAAGGTGTACGACGTGCGGAAGATGATCGCCAAGAGC

GAGCAGGAAATCGGCAAGGCTACCGCCAAGTACTTCTTCTACAGCAACATCATGAAC

TTTTTCAAGACCGAGATTACCCTGGCCAACGGCGAGATCCGGAAGCGGCCTCTGATC

GAGACAAACGGCGAAACCGGGGAGATCGTGTGGGATAAGGGCCGGGATTTTGCCAC

CGTGCGGAAAGTGCTGAGCATGCCCCAAGTGAATATCGTGAAAAAGACCGAGGTGC

AGACAGGCGGCTTCAGCAAAGAGTCTATCCTGCCCAAGAGGAACAGCGATAAGCTG

ATCGCCAGAAAGAAGGACTGGGACCCTAAGAAGTACGGCGGCTTCGACAGCCCCAC

CGTGGCCTATTCTGTGCTGGTGGTGGCCAAAGTGGAAAAGGGCAAGTCCAAGAAACT

GAAGAGTGTGAAAGAGCTGCTGGGGATCACCATCATGGAAAGAAGCAGCTTCGAGA

AGAATCCCATCGACTTTCTGGAAGCCAAGGGCTACAAAGAAGTGAAAAAGGACCTG

ATCATCAAGCTGCCTAAGTACTCCCTGTTCGAGCTGGAAAACGGCCGGAAGAGAATG

CTGGCCTCTGCCGGCGAACTGCAGAAGGGAAACGAACTGGCCCTGCCCTCCAAATAT

GTGAACTTCCTGTACCTGGCCAGCCACTATGAGAAGCTGAAGGGCTCCCCCGAGGAT

AATGAGCAGAAACAGCTGTTTGTGGAACAGCACAAGCACTACCTGGACGAGATCATC

GAGCAGATCAGCGAGTTCTCCAAGAGAGTGATCCTGGCCGACGCTAATCTGGACAAA

GTGCTGTCCGCCTACAACAAGCACCGGGATAAGCCCATCAGAGAGCAGGCCGAGAA

TATCATCCACCTGTTTACCCTGACCAATCTGGGAGCCCCTGCCGCCTTCAAGTACTTT

GACACCACCATCGACCGGAAGAGGTACACCAGCACCAAAGAGGTGCTGGACGCCAC

CCTGATCCACCAGAGCATCACCGGCCTGTACGAGACACGGATCGACCTGTCTCAGCT

GGGAGGCGACAAAAGGCCGGCGGCCACGAAAAAGGCCGGCCAGGCAAAAAAGAAA

AAGTAAGAAAAAAAAAAAAAAAAAAAAAAAAAAAAAAAAACC
```

-continued

```
>dsODN ligation insert fwd
                                              (SEQ ID NO: 252)
AGCAGGCCAATGGGGAGGACATCGATGTCACCTCCAATGACTAcTACCCATACGATG

TTCCAGATTACGCTATGGACTATAAGGACCACGACGGAGACTACAAGGATCATGATA

TTGATTACAAAGACGATGACGATAAGaagcttgaaATGGCATCAATGCAGAAGCTGATCT

CAGAGGAGGACCTGtaa

>dsODN ligation insert rev
                                              (SEQ ID NO: 253)
TAGTCATTGGAGGTGACATCGATGTCCTCCCCATTGGCCTGCTTTACAGGTCCTCCTC

TGAGATCAGCTTCTGCATTGATGCCATTTCAAGCTTCTTATCGTCATCGTCTTTGTAAT

CAATATCATGATCCTTGTAGTCTCCGTCGTGGTCCTTATAGTCCATAGCGTAATCTGG

AACATCGTATGGGTAG
```

Example 32: Further Characterization of Double Nicking by RNA-Guided CRISPR Cas9

Double nicking specificity: The targeting space for Cas9 multiplexed nicking can be increased by exploiting a relaxation in the stringency of Cas9 PAM recognition when the target DNA is targeted by multiple guide RNAs (sgRNAs). Applicants have demonstrated in Example 31 (Ran et al., Double nicking by RNA-guided CRISPR Cas9 for enhanced genome editing specificity, Cell. 2013 Sep. 12; 154(6):1380-9) that two appropriately offset sgRNAs can be targeted within a specific 'sgRNA offset' parameter to generate indels. Applicants demonstrate that efficient indels can be formed when offset sgRNAs are targeted with non-NGG PAMs (in particular NGN and NNG). It appears that Cas9 can potentially tolerate a shifted PAM or a PAM with only one G nucleotide in the 2nd or 3rd PAM base positions.

Cas9 mutagenesis for double nicking: Applicants tested the ability of Cas9 nickase mutants to generate indels when targeted by only one sgRNA. Single-stranded DNA breaks are repaired through high fidelity, non-NHEJ repair pathways. However, work by other groups may suggest significant mutagenesis by the Cas9(D10A) nickase and one sgRNA (Mali et al., Science 2013). Applicants generated mutations in the two additional (of 3 total) RuvC catalytic domains present within S. pyogenes Cas9, making a Cas9 3KO [Cas9(D10A, E762A, and D986A)] and tested it against the AAVS1 locus (sgRNA guide sequence: ggggccactagggacaggat (SEQ ID NO: 254)). Applicants found lower indel mutagenesis by the Cas9 3K0 vs. the D10A nickase mutant (see table below in which Data is average of 3 biological replicates.)

|  | Average indels | Standard error of mean |
|---|---|---|
| D10A | 0.0267 | 0.008854089 |
| 3KO | 0.0067 | 0.003340519 |
| wtCas9 | 9.5927 | 0.394065483 |

Specific editing of mouse embryos: Applicants titrated Cas9 dosage in mouse zygotes from 10 ng/uL to 0.01 ng/uL and determined the optimal dosage for specific Cas9 editing by double nicking. At the 10 ng/uL condition, Applicants demonstrated 88% editing with wild-type Cas9 and 83% editing by D10A double nicking. D10A+L sgRNA at 10 ng/uL exhibited 0% indels while wt Cas9 exhibited no indels at the 1, 0.1, and 0.01 ng/uL condition.

The experimental details for this example with regard to cell culture and transfection protocols and SURVEYOR nuclease assays for genome modification are further described in Example 31.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

REFERENCES

1. Ding, Q. et al. A TALEN genome-editing system for generating human stem cell-based disease models. Cell Stem Cell 12, 238-251 (2013).
2. Soldner, F. et al. Generation of isogenic pluripotent stem cells differing exclusively at two early onset Parkinson point mutations. Cell 146, 318-331 (2011).
3. Carlson, D. F. et al. Efficient TALEN-mediated gene knockout in livestock. Proc Natl Acad Sci USA 109, 17382-17387 (2012).
4. Geurts, A. M. et al. Knockout Rats via Embryo Microinjection of Zinc-Finger Nucleases. Science 325, 433-433 (2009).
5. Takasu, Y. et al. Targeted mutagenesis in the silkworm Bombyx mori using zinc finger nuclease mRNA injection. Insect Biochem Molec 40, 759-765 (2010).
6. Watanabe, T. et al. Non-transgenic genome modifications in a hemimetabolous insect using zinc-finger and TAL effector nucleases. Nat Commun 3 (2012).
7. Porteus, M. H. & Baltimore, D. Chimeric nucleases stimulate gene targeting in human cells. Science 300, 763 (2003).
8. Miller, J. C. et al. An improved zinc-finger nuclease architecture for highly specific genome editing. Nat Biotechnol 25, 778-785 (2007).
9. Sander, J. D. et al. Selection-free zinc-finger-nuclease engineering by context-dependent assembly (CoDA). Nat Methods 8, 67-69 (2011).
10. Wood, A. J. et al. Targeted genome editing across species using ZFNs and TALENs. Science 333, 307 (2011).

11. Christian, M. et al. Targeting DNA double-strand breaks with TAL effector nucleases. Genetics 186, 757-761 (2010).
12. Zhang, F. et al. Efficient construction of sequence-specific TAL effectors for modulating mammalian transcription. Nat Biotechnol 29, 149-153 (2011).
13. Miller, J. C. et al. A TALE nuclease architecture for efficient genome editing. Nat Biotechnol 29, 143-148 (2011).
14. Reyon, D. et al. FLASH assembly of TALENs for high-throughput genome editing. Nat Biotechnol 30, 460-465 (2012).
15. Boch, J. et al. Breaking the code of DNA binding specificity of TAL-type III effectors. Science 326, 1509-1512 (2009).
16. Moscou, M. J. & Bogdanove, A. J. A simple cipher governs DNA recognition by TAL effectors. Science 326, 1501 (2009).
17. Sanjana, N. E. et al. A transcription activator-like effector toolbox for genome engineering. Nat Protoc 7, 171-192 (2012).
18. Deveau, H., Garneau, J. E. & Moineau, S. CRISPR-Cas system and its role in phage-bacteria interactions. Annu Rev Microbiol 64, 475-493 (2010).
19. Horvath, P. & Barrangou, R. CRISPR-Cas, the immune system of bacteria and archaea. Science 327, 167-170 (2010).
20. Makarova, K. S. et al. Evolution and classification of the CRISPR-Cas systems. Nat Rev Microbiol 9, 467-477 (2011).
21. Bhaya, D., Davison, M. & Barrangou, R. CRISPR-Cas systems in bacteria and archaea: versatile small RNAs for adaptive defense and regulation. Annu Rev Genet 45, 273-297 (2011).
22. Cong, L. et al. Multiplex genome engineering using CRISPR-Cas systems. Science 339, 819-823 (2013).
23. Mali, P. et al. RNA-guided human genome engineering via Cas9. Science 339, 823-826 (2013b).
24. Jinek, M. et al. RNA-programmed genome editing in human cells. eLife 2, e00471 (2013).
25. Cho, S. W., Kim, S., Kim, J. M. & Kim, J. S. Targeted genome engineering in human cells with the Cas9 RNA-guided endonuclease. Nat Biotechnol 31, 230-232 (2013).
26. Garneau, J. E. et al. The CRISPR-Cas bacterial immune system cleaves bacteriophage and plasmid DNA. Nature 468, 67-71 (2010).
27. Jinek, M. et al. A programmable dual-RNA-guided DNA endonuclease in adaptive bacterial immunity. Science 337, 816-821 (2012).
28. Gasiunas, G., Barrangou, R., Horvath, P. & Siksnys, V. Cas9-crRNA ribonucleoprotein complex mediates specific DNA cleavage for adaptive immunity in bacteria. Proc Natl Acad Sci USA 109, E2579-2586 (2012).
29. Urnov, F. D., Rebar, E. J., Holmes, M. C., Zhang, H. S. & Gregory, P. D. Genome editing with engineered zinc finger nucleases. Nat Rev Genet 11, 636-646 (2010).
30. Hsu, P. D. & Zhang, F. Dissecting neural function using targeted genome engineering technologies. ACS Chem Neurosci 3, 603-610 (2012).
31. Perez, E. E. et al. Establishment of HIV-1 resistance in CD4(+) T cells by genome editing using zinc-finger nucleases. Nat Biotechnol 26, 808-816 (2008).
32. Cong, L. et al. Multiplex Genome Engineering Using CRISPR-Cas Systems. Science 339, 819-823 (2013).
33. Chen, F. Q. et al. High-frequency genome editing using ssDNA oligonucleotides with zinc-finger nucleases. Nat Methods 8, 753-U796 (2011).
34. Bedell, V. M. et al. In vivo genome editing using a high-efficiency TALEN system. Nature 491, 114-U133 (2012).
35. Saleh-Gohari, N. & Helleday, T. Conservative homologous recombination preferentially repairs DNA double-strand breaks in the S phase of the cell cycle in human cells. Nucleic Acids Res 32, 3683-3688 (2004).
36. Deltcheva, E. et al. CRISPR RNA maturation by trans-encoded small RNA and host factor RNase III. Nature 471, 602-607 (2011).
37. Sapranauskas, R. et al. The *Streptococcus thermophilus* CRISPR-Cas system provides immunity in *Escherichia coli*. Nucleic Acids Res 39, 9275-9282 (2011).
38. Hwang, W. Y. et al. Efficient genome editing in zebrafish using a CRISPR-Cas system. Nat Biotechnol 31, 227-229 (2013).
39. Wang, H. et al. One-Step Generation of Mice Carrying Mutations in Multiple Genes by CRISPR-Cas-Mediated Genome Engineering. Cell 153, 910-918 (2013).
40. Shen, B. et al. Generation of gene-modified mice via Cas9/RNA-mediated gene targeting. Cell Res 23, 720-723 (2013).
41. Qi, L. S. et al. Repurposing CRISPR as an RNA-guided platform for sequence-specific control of gene expression. Cell 152, 1173-1183 (2013).
42. Tuschl, T. Expanding small RNA interference. Nat Biotechnol 20, 446-448 (2002).
43. Smithies, O., Gregg, R. G., Boggs, S. S., Koralewski, M. A. & Kucherlapati, R. S. Insertion of DNA sequences into the human chromosomal beta-globin locus by homologous recombination. Nature 317, 230-234 (1985).
44. Thomas, K. R., Folger, K. R. & Capecchi, M. R. High frequency targeting of genes to specific sites in the mammalian genome. Cell 44, 419-428 (1986).
45. Hasty, P., Rivera-Perez, J. & Bradley, A. The length of homology required for gene targeting in embryonic stem cells. Mol Cell Biol 11, 5586-5591 (1991).
46. Wu, S., Ying, G. X., Wu, Q. & Capecchi, M. R. A protocol for constructing gene targeting vectors: generating knockout mice for the cadherin family and beyond. Nat Protoc 3, 1056-1076 (2008).
47. Guschin, D. Y. et al. A rapid and general assay for monitoring endogenous gene modification. Methods Mol Biol 649, 247-256 (2010).
48. Oliveira, T. Y. et al. Translocation capture sequencing: a method for high throughput mapping of chromosomal rearrangements. J Immunol Methods 375, 176-181 (2012).
49. Deltcheva, E. et al. CRISPR RNA maturation by trans-encoded small RNA and host factor RNase III. Nature 471, 602-607 (2011).
50. Bogenhagen, D. F. & Brown, D. D. Nucleotide sequences in *Xenopus* 5S DNA required for transcription termination. Cell 24, 261-270 (1981).
51. Bultmann, S. et al. Targeted transcriptional activation of silent oct4 pluripotency gene by combining designer TALEs and inhibition of epigenetic modifiers. Nucleic Acids Res 40, 5368-5377 (2012).
52. Valton, J. et al. Overcoming transcription activator-like effector (TALE) DNA binding domain sensitivity to cytosine methylation. J Biol Chem 287, 38427-38432 (2012).
53. Christian, M. et al. Targeting DNA double-strand breaks with TAL effector nucleases. Genetics 186, 757-761 (2010).

54. Mussolino, C. et al. A novel TALE nuclease scaffold enables high genome editing activity in combination with low toxicity. Nucleic acids research 39, 9283-9293 (2011).
55. Bobis-Wozowicz, S., Osiak, A., Rahman, S. H. & Cathomen, T. Targeted genome editing in pluripotent stem cells using zinc-finger nucleases. Methods 53, 339-346 (2011).
56. Jiang, W., Bikard, D., Cox, D., Zhang, F. & Marraffini, L. A. RNA-guided editing of bacterial genomes using CRISPR-Cas systems. Nat Biotechnol 31, 233-239 (2013).
57. Michaelis, L. M., Maud "Die kinetik der invertinwirkung.". Biochem. z (1913).
58. Mahfouz, M. M. et al. De novo-engineered transcription activator-like effector (TALE) hybrid nuclease with novel DNA binding specificity creates double-strand breaks. Proc Natl Acad Sci USA 108, 2623-2628 (2011).
59. Wilson, E. B. Probable inference, the law of succession, and statistical inference. J Am Stat Assoc 22, 209-212 (1927).
60. Tangri S, et al., Rationally engineered therapeutic proteins with reduced immunogenicity, J Immunol. 2005 Mar. 15; 174(6):3187-96.
61. REMINGTON'S PHARMACEUTICAL SCIENCES (Mack Pub. Co., N.J. 1991)
62. Lopes, V. S., etc al., Retinal gene therapy with a large MYO7A cDNA using adeno-associated virus. Gene Ther, 2013 Jan. 24. doi: 10.1038/gt 2013.3.[Epub ahead of print]
63. Kaplitt, M. G., et al., Safety and tolerability of gene therapy with an adeno-associated virus (AAV) borne GAD gene for Parkinson's disease: an open label, phase I trial. Lancet. 2007 Jun. 23; 369(9579):2097-105.
64. Nathwani, A. C., et al., Adenovirus-associated virus vector-mediated gene transfer in hemophilia B. N Engl J Med. 2011 Dec. 22; 365(25):2357-65. doi: 10.1056/NEJMoa1108046. Epub 2011 Dec. 10.
65. Gray S J, Foti S B, Schwartz J W, Bachaboina L, Taylor-Blake B, Coleman J, Ehlers M D, Zylka M J, McCown T J, Samulski R J. Optimizing promoters for recombinant adeno-associated virus-mediated gene expression in the peripheral and central nervous system using self-complementary vectors. Hum Gene Ther. 2011 September; 22(9):1143-53. doi: 10.1089/hum.2010.245.
66. Liu D, Fischer I. Two alternative promoters direct neuron-specific expression of the rat microtubule-associated protein 1B gene. J Neurosci. 1996 Aug. 15; 16(16): 5026-36.
67. Levitt N. Briggs D. Gil A. Proudfoot N.J. Definition of an efficient synthetic poly(A) site. Genes Dev. 1989; 3:1019-1025.
68. McClure C, Cole K L, Wulff P, Klugmann M, Murray A J. Production and titering of recombinant adeno-associated viral vectors. J Vis Exp. 2011 Nov. 27; (57):e3348. doi: 10.3791/3348.
69. Banker G, Goslin K. Developments in neuronal cell culture. Nature. 1988 Nov. 10; 336(6195):185-6.
70. Chang, N., Sun, C., Gao, L., Zhu, D., Xu, X., Zhu, X., Xiong, J. W., and Xi, J. J. (2013). Genome editing with RNA-guided Cas9 nuclease in zebrafish embryos. Cell research 23, 465-472.
71. Dianov, G. L., and Hubscher, U. (2013). Mammalian base excision repair: the forgotten archangel. Nucleic acids research 41, 3483-3490.
72. Friedland, A. E., Tzur, Y. B., Esvelt, K. M., Colaiacovo, M. P., Church, G. M., and Calarco, J. A. (2013). Heritable genome editing in *C. elegans* via a CRISPR-Cas9 system. Nature methods 10, 741-743.
73. Fu, Y., Foden, J. A., Khayter, C., Maeder, M. L., Reyon, D., Joung, J. K., and Sander, J. D. (2013). High-frequency off-target mutagenesis induced by CRISPR-Cas nucleases in human cells. Nature biotechnology.
74. Gratz, S. J., Cummings, A. M., Nguyen, J. N., Hamm, D. C., Donohue, L. K., Harrison, M. M., Wildonger, J., and O'Connor-Giles, K. M. (2013). Genome Engineering of *Drosophila* with the CRISPR RNA-Guided Cas9 Nuclease. Genetics 194, 1029-1035.
75. Hsu, P. D., Scott, D. A., Weinstein, J. A., Ran, F. A., Konermann, S., Agarwala, V., Li, Y., Fine, E. J., Wu, X., Shalem, O., et al. (2013). DNA targeting specificity of RNA-guided Cas9 nucleases. Nature biotechnology.
76. Mali, P., Aach, J., Stranges, P. B., Esvelt, K. M., Moosburner, M., Kosuri, S., Yang, L., and Church, G. M. (2013a). CAS9 transcriptional activators for target specificity screening and paired nickases for cooperative genome engineering. Nature biotechnology.
77. Maresca, M., Lin, V. G., Guo, N., and Yang, Y. (2013). Obligate ligation-gated recombination (ObLiGaRe): custom-designed nuclease-mediated targeted integration through nonhomologous end joining. Genome research 23, 539-546.
78. Pattanayak, V., Lin, S., Guilinger, J. P., Ma, E., Doudna, J. A., and Liu, D. R. (2013). High-throughput profiling of off-target DNA cleavage reveals RNA-programmed Cas9 nuclease specificity. Nature biotechnology.

What is claimed is:

1. A method of modifying a genomic locus of interest in a eukaryotic cell, comprising introducing into the eukaryotic cell an engineered composition comprising or encoding:
  (a) a Cas9, wherein the Cas9 comprises one or more mutations in a RuvC or HNH domain and is a nickase;
  (b) a first CRISPR-Cas system RNA comprising a first guide sequence capable of hybridizing to a first target sequence at the genomic locus of interest, a first tracr-mate sequence, and a first tracr sequence capable of hybridizing to the first tracr-mate sequence; and
  (c) a second CRISPR-Cas system RNA comprising a second guide sequence capable of hybridizing to a second target sequence at the genomic locus of interest, a second tracr-mate sequence, and a second tracr sequence capable of hybridizing to the second tracr-mate sequence;
  wherein the first and the second guide sequences direct sequence-specific binding of a first and a second CRISPR complexes to the first and second target sequences, respectively, wherein the first CRISPR complex comprises the Cas9 complexed with the first CRISPR-Cas system RNA, wherein the second CRISPR complex comprises the Cas9 complexed with the second CRISPR-Cas system RNA, wherein the first CRISPR complex cleaves one DNA strand of the genomic locus of interest to produce a first nick, wherein the second CRISPR complex cleaves the opposite DNA strand of the genomic locus of interest to produce a second nick, wherein the first nick is at least 26 nucleotides 5' of the second nick.

2. The method of claim 1, wherein the composition comprises a vector encoding the first and the second CRISPR-Cas system RNAs and the Cas9.

3. The method of claim 2, wherein the vector is a viral vector.

4. The method of claim 3, wherein the viral vector is an AAV vector.

5. The method of claim 1, wherein the composition comprises the first and the second CRISPR-Cas system RNAs and an mRNA encoding the Cas9.

6. The method of claim 1, wherein the Cas9 comprises one or more mutations in a RuvC domain.

7. The method of claim 6, wherein the Cas9 comprises one or more mutations selected from the group consisting of D10A, E762A and D986A.

8. The method of claim 6, wherein the Cas9 comprises a D10A mutation.

9. The method of claim 1, wherein the Cas9 comprises one or more mutations in a HNH domain.

10. The method of claim 9, wherein the Cas9 comprises one or more mutations selected from the group consisting of H840A, N854A and N863A.

11. The method of claim 9, wherein the Cas9 comprises a H840A mutation.

12. The method of claim 1, wherein the Cas9 is *S. pyogenes* Cas9.

13. The method of claim 1, wherein the Cas9 is *S. aureus* Cas9.

14. The method of claim 1, wherein the Cas9 comprises at least one nuclear localization sequence (NLS).

15. The method of claim 1, wherein the Cas9 comprises at least two NLSs.

16. The method of claim 1, wherein the Cas9 is fused to a heterologous functional protein domain.

17. The method of claim 1, wherein the first and the second CRISPR-Cas system RNAs are each a chimeric RNA comprising the guide sequence fused to the tracr mate sequence and the tracr sequence.

18. The method of claim 1, wherein the first nick is at least 30 nucleotides 5' of the second nick.

19. The method of claim 1, wherein the first nick is at most 100 nucleotides 5' of the second nick.

20. The method of claim 1, wherein the first nick is about 30-100 nucleotides 5' of the second nick.

21. The method of claim 1, wherein the first nick is about 34-50 nucleotides 5' of the second nick.

22. The method of claim 1, wherein the genomic locus of interest encodes a gene product.

23. The method of claim 22, wherein the gene product is a protein.

24. The method of claim 22, wherein expression of the gene product is decreased or increased, or activity or function of the gene product is altered.

25. The method of claim 1, wherein the eukaryotic cell is a mammalian cell.

26. The method of claim 1, wherein the eukaryotic cell is a human cell.

27. The method of claim 1, wherein the eukaryotic cell is a plant cell.

* * * * *